US012590288B2

(12) United States Patent
Rajagopal et al.

(10) Patent No.: US 12,590,288 B2
(45) Date of Patent: Mar. 31, 2026

(54) METHOD OF TREATING AN INFLAMMATORY DISEASE BY ADMINISTERING AN AGENT WHICH BINDS A SURFACE RECEPTOR ON A TUFT CELL THAT INDUCES AN ILC CLASS 2 INFLAMMATORY RESPONSE

(71) Applicants: The Broad Institute, Inc., Cambridge, MA (US); Massachusetts Institute of Technology, Cambridge, MA (US); The General Hospital Corporation, Boston, MA (US)

(72) Inventors: Jayaraj Rajagopal, Boston, MA (US); Aviv Regev, Cambridge, MA (US); Moshe Biton, Cambridge, MA (US); Adam Haber, Cambridge, MA (US); Daniel Montoro, Boston, MA (US); Ramnik Xavier, Boston, MA (US)

(73) Assignees: The Broad Institute, Inc., Cambridge, MA (US); Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 1554 days.

(21) Appl. No.: 16/604,589

(22) PCT Filed: Apr. 12, 2018

(86) PCT No.: PCT/US2018/027388
§ 371 (c)(1),
(2) Date: Oct. 11, 2019

(87) PCT Pub. No.: WO2018/191558
PCT Pub. Date: Oct. 18, 2018

(65) Prior Publication Data
US 2021/0040442 A1 Feb. 11, 2021

Related U.S. Application Data

(60) Provisional application No. 62/484,746, filed on Apr. 12, 2017.

(51) Int. Cl.
| | |
|---|---|
| *A61K 9/00* | (2006.01) |
| *C12N 5/071* | (2010.01) |
| *C12Q 1/6816* | (2018.01) |
| *C12Q 1/6881* | (2018.01) |

(52) U.S. Cl.
CPC .......... *C12N 5/0602* (2013.01); *A61K 9/0053* (2013.01); *A61K 9/0073* (2013.01); *C12Q 1/6816* (2013.01); *C12Q 1/6881* (2013.01); *C12N 2501/60* (2013.01); *C12Q 2563/185* (2013.01); *C12Q 2565/626* (2013.01); *C12Q 2565/627* (2013.01); *C12Q 2565/629* (2013.01); *C12Q 2600/158* (2013.01)

(58) Field of Classification Search
CPC .............. C12N 5/0602; C12N 2501/60; A61K 9/0053; A61K 9/073; C12Q 1/6816; C12Q 2563/185; C12Q 2565/626; C12Q 2565/627; C12Q 2565/629
See application file for complete search history.

(56) References Cited

U.S. PATENT DOCUMENTS

| | | | |
|---|---|---|---|
| 4,737,323 A | 4/1988 | Martin et al. |
| 4,816,567 A | 3/1989 | Cabilly et al. |
| 4,837,028 A | 6/1989 | Allen |
| 5,270,163 A | 12/1993 | Gold et al. |
| 5,686,281 A | 11/1997 | Roberts |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |

(Continued)

FOREIGN PATENT DOCUMENTS

| | | |
|---|---|---|
| EP | 2 784 162 A1 | 10/2014 |
| EP | 2 771 468 B1 | 2/2015 |

(Continued)

OTHER PUBLICATIONS

Gerbe et al (Intestinal epithelial tuft cells initiate type 2 mucosal immunity to helminth parasites. Nature, vol. 529, Jan. 2016; cited in IDS dated Oct. 11, 2019) (Year: 2016).*

(Continued)

*Primary Examiner* — Robert S Landsman

(74) *Attorney, Agent, or Firm* — Foley & Lardner LLP; Sunit Talapatra

(57) ABSTRACT

An atlas of intestinal epithelial cells, intestinal epithelial stem cells and intestinal immune cells identifies new cell populations, markers, networks, and responses to stimuli. Intestinal epithelial cell sub-types are also found in the trachea. Accordingly, disclosed are methods of modulating epithelial cell differentiation, maintenance and/or function, related methods for the treatment of disease, including IBD and asthma. Also disclosed are methods and kits for identifying cell types, their differentiation, homeostasis and activation.

20 Claims, 131 Drawing Sheets
Specification includes a Sequence Listing.

(56)         References Cited

U.S. PATENT DOCUMENTS

| | | |
|---|---|---|
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang et al. |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0171156 A1 | 9/2004 | Hartley et al. |
| 2004/0224402 A1 | 11/2004 | Bonyhadi et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang et al. |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0082470 A1 | 3/2015 | Heintz et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208243 A1 | 7/2016 | Zhang et al. |
| 2017/0047193 A1 | 2/2017 | Jiang et al. |
| 2017/0211142 A1 | 7/2017 | Smargon et al. |
| 2019/0093107 A1 | 3/2019 | Zhang et al. |
| 2019/0263912 A1 | 8/2019 | Haber et al. |

FOREIGN PATENT DOCUMENTS

| | | |
|---|---|---|
| EP | 2 764 103 B1 | 8/2015 |
| EP | 3 009 511 A2 | 4/2016 |
| WO | 92/15322 A1 | 9/1992 |
| WO | 96/40281 A2 | 12/1996 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |

(56) References Cited

FOREIGN PATENT DOCUMENTS

| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2016/000304 A1 | 1/2016 |
| WO | 2016/011210 A2 | 1/2016 |
| WO | 2016/028682 A1 | 2/2016 |
| WO | 2016/040476 A1 | 3/2016 |
| WO | 2016/049024 A2 | 3/2016 |
| WO | 2016/049163 A2 | 3/2016 |
| WO | 2016/049258 A2 | 3/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/106236 A1 | 6/2016 |
| WO | 2016/106244 A1 | 6/2016 |
| WO | 2016/161516 A1 | 10/2016 |
| WO | 2016/168584 A1 | 10/2016 |
| WO | 2017/070605 A1 | 4/2017 |
| WO | 2017/075294 A1 | 5/2017 |
| WO | 2017/164936 A1 | 9/2017 |
| WO | 2017/219027 A1 | 12/2017 |
| WO | 2018/035250 A1 | 2/2018 |
| WO | 2018/089386 A1 | 5/2018 |
| WO | 2018/170333 A1 | 9/2018 |
| WO | 2018/191558 A1 | 10/2018 |
| WO | 2019/005866 A1 | 1/2019 |

OTHER PUBLICATIONS

Van Es, et al., "Notch/Gamma-Secretase Inhibition Turns Proliferative Cells in Intestinal Crypts and Adenomas into Goblet Cells", Nature, vol. 435, No. 7044, Jun. 16, 2005, 959-963.

Jonz, et al., "Epithelial Mitochondria-Rich Cells and Associated Innervation in Adult and Developing Zebrafish", The Journal of Comparative Neurology, vol. 497, No. 5, Aug. 10, 2006, 817-832.

Kaser, et al., "XBP1 Links Er Stress to Intestinal Inflammation and Confers Genetic Risk for Human Inflammatory Bowel Disease", Cell, vol. 134, No. 5, Sep. 5, 2008, 743-756.

Katz, et al., "The Zinc-Finger Transcription Factor Klf4 is Required for Terminal Differentiation of Goblet Cells in the Colon", Development, vol. 129, No. 11, Jun. 2002, 2619-2628.

Kim, et al., "Single-Cell Transcript Profiles Reveal Multilineage Priming in Early Progenitors Derived from Lgr5(+) Intestinal Stem Cells", Cell Reports, vol. 16, No. 8, Aug. 23, 2016, 2053-2060.

Kobayashi, et al., "Identification of Novel Genes Selectively Expressed in the Follicle-associated Epithelium from the Meta-Analysis of Transcriptomics Data from Multiple Mouse Cell and Tissue Populations", DNA Research : An International Journal for Rapid Publication of Reports on Genes and Genomes, vol. 19, No. 5, Oct. 2012, 407-422.

Kohlnhofer, et al., "GATA4 Regulates Epithelial Cell Proliferation to Control Intestinal Growth and Development in Mice", Cellular and Molecular Gastroenterology and Hepatology, vol. 2, No. 2, Mar. 2016, 189-209.

Krasteva, et al., "Cholinergic Brush Cells in the Trachea Mediate Respiratory Responses to Quorum Sensing Molecules", Life Sciences, vol. 91, No. (21-22), Nov. 27, 2012, 992-996.

Krasteva, et al., "Cholinergic Chemosensory Cells in the Trachea Regulate Breathing", Proceedings of the National Academy of Sciences of the United States of America, vol. 108, No. 23, Jun. 7, 2011, 9478-9483.

Lee, et al., "T2R38 Taste Receptor Polymorphisms Underlie Susceptibility to Upper Respiratory Infection", Journal of Clinical Investigation, vol. 122, No. 11, Nov. 2012, 4145-4159.

Lei, et al., "Intestinal Subepithelial Myofibroblasts Support the Growth of Intestinal Epithelial Stem Cells", PLoS One, vol. 9, No. 1, Jan. 6, 2014, 11 pages.

Lindemans, et al., "Interleukin-22 Promotes Intestinal-Stem-Cell-Mediated Epithelial Regeneration", Nature, vol. 528, Dec. 24, 2015, 560-564.

Lopez Jimenez, et al., "Two Novel Genes, Gpr113, which Encodes a Family 2 G-protein-coupled Receptor, and Trcg1, are Selectively Expressed in Taste Receptor Cells", Genomics, vol. 85, No. 4, Apr. 2005, 472-482.

Mabbott, et al., "Microfold (M) Cells: Important Immunosurveillance Posts in the Intestinal Epithelium", Mucosal Immunology, vol. 6, No. 4, Jul. 2013, 666-677.

Martinez Rodriguez, et al., "Expansion of Paneth Cell Population in Response to Enteric Salmonella enterica Serovar Typhimurium Infection", Infection and immunity, vol. 80, No. 1, Jan. 2012, 266-275.

Miklavc, et al., "A New Role for P2X4 Receptors as Modulators of Lung Surfactant Secretion", Frontiers in Cellular Neuroscience, vol. 7, Article 171, Oct. 8, 2013, 6 pages.

Miyoshi, et al., "In Vitro Expansion and Genetic Modification of Gastrointestinal Stem Cells in Spheroid Culture", Nature Protocols, vol. 8, No. 12, Dec. 2013, 2481-2482.

Mombaerts, et al., "Spontaneous Development of Inflammatory Bowel Disease in T Cell Receptor Mutant Mice", Cell, vol. 75, No. 2, Oct. 22, 1993, 274-282.

Mukherjee, et al., "Antimicrobial Defense of the Intestine", Immunity, vol. 42, No. 1, Jan. 20, 2015, 28-39.

Mullins, et al., "Identification of a Human Ortholog of the Mouse Depp Gene Locus, Encoding a Novel Member of the Csp-1/Dcpp Salivary Protein Family", Physiological Genomics—American Journal of Physiology, vol. 28, No. 1, Dec. 13, 2006, 129-140.

Munitz, et al., "Distinct Roles for IL-13 and IL-4 Via IL-13 Receptor Alpha1 and the Type II IL-4 Receptor in Asthma Pathogenesis", Proceedings of the National Academy of Sciences of the United States of America, vol. 105, No. 20, May 20, 2008, 7240-7245.

Munoz, et al., "The LGR5 Intestinal Stem Cell Signature: Robust Expression of Proposed Quiescent '+4' Cell Markers", The EMBO Journal, vol. 31, No. 14, Jun. 12, 2012, 3079-3091.

Ng, et al., "Annexin-1-Deficient Mice Exhibit Spontaneous Airway Hyperresponsiveness and Exacerbated Allergen—Specific Antibody Responses in a Mouse Model of Asthma", Clinical and Experimental Allergy, vol. 41, No. 12, Dec. 2011, 1793-1803.

Noah, et al., "Intestinal Development and Differentiation", Experimental Cell Research, vol. 317, No. 19, Nov. 15, 2011, 2702-2710.

Overdier, et al., "The Winged Helix Transcriptional Activator Hfh-3 is Expressed in the Distal Tubules of Embryonic and Adult Mouse Kidney", Journal of Biological Chemistry, vol. 272, No. 21, May 23, 1997, 13725-13730.

Overton, et al., "GPR119 a Novel G Protein-Coupled Receptor Target for the Treatment of Type 2 Diabetes and Obesity", British Journal of Pharmacology, vol. 153, Mar. 2008, S76-S81.

(56) References Cited

OTHER PUBLICATIONS

Pardo-Saganta, et al., "Parent Stem Cells Can Serve as Niches for their Daughter Cells", Nature, vol. 523, No. 7562, Jul. 30, 2015, 597-601.

Pelaseyed, et al., "The Mucus and Mucins of the Goblet Cells and Enterocytes Provide the First Defense Line of the Gastrointestinal Tract and Interact with the Immune System", Immunological Reviews, vol. 260, No. 1, Jul. 2014, 8-20.

Peterson, et al., "Intestinal Epithelial Cells: Regulators of Barrier Function and Immune Homeostasis", Nature Reviews Immunology, vol. 14, No. 3, Mar. 2014, 141-153.

Py, et al., "Cochlin Produced by Follicular Dendritic Cells Promotes Antibacterial Innate Immunity", Immunity, vol. 38, No. 5, May 23, 2013, 1063-1072.

Quigley, et al., "Specification of Ion Transport Cells in the Xenopus Larval Skin", Development, vol. 138, No. 4, Feb. 2011, 705-714.

Rawlins, et al., "The Role of Scgb1A1+ Clara Cells in the Long-term Maintenance and Repair of Lung Airway, but not Alveolar, Epithelium", Cell Stem Cell, vol. 4, No. 6, Jun. 5, 2009, 525-534.

Rock, et al., "Basal Cells as Stem Cells of the Mouse Trachea Aand Human Airway Epithelium", Proceedings of the National Academy of Sciences of the United States of America, vol. 106, No. 31, Aug. 4, 2009, 12771-12775.

Rodenburg, et al., "*Salmonella* Induces Prominent Gene Expression in the Rat Colon", BMC Microbiology, vol. 7, Sep. 12, 2007, 16 pages.

Roy, et al., "Muc5B is Required for Airway Defence", Nature, vol. 505, No. 7483, Jan. 16, 2014, 412-416.

Saha, et al., "Macrophage-Derived Extracellular Vesicle-ackaged WNTS Rescue Intestinal Stem Cells and Enhance Survival After Radiation Injury", Nature Communications, vol. 7, Oct. 13, 2016, 16 pages.

Sakaguchi, et al., "S100A11, A Dual Growth Regulator of Epidermal Keratinocytes", Amino Acids, vol. 41, No. 4, Oct. 2011, 797-807.

Salzman, et al., "Protection Against Enteric *Salmonellosis* in Transgenic Mice Expressing a Human Intestinal Defensin", Nature, vol. 422, No. 6931, Apr. 3, 2003, 522-526.

Sato, et al., "Single Lgr5 Stem Cells Build Crypt-Villus Structures In Vitro without a Mesenchymal Niche", Nature, vol. 459, No. 7244, May 14, 2009, 262-265.

Saunders, et al., "Chemosensory Brush Cells of the Trachea. A Stable Population in a Dynamic Epithelium", American Journal of Respiratory Cell and Molecular Biology, vol. 49, No. 2, Aug. 2013, 190-196.

Shindo, et al., "FXYD6, a Na,K-ATPase Regulator, is Expressed in Type II Taste Cells", Bioscience, Biotechnology and Biochemistry, vol. 75, No. 6, 2011, 1061-1066.

Stappenbeck, et al., "The Role of Stromal Stem Cells in Tissue Regeneration and Wound Repair", Science, vol. 324, No. 5935, Jun. 26, 2009, 5 pages.

Strober, et al., "Chronic Intestinal Inflammation: An Unexpected Outcome in Cytokine or T Cell Receptor Mutant Mice", Cell, vol. 75, No. 2, Oct. 22, 1993, 203-205.

Tata, et al., "Dedifferentiation of Committed Epithelial Cells into Stem Cells in Vivo", Nature, vol. 503, No. 7475, Nov. 14, 2013, 218-223.

Terahara, et al., "Comprehensive Gene Expression Profiling of Peyer's Patch M Cells, Villous M-Like Cells, and Intestinal Epithelial Cells", Journal of Immunology, vol. 180, No. 12, Jun. 15, 2008, 7840-7846.

Tetteh, et al., "Replacement of Lost Lgr5-Positive Stem Cells through Plasticity of Their Enterocyte-Lineage Daughters", Cell Stem Cell, vol. 18, No. 2, Feb. 4, 2016, 203-213.

Treutlein, et al., "Reconstructing Lineage Hierarchies of the Distal Lung Epithelium Using Single-cell Rna-seq", Nature, vol. 509, No. 7500, May 15, 2014, 371-375.

Troy, et al., "Claudin Immunolocalization in Neonatal Mouse Epithelial Tissues", Cell and Tissue Research, vol. 330, No. 2, Nov. 2007, 381-388.

Van Der Flier, et al., "Stem Cells, Self-Renewal, and Differentiation in the Intestinal Epithelium", Annual Review of Physiology, vol. 71, 2009, 241-260.

Vassen, et al., "Gfi1B:Green Fluorescent Protein Knock-In Mice Reveal a Dynamic Expression Pattern of Gfi1B during Hematopoiesis that is Largely Complementary to Gfi1", Blood, vol. 109, No. 6, Mar. 15, 2007, 2356-2364.

Bezencon, et al., "Murine Intestinal Cells Expressing Trpm5 are Mostly Brush Cells and Express Markers of Neuronal and Inflammatory Cells," Journal of Comparative Neurology, Aug. 10, 2008, pp. 514-525.

Gerbe, et al., "Intestinal Epithelial Tuft Cells Initiate Type 2 Mucosal Immunity to Helminth Parasites", Nature, vol. 529, No. 7585, Jan. 14, 2016, 226-230.

Haber, et al., "A Single-Cell Survey of the Small Intestinal Epithelium," Nature, Nov. 8, 2017, pp. 333-338.

Harris, et al., "The Enigmatic Tuft Cell in Immunity," Science, Mar. 18, 2016, pp. 1264-1265.

Howitt, et al., "Tuft Cells Taste-Chemosensory Cells, Orchestrate Parasite Type 2 Immunity in the Gut," Science, vol. 351, No. 6279, Mar. 18, 2016, 1329-1333.

Reid, et al., "The Mysterious Pulmonary Brush Cell a Cell in Search of a Function," American Journal of Respiratory and Critical Care Medicine, Jul. 1, 2005, pp. 136-139.

The Broad Institute, Inc., "Notification of Transmittal of the International Search Report and the Written Opinion of the International Searching Authority, or the Declaration", Jul. 10, 2018, 11 pages.

Verzi, et al. "Transcription Factor Foxq1 Controls Mucin Gene Expression and Granule Content in Mouse Stomach Surface Mucous Cells", Gastroenterology, vol. 135, No. 2, Aug. 2008, 591-600.

Vidarsson, et al. "The Forkhead Transcription Factor Foxi1 is a Master Regulator of Vacuolar H-atpase Proton Pump Subunits in the Inner Ear, Kidney and Epididymis", PLoS One, vol. 4, No. 2, 2009, 11 pages.

Von Moltke, et al. "Tuft-Cell-Derived IL-25 Regulates an Intestinal ILC2-Epithelial Response Circuit", Nature, vol. 529, No. 7585, Jan. 14, 2016, 221-225.

Warburton, et al. "The Molecular Basis of Lung Morphogenesis", Mechanisms of Development, vol. 92, No. 1, Mar. 15, 2000, 55-81.

Watson, et al. "Clonal Dynamics Reveal Two Distinct Populations of Basal Cells in Slow-Turnover Airway Epithelium", Cell Reports, vol. 12, No. 1, Jul. 7, 2015, 90-101.

Worthington, et al. "Enteroendocrine Cells-Sensory Sentinels of the Intestinal Environment and Orchestrators of Mucosal Immunity", Mucosal Immunology, vol. 11, No. 1, Jan. 2018, 3-20.

Yan, et al. "Non-Equivalence of Wnt and R-Spondin Ligands During Lgr5+ Intestinal Stem Cell Self-renewal", Nature, vol. 545, No. 7653, May 11, 2017, 238-242.

Yoon, et al. "Association between Polymorphisms in Bitter Taste Receptor Genes and Clinical Features in Korean Asthmatics", Respiration, vol. 91, No. 2, 2016, 141-150.

Young, et al. "Expression of Taste Molecules in the Upper Gastrointestinal Tract in Humans with and Without Type 2 Diabetes", Gut, vol. 58, No. 3, Mar. 2009, 337-346.

Zech, et al. "P2rx4 Deficiency in Mice Alleviates Allergen-Induced Airway Inflammation", Oncotarget, vol. 7, No. 49, Dec. 6, 2016, 80288-80297.

Ziegler, et al. "Sensing The Outside World: TSLP Regulates Barrier Immunity", Nature Immunology, vol. 11, No. 4, Apr. 2010, 289-293.

Zuberi, et al. "Critical Role For Galectin-3 in Airway Inflammation and Bronchial Hyperresponsiveness in a Murine Model of Asthma", The American Journal of Pathology, vol. 165, No. 6, Dec. 2004, 2045-2053.

The Broad Institute, Inc., "International Preliminary Report on Patentability issued in International Application No. PCT/ US2018/ 027388", mailed on Oct. 24, 2019, 8 pages.

Adappa, et al., "Genetics of the Taste Receptor T2R38 Correlates With Chronic Rhinosinusitis Necessitating Surgical Intervention", International Forum of Allergy & Rhinology, vol. 3, No. 3, Mar. 2013, 184-187.

(56) References Cited

OTHER PUBLICATIONS

Ardini-Poleske, et al., "LungMAP: The Molecular Atlas of Lung Development Program", The American Journal of Physiology-Lung Cellular and Molecular Physiology, vol. 313, No. 5, Nov. 1, 2017, L733-L740.

Artis, et al., "RELMbeta/FIZZ2 is a Goblet Cell-Specific Immune-Effector Molecule in the Gastrointestinal Tract", Proceedings of the National Academy of Sciences of the United States of America, vol. 101, No. 37, Sep. 14, 2004, 13596-13600.

Bansal, et al., "Suppression of Immunoglobulin E-mediated Allergic Responses by Regulator of G Protein Signaling 13", Nature Immunology, vol. 9, No. 1, Jan. 2008, 73-80.

Barker, et al., "Adult Intestinal Stem Cells: Critical Drivers of Epithelial Homeostasis and Regeneration", Nature Reviews Molecular Cell Biology, vol. 15, No. 1, Jan. 2014, 19-33.

Barker, et al., "Identification of Stem Cells in Small Intestine and Colon by Marker Gene Lgr5", Nature, vol. 449, No. 7165, Oct. 25, 2007, 1003-1007.

Barker, et al., "Identifying the Stem Cell of the Intestinal Crypt: Strategies and Pitfalls", Cell Stem Cell, vol. 11, Issue 5, Oct. 5, 2012, 452-460.

Barriga, et al., "Mex3a Marks a Slowly Dividing Subpopulation of Lgr5+ Intestinal Stem Cells", Cell Stem Cell, vol. 20, No. 6, Jun. 1, 2017, 801-816.

Basak, et al., "Induced Quiescence of Lgr5+ Stem Cells in Intestinal Organoids Enables Differentiation of Hormone-Producing Enteroendocrine Cells", Cell Stem Cell, vol. 20, No. 2, Feb. 2, 2017, 177-190.

Basak, et al., "Mapping Early Fate Determination in Lgr5+ Crypt Stem Cells Using a Novel Ki67-RFP Allele", The EMBO Journal, vol. 33, No. 18, 2057-2068., Sep. 17, 2014.

Battle, et al., "GATA4 is Essential for Jejunal Function in Mice", Gastroenterology, vol. 135, No. 5, Nov. 2008, 1676-1686.

Bergstrom, et al., "Gram-Positive Bacteria are Held at a Distance in the Colon Mucus by the Lectin-like Protein 7g16", Proceedings of the National Academy of Sciences of the United States of America, vol. 113, No. 48, Nov. 29, 2016, 13833-13838.

Beuling, et al., "GATA Factors Regulate Proliferation, Differentiation, and Gene Expression in Small Intestine of Mature Mice", Gastroenterology, vol. 140, No. 4, Apr. 2011, 1219-1229.

Birchenough, et al., "New Developments in Goblet Cell Mucus Secretion and Function", Mucosal Immunology, vol. 3, No. 4, Jul. 2015, 712-719.

Biton, et al., "Epithelial Micrornas Regulate Gut Mucosal Immunity Via Epithelium-t Cell Crosstalk", Nature Immunology, vol. 12, No. 3, Mar. 2011, 239-246.

Blomqvist, et al., "Epididymal Expression of the Forkhead Transcription Factor Foxi1 is Required for Male Fertility", The EMBO Journal, vol. 25, No. 17, Sep. 6, 2006, 4131-4141.

Bochkov, et al., "Cadherin-Related Family Member 3, a Childhood Asthma Susceptibility Gene Product, Mediates Rhinovirus C Binding and Replication", Proceedings of the National Academy of Sciences of the United States of America, vol. 112, No. 17, Apr. 28, 2015, 5485-5490.

Bonnelykke, et al., "A Genome-Wide Association Study Identifies Cdhr3 as a Susceptibility Locus for Early Childhood Asthma With Severe Exacerbations", Nature Genetics, vol. 46, No., 1, Jan. 2014, 51-55.

Shale, et al. "CD4(+) T-Cell Subsets in Intestinal Inflammation", Immunological Reviews, vol. 252, No. 1, Mar. 2013, 164-82.

Chan, "The Role of Extracellular Matrix Protein 1 in Human Skin", Clinical and Experimental Dermatology, vol. 29, No. 1, Jan. 2004, 52-56.

Chen, et al., "In Silico Cloning of Mouse Muc5B Gene and Upregulation of Its Expression in Mouse Asthma Model", American Journal of Respiratory and Critical Care Medicine, vol. 164, No. 6, Sep. 15, 2001, 1059-1066.

Clevers, et al., "The Intestinal Crypt, a Prototype Stem Cell Compartment", Cell, vol. 154, No. 2, Jul. 18, 2013, 274-284.

Clevers, et al., "Wnt/Beta-Catenin Signaling in Development and Disease", Cell, vol. 127, No. 3, Nov. 3, 2006, 469-480.

D'Acquisto, et al., "Annexin-1 Modulates T-Cell Activation and Differentiation", Blood, vol. 109, No. 3, Feb. 1, 2007, 1095-1102.

Danahay, et al., "Notch2 is Required for Inflammatory Cytokine-driven Goblet Cell Metaplasia in the Lung", Cell Reports, vol. 10, No. 2, Jan. 13, 2015, 239-252.

Datta, et al., "Identification of Novel Genes in Intestinal Tissue that are Regulated after Infection with an Intestinal Nematode Parasite", Infection and Immunity, vol. 73, No. 7, Jul. 2005, 4025-4033.

Davies, et al., "Targeted Deletion of the Epididymal Receptor HE6 Results in Fluid Dysregulation and Male Infertility", Molecular and Cellular Biology, vol. 24, No. 19, Oct. 2004, 8642-8648.

De Lau, et al., "Peyer's Patch M Cells derived from Lgr5(+) Stem Cells Require SpiB and are Induced by RankL in Cultured "Miniguts"", Molecular and Cellular Biology, vol. 32, No. 18, Sep. 2012, 3639-3647.

Dixon, et al., "Requirement of a 5-Lipoxygenase-Activating Protein for Leukotriene Synthesis", Nature, vol. 343, No. 6255, Jan. 18, 1990, 282-284.

Duboc, et al., "The Bile Acid TGR5 Membrane Receptor: From Basic Research to Clinical Application", Digestive and Liver Disease, vol. 46, No. 4, Apr. 2014, 302-312.

Eckhardt, et al., "Intestinal Epithelial Serum Amyloid a Modulates Bacterial Growth in Vitro and Pro-Inflammatory Responses in Mouse Experimental Colitis", BMC Gastroenterology, vol. 10, Nov. 10, 2010.

Egerod, et al., "A Major Lineage of Enteroendocrine Cells Coexpress CCK, Secretin, GIP, GLP-1, PYY, and Neurotensin but not Somatostatin", Endocrinology, vol. 153, No. 12, Dec. 2012, 5782-5795.

Engelhardt, et al., "Submucosal Glands are the Predominant Site of Cftr Expression in the Human Bronchus", Nature Genetics, vol. 2, No. 3, Nov. 1992, 240-248.

Esaki, et al., "Mechanism of Development of Ionocytes Rich in Vacuolar-type H(+)-atpase in Tthe Skin of Zebrafish Larvae", Developmental Biology, vol. 329, No. 1, May 1, 2009, 116-129.

Ferraris, et al., "Regulation of Brush-Border Enzyme Activities and Enterocyte Migration Rates in Mouse Small Intestine", The American Journal of Physiology , vol. 262, Jun. 1992, G1047-G1059.

Furness, et al., "The Gut as a Sensory Organ", Nature Reviews Gastroenterology & Hepatology, vol. 10, No. 12, Dec. 2013, 729-740.

Garabedian, et al., "Examining the Role of Paneth Cells in the Small Intestine by Lineage Ablation in Transgenic Mice", Journal of Biological Chemistry, vol. 272, No. 38, Sep. 19, 1997, 23729-23740.

Gerbe, et al., "Intestinal Tuft Cells: Epithelial Sentinels Linking Luminal Cues to the Immune System", Mucosal Immunology, vol. 9, No. 6, Nov. 2016, 1353-1359.

Gerbe, et al., "The Intestinal Epithelium Tuft Cells: Specification and Function", Cellular and Molecular Life Sciences, vol. 69, No. 17, Sep. 2012, 2907-2917.

Ghaleb, et al., "Krüppel-like Factors 4 and 5: The Yin and Yang Regulators of Cellular Proliferation", Cell Research, vol. 15, No. 2, Feb. 2005, 92-96.

Gribble, et al., "Enteroendocrine Cells: Chemosensors in the Intestinal Epithelium", Annual review of physiology, vol. 78, 2016, 277-299.

Grun, et al., "Single-Cell Messenger RNA Sequencing Reveals Rare Intestinal Cell Types", Nature, vol. 525, Sep. 10, 2015, 251-273.

Habib, et al., "Co-localisation and Secretion of Glucagon-Like Peptide 1 and Peptide YY from Primary Cultured Human L Cells", Diabetologia, vol. 56, No. 6, Jun. 2013, 1413-1416.

Hase, et al., "Uptake Through Glycoprotein 2 of FimH(+) Bacteria by M Cells Initiates Mucosal Immune Response", Nature, vol. 462, No. 7270, Nov. 12, 2009, 226-230.

Heitzmann, et al., "The in Vivo Respiratory Phenotype of the Adenosine A1 Receptor Knockout Mouse", Respiratory Physiology and Neurobiology Journal Elsevier, vol. 222, Feb. 1, 2016, 16-28.

Hoegger, et al., "Impaired Mucus Detachment Disrupts Mucociliary Transport in a Piglet Model of Cystic Fibrosis", Science, vol. 345, No. 6198, Aug. 15, 2014, 818-822.

(56)           References Cited

OTHER PUBLICATIONS

Ichimura, et al., "Free Fatty Acid Receptors Act as Nutrient Sensors to Regulate Energy Homeostasis", Prostaglandins and Other Lipid Mediators—Journal—Elsevier, vol. 89, No. (3-4), Sep. 2009, 82-88.
Jakobsson, et al., "Identification and Characterization of a Novel Microsomal Enzyme With Glutathione-Dependent Transferase and Peroxidase Activities", Journal of Biological Chemistry, vol. 272, No. 36, Sep. 5, 1997, 22934-22939.
Jang, et al., "Intestinal Villous M Cells: An Antigen Entry Site in the Mucosal Epithelium", Proceedings of the National Academy of Sciences of the United States of America, vol. 101, No. 16, Apr. 20, 2004, 6110-6115.
Abudayyeh et al., "A cytosine deaminase for programmable single-base RNA editing," Science, Jul. 26, 2019, vol. 365, No. 6451 (pp. 382-386).
Adamson et al., "A Multiplexed Single-Cell CRISPR Screening Platform Enables Systematic Dissection of the Unfolded Protein Response," Cell, Dec. 15, 2016, vol. 167 (pp. 1867-1882).
Ali et al., "Regulatory T Cells in Skin Facilitate Epithelial Stem Cell Differentiation," Cell, Jun. 2017, vol. 169, No. 6 (pp. 1119-1129).
Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).
Altman et al., "Phenotypic Analysis of Antigen-specific T Lymphocytes," Science, Oct. 4, 1996, vol. 274, No. 5284 (pp. 94-96).
Amir et al., "viSNE Enables Visualization of High Dimensional Single-Cell Data and Reveals Phenotypic Heterogeneity of Leukemia," Nature Biotechnology, Jun. 2013, vol. 31, No. 6 (25 pages).
Andersen et al., "Parallel detection of antigen-specific T cell responses by combinatorial encoding of MHC multimers," Nature Protocols, vol. 7, No. 5, 2012 (pp. 891-902).
Arpaia et al., "A Distinct Function of Regulatory T Cells in Tissue Protection," Cell, Aug. 27, 2015, vol. 162, No. 5 (pp. 1078-1089).
Aurora et al., "Immune modulation of stem cells and regeneration," Cell Stem Cell, Jul. 3, 2014, vol. 15, No. 1 (pp. 14-25).
Bartel et al., "MicroRNAs: Genomics, Biogenesis, Mechanism, and Function," Cell, Jan. 23, 2004, vol. 116, No. 2 (pp. 281-297).
Bartunek et al., Avian stem cell factor (SCF): production and characterization of the recombinant His-tagged SCF of chicken and its neutralizing antibody, Cytokine, Jan. 1996, vol. 8, Issue 1 (pp. 14-20).
Bendall et al., "Single-cell Trajectory Detection Uncovers Progression and Regulatory Coordination in Human B Cell Development", Cell, Apr. 24, 2014, vol. 157, No. 3 (pp. 714-725).
Benjamin et al., "Controlling the False Discovery Rate: A Practical and Powerful Approach to Multiple Testing," Journal of the Royal Statistical Society, 1995 Series B, vol. 57, No. 1 (pp. 289-300).
Besser et al., "Clinical responses in a phase II study using adoptive transfer of short-term cultured tumor infiltration lymphocytes in metastatic melanoma patients," Clinical Cancer Research, May 1, 2010, vol. 16, No. 9 (pp. 2646-2655).
Beyaz et al., "High-fat diet enhances sternness and tumorigenicity of intestinal progenitors," Nature, 2016, vol. 531, No. 7592 (pp. 53-58).
Binz et al., "Engineering novel binding proteins from nonimmunoglobulin domains," Nature Biotechnology, 2005, vol. 23 (pp. 1257-1268).
Birket et al., "A Functional Anatomic Defect of the Cystic Fibrosis Airway," American Journal of Respiratory and Critical Care Medicine, Aug. 15, 2014, vol. 190, No. 4 (pp. 421-432).
Birket et al., "Combination Therapy with Cystic Fibrosis Transmembrane Conductance Regulator Modulators Augment the Airway Functional Microanatomy," The American Journal of Physiology-Lung Cellular and Molecular Physiology, May 15, 2016, vol. 310, No. 10 (pp. L 928-L 939).
Birket et al., "Development of an Airway Mucus Defect in the Cystic Fibrosis Rat," JCI Insight, Jan. 11, 2018, vol. 3, No. 1 (14 pages).

Bland et al., "MHC Class II Expression by the Gut Epithelium," Immunology Today, vol. 9, No. 6, 1988, 174-178.
Boch et al., "Breaking the Code of DNA Binding Specificity of TAL-Type III Effectors," Science, Dec. 11, 2009, vol. 326 (pp. 1509-1512).
Boes et al., "T-cell engagement of dendritic cells rapidly rearranges MHC class II transport," Nature, Aug. 29, 2002, vol. 418 (pp. 983-988).
Boni et al., "Adoptive transfer of allogeneic tumor-specific T cells mediates effective regression of large tumors across major histocompatibility barriers," Blood, Dec. 1, 2008, vol. 112, No. 12 (pp. 4746-4754).
Bosse et al., "Gata4 is essential for the maintenance of jejunal-ileal identities in the adult mouse small intestine," Molecular and Cellular Biology, Dec. 2006, vol. 26, No. 23 (pp. 9060-9070).
Bramsen et al., "Development of Therapeutic-Grade Small Interfering RNAs by Chemical Engineering," Frontiers in Genetics, Aug. 20, 2012, vol. 3, Article 154 (pp. 1-22).
Brennecke et al., "Accounting for Technical Noise in Single-Cell RNA-seq Experiments," Nature Methods, Sep. 22, 2013, vol. 10, No. 11 (pp. 1093-1095).
Brown et al., "Propellant-Driven Aerosols of Proteins," Aerosol Science and Technology, Jan. 1996, vol. 24 (pp. 45-56).
Buczacki et al., "Intestinal label-retaining cells are secretory precursors expressing Lgr5," Nature, Mar. 7, 2013, vol. 495, No. 7439 (pp. 65-96).
Budde et al., "Combining a CD20 Chimeric Antigen Receptor and an Inducible Caspase 9 Suicide Switch to Improve the Efficacy and Safety of T Cell Adoptive Immunotherapy for Lymphoma, " PLoS One, 2013, vol. 8, No. 12, e82742 (10 pages).
Buettner et al., "Computational analysis of cell-to-cell heterogeneity in single-cell RNA-sequencing data reveals hidden subpopulations of cells," Nature Biotechnology, Feb. 2015, vol. 33, No. 2 (pp. 155-160).
Buja et al., "Remarks on Parallel Analysis," published in: Multivariate Behavioral Research, 1992, vol. 27, No. 4 (26 pages).
Burzyn et al., "A special population of regulatory T cells potentiates muscle repair," Cell, Dec. 5, 2013, vol. 155 (pp. 1282-1295).
Canver et al., "BCL11A enhancer dissection by Cas9-mediated in situ saturating mutagenesis," Nature, vol. 527, 2015 [including Supplementary Material] (pp. 192-197).
Cao et al., "Comprehensive single cell transcriptional profiling of a multicellular organism by combinatorial indexing," bioRxiv preprint first posted online Feb. 2, 2017 (35 pages).
Cao et al., "Comprehensive single-cell transcriptional profiling of a multicellular organism," Science, Aug. 18, 2017, vol. 357, No. 6352 (pp. 661-667).
Carlson et al., "Identification of Amino Acids in the Glutamate Receptor, GluR3, Important for Antibody-binding and Receptor-specific Activation," The Journal of Biological Chemistry, Apr. 25, 1997, vol. 272, No. 17 (pp. 11295-11301).
Carr et al., "Genome Engineering," Nature Biotechnology, Dec. 2009, vol. 27, No. 12 (pp. 1151-1162).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Charman, "Lipids, Lipophilic Drugs, and Oral Drug Delivery-Some Emerging Concepts," Journal of Pharmaceutical Sciences, 2000, vol. 89, No. 8 (pp. 967-978).
Chen et al., "Dynamic Imaging of Genomic Loci in Living Human Cells by an Optimized CRISPR/Cas System," Cell, 2013, vol. 155 (pp. 1479-1491).
Chen et al., "Genome-wide CRISPR Screen in a Mouse Model of Tumor Growth and Metastasis," Cell, 2015, vol. 160 (pp. 1-15).
Chen et al., Effects of Interleukin-1a, Interleukin-1 Receptor Antagonist, and Neutralizing Antibody on Proinflammatory Cytokine Expression by Human Squamous Cell Carcinoma Lines, Cancer Research, Aug. 15, 1998, vol. 58, No. 16 (pp. 3668-3678).
Cheng et al., "Epithelial interleukin-25 is a key mediator in Th2-high, corticosteroid-responsive asthma," American Journal of Respiratory and Critical Care Medicine, Sep. 15, 2014, vol. 190, No. 6 (pp. 639-648).

(56) References Cited

OTHER PUBLICATIONS

Cheng et al., "Origin, Differentiation and Renewal of the Four Main Epithelial Cell Types in the Mouse Small Intestine III. Entero-Endocrine Cells," The American Journal of Anatomy, 1974, vol. 141, (pp. 503-519).

Chu et al., "Efficient Generation of Rosa26 Knock-in Mice using Crispr/Cas9 in C57bl/6 Zygotes," BMC Biotechnology, Jan. 16, 2016, vol. 16, No. 4 (15 pages).

Chung et al., "Polycistronic RNA polymerase II expression vectors for RNA interference based on BIC/miR-155," Nucleic Acids Research, 2006, vol. 34, No. 7 (14 pages).

Clackson et al., "Making antibody fragments using phage display libraries," Nature, Aug. 1991, vol. 352 (pp. 624-628).

Coburn et al., "*Salmonella*, the host and disease: a brief review," Immunology and Cell Biology, 2007, vol. 85 (pp. 112-118).

Coifman et al., "Geometric diffusions as a tool for harmonic analysis and structure definition of data: diffusion maps," Proceedings of the National Academy of Sciences, USA, May 24, 2005, vol. 102, No. 21 (pp. 7426-7431).

Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].

Cook et al., "Characterization and development of RGD-peptide-modified poly(lactic acid-co-lysine) as an interactive, resorbable biomaterial," Journal of Biomedical Materials Research, Jun. 15, 1997 (pp. 513-523).

Cordier et al., "Development of thymus, parathyroids, and ultimobranchial bodies in NMRI and nude mice," The American Journal of Anatomy, 1980, vol. 157 (pp. 227-263).

Cox et al., "RNA editing with CRISPR-Cas13," Science, Nov. 24, 2017, vol. 358, No. 6366 (pp. 1019-1027).

Darwin et al., "Molecular basis of the interaction of *Salmonella* with the intestinal mucosa," Clinical Microbiology Review, Jul. 1999, vol. 12, No. 3 (pp. 505-428).

Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (pp. 11540-11556).

Deng et al., "An Agonist Murine Monoclonal Antibody to the Human c-Mpl Receptor Stimulates Megakaryocytopoiesis," Blood, Sep. 1998, vol. 92, No. 6 (pp. 1981-1988).

Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).

Di Stasi et al., "Inducible apoptosis as a safety switch for adoptive cell therapy," Clinical Trial, New England Journal of Medicine, Nov. 3, 2011, vol. 365, No. 18 (pp. 1673-1683).

Dixit et al., "Perturb-Seq: Dissecting Molecular Circuits with Scalable Single-Cell RNA Profiling of Pooled Genetic Screens," Cell, Dec. 15, 2016, vol. 167, No. 7 (pp. 1853-1866).

Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].

Dombrowski et al., "Regulatory T cells promote myelin regeneration in the central nervous system," Nature Neuroscience, May 2017, vol. 20, No. 5 (pp. 674-680).

Doyon et al., "Enhancing zinc-finger-nuclease activity with improved obligate heterodimeric architectures," Nature Methods, Jan. 2011, vol. 8, No. 1 (pp. 74-79).

Du Clos,"Pentraxins: structure, function, and role in inflammation," ISRN Inflammation, Sep. 14, 2013, vol. 2013, Article ID 379040 (pp. 1-22).

Dudley et al., "Adoptive Cell Transfer Therapy Following Non-Myeloablative but Lymphodepleting Chemotherapy for the Treatment of Patients with Refractory Metastatic Melanoma," Journal of Clinical Oncology, Apr. 1, 2005, vol. 23, No. 10 (pp. 2346-2357).

Dudley et al., "Cancer regression and autoimmunity in patients after clonal repopulation with antitumor lymphocytes," Science, 2002, vol. 298, No. 5594 (pp. 850-854).

East-Seletsky et al., "Two distinct RNase activities of CRISPR-C2c2 enable guide-RNA processing and RNA detection," Nature, Oct. 13, 2016, vol. 538, No. 7624 (pp. 270-273).

Ellington et al, "In vitro selection of RNA molecules that bind specific ligands," Nature, 1990, vol. 346, No. 6287 (pp. 818-822).

Erichson et al., "Randomized Matrix Decompositions using R," Journal of Statistical Software, May 2019, vol. 89, Issue 11 (47 pages).

Esplunges et al., "Control of TH17 cells occurs in the small intestine," Nature, vol. 475, No. 7357 (pp. 514-518).

Ester et al., "A density-based algorithm for discovering clusters a density-based algorithm for discovering clusters in large spatial databases with noise," Proceedings of the Second International Conference on Knowledge Discovery and Data Mining, 1996 (pp. 226-231).

Farin et al., "Paneth cell extrusion and release of antimicrobial products is directly controlled by immune cell-derived IFN-gamma," Journal of Experimental Medicine, 2014, vol. 211, No. 7 (pp. 1393-1405).

Finak et al., "MAST: a flexible statistical framework for assessing transcriptional changes and characterizing heterogeneity in single-cell RNA sequencing data," Genome Biology, Dec. 10, 2015, vol. 16 (pp. 1-13).

Gao et al., "Engineered Cpf1 Enzymes with Altered PAM Specificities," Nature Biotechnology, Aug. 2017, vol. 35, No. 8 (pp. 789-792).

Gebauer and Skerra, "Engineered protein scaffolds as next-generation antibody therapeutics," Current Opinion in Chemical Biology, Jun. 2009, vol. 13, No. 3 (pp. 245-255).

Geiss et al., "Direct multiplexed measurement of gene expression with color-coded probe pairs," Nature Biotechnology, 2008, vol. 26, No. 3 (pp. 317-325).

Gershon et al., "The serotonin signaling system: from basic understanding to drug development for functional GI disorders," Gastroenterology, Jan. 2007, vol. 132, No. 1 (pp. 397-414).

Gierahn et al., "Seq-Well: Portable, Low-Cost RNA Sequencing of Single Cells at High Throughput," Nature Methods, Apr. 2017, vol. 14, No. 4 (8 pages).

Gill et al., "Biopharmaceutical drug discovery using novel protein scaffolds," Current Opinion in Biotechnology, 2006, vol. 17, No. 6 (653-658).

Graham et al., "From Genetics of Inflammatory Bowel Disease Towards Mechanistic Insights," Trends in Immunology Aug. 2013, vol. 34, No. 8 (pp. 371-378).

Graham et al., "Functional genomics identifies negative regulatory nodes controlling phagocyte oxidative burst," Nature Communications, 2015, vol. 6, No. 7838 (pp. 1-12).

Greco et al., "Improving the safety of cell therapy with the TK-suicide gene," Frontiers in Pharmacology, May 5, 2015, vol. 6, No. 95 (13 pages).

Griffin et al., "Development of protective immunity to *Salmonella*, a mucosal pathogen with a systemic agenda," Mucosal Immunol Jul. 2011, vol. 4, No. 4 (pp. 371-382).

Grubb et al., "Anomalies in Ion Transport in CF Mouse Tracheal Epithelium," American Journal of Physiology, Jul. 1994, vol. 267 (pp. C293-C300).

Gruber et al., "The Vienna RNA Websuite," Nucleic Acids Research, Apr. 19, 2008, vol. 36 (pp. W70-W74).

Gudbjartsson et al., "Sequence variants affecting eosinophil numbers associate with asthma and myocardial infarction," Nature Genetics, Mar. 2009, vol. 41, No. 3 (pp. 342-347).

Habib et al., "Div-Seq: Single-nucleus RNA-Seq reveals dynamics of rare adult newborn neurons," Science, Aug. 26, 2016, vol. 353, No. 6302 (pp. 925-928).

Habib et al., "Massively parallel single-nucleus RNA-seq with DroNc-seq," Nature Methods, Oct. 2017, vol. 14, No. 10 (pp. 955-958).

Haghverdi et al., "Diffusion maps for high-dimensional single-cell analysis of differentiation data," Bioinformatics, 2015, vol. 31, No. 18 (pp. 2989-2998).

(56)        References Cited

OTHER PUBLICATIONS

Hajeri et al., "siRNAs: their potential as therapeutic agents—Part I. Designing of siRNAs," Drug Discovery Today, Sep. 2009, vol. 14, Nos. 17-18 (pp. 851-858).

Harrop et al., "Antibodies to TR2 (Herpesvirus Entry Mediator), a New Member of the TNF Receptor Superfamily, Block T Cell Proliferation, Expression of Activation Markers, and Production of Cytokines," Journal of Immunology, 1998, vol. 161, No. 4 (pp. 1786-1794).

Hashimoto et al., "A conditional null allele of the major histocompatibility IA-beta chain gene," Genesis, 2002, vol. 32 (pp. 152-153).

Hayami et al., "Overexpression of the JmjC histone demethylase KDM5B in human carcinogenesis: involvement in the proliferation of cancer cells through the E2F/RB pathway," Molecular Cancer, Mar. 13, 2010, vol. 9, No. 59 (pp. 1-14).

Heinz et al., "The selection and function of cell type-specific enhancers," Nature Reviews Molecular Cell Biology, Mar. 2015, vol. 16, No. 3 (pp. 144-154).

Hendel et al., "Chemically modified guide RNAs enhance CRISPR-Cas genome editing in human primary cells," Nature Biotechnology Sep. 2015, vol. 33, No. 9 (pp. 985-989).

Hicke et al., "Escort aptamers: a delivery service for diagnosis and therapy," The Journal of Clinical Investigation, Oct. 2000, vol. 106, No. 8 (pp. 923-928).

Horwell et al., "The 'peptoid' approach to the design of non-peptide, small molecule agonists and antagonists of neuropeptides," Trends in Biotechnology, Apr. 1995, vol. 13, No. 4 (pp. 132-134).

Howard et al., "Intracerebral drug delivery in rats with lesion-induced memory deficits," Journal of Neurosurgery, Jul. 1989, vol. 71, No. 1 (pp. 105-112).

Howie et al., "Secreted and transmembrane 1A is a novel co-stimulatory ligand," PLoS One, Sep. 2013, vol. 8, No. 9 (pp. 1-9).

Hsu et al., "Development and Applications of CRISPR-Cas9 for Genome Engineering," Cell, 2014, vol. 157 (pp. 1262-1278).

Hsu et al., "DNA targeting specificity of RNA-guided Cas9 nucleases," Nature Biotechnology, Sep. 2013, vol. 31, No. 9 (pp. 827-832).

Huang et al., "IL-25-responsive, lineage-negative KLRG1hi cells are multipotential 'inflammatory' type 2 innate lymphoid cells," Nature Immunology, Feb. 2015, vol. 16, No. 2 (pp. 161-169).

Huch et al., "In vitro expansion of single Lgr5+ liver stem cells induced by Wnt-driven regeneration," Nature, Feb. 14, 2013, vol. 494, No. 7436 (pp. 247-250).

Inoue et al., "An inducible translocation strategy to rapidly activate and inhibit small GTPase signaling pathways," Nature Methods, Jun. 2005, vol. 2, No. 6 (pp. 415-418).

Ivanov et al., "Induction of intestinal Th17 cells by segmented filamentous bacteria," Cell, Oct. 30, 2009, vol. 139, No. 3 (pp. 485-498).

Iwata et al., "Retinoic acid imprints gut-homing specificity on T cells," Immunity, Oct. 2004, vol. 21, No. 4 (pp. 527-538).

Jager et al., "Th1, Th17, and Th9 effector cells induce experimental autoimmune encephalomyelitis with different pathological phenotypes," The Journal of Immunology, Nov. 2009, vol. 183 (pp. 7169-7177).

Jensen et al., "Design and Implementation of Adoptive Therapy with Chimeric Antigen Receptor-Modified T Cells," Immunological Reviews, Jan. 2014, vol. 257, No. 1 (32 pages).

Jiang et al., "RNA-guided editing of bacterial genomes using CRISPR-Cas systems," Nature Biotechnology, Mar. 2013, vol. 31 [including supplementary information—30 pages] (pp. 233-239).

Johnson et al., "Adjusting batch effects in microarray expression data using empirical Bayes methods," Biostatistics, Jan. 2007, vol. 8, No. 1 (pp. 118-127).

Johnson et al., "Gene therapy with human and mouse T-cell receptors mediates cancer regression and targets normal tissues expressing cognate antigen," Blood, Jul. 2009, vol. 114, No. 3 (pp. 535-546).

Kalos et al., "T Cells with Chimeric Antigen Receptors Have Potent Antitumor Effects and Can Establish Memory in Patients with Advanced Leukemia," Science Translational Medicine, Aug. 10, 2011, vol. 3, No. 95 (12 pages).

Kambayashi et al., "Atypical MHC class II-expressing antigenpresenting cells: can anything replace a dendritic cell?" Immunology, Nov. 2014, vol. 14, (pp. 719-730).

Karra et al., "The role of peptide YY in appetite regulation and obesity," The Journal of Physiology, Jan. 15, 2009, vol. 587, No. 1 (pp. 19-25).

Kaser et al., "XBPI links ER stress to intestinal inflammation and confers genetic risk for human inflammatory bowel disease," Cell, Sep. 2008, vol. 134 (pp. 743-756).

Keefe et al., "Aptamers as therapeutics," Nature Reviews, Jul. 2010, vol. 9 (pp. 537-550).

Kelley et al., "Versatility of chemically synthesized guide RNAs for CRISPR-Cas9 genome editing," Journal of Biotechnology, Sep. 2016, vol. 233, 10 (pp. 74-83).

Kim et al., "Chimeric restriction endonuclease," Proceedings of the National Academy of Sciences, USA, Biochemistry, Feb. 1994, vol. 91 (pp. 883-887).

Kim et al., "Hybrid restriction enzymes: Zinc finger fusions to Fok I cleavage domain," Proceedings of the National Academy of Science, USA, Feb. 1996, vol. 93, No. 3 (pp. 1156-1160).

Kim et al., "Regulatory T cells prevent catastrophic autoimmunity throughout the lifespan of mice," Nature Immunology, Feb. 2007, vol. 8, No. 2 (pp. 191-197).

Kim et al., "Highly efficient RNA-guided genome editing in human cells via delivery of purified Cas9 ribonucleoproteins," Genome Research, Jun. 2014, vol. 24, No. 6 (pp. 1012-1019).

Klein et al., "Droplet Barcoding for Single-Cell Transcriptomics Applied to Embryonic Stem Cells," Cell, 2015, vol. 161, No. 5 (pp. 1187-1201).

Kleinstiver et al., "Engineered CRISPR-Cas9 nucleases with altered PAM specificities," Nature, Jul. 23, 2015, vol. 523, No. 7561 (pp. 481-485).

Klok et al., "The role of leptin and ghrelin in the regulation of food intake and body weight in humans: a review," Obesity Reviews, Jan. 2007, vol. 8, No. 1 (pp. 21-34).

Koenker et al., "Quantile Regression," The Journal of Economic Perspectives, Fall 2001, vol. 15, No. 4 (pp. 143-156).

Kohler et al., "Continuous cultures of fused cells secreting antibody of predefined specificity," Nature, 1975, vol. 256 (pp. 495-497).

Kolmar, "Alternative binding proteins: biological activity and therapeutic potential of cystine-knot miniproteins," The FEBS Journal, 2008, 275 (pp. 2684-2690).

Konermann et al., "Genome-scale transcriptional activation by an engineered CRISPR-Cas9 complex," Nature, 2015, vol. 517 (pp. 583-588) [Including Supplemental information, 12 pages].

Konermann et al., "Optical control of mammalian endogenous transcription and epigenetic states," Nature, Aug. 22, 2013, vol. 500, Includes Supplemental Information (pp. 472-476).

Kowalczyk et al., "Single-cell RNA-seq reveals changes in cell cycle and differentiation programs upon aging of hematopoietic stem cells," Genome Research, 2015, vol. 25 (pp. 1860-1872).

Kurrecka et al., "Antisense technologies: improvement through novel chemical modifications," European Journal of Biochemistry, 2003, vol. 270 (pp. 1628-1644).

Lagos-Quintana et al., "Identification of Novel Genes Coding for Small Expressed RNAs," Science, Oct. 26, 2001, vol. 294 (pp. 853-858).

Lagos-Quintana et al., "Identification of tissue-specific microRNAs from mouse," Current Biology, Apr. 30, 2002, vol. 12, (pp. 735-739).

Lagos-Quintana et al., "New microRNAs from mouse and human," RNA, 2003, vol. 9 (pp. 175-179).

Langmead et al., "Ultrafast and memory-efficient alignment of short DNA sequences to the human genome", Genome Biology, Mar. 4, 2009, vol. 10, No. 3 (pp. 1-10).

Lau et al., "An Abundant Class of Tiny RNAs with Probably Regulatory Roles in Caenorhabditis elegans," Science, Oct. 26, 2001, vol. 294 (pp. 858-861).

(56) References Cited

OTHER PUBLICATIONS

Le Mercier et al., "Beyond CTLA-4 and PD-1, the generation Z of negative checkpoint regulators," Frontiers in Immunology, Aug. 21, 2015, vol. 6, Article 418 (15 pages).

Lee et al., "An Extensive Class of Small RNAs in Caenorhabditis elegans," Science, Oct. 26, 2001, vol. 294 (pp. 862-864).

Lee et al., "Synthetically modified guide RNA and donor DNA are a versatile platform for CRISPR-Cas9 engineering," Elife, May 2, 2017, vol. 6 e25312 (17 pages).

Leek et al., "The sva package for removing batch effects and other unwanted variation in high-throughput experiments," Bioinformatics, Mar. 15, 2012, vol. 28, No. 6 (pp. 882-883).

Levine et al., "Data-Driven Phenotypic Dissection of AML Reveals Progenitor-like Cells that Correlate with Prognosis," Cell, 2015, vol. 162, No. 1 (pp. 184-197).

Levy-Nissenbaum et al., Nanotechnology and aptamers: applications in drug delivery, Trends in Biotechnology, Aug. 2008, vol. 26, No. 8 (pp. 442-449).

Li et al., "Engineering CRISPR-Cpf1 crRNAs and mRNAs to maximize genome editing efficiency," Nature Biomedical Engineering, May 2017, vol. 1, No. 5 (21 pages).

Li et al., "Gwasdb V2: An Update Database for Human Genetic Variants Identified by Genome-wide Association Studies," Nucleic Acids Research, Jan. 4, 2016, vol. 44 (pages D869-D876).

Li et al., "RSEM: accurate transcript quantification from RNA-Seq data with or without a reference genome," BMC Bioinformatics, 2011, vol. 12, No. 323 (16 pages).

Liautard et al., "Specific Inhibition of IL-6 Signalling with Monoclonal Antibodies Against the gp130 Receptor," Cytokine, Apr. 1997, vol. 9, No. 4 (pp. 233-241).

Liberzon et al. Molecular signatures database (MSigDB) 3.0, Bioinformatics, 2011, vol. 27 (pp. 1739-1740).

Liberzon et al., "Molecular signatures database (MSigDB) 3.0," Bioinformatics Jun. 15, 2011, vol. 27, No. 12 (pp. 1739-1740).

Lim et al., "The microRNAs of Caenorhabditis elegans," Genes & Development, Apr. 15, 2003, vol. 17, No. 8 (pp. 991-1008).

Lim et al., "Vertebrate microRNA genes," Science, Mar. 7, 2003, vol. 299, No. 5612 (p. 1540).

Liu et al., "An Autoregulatory Mechanism Governing Mucociliary Transport is Sensitive to Mucus Load", American Journal of Respiratory Cell and Molecular Biology, Oct. 2014, vol. 51, No. 4 (pp. 485-493).

Liu et al., "Method for Quantitative Study of Airway Functional Microanatomy Using Micro-Optical Coherence Tomography," Plos One, Jan. 2013, vol. 8, Issue 1 (pp. 1-8).

Loonen et al., "REG3-gamma-deficient mice have altered mucus distribution and increased mucosal inflammatory responses to the microbiota and enteric pathogens in the ileum," Mucosal Immunology, Jul. 2014, vol. 7, No. 4 (pp. 939-947).

Macosko et al., "Highly Parallel Genome-wide Expression Profiling of Individual Cells Using Nanoliter Droplets," Cell, May 21, 2015, vol. 161 (pp. 1202-1214).

Madsen et al., "Mice lacking all conventional MHC class II genes," Proceeding of the National Academy of Sciences, USA, Aug. 1999, vol. 96 (pp. 10338-10343).

Man et al., "*Salmonella* infection induces recruitment of Caspase-8 to the inflammasome to modulate IL-beta production," Journal of Immunology, Nov. 15, 2013, vol. 191, No. 10 (pp. 1-18).

Marasco et al., Design, intracellular expression, and activity of a human anti-human immunodeficiency virus type 1 gp120 single-chain antibody, Proceedings of the National Academy of Sciences, Aug. 15, 1993, vol. 90 (pp. 7889-7893).

Marjou et al., "Tissue-specific and inducible Cre-mediated recombination in the gut epithelium," Genesis, Jul. 2004 Vol. 39, No. 3 (pp. 186-193).

Marks et al., "By-passing immunization: Human antibodies from V-gene libraries displayed on phage," Journal of Molecular Biology, Dec. 1991, vol. 222, No. 3 (pp. 581-597).

Maruyama et al., "Targetability of novel immunoliposomes modified with amphipathic poly (ethylene glycol) s conjugated at their distal terminals to monoclonal antibodies," Biochimica et Biophysica Acta, 1995, vol. 1234 (pp. 74-80).

Matsuda et al., "Controlled expression of transgenes introduced by in vivo electroporation," Proceedings of the National Academy of Sciences, Jan. 16, 2007, vol. 104, No. 3 (pp. 1027-1032).

Matsumoto et al., "Retinal Promotes In Vitro Growth of Proximal Colon Organoids through a Retinoic Acid-Independent Mechanism," PLoS One, Aug. 26, 2016, vol. 11, No. 8 (pp. 1-15).

Maus et al., "Adoptive immunotherapy for cancer or viruses," Annual Review of Immunology, 2014, vol. 32 (pp. 189-225).

Mikos et al., "Laminated three-dimensional biodegradable foams for use in tissue engineering," Biomaterials, Apr. 1993, vol. 14, No. 5 (pp. 323-330).

Mikos et al., "Preparation and characterization of poly (L-lactic acid) foams," Polymer, 1994, vol. 35, 1068 (pages.

Miyamoto et al., "Rapid and orthogonal logic gating with a gibberellin-induced dimerization system," Nature Chemical Biology, 2012, vol. 8, No. 5 (pp. 465-470).

Mombaerts et al., "Mutations in T-cell antigen receptor genes alpha and beta block thymocyte development at different stages," Nature, Nov. 19, 1992, vol. 360 (pp. 225-231).

Monticelli et al., "Innate lymphoid cells promote lung-tissue homeostasis after infection with influenza virus," Nature Immunology, Sep. 25, 2011, vol. 12 (pp. 1045-1054).

Morgan et al., "Cancer Regression in Patients After Transfer of Genetically Engineered Lymphocytes," Science, Oct. 6, 2006, vol. 314, No. 5796 (pp. 126-129).

Morita et al., "Innate lymphoid cells in allergic and nonallergic inflammation," Journal of Allergy and Clinical Immunology, Nov. 2016, vol. 138, No. 5 (pp. 1253-1264).

Moriyama et al., "Multiple Roles of Notch Signaling in The Regulation of Epidermal Development," Developmental Cell, Apr. 2008, vol. 14, No. 4 (pp. 594-604).

Moro et al., "Innate production of TH2 cytokines by adipose tissue-associated c-Kit+Sca-1+ lymphoid cells," Nature, 2010, vol. 463 (pp. 540-544).

Morocz et al., "Brain edema development after MRI-guided focused ultrasound treatment," Journal of Magnetic Resonance Imaging, Jan.-Feb. 1998, vol. 8, No. 1 (pp. 136-142).

Moscou et al., "A Simple Cipher Governs DNA Recognition by TAL Effectors", Science, Dec. 11, 2009, vol. 326 (p. 1501).

Mou et al., "Dual SMAD Signaling Inhibition Enables Long-Term Expansion of Diverse Epithelial Basal Cells," Cell Stem Cell, 2016, vol. 19 (pp. 217-231).

Moussatov et al., "A Possible Approach to the Treatment of Polycystic Ovarian Syndrome Using Focused Ultrasound," Ultrasonics, 1998, vol. 36, No. 8 (pp. 893-900).

Muller et al., "VEGF and the Fab fragment of a humanized neutralizing antibody: crystal structure of the complex at 2.4 A resolution and mutational analysis of the interface," Structure, 1998, vol. 6, No. 9 (pp. 1153-1167).

Nakamura et al., "Codon usage tabulated from the international DNA sequence databases: status for the year 2000," Nucleic Acids Research, 2000, vol. 28, No. 1 (p. 292).

Neill et al., "Nuocytes represent a new innate effector leukocyte that mediates type-2 immunity," Nature, Apr. 29, 2010, vol. 464, No. 7293 (pp. 1367-1370).

Ng et al., "Human leucine-rich repeat proteins: a genome-wide bioinformatic categorization and functional analysis in innate immunity," Proceedings of the National Academy of Sciences, USA, Mar. 15, 2011, vol. 108, Suppl. 1 (pp. 4631-4638).

Nishimasu et al., "Crystal Structure of Cas9 in Complex with Guide RNA and Target DNA," Cell, Feb. 27, 2014, vol. 156 (pp. 935-949).

Nishimasu et al., "Crystal Structure of Staphylococcus aureus Cas9", Cell, 2015, vol. 162 (pp. 1113-1126).

Nixon et al., "Engineered protein inhibitors of proteases," Current Opinion in Drug Discovery & Development, Mar. 1, 2006, vol. 9, No. 2 (pp. 261-268).

Nowak et al., "Survey and Summary—Guide RNA engineering for versatile Cas9 functionality," Nucleic Acids Research, Oct. 12, 2016, vol. 44, No. 20 (pp. 9555-9564).

(56) References Cited

OTHER PUBLICATIONS

Nozaki et al., "Co-culture with intestinal epithelial organoids allows efficient expansion and motility analysis of intraepithelial lymphocytes," Journal of Gastroenterology, Mar. 2016, vol. 51, No. 3 (pp. 206-213).

Nygren, "Alternative binding proteins: Affibody binding proteins developed from a small three-helix bundle scaffold," The FEBS Journal, 2008, vol. 275 (pp. 2668-2676).

Oki et al., "A novel cell-cycle-indicator, mVenus-p27K-, identifies quiescent cells and visualizes GO-GI transition," Scientific Reports, 2014, vol. 4 (pp. 1-10).

Paige et al., "RNA mimics of green fluorescent protein," Science, Jul. 29, 2011, vol. 333, No. 6042 (pp. 642-646).

Paix et al., "High Efficiency, Homology-Directed Genome Editing in Caenorhabditis elegans Using CRISPR-Cas9 Ribonucleoprotein Complexes," Genetics, Sep. 2015, vol. 201 (pp. 47-54).

Parker et al., "Scheme for ranking potential HLA-A2 binding peptides based on independent binding of individual peptide side-chains," The Journal of Immunology, Jan. 1, 1994, vol. 152, No. 1 (pp. 163-175).

Parnas et al., "A Genome-Wide CRISPR Screen in Primary Immune Cells to Dissect Regulatory Networks," 2015, vol. 162 (pp. 675-686) [with Supplementary Information].

Pashine et al., "Th1 dominance in the immune response to live *Salmonella typhimurium* requires bacterial invasiveness but not persistence," International Immunology, Apr. 1999, vol. 11, No. 4, (pp. 481-489).

Patel et al., "Single-cell RNA-seq highlights intratumoral heterogeneity in primary glioblastoma," Science, Jun. 20, 2014, vol. 344, No. 6190 (pp. 1396-1401).

Piazza et al., "Immunotherapy of Respiratory Syncytial Virus Infection in Cotton Rats (*Sigmodon fulviventer*) Using IgG in a Small-Particle Aerosol," Journal of Infectious Diseases, 1992, vol. 166 (pp. 1422-1424).

Picelli et al. "Full-length RNA-seq from single cells using Smart-seq2," Nature Protocols, Jan. 2014, vol. 9, No. 1 (pp. 171-181).

Pitard et al., "Production and characterization of monoclonal antibodies against the leukemia inhibitory factor low affinity receptor, gp190," Journal of Immunological Methods, 1997, vol. 205 (pp. 177-190).

Platt et al., "CRISPR-Cas9 Knockin Mice for Genome Editing and Cancer Modeling," Cell, 2014, vol. 159 (pp. 440-455).

Poirot et al., "Multiplex Genome-Edited T-cell Manufacturing Platform for Off-the-Shelf Adoptive T-cell Immunotherapies," Cancer Research, Jul. 16, 2015, vol. 75, No. 18 (pp. 3853-3864).

Potten et al., "Intestinal stem cells protect their genome by selective segregation of template DNA strands," Journal of Cell Science, 2002, vol. 115, No. 11 (pp. 2381-2388).

Powell et al. "Compendium of Excipients for Parenteral Formulations," PDA Journal of Pharmaceutical Science and Technology, Sep./Oct. 1998, vol. 52, No. 2 (pp. 238-311).

Prat et al., "Agonistic monoclonal antibodies against the Met receptor dissect the biological responses to HGF," Journal of Cell Science, 1998, vol. 111 (pp. 237-247).

Pujana et al., "Network modeling links breast cancer susceptibility and centrosome dysfunction," Nature Genetics, 2007, vol. 39 (pp. 1338-1349).

Rahdar et al., "Synthetic CRISPR RNA-Cas9-guided genome editing in human cells," Proceedings of the American Academy of Sciences, U.S.A. Nov. 16, 2015 (pp. E7110-E7117).

Ramage et al., "5-hydroxytryptamine and cardiovascular regulation," Trends in Pharmacological Sciences, Sep. 2008, vol. 29, No. 9 (pp. 472-481).

Ramanan et al., "CRISPR-Cas9 cleavage of viral DNA efficiently suppresses hepatitis B virus," Nature/Scientific Reports, Jun. 2015 (9 pages).

Ramilowski et al., "A draft network of ligand-receptor-mediated multicellular signalling in human," Nature Communications, 2016, vol. 6, No. 7866 (pp. 1-11).

Ramos et al., "An inducible caspase 9 suicide gene to improve the safety of mesenchymal stromal cell therapies," Stem Cells, Jun. 2010, vol. 28, No. 6 (pp. 1107-1115).

Ran et al., "Double Nicking by RNA-guided CRISPR Cas9 for enhanced genome editing specificity," Cell, Sep. 12, 2013, vol. 154 (pp. 1380-1389).

Ran et al., "Genome engineering using the CRISPR-Cas9 system," Nature Protocols, 2013, vol. 8 (pp. 2281-2308).

Ran et al., "In vivo genome editing using *Staphylococcus aureus* Cas9," Nature, 2015, vol. 520 (pp. 186-191). [Includes Supplemental information, 12 pages].

Regev et al., "Science Forum: The Human Cell Atlas," eLife, Dec. 5, 2017, vol. 6 (pp. 1-30).

Reigstad et al., "Gut microbes promote colonic serotonin production through an effect of short-chain fatty acids on enterochromaffin cells," The Journal of the federation of American Societies for Experimental Biology, Apr. 2015, vol. 29, No. 4 (pp. 1395-1403).

Restifo et al., "Adoptive Immunotherapy for Cancer: Harnessing the T Cell Response," Nature Reviews Immunology, Mar. 22, 2012, vol. 12, No. 4 (pp. 269-281).

Reynolds et al., "Immunity to the model intestinal helminth parasite Heligmosomoides polygyrus", Seminars in immunopathology, 2012, vol. 34 (pp. 829-846).

Ritsma et al., "Intestinal crypt homeostasis revealed at single-stem-cell level by in vivo live imaging," Nature, Mar. 20, 2014, vol. 507, No. 7492 (pp. 362-365).

Rivas et al., "IL-4 production by group 2 innate lymphoid cells promotes food allergy by blocking regulatory T-cell function," Journal of Allergy and Clinical Immunology, Sep. 2016, vol. 138, No. 3 (pp. 801-811).

Rodenburg et al., "Gene expression response of the rat small intestine following oral *Salmonella* infection," Physiological Genomics, First published Mar. 27, 2007, vol. 30 (pp. 123-133).

Rodriguez et al., "Machine learning. Clustering by fast search and find of density peaks," Science, Jun. 27, 2014, vol. 344, No. 6191 (pp. 1492-1496).

Roesch et al., "A Temporarily Distinct Subpopulation of Slow-Cycling Melanoma Cells Is Required for Continuous Tumor Growth," Cell, May 14, 2010, vol. 141 (pp. 583-594).

Rosenberg et al., "Adoptive cell transfer as personalized immunotherapy for human cancer," Cancer Immunology and Immunotherapy, Apr. 2015, vol. 348, Issue 6230 (pp. 62-69).

Rosenberg et al., "Scaling single cell transcriptomics through split pool barcoding," bioRxiv preprint first posted online Feb. 2, 2017 (13 pages).

Rosvall et al., "Maps of Random Walks on Complex Networks Reveal Community Structure," Proceedings of the National Academy of Sciences, USA, Jan. 29, 2008, vol. 105, No. 4 (pp. 1118-1123).

Rubin,"The Bayesian Bootstrap," The Annals of Statistics, 1981, vol. 9, No. 1 (pp. 130-134).

Sadelain et al., "Eliminating Cells Gone Astray," New England Journal of Medicine, Nov. 3, 2011, vol. 365, No. 18 (pp. 1735-1737).

Salic et al., "A chemical method for fast and sensitive detection of DNA synthesis in vivo," Proceedings of the National Academy of Sciences, USA, 2008, vol. 105 (pp. 2415-2420).

Salomon et al., "The expression and regulation of class II antigens in normal and inflammatory bowel disease peripheral blood monocytes and intestinal epithelium," Autoimmunity, 1991, vol. 9 (pp. 141-149).

Sangiorgi et al., "Bmi1 is expressed in vivo in intestinal stem cells," Nature Genetics, Jul. 2008, vol. 40, No. 7 (pp. 915-920).

Sato et al., "Growing self-organizing mini-guts from a single intestinal stem cell: mechanism and applications," Science, Jun. 7, 2013, vol. 340, No. 6137 (pp. 1190-1194).

Saudek et al., "A preliminary trial of the programmable implantable medication system for insulin delivery," New England Journal of Medicine, Aug. 31, 1989, vol. 321 (pp. 574-579).

Scaringe et al., "Advanced 5'-silyl-2'-orthoester approach to RNA oligonucleotide synthesis," Methods in Enzymology, 2000, vol. 317 (pp. 3-18).

(56)                    References Cited

OTHER PUBLICATIONS

Scaringe et al., "Novel RNA Synthesis Method Using 5'-O-Silyl-2'-O-orthoester Protecting Groups," Journal of the American Chemical Society, 1998, vol. 120, No. 45 (pp. 11820-11821).

Schneider et al., "NIH Image to ImageJ: 25 years of image analysis," Nature Methods, Jul. 2012, vol. 9, No. 7 (pp. 671-675).

Shah et al., "Airway Acidification Initiates Host Defense Abnormalities in Cystic Fibrosis Mice," Science, Jan. 29, 2016, vol. 351, No. 6272 (pp. 503-507).

Shalek et al., "Single-Cell RNA-Seq Reveals Dynamic Paracrine Control of Cellular Variation," Nature, Jun. 19, 2014, vol. 510 (pp. 363-369).

Shalem et al., "Genome-Scale CRISPR-Cas9 Knockout Screening in Human Cells," Science, Jan. 3, 2014, vol. 343 (pp. 84-87).

Shalem et al., "High-throughput functional genomics using CRISPR-Cas9" Nature Review Genetics, 2015, vol. 16, No. 5 (pp. 299-311).

Sharma et al., "Antisense oligonucleotides: modifications and clinical trials," Medical Chemistry Journal, 2014, vol. 5 (pp. 1454-1471).

Shekhar et al., "Comprehensive Classification of Retinal Bipolar Neurons by Single-Cell Transcriptomics," Cell, Aug. 25, 2016 Vol. 166, No. 5 (pp. 1308-1323).

Shields et al., "Microfluidic cell sorting: a review of the advances in the separation of cells from debulking to rare cell isolation," Lab Chip, Mar. 7, 2015 Vol. 15, No. 5 (pp. 1230-1249).

Shmakov et al., "Discovery and Functional Characterization of Diverse Class 2 CRISPR-Cas Systems," Molecular Cell, Nov. 1, 2015, vol. 60, No. 3 (pp. 385-397).

Silverman et al., "Multivalent avimer proteins evolved by exon shuffling of a family of human receptor domains," Nature Biotechnology, 2005, vol. 23, No. 12 (pp. 1556-1561).

Sjolund et al., "Endocrine Cells in Human Intestine: An Immunocytochemical Study," Gastroenterology, Nov. 1983, vol. 85, No. 5 (pp. 1120-1130).

Skerra et al., "Alternative binding proteins: Anticalins-harnessing the structural plasticity of the lipocalin ligand pocket to engineer novel binding activities," The FEBS Journal, 2008, vol. 275 (pp. 2677-2683).

Skerra et al., "Alternative non-antibody scaffolds for molecular recognition." Current Opinion in Biotechnology, 2007, vol. 18 (pp. 295-303).

Skerra, "Engineered protein scaffolds for molecular recognition," Journal of Molecular Recognition, 2000, vol. 13 (pp. 167-187).

Slaymaker et al., "Rationally engineered Cas9 nucleases with improved specificity," Science, Jan. 1, 2016, vol. 351, No. 6268 (pp. 84-88).

Smargon et al., "Cas13b Is a Type VI-B CRISPR-Associated RNA-Guided RNases Differentially Regulated by Accessory Proteins Csx27 and Csx28," Cell Press: Molecular Cell, Feb. 16, 2017, vol. 65, No. 4 (pp. 618-630).

Snippert et al., "Intestinal crypt homeostasis results from neutral competition between symmetrically 5 stem cells," Cell, 2010, vol. 143 (pp. 134-144).

Sokol et al., "Basophils function as antigen-presenting cells for an allergen-induced T helper type 2 response," Nature Immunology, Jul. 2009, vol. 10, No. 7 (pp. 713-720).

Sriuranpong et al., "Notch signaling induces rapid degradation of achaete-scute homolog 1," Molecular and Cellular Biology, May 2002, vol. 22 (pp. 3129-3139).

Stijnen et al., "Random effects meta-analysis of event outcome in the framework of the generalized linear mixed model with applications in sparse data," Statistics in Medicine, Jun. 25, 2010, vol. 29 (pp. 3046-3067).

Stumpp et al., "DARPins: a new generation of protein therapeutics," Drug Discovery Today, Aug. 2008, vol. 13, Nos. 15/16 (pp. 695-701).

Su et al., "Coinfection with an intestinal helminth impairs host innate immunity against *Salmonella enterica* serovar Typhimurium and exacerbates intestinal inflammation in mice," Infection and Immunity, Sep. 2014, vol. 82, No. 9 (pp. 3855-3866).

Su et al., "Development of fatal intestinal inflammation in MyD88 deficient mice co-infected with helminth and bacterial enteropathogens," PLoS Neglected Tropical Diseases, Jul. 2014, vol. 8, No. 7 (pp. 1-13).

Sun et al., "Disease Phenotype of a Ferret Cftr-Knockout Model of Cystic Fibrosis," Journal of Clinical Investigation, Sep. 2010, vol. 120, No. 9 (pp. 3149-3160).

Sun et al., "Lung Phenotype of Juvenile and Adult Cystic Fibrosis Transmembrane Conductance Regulator-Knockout Ferrets," American Journal of Respiratory Cell and Molecular Biology, Mar. 2014, vol. 50, No. 3 (pp. 502-512).

Swiech et al., "In vivo interrogation of gene function in the mammalian brain using CRISPR-Cas9," Nature Biotechnology, 2014, vol. 33 (pp. 102-106) [Including Supplemental information, 4 pages].

Tang et al., "Acidic pH Increases Airway Surface Liquid Viscosity in Cystic Fibrosis," The Journal of Clinical Investigation, Mar. 1, 2016, vol. 126, No. 3 (pp. 879-891).

Tanoue et al., "Development and maintenance of intestinal regulatory T cells," Nature Reviews Immunology, May 2016, vol. 16, No. 5 (pp. 295-309).

Tarran et al., "Regulation of Murine Airway Surface Liquid Volume by Cftr and Ca2+-activated CI-Conductances," The Journal of General Physiology, Sep. 2002, vol. 120, No. 3 (pp. 407-418).

Thelemann et al., "Interferon-gamma induces expression of MHC class II on intestinal epithelial cells and protects mice from colitis," PLoS One, Jan. 28, 2014, vol. 9, No. 1 (pp. 1-10).

Tirosh et al., "Dissecting The Multicellular Ecosystem of Metastatic Melanoma By Single-Cell RNA-Seq," Science, Apr. 8, 2016, vol. 352, No. 6282 (pp. 189-196).

Tran-Huu-Hue et al., "Practical Systems for the Generation of High Power Continuous Wave-Non Focused Ultrasound in the MHz Range," Acustica, acta acustica, 1997, vol. 83 (pp. 1103-1106).

Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).

Tsai et al., "Dimeric CRISPR RNA-guided FokI nucleases for highly specific genome editing," Nature Biotechnology, 2014, vol. 32, No. 6 (pp. 569-576).

Tuerk et al., "Systematic evolution of ligands by exponential enrichment: RNA ligands to bacteriophage T4 DNA polymerase," Science, Aug. 3, 1990, vol. 249, No. 4968 (pp. 505-510).

Twyman et al., "Glutamate Receptor Antibodies Activate a Subset of Receptors and Reveal an Agonist Binding Site," Neuron, Apr. 1995, vol. 14 (pp. 755-762).

Van Ampting et al., "Intestinally secreted C-type lectin Reg3b attenuates *Salmonellosis* but not listeriosis in mice," Infection and Immunity, vol. 80 (pp. 1115-1120).

Van Der Maaten et al., "Visualizing Data Using t-SNE," Journal of Machine Learning Research, Nov. 2008, vol. 9 (pp. 2579-2605).

Van Der Maaten, "Accelerating t-SNE using Tree-Based Algorithms", Journal of Machine Learning Research, Oct. 2014, vol. 15, No. 1 (pp. 3221-3245).

Van Der Meer Van-Kraaj et al., "Dietary modulation and structure prediction of rat mucosal pentraxin (Mptx) protein and loss of function in humans," Genes and Nutrition, Dec. 2007, vol. 2, No. 3 (pp. 275-285).

Van Keymeulen et al., "Distinct stem cells contribute to mammary gland development and maintenance," Nature, 2011, vol. 479 (pp. 189-193).

Van Rijt et al., "Type 2 innate lymphoid cells: at the cross-roads in allergic asthma," Seminars in Immunopathology, Jul. 2016, vol. 38, No. 4 (pp. 483-496).

Vitak et al., "Sequencing thousands of single-cell genomes with combinatorial indexing," Nature Methods, Mar. 2017, vol. 14, No. 3 (pp. 302-308).

Von Essen, "Constitutive and ligand-induced TCR degradation," Journal of Immunology, vol. 173, No. 1 (pp. 384-393).

Wagner et al., "Revealing the vectors of cellular identity with single-cell genomics," Nature Biotechnology, Nov. 8, 2016, vol. 34, No. 11 (pp. 1145-1160).

Wang et al., "Genetic Screens in Human Cells Using the CRISPR-Cas9 System," Science, 2014, vol. 343 (pp. 80-84).

(56) References Cited

OTHER PUBLICATIONS

Wang et al., "One-Step Generation of Mice Carrying Mutations in Multiple Genes by CRISPR/Cas-Mediated Genome Engineering," Cell, May 9, 2013, vol. 153 (pp. 910-918).

Wang, Wei, "Lyophilization and development of solid protein pharmaceuticals," International Journal of Pharmaceutics, Aug. 2000, vol. 203, Issues 1-2 (pp. 1-60).

Watson et al., "SHP-1: the next checkpoint target for cancer immunotherapy?" Biochemical Society Transactions, Apr. 15, 2016, vol. 44, No. 2 (pp. 356-362).

Westphalen et al., Long-lived intestinal tuft cells serve as colon cancer-initiating cells, The Journal of Clinical Investigation, 2014, vol. 124, No. 3 (pp. 1-14).

Wlodarska et al., "NLRP6 inflammasome orchestrates the colonic host-microbial interface by regulating goblet cell mucus secretion," Cell, Feb. 27, 2014 (vol. 156, No. 5 (pp. 1045-1059).

Wu et al., "Remote control of therapeutic T cells through a small molecule-gated chimeric receptor," Science, Oct. 16, 2015, vol. 350, No. 6258 (pp. 1-21).

Wu et al., "Genome-wide binding of the CRISPR endonuclease Cas9 in mammalian cells," Nature Biotechnology, 2014, Including Supplemental information (pp. 1-9).

Xu et al., "Sequence determinants of improved CRISPR sgRNA design," Genome Research, Aug. 2015, vol. 25 (pp. 1147-1157).

Yan et al., "Cas13d Is a Compact RNA-Targeting Type Vi CRISPR Effector Positively Modulated by a WYL-Domain-Containing Accessory Protein," Molecular Cell, Apr. 19, 2018, vol. 70, No. 2 (pp. 327-339).

Yan et al., "Intestinal Enteroendocrine Lineage Cells Possess Homeostatic and Injury-Inducible Stem Cell Activity," Cell Stem Cell, Jul. 6, 2017, vol. 21, No. 1 (pp. 78-90).

Yan et al., "Optimization of Recombinant Adena-Associated Virus-Mediated Expression for Large Transgenes, Using a Synthetic Promoter and Tandem Array Enhancers," Human Gene Therapy, Jun. 2015, vol. 26 (pp. 334-346).

Yoon et al., "Antibodies to Domains II and III of the IL-1 Receptor Accessory Protein Inhibit IL-1-Beta Activity But Not Binding: Regulation of IL-1 Responses is Via Type I Receptor, Not the Accessory Protein," The Journal of Immunology, 1998, vol. 160 (pp. 3170-3179).

Young et al., "A Gene ontology analysis for RNA-seq: accounting for selection bias," Genome Biology, 2010, vol. 11, No. R14 (pp. 1-12).

Zeisel et al., Brain Strcuture: "Cell Types in the Mouse Cortex and Hippocampus Revealed by Single-cell RNA-seq," Science, Mar. 6, 2015, vol. 347, No. 6226 (pp. 1138-1142).

Zetsche et al., "A split-Cas9 architecture for inducible genome editing and transcription modulation," Nature Biotechnology, Feb. 2015, vol. 33, No. 2 (pp. 139-142).

Zetsche et al., "Cpf1 is a single RNA-guided endonuclease of a Class 2 CRISPR-Cas system," Cell, Oct. 22, 2015, vol. 163, No. 3 (pp. 759-771) [with Supplemental Information]—36 Pages).

Zhang et al., "AnimalTFDB: a comprehensive animal transcription factor database," Nucleic Acids Research, 2012, vol. 40 (pp. 1-6).

Zhang et al., "Efficient Construction of Sequence-Specific TAL Effectors for Modulating Mammalian Transcription," Nature Biotechnology, Feb. 2011, vol. 29, No. 2 (pp. 149-154).

Zheng et al. "Haplotyping germline and cancer genomes with high-throughput linked-read sequencing," Nature Biotechnology, Feb. 1, 2016, vol. 34, No. 3 (pp. 303-311) [with Supplemental Material].

Zheng et al., "Massively parallel digital transcriptional profiling of single cells," Nature Communications, Jan. 16, 2017, vol. 8, No. 14049 (12 pages).

Zhou et al., "Aptamer-targeted cell-specific RNA interference," Silence, Feb. 1, 2010, vol. 1, No. 4 (10 pages).

Zhou et al., "Long-term outcome after haploidentical stem cell transplant and infusion of T cells expressing the inducible caspase 9 safety transgene," Blood, Jun. 19, 2014, vol. 123, No. 25 (pp. 3895-3905).

Zhu et al., "Inhibition of Vascular Endothelial Growth Factor-induced Receptor Activation with Anti-Kinase Insert Domain-containing Receptor Single-Chain Antibodies from a Phage Display Library," Cancer Research, Aug. 1998, vol. 58 (pp. 3209-3214).

Zilionis et al., "Single-cell barcoding and sequencing using droplet microfluidics," Nature Protocols, 2017, vol. 12, No. 1 (pp. 44-73).

Zuker et al., "Optimal computer folding of large RNA sequences using thermodynamics and auxiliary information," Nucleic Acids Research, Jan. 10, 1981, vol. 9, No. 1 (pp. 133-148).

* cited by examiner

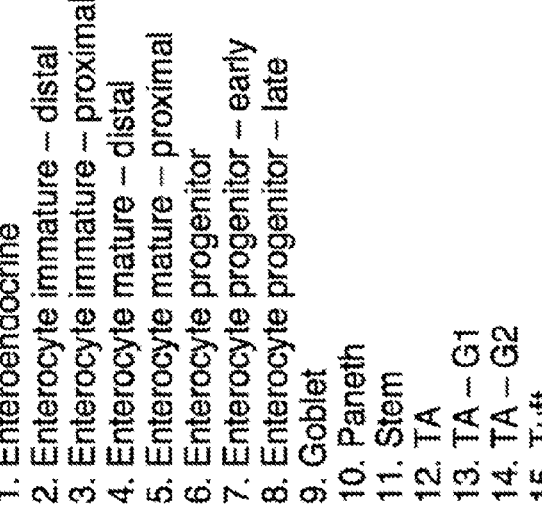
1. Enteroendocrine
2. Enterocyte immature – distal
3. Enterocyte immature – proximal
4. Enterocyte mature – distal
5. Enterocyte mature – proximal
6. Enterocyte progenitor
7. Enterocyte progenitor – early
8. Enterocyte progenitor – late
9. Goblet
10. Paneth
11. Stem
12. TA
13. TA – G1
14. TA – G2
15. Tuft
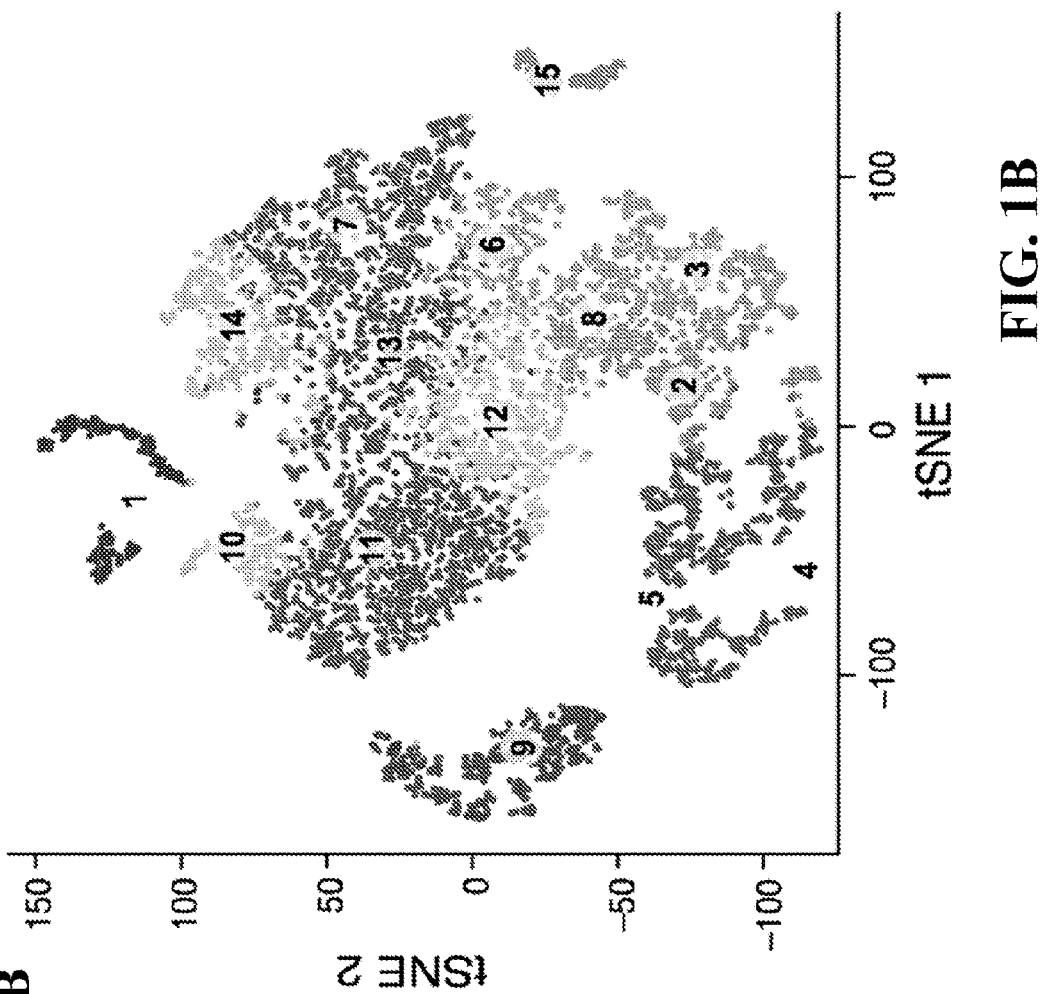
FIG. 1B

D
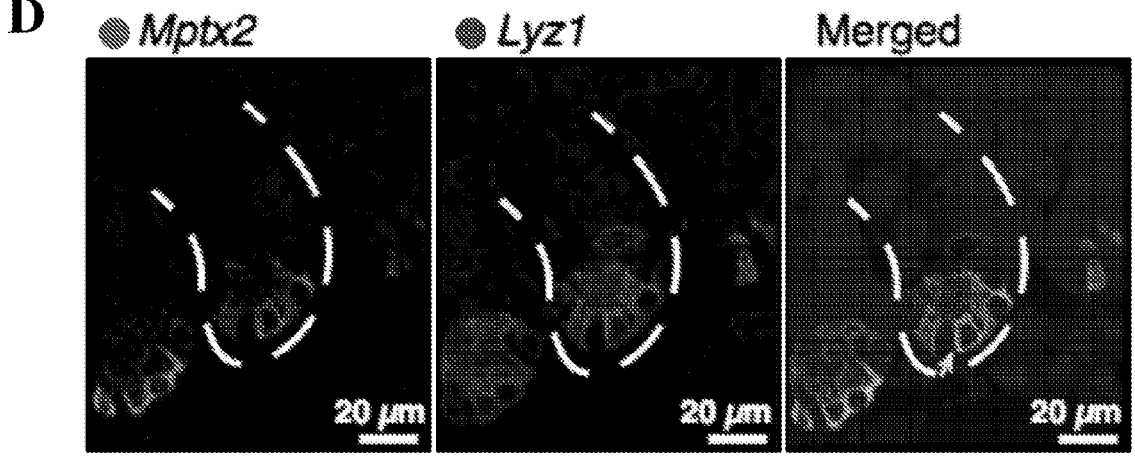
E
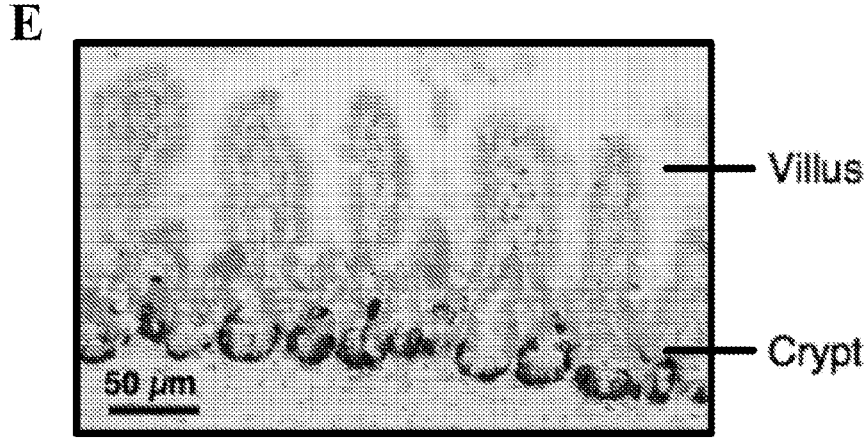
FIG. 1D-E

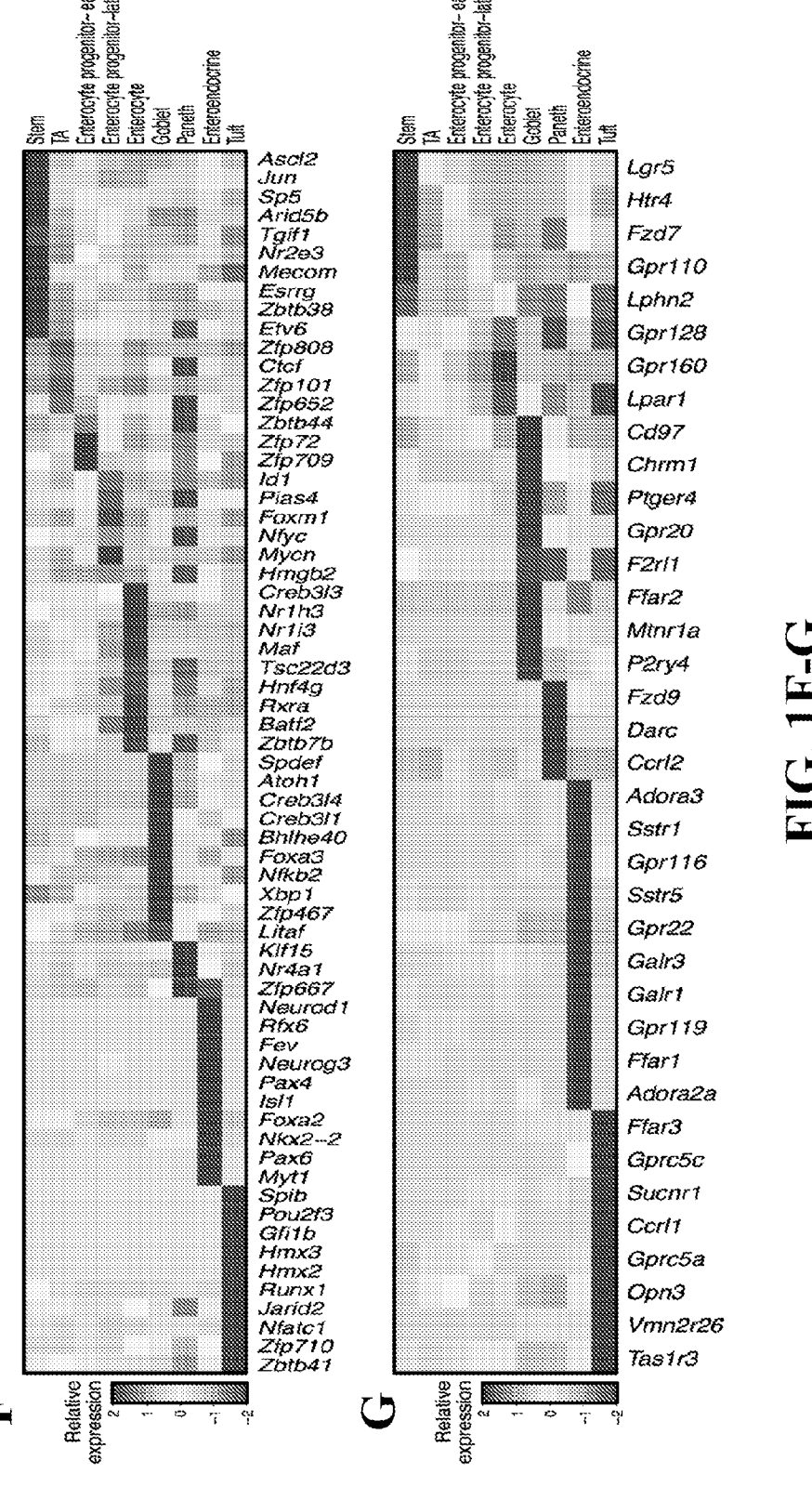
FIG. 1F-G

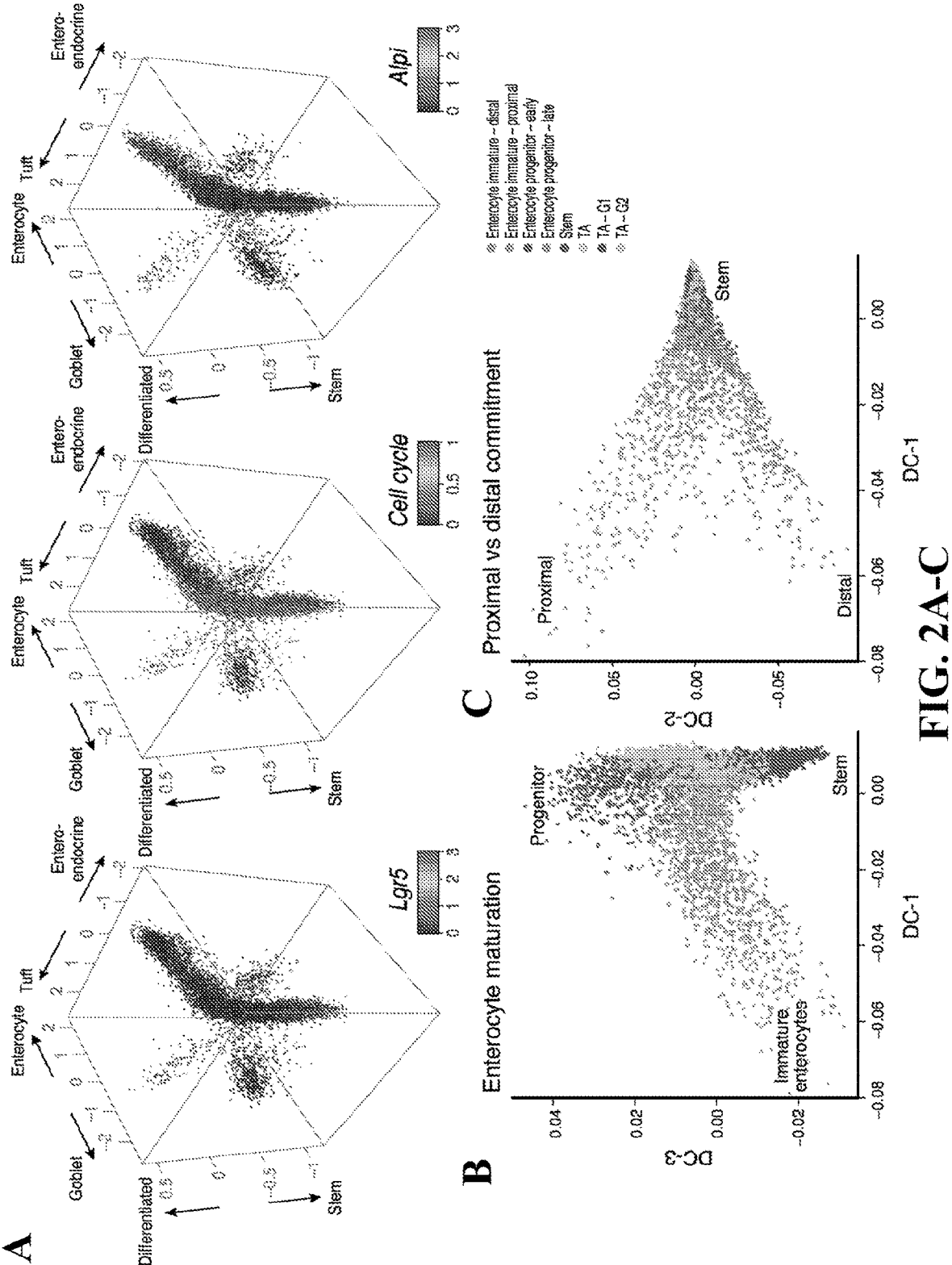
FIG. 2A-C

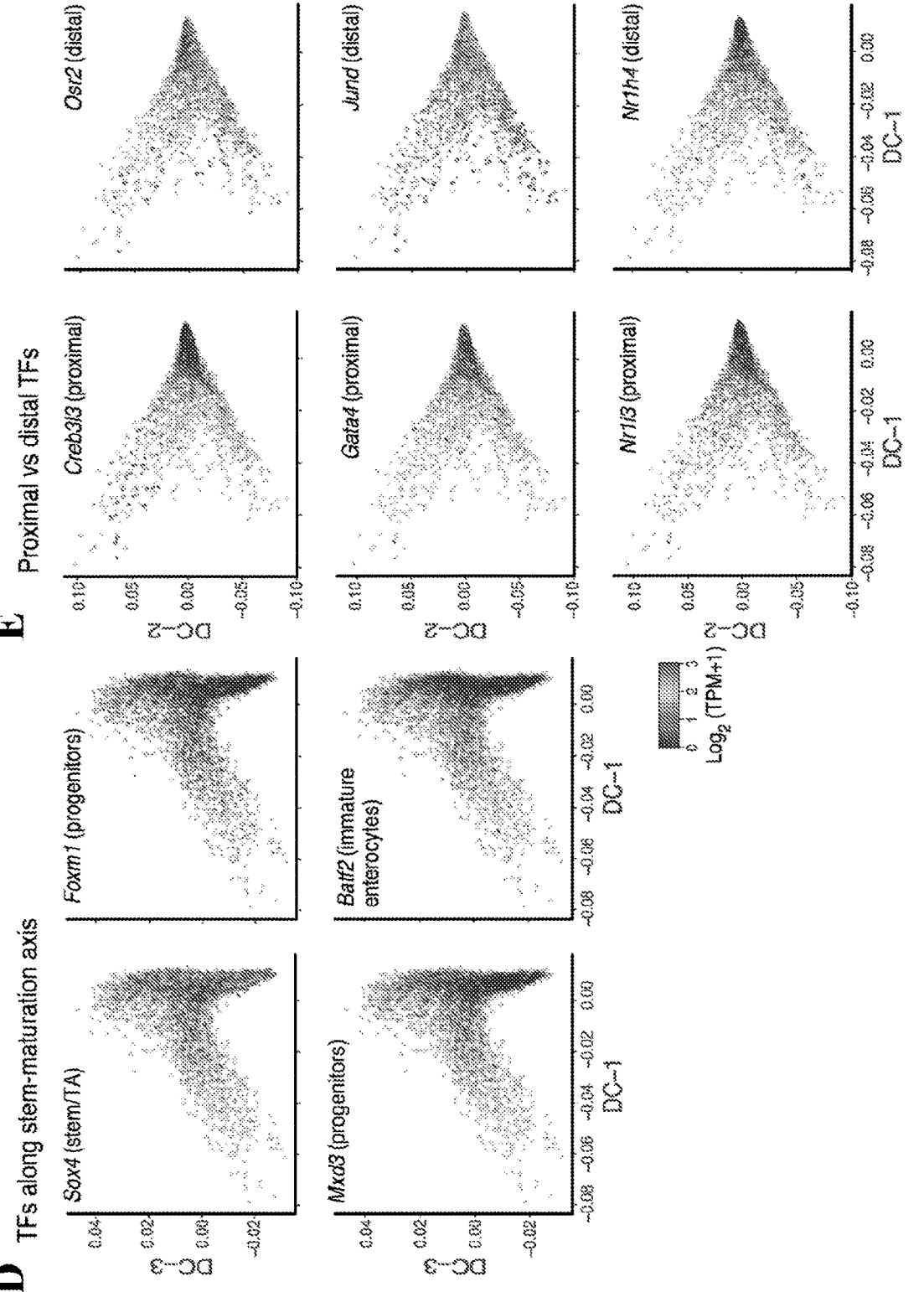
FIG. 2D-E

A

1. EC
2. EC–*Reg4*
3. Prog. A
4. Prog.-early
5. SAKD
6. SILA
7. SIK
8. SIK-P
9. SIL-P
10. SIN
11. Prog.-middle
12. Prog.-late

B

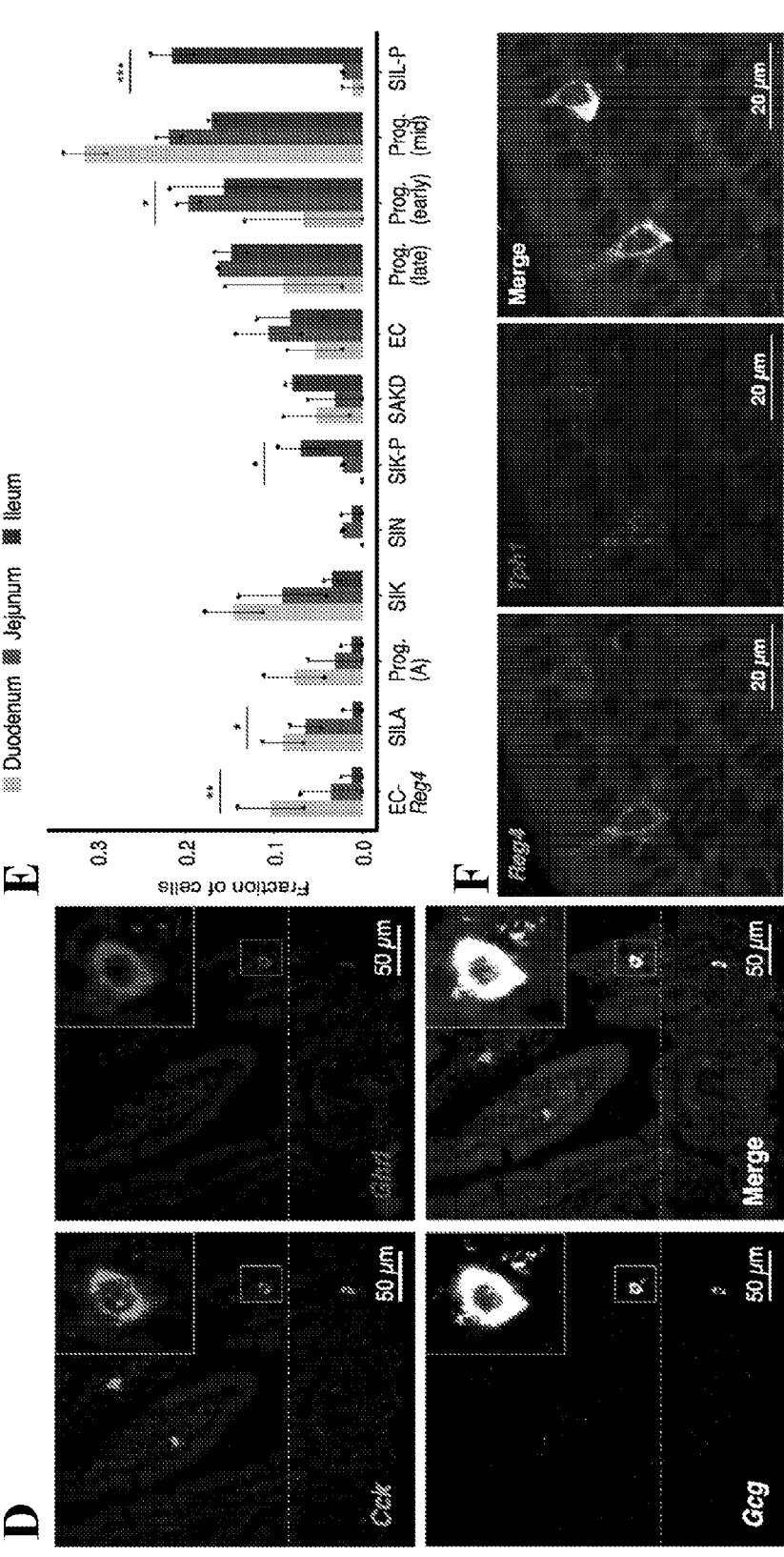
FIG. 3D-F

A

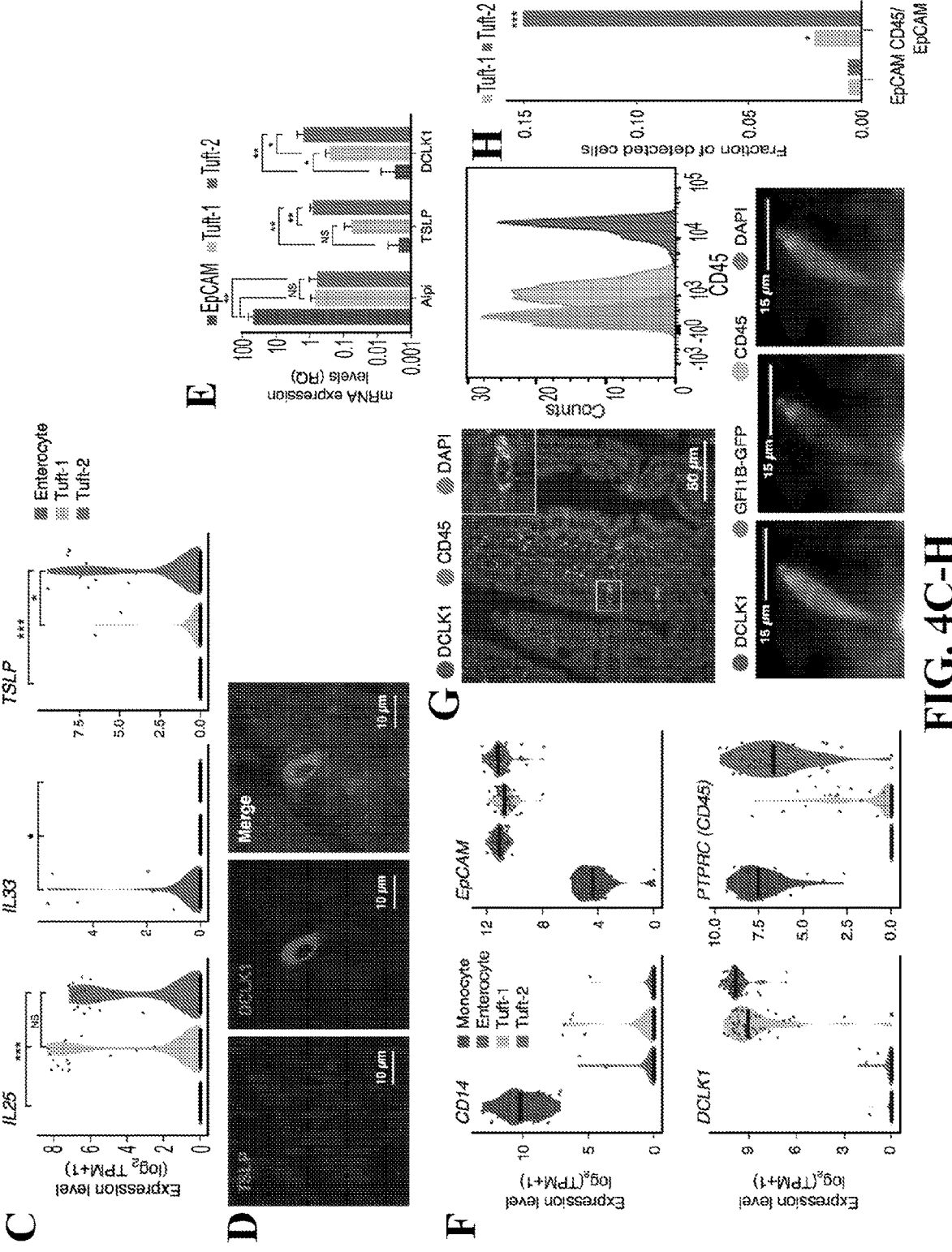
FIG. 4C-H

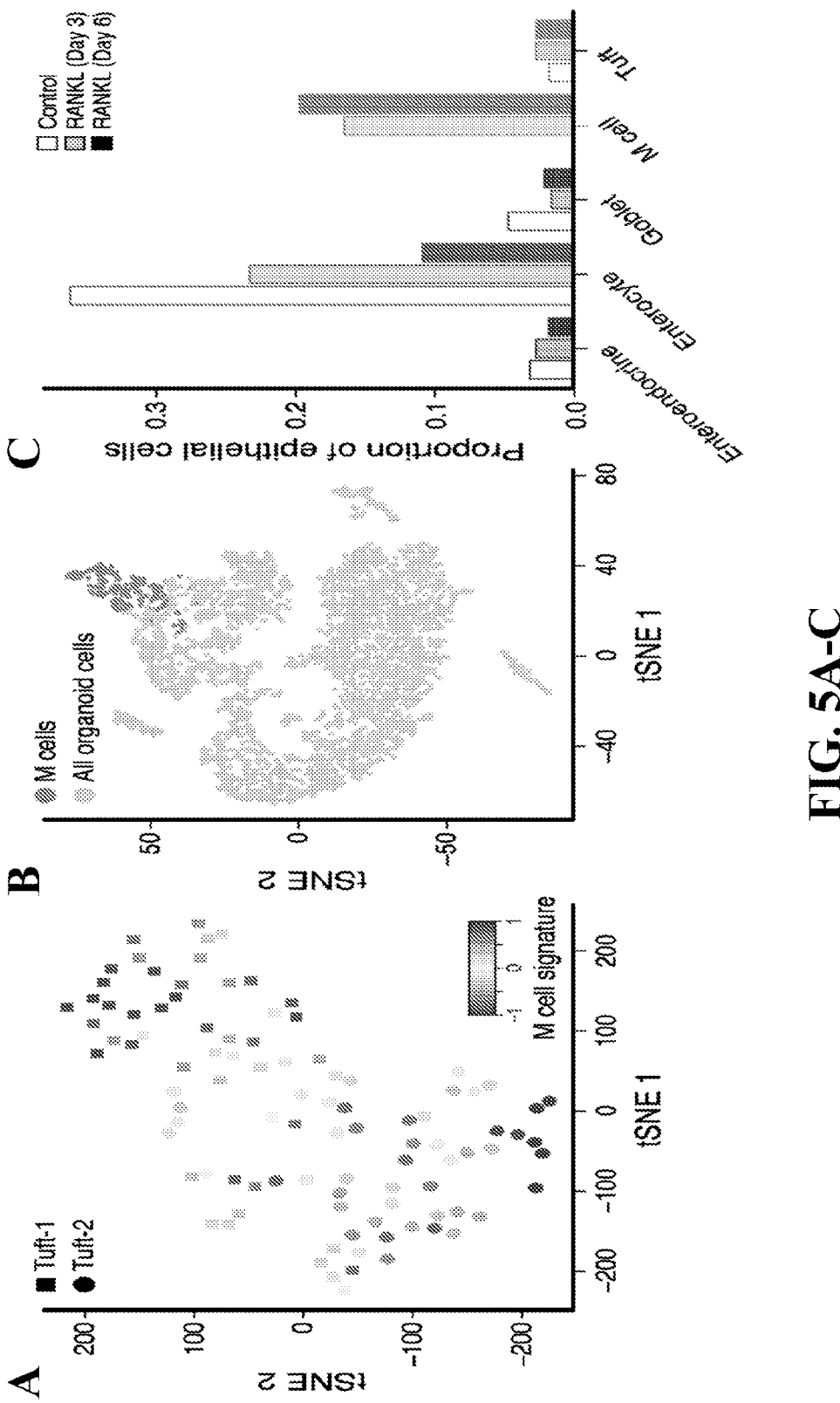
FIG. 5A-C

D

Stem and TA
Enterocyte (proximal)
Enterocyte (distal)
SAKD
SIK
Enteroendrocrine
EC–*Reg4*
M cell
Tuft
Goblet Pearson
correlation

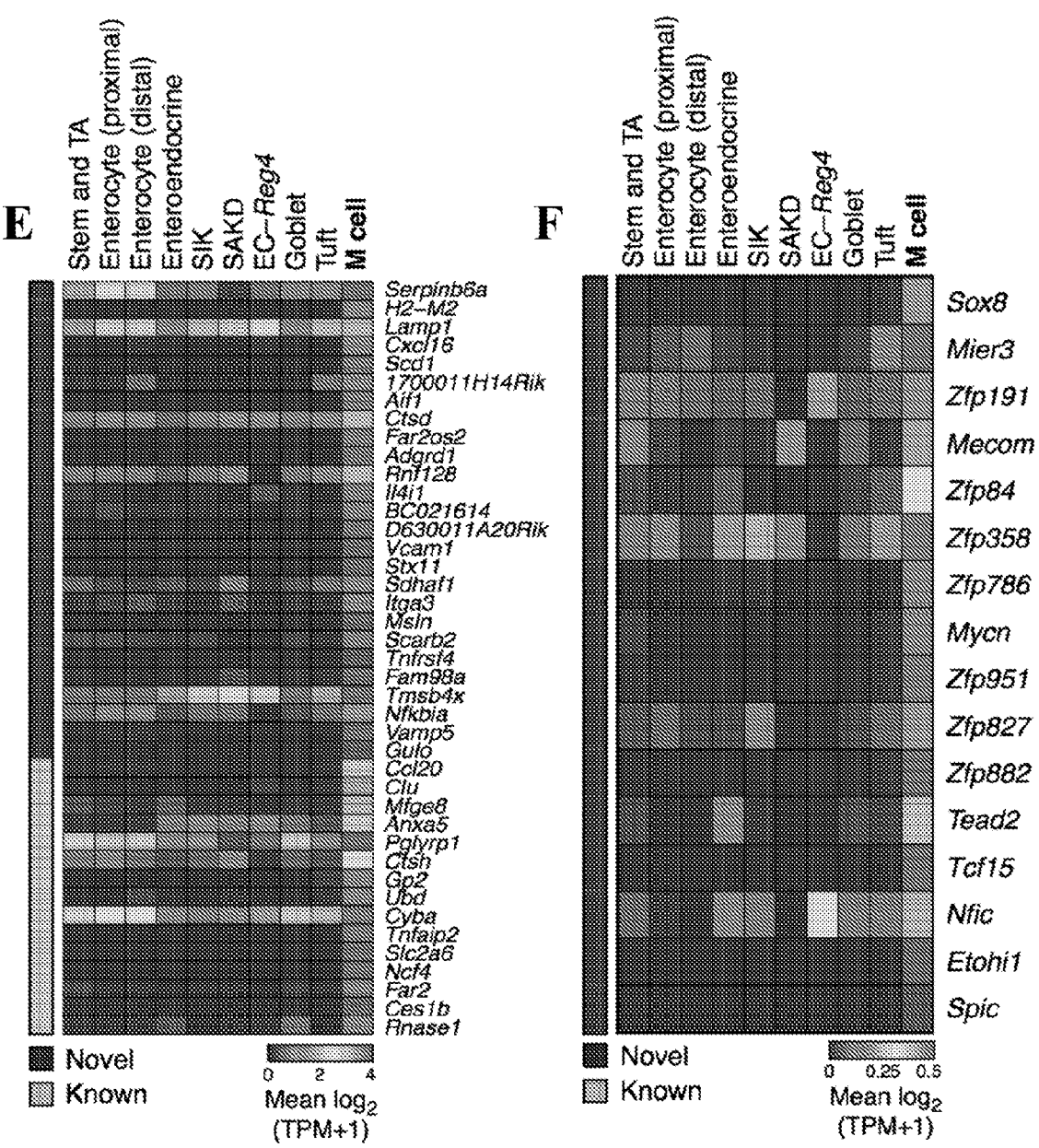
FIG. 5E-F

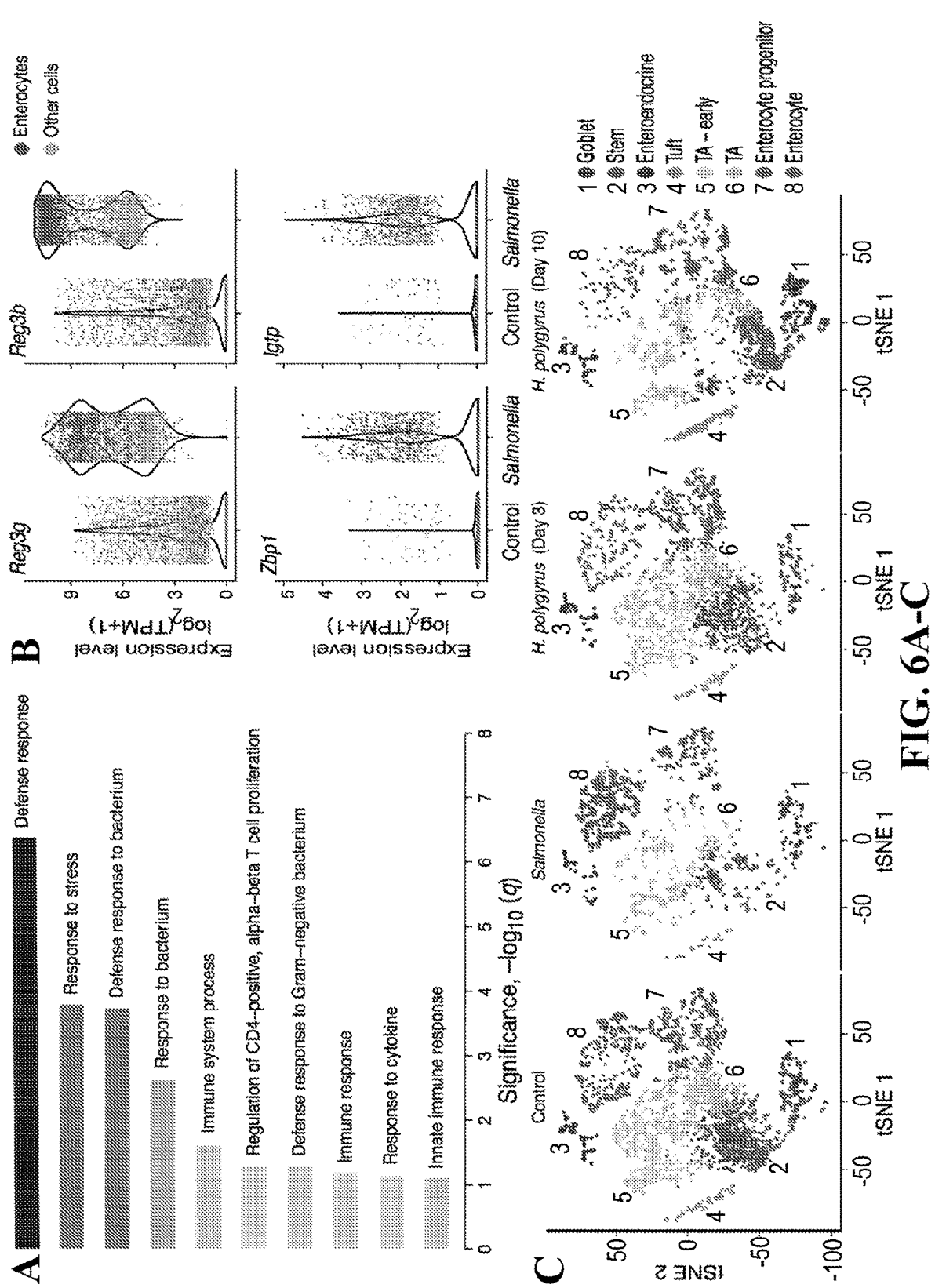
FIG. 6A–C

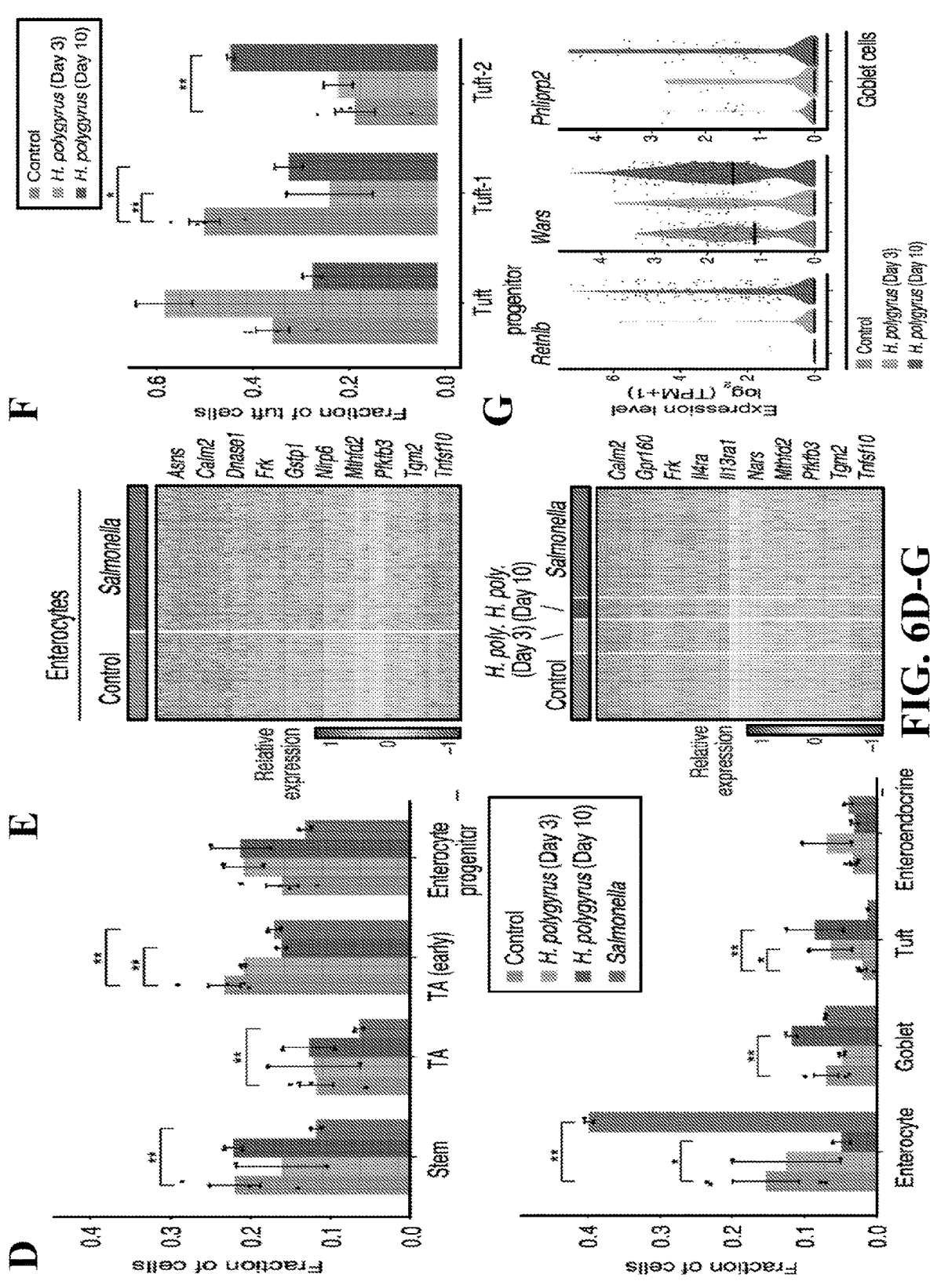
FIG. 6D-G

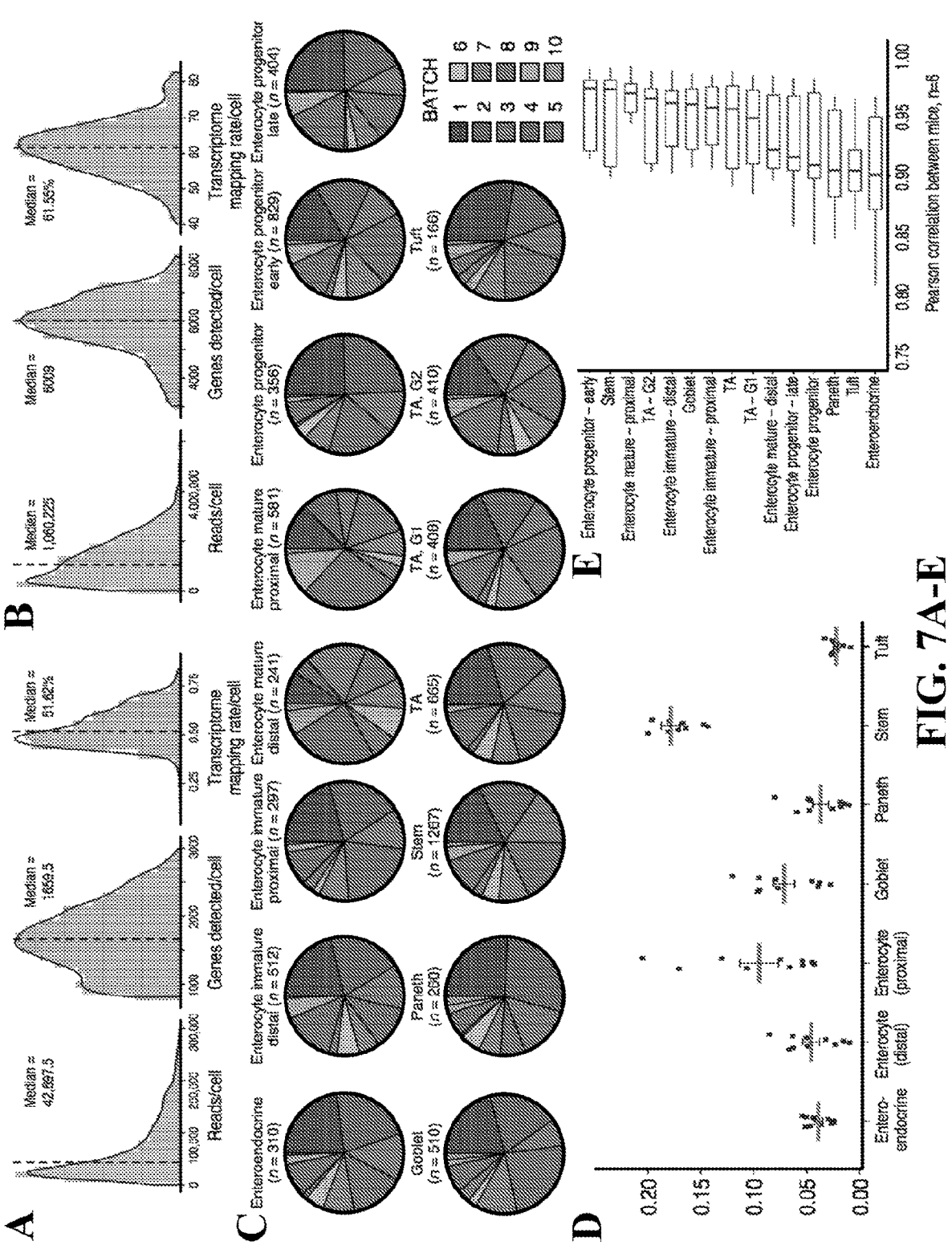
FIG. 7A-E

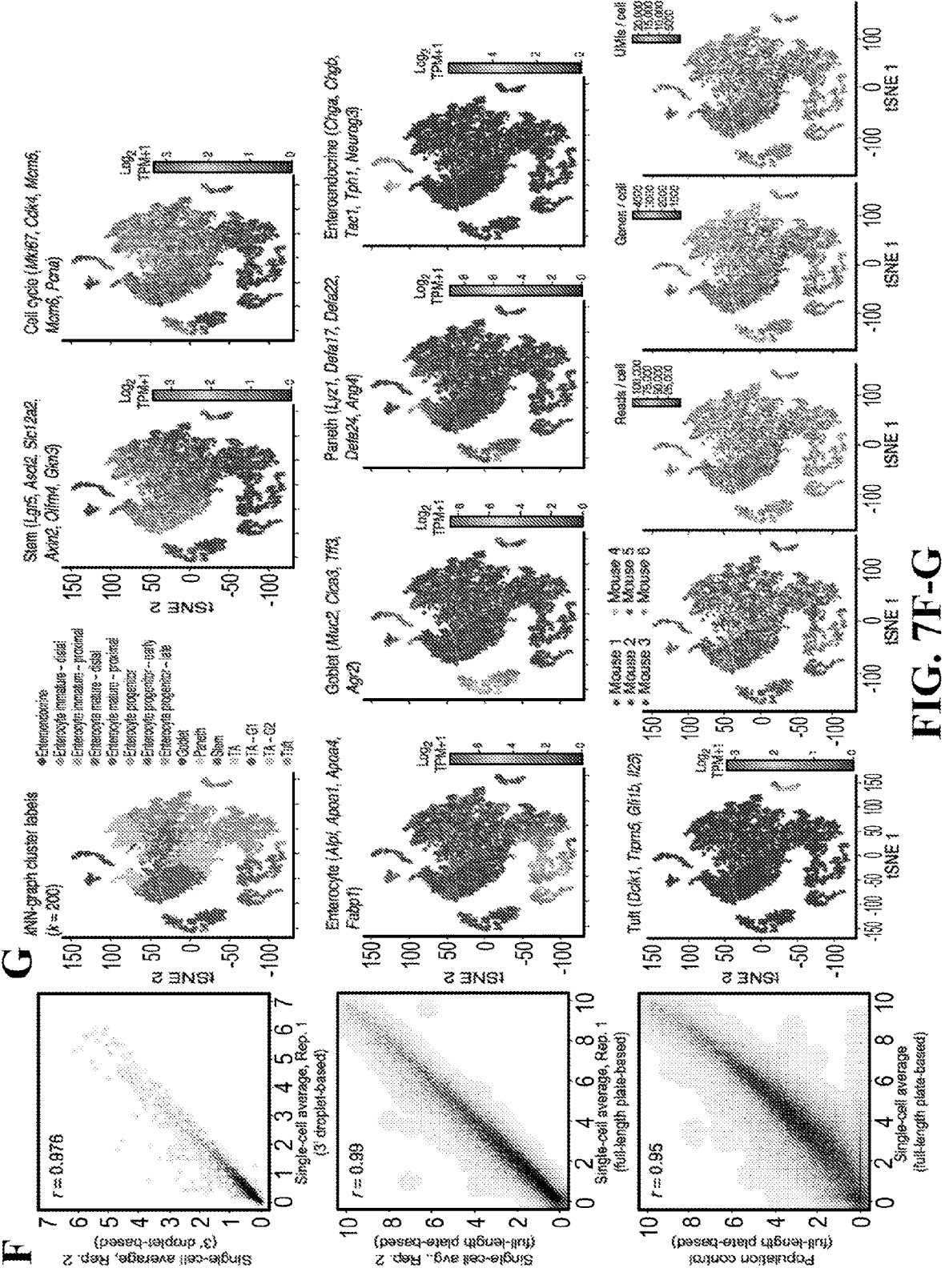
FIG. 7F-G

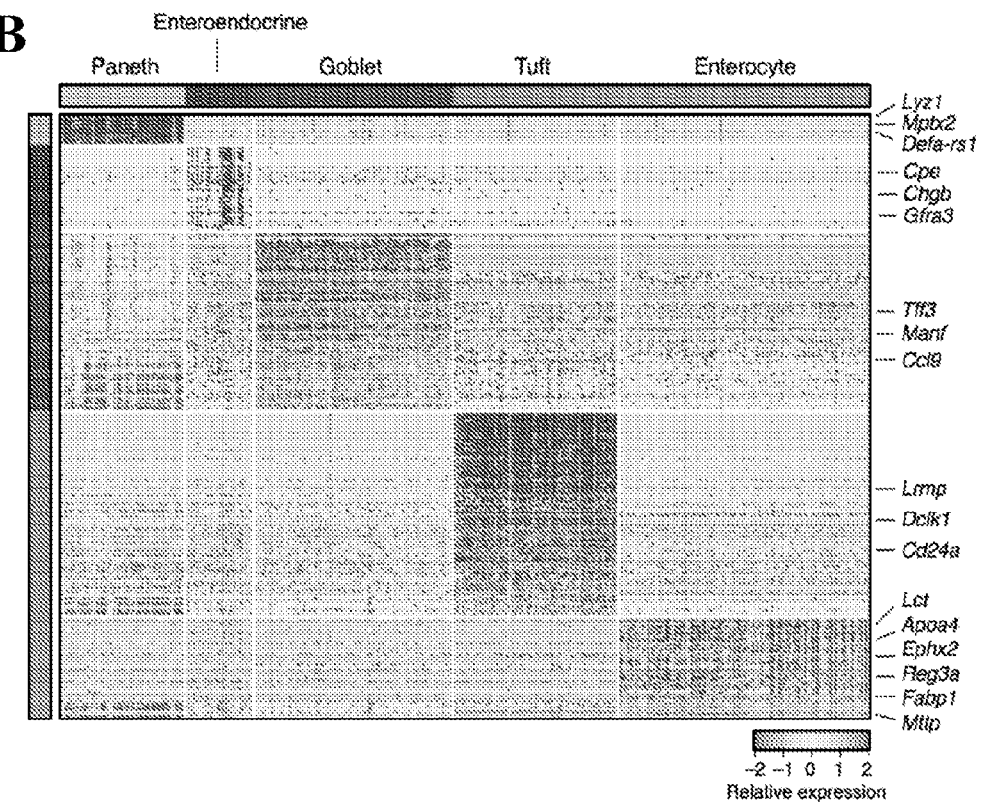
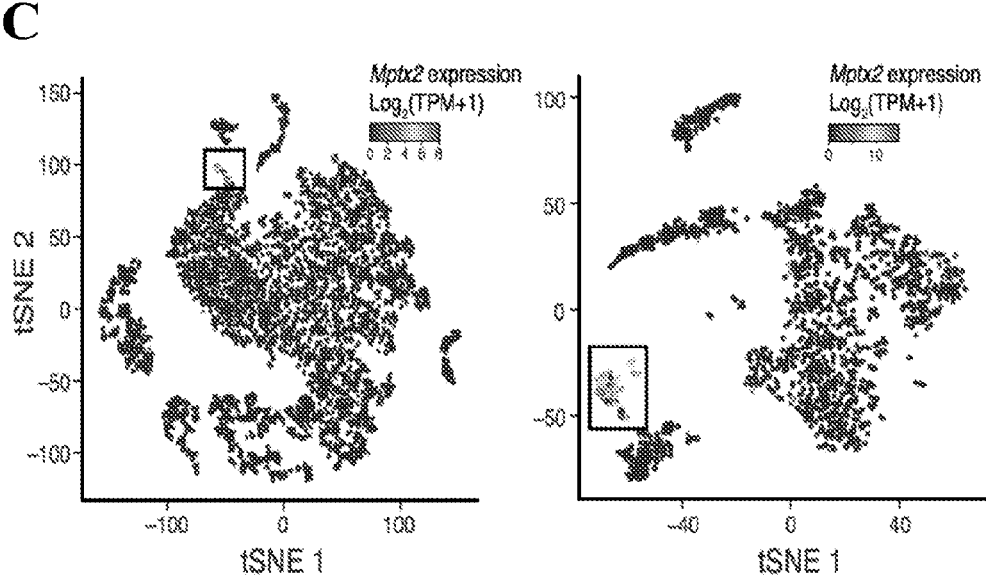
FIG. 8B-C

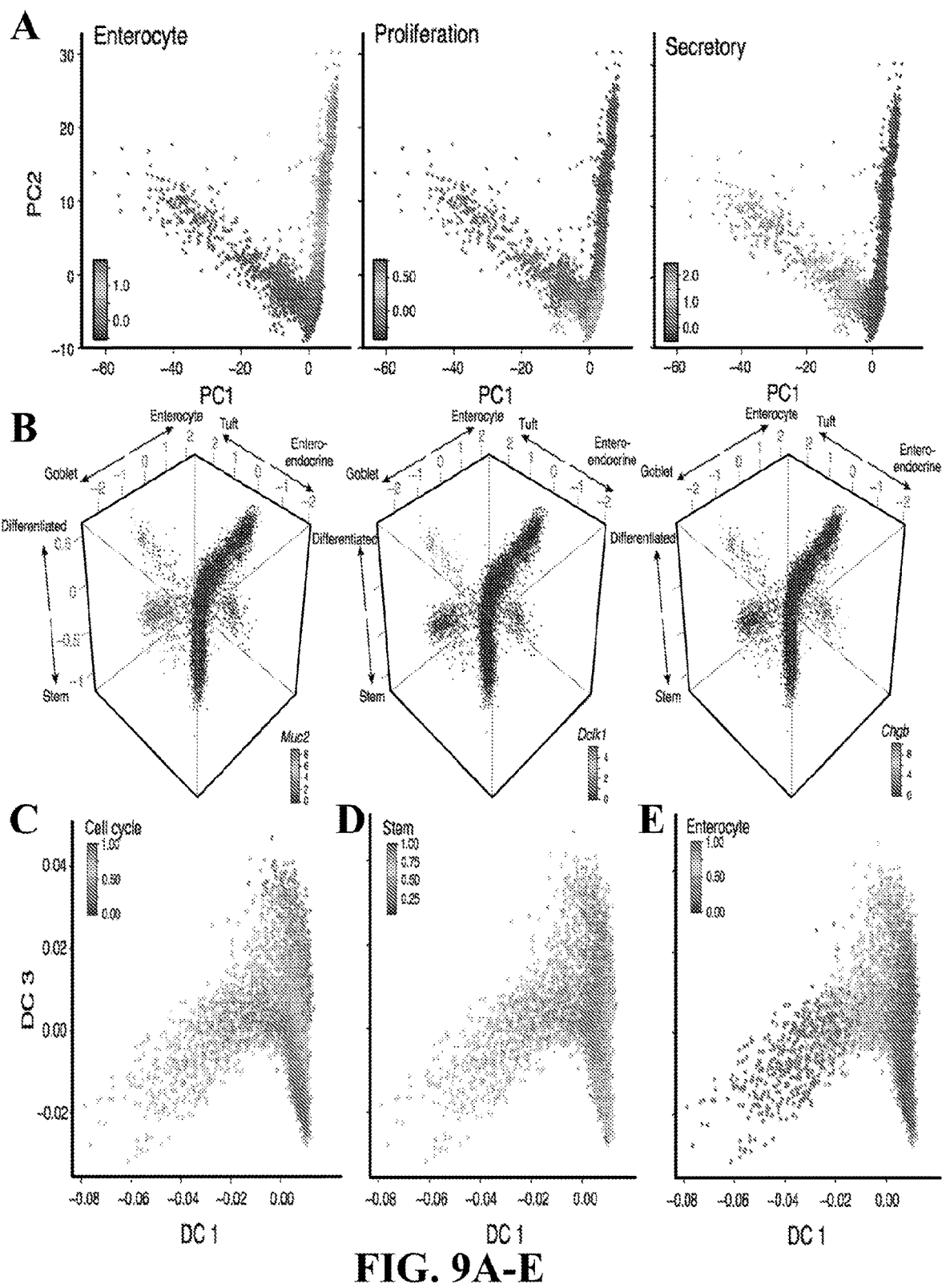
FIG. 9A-E

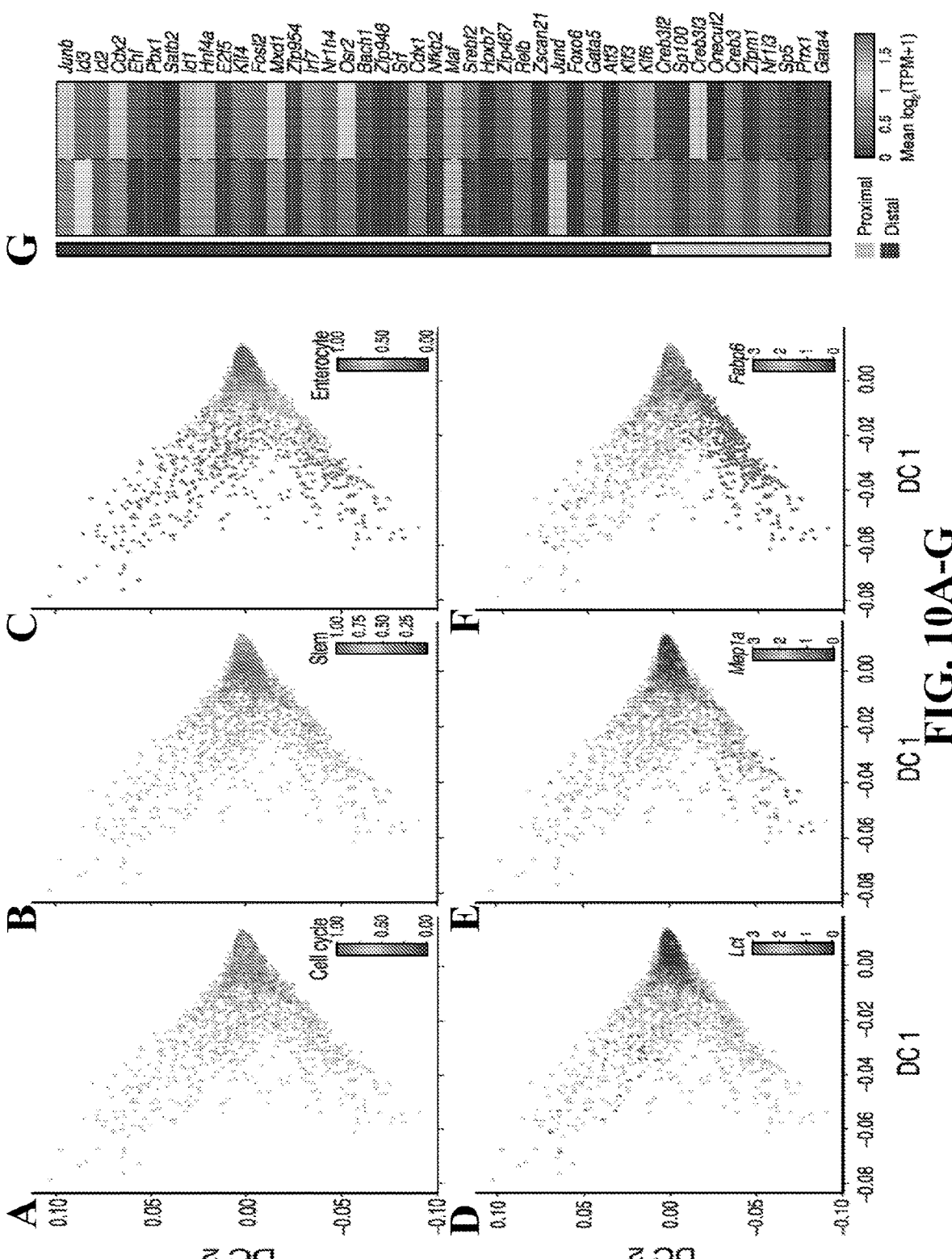
FIG. 10A-G

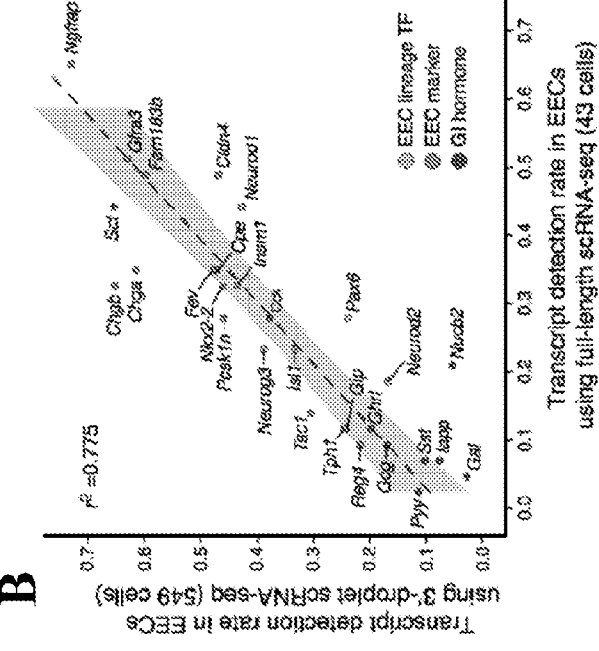
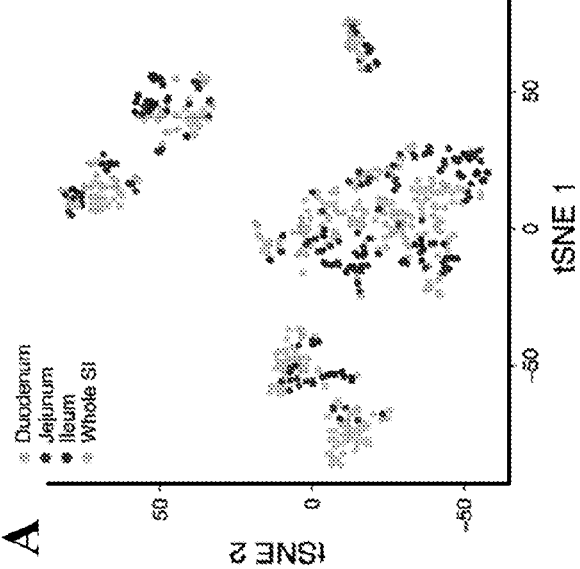
FIG. 11A-B

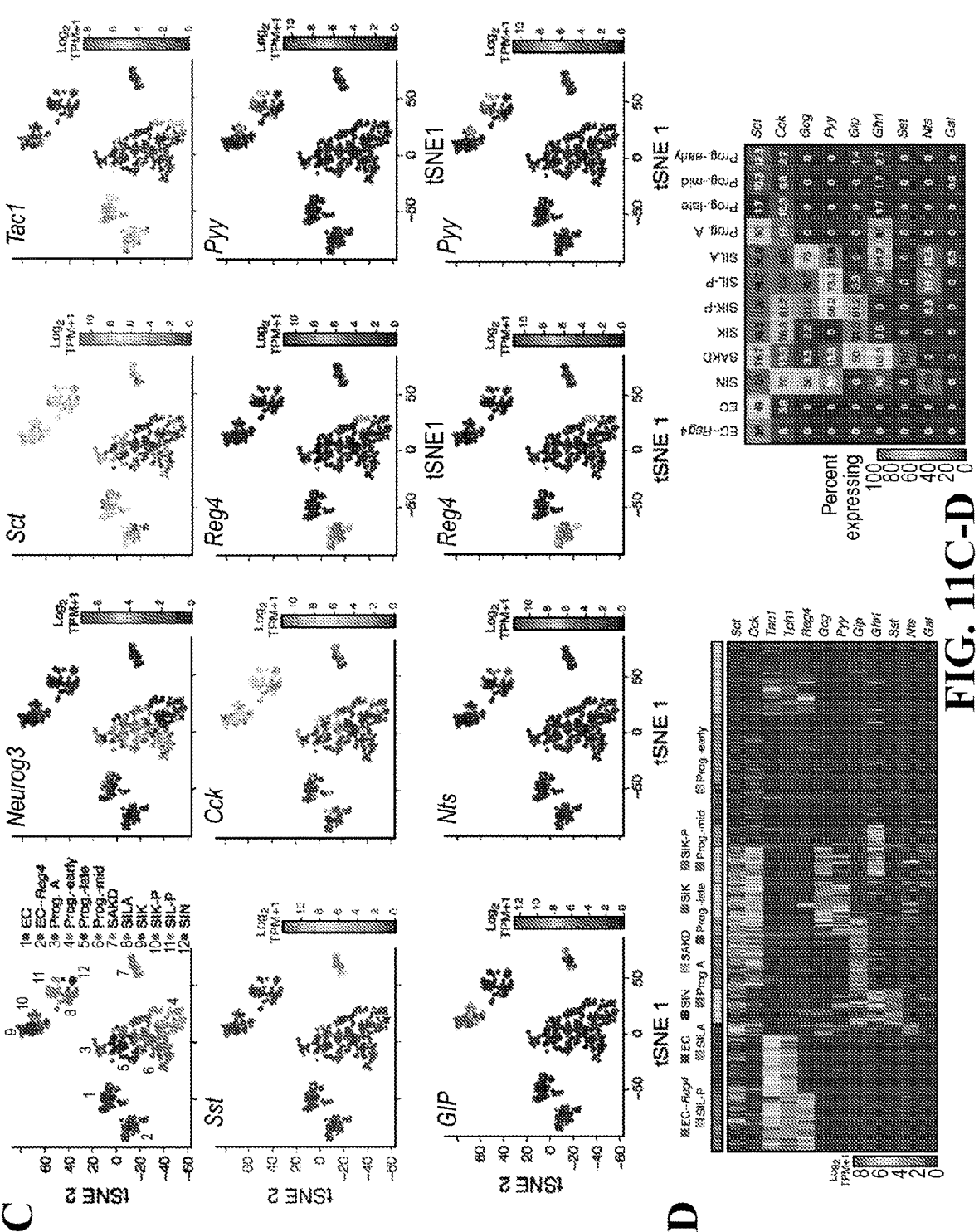
FIG. 11C-D

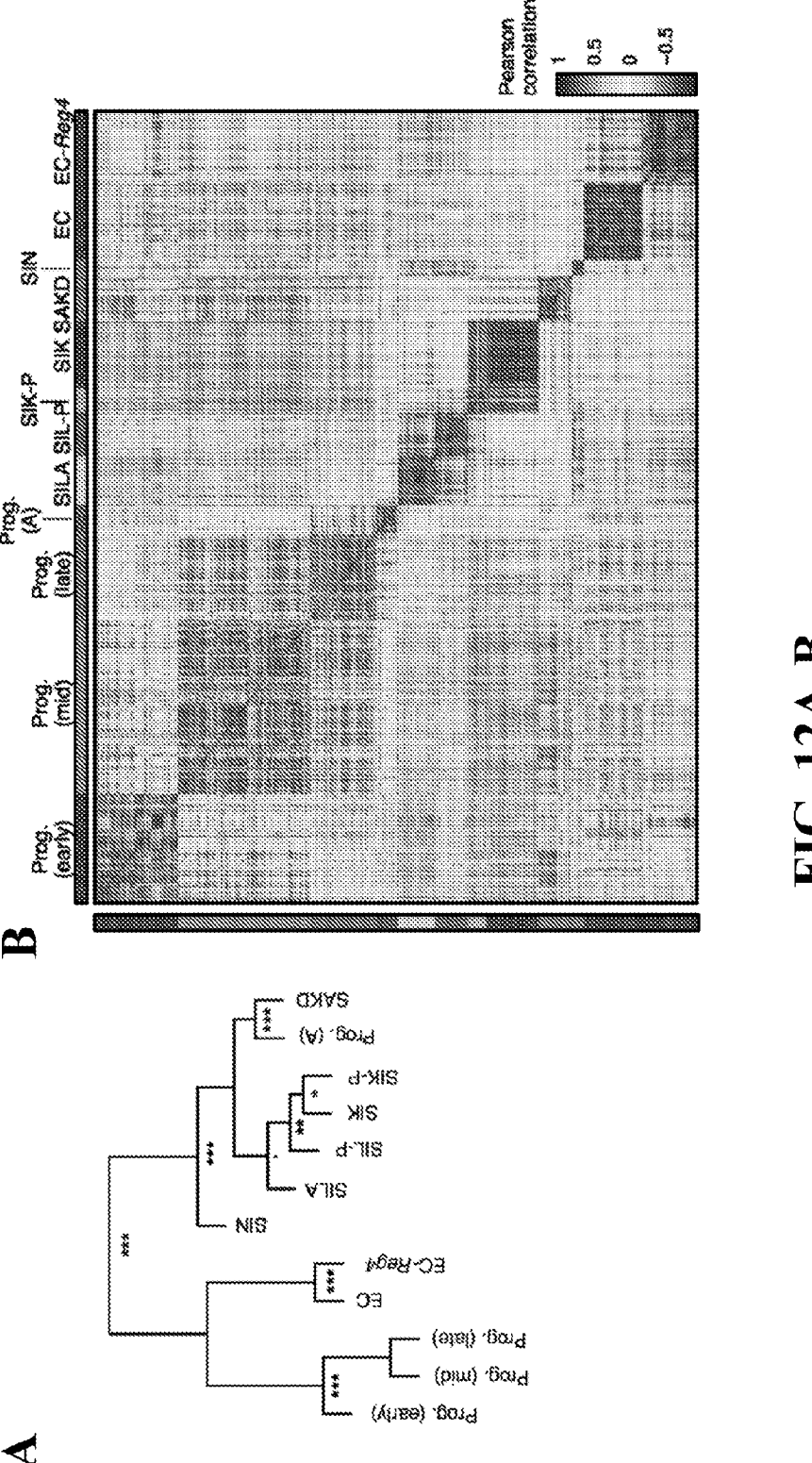
FIG. 12A-B

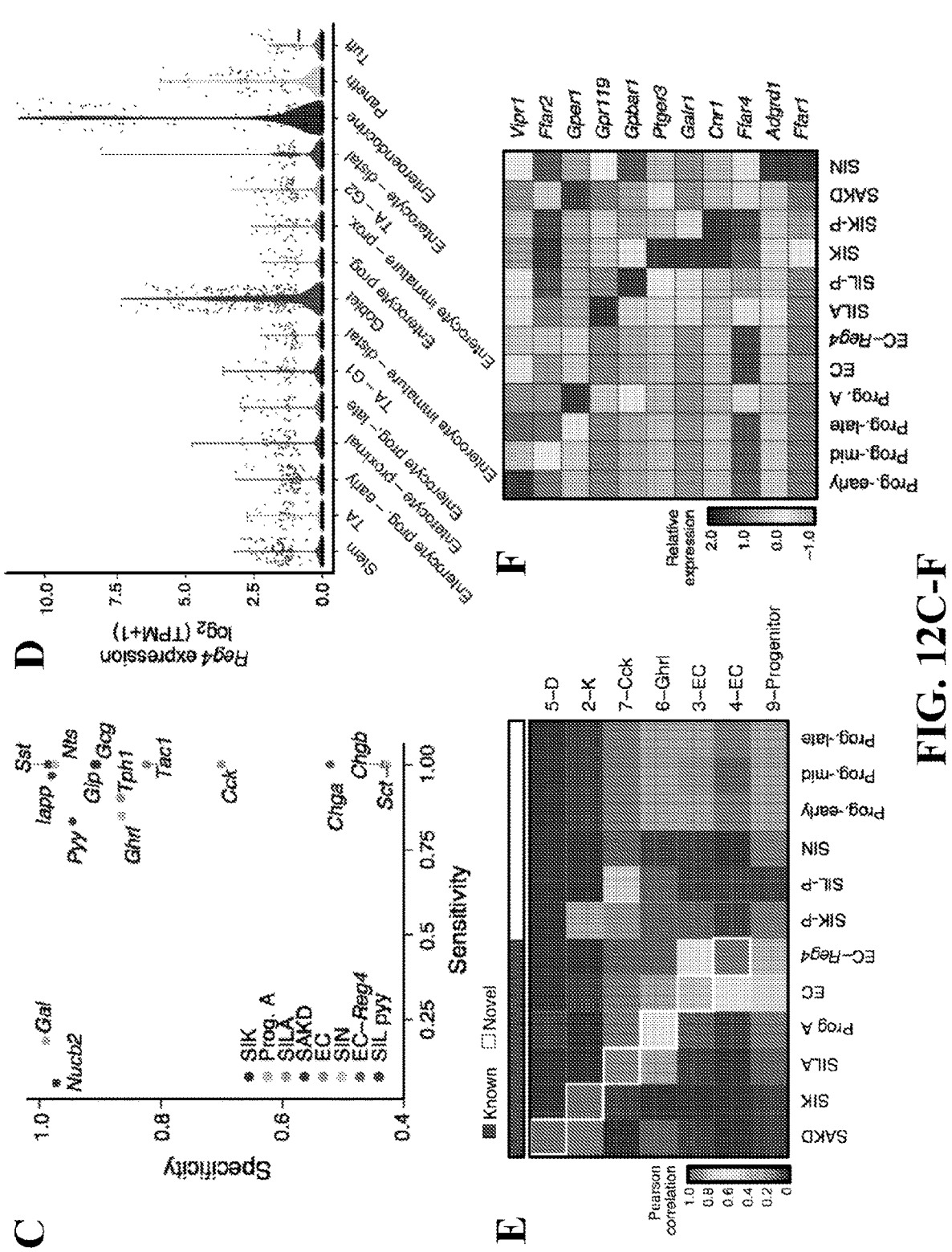
FIG. 12C-F

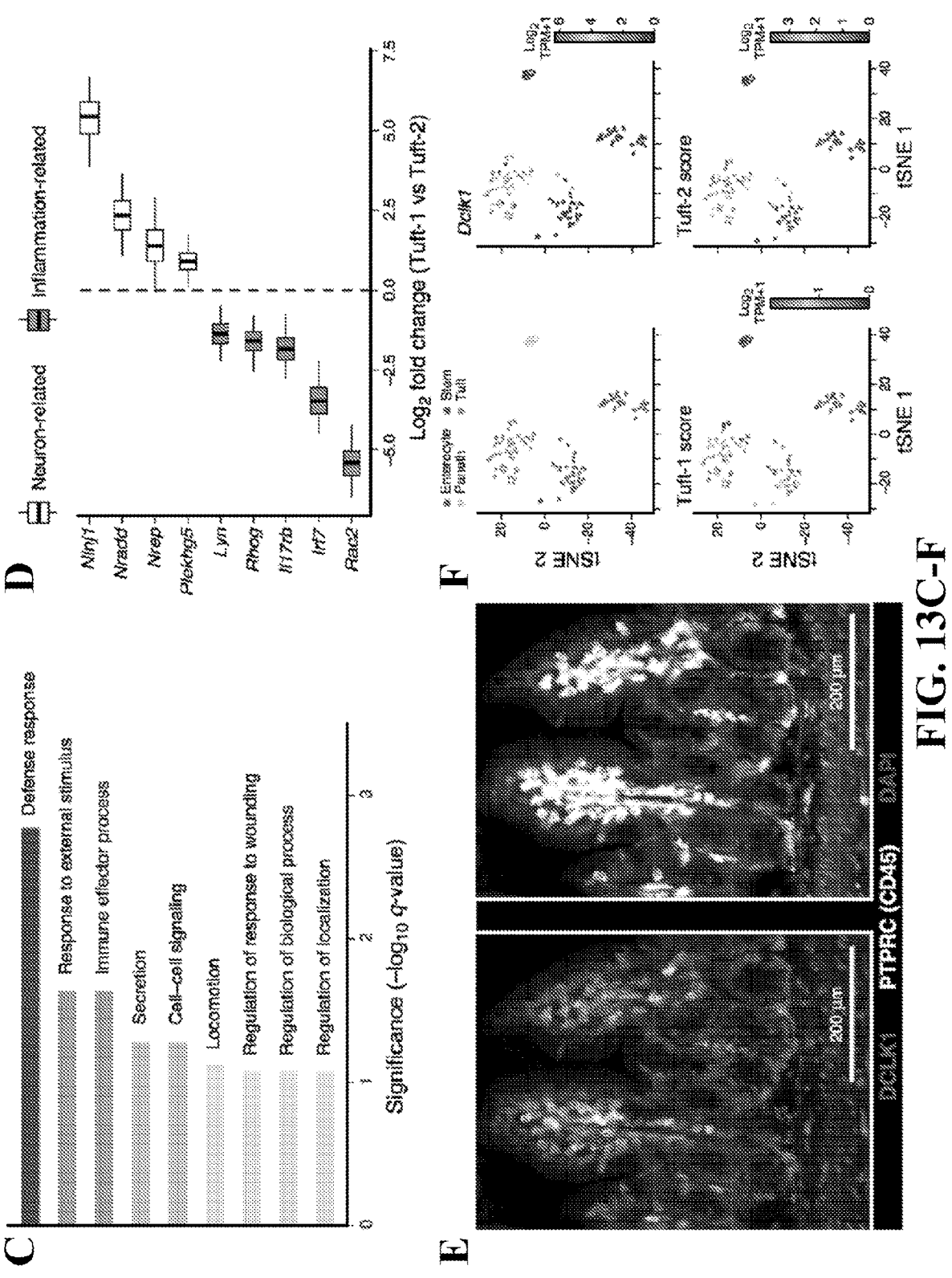
FIG. 13C-F

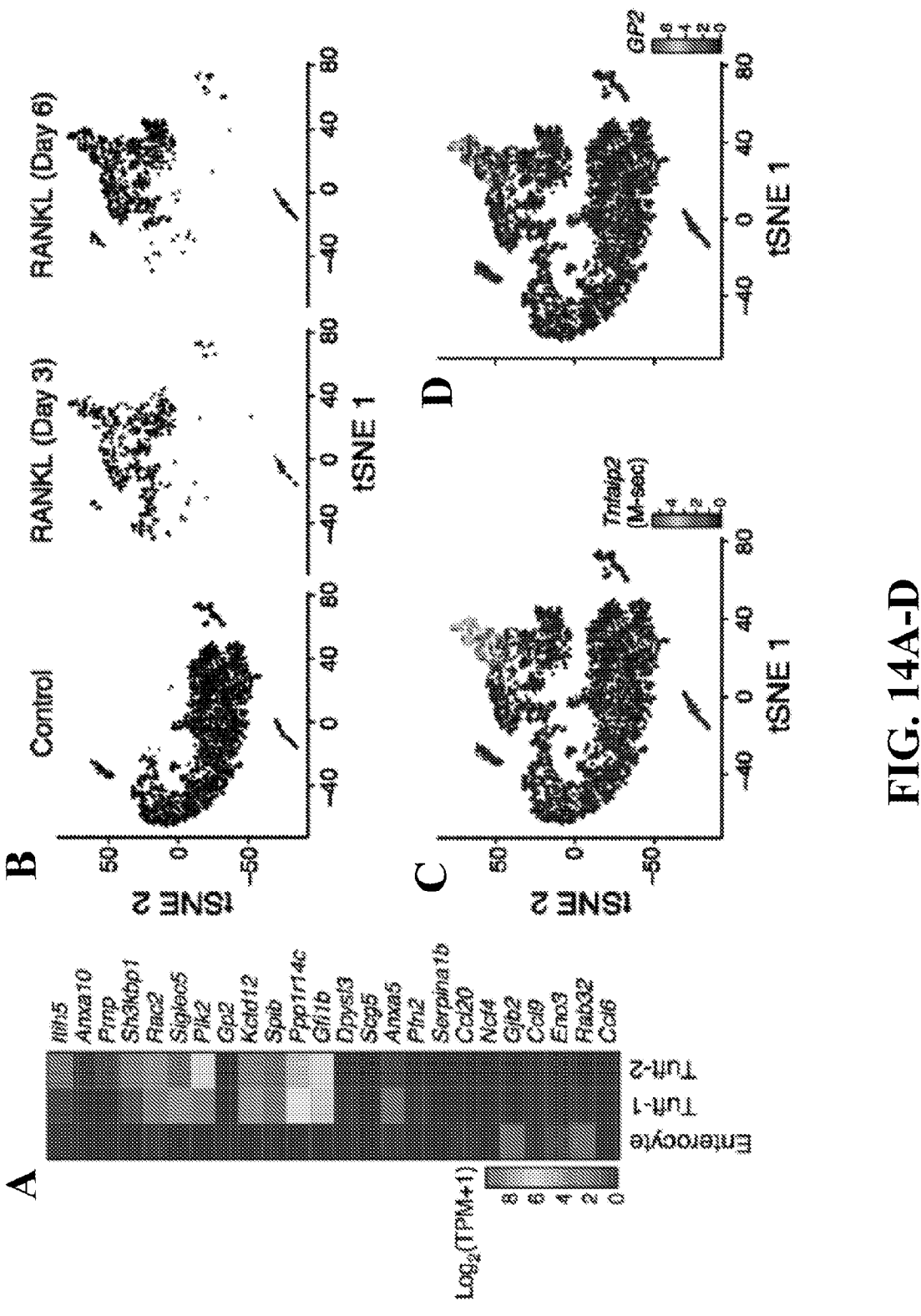
FIG. 14A-D

F

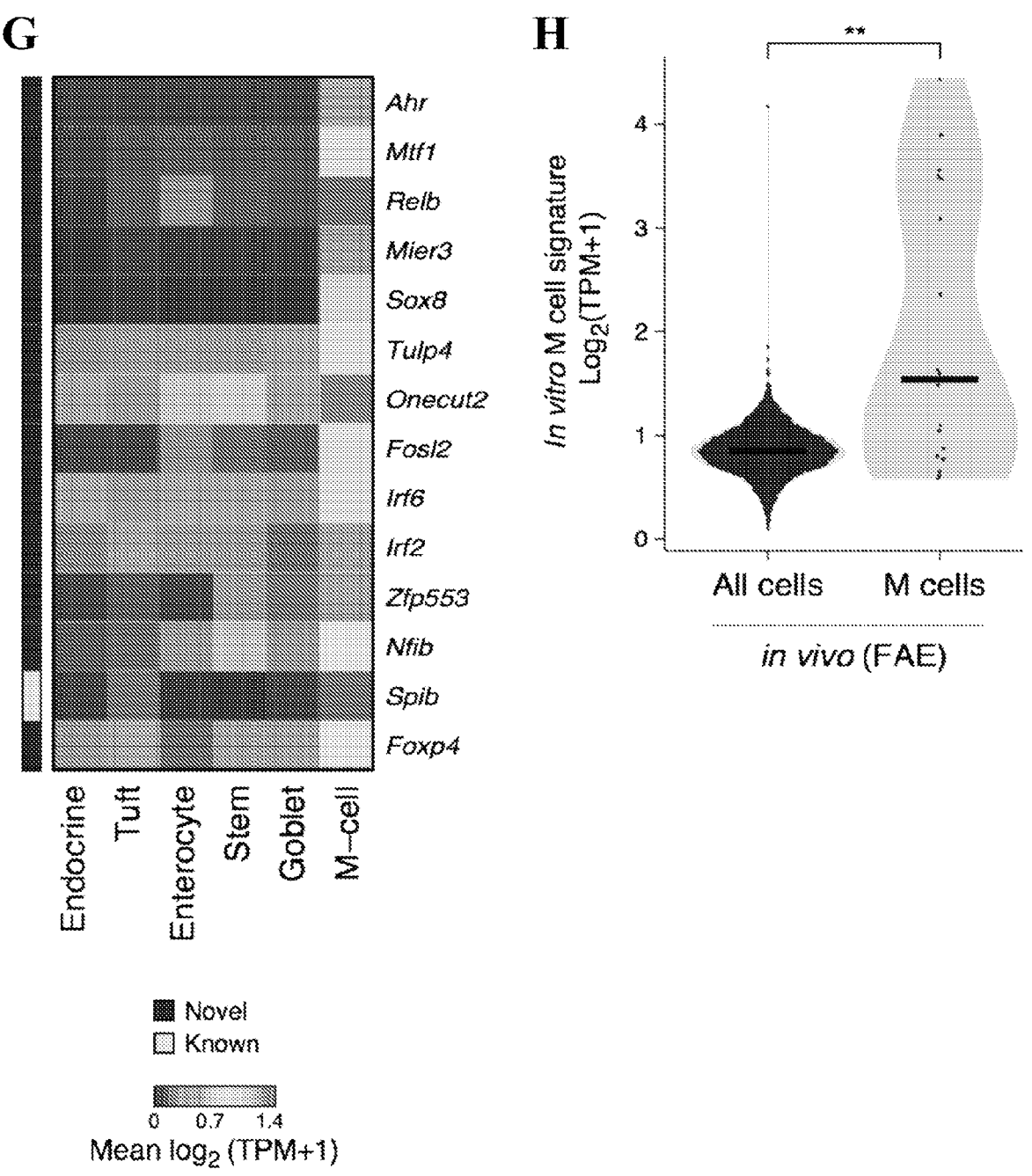
FIG. 14G-H

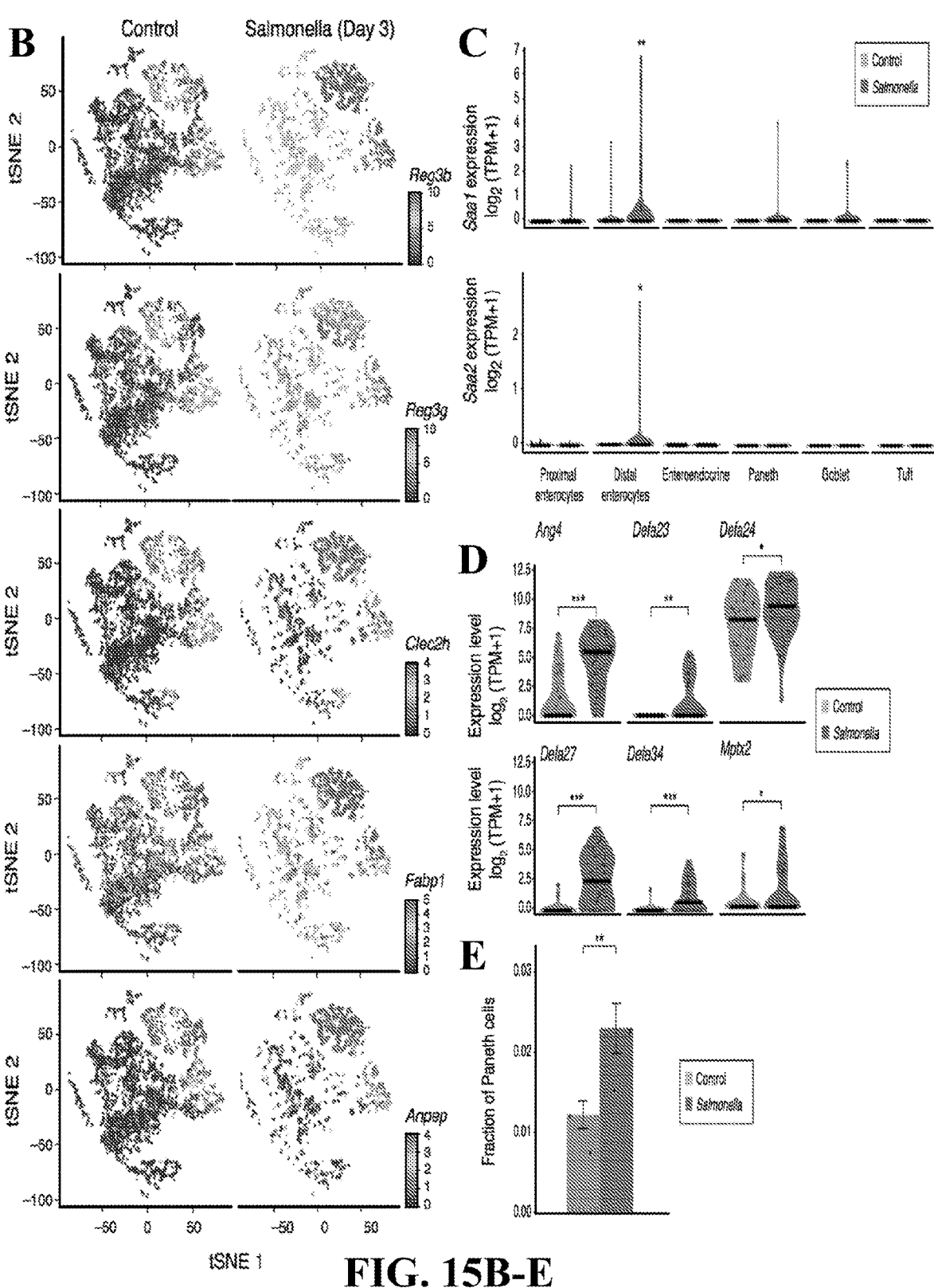
FIG. 15B-E

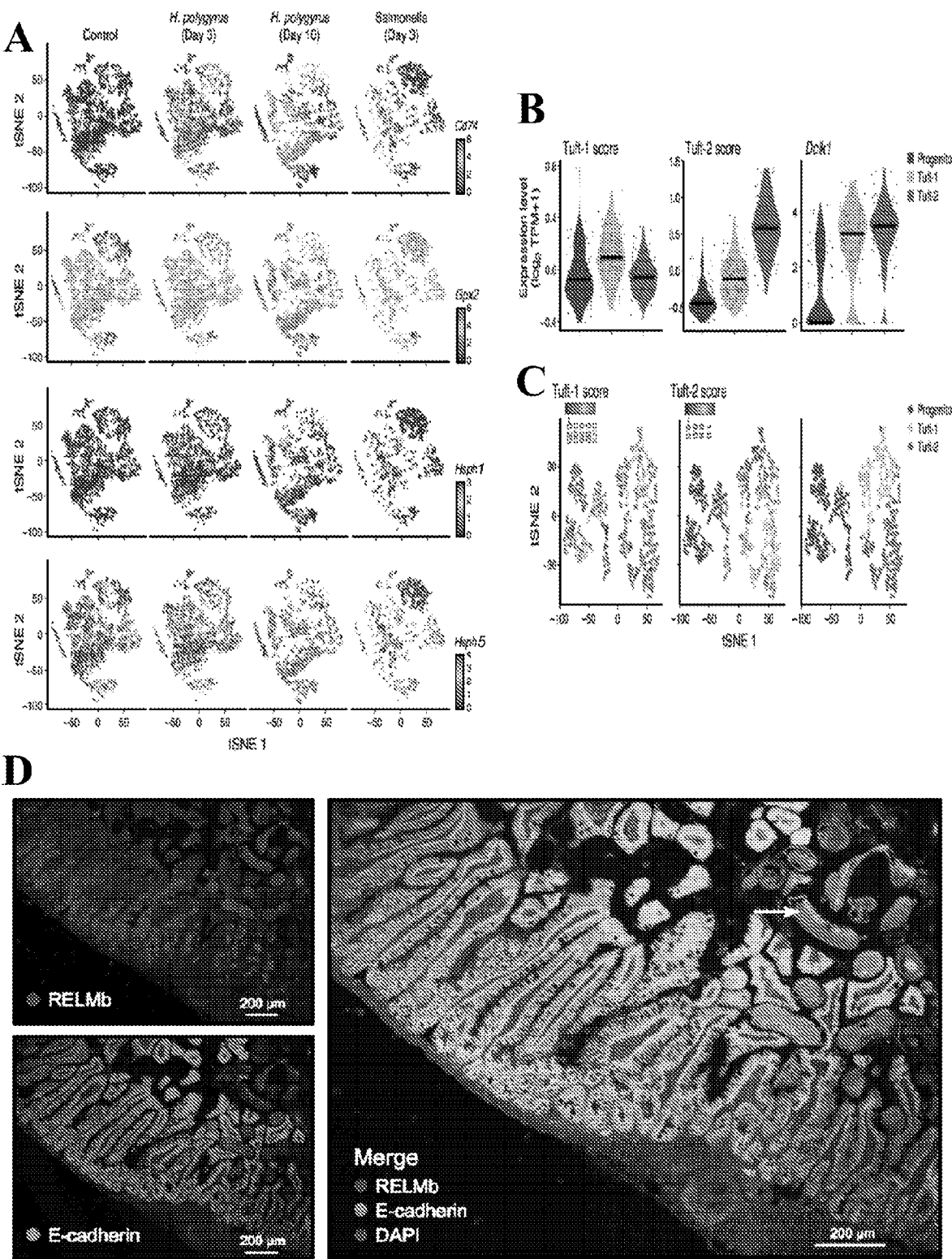
FIG. 16A-D

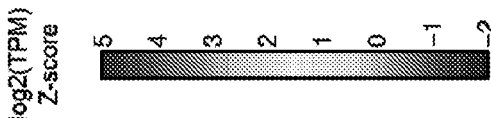
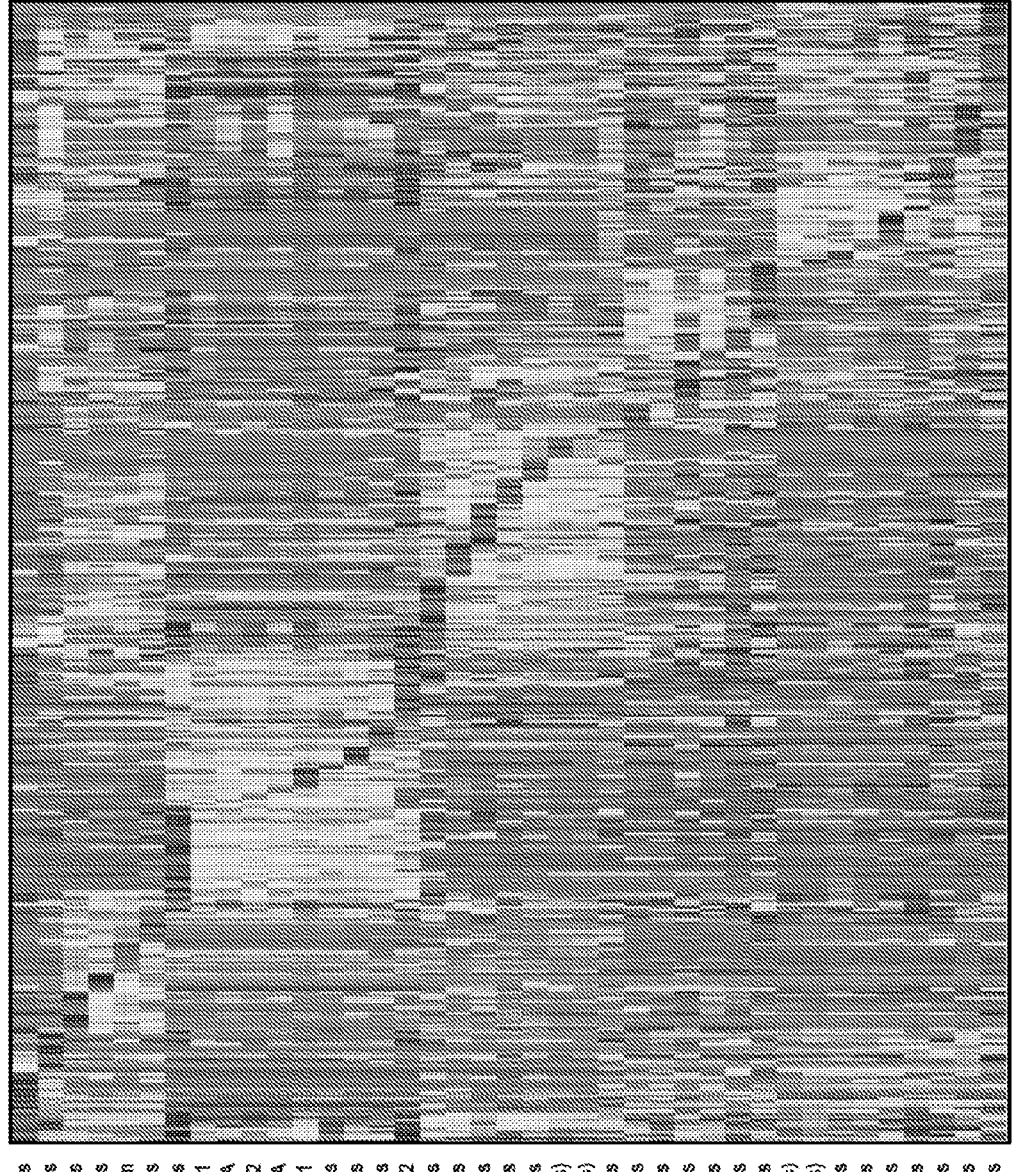
FIG. 20

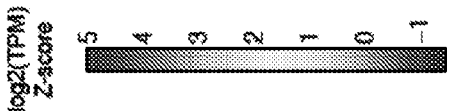
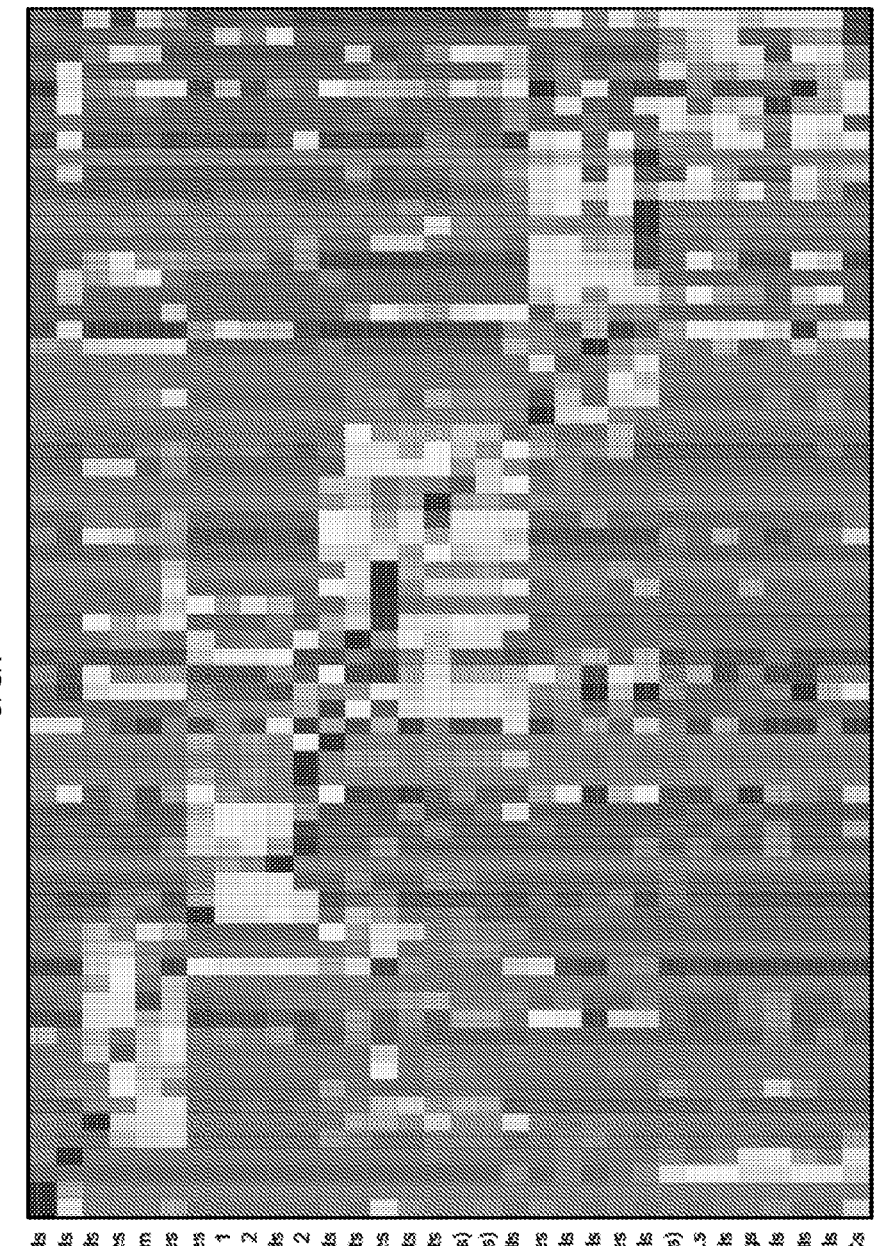
FIG. 21

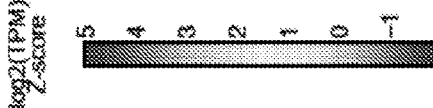
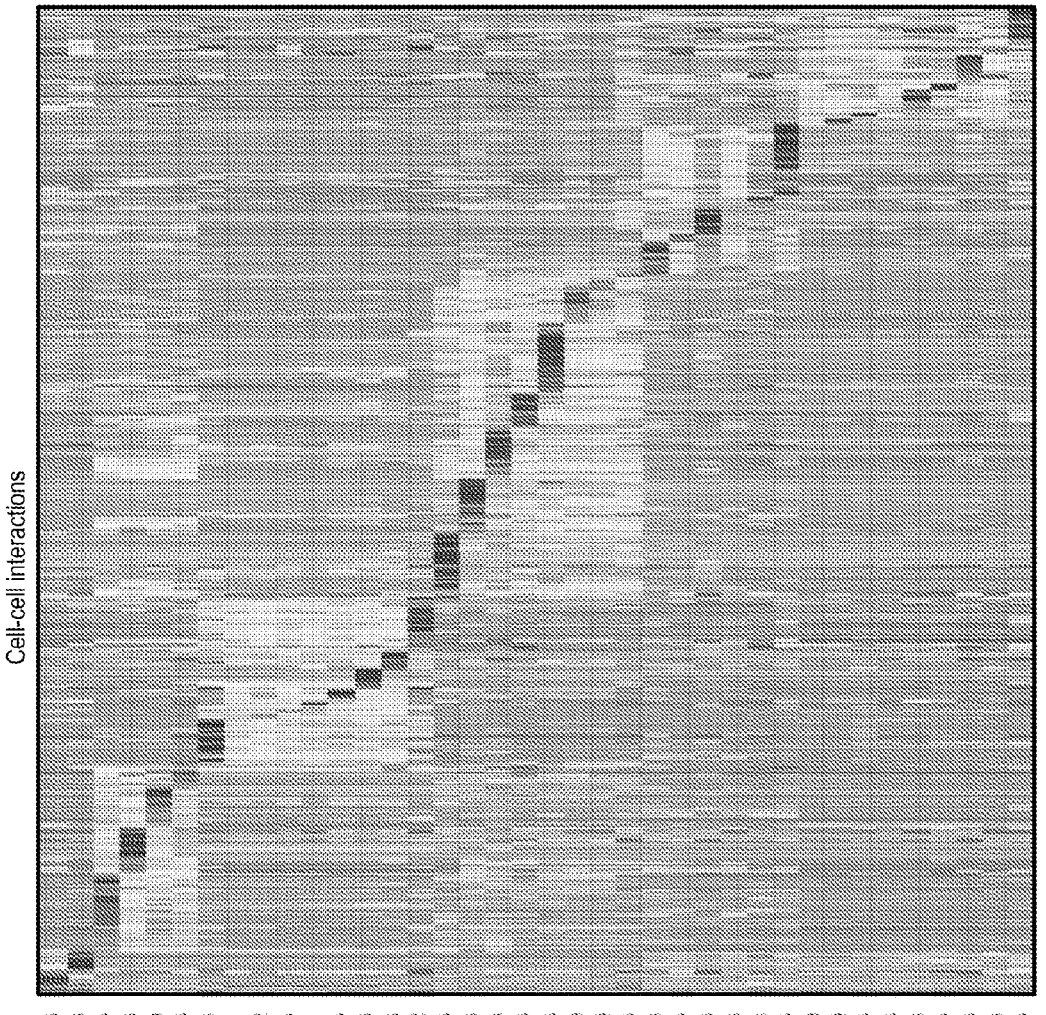
FIG. 22

D
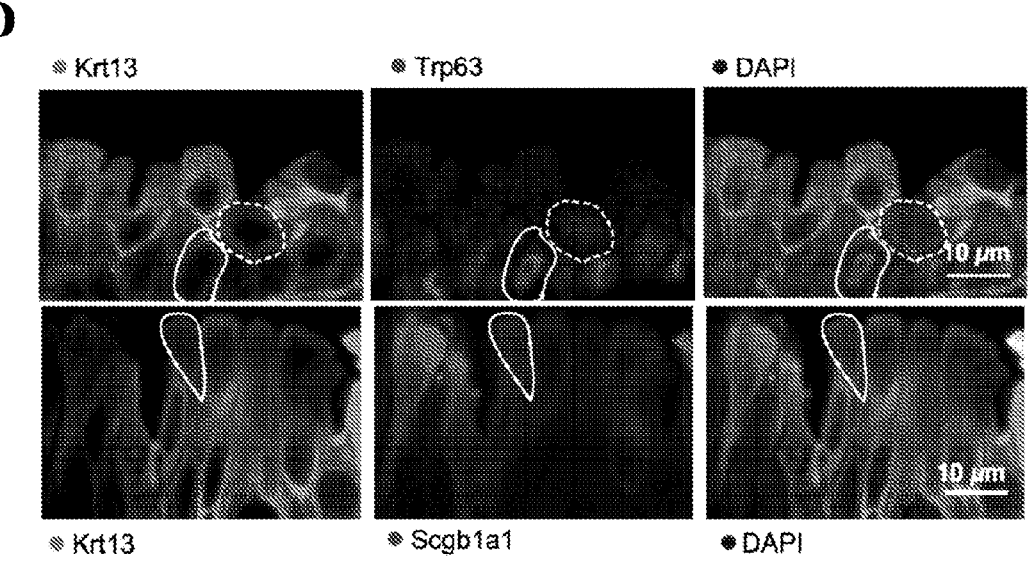
E
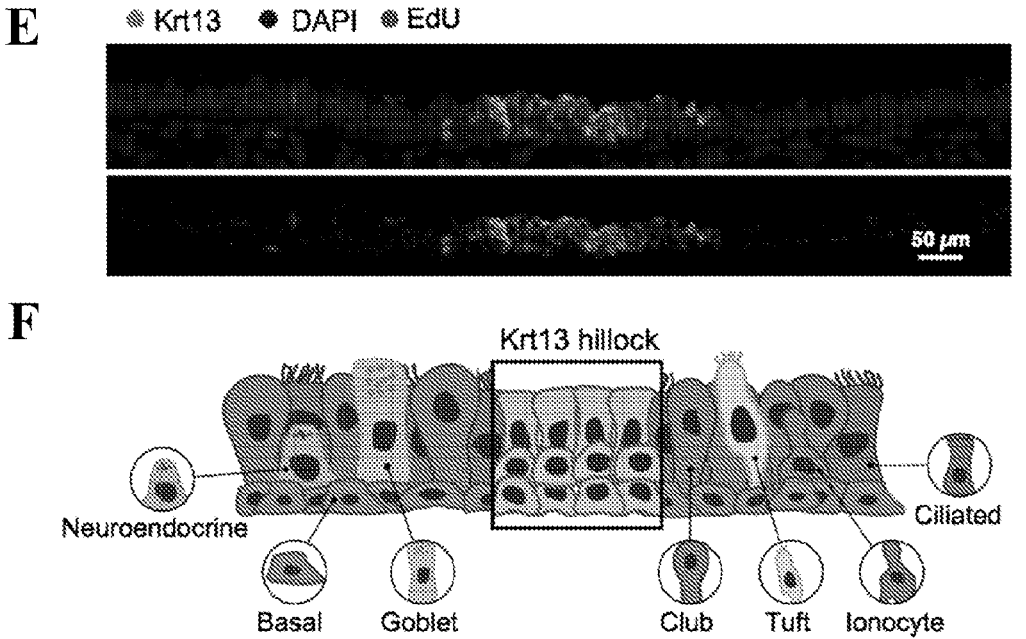
FIG. 38

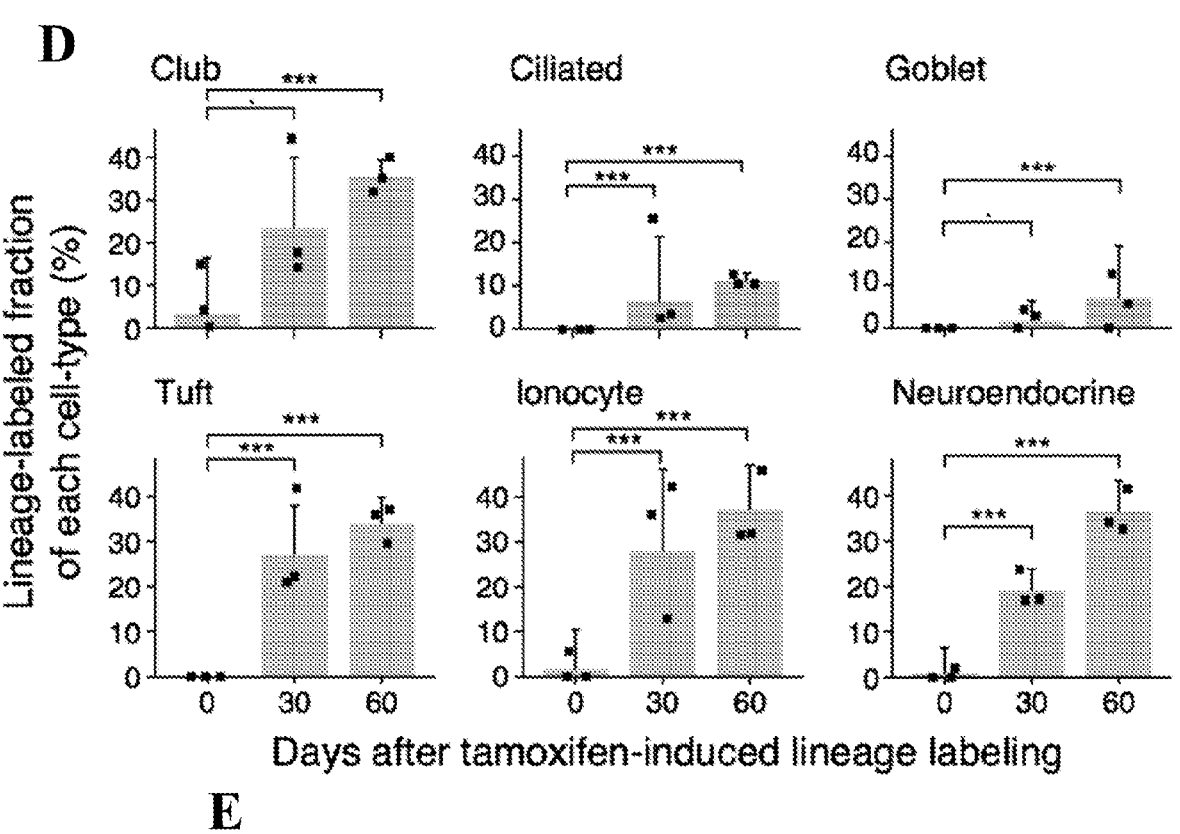
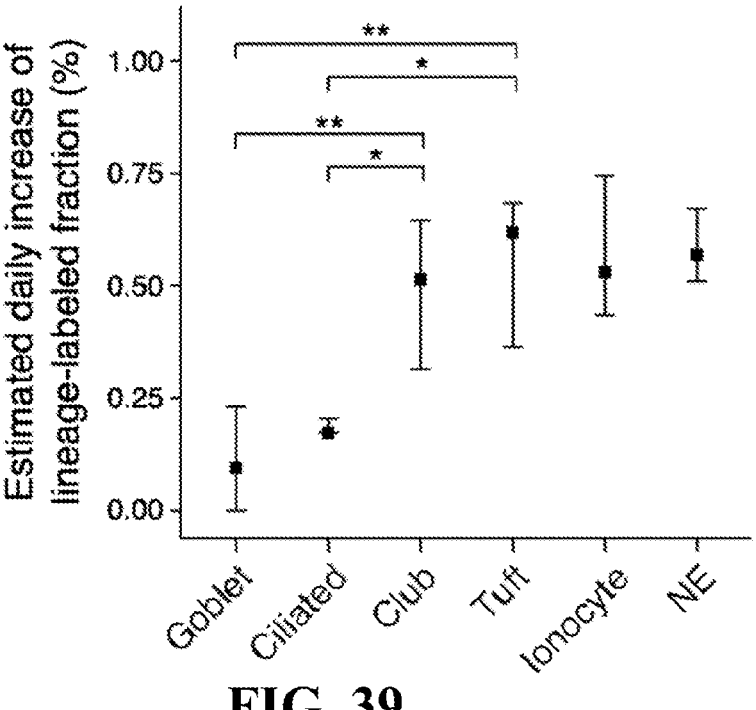
FIG. 39

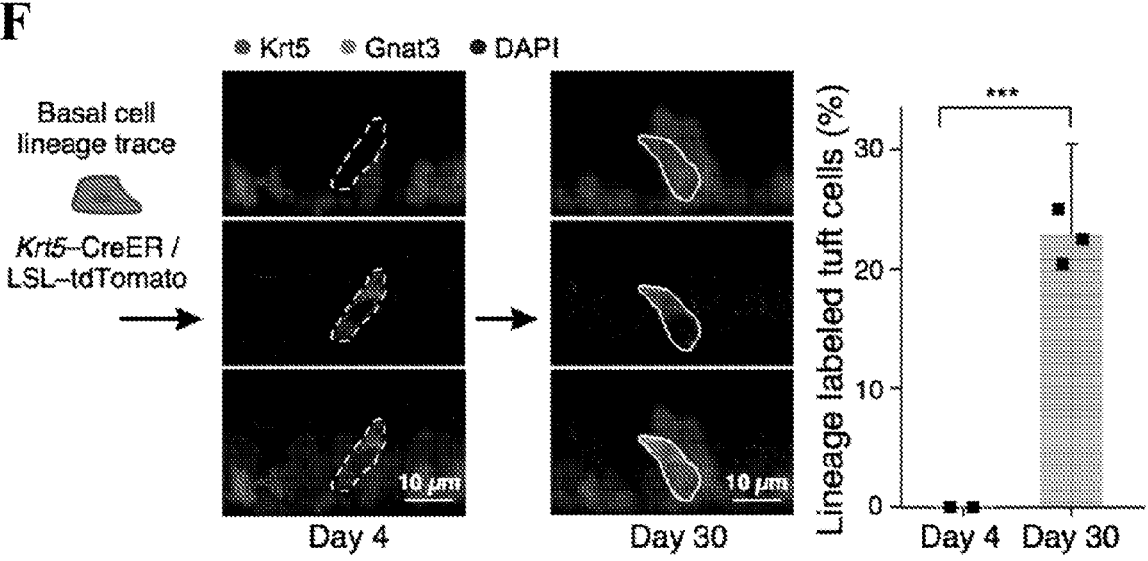
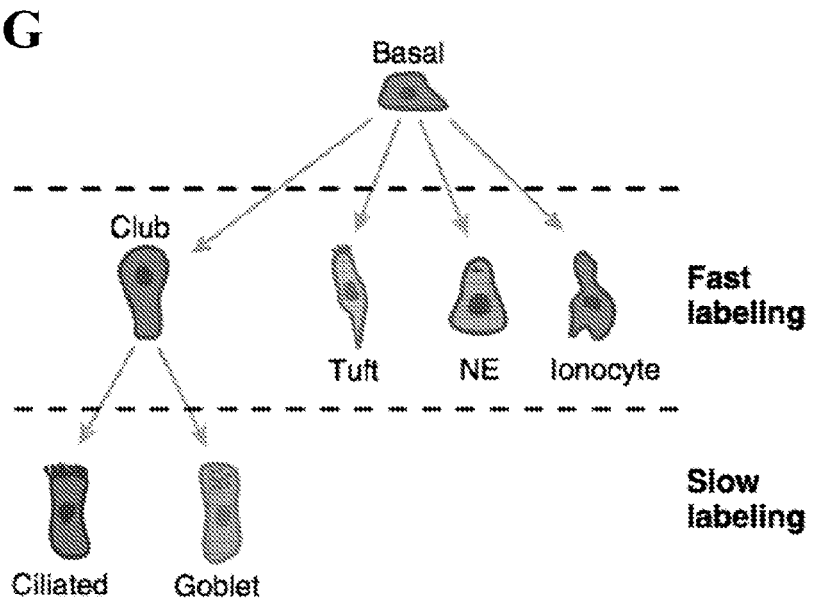
FIG. 39

D
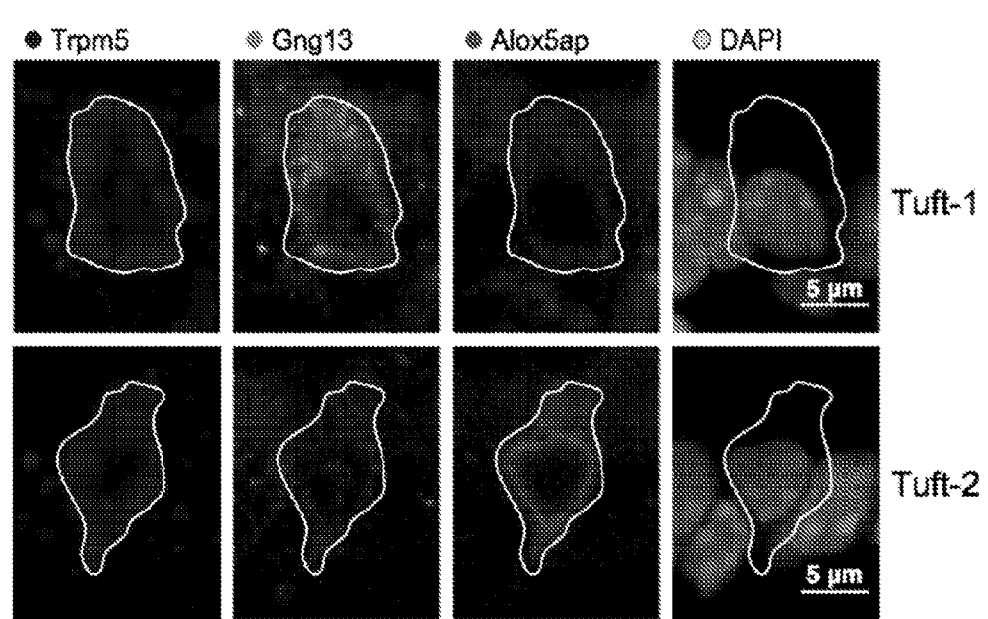
E
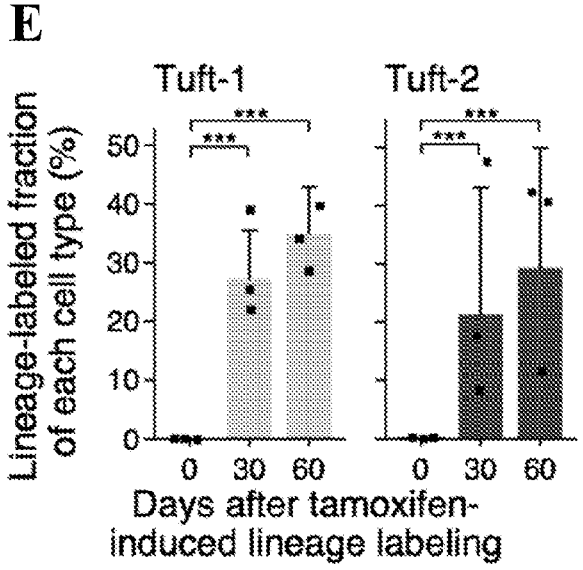
FIG. 40

A
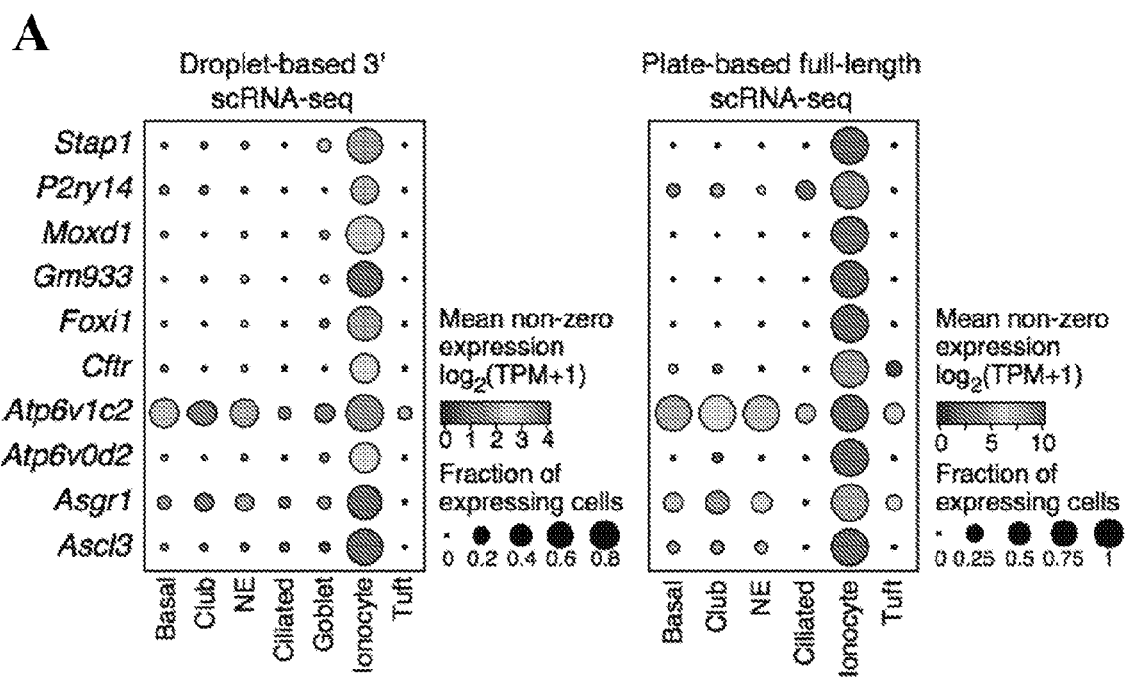
B
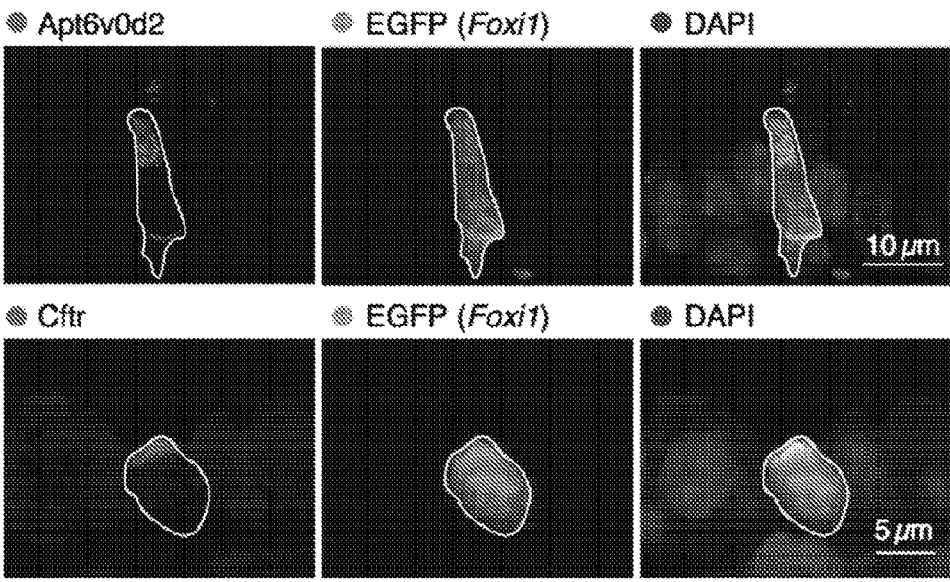
FIG. 41

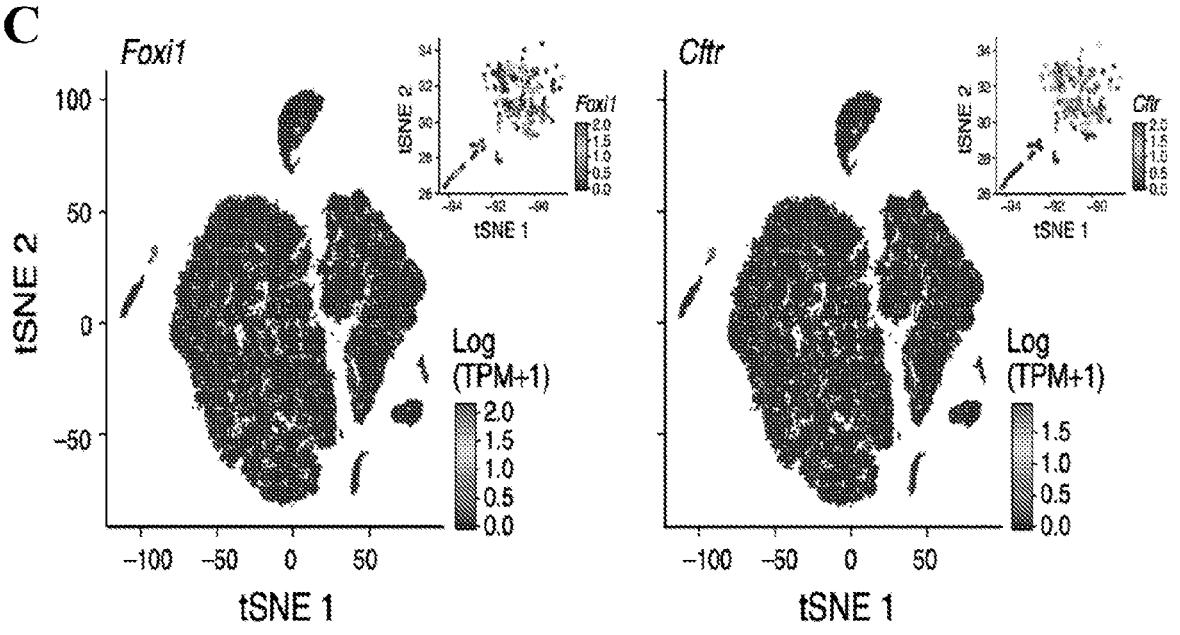
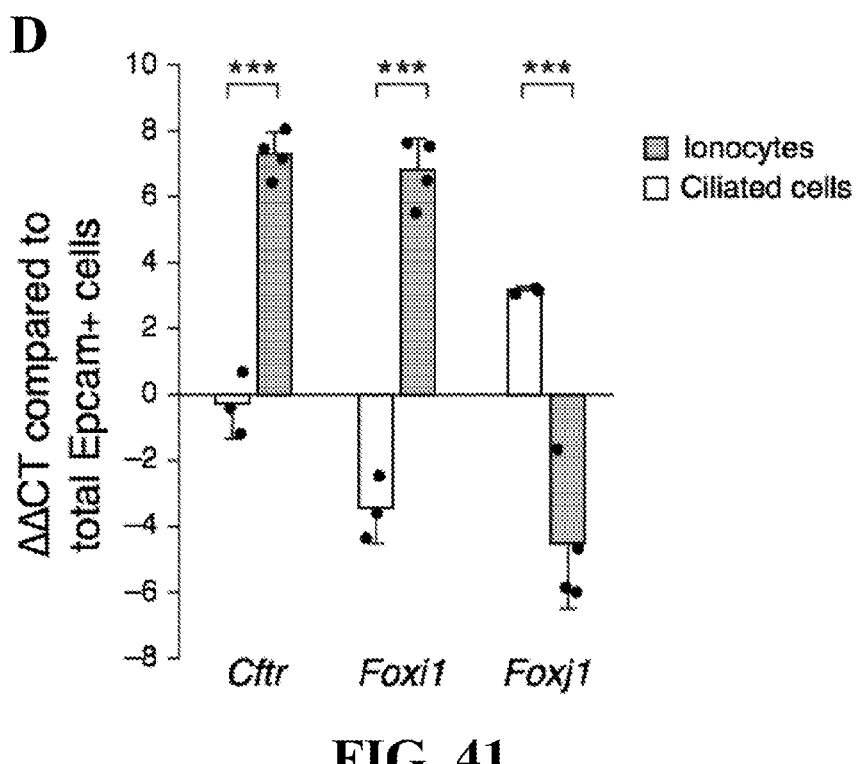
FIG. 41

H
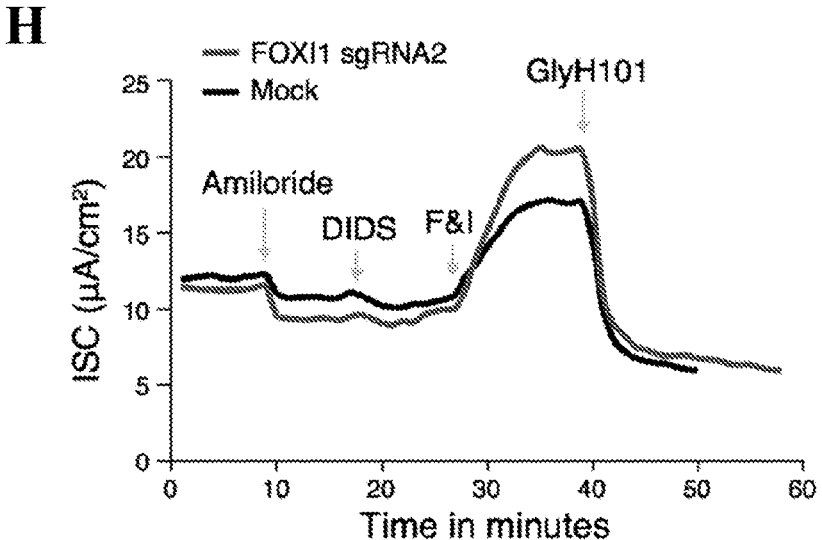
I
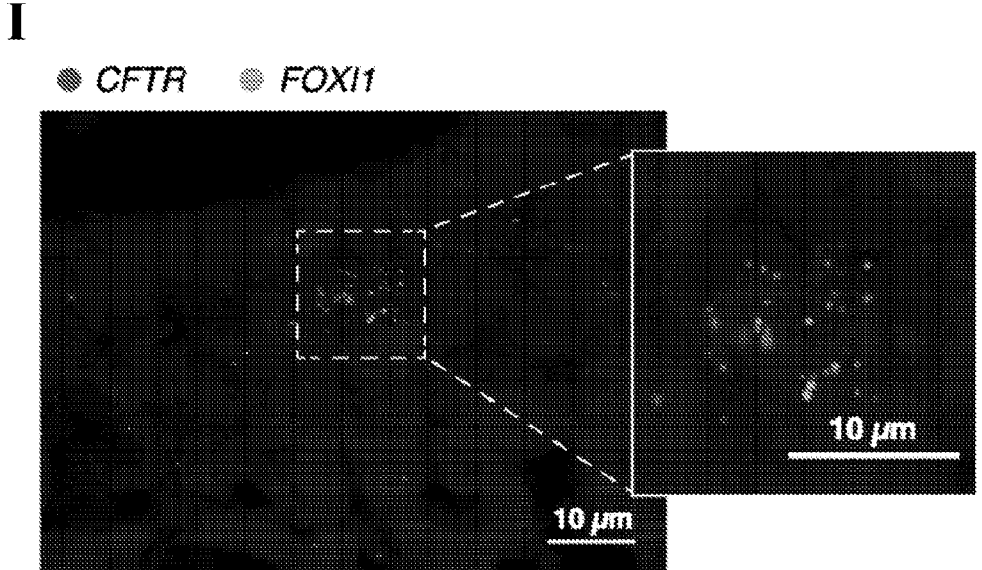
FIG. 41

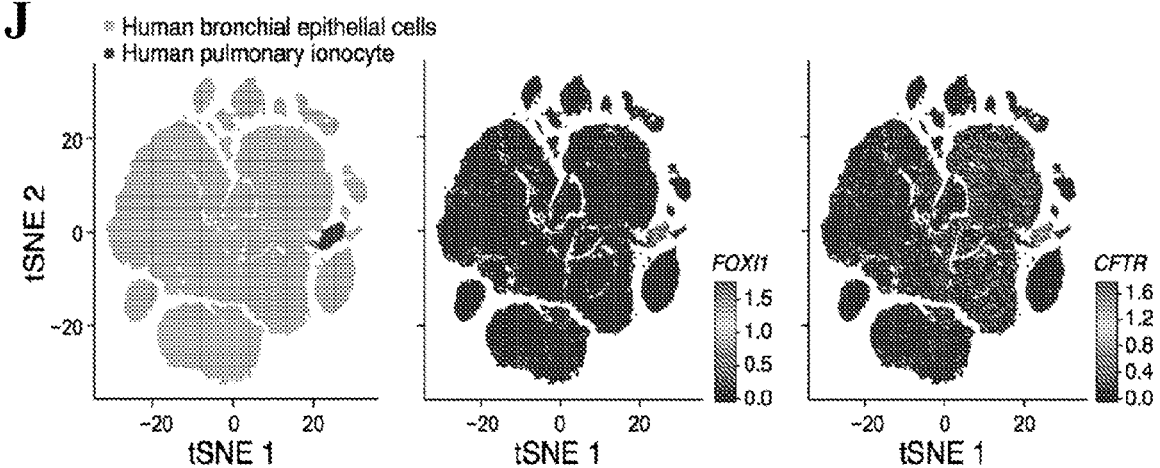
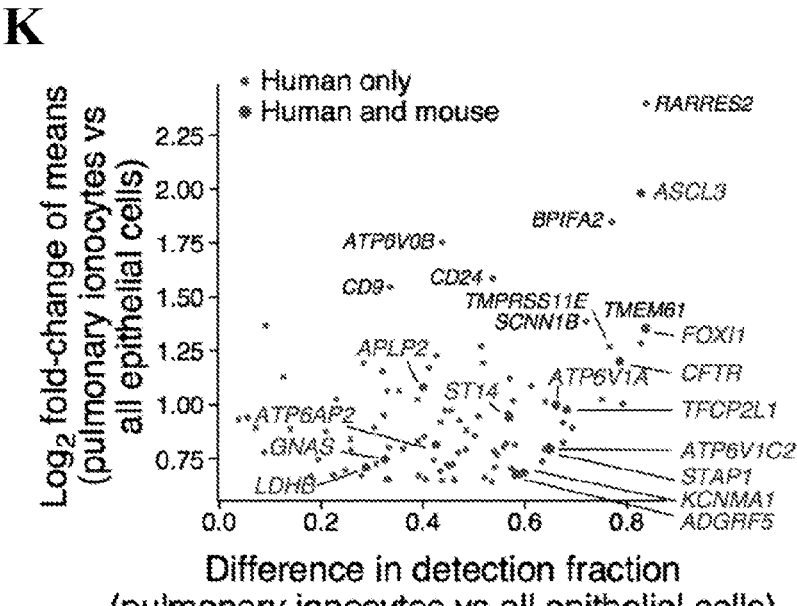
FIG. 41

D
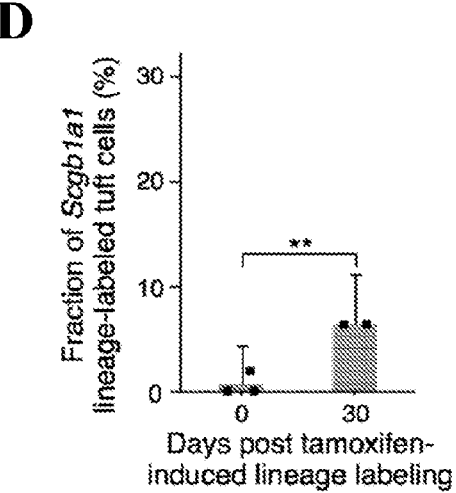
E
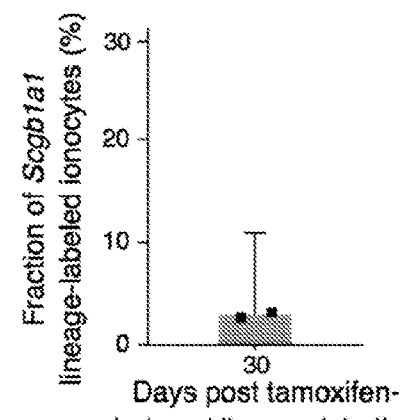
F
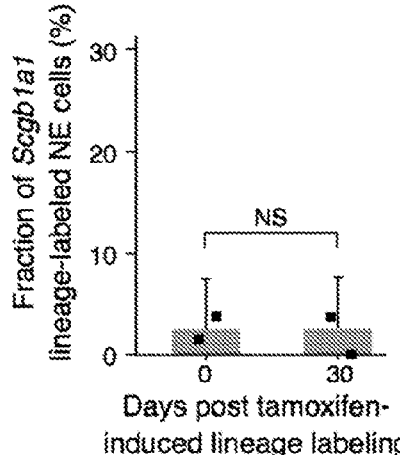
FIG. 48

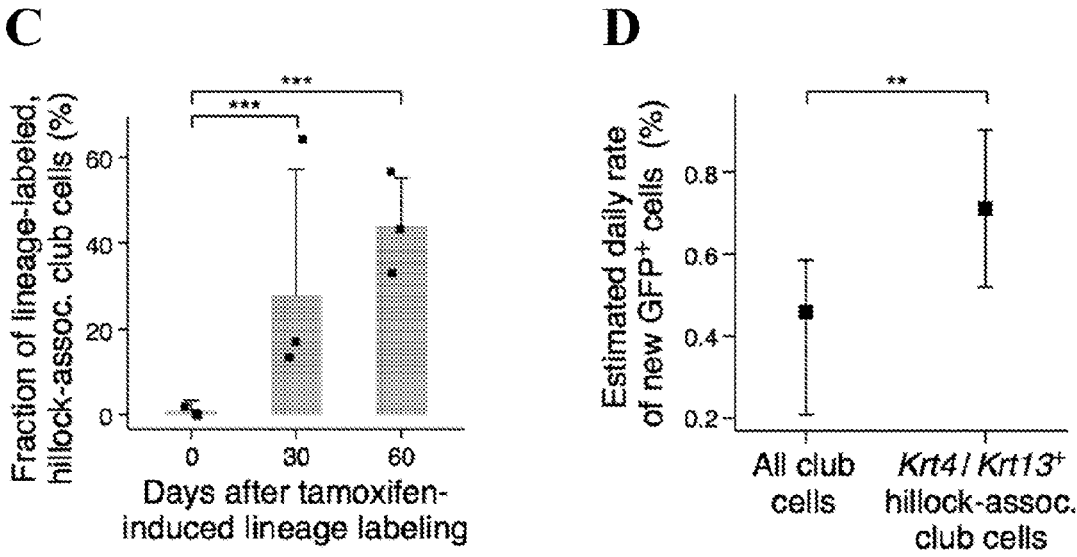
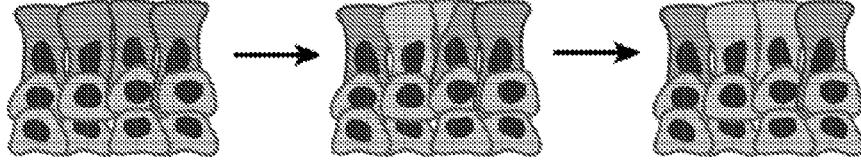
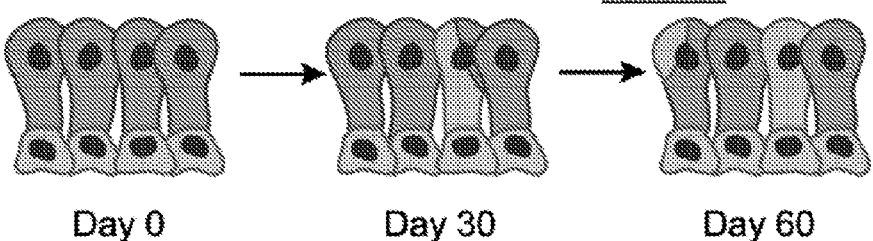
FIG. 49

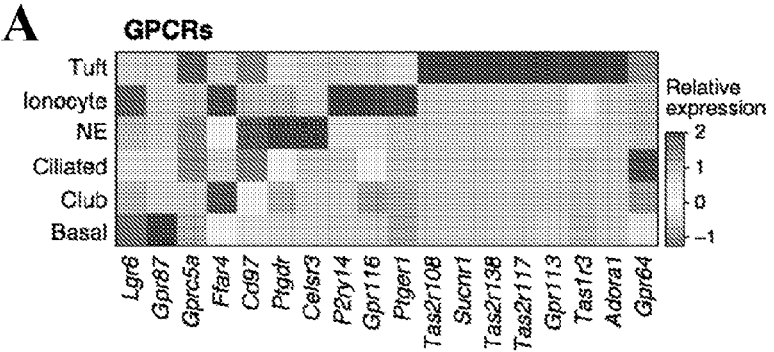
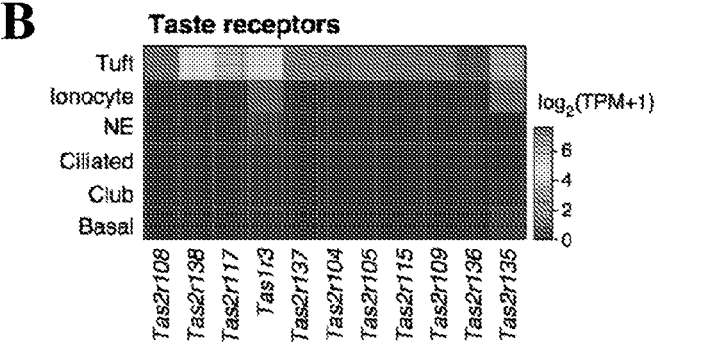
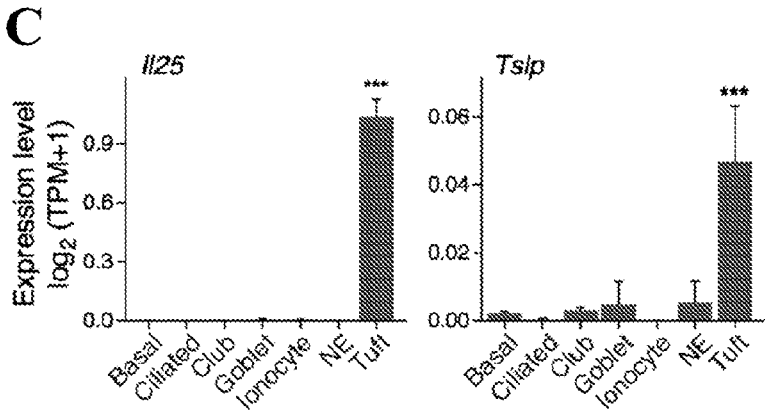
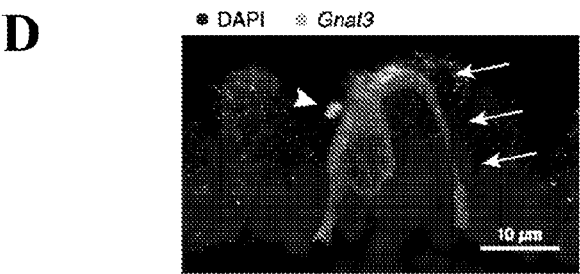
FIG. 50

G

A
B
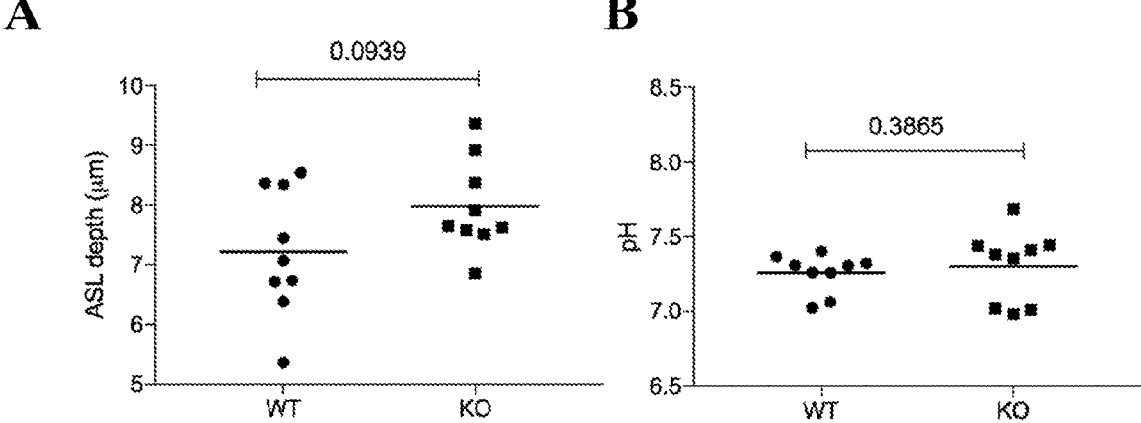
C
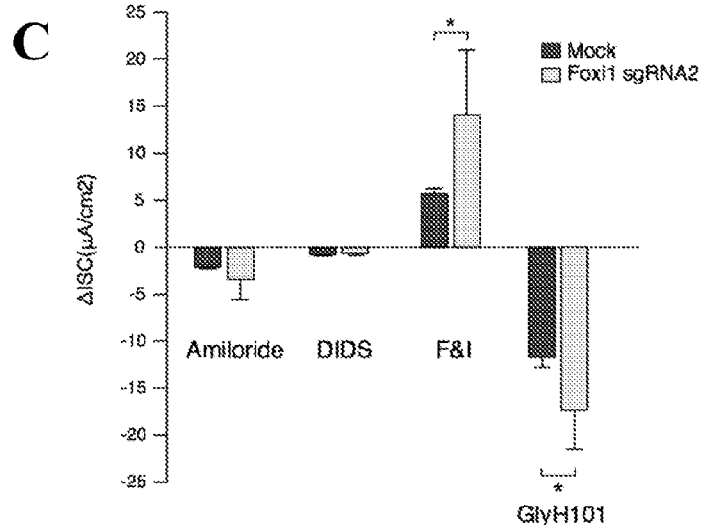
FIG. 52

METHOD OF TREATING AN INFLAMMATORY DISEASE BY ADMINISTERING AN AGENT WHICH BINDS A SURFACE RECEPTOR ON A TUFT CELL THAT INDUCES AN ILC CLASS 2 INFLAMMATORY RESPONSE

CROSS-REFERENCE TO RELATED APPLICATIONS

This application is a national phase of International Application No. PCT/US2018/027388, filed Apr. 12, 2018, which claims the benefit of U.S. Provisional Application No. 62/484,746, filed Apr. 12, 2017. The entire contents of the above-identified applications are hereby fully incorporated herein by reference.

STATEMENT REGARDING FEDERALLY SPONSORED RESEARCH

This invention was made with government support under Grant Nos. OD020839, DK114784, DK043351 and DK097485 awarded by the National Institutes of Health. The government has certain rights in the invention.

TECHNICAL FIELD

The subject matter disclosed herein is generally directed to compositions and methods for modulating, controlling or otherwise influencing epithelial cell differentiation, homeostasis and activation in the gut and respiratory system. This invention also relates generally to identifying and exploiting target genes and/or target gene products that modulate, control or otherwise influence epithelial cell differentiation, homeostasis and activation in a variety of therapeutic and/or diagnostic indications. This invention also relates generally to a gut and trachea atlas identifying novel cell types and markers for detecting, quantitating and isolating said cell types.

BACKGROUND

The functional balance between the epithelium and the constituents within the lumen plays a central role in both maintaining the normal mucosa and in disease. Intestinal epithelial cells (IECs) of the small intestinal epithelium comprise two major lineages—absorptive and secretory[1]—reflecting its dual roles to absorb nutrients and form a flexible barrier, monitoring and titrating responses to a variety of noxious substances or pathogens[2]. Enterocytes of the absorptive lineage comprise approximately 80% of the epithelium and are specialized for digestion and transport of nutrients[3]. The secretory lineage comprises five further terminally differentiated types of IECs: goblet, Paneth, enteroendocrine, tuft and microfold (M) cells[4-6]—each with distinct and specialized sensory and effector functions.

The epithelium is organized in a repeating structure of villi, which project toward the lumen, and nearby crypts (FIG. 1a). The crypts of the small intestine are the proliferative part of the epithelium, in which intestinal stem cells (ISCs) and progenitors, termed transit-amplifying cells (TAs), reside[6,7]. In contrast, only fully differentiated cells are found on the villi[2,7]. The crypt also contains Paneth cells, which secrete anti-microbial peptides (AMPs), such as defensins and lysozyme, into the lumen to keep the microbiota in check[8,9]. The highly proliferative TA cells migrate along the crypt-villus axis and differentiate into functionally distinct epithelial cell types that subsequently reach the tip of the villus, where mature cells undergo apoptosis and shed to the lumen[1].

Epithelial tissue turns over rapidly (~5 days)[8], allowing it to dynamically shift its composition in response to stress or pathogens. For example, parasitic infection typically induces hyperplasia of goblet cells, which produce and secrete mucins to prevent pathogen attachment, strengthening the epithelial barrier and facilitating parasite expulsion[10]. Rare (0.5-1%) enteroendocrine cells (EECs) secrete over 20 individual hormones and are key mediators of intestinal response to nutrients[11,12] by directly detecting fluctuations in luminal nutrient concentrations via G-protein-coupled receptors (GPCRs)[11]. Finally, IECs communicate with immune cells to initiate either inflammatory responses or tolerance in response to lumen signals[2,13]. Tuft cells[5], a rare IEC population, promote type-2 immunity in response to intestinal parasites by expressing interleukin-25 (Il25), which in turn mediates the recruitment of group 2 of innate lymphoid cells (ILC2s) that initiate the expansion of T-helper type 2 (Th2) cells upon parasite infection[14-16]. M cells, which reside exclusively in follicle-associated epithelia (FAE)[17], play an important role in immune sensing by transporting luminal content to immune cells found directly below them[18] in Peyer's patches, gut associated lymphoid follicles. Disruption in any of the major innate immune sensors and proximity effector functions of IECs may result in increased antigenic load through weakening of the epithelial barrier, and may lead to the onset of acute or chronic inflammation.

Despite this extensive knowledge, given the complexity of the epithelial cellular ecosystem, many questions remain open. First, do we know all the discrete epithelial cell types of the gut, or are there additional types, or new sub-types that have eluded previous studies. Second, what are the molecular characteristics of each type. For example, mapping the GPCRs and hormones expressed by EECs has important therapeutic applications; charting known and new specific cell surface markers would provide handles for specific cell isolation, and help assess the validity of legacy ones; and finding differentially expressed transcription factors (TFs) will open the way to study the molecular processes that accompany the differentiation of IECs, such as tuft or enteroendocrine cells. Third, we still know little about the response of individual cell populations to pathogenic insult, both in terms of changes in cellular proportions and cell-intrinsic responses.

A systematic atlas of single-cell RNA profiles can help address these questions, as the gene-expression program of a given cell closely reflects both its identity and function[19,20] Most previous studies have examined the gene-expression profiles of IECs, but relied on known markers to purify cell populations[6, 15, 21, 22], which may isolate either a mixed population if marker expression is more promiscuous than assumed, or a subset of a larger group if overly specific. They may further fail to detect rare cellular populations or intermediate, transient states on a continuum. A recent study[23] attempted to overcome these limitations using single-cell RNAseq (scRNA-seq), but analyzed only several hundred single cells, which may be insufficient to address the diversity of IECs, especially for subtypes that occur at a frequency of less than 0.1%[11,12] Additional, studies[53, 30, 145] also attempted to overcome these limitations using single-cell RNAseq (scRNA-seq). All of these studies have not yet extensively characterized intestinal epithelial cellular diversity.

The intestinal mucosa maintains a functional equilibrium with the complex luminal milieu, which is dominated by a spectrum of gut microbial species and their products. The functional balance between the epithelium and the lumen plays a central role in maintaining the normal mucosa and in the pathophysiology of many gastrointestinal disorders[2]. To maintain barrier integrity and tissue homeostasis in response to immune signals and luminal contents[2], the gut epithelium constantly regenerates by rapid proliferation and differentiation[149]. This process is initiated by intestinal stem cells (ISCs), which give rise to committed progenitors that in turn differentiate to specific IEC types[103,39].

ISC differentiation depends on external signals from an ecosystem of non-epithelial cells in the gut niche. In particular, canonical signal transduction pathways, such as Wnt and Notch[113,114], are essential to ISC maintenance and differentiation, and rely on signals from stromal cells[115,150]. The intestinal tract is also densely populated by innate and adaptive immune cells, which maintain the balance between immune activation and tolerance[2,151]. However, it is unknown if and how immune cells and the adjacent ISCs interact.

Several studies suggest an important role for immune cells in tissue homeostasis. Tissue-resident innate immune cells, such as macrophages and type 3 innate lymphoid cells (ITLC3s), can play a role in regeneration of the gut[115,116] and other tissues[117,119]. Among adaptive immune cells, recent studies have implicated T regulatory cells ($T_{regs}$) in regeneration within muscles, lungs, and the central nervous system[118, 152, 153] Skin-resident $T_{regs}$ were very recently shown to be involved in maintaining hair follicle stem cell (HFSC) renewal through Jagged1-mediated Notch signaling[154]. In the gut, mouse models of intestinal infection, T cell depletion, and inflammatory bowel disease (IBD) all display aberrant epithelial cell composition, such as goblet cell hypoplasia or tuft cell expansion[13, 14, 155]. These phenotypes have been primarily interpreted as reflecting intestinal epithelial cell dysfunction and changes in gut microbial populations[13, 151, 156, 157].

The small intestinal mucosa is a complex system. The mucosa comprises multiple cell types involved in absorption, defense, secretion and more. These cell types are rapidly renewed from intestinal stem cells. The types of cells, their differentiation, and signals controlling differentiation and activation are poorly understood. The small intestinal mucosa also possesses a large and active immune system, poised to detect antigens and bacteria at the mucosal surface and to drive appropriate responses of tolerance or an active immune response. Finally, there is complex luminal milieu which comprises a combination of diverse microbial species and their products as well as derivative products of the diet. It is increasingly clear that a functional balance between the epithelium and the constituents within the lumen plays a central role in both maintaining the normal mucosa and the pathophysiology of many gastrointestinal disorders. Many disorders, such as irritable bowel disease, Crohn's disease, and food allergies, have proven difficult to treat. The manner in which these multiple factors interact remains unclear. Furthermore, studying the small intestinal mucosa can provide insight into the mucosa of the respiratory system. Airways conduct gases to the distal lung and are the sites of disease in asthma and cystic fibrosis.

SUMMARY

In one aspect, the present invention provides for an isolated tuft cell characterized in that the tuft cell comprises expression of any one or more genes or polypeptides selected from the group consisting of: a) Lrmp, Dclk1, Cd24a, Tas1r3, Ffar3, Sucnr1, Gabbr1, Drd3, Etv1, Gfi1b, Hmx2, Hmx3, Runx1, Jarid2, Nfatc1, Zfp710, Zbtb41, Spib, Foxe1, Sox9, Pou2f3, Ascl2, Ehf Tcf4, Gprc5c, Sucnr1, Ccrl1, Gprc5a, Opn3, Vmn2r26 and Tas1r3; or b) Cd24a, Tas1r3, Ffar3, Sucnr1, Gabbr1 and Drd3; or c) Etv1, Gfi1b, Hmx2, Hmx3, Runx1, Jarid2, Nfatc1, Zfp710, Zbtb41, Spib, Foxe1, Sox9, Pou2f3, Ascl2, Ehf and Tcf4; or d) Etv1, Hmx2, Spib, Foxe1, Sox9, Pou2f3, Ascl2, Ehf and Tcf4; or e) Ffar3, Gprc5c, Sucnr1, Ccrl1, Gprc5a, Opn3, Vmn2r26 and Tas1r3; or f) Etv1, Hmx2, Spib, Foxe1, Pou2f3, Sox9, Ascl2, Hoxa5, Hivep3, Ehf Tcf4, Mxd4, Hmx3, Hoxa3 and Nfatc1; g) or Lrmp, Gnat3, Gnb3, Plac8, Trpm5, Gng13, Ltc4s, Rgs13, Hck, Alox5ap, Avil, Alox5, Ptpn6, Atp2a3 and Plk2; or h) Rgs13, Rpl41, Rps26, Zmiz1, Gpx3, Suox, Tslp and Socs1; or i) tuft cell marker genes in any of Tables 3-6 or 15A.

In one embodiment, the tuft cell may be an immune-like tuft cell and the cell may further comprise expression of any one or more genes or polypeptides selected from the group consisting of: a) Ptprc (CD45) and Tslp; or b) Siglec5, Rac2, Ptprc, Sf6galnac6, Tm4sf4, Smpx, Ptgs1, C2, Gde1, Cpv1, S100a1, Fcna, Fbxl21, Ceacam2, Sucnr1, Spa17, Kcnj16, AA467197, Cd300lf Trim38, Vmn2r26, Gcnt1, Irf7, Plk2, Glyctk and Tslp; or c) Lyn, Rhog, Il17rb, Irf7 and Rac2; or d) tuft-2 cell marker genes in Table 8.

In one embodiment, the tuft cell may be a neuronal-like tuft cell and the cell may further comprise expression of any one or more genes or polypeptides selected from the group consisting of: a) Nrep, Nradd, Ninj1, and Plekhg5; or b) Nradd, Endod1, Gga2, Rbm38, Sic44a2, Cbr3, Ninj1, Mblac2, Usp11, Sphk2, Atp4a, Uspl1, Mical1, Mta2, Inpp5j, Svil, Kcnn4, Dnahc8, Anxa11, Zjhx3, Lnpp5b, Tip3, Jup, and St5; or c) tuft-1 cell marker genes in Table 8.

The tuft cell may be a gastrointestinal tuft cell or subset of a gastrointestinal tuft cell, or a respiratory tuft cell or a subset of respiratory tuft cells. The tuft cell may be a respiratory or digestive system tuft cell. The digestive system tuft cell may comprise an esophageal epithelial cell, a stomach epithelial cell, or an intestinal epithelial cell. The respiratory tuft cell may comprise a laryngeal epithelial cell, a tracheal epithelial cell, a bronchial epithelial cell, or a submucosal gland cell.

In another aspect, the present invention provides for a method of detecting tuft cells in a biological sample, comprising determining the expression or activity of any one or more genes or polypeptides selected from the group consisting of: a) Lrmp, Dclk1, Cd24a, Tas1r3, Ffar3, Sucnr1, Gabbr1, Drd3, Etv1, Gfi1b, Hmx2, Hmx3, Runx1, Jarid2, Nfatc1, Zfp710, Zbtb41, Spib, Foxe1, Sox9, Pou2f3, Ascl2, Ehf Tcf4, Gprc5c, Sucnr1, Ccrl1, Gprc5a, Opn3, Vmn2r26 and Tas1r3; or b) Cd24a, Tas1r3, Ffar3, Sucnr1, Gabbr1 and Drd3; or c) Etv1, Gfi1b, Hmx2, Hmx3, Runx1, Jarid2, Nfatc1, Zfp710, Zbtb41, Spib, Foxe1, Sox9, Pou2f3, Ascl2, Ehf and Tcf4; or d) Etv1, Hmx2, Spib, Foxe1, Sox9, Pou2f3, Ascl2, Ehf and Tcf4; or e) Ffar3, Gprc5c, Sucnr1, Ccrl1, Gprc5a, Opn3, Vmn2r26 and Tas1r3; or f) Etv1, Hmx2, Spib, Foxe1, Pou2f3, Sox9, Ascl2, Hoxa5, Hivep3, Ehf Tcf4, Mxd4, Hmx3, Hoxa3 and Nfatc1; or g) Lrmp, Gnat3, Gnb3, Plac8, Trpm5, Gng13, Ltc4s, Rgs13, Hck, Alox5ap, Avil, Alox5, Ptpn6, Atp2a3 and Plk2; or h) Rgs13, Rpl41, Rps26, Zmiz1, Gpx3, Suox, Tslp and Socs1; or i) tuft cell marker genes in any of Tables 3-6 or 15A, whereby said expression indicates tuft cells. The tuft cells may be immune-like tuft cells and the method may further comprise detecting the expression of any one or more genes or polypeptides selected from the group consisting of: a) Ptprc (CD45) and Tslp; or b) Siglec5, Rac2, Ptprc, Sf6galnac6, Tm4sf4, Smpx, Ptgs1, C2, Gde1, Cpv1, S100a1, Fcna, Fbxl21, Ceacam2, Sucnr1, Spa17, Kcnj16, AA467197, Cd300lf Trim38, Vmn2r26, Gcnt1, Irf7, Plk2, Glyctk and Tslp; or c) Lyn, Rhog, Il17rb, Irf7 and Rac2; or d) tuft-2 cell marker genes in Table 8. The tuft cells may be neuronal-like tuft cells and the method may further comprise detecting the expression of any one or more genes or polypeptides selected from the group consisting of: a) Nrep, Nradd, Ninj1, and Plekhg5; or b) Nradd, Endod1, Gga2, Rbm38, Sic44a2, Cbr3, Nmj1, Mblac2, Usp11, Sphk2, Atp4a, Uspl1, Mical1, Mta2, Inpp5j, Svil, Kcnn4, Dnahc8, Anxa11, Zjhx3, Lnpp5b, Tip3, Jup, and St5; or c) tuft-1 cell marker genes in Table 8. The tuft cell may be a gastrointestinal tuft cell or a subset of a gastrointestinal tuft cell, or a respiratory tuft cell or subset of respiratory tuft cells. The tuft cell may be a respiratory or digestive system tuft cell. The digestive system tuft cell may comprise an esophageal epithelial cell, a stomach epithelial cell, or an intestinal epithelial cell. The respiratory tuft cell may comprise a laryngeal epithelial cell, a tracheal epithelial cell, or a bronchial epithelial cell. The expression or activity of one or more genes or polypeptides may be detected in a bulk sample, whereby a gene signature is detected by deconvolution of the bulk data.

In another aspect, the present invention provides for a method for detecting or quantifying tuft cells in a biological sample of a subject, the method comprising: a) providing a biological sample of a subject; and b) detecting or quantifying in the biological sample tuft cells as defined herein. The biological sample may be a biopsy sample and wherein quantifying may comprise staining for one or more tuft cell genes or polypeptides.

In another aspect, the present invention provides for a method for isolating tuft cells from a biological sample of a subject, the method comprising: a) providing a biological sample of a subject; and b) isolating from the biological sample tuft cells as defined herein. The isolating may comprise labeling one or more surface markers and sorting cells in the biological sample. The sorting may be by FACS. The isolating may comprise binding an affinity reagent to one or more surface markers expressed on cells in the biological sample. The affinity reagent may be an antibody coated magnetic bead.

In another aspect, the present invention provides for a method for modulating epithelial cell proliferation, differentiation, maintenance, and/or function, the method comprising contacting an epithelial tuft cell or a population of epithelial tuft cells as defined herein with a tuft cell modulating agent in an amount sufficient to modify proliferation, differentiation, maintenance, and/or function of the epithelial tuft cell or population of epithelial tuft cells. The tuft cell may be an immune-like tuft cell. The tuft cell may be a neuronal-like tuft cell. Not being bound by a theory, the present invention allows for these previously unknown tuft cells to be targeted specifically. The epithelial tuft cell may be a laryngeal epithelial cell, a tracheal epithelial cell, a bronchial epithelial cell, a submucosal gland cell, a gut epithelial cell, an intestinal epithelial cell, or an esophageal epithelial cell. The modulating of the epithelial cell proliferation, differentiation, maintenance, and/or function may comprise modulating inflammation. The inflammation may comprise an ILC2 inflammatory response. The modulating may be for the treatment of asthma (e.g., allergic asthma, therapy resistant-asthma, steroid-resistant severe allergic airway inflammation, systemic steroid-dependent severe eosinophilic asthma, chronic rhino-sinusitis (CRS)), bronchitis, cystic fibrosis, infection (e.g., pneumonia or tuberculosis), emphysema, lung cancer, pulmonary hypertension, chronic obstructive pulmonary disease, idiopathic pulmonary fibrosis, α-1-anti-trypsin deficiency, congestive heart failure, atopic dermatitis, food allergy, chronic airway inflammation, or primary eosinophilic gastrointestinal disorder (EGID) (e.g., eosinophilic esophagitis (EoE), eosinophilic gastritis, eosinophilic gastroenteritis, and eosinophilic colitis) in a subject in need thereof. The modulating may comprise inhibiting the activity of a tuft cell.

The tuft cell modulating agent may comprise a therapeutic antibody, antibody fragment, antibody-like protein scaffold, aptamer, protein, genetic modifying agent or small molecule. The tuft cell modulating agent may comprise an agent capable of binding to a surface receptor on the tuft cell. The agent may block activation of the surface receptor. The agent may block binding of a ligand to the surface receptor. The agent may be a blocking antibody. The tuft cell modulating agent may comprise an agent capable of modulating the expression or activity of a transcription factor selected from the group consisting of Etv1, Hmx2, Spib, Foxe1, Pou2f3, Sox9, Ascl2, Hoxa5, Hivep3, Ehf, Tcf4, Mxd4, Hmx3, Hoxa3 and Nfatc1. The agent may be administered to a mucosal surface. The agent may be administered to the lung, nasal passage, trachea, gut, intestine, or esophagus. The agent may be administered by aerosol inhalation. The agent may be administered by swallowing.

In another aspect, the present invention provides for a kit comprising reagents to detect at least one tuft cell gene or polypeptide as described herein. The kit may comprise at least one antibody, antibody fragment, or aptamer. The kit may comprise primers and/or probes for quantitative RT-PCR or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25).

The ability to identify cell types, metabolic state, cycling state and the like has many utilities—for example, identifying the source of a cancer cell type; identifying disease states; screening for drug effects; and applied and basic research.

In another embodiment provided is a method for identifying tuft cells in a sample, comprising detecting expression of any one or more of Cd24a, Tas1r3, Ffar3, Sucnr1, Gabbr1 or Drd3 protein or mRNA, wherein the expression indicates tuft cells. Such a method may further comprise detecting expression of any one or more of Ptprc or Tslp protein or mRNA, wherein the expression indicates a subset of tuft cells, and may further comprise detecting expression of any one or more of Nrep, Nradd, Ninj1, and Plekhg5 protein or mRNA, wherein the expression indicates a subset of tuft cells.

In another embodiment provided is an isolated gastrointestinal tract cell characterized by expression of one or markers for a cell type selected from any of Tables 3 to 10 or 15 A to D.

In another embodiment provided is a method for detecting or quantifying gastrointestinal tract cells in a biological sample of a subject, the method comprising detecting or quantifying in the biological sample gastrointestinal tract cells as defined in herein. The gastrointestinal tract cell may be detected or quantified using one or more markers for a cell type selected from any of Tables 3 to 10 or 15 A to D.

In another embodiment provided is a method of isolating a gastrointestinal tract cell from a biological sample of a subject, the method comprising isolating from the biological sample gastrointestinal tract cells as defined herein. The gastrointestinal tract cell may be isolated using one or more surface markers for a cell type selected from any of Tables 3 to 10 or 15 A to D.

The gastrointestinal tract cells may be isolated, detected or quantified using a technique selected from the group consisting of RT-PCR, RNA-seq, single cell RNA-seq, western blot, ELISA, flow cytometry, mass cytometry, fluorescence activated cell sorting, fluorescence microscopy, affinity separation, magnetic cell separation, microfluidic separation, and combinations thereof.

The ability to identify cell types, metabolic state, cycling state and the like has many utilities—for example, identifying the source of a cancer cell type; identifying disease states; screening for drug effects; and applied and basic research.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIGS. 1A-G—A single-cell expression atlas of intestinal epithelial cells. FIG. 1A shows a schematic overview. Two complementary scRNA-seq methods used to create a high-resolution atlas of the mouse small intestinal epithelium. FIG. 1B shows cell type clusters. t-distributed stochastic nearest-neighbor embedding (tSNE) visualization of 7,216 single cells. Individual points correspond to single cells shaded by their assignment to clusters using a k-nearest neighbor (kNN) graph-based algorithm (see Methods). Although EECs are classified as a single group by clustering, the tSNE embedding separates out the enterochromaffin subset (small left-hand cluster, top of figure). This heterogeneity is fully characterized in (FIG. 3). Legend shows the cluster post-hoc annotation to cell types. FIG. 1C shows cell type-specific signatures. Heatmap shows the relative expression level (row-wise Z-score of $log_2(TPM+1)$ expression values, (bar) of genes (rows) in high confidence cell-type-specific signatures based on both full-length and 3' scRNA-seq data, across the individual post-mitotic IECs (columns). Shading code marks the cell types and their associated signatures. FIGS. 1D-E show Mptx2 is a novel Paneth cell marker. (D) Shown is combined single-molecule fluorescence in situ hybridization (smFISH) with immunofluorescence assay (IFA) of FFPE sections of Mptx2 co-stained with the canonical Paneth cell Lyz1 protein marker. Scale bar, 20 μm. (E) In situ hybridization (ISH) of Mptx2 at lower magnification. Scale bar, 50 μm. FIGS. 1F-G show cell type-specific transcription factors (TFs) and G protein-coupled receptors (GPCRs). Heatmaps depict the average relative expression (Z-score of mean $log_2(TPM+1)$, bar) of the top 10 TFs (F) and GPCRs (G) (columns) that are specifically expressed in the cells of each IEC type (rows) based on the higher depth, full-length scRNA-seq data.

FIGS. 2A-F—Differentiation from stem cells to mature enterocytes. FIG. 2A shows gene signature-based embedding of the IEC lineage. Shown are 7,216 single IECs (see main text and Methods) positioned by signature scores for key cell types: the difference between the signature scores for tuft and enteroendocrine cells (x-axis); between enterocyte and goblet cell scores (y-axis), and the stem cell score (z-axis). Each signature score was computed using 50 genes (Methods). Cells are shaded by expression levels of the stem cell marker Lgr5 (left), cell-cycle gene set (center), and the enterocyte marker Alpi (right). FIGS. 2B-E show diffusion-map embedding of 5,282 cells progressing through stages of enterocyte differentiation (Methods). (B-C) Cells are shaded by their cluster assignment (FIG. 1B). Diffusion component 1 and 3 (DC-1 and DC-3) are associated with the transition from stem cells to progenitors (B), while DC-2 distinguishes between proximal and distal enterocyte fate commitment (C). (D-E) Cells are shaded by the expression ($log_2(TPM+1)$, bar) of known and novel TFs associated with stages of differentiation (D), or with proximal or distal enterocyte differentiation (E). FIG. 2F shows the top 10 markers for absorptive and secretory IECs. Heatmap shows the mean expression level (bar, $Log_2(TPM+1)$) for genes (rows) in cells in the two subsets (columns).

FIGS. 3A-F—Novel classification of rare enteroendocrine subtypes. FIG. 3A shows type discovery by unsupervised clustering. Shown is a tSNE embedding of the 533 enteroendocrine cells (EECs) from the droplet-based dataset. Cells are numbered and shaded based on the 12 clusters determined through kNN-graph based clustering (Methods), and labeled by post-hoc analysis based on known genes (B-C). FIG. 3B shows EEC subtype signatures. Heatmap of the relative expression level (row-wise Z-scores, bar) of the most specific (FDR<0.01, $log_2(fold change) > 0.1$) genes (rows) for the cells (columns) in each of the 12 detected clusters (coded as in A). FIG. 3C shows marker based classification of EECs. Violin plots show the distribution of expression ($log_2(TPM+1)$) of genes (columns) encoding major EEC TFs, markers genes, and hormones in the cells (dots) from each of the 12 subtype clusters (rows), coded as in A. Grey bars indicate traditional nomenclature for EEC subtypes based on hormone expression (S, I, L, K, A). FIG. 3D shows smFISH of the co-expression of gut hormones Cck ("I"), Ghrl ("A") and Gcg ("L") by individual EECs. Scale bar, 50 μm. Inset (×5) of triple positive SILA cell FIG. 3E shows distribution of EEC subtypes in different SI regions. Proportion (y axis) of each EEC subset in cells sampled from each of three regions of the small intestine, duodenum, jejunum and ileum (legend) in each mouse (dots, n=2 mice per region). Error bars: standard error of the mean (SEM). (*FDR<0.25, FDR<0.1, *FDR<0.01, $\chi^2$ test, Methods) FIG. 3F shows combined smFISH and IFA of enterochromaffin cells with Reg4 (left) and Tph1 (middle) co-stained with ChgA antibody (right). Scale bar, 20 μm.

FIGS. 4A-H—A CD45-positive subset of tuft cells expresses the epithelial cytokine TSLP. FIG. 4A shows tuft cell subsets. tSNE embedding of 166 tuft cells from the droplet-based dataset (FIG. 1B). Cells are shaded by their subtype assignment based on kNN-graph-clustering (Methods), and annotatedpost-hoc (legend, top right). FIG. 4B shows gene signatures for Tuft-1 and Tuft-2 cells. Heatmap shows the relative expression (row-wise Z-scores, −bar) of the consensus marker genes for Tuft-1 and Tuft-2 cells (rows) across single cells from the droplet-based dataset (columns) assigned to Tuft-1 and Tuft-2 cell clusters. The top 25 genes are shown, all FDR<0.01 and log 2 fold change >0.1 in both plate- and droplet-based datasets). FIG. 4C shows TSLP expression in Tuft-2 cells. Violin plots show the distribution of expression of epithelial cytokines (1125, left; 1133, middle; TSLP: right) in the cells (dots) in enterocytes, Tuft-1- and Tuft-2 subsets, in full-length scRNA-seq data. Both tuft cell subsets express 1125, but TSLP is enriched in the Tuft-2 subset. (*FDR<0.1, ***FDR<0.0001, Mann-Whitney U-test). FIGS. 4D-E shows validation of high TSLP expression by Tuft-2 cells. (D) Combined smFISH and IFA of TSLP co-stained with DCLK1, scale bar 10 μm. (E) qPCR (y axis, relative quantification compared to Tuft-2 group) of Alpi (enterocyte marker), TSLP and Dclk1 (tuft cell markers) from cells defined as Tuft-1, Tuft-2 or randomly selected single cells from processed plates of the full-length scRNA-seq data (16 cells per group). (*p<0.05, p<0.005, t-test). FIG. 4F shows high expression of Ptprc (CD45) by Tuft-2 cells. Violin plots show the distribution of expression of Cd14 (top-left), EpCAMf (top-right), Dclk1 (bottom-left) and Ptprc (CD45; bottom-right) in the cells (dots) of enterocyte, Tuft-1 and Tuft-2 subsets as well as monocytes based on the deeper-coverage full-length scRNA-seq data. FIG. 4G shows validation of CD45 expression by tuft cells. Top left: smFISH imaging ofPtprc (encoding CD45) co-stained with DCLK1 antibody. Scale bar 50 μm. Top right: Distribution of CD45 protein levels within Gfi1b-GFP labeled cells, compared to background (light grey) and monocytes (dark grey) based on FACS. Bottom: IFA co-staining of DCLK1, Gfi1b-GFP and CD45 within the same tuft cell. Scale bar 15 μm. FIG. 4H** shows isolation of Tuft-2 cells using FACS based on CD45 expression. Proportion (y axis) of detected Tuft-1 and Tuft-2 cells (shaded as in a-f) in 3' droplet scRNAseq data (n=3 pooled mice) from cells sorted using EpCAM alone (left) or using EpCAM and CD45 (right) (*p<0.05, *** p<0.0005, hypergeometric test).

FIGS. 5A-F—Microfold (M) cell-specific gene signatures. FIG. 5A shows Tuft-2 cells express a higher level of known M cell genes. tSNE embedding of 101 tuft cells (squares: Tuft-1; circles: Tuft-2) extracted from full-length scRNA-seq data (FIG. 8A). Cells are shaded by their relative score (bar, Methods) for the expression of 20 known M cell genes[17]. FIGS. 5B-C show RANKL-mediated in-vitro differentiation of M cells. (B) tSNE embedding of 5,434 epithelial cells profiled from intestinal organoids with and without treatment of RANKL. Blue: 384 differentiated M cells, identified by unsupervised clustering (FIG. 14E). (C) Shown are the proportions of epithelial cells (y axis) in each cell subset (x axis; subsets identified by graph-clustering and labeled post-hoc; Methods) from organoids grown under control conditions (white bars) or treated with RANKL for 3 days (light shaded bars) or 6 days (dark shaded bars). FIGS. 5D-F show M cells from follicular-associated epithelium (FAE) in vivo. (D) M cell cluster. Heatmap shows the Pearson correlation coefficient (bar) between expression profiles from each pair of cells (rows, columns), for 4,700 FAE derived epithelial cells (n=5 mice). Cells are ordered by unsupervised clustering (Methods), with large clusters down-sampled to a maximum of 250 cells for visualization only. Arrow marks a group of 18 M cells. (E-F). Gene signatures of in vivo M cells. Heat maps show the mean expression (−bar) in each FAE cell type cluster (columns) of genes (rows) for known (grey bars) or novel (black bars) cell surface markers (E) or transcription factors (F), identified as specific (FDR<0.05, Mann-Whitney U-test) to M cells in vivo.

FIGS. 6A-I—Tailored remodeling of the proportion and transcriptional programs of intestinal epithelial cells in response to different infections. FIG. 6A shows functional changes in IEC transcriptional programs in *Salmonella* infection. Shown are the significance (−log$_{10}$(q), x axis) for the top 10 enriched GO terms among genes in *Salmonella*-treated IECs compared to control IECs. FIG. 6B shows up-regulation of Reg3b and Reg3b expression in both enterocytes and other epithelial cells during *Salmonella* infection. Violin plots show the distribution of expression levels (log$_2$(TPM+1), y axis) of antimicrobial C-type lectins Reg3 g (top left) and Reg3b (top right), and interferon inducible and regulatory proteins Zbp1 (bottom left) and Igtp (bottom right) in control and *Salmonella*-treated enterocytes and all other cells (grey). FIGS. 6C-D show changes in cell composition during *Salmonella* and helminth infection. (C) tSNE visualization of IECs subsets (numbered and shaded according to their assignment to cell-type clusters using unsupervised clustering; legend) in controls (left; n=4 mice), *Salmonella* infected mice (n=2, center left), and mice infected with the intestinal parasite *H. polygyrus* for 3 (n=2, center right) or 10 (n=2, right) days. FIG. 6D shows frequencies (y axis) of cells of each subtype (as in c) in each mouse (dots) under each infection condition (*FDR<1× 10$^{-5}$; FDR<1×10$^{-10}$, Wald test). Error bars: standard error of the mean (SEM). FIG. 6E** shows cell-intrinsic changes in enterocyte transcriptional programs following *Salmonella* infection. Heatmap shows the relative expression (row-wise Z-scores, bar) of 104 genes (left panel, rows) of which 58 (right panel) are specific to *Salmonella* infection (Methods), significantly up-regulated (FDR<0.05, Mann-Whitney U-test, log 2 fold-change >0.1) in individual enterocytes (columns) from the *Salmonella* infected mice compared to controls (grey). Enterocytes from *H. polygyrus*-treated mice (3 days; 10 days) are shown (right panel) for comparison. Labels indicate 10 representative up-regulated genes. FIG. 6F shows shifts in composition of tuft cell subsets in response to *H. polygyrus* infection. Frequencies (y axis) of cells in each subset (FIG. 16B-C) after 3 (left) and 10 (days) of infection in each mouse (dots, n=2 mice). Error bars: standard error of the mean (SEM). (*FDR<0.25; FDR<0.05, Wald test). FIG. 6G** shows up-regulation of anti-parasitic genes by goblet cells in response to *H. polygyrus* infection. Violin plots show the distribution of expression levels (log$_2$(TPM+1), y axis) of three genes, previously implicated in anti-parasitic immunity[70], which are up-regulated by goblet cells from control mice (grey) and mice infected by *H. polygyrus* for 3 and 10 days (light and dark, respectively) (FDR<0.05, Mann-Whitney U-test, 3' scRNA-seq dataset). FIG. 6H shows cell intrinsic changes in enterocyte transcriptional programs following *Salmonella* infection. Heatmap shows the relative expression (row-wise Z-scores, bar) of 104 (left) genes (rows) of which 58 are specific to *Salmonella* infection (right, Methods) significantly up-regulated (FDR<0.05, Mann-Whitney U-test, Log$_2$ fold-change >0.1) in individual enterocytes (columns) from the *Salmonella* infected mice compared to controls (grey). Enterocytes from *H. polygyrus*-treated mice (3 days; 10 days) are shown (right) for comparison, labels indicate 10 representative up-regulated genes. FIG. 6I shows cell intrinsic changes in goblet cell transcriptional programs following helminth infection. Heatmap shows the relative expression (row-wise Z-scores, bar) of 20 genes (left panel, rows) of which 14 are specific to *H. polygyrus* infection (right panel, Methods) significantly up-regulated in individual goblet cells (columns, FDR<0.05, Mann-Whitney U-test, Log$_2$ fold-change >0.1) from *H. polygyrus* infected mice (3 days; 10 days) compared to control (grey). Goblet cells from *Salmonella*-treated mice are shown (right) for comparison, labels indicate 10 representative up-regulated genes.

FIGS. 7A-G—Identifying intestinal epithelial cell-types in scRNA-seq data by unsupervised clustering, related to FIG. 1. FIGS. 7A-B show quality metrics for scRNA-seq data. Shown are distributions of the number of reads per cell (left), the number of genes detected with non-zero transcript counts per cell (center) and the fraction of reads mapping to the mm10 mouse transcriptome per cell (right) in the droplet-based 3' scRNA-seq data (A) and the plate-based full-length scRNA-Seq data (B). FIG. 7C-F show agreement across batches. (C) Contribution of batches to each cluster.

Each pie chart shows the batch composition (legend) of each detected cluster (post-hoc annotation and number of cells are marked on top) in the droplet-based 3' scRNA-seq dataset. All 10 biological replicates contribute to all clusters, and no major batch effect is observed. (n=6 mice). (D) Contribution of each mouse to each cluster. Shown is the proportion of detected cells (y axis) in each major cell type (x axis) in the droplet-based 3' scRNA-seq dataset in each of six mice (dots). Grey bar: mean; error bars: standard error of the mean (SEM). (E) Agreement in expression profiles across mice. Box and whisker plot shows the Pearson correlation coefficients (x axis) in average expression profiles (average $\log_2$(TPM+1)) for cells in each cluster (y axis), across all pairs of mice. Black bar indicates median value, box edges correspond to the 25th and 75th percentiles, while whiskers indicate a further 1.5*IQR where IQR is the interquartile range. Note that clusters with additional sub-types (e.g., Tuft, enteroendocrine cells) show more variation, as expected. (F) Scatter plots compare the average $\log_2$(TPM+1) gene expression values between two scRNA-seq experiments from the droplet-based 3' scRNA-seq dataset (top, x and y axis), two scRNA-seq experiments from the plate-based full length scRNA-seq dataset (center, x and y axis), or between the average of a plate-based full-length scRNA-seq (x axis) and a population control (y axis) (bottom). Pearson correlation is marked top left. FIG. 7G shows additional QC metrics and post-hoc cluster annotation by the expression of known cell-type markers. tSNE visualization of 7,216 single cells, where individual points correspond to single cells. Top left corner to bottom right corner, in order: Cells are shaded by their assignment to clusters (top left, identical to FIG. 1B), mean expression ($\log_2$(TPM+1), bar) of several known marker genes for a particular cell type or state (indicated on top), the mouse from which they originate (legend), the number of reads per cell (bar), the number of genes detected per cell (bar) and the number of transcripts as measured by unique molecular identifiers (UMIs) per cell.

FIGS. 8A-F—Identification and characterization of intestinal epithelial cell-types in plate-based full-length scRNA-seq data by unsupervised clustering, related to FIG. 1. FIG. 8A shows QC metrics and post-hoc cluster annotation by the expression of known cell-type markers. tSNE visualization of 1,522 single cells where individual points correspond to single cells. Top left corner to bottom right corner, in order: Cells are numbered and shaded by their assignment to clusters, using a k-nearest neighbor (kNN) graph-based algorithm (Methods; Legend shows the cluster post-hoc annotation to cell types); mean expression ($\log_2$(TPM+1), bar) of several known marker genes for a particular cell type or state (indicated on top; same as in FIG. 7G); the mouse from which they originate (legend) and its genotype, the FACS gate used to sort them (legend), the number of reads per cell (bar) and the number of genes detected per cell (bar). FIG. 8B shows cell-type-specific signatures. Heatmap shows the relative expression level (row-wise Z-scores, bar) of genes (rows) in consensus cell-type-specific signatures (same genes as FIG. 1C, with the exception of enterocytes), across the individual post-mitotic IECs (columns) in the full-length scRNA-seq data. Shading marks the cell types and their associated signatures. FIG. 8C shows Mptx2, a novel Paneth cell marker. tSNE of the cells from the droplet-based 3' scRNA-seq (left, as in FIG. 1B) and plate-based full-length scRNA-seq (right, as in A) datasets, shaded by expression ($\log_2$(TPM+1), bar) of the mucosal pentraxin Mptx2. FIG. 8D shows cell-type-enriched GPCRs. Heatmap shows the relative expression (row-wise Z-scores, bar) of genes encoding GPCRs (rows) that are significantly (FDR<0.001, Mann-Whitney U-test) up- or down-regulated in the cells (columns) in a given cell-type (top, coded as in A) compared to all other cells, in the plate-based full-length scRNA-seq data. FIG. 8E shows cell type specific Leucine-rich repeat (LRR) proteins. Heatmap depicts the mean relative expression (column-wise Z-score of mean $\log_2$ (TPM+1) values, bar) of genes (columns) encoding LRR proteins that are significantly (FDR<0.001, Mann-Whitney U-test) up- or down-regulated in a given cell-type (rows) compared to all other cells, in the plate-based full length scRNA-seq data. FIG. 8F shows violin plots displaying the distribution of expression levels of Selm, Fxyd3, Hepacam2, Cd24a and Tm4sf4 across intestinal epithelial cell types.

FIGS. 9A-E—Mapping of differentiation processes using low-dimensional embedding, related to FIG. 2 FIG. 9A shows principal components analysis (PCA) of IECs. Shown are the first two PCs (x and y axis) of a PCA of 7,216 IECs. Cells (points) are shaded by the signature scores of enterocytes (left), cell-cycle (middle) and secretory cells (right). The secretory signature score is the sum of the Paneth, goblet, enteroendocrine and tuft signature scores (Methods). FIG. 9B shows gene signature-based embedding of the IEC lineage. Shown are 7,216 single IECs positioned by signature scores for key cell types: the difference between the signature scores for enterocyte and enteroendocrine cells (x axis); the difference between goblet and tuft cell scores (y axis), and the stem cell score (z axis) (as in FIG. 2B). Each signature score was computed using 50 genes (Methods). Cells are shaded by $\log_2$(TPM+1) expression (bar) of the goblet cell markerMuc2 (left), the tuft cell marker Dclk1 (middle), and the enteroendocrine marker Chgb (right). FIGS. 9C-E show that DC-3 reflects the distinction between stem cells and enterocyte progenitors. Diffusion-map embedding of 5,282 cells progressing through stages of enterocyte differentiation (see also FIG. 2C). Shown are DC-1 (x axis) and DC-3 (y axis) with cells (points) shaded by the score (bar, Methods) for gene signatures of the cell-cycle (C), stem cells (D), and enterocytes (E).

FIGS. 10A-Q—Enterocyte differentiation toward proximal and distal fates, related to FIG. 2. FIGS. 10A-F show DC-1 is driven by enterocyte differentiation and DC-2 distinguished proximal and distal enterocytes. Diffusion-map embedding of 5,282 cells through stages of enterocyte differentiation. Shown are DC-1 (x axis) and DC-2 (y axis) with cells (points) shaded by the score (bar, Methods) for gene signatures of the cell cycle (A), stem cells (B), enterocytes (C), or by the expression levels ($\log_2$(TPM+1), bar) of the proximal enterocyte marker Lct (D), and the distal markers Mep1a (E) and Fabp6(F). FIG. 10G shows TF genes differentially expressed between proximal and distal cell fate. Heatmap shows the mean expression level (bar) of 44 TFs differentially expressed between the proximal and distal (legend) enterocyte clusters of FIG. 1B (FDR<0.05, Mann-Whitney U-test). FIGS. 10M-N show Paneth cell subsets. (M) tSNE of 10,396 single cells (points) obtained using a large cell-enriched protocol (Methods), numbered and shaded by clusters annotated post-hoc. n=2 mice. FIGS. 10N-0 show Paneth cell subset markers. (N) Expression (row-wise Z-score, bar) of genes specific (FDR<0.05, Mann-Whitney U-test, log$_2$ fold-change >0.5) to each of the two Paneth cell subsets (average of 724.5 cells per subtype, down-sampled to 500 for visualization) shown in (M). FIG. 10O shows two Paneth subsets reflect regional diversity. Expression of the same genes (rows) as in (N) but in Paneth cells from each of three small intestinal regions (176.3 cells obtained per each of the regions on average, columns; FIG. 10H); 11 of 11 Paneth-1 markers are enriched in the ileal Paneth cells, while 7/10 Paneth-2 markers are enriched in duodenal or jejunal Paneth cells (FDR<0.05, Mann-Whitney U-test). FIG. 10P shows regional variation of intestinal stem cells. Expression (row-wise Z-score) of genes specific to stem cells from each intestinal region (FDR<0.05, Mann-Whitney U-test, log 2 fold-change >0.5). There are 1,226.3 obtained cells per each of the three regions on average, down-sampled to 500 for visualization. FIG. 10Q shows novel regional stem cell markers (P) identify distinct populations in diffusion map space. Close-up of stem-cell region of diffusion space (FIG. 2C) shaded by expression level (log$_2$(TPM+1), bars) pan-ISC marker Lgr5 (left), proximal ISC marker Gkn3 (center) and distal ISC marker (Bex1). Dashed line is a visual guide.

FIGS. 11A-E—Heterogeneity within EECs, related to FIG. 3. FIG. 11A shows EEC subset discovery and spatial location. Shown is a tSNE embedding of the 533 enteroendocrine cells (EECs) identified from the droplet-based datasets for whole SI and regional samples (Methods). FIG. 11B shows agreement in hormone detection rates between 3' droplet and full-length scRNA-seq. Scatter plot shows the detection rate (fraction of cells with non-zero expression of a given transcript) for a set of known EEC hormones, TFs and marker genes (legend) in EECs from the full-length dataset (x axis), and from the 3' droplet-based dataset (y axis). Linear fit (dashed line) and 95% confidence interval (shaded) are shown. FIG. 11C shows expression of key genes across subset clusters. tSNE plot shows cells numbered and shaded by either by their assignment to 12 clusters (top left plot; identical to FIG. 3A) or by the expression (log$_2$(TPM+1), bar) of genes encoding either gut hormones (Sct, Sst, Cck, Gcg, Ghrl, GIP, Nts), or markers of immature EECs (Neurog3), mature EECs (Chgb) or enterochromaffin cells (Tac1, Reg4). FIG. 11D shows co-expression of GI hormones by individual cells. Left: Heatmap shows the expression (bar) of canonical gut hormone genes (rows) in each of 533 individual EECs (columns), ordered by their assignment to the clusters in a (bar, top). Right: Heatmap shows for each cluster (columns) the percentage of cells (bar, inset text) in which the transcript for each hormone (rows) is detected. FIG. 11E shows potential markers for the enteroendocrine (EEC) lineage. Shown is a Volcano plot of the differential expression of each gene (dot) between 310 of the EECs and 6,906 remaining IECs (x axis), and the significance (−log$_{10}$(Q value)) of each such test (y axis). Genes (points) are shaded by their expression level (Log$_2$ (TPM+1), bar)). The names of known lineage TFs and of gut hormone genes are indicated.

FIGS. 12A-F—Classification and specificity of enteroendocrine subsets related to FIG. 3. FIG. 12A shows relationships between EEC subsets. Dendrogram shows the relationship between EEC clusters as defined by hierarchical clustering of mean expression profiles of all the cells in a subset (Methods). Estimates for the significance of each split are derived from 100,000 bootstrap iterations using the R package pvclust (*p<0.05; ** p<0.01, p<0.001, χ$^2$ test). Heat map (B) shows cell-cell Pearson correlations (r, bar) between the scores across 11 significant PCs (p<0.05, Methods) across the 533 EECs (rows, columns). Rows and columns are ordered using cluster labels obtained using unsupervised clustering (Methods). FIG. 12C shows subset specificity of gut hormones and related genes. Scatter plot shows for each gene its specificity to its marked cell subset (y axis; defined as the proportion of cells not in a given subset which do not express a given gene) and its sensitivity in that subset (defined as the fraction of cells of a given type which do express the gene, Methods). Subsets are coded as in the legend. Genes are assigned to the subset where they are most highly expressed on average. Genes were chosen based on their known annotation as gut hormones (Cck, Gal, Gcg, Ghrl, GIP, Iapp, Nucb2, Nts, Pyy, Sct, Sst), enterochromaffin markers (Tph1, Tac1) and canonical EEC markers (Chga, Chgb). FIG. 12D shows the enteroendocrine marker Reg4 is substantially expressed in enteroendocrine, goblet and Paneth cells. Violin plots show the distribution of expression (log$_2$(TPM+1), y axis) of Reg4 in each of the IEC subsets (x axis). FIG. 12E shows mapping the in vivo-identified EEC subsets to EEC subsets in organoid[53]. Heatmap shows the Pearson correlation (bar) between average expression profiles of the cells of each of 12 subsets in the study (columns), and seven recently reported clusters (rows) from organoids[53]. Cluster-pairs that are maximal across both a row and a column are highlighted (white border). FIG. 12F shows GPCRs enriched in different EEC subtypes. Heatmap shows the expression levels (row-wise Z-score, bar) averaged across the cells in each of the EEC sub-types (columns) of 11 GPCR-encoding genes (rows) that are differentially expressed (FDR<0.25, Mann-Whitney U-test) in one of the EEC subtype clusters.

FIGS. 13A-F—Characterization of tuft cell heterogeneity and identification of hematopoietic lineage marker Ptprc (CD45) in a subset of tuft cells, related to FIG. 4. FIG. 13A shows Tuft-1 and Tuft-2 cells. tSNE visualization of 102 tuft cells (points) from the plate-based full-length scRNA-seq dataset (FIG. 7F), labeled by their sub-clustering into Tuft-1 and Tuft-2 subtypes. FIG. 13B shows gene signatures for Tuft-1 and Tuft-2 cells. Heatmap shows the relative expression (row-wise Z-scores, bar) of the consensus Tuft-1 and Tuft-2 marker genes (rows), across single cells from the plate-based dataset (columns) assigned to Tuft-1 and Tuft-2 cell clusters. Top 25 genes shown for each subtype (all FDR<0.01 and log 2 fold change >0.1 in both plate- and droplet-based datasets). FIG. 13C shows Tuft-2 signature genes are enriched in immune functions. Shown are the significantly enriched (Methods, FDR<0.1, −log$_{10}$(Q-value), x axis) GO terms (y axis) in the gene signature for the Tuft-2 subset. FIG. 13D shows expression of neuron- and immune-related genes in Tuft-1 and Tuft-2 subsets, respectively. Plot shows for each gene (y axis) its differential expression (x axis) between Tuft-1 and Tuft-2 cells. Bar indicates Bayesian bootstrap[74] estimates of log 2 (fold change), and hinges and whiskers indicate 25% and 95% confidence intervals, respectively. FIG. 13E shows validation of CD45 expression in some Tuft cells. IFA showing co-expression of a specific tuft cell marker, DCLK1 and CD45 (white). Scale bar, 200 μm. FIG. 13F shows isolation of Tuft-2 cells using FACS based on CD45 expression. tSNE embedding of 332 EpCAM$^+$/CD45$^+$ FACS-sorted single cells (points, n=3 pooled mice), shaded by unsupervised clustering (top left), the expression of the Tuft cell marker Dclk1 (top right), or the signature scores for Tuft-1 and Tuft-2 cells (bottom left and right, respectively).

FIGS. 14A-I—Microfold (M) cells from RANKL-treated intestinal organoids and in vivo, related to FIG. 5. FIG. 14A shows previously reported[17] M cell signature genes expressed in Tuft-2 cells. Heat map shows the mean expression level (log$_2$(TPM+1), bar) of M cell signature genes[17] (rows) in cells from the Tuft-1 and Tuft-2 subsets (columns) and in mature enterocytes, shown for comparison, based on the high-coverage full-length scRNA-seq data. Cells in the Tuft-2 subset express a significantly higher level of these genes on average (p<1×10$^{-5}$, Mann-Whitney U-test). FIGS. 14B-E show scRNA-seq identifies M cells in RANKL treated organoids. tSNE embedding of 5,434 single cells (dots) from organoids, highlighting (B) those from control (left) or RANKL-treated (middle, right) intestinal organoids; or coloring each cell (C-D) by the expression (log$_2$(TPM+1), bar) of the canonical M cell markers TNF-alpha induced protein 2 (Tnfaip2, M-sec, C) and glycoprotein 2 (Gp2, D). FIG. 14E shows expression of M cell marker genes[17, 58, 75] in each of the organoid cell clusters. Violin plots show the distribution of expression levels (log$_2$(TPM+1)) for each of 10 previously reported M cell marker genes[58] (columns), in the cells (dots) in each of 13 clusters identified by k-NN clustering of the 5,434 scRNA-seq profiles from organoids. FIGS. 14F-G show M cell gene signature in vitro. Heat maps show for each cell type cluster of organoid-derived intestinal epithelial cells (columns) the mean expression (bar) of genes (rows) for known (grey bars) or novel (black bars) M cell markers (F) or transcription factors (G), identified as specific (FDR<0.05, Mann-Whitney U-test) to M cells both in vitro and in vivo (Methods). FIG. 14H shows congruence of in vitro and in vivo-derived M cell gene signatures. Violin plot shows the distribution of the mean expression of the in vitro-derived signature genes (y-axis) across the in vivo M cells (blue) and all other cells derived from the FAE (grey). FIG. 14I shows in vivo expression of the M cell signature genes from organoids. Heatmaps show the mean expression level (Log$_2$(TPM+1), bar) each of the genes specific to M cells (FDR<0.05, Mann-Whitney U-test, Log$_2$ fold change >0.5) in the organoid data (rows), in the cells from each of the cell type clusters (columns) from the organoids (left) or from in vivo IECs (right). Known and novel M cell markers are marked (left). Genes that are specific to M cells in vitro but expressed by IECs in vivo (grey) are filtered out, and a refined set of 18 specific M cell markers (black) that are not expressed by in vivo IECs is retained.

FIGS. 15A-E—Intestinal epithelial cell response to pathogenic stress, related to FIG. 6. FIG. 15A shows generalized and pathogen-specific response genes. Volcano plots show for each gene (dot) the differential expression (DE, x axis), and its associated significance (y axis; (−log$_{10}$(Q value); Likelihood-ratio test) in response to either *Salmonella* (top) or *H. polygyrus* (bottom). Genes strongly up-regulated in *Salmonella* (FDR<10$^{-6}$) or *H. polygyrus* (FDR<5×10$^{-3}$) are highlighted by shading, respectively. (All highlighted genes were significantly differentially expressed (FDR<0.05) in both the 3' scRNA-seq and the higher depth full-length scRNA-seq datasets.) Left panels: all genes differentially expressed in the noted parasite infection vs. uninfected controls; middle panels: the subset differentially expressed in both parasites vs. control; right panels: the subset differentially expressed only in the noted parasite but not the other (Methods). FIG. 15B shows global induction of enterocyte-specific genes across cells during *Salmonella* infection. tSNE embedding of 9,842 single IECs from control wild-type mice (left) and mice infected with *Salmonella* (right). Cells are shaded by the expression of the indicated genes, all specific to enterocytes in control mice (Tables 3-5) and strongly up-regulated by infection (FDR<10$^{-10}$ in both the 3' scRNA-seq datasets and in the higher depth full length scRNA-seq dataset). FIG. 15C shows up-regulation of pro-inflammatory apolipoproteins Serum Amyloid A 1 and 2 (Saa1 and Saa2) in distal enterocytes under *Salmonella* infection. Violin plot shows log$_2$(TPM+1) expression level (y axis) of Saa1 (top) and Saa2 (bottom) across all post-mitotic cell-types from control and *Salmonella*-treated mice (n=4 mice, sample identity shown by legend) (*FDR<0.01; FDR<0.0001, Mann-Whitney U-test). FIG. 15D** shows up-regulation of antimicrobial peptides by Paneth cells following *Salmonella* infection. Violin plots show log 2 (TPM+1) expression levels (y axis) of genes encoding antimicrobial peptides (panels, marked on top left) and the mucosal pentraxin Mptx2 (bottom right) in the cells (dots) from control and *Salmonella*-infected mice (n=4 mice, sample identity shown by legend) (*FDR<0.1; FDR<0.01, FDR<0.0001, Mann-Whitney U-test). FIG. 15E shows paneth cell numbers detected (using graph-clustering, Methods) after *Salmonella*. Frequencies (y-axis) of Paneth cells in each mouse (dots) under each condition (legend). Error bars: standard error of the mean (SEM). (**FDR<0.01, Wald test).

FIGS. 16A-D—Goblet and tuft cell responses to *H. polygyrus* show a unique defense mechanism, related to FIG. 6. FIG. 16A shows genes significantly induced in response to *H. polygyrus* infection in a non-cell-type specific manner. tSNE visualization of 9,842 single IECs (dots) from control wild-type mice (left) and mice infected with *H. polygyrus* for three (middle) or ten (right) days. Cells are shaded by the expression (log$_2$(TPM+1), bar) of the indicated genes. Genes were selected as significantly differentially expressed in response to infection in a non-cell-type specific manner (FDR<0.001 in both the 3' scRNA-seq and full-length scRNA-seq datasets). Ifitm3 is specific to *H. polygyrus* infection, while others are up-regulated in both pathogenic infections. FIGS. 16B-C show expression of the Tuft-1 signature (left), Tuft-2 signature (middle) and Dclk1 (right) in the combined dataset of control, *Salmonella* and *H. polygyrus* infected cells in tuft cell subgroups defined by cluster analysis. (B) Violin plots of the distribution of the respective signature scores (left and middle) and the expression of Dclk1 (right, log 2 (TPM+1, y axis) in cells (dots) in each of the tuft subsets (x axis). (C) tSNE mapping of the 409 tuft progenitor, Tuft-1 and Tuft-2 cells, shaded by the scores for each signature (bar, left and middle) and their assignment to subtype clusters via kNN-graph clustering (right). FIG. 16D shows anti-parasitic protein secretion by goblet cells during *H. polygyrus* infection. Immunofluorescence assay (IFA) of FFPE sections of RELMb (top-left), E-cadherin (Bottom left) and their merged view (right) after 10 days of helminth infection. White arrow: sections of *H. polygyrus*. Scale bar, 200 μm.

FIG. 20—illustrates the cell-of-origin for key IBD GWAS genes.

FIG. 21—illustrates the cell-of-origin for key IBD GWAS G-protein coupled receptor (GPCR) genes.

FIG. 22—illustrates the cell-of-origin for key IBD GWAS cell-cell interaction genes.

FIG. 33—shows the Tuft Cell is dynamically maintained by the Stem Cell lineage.

FIG. 37A shows a schematic overview. Two complementary scRNA-seq methods used to create an atlas of the mouse tracheal epithelium. FIG. 37B shows cell type clusters. t-distributed stochastic nearest-neighbor embedding (tSNE) visualization of 7,193 3' scRNA-seq profiles. Single cells (points) are shaded by their assignment to clusters (Methods; tSNE plot used for visualization only) and annotated post hoc (legend). Dashed circle: ionocyte cluster. FIG. 37C shows cell type clusters. Left: Pearson correlation coefficients (r, bar) between every pair of 7,193 cells (rows and columns) ordered by cluster assignment (bar, rows and columns). Inset (right): zoom of 288 cells from the rare types (black border on left). FIG. 37D shows gene signatures. Relative expression level (row-wise Z-score of $\log_2$(TPM+1) expression values, bar) of cell type-specific genes (rows) in each epithelial cell (columns). Large clusters (basal, club) are down-sampled to 500 cells. FIG. 37E shows cluster-specific transcription factors (TFs). Mean relative expression (row-wise Z-score of mean $\log_2$(TPM+1), bar) of the top TFs (rows) that are enriched (FDR<0.01, likelihood-ratio test) in cells (columns) of each cluster.

FIGS. 38A-B show alternative putative developmental paths to club cells. Diffusion map embedding of 6,905 cells inferred to differentiate from basal to club to ciliated cells (Methods), shaded by either cluster assignment (left) or expression ($\log_2$(TPM+1), bar) of specific genes (all other panels). FIG. 38B shows cell fate trajectories. Schematic of the number of individual cells associated with each cell fate trajectory (Methods). Krt13$^+$ cells occur in hillock structures. FIG. 38C shows whole-mount stain of Krt13 (magenta) and ciliated cell marker Acetylated tubulin (AcTub) shows the distribution of hillocks (which lack ciliated cells) throughout the trachea. FIG. 38D shows immunofluorescence stainings of Krt13 and either basal (Trp63$^+$, solid white line top panel), suprabasal (Trp63$^+$, dashed white line top panel) or luminal (Scgb1a1$^+$, solid white line, bottom panel) markers (magenta, both panels), showing distinct strata of basal Trp63$^+$Krt13$^+$ cells and luminal Scgb1a1$^+$Krt13$^+$ cells. FIG. 38E shows Hillocks are proliferative. Co-stain of EdU (magenta) and Krt13. FIG. 38F shows a schematic of hillocks within pseudostratified ciliated epithelium. FIGS. 38G-I show proximal vs. distal specific club cell expression. Relative expression level (row-wise Z-score, bar) for genes (rows) enriched in proximal and distal tracheal club cells (FDR<0.05, likelihood-ratio test) in the full-length scRNA-seq data. FIGS. 38H-I show ucous metaplasia in distally-derived epithelia. FIG. 38H shows Muc5ac (goblet cell stain) and AcTub (ciliated cell stain) levels in cultured epithelia from proximal (top) or distal (bottom) trachea stimulated with recombinant IL-13 (rIL-13, 25 ng/mL, right) vs. control (left). FIG. 38I shows goblet cell quantification (ln(Muc5ac$^+$/GFP$^+$ ciliated cells, y-axis) in Foxj1-GFP mice (n=6, dots) in each of four conditions in (h) (x-axis). p<0.01, *p<0.001, Tukey's HSD test, black bars: mean, error bars: 95% CI.

FIG. 39A shows Pulse-Seq. Tmx: tamoxifen, mT: tdTomato, mG: mGFP. FIG. 39B-C show cell type clusters and lineage labeling. tSNE visualization of 66,265 scRNA-seq profiles from Pulse-Seq. Cells shaded by assignment to clusters (B, Methods), or by the presence of a lineage label (C). FIG. 39D shows lineage tracing of each tracheal epithelial cell type. Estimated fraction (%, y-axis, Methods) of cells of each type that are positive for the fluorescent lineage label (by FACS) from n=3 mice per time-point (x-axis). Points: individual mice. *p<0.1, *p<0.05, p<0.01, *p<0.001, likelihood-ratio test (Methods), error bars: 95% CI. FIG. 39E shows ciliated and goblet cells are produced later than club and rare epithelial cell types. Estimated daily rate of new lineage labeled cells (%, y-axis, Methods, FIG. 42C) for each type (x-axis). *p<0.05, p<0.01, rank test (Methods), error bars: 95% CI. FIG. 39F shows conventional lineage trace of Gnat3$^+$ tuft cells confirms they are generated by basal cells. Left: Representative images and basal cell lineage labeling quantification (bar plot, right) of Gnat3$^+$ tuft cells at Day 4 (0%, n=2 mice, dots) and Day 30 (22.9%, 95% CI [0.17, 0.30], n=3 mice) post-labeling. Dashed white lines: unlabeled tuft cells; solid white lines: labeled tuft cells. *p<0.001, likelihood-ratio test. Error bars: 95% CI. FIG. 39G shows cell types, lineage, and cellular dynamics inferred using Pulse-Seq.

FIG. 40A shows tuft-1 and tuft-2 sub-clusters. tSNE visualization of 892 tuft cells (points) shaded either by their cluster assignment (left, legend), or by the expression level ($\log_2$(TPM+1), bar, remaining panels) of marker genes for mature tuft cells (Trpm5), tuft-1 (Gng13), tuft-2 (Alox5ap) subsets. FIG. 40B-D show gene signatures for tuft-1 and tuft-2 subsets. FIG. 40B shows distribution of expression levels (y-axis, $\log_2$(TPM+1)) of the top markers for each subset (x-axis). NS: FDR>0.05, **FDR<$10^{-10}$, likelihood-ratio test. FIG. 40C shows relative expression level (row-wise Z-scores, bar) of genes (rows) differentially expressed (FDR<0.25, likelihood-ratio test) in tuft cells (columns) of each sub-cluster (bar, top). FIG. 40D shows validation of tuft-1 and tuft-2 markers in vivo. Immunofluorescence staining of expression of the respective tuft-1 and tuft-2 cell markers Gng13 and Alox5ap (magenta) by distinct tuft cells (solid white lines), along with pan-tuft marker Trpm5 (blue) and DAPI (grey). FIG. 40E shows tuft-1 and tuft-2 subtypes are each generated from basal cell parents. Estimated fraction (%, y-axis, Methods) of cells of each type that are positive for the basal-cell lineage label (by FACS) from n=3 mice (points) per time-point (x-axis) in the Pulse-Seq experiment. *p<0.001, likelihood-ratio test (Methods), error bars: 95% CI. FIGS. 40F-G show tuft-1 and tuft-2 respectively express chemosensory and inflammatory gene modules. Differential expression between tuft subtypes for all genes (F, left), those involved in leukotriene synthesis (F, center left), taste transduction (F, right), and transcription factors (G). Labeled genes are differently expressed in the tuft cell subsets (FDR<0.01, likelihood-ratio test). FIG. 40H shows validation of goblet cell subtype markers. Immunofluorescence staining of the goblet-1 (Tff2, magenta) and goblet-2 Lipf markers along with DAPI (blue) in distinct cells (solid white lines).

FIGS. 41A-K—The pulmonary ionocyte is a novel mouse and human airway epithelial cell type that specifically expresses CFTR. FIG. 41A shows mouse ionocyte markers. Expression level (mean $\log_2$(TPM+1), bar) of ionocyte markers (columns, FDR<0.05 in both 3' and full-length scRNA-seq datasets, likelihood-ratio test and Supplementary Table 3) in the 3' scRNA-seq dataset of each airway epithelial cell type (rows). Dot size: proportion of cells with non-zero expression. intensity: mean expression in those cells with non-zero expression. FIG. 41B shows ionocytes specifically express V-ATPase and Cftr. Immunofluorescent co-labeling of EGFP (Foxi1⁺) ionocytes and a V-ATPase subunit (Atp6v0d2, top left, solid white line) and Cftr (bottom left, solid white line). FIG. 41C shows tSNE visualization shaded by expression level of ionocyte markers Foxi1 (left) and Cftr (right) across all 66,265 trachea epithelial cells from the Pulse-Seq experiment and in the subset of 276 ionocytes (inset). FIG. 41D shows qRT-PCR confirms ionocyte enrichment of Cftr relative to ciliated cells and EpCAM⁺ populations. Expression ($\Delta\Delta$CT, y-axis) of ionocyte (Cftr, Foxi1) and ciliated cell (Foxj1) markers (x-axis) detected using qRT-PCR of prospectively isolated populations of ionocytes and ciliated cells from Foxi1−(n=4, dots) and Foxj1-GFP mice (n=3), respectively. All values normalized relative to EpCAM⁺ populations from wild type mice (n=6; 7.30 $\Delta\Delta$CT, 95% CI [±0.66]), *p<0.001, Dunn's Method, error bars: 95% CI. FIG. 41F shows ionocyte depletion via Foxi1-KO disrupts mucosal homeostasis in ALI cultured epithelia. Effective viscosity (cP, left) and ciliary beat frequency (Hz, right) from optical coherence tomography (OCT) in homozygous Foxi1-KO (n=9, dots) vs. wild type littermates (x-axis, n=3 mice). *p<0.001, **p<0.0001, Mann-Whitney U-test. g-h. shows Foxi1 transcriptional activation (Foxi1-TA) in ferret increases Cftr expression and chloride transport. FIG. 41G shows qRT-PCR expression quantification ($\Delta\Delta$CT, y-axis) of ionocyte markers (x-axis) in ferret Foxi1-TA ALI (n=4) normalized to mock transfection (Cftr: −1.39 $\Delta\Delta$CT, 95% CI [±0.44], Foxi1: −5.37 $\Delta\Delta$CT, 95% CI [±0.91], Methods), error bars: 95% CI. FIG. 41H shows Foxi1 activation in ferret cell cultures results in a CFTR inhibitor-sensitive short-circuit current ($\Delta I_{sc}$). Representative trace of short-circuit current ($I_{sc}$, y-axis) tracings from Foxi1-TA ferret ALI after sgRNA reverse transfection (n=4, light blue) vs. mock transfection (n=4, black). FIG. 41I shows ionocytes are sparsely distributed in human bronchial epithelium. In situ hybridization shows cells co-labeled for Foxi1 and Cftr (20 double Z probe pairs spanning 960 nucleotides including the only documented CFTR splice site). FIGS. 41J-K show human pulmonary ionocytes are the major source of Cftr in the bronchial epithelium. FIG. 41J shows tSNE of 765 human pulmonary ionocytes (points) identified using clustering of 78,217 3' droplet scRNA-seq profiles (grey points) from human bronchial epithelium (n=1 patient). FIG. 41**K shows Difference in fraction of cells in which transcript is detected (x axis) and $\log_2$ fold-change (y-axis) between human ionocytes and all other bronchial epithelial cells. All labeled genes are differentially expressed ($\log_2$ fold-change >0.25 and FDR<<$10^{-10}$, Mann-Whitney U-test). Shading: consensus ionocyte markers in mouse (log 2 fold-change >0.25, FDR<$10^{-5}$, likelihood-ratio test) and human.

FIG. 42—Shows that a new lineage hierarchy of the airway epithelium reframes our understanding of the cellular basis of airways disease. Specific cells are associated with novel cell-type markers and disease-relevant genes.

FIG. 43A shows quality metrics for the initial droplet-based 3' scRNA-seq data. Distributions (y axis) of the number of reads per cell (x-axis, left), the number of the genes detected with non-zero transcript counts per cell (x-axis, center), and the fraction of reads mapping to the mm10 transcriptome per cell (x-axis, right). Dashed and blue lines: median value and kernel density estimate, respectively. FIG. 43B shows cell type clusters are composed of cells from multiple biological replicates. Fraction of cells in each cluster that originate from a given biological replicate (legend, bottom right, n=6 mice); post hoc annotation and number of cells are indicated above each pie chart. All biological replicates contribute to all clusters (except for WT mouse 1 which did not contain any of the very rare ionocytes), and no significant batch effect was observed. FIG. 43C shows reproducibility between biological replicates. Average gene expression values ($\log_2$(TPM+1), x and y axes) across all cells of two representative 3' scRNA-seq replicate experiments (Pearson correlation coefficient, top left), blue shading: gene (point) density. FIG. 43D shows Post hoc cluster interpretation based on the expression of known cell type markers[4]. tSNE of 7,193 scRNA-seq profiles (points), shaded by cluster assignment (Methods, top left) or by the expression ($\log_2$(TPM+1), bar) of a single marker genes or the mean expression of several marker genes[4] for a particular cell type.

FIG. 44A shows quality metrics for full-length, plate-based scRNA-seq data. Distributions (y axis) of the number of reads per cell (x-axis, left), the number of the genes detected with non-zero transcript counts per cell (x-axis, center), and the fraction of reads mapping to the mm10 transcriptome per cell (x-axis, right). FIG. 44B-C show high reproducibility between plate-based scRNA-seq data from biological replicates of tracheal epithelial cells. Average expression values (x and y axes; $\log_2(TPM+1)$) in two representative full-length scRNA-seq replicate experiments (left panel, x and y axes) and in the average of a full-length scRNA-seq dataset (right panel, x axis) and a population control (right panel, y axis) for cells extracted from proximal (B) and distal (C) mouse trachea. Blue shading: density of genes (points); r-Pearson correlation coefficient. FIG. 44D shows Post hoc cluster annotation by the expression of known cell-type markers. tSNE of 301 scRNA-seq profiles (points) shaded by region of origin (top left panel), cluster assignment (top second panel, Methods), or, for the remaining plots, the expression level ($\log_2(TPM+1)$, –bar) of a single marker genes or the mean expression of several marker genes[4] for a particular cell type. All clusters are populated by cells from both proximal and distal epithelium except rare NE cells, which were only detected in proximal experiments (top left panel).

FIG. 45A shows cell type clusters in full-length plate-based scRNA-seq data. Cell-cell Pearson correlation coefficient (r, bar), between all 301 cells (individual rows and columns) ordered by cluster assignment (bar, as in FIG. 38d). Right: zoomed in view of 17 cells (black border on left) from the rare types. FIG. 45B shows high confidence consensus markers. Relative expression level (row-wise Z-score of mean $\log_2(TPM+1)$, bar at bottom) of consensus marker genes (rows, FDR<0.01 in both 3'-droplet and full-length plate-based scRNA-seq datasets, likelihood-ratio test) for each cell type (flanking bar) across 7,193 cells in the 3' droplet data (columns, left) and the 301 cells in the plate-based dataset (columns, right). FIG. 45C-E show cell type-specific expression of genes associated with asthma by GWAS. c. Relative expression (Z-score of mean $\log_2(TPM+1)$, bar bottom right) of genes (rows) that are associated with asthma in GWAS and enriched (FDR<0.01, likelihood-ratio test) for cell type (columns) specific expression in our 3' scRNA-seq data. FIG. 45D for each gene from (c) shown is the significance ($-\log_{10}(FDR)$, Fisher's combined p-value, likelihood-ratio test, y axis) and effect size (point size, mean $\log_2(\text{fold-change})$) of cell type specific expression in the relevant cell (legend) and its genetic association strength from GWAS[15] (x axis). FIG. 45E shows distribution of expression levels (y axis, $\log_2(TPM+1)$) in the cells in each cluster (x axis, legend) for two asthma GWAS genes: Cdhr3 (left; specific to ciliated cells) and Rgs13 (right; specific to tuft cells). **FDR<0.0001, likelihood-ratio test.

FIG. 46A shows Krt8 does not distinguish pseudostratified club cell development from hillock-associated club cell development. Diffusion map embedding of 6,905 cells (as in FIG. 38A) shaded either by their Krt13[+] hillock membership (top left), or by expression ($\text{Log}_2(TPM+1)$, shaded bar) of specific genes (all other panels). FIG. 46B shows Hillocks are more proliferative. Fraction of EdU[+] epithelial cells (%, y-axis; representative image in FIG. 38E) in hillocks and non-hillock areas (x axis). ***p<0.001, likelihood-ratio test, black bar: mean, error bars: 95% CI. shows Krt13[+] hillock cells are turned over rapidly. Fraction of Krt13[+] cells that are club cell lineage labeled (%, y axis) at day 5 (10.2%, 95% CI [0.07, 0.16]) and its dilution at day 80 (5.2%, 95% CI

[0.03, 0.08]). Error bars: 95% confidence interval, n=3 mice (dots). *p<0.05, likelihood-ratio test. shows Genes and processes associated with Krt13[+] cells. FIG. 46D shows the differential expression (x axis, $\log_2(\text{fold-change})$) and its associated significance (y axis, $\log_{10}(FDR)$) for each gene (dot) that is differentially expressed in Krt13[+] cells (identified using clustering in diffusion map space, Methods) as compared to all cells (FDR<0.05, likelihood-ratio test). Shaded: cell type with highest expression (genes whose highest expression is in Krt13[+] cells). Dots show all the genes differentially expressed (FDR<0.05) between Krt13[+] hillock cells and other cells. Those genes with absolute effect sizes greater than $\log_2(\text{fold-change})>1$ are marked with large points, while others are identified as small points (grey). FIG. 46E shows Krt13[+] cell type-enriched pathways. Representative MSigDB[78] gene sets (rows) that are significantly enriched (x axis and bar, $-\log_{10}(FDR)$, hypergeometric test) in Krt13[+] cells.

FIGS. 47A-H show Relative mean expression (loess-smoothed row-wise Z-score of mean $\log_2(TPM+1)$, bar at bottom) of significantly (p<0.001, permutation test) varying genes (A-D) and TFs (E-H) (rows) across subsets of 6,905 (columns) basal, club and ciliated cells. Cells are pseudotemporally ordered (x axis, all plots) using diffusion maps (FIG. 38A). Each cell was assigned to a cell fate transition if it was within d<0.1 of an edge of the convex hull of all points (where dis the Euclidean distance in diffusion-space) is assigned to that edge (Methods).

FIG. 48A shows Post hoc cluster annotation by known cell type markers[4]. tSNE of 66,265 scRNA-seq profiles (points) from Pulse-Seq, shaded by the expression ($\log_2(TPM+1)$, bar) of single marker genes for a particular cell type or cell-cycle score[79] (bottom right) FIG. 48B shows Labeled fraction of basal cells is unchanged during Pulse-Seq time course, as expected. Estimated fraction (%, y-axis, Methods) of cells of each type that are positive for the fluorescent lineage label (by FACS) in each of n=3 mice (points) per time-point (x axis). NS: p>0.1, likelihood-ratio test (Methods), error bars: 95% CI. FIG. 48C shows Pulse-Seq lineage-labeled fraction of various cell populations over time. Linear quantile regression fits (trendline, Methods) to the fraction of lineage-labeled cells of each type (n=3 mice per time point, dots, y-axis) as a function of the number of days post tamoxifen-induced labeling (x-axis). β: estimated regression coefficient, interpreted as daily rate of new lineage-labeled cells, p: p-value for the significance of the relationship, Wald test (Methods). As expected, goblet and ciliated cells are labeled more slowly than club cells (FIG. 39E). FIGS. 48D-F show Conventional Scgb1a1 (CC10) lineage trace of rare epithelial types shows minimal contribution to rare cell lineages. Fraction of Scb1a1 labeled (club cell trace) cells (y axis, %) of Gnat3[+] tuft cells (D) at day 4 (0.6%, 95% CI [0.00, 0.04]) and day 30 (6.3%, 95% CI [0.04, 0.11]), Foxi1-GFP[+] ionocytes at day 30 (2.9%, 95% CI [0.01, 0.11]) (E), and Chga[+] neuroendocrine (NE) cells at day 4 (2.5%, 95% CI [0.01, 0.08]) and day 30 (2.6%, 95% CI [0.01, 0.08]) (F) after club cell lineage labeling. ** p<0.01, likelihood-ratio test. Error bars: 95% confidence interval. Each time point cell type combination has at least n=2 mice.

FIGS. 49A-B show PC-1 and PC-2 are associated with basal to club differentiation and both proximodistal heterogeneity and hillock gene modules respectively. FIG. 49A shows PC-1 (x-axis) vs. PC-2 (y-axis) for a PCA of 17,700 scRNAseq profiles of club cells (points) in the Pulse-Seq dataset, shaded by signature scores (legends, Methods) for basal (left), proximal club cells (center left), distal club cells (center right), the $Krt13^+/Krt4^+$ hillock (right), or their cluster assignment (inset, right). FIG. 49B shows bar plots show the extent (normalized enrichment score, y-axis, Methods) and significance of association of PC-1 (left) and PC-2 (right) for gene sets associated with different airway epithelial types (x-axis), or gene modules associated with proximodistal heterogeneity (FIG. 2g). Heatmaps shows the relative expression level (row-wise Z-score of $\log_2(TPM+1)$ expression values, bar) of the 20 genes (rows) with the highest and lowest loadings on PC-1 (left) and PC-2 (right) in each club cell (columns, down-sampled to 1,000 cells for visualization only). NS $p>0.05$, $*p<0.05$, $p<0.01$, $*p<0.001$, permutation test (Methods). FIG. 49C shows lineage tracing of hillock-associated cells. Estimated fraction (%, y-axis, Methods) of cells of each type that are positive for the fluorescent lineage label (by FACS) from $n=3$ mice (points) per time-point (x axis). $*p<0.001$, likelihood-ratio test (Methods), error bars: 95% CI. FIG. 49D shows Hillock-associated club cells are produced at a greater rate than all club cells. Estimated rate (%, y-axis) based on the slope of quantile regression fits (Methods) to the fraction of lineage-labeled cells of each type (x-axis). $p<0.01$, rank test (Methods), error bars: 95% CI. FIG. 49E shows schematic of the more rapid turnover of basal to club cells inside (top) and outside (bottom) hillocks.

FIG. 50A shows cell type-enriched GPCRs. Relative expression (Z-score of mean $\log_2(TPM+1)$, bar) of the GPCRs (columns) that are most enriched (FDR<0.001, likelihood-ratio test) in the cells of each trachea epithelial cell type (rows) based on full-length scRNA-seq data. FIG. 50B shows tuft cell-specific expression of Type I and Type II taste receptors. Expression level (mean $\log_2(TPM+1)$, bar) of tuft-cell enriched (FDR<0.05, likelihood-ratio test) taste receptor genes (columns) in each trachea epithelial cell type (rows, labeled as in e) based on full-length scRNA-seq data. FIG. 50C shows tuft cell-specific expression of the Type-2 immunity-associated alarmins Il25 and Tslp. Mean expression level (y-axis, $\log_2(TPM+1)$), of Il-25 (left) and Tslp (right) in each cell type (x axis). $*FDR<10^{-10}$, likelihood-ratio test. FIG. 50D shows morphological features of tuft cells. Immunofluorescence staining of the tuft-cell marker Gnat3 along with DAPI. Arrowhead: "tuft", arrows: cytoplasmic extension. FIGS. 50E-F** show mature and immature subsets are identified using marker gene expression. The distribution of expression of scores (y-axis, using top 20 marker genes, Supplementary Table 1, Methods) for tuft (e) goblet (f), basal and club cells (label on top) in each cell subset (x axis) (basal and club cells downsampled to 1,000 cells). $*p<0.05$, $*p<0.001$, Mann-Whitney U-test. FIGS. 50G-H show gene signatures for goblet-1 and goblet-2 subsets. The distribution (G) and relative expression level (H, row-wise Z-scores, bar) of marker genes that distinguish (log 2 fold-change >0.1, FDR<0.001, likelihood-ratio test) cells in the goblet-1 and goblet-2 sub-clusters (bar, top and left) from the combined 3' scRNA-seq datasets. FIG. 50I** shows immunofluorescence staining of the goblet-1 marker Tff2 (magenta), the known goblet cell marker Muc5ac, and DAPI (blue). Solid white line: boundary of a goblet-1 cell.

FIG. 51A shows Immunofluorescent characterization of ionocytes. Ionocytes visualized with EGFP(Foxi1) mouse. EGFP appropriately marks Foxi1 antibody-positive cells (left panel, solid white line). $EGFP^+$ cells express canonical airway markers Ttf1 (Nkx2-1) and Sox2 (solid white lines). $EGFP(Foxi1)^+$ cells do not label with basal (Trp63), club (Scgb1a1), ciliated (Foxj1), tuft (Gnat3), neuroendocrine (NE) (Chga), or goblet (Tff2) cell markers (dashed white lines). FIG. 51B shows ionocytes are sparsely distributed in the surface epithelium. Representative whole mount confocal image of ionocytes EGFP(Foxi1) and ciliated cells (AcTub). FIG. 51C shows $GFP(Foxi1)^+$ ionocytes extend cytoplasmic appendages (arrows). FIG. 51F shows immunofluorescent labeling of $GFP(Foxi1)^+$ cells in the submucosal gland. Dotted line separates surface epithelium (SA) from submucosal gland (SMG). FIG. 51E shows Ascl3-KO moderately decreases ionocyte TFs and Cftr in ALI cultured epithelia. Expression quantification ($\Delta\Delta CT$, y-axis) of ionocyte (Cftr: −0.82 $\Delta\Delta CT$, 95% CI [±0.20], Foxi1: −0.75 $\Delta\Delta CT$, 95% CI [±0.28], Ascl3: −10.28 $\Delta\Delta CT$, 95% CI [±1.85]) and basal (Trp63), club (Scgb1a1), or ciliated (Foxj1) markers (x-axis) in hetero- and homozygous KO (legend) are normalized to wild type littermates. The mean of independent probes (p1 and p2) was used for Cftr. $n=10$ and 5 hetero- and homozygous KO, respectively and $n=4$ wild type mice. $*p<0.05$, $p<0.01$, Dunn's Method, error bars: 95% CI. FIG. 51F shows increased depth of airway surface liquid (ASL) in Foxi1-KO ALI culture compared to WT. Representative OCT image of ASL. bar: airway surface liquid and mucous layer depth. Scale bar (white): 10 m. FIGS. 51G-H** show increased forskolin $\Delta I_{eq}$ in heterozygous and KO epithelia. $\Delta I_{eq}$ (y axis) in ALI cultures of wild type (WT), heterozygous (HET) and Foxi1 knock-out (KO) mice ($n=5$ WT, $n=4$ HET, $n=6$ KO, dots) that were characterized for their forskolin-inducible equivalent currents (G, $I_{eq}$) and for currents sensitive to $CFTR_{inh}$-172 (H). The inhibitor-sensitive $\Delta I_{eg}$s reported may be somewhat underestimating the true inhibitor-sensitive current, since not for all filters the inhibitor response reached a steady plateau on the time scale of the experiment.

FIGS. 52A-C—Ionocyte characterization. FIGS. 52A-B show ionocyte depletion or disruption via Foxi1-KO disrupts mucosal homeostasis in ALI cultured epithelia. ASL depth determined via OCT (A) and pH (B) in homozygous Foxi1-KO ($n=9$, dots) vs. wild type littermates (x-axis, $n=3$ mice). p values: Mann-Whitney U-test. FIG. 52C shows Foxi1-TA results in increased Cftr short-circuit current ($\Delta I_{sc}$, y-axis) in ferret ALI vs. mock transfected controls (Methods). $n=5$, $*p<0.05$, t-test, error bars: 95% CI.

DETAILED DESCRIPTION OF THE EXAMPLE EMBODIMENTS

General Definitions

Figure 1A:
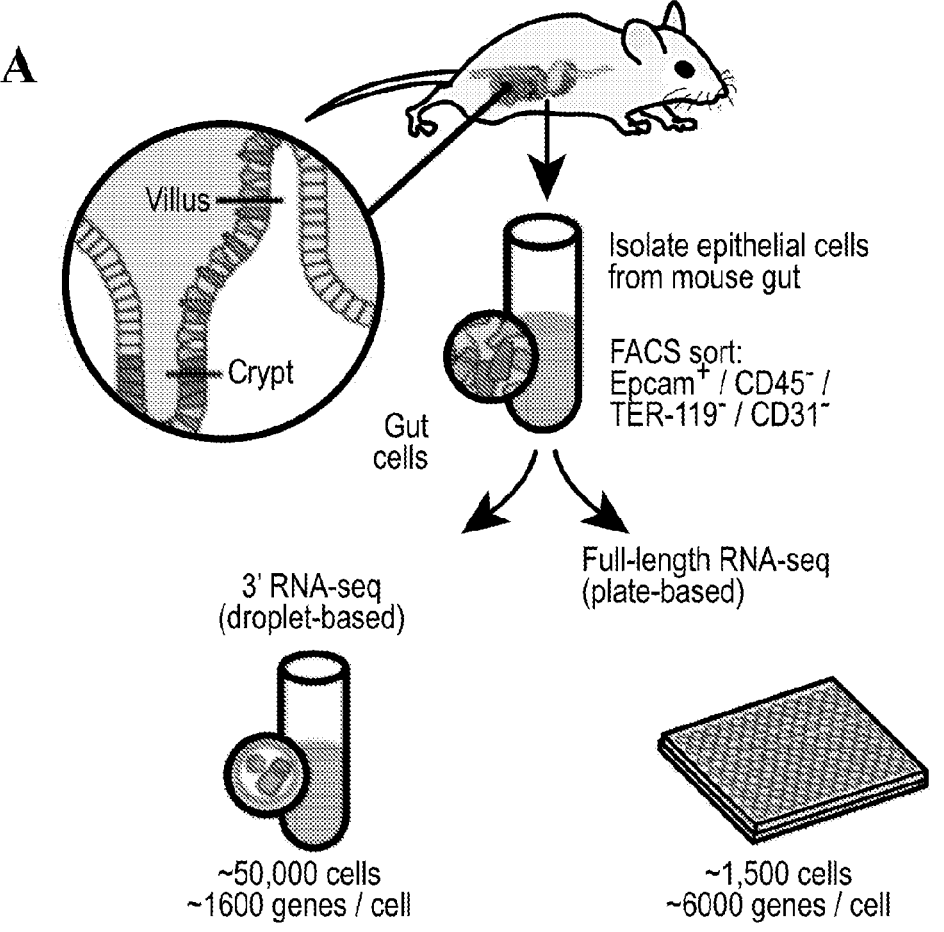

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011)

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Whereas the terms "one or more" or "at least one", such as one or more members or at least one member of a group of members, is clear per se, by means of further exemplification, the term encompasses inter alia a reference to any one of the members, or to any two or more of the members, such as, e.g., any ≥3, ≥4, ≥5, ≥6 or ≥7 etc. of the members, and up to all members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

The term "isolated" as used throughout this specification with reference to a particular component generally denotes that such component exists in separation from—for example, has been separated from or prepared and/or maintained in separation from—one or more other components of its natural environment. More particularly, the term "isolated" as used herein in relation to a cell or cell population denotes that such cell or cell population does not form part of an animal or human body.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The terms "sample" or "biological sample" as used throughout this specification include any biological specimen obtained from a subject. Particularly preferred are samples from the intestinal tissue, but may also include samples from intestinal lumen, faeces, or blood. The term "tissue" as used throughout this specification refers to any animal tissue types, but particularly preferred is intestinal tissue. The tissue may be healthy or affected by pathological alterations. The tissue may be from a living subject or may be cadaveric tissue. The tissue may be autologous tissue or syngeneic tissue or may be allograft or xenograft tissue.

Reference is made to U.S. Provisional application Ser. No. 62/533,653, filed Jul. 17, 2017 and International application serial number PCT/US2017/060469, filed Nov. 7, 2017.

All publications, published patent documents, and patent applications cited herein are hereby incorporated by reference to the same extent as though each individual publication, published patent document, or patent application was specifically and individually indicated as being incorporated by reference.

OVERVIEW

The inventors have identified novel markers capable of identifying new subpopulations of cells, have developed an atlas of the cells in the small intestine and trachea. Additionally, the inventors have validated the population of tuft cells in the trachea (i.e., a subset of epithelial cells). The present invention provides isolated and modified cells, including therapeutic compositions thereof, as well as methods for identifying said cells types and method for modulating said cells for the treatment of gastrointestinal disorders, such as irritable bowel disease, Crohn's disease, and food allergies and respiratory disorders, such as asthma.

As disclosed further herein, Applicants combined single-cell RNA-sequencing (scRNA-Seq) and in vivo lineage tracing to study the cellular composition and hierarchy of the murine tracheal epithelium. Applicants identified new tuft cell types. Applicants revised the cellular hierarchy of the epithelium and demonstrated that tuft cells, neuroendocrine cells, and ionocytes are all direct descendants of basal cells and that they continually turn over. Applicants further discovered a novel cell population that resides in "hillocks", previously unrecognized epithelial structures. Applicants found that club cells functionally vary based on their location within the respiratory tree and identify disease-relevant subsets of tuft and goblet cells. By associating cell type-specific gene expression programs with key disease genes, Applicants establish a new cellular narrative for airways disease.

Embodiments disclosed herein provide markers and gene signatures for identifying, isolating and modulating cells for the treatment of diseases and disorders associated with the gut and the respiratory system. Understanding the development, differentiation and function of an organ, such as the intestine, requires the identification and characterization of all of its component cell types. In the small bowel, intestinal epithelial cells (IECs) sense and respond to microbial stimuli and noxious substances, provide crucial barrier function and participate in the coordination of immune responses. Here, Applicants profiled 53,193 individual IECs from mouse small intestine and intestinal organoid cultures. Using unsupervised clustering, Applicants defined specific gene signatures for major IEC lineages, including the identification of Mptx2, a mucosal pentraxin, as a novel Paneth cell marker. In addition, Applicants identified unexpected diversity of hormone-secreting enteroendocrine populations, revealing co-expression programs of gut hormone genes, previously thought to represent different enteroendocrine subtypes, and constructed a novel hierarchical taxonomy of these cells. Applicants also distinguished two subtypes of Dclk1-positive tuft cells, one of which (Tuft-2) expresses both the epithelial cytokine Tslp and the pan-immune cell marker Ptprc (CD45), which has not been previously associated with any non-hematopoietic cell type. Finally, Applicants characterized how the intrinsic states and proportions of these cell types are reshaped in response to infections, e.g. *Salmonella enterica* and *Heligmosomoides polygyrus* infections. *Salmonella* infection led to an increased number of Paneth cells and enterocytes, and Paneth cell-specific up-regulation of both defensins and Mptx2. In addition, an absorptive enterocyte-specific antimicrobial program was broadly activated across all IEC types, demonstrating previously uncharacterized cellular response to pathogens. In contrast, *H. polygyrus* led to expansion of goblet and tuft cell populations, with a particular expansion of the Cd45⁺ Tuft-2 group. The high-resolution atlas highlights new markers and transcriptional programs, novel allocation of sensory molecules to cell types and organizational principles of gut homeostasis and physiology.

Here, Applicants use scRNA-seq to chart a comprehensive atlas of the epithelial cells of the small intestine. Applicants identified gene signatures, key TFs and specific GPCRs for each of the major small intestinal differentiated cell types, and traced their differentiation from ISCs. Applicants identified and characterized cellular heterogeneity within specific cell-types, and validated individual genes and signatures in situ. Applicants found a transcriptional signature distinguishing proximal and distal enterocytes, established a novel classification of the different subtypes of the enteroendocrine cells and their differential deployment at different locations, and identified a previously unrecognized separation of tuft cells to two sub-types, one with a neuron-like and one with an immune-like gene signature, expressing Ptprc (CD45) and TSLP, a pan-immune cell marker and epithelial cytokine, respectively. Finally, Applicants demonstrated how these cell types and states change dynamically as the small intestine adapts to infection by distinct classes of pathogens. The high resolution cell atlas better defines the composition of the gut, highlights novel key molecules, TFs and GPCRs that can impact gut function and shows how changes in gut composition can play a key role in maintaining homeostasis in response to pathogens.

Airways conduct gases to the distal lung and are the sites of disease in asthma and cystic fibrosis. Here, Applicants further combined single-cell RNA-sequencing (scRNA-Seq) and in vivo lineage tracing to study the cellular composition and hierarchy of the murine tracheal epithelium. Applicants identified a new rare cell, the pulmonary ionocyte. Applicants revised the cellular hierarchy of the epithelium and demonstrated that tuft cells, neuroendocrine cells, and ionocytes are all direct descendants of basal cells and that they continually turn over. Applicants further discovered a novel cell population that resides in "hillocks", previously unrecognized epithelial structures. Applicants found that club cells functionally vary based on their location within the respiratory tree and identify disease-relevant subsets of tuft and goblet cells. Remarkably, Applicants found that the cystic fibrosis gene, CFTR, is predominantly expressed in pulmonary ionocytes in both mouse and human. Loss of ionocytes in mouse epithelia results in the loss of Cftr expression, abnormal surface fluid, and increased mucus viscosity, all of which are altered in cystic fibrosis. By associating cell type-specific gene expression programs with key disease genes, Applicants establish a new cellular narrative for airways disease.

Isolated Cells, Markers, and Gene Signatures

The small intestinal mucosa is at equipoise with a complex luminal milieu which comprises a combination of diverse microbial species and their products as well as derivative products of the diet. It is increasingly clear that the functional balance between the epithelium and the constituents within the lumen plays a central role in both maintaining the normal mucosa and the pathophysiology of many gastrointestinal disorders. The barrier function is part fulfilled by anatomic features that partly impede penetration of macromolecules and diverse set of specialized cells that monitor and titrate responses to a variety of noxious substances or pathogens (Peterson and Artis, 2014). The underlying mucosal immune system is poised to detect antigens and bacteria at the mucosal surface and to drive appropriate responses of tolerance or an active immune response.

IECs of the small intestinal epithelium comprise two major lineages—absorptive and secretory (Clevers, 2006)—reflecting its dual roles. Enterocytes of the absorptive lineage comprise approximately 80% of the epithelium and are specialized for digestion and transport of nutrients (Ferraris et al., 1992). The secretory lineage comprises five further terminally differentiated types of IECs: goblet, Paneth, enteroendocrine, tuft and microfold (M) cells (Barker et al., 2007; Gerbe et al., 2012; Sato et al., 2009)—each with distinct and specialized sensory and effector functions.

The epithelium is organized in a repeating structure of villi, which project toward the lumen, and nearby crypts (FIG. 1a). The crypts of the small intestine are the proliferative part of the epithelium, in which intestinal stem cells (ISCs) and progenitors, termed transit-amplifying cells (TAs), reside (Barker et al., 2007; Barker et al., 2012; Miyoshi and Stappenbeck, 2013). In contrast, only fully differentiated cells are found on the villi (Barker, 2014; Clevers, 2013; Peterson and Artis, 2014). The crypt also contains Paneth cells, which secrete anti-microbial peptides (AMPs), such as defensins and lysozyme, into the lumen to keep the microbiota in check (Cheng and Leblond, 1974b;

Clevers, 2013; Salzman et al., 2003). The highly prolifera-tive TA cells migrate along the crypt-villus axis and differ-entiate into functionally distinct epithelial cell types that subsequently reach the tip of the villus, where mature cells undergo apoptosis and shed to the lumen (Clevers, 2006). Epithelial tissue turns over rapidly (~5 days) (Barker, 2014; Clevers, 2013; van der Flier et al., 2009), allowing it to dynamically shift its composition in response to stress or pathogens.

For example, parasitic infection typically induces hyper-plasia of goblet cells, which produce and secrete mucins to prevent pathogen attachment, strengthening the epithelial barrier and facilitating parasite expulsion (Pelaseyed et al., 2014). Rare (0.5-1%) enteroendocrine cells (EECs) secrete over 20 individual hormones and are key mediators of intestinal response to nutrients (Furness et al., 2013; Gribble and Reimann, 2016) by directly detecting fluctuations in luminal nutrient concentrations via G-protein-coupled receptors (GPCRs)(Gribble and Reimann, 2016). Mapping these GPCRs and hormones has important therapeutic appli-cations. Finally, IECs communicate with immune cells to initiate either inflammatory responses or tolerance in response to lumen signals (Biton et al., 2011; Peterson and Artis, 2014).

A rare IEC population, tuft cells (Gerbe et al., 2012) promote type-2 immunity in response to intestinal parasites by expressing interleukin-25 (1125), which in turn mediates the recruitment of group 2 of innate lymphoid cells (ILC2s) that initiate the expansion of T-helper type 2 cells upon parasite infection (Gerbe et al., 2016; Howitt et al., 2016; von Moltke et al., 2016). Furthermore, M cells reside exclusively in follicle-associated epithelia found only above Peyer's patches, which are gut associated lymphoid follicles (de Lau et al., 2012). M cells play an important role in immune sensing by transporting luminal content to immune cells found directly below them (Mabbott et al., 2013). Disruption in any of the major innate immune sensors and proximity effector functions of IECs may result in increased antigenic load through weakening of the epithelial barrier, and may lead to the onset of acute or chronic inflammation. Despite this extensive knowledge, given the complexity of the epithelial cellular ecosystem, many questions remain open.

The present invention identifies discrete epithelial cell types of the gut and respiratory tract, additional types, or new sub-types that have eluded previous studies. The pres-ent invention also provides a molecular characterization of each type. For example, mapping the GPCRs and hormones expressed by EECs has important therapeutic applications; charting known and new specific cell surface markers can provide handles for specific cell isolation, and help assess the validity of legacy ones; and finding differentially expressed transcription factors (TFs) can open the way to study the molecular processes that accompany the differen-tiation of IECs, such as tuft or enteroendocrine cells. The present invention also identifies targets and pathways involved in the response of individual cell populations to pathogenic insult, both in terms of changes in cellular proportions and cell-intrinsic responses.

Tuft Cells: Tuft cells, sometimes referred to as brush cells, are chemosensory cells in the epithelial lining of the intes-tines and respiratory tract. The names "tuft" and "brush" refer to the microvilli projecting from the cells. Ordinarily there are very few tuft cells present but they have been shown to greatly increase at times of a infection, including parasitic infection. Several studies have proposed a role for tuft cells in defense against parasitic infection. In the intes-tine, tuft cells are the sole source of secreted interleukin 25 (IL-25), a cytokine involved in type 2 immunity (Harris, Science (2016) Vol. 351, Issue 6279, pp. 1264-1265; and Howitt and Lavoie (2016) Science. 351: 1329-33). Appli-cants have discovered for the first time signature genes specific for tuft cells in the gut and respiratory tract that can be used to isolate, detect and target tuft cells, specifically novel subtypes of tuft cells (e.g., neuronal, immune). Prior to the present invention, the specific subtypes of tuft cells could not be detected or modulated.

Type 2 innate lymphoid cells (ILC2s) regulate the initia-tion of allergic tissue inflammation at mucosal surfaces, in large part due to their ability to rapidly produce effector cytokines such as IL-5 and IL-13 (Neill, D. R. et al. Nature 464, 1367-1370, (2010); and Moro, K. et al. Nature 463, 540-544, (2010)). ILCs are also vital in maintaining tissue homeostasis by promoting epithelial cell proliferation, sur-vival, and barrier integrity (Monticelli, L. A. et al. Nature immunology 12, 1045-1054, (2011)). Alarmin cytokines, such as IL-25 and IL-33, activate ILC2s to promote tissue homeostasis in the face of epithelial injury, but also play critical roles in initiating allergic inflammatory responses (Huang, Y. et al. Nature immunology 16, 161-169, (2015); Cheng, D. et al. American journal of respiratory and critical care medicine 190, 639-648, (2014); and Gudbjartsson, D. F. et al. Nature genetics 41, 342-347, (2009)).

Accordingly, one aspect, embodiment disclosed herein provide isolated cells, in particular isolated tuft cells. The isolated tuft cell may be a gastrointestinal tuft cell or subset of a gastrointestinal tuft cell, or a respiratory tuft cell or a subset of respiratory tuft cells. The tuft cell may be a respiratory or digestive system tuft cell. The digestive sys-tem tuft cell may comprise an esophageal epithelial cell, a stomach epithelial cell, or an intestinal epithelial cell. The respiratory tuft cell may comprise a laryngeal epithelial cell, a tracheal epithelial cell, a bronchial epithelial cell, or a submucosal gland cell.

The isolated cells disclosed herein may be defined by the presence of certain markers or gene signatures unique to that isolated cell type or sub-type, or a particular cell state of said cell type or sub-type. As used herein a "cell state" refers to a particular functional state, for example the cell state of a tuft cell in homeostasis, may be differentiated from the cell state of a tuft cell after exposure to certain external stimuli such exposure to certain cytokines after an infection, based on the presence of certain markers or gene signatures.

Markers: The term "marker" is widespread in the art and commonly broadly denotes a biological molecule, more particularly an endogenous biological molecule, and/or a detectable portion thereof, whose qualitative and/or quanti-tative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoroarabinose, etc.).

Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof.

A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Unless otherwise apparent from the context, reference herein to any marker, such as a peptide, polypeptide, protein, or nucleic acid, may generally also encompass modified forms of the marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of the peptide, polypeptide, or protein. For example, insofar not exceeding the length of the full-length peptide, polypeptide, or protein, a fragment may include a sequence of $\geq 5$ consecutive amino acids, or $\geq 10$ consecutive amino acids, or $\geq 20$ consecutive amino acids, or $\geq 30$ consecutive amino acids, e.g., $\geq 40$ consecutive amino acids, such as for example $\geq 50$ consecutive amino acids, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of the nucleic acid. For example, insofar not exceeding the length of the full-length nucleic acid, a fragment may include a sequence of $\geq 5$ consecutive nucleotides, or $\geq 10$ consecutive nucleotides, or $\geq 20$ consecutive nucleotides, or $\geq 30$ consecutive nucleotides, e.g., $\geq 40$ consecutive nucleotides, such as for example $\geq 50$ consecutive nucleotides, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis. The phrase "gene or gene product signature" as intended throughout this specification refers to a set, group or collection of one or more, preferably two or more markers, such as genes or gene products, the expression status or profile of which is associated with or identifies a specific cell type, cell subtype, or cell state of a specific cell type or subtype. Such gene or gene product signatures can be used for example to indicate the presence of a specific cell type, cell subtype, or cell state of a specific cell type or subtype in a population of cells, and/or the overall cell type composition or status of an entire cell population. Such gene or gene product signatures may be indicative of cells within a population of cells in vivo. Preferably, a reference herein to a gene or gene product signature comprising or consisting of one or more genes or gene products from a discrete list of genes or gene products may denote that the genes or gene products said to be comprised by or constituting the signature are expressed in a specific cell type, cell subtype, or cell state of a specific cell type or subtype, i.e., that cells of the specific cell type, cell subtype, or cell state of the specific cell type or subtype are positive for the genes or gene products comprised by the signature.

Gene Signatures: Typically, a gene signature may comprise or consist of two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more, or 200 or more, or 300 or more, or 400 or more, or 500 or more genes or gene products. Where the present specification refers to a signature as comprising or consisting of one or more genes set forth in a given Table, the signature may comprise of consist of, by means of example and without limitation, one, or two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more (provided that the recited number does not exceed the number of genes or gene products listed in the Table) or substantially all or all genes or gene products as set forth in the Table. In certain embodiments, the signature may comprise or consist of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or at least 95%, e.g., 96%, 97%, 98%, 99%, or up to 100% (by number) of the genes or gene products set forth in the Table (rounded up or down as conventional to the closest integer).

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (be it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to further modulate intestinal epithelial cells. The signatures of the present invention may be discovered by analysis of expression profiles of single-cells within a population of cells from isolated samples (e.g. biopsy), thus allowing the discovery of novel cell subtypes or cell states that were previously invisible or unrecognized.

The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular phenotype of an intestinal epithelial cell, intestinal epithelial stem cell, or intestinal immune cell. Induction or suppression of a particular signature may consequentially be associated with or causally drive a particular phenotype.

Various aspects and embodiments of the invention may involve analyzing gene signature(s), protein signature(s), and/or other genetic signature(s) based on single cell analyses (e.g. single cell RNA sequencing) or alternatively based on cell population analyses, as is defined herein elsewhere.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type.

Markers as taught herein or genes or gene products comprised by or constituting gene or gene product signatures as taught herein, or the gene or gene product signatures as taught herein, may display AUC (area under the receiver-operating curve (ROC) as well-established in the art) value of 0.70 or more, e.g., 0.75 or more, preferably 0.80 or more, more preferably 0.85 or more, even more preferably 0.90 or more, and still more preferably 0.95 or more, e.g., 0.96, 0.97, 0.98, 0.99, or 1.00. An AUC value of 1 implies that the marker, gene, gene product or signature is a perfect classifier for a given outcome (e.g., a cell type or cluster). An AUC value of 0.50 implies no predictive value for the outcome.

A marker, for example a gene or gene product, for example a peptide, polypeptide, protein, or nucleic acid, or a group of two or more markers, is "measured" in a tested object (e.g., in or on a cell, cell population, tissue, organ, or organism, e.g., in a biological sample of a subject) when the presence or absence and/or quantity of the marker or the group of markers is detected or determined in the tested object, preferably substantially to the exclusion of other molecules and analytes, e.g., other genes or gene products.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to another value, such as relative to a reference value. Performing a relative comparison between first and second variables (e.g., first and second quantities) may but need not require determining first the absolute values of the first and second variables. For example, a measurement method may produce quantifiable readouts (such as, e.g., signal intensities) for the first and second variables, wherein the readouts are a function of the value of the variables, and wherein the readouts may be directly compared to produce a relative value for the first variable vs. the second variable, without the actual need to first convert the readouts to absolute values of the respective variables.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed for example as a percentage or fraction (by number) of cells comprised in the population that are positive for the marker, or as percentages or fractions (by number) of cells comprised in the population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample of a subject).

In certain examples, such methods may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI- (MS)$^n$; atmospheric pressure photoionization mass spectrometry (APPI-MS); APPI-MS/MS; and APPI- (MS)$^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between the mobile phase and the stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from.

In certain embodiments, the invention involves plate based single cell RNA sequencing (see, e.g., Picelli, S. et al., 2014, "Full-length RNA-seq from single cells using Smartseq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain example embodiments, the tuft cell may be characterized by the expression one or more, two or more, three or more, four or more, five or more, six or more, seven or more, eight or more, nine or more, or ten or more genes or polypeptides listed in any one of Table 3-6 or 15A below. In certain example embodiments, the tuft cell is characterized by expression of 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in any one of Tables 3-6 or 15A below.

In another example embodiment, the tuft cell may be characterized by the expression 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in Table 3.

In another example embodiment, the tuft cell may be characterized by the expression 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in Table 4.

In another example embodiment, the tuft cell may be characterized by the expression 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in Table 5.

In another example embodiment, the tuft cell may be characterized by the expression 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in Table 6.

In another example embodiment, the tuft cell may be characterized by the expression 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of the genes or polypeptides listed in Table 15A.

In another example embodiment, the tuft cell may be characterized by the expression of the genes or polypeptides listed in Table 3, Table 4, Table 5, Table 6, Table 8 or Table 15A.

In certain example embodiments, the tuft cell may be characterized by expression of Lrmp, Dclk1, Cd24a, Tas1r3, Ffar3, Sucnr1, Gabbr1, Drd3, Etv1, Gfi1b, Hmx2, Hmx3, Runx1, Jarid2, Nfatc1, Zfp710, Zbtb41, Spib, Foxe1, Sox9, Pou2f3, Ascl2, Ehf, Tcf4, Gprc5c, Sucnr1, Ccrl1, Gprc5a, Opn3, Vmn2r26 and Tas1r3. In another example embodiment, the tuft cell may be characterized by expression of Cd24a, Tas1r3, Ffar3, Sucnr1, Gabbr1 and Drd3. In another example embodiment, the tuft cell may be characterized by expression of Etv1, Gfi1b, Hmx2, Hmx3, Runx1, Jarid2, Nfatc1, Zfp710, Zbtb41, Spib, Foxe1, Sox9, Pou2f3, Ascl2, Ehf and Tcf4. In another example embodiment, the tuft cell may be characterized by expression of Etv1, Hmx2, Spib, Foxe1, Sox9, Pou2f3, Ascl2, Ehf and Tcf4. In another example embodiment, the tuft cell may be characterized by expression of Ffar3, Gprc5c, Sucnr1, Ccrl1, Gprc5a, Opn3, Vmn2r26 and Tas1r3. In another example embodiment, the tuft cell may be characterized by the expression of Etv1, Hmx2, Spib, Foxe1, Pou2f3, Sox9, Ascl2, Hoxa5, Hivep3, Ehf Tcf4, Mxd4, Hmx3, Hoxa3 and Nfatc1. In another example embodiment, the tuft cell may be characterized by expression of Lrmp, Gnat3, Gnb3, Plac8, Trpm5, Gng13, Ltc4s, Rgs13, Hck, Alox5ap, Avil, Alox5, Ptpn6, Atp2a3 and Pik2. In another example embodiment, the tuft cell may be characterized by expression of Rgs13, Rpl41, Rps26, Zmiz1, Gpx3, Suox, Tslp and Socs1.

In certain example embodiments, the tuft cell may be characterized by primarily a chemosensory cell state. In certain example embodiments, the chemosensory cell state may be characterized by the expression of Trpm5, Pou2fs, Gnb3, Gng13, Atpb1b1, Fxyd6, Tas2R38, Tas2R105, Tas2R108, Tas1r3, or combinations thereof. In additional to a chemosensory role such tuft cells may play a role in sensing of bacterial infection, in particular gram-negative infection, as characterized by expression of Tas2R38, and/or regulation of breathing as characterized by expression of Tas2R105, Tas2R108, Tas1r3, or a combination thereof.

In certain other example embodiments, the tuft cell may be characterized by having primarily immune and/or inflammatory state characterized by the expression of Gfi1B, Spib, Sox9, Mgst3, Alox5ap. Ptprc (CD45), or a combination thereof.

Methods of Detecting and Isolating Cells

A further aspect of the invention thus relates to a method for detecting or quantifying intestinal epithelial cells, intestinal epithelial stem cells, intestinal immune cells or respiratory epithelial cells in a biological sample of a subject, or for isolating such cells from a biological sample of a subject, the method comprising: a) providing a biological sample of a subject; and b) detecting or quantifying in the biological sample intestinal epithelial cells, intestinal epithelial stem cells, or preferably intestinal epithelial cells as disclosed herein, or isolating from the biological sample such cells as disclosed herein.

The method may allow for detecting or concluding the presence or absence of the specified intestinal epithelial cells, intestinal epithelial stem cells, intestinal immune cells, or respiratory (e.g., airway) epithelial cells (preferably epithelial cells, e.g., tuft cells) in a tested object (e.g., in a cell population, tissue, organ, organism, or in a biological sample of a subject). The method may also allow to quantify the specified intestinal epithelial cells, intestinal epithelial stem cells, intestinal immune cells, or respiratory epithelial cells (preferably epithelial cells, e.g., tuft cells) in a tested object (e.g., in a cell population, tissue, organ, organism, or in a biological sample of a subject). The quantity of the specified cells in the tested object such as the biological sample may be suitably expressed for example as the number (count) of the specified cells per standard unit of volume (e.g., ml, µl or nl) or weight (e.g., g or mg or ng) of the tested object such as the biological sample ormay also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) intestinal epithelial cells, intestinal epithelial stem cells, intestinal immune cells, or respiratory epithelial cells (preferably epithelial cells, e.g., tuft cells) and of different (sub) types comprised in the tested object such as the biological sample (e.g., neuronal or immune tuft cells). The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

In certain embodiments, methods to detect or conclude the presence or absence of a specified cell may be used to diagnose a disease or disorder. Specifically, the methods disclosed herein may be used to identify a particular tuft cell type, sub-type, cell state associated with presence or absence of a particular disease or disorder. For example, detection of increased tuft cells associated with an immune-like cell state may indicate the presence of inflammation, infection, or any other other diseases or conditions described herein.

The method may allow to isolate or purify the specified intestinal epithelial cells, intestinal epithelial stem cells, intestinal immune cells, or respiratory epithelial cells (preferably epithelial cells, e.g., tuft cells) from the tested object such as the biological sample. The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc.

In some aspects the present disclosure refers to a method of identifying a cell or cell marker identified above, comprising: a) isolating target cells based on a marker specifically expressed in or on the cell or by label-free imaging flow cytometry; b) quantifying gene expression in the target cells by single cell sequencing, and c) clustering the target cells based on the gene expression by application of one or more algorithms, d) optionally determining a transcription signature for each cluster based at least in part on identifying differentially expressed genes between two or more clusters and between each cluster and the remaining cells as background, and e) optionally validating gene expression against cellular morphology.

In some examples of the present disclosure identifying differentially expressed transcripts comprises application of a supervised or unsupervised machine-learning model. A supervised machine learning model is for example selected from the group consisting of an analytical learning model, an artificial neural network model, a back propagation model, a boosting model, a Bayesian statistics model, a case-based model, a decision tree learning model, an inductive logic programming model, a Gaussian process regression model, a group method of data handling model, a kernel estimator model, a learning automata model, a minimum message length model, a multilinear subspace learning, a naïve bayes classifer model, a nearest neighbor model, a probably approximately correct (PAC) learning model, a ripple down rules model, a symbolic machine learning model, a subsymbolic machine learning model, a support vector machine learning model, a minimum complexity machine model, a random forest model, an ensemble of classifiers model, an ordinal classification model, a data pre-processing model, a handling imbalanced datasets model, a statistical relational learning model, a Proaftn model. An unsupervised machine learning model is for example selected from the group consisting of a k-means model, a mixture model, a hierarchical clustering model, an anomaly detection model, a neural network model, an expectation-maximization (EM) model, a method of moments model, or a blind signal separation technique.

These models are used separately or in combination with each other or in combination with any other machine-learning model, wherein a supervised model is combined with a supervised model, or an unsupervised model is combined with an unsupervised model or a supervised model is combined with an unsupervised model.

In other examples of the previous aspects (optional) validating gene expression against cellular morphology comprises sparse labeling the cell to enhance the expression of a fluorescent protein in the cell and combining the sparse labeling with fluorescent in situ hybridization (FISH) to validate the marker against cellular morphology in step e). In examples of the previous aspects FISH is for example combined with a specific antibody, double FISH or a transgenic reporter mouse line directed to a previously identified marker in the cell. For example, an enhancer element is inserted into a lentivirus or an adeno-associated virus (AAV) vector upstream of the fluorescent protein to enhance its expression.

A further aspect of the invention thus relates to a method for detecting or quantifying intestinal epithelial cells, intestinal epithelial stem cells, intestinal immune cells, or respiratory epithelial cells in a biological sample of a subject, or for isolating such cells from a biological sample of a subject, the method comprising: a) providing a biological sample of a subject; and b) detecting or quantifying in the biological sample intestinal epithelial cells, intestinal epithelial stem cells, or preferably intestinal epithelial cells as disclosed herein, or isolating from the biological sample such cells as disclosed herein.

The method may allow for detecting or concluding the presence or absence of the specified intestinal epithelial cells, intestinal epithelial stem cells, intestinal immune cells, or respiratory (e.g., airway) epithelial cells (preferably epithelial cells, e.g., tuft cells) in a tested object (e.g., in a cell population, tissue, organ, organism, or in a biological sample of a subject). The method may also allow to quantify the specified intestinal epithelial cells, intestinal epithelial stem cells, intestinal immune cells, or respiratory epithelial cells (preferably epithelial cells, e.g., tuft cells) in a tested object (e.g., in a cell population, tissue, organ, organism, or in a biological sample of a subject). The quantity of the specified cells in the tested object such as the biological sample may be suitably expressed for example as the number (count) of the specified cells per standard unit of volume (e.g., ml, µl or nl) or weight (e.g., g or mg or ng) of the tested object such as the biological sample ormay also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) intestinal epithelial cells, intestinal epithelial stem cells, intestinal immune cells, or respiratory epithelial cells (preferably epithelial cells, e.g., tuft cells) and of different (sub) types comprised in the tested object such as the biological sample (e.g., neuronal or immune tuft cells). The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

The method may allow to isolate or purify the specified intestinal epithelial cells, intestinal epithelial stem cells, intestinal immune cells, or respiratory epithelial cells (preferably epithelial cells, e.g., tuft cells) from the tested object such as the biological sample. The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc.

Isolating or purifying the specified intestinal epithelial cells, intestinal epithelial stem cells, intestinal immune cells, or respiratory epithelial cells (preferably epithelial cells, e.g., tuft cells) from the tested object such as the biological sample may increase the abundance of the specified cells relative to all other cells comprised in the tested object such as the biological sample, or relative to other cells of a select subset of the cells comprised in the tested object such as the biological sample.

By means of example, isolating or purifying the specified cells from the tested object such as the biological sample may yield a cell population, in which the specified cells constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The intestinal epithelial cells, intestinal epithelial stem cells, intestinal immune cells, or respiratory epithelial cells (preferably epithelial cells, e.g., tuft cells) disclosed herein are generally described or characterized with reference to certain marker(s) or combination(s) of markers (such as genes or gene products, e.g., peptides, polypeptides, proteins, or nucleic acids) expressed or not expressed by the cells, or with reference to certain gene or gene product signature(s) comprised by the cells. Accordingly, the present methods for detecting, quantifying or isolating the specified cells may be marker-based or gene or gene product signature-based, i.e., may involve detection, quantification or isolation of cells expressing or not expressing marker(s) or combination(s) of markers the expression or lack of expression of which is taught herein as typifying or characterising the specified cells, or may involve detection, quantification or isolation of cells comprising gene or gene product signature(s) taught herein as typifying or characterising the specified cells.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified intestinal epithelial cells, intestinal epithelial stem cells, intestinal immune cells, or respiratory epithelial cells (preferably epithelial cells, e.g., tuft cells) in, or to isolate the specified cells from, a tested object (e.g., a cell population, tissue, organ, organism, or a biological sample of a subject). Such methods allow to detect, quantify or isolate the specified cells in or from the tested object (e.g., a cell population, tissue, organ, organism, or a biological sample of a subject) substantially to the exclusion of other cells comprised in the tested object.

Such methods may allow to detect, quantify or isolate the specified cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified cells.

In certain embodiments, methods for detecting, quantifying or isolating the specified cells may comprise treatment(s) or step(s) which diminish or eliminate the viability of the cells. For example, methods which comprise measuring intracellular marker(s) typically necessitate permeabilization of the cell membrane and possibly fixation of the cells; and methods which comprise measuring nucleic acid marker(s) may typically necessitate obtaining nucleic acids (such as particularly RNA, more particularly mRNA) from the cells. In certain other embodiments, methods for detecting, quantifying or isolating the specified cells may substantially preserve the viability of the cells. For example, methods which comprise measuring extracellular or cell surface marker(s) need not disturb the integrity of the cell membrane and may not require fixation/permeabilization of the cells. By means of an example, methods for detecting, quantifying or isolating the specified cells may be configured such that at least 40% (by number), for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of the detected, quantified or isolated cells remain viable. The term "viable cells" as used throughout this specification refers to cells that can be qualified as viable by tests and assays known per se. For instance, the viability of cells may be measured using conventional dye exclusion assays, such as Trypan Blue exclusion assay or propidium iodide exclusion assay. In such assays, viable cells exclude the dye and hence remain unstained, while non-viable cells take up the dye and are stained. The cells and their uptake of the dye can be visualised and revealed by suitable techniques (e.g., conventional light microscopy, fluorescence microscopy, or flow cytometry), and viable (unstained) and non-viable (stained) cells in the tested sample can be counted.

In certain embodiments, methods for detecting, quantifying or isolating the specified intestinal epithelial cells, intestinal epithelial stem cells, intestinal immune cells, or respiratory epithelial cells (preferably epithelial cells, e.g., tuft cells) may be single-cell-based, i.e., may allow to discretely detect, quantify or isolate the specified cells as individual cells. In other embodiments, methods for detecting, quantifying or isolating the specified cells may be cell population-based, i.e., may only allow to detect, quantify or isolate the specified cells as a group or collection of cells, without providing information on or allowing to isolate individual cells.

Methods for detecting, quantifying or isolating the specified intestinal epithelial cells, intestinal epithelial stem cells, intestinal immune cells, or respiratory epithelial cells (preferably epithelial cells, e.g., tuft cells) may employ any of the above-described techniques for measuring markers, insofar the separation or the qualitative and/or quantitative measurement of the marker(s) can be correlated with or translated into detection, quantification or isolation of the specified cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified cells.

In certain embodiments, the intestinal epithelial cells, intestinal epithelial stem cells, intestinal immune cells, or respiratory epithelial cells (preferably epithelial cells, e.g., tuft cells) are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analysed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyse cells by replacing fluorochrome-labelled binding reagents with mass tagged binding reagents, i.e., tagged with an element or isotope having a defined mass. In these methods, labelled particles are introduced into a mass cytometer, where they are individually atomised and ionised. The individual particles are then subjected to elemental analysis, which identifies and measures the abundance of the mass tags used. The identities and the amounts of the isotopic elements associated with each particle are then stored and analysed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analysed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 $\mu$m, more preferably less than 400 $\mu$m, more preferably less than 300 $\mu$m, more preferably less than 200 $\mu$m, e.g., 100 $\mu$m or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

In certain embodiments, the aforementioned methods and techniques may employ agent(s) capable of specifically binding to one or more gene products, e.g., peptides, polypeptides, proteins, or nucleic acids, expressed or not expressed by the intestinal epithelial cells, intestinal epithelial stem cells, intestinal immune cells, or respiratory epithelial cells (preferably epithelial cells, e.g., tuft cells) as taught herein. In certain preferred embodiments, such one or more gene products, e.g., peptides, polypeptides, or proteins, may be expressed on the cell surface (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridisation probes or amplification or sequencing primers and primer pairs), small molecules, or combinations thereof.

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant ($K_A$) of such binding $K_A \geq 1 \times 10^6$ $M^{-1}$, more preferably $K_A \geq 1 \times 10^7$ $M^{-1}$, yet more preferably $K_A \geq 1 \times 10^8$ $M^{-1}$, even more preferably $K_A \geq 1 \times 10^9$ $M^{-1}$, and still more preferably $K_A \geq 1 \times 10^{10}$ $M^{-1}$ or $K_A \geq 1 \times 10^{11}$ $M^{-1}$ or $K_A \geq 1 \times 10^{12}$ $M^{-1}$, wherein $K_A = [SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immuno-globulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos*, *Lama glama* or *Lama vicugna*) or horse. An antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_d$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

The term "oligonucleotide" as used throughout this specification refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, increased stability in the presence of nucleases and increased hybridization affinity, increased tolerance for mismatches, etc. The reference to oligonucleotides may in particular but without limitation include hybridisation probes and/or amplification primers and/or sequencing primers, etc., as commonly used in nucleic acid detection technologies.

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to the target nucleic acid sequence. Antisense agents suitable for use herein, such as hybridisation probes or amplification or sequencing primers and primer pairs) may typically be capable of annealing with (hybridising to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In certain embodiments, the one or more binding agents may be one or more antibodies. In other embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni^{2+}$), maltose:maltose binding protein, etc. In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof. In certain embodiments, the one or more binding agents are one or more antibodies.

A marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

Inflammatory Diseases of the Gut and Respiratory System

In certain embodiments, tuft cells are modulated to treat inflammatory diseases. In certain embodiments, tuft cells are modulated to shift immune-like tuft-2 cells to be more tuft-1 neuronal like. In certain embodiments, tuft cells are modulated to shift tuft-1 neuronal cells to be more immune-like tuft-2 like. In certain embodiments, a signature gene specific for a tuft cell is targeted to modulate tuft cells in vivo. In certain embodiments, specific tuft cells are targeted to reduce an inflammatory response. Targeted cells may be activated or inhibited. In certain embodiments, basal cells are targeted to differentiate into a specific subset of tuft cells. In certain embodiments, a signature gene specific for a tuft cell is targeted to modulate basal cells in vivo.

Inflammatory bowel disease (IBD) is a group of inflammatory conditions of the colon and small intestine, principally including Crohn's disease and ulcerative colitis, with other forms of IBD representing far fewer cases (e.g., collagenous colitis, lymphocytic colitis, diversion colitis, Behçet's disease and indeterminate colitis). Pathologically, Crohn's disease affects the full thickness of the bowel wall (e.g., transmural lesions) and can affect any part of the gastrointestinal tract, while ulcerative colitis is restricted to the mucosa (epithelial lining) of the colon and rectum.

Graft-versus-host disease (GVHD) is an immune-related disease that can occur following an allogeneic tissue transplant. It is commonly associated with stem cell or bone marrow transplants, but GVHD also applies to other forms of tissue graft. In GVHD immune cells of the tissue graft recognize the recipient host as foreign and attack the host's cells.

It has long been recognized that IBD and GVHD are diseases associated with increased immune activity. The causes of IBD, while not well understood, may be related to an aberrant immune response to the microbiota in genetically susceptible individuals. IBD affects over 1.4 million people in the United States and over 2.2 million in Europe and is on the increase. With both environmental and genetic factors playing a role in the development and progression of IBD, response to current treatments (e.g., anti-inflammatory drugs, immune system suppressors, antibiotics, surgery, and other symptom specific medications) are unpredictable.

Similarly, a fundamental feature of GVHD is increased immune activity. As yet, the pathophysiology underlying GVHD is not well understood. It is a significant cause of morbidity and mortality following allogenic haematopoietic stem-cell transplantation and thus the focus of much ongoing research. Despite the advances in understanding the pathophysiology (e.g., predisposing factors), a standardized therapeutic strategy is still lacking. Currently both acute and chronic forms of GVHD are treated using corticosteroids (e.g., anti-inflammatory treatments). There is a need for new approaches to treating IBD and GVHD.

Some of the genetic factors predisposing one to IBD are known, as explored in Daniel B. Graham and Ramnik J. Xavier "From Genetics of Inflammatory Bowel Disease Towards Mechanistic Insights" *Trends Immunol.* 2013

August; 34(8): 371-378 (incorporated herein). This disclosure provides a rationale for modulating intestinal epithelial cell balance, function, differentiation and/or activity for the treatment of both IBD and GVHD, and other disorders.

In certain embodiments, the IBD is Crohn's disease or ulcerative colitis. In certain embodiments, the IBD is collagenous colitis, lymphocytic colitis, diversion colitis, Behçet's disease, or indeterminate colitis.

In other embodiments, the GVHD is acute graft- versus-host disease (aGVHD) or chronic graft-versus-host disease (cGVHD).

Asthma is characterized by recurrent episodes of wheezing, shortness of breath, chest tightness, and coughing. Sputum may be produced from the lung by coughing but is often hard to bring up. During recovery from an attack, it may appear pus-like due to high levels of eosinophils. Symptoms are usually worse at night and in the early morning or in response to exercise or cold air. Some people with asthma rarely experience symptoms, usually in response to triggers, whereas others may have marked and persistent symptoms. Chronic rhino-sinusitis (CRS) is characterized by inflammation of the mucosal surfaces of the nose and para-nasal sinuses, and it often coexists with allergic asthma. Atopic dermatitis is a chronic inflammatory skin disease that is characterized by eosinophilic infiltration and high serum IgE levels. Similar to allergic asthma and CRS, atopic dermatitis has been associated with increased expression of TSLP, IL-25, and IL-33 in the skin. Primary eosinophilic gastrointestinal disorders (EGIDs), including eosinophilic esophagitis (EoE), eosinophilic gastritis, eosinophilic gastroenteritis, and eosinophilic colitis, are disorders that exhibit eosinophil-rich inflammation in the gastrointestinal tract in the absence of known causes for eosinophilia such as parasite infection and drug reaction.

In certain embodiments, tuft cells induce an TLC2 inflammatory response. A skilled person can readily determine diseases that can be treated by reducing an ILC2 inflammatory response. ILC2 cells and ILC2 inflammatory responses have been associated with allergic asthma, therapy resistant-asthma, steroid-resistant severe allergic airway inflammation, systemic steroid-dependent severe eosinophilic asthma, chronic rhino-sinusitis (CRS), atopic dermatitis, food allergies, persistence of chronic airway inflammation, and primary eosinophilic gastrointestinal disorders (EGIDs), including but not limited to eosinophilic esophagitis (EoE), eosinophilic gastritis, eosinophilic gastroenteritis, and eosinophilic colitis (see, e.g., Van Rijt et al., Type 2 innate lymphoid cells: at the cross-roads in allergic asthma, Seminars in Immunopathology July 2016, Volume 38, Issue 4, pp 483-496; Rivas et al., IL-4 production by group 2 innate lymphoid cells promotes food allergy by blocking regulatory T-cell function, J Allergy Clin Immunol. 2016 September; 138(3):801-811.e9; and Morita, Hideaki et al. Innate lymphoid cells in allergic and nonallergic inflammation, Journal of Allergy and Clinical Immunology, Volume 138, Issue 5, 1253-1264). In certain embodiments, modulation of tuft cells can be used to modulate ILC2 inflammatory responses.

In certain embodiments, tuft cells may be modulated to treat other diseases. In certain embodiments, the diseases are localized to a mucosal surface. The terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy.

The term "infection" as used herein refers to presence of an infective agent, such as a pathogen, e.g., a microorganism, in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

The term "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less); tachycardia (at least 90 beats per minute); tachypnea (at least 20 breaths per minute or $PaCO_2$ less than 4.3 kPa (32.0 mm Hg) or the need for mechanical ventilation); and an altered white blood cell (WBC) count of $12 \times 10^6$ cells/mL or more, or an altered WBC count of $4 \times 10^6$ cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteraemia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

The term "proliferative disease" generally refers to any disease or disorder characterised by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterised by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor. The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

Diagnosis, Prognosis, Monitoring

In certain embodiments, the markers described herein are used to make a diagnosis, prognosis or used to monitor a disease according to the methods described herein. In certain embodiments, markers are detected and/or quantified. In certain embodiments, cells are detected and/or quantified.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having the disease or condition. For example, a prediction of a disease or condition in a subject may indicate a probability, chance or risk that the subject will develop the disease or condition, for example within a certain time period or by a certain age. The probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Cell-Based Therapeutics

The embodiments disclosed herein also provide cell-based therapeutic compositions comprising the isolated and/or modified tuft cells. The cell-based therapeutics may be used to restore homeostatic balance in one of the diseased tissues disclosed herein. For example, cell-based therapeutics may be used to deliver tuft cells modified to be primarily chemosensory or immune-like depending on the condition that needs to be treated. The isolated cells used in the cell based therapeutics may be allogenic or autologous. Tuft cells may be modified ex vivo and transferred to a subject in need thereof. In certain embodiments, a signature gene specific for a tuft cell is targeted to modulate tuft cells ex vivo. In certain embodiments, a signature gene specific for a tuft cell is targeted to modulate basal cells ex vivo. In certain embodiments, basal cells are differentiated into a specific subset of tuft cells.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatizers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, antiapoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

In some embodiments, the tuft cells or their progenitor cells are implanted in the subject as part of a composition further comprising a scaffold. In some embodiments, the scaffold is biodegradable.

In some embodiments, the scaffold comprises a natural fiber, a synthetic fiber, decellularized lung tissue, or a combination thereof.

In some embodiments, the natural fiber is selected from the group consisting of collagen, fibrin, silk, thrombin, chitosan, chitin, alginic acid, hyaluronic acid, and gelatin.

In some embodiments, the synthetic fiber is selected from the group consisting of: representative bio-degradable aliphatic polyesters such as polylactic acid (PLA), polyglycolic acid (PGA), poly(D,L-lactide-co-glycolide) (PLGA), poly (caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified intestinal or respiratory epithelial cells, epithelial stem cells, or immune cells (preferably epithelial cells, e.g., tuft cells) and/or other active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a population of the intestinal or respiratory epithelial cells, epithelial stem cells, or immune cells (preferably epithelial cells, e.g., tuft cells) as taught herein. The terms "cell population" or "population" denote a set of cells having characteristics in common. The characteristics may include in particular the one or more marker(s) or gene or gene product signature(s) as taught herein. The intestinal or respiratory epithelial cells, epithelial stem cells, or immune cells (preferably epithelial cells, e.g., tuft cells) cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated intestinal or respiratory epithelial cells, epithelial stem cells, or immune cells (preferably epithelial cells, e.g., tuft cells) of populations thereof as disclosed throughout this specification may be suitably cultured or cultivated in vitro. The term "in vitro" generally denotes outside, or external to, a body, e.g., an animal or human body. The term encompasses "ex vivo".

The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Methods of Modulating, Differentiation, and Treating

Embodiments disclosed herein provide methods of modulating epithelial cell proliferation, differentiation, maintenance, and/or function comprising administering to a subject in need thereof a tuft cell modulating agent. The methods may induce differentiation of progenitor cells into tuft cells or particular tuft cell sub-types disclosed herein. The methods may be used to induce shift in the relative amount of tuft cells in a given tissue as a whole or to push the balance of particular population of tuft cells towards one cell type or another. For example, in inflammatory disease, modulating agents may be used to reduce the number of inflammatory tuft cells and/or increase the number of non-inflammatory tuft cells or in order to reduce or mitigate tuft cell contributions to or induction of said inflammatory response.

Within the present specification, the terms "differentiation", "differentiating" or derivatives thereof, denote the process by which an unspecialised or relatively less specialised cell becomes relatively more specialised. In the context of cell ontogeny, the adjective "differentiated" is a relative term. Hence, a "differentiated cell" is a cell that has progressed further down a certain developmental pathway than the cell it is being compared with. The differentiated cell may, for example, be a terminally differentiated cell, i.e., a fully specialised cell capable of taking up specialised functions in various tissues or organs of an organism, which may but need not be post-mitotic; or the differentiated cell may itself be a progenitor cell within a particular differentiation lineage which can further proliferate and/or differentiate.

A relatively more specialized cell may differ from an unspecialized or relatively less specialized cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, electrophysiological behaviour, etc., wherein such characteristics signify the progression of the relatively more specialised cell further along the developmental pathway. Non-limiting examples of differentiation may include, e.g., the change of a pluripotent stem cell into a given type of multipotent progenitor or stem cell, the change of a multipotent progenitor or stem cell into a given type of unipotent progenitor or stem cell, or the change of a unipotent progenitor or stem cell to more specialized cell types or to terminally specialised cells within a given cell lineage.

Any one or more of the several successive molecular mechanisms involved in the expression of a given gene or polypeptide may be targeted in the intestinal epithelial cells, intestinal epithelial stem cells, intestinal immune cells, or respiratory cells (preferably epithelial cells, e.g., tuft cells) cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localization of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalized polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell. Functional genomics can be used to modify cells for therapeutic purposes, and identify networks and pathways. For example, Graham et al. ("Functional genomics identifies negative regulatory nodes controlling phagocyte oxidative burst," *Nature Communications* 6, Article number: 7838 (2015)) describes functional genetic screens to identify the phagocytic oxidative burst.

With the rapid advancement of genomic technology, it is now possible to associate genetic variation with phenotypes of intestinal epithelial cells, intestinal epithelial stem cells, intestinal immune cells, or respiratory epithelial cells (preferably epithelial cells, e.g., tuft cells) at the population level. In particular, genome-wide association studies (GWAS) have implicated genetic loci associated with risk for IBD and allowed for inference of new biological processes that contribute to disease. These studies highlight innate defense mechanisms such as antibacterial autophagy, superoxide generation during oxidative burst and reactive nitrogen species produced by iNOS. However, GWAS requires functional analysis to unlock new insights. For example, many risk loci are densely populated with coding genes, which complicates identification of causal genes. Even when fine mapping clearly identifies key genes, a majority have poorly defined functions in host immunity. Moreover, any given gene may have multiple functions depending on the cell type in which it is expressed as well as environmental cues. Such context-specific functions of regulatory genes are largely unexplored. Thus, human genetics offers an opportunity to leverage insight from large amounts of genetic variation within healthy and patient populations to interrogate mechanisms of immunity. Irrespective of their putative roles in IBD pathology, genes within risk loci are likely to be highly enriched for genes controlling signaling pathways. In certain embodiments, any gene as described herein is targeted. In certain embodiments, a GWAS gene is targeted. In certain embodiments, the gene is modulated by increasing or decreasing expression or activity of the gene.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

It will be understood by the skilled person that treating as referred to herein encompasses enhancing treatment, or improving treatment efficacy. Treatment may include inhibition of an inflammatory response, tumor regression as well as inhibition of tumor growth, metastasis or tumor cell proliferation, or inhibition or reduction of otherwise deleterious effects associated with the tumor.

As used throughout this specification, the terms "treat", "treating" and "treatment" refer to the alleviation or measurable lessening of one or more symptoms or measurable markers of a pathological condition such as a disease or disorder. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

As used throughout this specification, the terms "prevent", "preventing" and "prevention" refer to the avoidance or delay in manifestation of one or more symptoms or measurable markers of a pathological condition, such as a disease or disorder. A delay in the manifestation of a symptom or marker is a delay relative to the time at which such symptom or marker manifests in a control or untreated subject with a similar likelihood or susceptibility of developing the pathological condition. The terms "prevent", "preventing" and "prevention" include not only the avoidance or prevention of a symptom or marker of the pathological condition, but also a reduced severity or degree of any one of the symptoms or markers of the pathological condition, relative to those symptoms or markers in a control or non-treated individual with a similar likelihood or susceptibility of developing the pathological condition, or relative to symptoms or markers likely to arise based on historical or statistical measures of populations affected by the disease or disorder. By "reduced severity" is meant at least a 10% reduction in the severity or degree of a symptom or measurable marker relative to a control or reference, e.g., at least 15%, 20%, 30%, 40%, 50%, 60%, 70%, 80%, 90%, 95%, 99% or even 100% (i.e., no symptoms or measurable markers).

Efficaciousness of treatment is determined in association with any known method for diagnosing or treating the particular disease. The invention comprehends a treatment method comprising any one of the methods or uses herein discussed.

The phrase "therapeutically effective amount" as used herein refers to a sufficient amount of a drug, agent, or compound to provide a desired therapeutic effect.

As used herein "patient" refers to any human being receiving or who may receive medical treatment and is used interchangeably herein with the term "subject".

Modulating Agents

In certain embodiments, the tuft cell modulating agent may comprise a therapeutic antibody, antibody fragment, antibody-like protein scaffold, aptamer, protein, genetic modifying agent or small molecule.

The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

In certain embodiments, the tuft cell modulating agent can refer to a protein-binding agent that permits modulation or activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof.

As used herein, a "blocking" antibody or an antibody "antagonist" is one which inhibits or reduces biological activity of the antigen(s) it binds. For example, an antagonist antibody may bind a surface receptor or ligand and inhibit the ability of the receptor and ligand to induce an ILC class 2 inflammatory response. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Methods for administering antibodies for therapeutic use is well known to one skilled in the art. In certain embodiments, small particle aerosols of antibodies or fragments thereof may be administered, preferably for treating a respiratory inflammatory disease (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as inhibitors or antagonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention (e.g. NMU antibodies) may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetearyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 µg to 1 g, preferably 1-1000 µg, more preferably 2-500, even more preferably 5-50, most preferably 10-20 µg per unit dosage form. In certain embodiments, infusion of antibodies of the present invention may range from 10-500 mg/m$^2$.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The disclosure also encompasses nucleic acid molecules, in particular those that inhibit a target gene. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of poly-nucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxford-journals. org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, *PNAS, E*7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine(5moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas proten (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the compelementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm². In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., nature.com/nmeth/joumal/v2/n6/full/nmeth763.html), 3. GID1-GAIbased system inducibleby Gibberellin (GA) (see, e.g., nature.com/nchembio/joumal/v8/n5/full/nchembio.922.html).

A chemical inducible system can be an estrogen receptor (ER) based system inducible by 4-hydroxytamoxifen (4OHT) (see, e.g., pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogren receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in ortho-pedic therapy. Furthermore, instruments suitable for the application of ultrasound to a subject vertebrate are widely available and their use is well known in the art.

In particular embodiments, the guide molecule is modi-fied by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complemen-tary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodi-ments of the invention, additional sequences comprising an extented length may also be present within the guide mol-ecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advan-tageous that the protected portion does not impede thermo-dynamics of the CRISPR-Cas system interacting with its target. By providing such an extension including a partially double stranded guide molecule, the guide molecule is considered protected and results in improved specific bind-ing of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector pro-teins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-target-ing CRISPR effector"; Science; DOI: 10.1126/sci-ence.aaf5573; and Shmakov et al. (2015) "Discovery and Functional Characterization of Diverse Class 2 CRISPR-Cas Systems", Molecular Cell, DOI: dx.doi.org/10.1016/j.mol-cel.2015.10.008; which are incorporated herein in their entirety by reference. Cas13b has been described in Smar-gon et al. (2017) "Cas13b Is a Type VI-B CRISPR-Associ-ated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by compari-son to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein com-prise one or more HEPN domains comprising a RxxxxH motif sequence. The RxxxxH motif sequence can be, with-out limitation, from a HEPN domain described herein or a HEPN domain known in the art. RxxxxH motif sequences further include motif sequences created by combining por-tions of two or more HEPN domains. As noted, consensus sequences can be derived from the sequences of the orthologs disclosed in U.S. Provisional Patent Application 62/432,240 entitled "Novel CRISPR Enzymes and Sys-tems," U.S. Provisional Patent Application 62/471,710 entitled "Novel Type VI CRISPR Orthologs and Systems" filed on Mar. 15, 2017, and U.S. Provisional Patent Appli-cation 62/484,786 entitled "Novel Type VI CRISPR Orthologs and Systems," filed on Apr. 12, 2017.

In certain other example embodiments, the CRISPR sys-tem effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional 62/432,240 entitled "Novel Crispr Enzymes and Systems" filed Dec. 9, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria*, Corynebacter, Sutterella, *Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: *Leptotrichia shahii, Leptotrichia, wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYLL. WYL1 is a single WYL-domain protein associated primarily with *Ruminococcus*.

In other example embodiments, the Type VI RNA-targeting Cas enzyme is Cas13d. In certain embodiments, Cas13d is *Eubacterium* siraeum DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytindine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)A-DAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenonsine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of. Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient. In one embodiment, the modified cell for cell therapy is a epithelial cell (e.g., tuft cell).

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of Staphylococcus aureus Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both Streptococcus thermophilus Cas9 and also Streptococcus pyogenes Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcus pneumoniae and Escherichia coli. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli,* 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054, 675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054, 528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNC-TIONAL CRISPR-CAS SYSTEMS; U.S. application 62/055,487, 25 Sep. 2014, FUNCTIONAL SCREENING WITH OPTIMIZED FUNCTIONAL CRISPR-CAS SYS-TEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. applica-tion 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Men-tion is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. applica-tion 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGI-NEERING OF SYSTEMS, METHODS AND OPTIMIZED GUIDE COMPOSITIONS WITH NEW ARCHITEC-TURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDIT-ING USING CAS9 NICKASES.

Each of these patents, patent publications, and applica-tions, and all documents cited therein or during their pros-ecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorpo-rated by reference.

In particular embodiments, pre-complexed guide RNA and CRISPR effector protein, (optionally, adenosine deami-nase fused to a CRISPR protein or an adaptor) are delivered as a ribonucleoprotein (RNP). RNPs have the advantage that they lead to rapid editing effects even more so than the RNA method because this process avoids the need for transcrip-tion. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is deliv-ered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypep-tides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcrip-tion. Nat Biotechnol. 2011; 29:149-153 and U.S. Pat. Nos. 8,450,471, 8,440,431 and 8,440,432, all of which are spe-cifically incorporated by reference.

In advantageous embodiments of the invention, the meth-ods provided herein use isolated, non-naturally occurring, recombinant or engineered DNA binding proteins that com-prise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypep-tide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}-(X_{12}X_{13})-X_{14-33}$ or 34 or 35, where the subscript indicates the amino acid position and X represents any amino acid. $X_{12}X_{13}$ indicate the RVDs. In some polypep-tide monomers, the variable amino acid at position 13 is missing or absent and in such polypeptide monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}-(X_{12}X_{13})-X_{14-33}$ or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                    (SEQ. I.D. No. 1)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

```
                                    (SEQ. I.D. No. 2)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains.

The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. The two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

In certain embodiments, a modulant may comprise silencing one or more endogenous genes.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In certain embodiments, a modulant may comprise (i) a DNA-binding portion configured to specifically bind to the endogenous gene and (ii) an effector domain mediating a biological activity.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments, the effector domain may be a transcriptional inhibitor (i.e., a repressor domain), such as an mSin interaction domain (SID). SID4X domain or a Kruppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity.

Other preferred embodiments of the invention may include any combination the activities described herein. In certain embodiments, a modulant may comprise introducing one or more endogenous genes and/or one or more exogenous genes in expressible format into an immune cell, in accordance with the practice of transgenesis as taught elsewhere in this specification.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T cells (including, e.g., thymocytes, Th or Tc; Th1, Th2, Th17, Thαβ, CD4+, CD8+, effector Th, memory Th, regulatory Th, CD4+/CD8+ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

The invention provides compositions and methods for modulating T cell and intestinal or respiratory epithelial cell balance. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products. The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without the modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without the modulation. Preferably, modulation may be specific or selective, hence, one or more desired phenotypic aspects of a cell or cell population may be modulated without substantially altering other (unintended, undesired) phenotypic aspect(s).

In certain embodiments, a modulant may comprise altering expression and/or activity of one or more endogenous genes of the cell. The term "altered expression" denotes that the modification of the cell alters, i.e., changes or modulates, the expression of the recited gene(s) or polypeptides(s). The term "altered expression" encompasses any direction and any extent of the alteration. Hence, "altered expression" may reflect qualitative and/or quantitative change(s) of expression, and specifically encompasses both increase (e.g., activation or stimulation) or decrease (e.g., inhibition) of expression.

"Modulating" can also involve effecting a change (which can either be an increase or a decrease) in affinity, avidity, specificity and/or selectivity of a target gene or cell, such as a cell surface gene (e.g., receptor or ligand). "Modulating" can also mean effecting a change with respect to one or more biological or physiological mechanisms, effects, responses, functions, pathways or activities in which the target gene or cell (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target gene or cell involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

As used herein, the term "modulating T cell balance" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell; controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other CD4+ T cell differentiation; controlling or otherwise influencing the networks that regulate other CD4+ T cell maintenance; controlling or otherwise influencing the networks that regulate other CD4+ T cell function; manipulating or otherwise influencing the ratio of T cells such as, for example, manipulating or otherwise influencing the ratio of Th17 cells to other T cell types such as Tregs or other CD4+ T cells; manipulating or otherwise influencing the ratio of different types of Th17 cells such as, for example, pathogenic Th17 cells and non-pathogenic Th17 cells; manipulating or otherwise influencing at least one function or biological activity of a T cell; manipulating or otherwise influencing at least one function or biological activity of Th cell; manipulating or otherwise influencing at least one function or biological activity of a Treg cell; manipulating or otherwise influencing at least one function or biological activity of a Th17 cell; and/or manipulating or otherwise influencing at least one function or biological activity of another CD4+ T cell.

As used herein, the term "modulating enteric cell balance" comprises cell differentiation types, rates, activity levels, death rate, and more.

The invention provides T cell modulating agents that modulate T cell balance. For example, in some embodiments, the invention provides T cell modulating agents and methods of using these T cell modulating agents to regulate, influence or otherwise impact the level(s) of and/or balance between T cell types, e.g., between Th17 and other T cell types, for example, regulatory T cells (Tregs), and/or Th17 activity and inflammatory potential.

As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

For example, in some embodiments, the invention provides T cell modulating agents and methods of using these T cell modulating agents to regulate, influence or otherwise impact the level of and/or balance between Th17 phenotypes, and/or Th17 activity and inflammatory potential. Suitable T cell modulating agents include an antibody, a soluble polypeptide, a polypeptide agent, a peptide agent, a nucleic acid agent, a nucleic acid ligand, or a small molecule agent.

For example, in some embodiments, the invention provides T cell modulating agents and methods of using these T cell modulating agents to regulate, influence or otherwise impact the level of and/or balance between Th17 cell types, e.g., between pathogenic and non-pathogenic Th17 cells. For example, in some embodiments, the invention provides T cell modulating agents and methods of using these T cell modulating agents to regulate, influence or otherwise impact the level of and/or balance between pathogenic and non-pathogenic Th17 activity.

For example, in some embodiments, the invention provides T cell modulating agents and methods of using these T cell modulating agents to influence or otherwise impact the differentiation of a population of T cells, for example toward Th17 cells, with or without a specific pathogenic distinction, or away from Th17 cells, with or without a specific pathogenic distinction.

For example, in some embodiments, the invention provides T cell modulating agents and methods of using these T cell modulating agents to influence or otherwise impact the differentiation of a population of T cells, for example toward a non-Th17 T cell subset or away from a non-Th17 cell subset. For example, in some embodiments, the invention provides T cell modulating agents and methods of using these T cell modulating agents to induce T cell plasticity, i.e., converting Th17 cells into a different subtype, or into a new state.

For example, in some embodiments, the invention provides T cell modulating agents and methods of using these T cell modulating agents to induce T cell plasticity, e.g., converting Th17 cells into a different subtype, or into a new state.

For example, in some embodiments, the invention provides T cell modulating agents and methods of using these T cell modulating agents to achieve any combination of the above.

The terms "pathogenic" or "non-pathogenic" as used herein are not to be construed as implying that one cell phenotype is more desirable than the other.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal.

One skilled in the art will appreciate that the T cell modulating agents have a variety of uses. For example, the T cell modulating agents are used as therapeutic agents as described herein. The T cell modulating agents can be used as reagents in screening assays, diagnostic kits or as diagnostic tools, or these T cell modulating agents can be used in competition assays to generate therapeutic reagents.

Adoptive Cell Transfer (ACT)

In certain embodiments, a cell-based therapeutic includes engraftment of the cells of the present invention (e.g., tuft cells). As used herein, the term "engraft" or "engraftment" refers to the process of cell incorporation into a tissue of interest in vivo through contact with existing cells of the tissue.

Given the linkage between T cells and epithelial cell differentiation, function and activity, the invention also contemplates the adoptive cell transfer for the modulation of epithelial cells. Adoptive cell therapy or adoptive cell transfer (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may, for example, be employed to genetically modify T cells by altering the specificity of the T cell receptor (TCR), for example, by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761).

Third-generation CARs include a combination of costimulatory endodomains, such a CD3ζ-chain, CD97, GDI1a-CD18, CD2, ICOS, CD27, CD2, CD7, LIGHT, LFA-1, NKG2C, B7-H3, CD30, CD40, PD-1, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T cell attack and/or minimize side effects.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may be eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Various techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3 (and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-

1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T cell manufacturing platform for "off-the-shelf" adoptive T cell immunotherapies, Cancer Res 75 (18): 3853). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T cell receptors (TCR), disrupt the target of a chemotherapeutic agent, block an immune checkpoint, activate a T cell, and/or increase the differentiation and/or proliferation of functionally exhausted or dysfunctional CD8+ T cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system can specifically catalyze cleavage in one targeted gene thereby inactivating the targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via NHEJ often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRa or TCRO can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT. In preferred embodiments, the novel genes or gene combinations described herein are targeted or modulated.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNA-BEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., *Science*. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MHIC-bound antigen peptide presented on the surface of the immune cell as taught herein) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and immune cells may be may be suitably contacted by admixing the T cells and immune cells in an aqueous composition, e.g., in a culture medium, in sufficient numbers and for a sufficient duration of time to produce the desired T cell activation.

Use of T Cell Modulating Agents

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown below in Table 1.

TABLE 1

| T cell Modulating Agents | |
|---|---|
| Target | Agent |
| CCR6 | prostaglandin E2, lipopolysaccharide, mip-3alpha, vegf, rantes, calcium, bortezomib, ccl4, larc, tarc, lipid, *E. coli* B5 lipopolysaccharide |
| CCR5 | cholesterol, cyclosporin a, glutamine, methionine, guanine, simvastatin, threonine, indinavir, lipoxin A4, cysteine, prostaglandin E2, zinc, dapta, 17-alpha-ethynylestradiol, polyacrylamide, progesterone, zidovudine, rapamycin, rantes, glutamate, alanine, valine, ccl4, quinine, NSC 651016, methadone, pyrrolidine dithiocarbamate, palmitate, nor-binaltorphimine, interferon beta-1a, vitamin-e, tak779, lipopolysaccharide, cisplatin, albuterol, fluvoxamine, vicriviroc, bevirimat, carbon tetrachloride, galactosylceramide, ATP-gamma-S, cytochalasin d, hemozoin, CP 96345, tyrosine, etravirine, vitamin d, mip 1alpha, ammonium, tyrosine sulfate, isoleucine, isopentenyl diphosphate, il 10, serine, N-acetyl-L-cysteine, histamine, cocaine, ritonavir, tipranavir, aspartate, atazanavir, tretinoin, ATP, ribavirin, butyrate, N-nitro-L-arginine methyl ester, larc, buthionine sulfoximine, DAPTA, aminooxypentane-rantes, triamcinolone acetonide, shikonin, actinomycin d, bucladesine, aplaviroc, nevirapine, N-formyl-Met-Leu-Phe, cyclosporin A, lipoarabinomannan, nucleoside, sirolimus, morphine, mannose, calcium, heparin, c-d4i, pge2, beta-estradiol, mdms, dextran sulfate, dexamethasone, arginine, ivig, mcp 2, cyclic amp, U 50488H, N-methyl-D-aspartate, hydrogen peroxide, 8-carboxamidocyclazocine, latex, groalpha, xanthine, ccl3, retinoic acid, Maraviroc, sdf 1, opiate, efavirenz, estrogen, bicyclam, enfuvirtide, filipin, bleomycin, polysaccharide, tarc, pentoxifylline, *E. coli* B5 lipopolysaccharide, methylcellulose, maraviroc |
| ITGA3 | SP600125, paclitaxel, decitabine, e7820, retinoid, U0126, serine, retinoic acid, tyrosine, forskolin, Ca2+ |
| IRF4 | prostaglandin E2, phorbol myristate acetate, lipopolysaccharide, A23187, tacrolimus, trichostatin A, stallimycin, imatinib, cyclosporin A, tretinoin, bromodeoxyuridine, ATP-gamma-S, ionomycin |
| BATF | Cyclic AMP, serine, tacrolimus, beta-estradiol, cyclosporin A, leucine |
| RBPJ | zinc, tretinoin |
| PROCR | lipopolysaccharide, cisplatin, fibrinogen, 1,10-phenanthroline, 5-N-ethylcarboxamido adenosine, cystathionine, hirudin, phospholipid, Drotrecogin alfa, vegf, Phosphatidylethanolamine, serine, gamma-carboxyglutamic acid, calcium, warfarin, endotoxin, curcumin, lipid, nitric oxide |
| ZEB1 | resveratrol, zinc, sulforafan, sorafenib, progesterone, PD-0332991, dihydrotestosterone, silibinin, LY294002, 4-hydroxytamoxifen, valproic acid, beta-estradiol, forskolin, losartan potassium, fulvestrant, vitamin d |
| POU2AF1 | terbutaline, phorbol myristate acetate, bucladesine, tyrosine, ionomycin, KT5720, H89 |
| EGR1 | ghrelin, ly294002, silicone, sodium, propofol, 1,25 dihydroxy vitamin d3, tetrodotoxin, threonine, cyclopiazonic acid, urea, quercetin, ionomycin, 12-o-tetradecanoylphorbol 13-acetate, fulvestrant, phenylephrine, formaldehyde, cysteine, leukotriene C4, prazosin, LY379196, vegf, rapamycin, leupeptin, pd 98, 059, ruboxistaurin, pCPT-cAMP, methamphetamine, nitroprusside, H-7, Ro31-8220, phosphoinositide, lysophosphatidylcholine, bufalin, calcitriol, leuprolide, isobutylmethylxanthine, potassium chloride, acetic acid, cyclothiazide, quinolinic acid, tyrosine, adenylate, resveratrol, topotecan, genistein, thymidine, D-glucose, mifepristone, lysophosphatidic acid, leukotriene D4, carbon monoxide, poly rI:rC-RNA, sp 600125, agar, cocaine, 4-nitroquinoline-1-oxide, tamoxifen, lead, fibrinogen, tretinoin, atropine, mithramycin, K+, epigallocatechin-gallate, ethylenediaminetetraacetic acid, h2o2, carbachol, sphingosine-1-phosphate, iron, 5-hydroxytryptamine, amphetamine, SP600125, actinomycin d, SB203580, cyclosporin A, norepinephrine, okadaic acid, ornithine, LY294002, pge2, beta-estradiol, glucose, erlotinib, arginine, 1-alpha, 25-dihydroxy vitamin D3, dexamethasone, pranlukast, phorbol myristate acetate, nimodipine, desipramine, cyclic amp, N-methyl-D-aspartate, atipamezole, acadesine, |

TABLE 1-continued

T cell Modulating Agents

| Target | Agent |
| --- | --- |
| | losartan, salvin, methylnitronitrosoguanidine, EGTA, gf 109203x, nitroarginine, 5-N-ethylcarboxamido adenosine, 15-deoxy-delta-12,14 -PGJ 2, dbc-amp, manganese superoxide, di(2-ethylhexyl) phthalate, egcg, mitomycin C,6,7-dinitroquinoxaline-2,3-dione, GnRH-A, estrogen, ribonucleic acid, imipramine, bapta, L-triiodothyronine, prostaglandin, forskolin, nogalamycin, losartan potassium, lipid, vincristine, 2-amino-3-phosphonopropionic acid, prostacyclin, methylnitrosourea, cyclosporin a, vitamin K3, thyroid hormone, diethylstilbestrol, D-tubocurarine, tunicamycin, caffeine, phorbol, guanine, bisindolylmaleimide, apomorphine, arachidonic acid, SU6656, prostaglandin E2, zinc, ptx1, progesterone, cyclosporin H, phosphatidylinositol, U0126, hydroxyapatite, epoprostenol, glutamate, 5fluorouracil, indomethacin, 5-fluorouracil, RP 73401, Ca2+, superoxide, trifluoperazine, nitric oxide, lipopolysaccharide, cisplatin, diazoxide, tgf beta1, calmidazolium, anisomycin, paclitaxel, sulindac sulfide, ganciclovir, gemcitabine, testosterone, ag 1478, glutamyl-Se-methylselenocysteine, doxorubicin, tolbutamide, cytochalasin d, PD98059, leucine, SR 144528, cyclic AMP, matrigel, haloperidol, serine, sb 203580, triiodothyronine, reverse, N-acetyl-L-cysteine, ethanol, s-nitroso-n-acetylpenicillamine, curcumin, l-nmma, H89, tpck, calyculin a, chloramphenicol, A23187, dopamine, platelet activating factor, arsenite, selenomethylselenocysteine, ropinirole, saralasin, methylphenidate, gentamicin, reserpine, triamcinolone acetonide, methyl methanesulfonate, wortmannin, thapsigargin, deferoxamine, calyculin A, peptidoglycan, dihydrotestosterone, calcium, phorbol-12-myristate, ceramide, nmda, 6-cyano-7-nitroquinoxaline-2,3-dione, hydrogen peroxide, carrageenan, sch 23390, linsidomine, oxygen, clonidine, fluoxetine, retinoid, troglitazone, retinoic acid, epinephrine, n acetylcysteine, KN-62, carbamylcholine, 2-amino-5-phosphonovaleric acid, oligonucleotide, gnrh, rasagiline, 8-bromo-cAMP, muscarine, tacrolimus, kainic acid, chelerythrine, inositol 1,4,5 trisphosphate, yohimbine, acetylcholine, atp, 15-deoxy-delta-12,14-prostaglandin j2, ryanodine, CpG oligonucleotide, cycloheximide, BAPTA-AM, phenylalanine |
| ETV6 | lipopolysaccharide, retinoic acid, prednisolone, valproic acid, tyrosine, cerivastatin, vegf, agar, imatinib, tretinoin |
| IL17RA | rantes, lipopolysaccharide, 17-alpha-ethinylestradiol, camptothecin, *E. coli* B5 lipopolysaccharide |
| EGR2 | phorbol myristate acetate, lipopolysaccharide, platelet activating factor, carrageenan, edratide, 5-N-ethylcarboxamido adenosine, potassium chloride, dbc-amp, tyrosine, PD98059, camptothecin, formaldehyde, prostaglandin E2, leukotriene C4, zinc, cyclic AMP, GnRH-A, bucladesine, thapsigargin, kainic acid, cyclosporin A, mifepristone, leukotriene D4, LY294002, L-triiodothyronine, calcium, beta-estradiol, H89, dexamethasone, cocaine |
| SP4 | betulinic acid, zinc, phorbol myristate acetate, LY294002, methyl 2-cyano-3, 12-dioxoolean-1,9-dien-28-oate, beta-estradiol, Ca2+ |
| IRF8 | oligonucleotide, chloramphenicol, lipopolysaccharide, estrogen, wortmannin, pirinixic acid, carbon monoxide, retinoic acid, tyrosine |
| NFKB1 | Bay 11-7085, Luteolin, Triflusal, Bay 11-7821, Thalidomide, Caffeic acid phenethyl ester, Pranlukast |
| TSC22D3 | phorbol myristate acetate, prednisolone, sodium, dsip, tretinoin, 3-deazaneplanocin, gaba, PD98059, leucine, triamcinolone acetonide, prostaglandin E2, steroid, norepinephrine, U0126, acth, calcium, ethanol, beta-estradiol, lipid, chloropromazine, arginine, dexamethasone |
| PML | lipopolysaccharide, glutamine, thyroid hormone, cadmium, lysine, tretinoin, bromodeoxyuridine, etoposide, retinoid, pic 1, arsenite, arsenic trioxide, butyrate, retinoic acid, alpha-retinoic acid, h2o2, camptothecin, cysteine, leucine, zinc, actinomycin d, proline, stallimycin, U0126 |
| IL12RB1 | prostaglandin E2, phorbol myristate acetate, lipopolysaccharide, bucladesine, 8-bromo-cAMP, gp 130, AGN194204, galactosylceramide-alpha, tyrosine, ionomycin, dexamethasone, il-12 |
| IL21R | azathioprine, lipopolysaccharide, okadaic acid, *E. coli* B5 lipopolysaccharide, calyculin A |
| NOTCH1 | interferon beta-1a, lipopolysaccharide, cisplatin, tretinoin, oxygen, vitamin B12, epigallocatechin-gallate, isobutylmethylxanthine, threonine, apomorphine, matrigel, trichostatin A, vegf, 2-acetylaminofluorene, rapamycin, dihydrotestosterone, poly rI:rC-RNA, hesperetin, valproic acid, asparagine, lipid, curcumin, dexamethasone, glycogen, CpG oligonucleotide, nitric oxide |
| ETS2 | oligonucleotide |
| MINA | phorbol myristate acetate, 4-hydroxytamoxifen |
| SMARCA4 | cyclic amp, cadmium, lysine, tretinoin, latex, androstane, testosterone, sucrose, tyrosine, cysteine, zinc, oligonucleotide, estrogen, steroid, trichostatin A, tpmp, progesterone, histidine, atp, trypsinogen, glucose, agar, lipid, arginine, vancomycin, dihydrofolate |
| FAS | hoechst 33342, ly294002, 2-chlorodeoxyadenosine, glutamine, cd 437, tetrodotoxin, cyclopiazonic acid, arsenic trioxide, phosphatidylserine, niflumic acid, gliadin, ionomycin, safrole oxide, methotrexate, rubitecan, cysteine, propentofylline, vegf, boswellic acids, rapamycin, pd 98, 059, |

TABLE 1-continued

| T cell Modulating Agents | |
|---|---|
| Target | Agent |

|  |  |
|---|---|
|  | captopril, methamphetamine, vesnarinone, tetrapeptide, oridonin, raltitrexed, pirinixic acid, nitroprusside, H-7, beta-boswellic acid, adriamycin, concanamycin a, etoposide, trastuzumab, cyclophosphamide, ifn-alpha, tyrosine, rituximab, selenodiglutathione, chitosan, omega-N-methylarginine, creatinine, resveratrol, topotecan, genistein, trichostatin A, decitabine, thymidine, D-glucose, mifepristone, tetracycline, Sn50 peptide, poly rI:rC-RNA, actinomycin D, sp 600125, doxifluridine, agar, ascorbic acid, acetaminophen, aspirin, tamoxifen, okt3, edelfosine, sulforafan, aspartate, antide, n, n-dimethylsphingosine, epigallocatechin-gallate, N-nitro-L-arginine methyl ester, h2o2, cerulenin, sphingosine-1-phosphate, SP600125, sodium nitroprusside, glycochenodeoxycholic acid, ceramides, actinomycin d, SB203580, cyclosporin A, morphine, LY294002, n(g)-nitro-l-arginine methyl ester, 4-hydroxynonenal, piceatannol, valproic acid, beta-estradiol, 1-alpha, 25-dihydroxy vitamin D3, arginine, dexamethasone, sulfadoxine, phorbol myristate acetate, beta-lapachone, nitrofurantoin, chlorambucil, methylnitronitrosoguanidine, CD 437, opiate, egcg, mitomycin C, estrogen, ribonucleic acid, fontolizumab, tanshinone iia, recombinant human endostatin, fluoride, L-triiodothyronine, bleomycin, forskolin, nonylphenol, zymosan A, vincristine, daunorubicin, prednisolone, cyclosporin a, vitamin K3, diethylstilbestrol, deoxyribonucleotide, suberoylanilide hydroxamic acid, orlistat, 3-(4,5-dimethylthiazol-2-yl)-2,5-diphenyltetrazolium bromide, rottierin, arachidonic acid, ibuprofen, prostaglandin E2, toremifene, depsipeptide, ochratoxin A, (glc)4, phosphatidylinositol, mitomycin c, rantes, sphingosine, indomethacin, 5fluorouracil, phosphatidylcholine, 5-fluorouracil, mg 132, thymidylate, trans-cinnamaldehyde, sterol, polyadenosine diphosphate ribose, nitric oxide, vitamin e succinate, lipopolysaccharide, cisplatin, herbimycin a, 5-aza-2'deoxycytidine, proteasome inhibitor PSI, 2,5-hexanedione, epothilone B, caffeic acid phenethyl ester, glycerol 3-phosphate, tgf beta1, anisomycin, paclitaxel, gemcitabine, medroxyprogesterone acetate, hymecromone, testosterone, ag 1478, doxorubicin, S-nitroso-N-acetylpenicillamine, adpribose, sulforaphane, vitamin d, annexin-v, lactate, reactive oxygen species, sb 203580, serine, N-acetyl-L-cysteine, dutp, infliximab, ethanol, curcumin, cytarabine, tpck, calyculin a, dopamine, gp 130, bromocriptine, apicidin, fatty acid, citrate, glucocorticoid, arsenite, butyrate, peplomycin, oxaliplatin, camptothecin, benzyloxycarbonyl-Leu-Leu-Leu aldehyde, clofibrate, carbon, wortmannin, fludarabine, N-(3-(aminomethyl)benzyl)acetamidine, sirolimus, peptidoglycan, c2ceramide, dihydrotestosterone, 7-aminoactinomycin d, carmustine, heparin, ceramide, paraffin, mitoxantrone, docosahexaenoic acid, vitamin a, ivig, hydrogen peroxide, 7-ethyl-10-hydroxy-camptothecin, oxygen, pydrin, bortezomib, retinoic acid, 1,4-phenylenebis(methylene)selenocyanate, teriflunomide, epinephrine, n acetylcysteine, noxa, irinotecan, oligonucleotide, d-api, rasagiline, 8-bromo-cAMP, atpo, agarose, fansidar, clobetasol propionate, teniposide, aurintricarboxylic acid, polysaccharide, CpG oligonucleotide, cycloheximide |
| IRF1 | tamoxifen, chloramphenicol, polyinosinic-polycytidylic acid, inosine monophosphate, suberoylanilide hydroxamic acid, butyrate, iron, gliadin, zinc, actinomycin d, deferoxamine, phosphatidylinositol, adenine, ornithine, rantes, calcium, 2',5'-oligoadenylate, pge2, poly(i-c), indoleamine, arginine, estradiol, nitric oxide, etoposide, adriamycin, oxygen, retinoid, guanylate, troglitazone, ifn-alpha, retinoic acid, tyrosine, adenylate, am 580, guanosine, oligonucleotide, estrogen, thymidine, tetracycline, serine, sb 203580, pdtc, lipid, cycloheximide |
| MYC | cd 437, 1, 25 dihydroxy vitamin d3, phenethyl isothiocyanate, threonine, arsenic trioxide, salicylic acid, quercetin, prostaglandin E1, ionomycin, 12-o-tetradecanoylphorbol 13-acetate, fulvestrant, phenylephrine, fisetin, 4-coumaric acid, dihydroartemisinin, 3-deazaadenosine, nitroprusside, pregna-4,17-diene-3,16-dione, adriamycin, bromodeoxyuridine, AGN194204, STA-9090, isobutylmethylxanthine, potassium chloride, docetaxel, quinolinic acid, 5,6,7,8-tetrahydrobiopterin, propranolol, delta 7-pga1, topotecan, AVI-4126, trichostatin A, decitabine, thymidine, D-glucose, mifepristone, poly rI:rC-RNA, letrozole, L-threonine, 5-hydroxytryptamine, bucladesine, SB203580, 1'-acetoxychavicol acetate, cyclosporin A, okadaic acid, dfmo, LY294002, hmba, piceatannol, 2',5'-oligoadenylate, 4-hydroxytamoxifen, butylbenzyl phthalate, dexamethasone, ec 109, phosphatidic acid, grape seed extract, phorbol myristate acetate, coumermycin, tosylphenylalanyl chloromethyl ketone, CD 437, di(2-ethylhexyl) phthalate, butyrine, cytidine, sodium arsenite, tanshinone iia, L-triiodothyronine, niacinamide, glycogen, daunorubicin, vincristine, carvedilol, bizelesin, 3-deazaneplanocin, phorbol, neplanocin a, panobinostat, [alcl], phosphatidylinositol, U0126, dichlororibofuranosylbenzimidazole, flavopiridol, 5-fluorouracil, verapamil, cyclopamine, nitric oxide, cisplatin, hrgbetal, 5,6-dichloro-1-beta-d-ribofuranosylbenzimidazole, amsacrine, gemcitabine, aristeromycin, medroxyprogesterone acetate, gambogic acid, leucine, alpha-naphthyl acetate, cyclic AMP, reactive oxygen species, PD 180970, curcumin, chloramphenicol, A23187, crocidolite asbestos, 6-hydroxydopamine, cb 33, arsenite, |

TABLE 1-continued

| T cell Modulating Agents | |
| --- | --- |
| Target | Agent |
| | gentamicin, benzyloxycarbonyl-Leu-Leu-Leu aldehyde, clofibrate, wortmannin, sirolimus, ceramide, melphalan, 3M-001, linsidomine, CP-55940, hyaluronic acid, ethionine, clonidine, retinoid, bortezomib, oligonucleotide, methyl 2-cyano-3,12-dioxoolean-1,9-dien-28-oate, tacrolimus, embelin, methyl-beta-cyclodextrin, 3M-011, folate, ly294002, PP1, hydroxyurea, aclarubicin, phenylbutyrate, PD 0325901, methotrexate, Cd2+, prazosin, vegf, rapamycin, alanine, phenobarbital, pd 98, 059, trapoxin, 4-hydroperoxycyclophosphamide, methamphetamine, s-(1,2-dichlorovinyl)-l-cysteine, aphidicolin, vesnarinone, ADI PEG20, pirinixic acid, wp631, H-7, carbon tetrachloride, bufalin, 2,2-dimethylbutyric acid, etoposide, calcitriol, trastuzumab, cyclophosphamide, harringtonine, tyrosine, N(6)-(3-iodobenzyl)-5'-N-methylcarboxamidoadenosine, resveratrol, thioguanine, genistein, S-nitroso-N-acetyl-DL-penicillamine, zearalenone, lysophosphatidic acid, Sn50 peptide, roscovitine, actinomycin D, propanil, agar, tamoxifen, acetaminophen, imatinib, tretinoin, mithramycin, ATP, epigallocatechin-gallate, ferric ammonium citrate, acyclic retinoid, L-cysteine, nitroblue tetrazolium, actinomycin d, sodium nitroprusside, 1,2-dimethylhydrazine, dibutyl phthalate, ornithine, 4-hydroxynonenal, beta-estradiol, 1-alpha, 25-dihydroxy vitamin D3, cyproterone acetate, nimodipine, nitrofurantoin, temsirolimus, 15-deoxy-delta-12,14-PGJ 2, estrogen, ribonucleic acid, ciprofibrate, alpha-amanitin, SB 216763, bleomycin, forskolin, prednisolone, cyclosporin a, thyroid hormone, tunicamycin, phosphorothioate, suberoylanilide hydroxamic acid, pga2, 3-(4,5-dimethylthiazol-2-yl)-2,5-diphenyltetrazolium bromide, benzamide riboside, bisindolylmaleimide, SU6656, prostaglandin E2, depsipeptide, zidovudine, cerivastatin, progesterone, sethoxydim, indomethacin, mg 132, mezerein, pyrrolidine dithiocarbamate, vitamin e succinate, herbimycin a, 5-aza-2'deoxycytidine, lipopolysaccharide, diazoxide, anisomycin, paclitaxel, sodium dodecylsulfate, nilotinib, oxysterol, doxorubicin, lipofectamine, PD98059, steroid, delta-12-pgj2, serine, H-8, N-acetyl-L-cysteine, ethanol, n-(4-hydroxyphenyl)retinamide, tiazofurin, cytarabine, H89, 10-hydroxycamptothecin, everolimus, lactacystin, n(1), n(12)-bis(ethyl)spermine, silibinin, glucocorticoid, butyrate, camptothecin, triamcinolone acetonide, tocotrienol, n-ethylmaleimide, phorbol 12,13-didecanoate, thapsigargin, deferoxamine, R59949, bryostatin 1, paraffin, romidepsin, vitamin a, docosahexaenoic acid, hydrogen peroxide, droloxifene, saikosaponin, fluoxetine, retinoic acid, n acetylcysteine, dithiothreitol, cordycepin, agarose, 8-bromo-cAMP, D-galactosamine, tachyplesin i, theophylline, metoprolol, SU6657, 15-deoxy-delta-12,14-prostaglandin j2, dmso, 2-amino-5-azotoluene, cycloheximide |

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In yet other embodiments, the methods of the disclosure include administering to a subject in need thereof an effective amount (e.g., therapeutically effective amount or prophylactically effective amount) of the treatments provided herein. Such treatment may be supplemented with other known treatments, such as surgery on the subject. In certain embodiments, the surgery is strictureplasty, resection (e.g., bowel resection, colon resection), colectomy, surgery for abscesses and fistulas, proctocolectomy, restorative proctocolectomy, vaginal surgery, cataract surgery, or a combination thereof.

Diseases that may be treated by the foregoing include, without limitation, infection, inflammation, immune-related disorders or aberrant immune responses.

Diseases with an abberant or pathologic immune response include include, for example, Acquired Immunodeficiency Syndrome (AIDS, which is a viral disease with an autoimmune component), Crohn's disease, systemic lupus erythematosus, ulcerative colitis, multiple sclerosis (MS), inflammatory bowel disease and chronic and acute inflammatory disorders. Examples of inflammatory disorders include asthma, atopic allergy, allergy, eczema, glomerulonephritis, graft vs. host disease.

Administration of a modulating agent to a patient suffering from a disorder or aberrant or condition considered successful if any of a variety of laboratory or clinical objectives is achieved, such as if symptoms associated with the disorder or condition is alleviated, reduced, inhibited or does not progress to a further, i.e., worse, state.

A therapeutically effective amount of an agent relates generally to the amount needed to achieve a therapeutic objective, and will depend on the specificity of agent for its specific target, the rate and route of administration, and the like. Where polypeptide-based agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing an inflammatory response (e.g., a person who is genetically predisposed or predisposed to allergies or a person having a disease characterized by episodes of inflammation) may receive prophylactic treatment to inhibit or delay symptoms of the disease.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., cells, agonists or antagonists) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), esto-late, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hyd-robromide, tannate, hydrochloride, tartrate, hydroxynaph-thoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

Methods of administrating the pharmacological compo-sitions, including agents, cells, agonists, antagonists, anti-bodies or fragments thereof, to an individual include, but are not limited to, intradermal, intrathecal, intramuscular, intra-peritoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary admin-istration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically accept-able carriers, with amphipathic agents such as lipids which exist in aggregated form as micelles, insoluble monolayers, liquid crystals, or lamellar layers in aqueous solution. Suit-able lipids for liposomal formulation include, without limi-tation, monoglycerides, diglycerides, sulfatides, lysoleci-thin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The pre-cise dose to be employed in the formulation will also depend on the route of administration, and the overall seriousness of the disease or disorder, and should be decided according to the judgment of the practitioner and each patient's circum-stances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range for a small molecule, protein or protein derivative thereof may be within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of an agent are generally about 5-500 micrograms ($\mu$g) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 $\mu$g/human and preferably approximately 5 to 500 $\mu$g/human as a single dose. Effective doses may be extrapolated from dose-re-sponse curves derived from in vitro or animal model test systems. Ultimately the attending physician will decide on the appropriate duration of therapy using compositions of the present invention. Dosage will also vary according to the age, weight and response of the individual patient.

Perturbation Screening

In certain embodiments, the gene signatures described herein are screened by perturbation of target genes within said signatures. Methods and tools for genome-scale screen-ing of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that signature genes may be perturbed and the perturbation may be iden-tified and assigned to the proteomic and gene expression readouts of single cells. In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a disease (e.g., inflammatory disease, cancer, autoimmune disease). Thus, in certain embodiments, perturb-seq is used to discover novel drug targets.

Orthologs and Homologs

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Thus, when reference is made to mouse genes and proteins, it is understood that the same is believed to apply to the corresponding ortholog in humans or other species.

Likewise, when referencing Cas9 and other proteins, it is understood to likewise apply to orthologs and homologs.

The CRISPR-CRISPR associated (Cas) systems of bacterial and archaeal adaptive immunity are some such systems that show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multi-subunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The effector protein may comprise a chimeric effector protein comprising a first fragment from a first effector protein ortholog and a second fragment from a second effector protein ortholog, and wherein the first and second effector protein orthologs are different. At least one of the first and second effector protein orthologs may comprise an effector protein from an organism comprising Bergeyella, *Prevotella, Porphyromonas, Bacteroides, Alistipes, Riemerella, Myroides, Flavobacterium, Capnocytophaga, Chryseobacterium, Paludibacter, Phaeodactylibacter* or *Psychroflexus*.

In certain embodiments, the effector protein, particularly a Group 29 or Group 30 effector protein effector protein may be at least 700 amino acids long. In preferred embodiments, the effector protein may be about 1100 to about 1500 amino acids long, e.g., about 1100 to about 1200 amino acids long, or about 1200 to about 1300 amino acids long, or about 1300 to about 1400 amino acids long, or about 1400 to about 1500 amino acids long, e.g., about 900, about 1000, about 1100, about 1200, about 1300, about 1400, about 1500, about 1600, about 1700, or about 1800 amino acids long.

In certain embodiments, the Group 29 or Group 30 effector proteins as intended herein may be associated with a locus comprising short CRISPR repeats between 30 and 40 bp long, more typically between 34 and 38 bp long, even more typically between 36 and 37 bp long, e.g., 30, 31, 32, 33, 34, 35, 36, 37, 38, 39, or 40 bp long. In certain embodiments the CRISPR repeats are long or dual repeats between 80 and 350 bp long such as between 80 and 200 bp long, even more typically between 86 and 88 bp long, e.g., 80, 81, 82, 83, 84, 85, 86, 87, 88, 89, or 90 bp long.

Orthologous proteins may but need not be structurally related, or are only partially structurally related. In particular embodiments, the homologue or orthologue of a Group 29 or Group 30 protein as referred to herein has a sequence homology or identity of at least 80%, more preferably at least 85%, even more preferably at least 90%, such as for instance at least 95% with the Group 29 or Group 30 effector protein. In a preferred embodiment, the Group 29 or Group 30 effector protein may be an ortholog of an organism of a genus which includes but is not limited to *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. Some methods of identifying orthologs of CRISPR system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species.

TABLE 1

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Paludibacter propionicigenes* WB4 (NC_014734.1) | WP_013446107.1 | NA | 8 | N | N | N | 1155 |
| *Prevotella* sp. P5-60 (NZ_JXQJ01000080.1) | WP_044074780.1 | NA | 5 | Y | ? | ? | 1091 |
| *Prevotella* sp. P4-76 (NZ_JXQI01000021.1) | WP_044072147.1 | NA | 0 | ? | ? | ? | 1091 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Prevotella* sp. P5-125 (NZ_JXQL01000055.1) | WP_044065294.1 | NA | 11 | ? | ? | ? | 1091 |
| *Prevotella* sp. P5-119 (NZ_JXQK01000043.1) | WP_042518169.1 | NA | 11 | ? | ? | ? | 1091 |
| *Capnocytophaga canimorsus* Cc5 (NC_015846.1) | WP_013997271.1 | WP_013997274.1 | 51 | Y | Y | Y | 1200 |
| *Phaeodactylibacter xiamenensis* (NZ_JPOS01000018.1) | WP_044218239.1 | WP_044218241.1 | 19 | ? | ? | ? | 1132 |
| *Porphyromonas gingivalis* W83 (NC_002950.2) | WP_005873511.1 | WP_005873518.1 | 7 | Y | Y | Y | 1136 |
| *Porphyromonas gingivalis* F0570 (NZ_KI259168.1) | WP_021665475.1 | WP_021665476.1 | 3 | ? | ? | ? | 1136 |
| *Porphyromonas gingivalis* ATCC 33277 (NC_010729.1) | WP_012458151.1 | WP_012458152.1 | 12 | Y | Y | Y | 1136 |
| *Porphyromonas gingivalis* F0185 (AWVC01000122.1) | ERJ81987.1 | ERJ81988.1 | 0 | ? | ? | ? | 1136 |
| *Porphyromonas gingivalis* F0185 (NZ_KI259960.1) | WP_021677657.1 | WP_021677658.1 | 6 | ? | ? | ? | 1136 |
| *Porphyromonas gingivalis* SJD2 (NZ_KI629875.1) | WP_023846767.1 | WP_005873518.1 | 4 | ? | ? | ? | 1136 |
| *Porphyromonas gingivalis* F0568 (AWUU01000145.1) | ERJ65637.1 | ERJ65638.1 | 3 | ? | ? | ? | 1136 |
| *Porphyromonas gingivalis* W4087 (AWVE01000130.1) | ERJ87335.1 | ERJ87336.1 | 2 | ? | ? | ? | 1136 |
| *Porphyromonas gingivalis* W4087 (NZ_KI260263.1) | WP_021680012.1 | WP_005873518.1 | 4 | ? | ? | ? | 1136 |
| *Porphyromonas gingivalis* F0568 (NZ_KI258981.1) | WP_021663197.1 | WP_021663198.1 | 6 | ? | ? | ? | 1136 |
| *Porphyromonas gingivalis* (NZ_LOEL01000010.1) | WP_061156637.1 | WP_005873518.1 | 11 | ? | ? | ? | 1136 |
| *Porphyromonas gulae* (NZ_JRAQ01000019.1) | WP_039445055.1 | WP_039445052.1 | 10 | ? | ? | ? | 1136 |
| *Bacteroides pyogenes* F0041 (KE993153.1) | ERI81700.1 | ERI81699.1 | 5 | ? | ? | ? | 1116 |
| *Bacteroides pyogenes* JCM 10003 (NZ_BAIU01000001.1) | WP_034542281.1 | WP_034542279.1 | 18 | ? | ? | ? | 1116 |
| *Alistipes* sp. ZOR0009 (NZ_JTLD01000029.1) | WP_047447901.1 | NA | 7 | ? | ? | ? | 954 |
| *Flavobacterium branchiophilum* FL-15 (NC_016001.1) | WP_014084666.1 | WP_014084665.1 | 19 | Y | N | Y | 1151 |
| *Prevotella* sp. MA2016 (NZ_JHUW01000010.1) | WP_036929175.1 | NA | 7 | ? | ? | ? | 1323 |
| *Myroides odoratimimus* CCUG 10230 (AGEC02000017.1) | EHO06562.1 | EHO06560.1 | 2 | ? | ? | ? | 1160 |
| *Myroides odoratimimus* CCUG 3837 (AGZK01000016.1) | EKB06014.1 | EKB06015.1 | 0 | ? | ? | ? | 1158 |
| *Myroides odoratimimus* CCUG 3837 (NZ_JH815535.1) | WP_006265509.1 | WP_006265510.1 | 0 | ? | ? | ? | 1158 |
| *Myroides odoratimimus* CCUG 12901 (NZ_JH590834.1) | WP_006261414.1 | WP_006261415.1 | 0 | ? | ? | ? | 1158 |
| *Myroides odoratimimus* CCUG 12901 (AGED01000033.1) | EHO08761.1 | EHO08762.1 | 0 | ? | ? | ? | 1158 |
| *Myroides odoratimimus* (NZ_CP013690.1) | WP_058700060.1 | WP_006261415.1 | 10 | Y | Y | Y | 1160 |
| *Bergeyella zoohelcum* ATCC 43767 (AGYA01000037.1) | EKB54193.1 | EKB54194.1 | 9 | ? | ? | ? | 1225 |
| *Capnocytophaga cynodegmi* (NZ_CDOD01000002.1) | WP_041989581.1 | WP_041989578.1 | 7 | ? | ? | ? | 1219 |
| *Bergeyella zoohelcum* ATCC 43767 (NZ_JH932293.1) | WP_002664492.1 | WP_034985946.1 | 8 | Y | Y | Y | 1225 |
| *Flavobacterium* sp. 316 (NZ_JYGZ01000003.1) | WP_045968377.1 | NA | 0 | ? | ? | ? | 1156 |
| *Psychroflexus torquis* ATCC 700755 (NC_018721.1) | WP_015024765.1 | NA | 16 | Y | Y | Y | 1146 |
| *Flavobacterium columnare* ATCC 49512 (NC_016510.2) | WP_014165541.1 | NA | 7 | Y | Y | Y | 1180 |
| *Flavobacterium columnare* (NZ_CP013992.1) | WP_060381855.1 | NA | 5 | Y | Y | Y | 1214 |
| *Flavobacterium columnare* (NZ_CP015107.1) | WP_063744070.1 | NA | 3 | Y | Y | Y | 1214 |
| *Flavobacterium columnare* (NZ_CP016277.1) | WP_065213424.1 | NA | 14 | Y | Y | Y | 1215 |
| *Chryseobacterium* sp. YR477 (NZ_KN549099.1) | WP_047431796.1 | NA | 0 | ? | ? | ? | 1146 |

TABLE 1-continued

| | | | | | | | |
|---|---|---|---|---|---|---|---|
| | | | | Representative Type VI-B Effectors and Accessory Proteins | | | |
| Species (Genome Accession) | Cas13b Accession | Csx27/28 Accession | # Spacers | CRISPR-Cas? | Cas1? | Cas2? | Cas13b size (aa) |
| *Riemerella anatipestifer* ATCC 11845 = DSM 15868 (NC__014738.1) | WP__004919755.1 | WP__004919758.1 | 12 | Y | Y | Y | 1096 |
| *Riemerella anatipestifer* RA-CH-2 (NC__020125.1) | WP__015345620.1 | WP__004919758.1 | 12 | Y | Y | Y | 949 |
| *Riemerella anatipestifer* (NZ__CP007504.1) | WP__049354263.1 | WP__004919758.1 | 11 | Y | Y | Y | 949 |
| *Riemerella anatipestifer* (NZ__LUDU01000012.1) | WP__061710138.1 | WP__061710139.1 | 13 | ? | ? | ? | 951 |
| *Riemerella anatipestifer* (NZ__LUDI01000010.1) | WP__064970887.1 | WP__064970885.1 | 4 | ? | ? | ? | 1096 |
| *Prevotella saccharolytica* F0055 (AMEP01000091.1) | EKY00089.1 | EKY00090.1 | 0 | ? | ? | ? | 1151 |
| *Prevotella saccharolytica* JCM 17484 (NZ__BAKN01000001.1) | WP__051522484.1 | NA | 5 | Y | Y | Y | 1152 |
| *Prevotella buccae* ATCC 33574 (AEPD01000005.1) | EFU31981.1 | EFU31982.1 | 16 | ? | ? | ? | 1128 |
| *Prevotella buccae* ATCC 33574 (NZ__GL586311.1) | WP__004343973.1 | WP__004343974.1 | 16 | Y | Y | Y | 1128 |
| *Prevotella buccae* D17 (NZ__GG739967.1) | WP__004343581.1 | WP__004343582.1 | 8 | ? | ? | ? | 1128 |
| *Prevotella* sp. MSX73 (NZ__ALJQ01000043.1) | WP__007412163.1 | WP__036927782.1 | 13 | ? | ? | ? | 1128 |
| *Prevotella pallens* ATCC 700821 (AFPY01000052.1) | EGQ18444.1 | EGQ18443.1 | 4 | ? | ? | ? | 1126 |
| *Prevotella pallens* ATCC 700821 (NZ__GL982513.1) | WP__006044833.1 | WP__050795200.1 | 4 | ? | ? | ? | 1126 |
| *Prevotella intermedia* ATCC 25611 = DSM 20706 (NZ__JAEZ01000017.1) | WP__036860899.1 | WP__050795200.1 | 11 | ? | ? | ? | 1127 |
| *Prevotella intermedia* (NZ__LBGT01000010.1) | WP__061868553.1 | NA | 27 | ? | ? | ? | 1121 |
| *Prevotella intermedia* 17 (CP003502.1) | AFJ07523.1 | AFJ07898.1 | 16 | N | N | N | 1135 |
| *Prevotella intermedia* (NZ__AP014926.1) | WP__050955369.1 | WP__014708440.1 | 16 | N | N | N | 1133 |
| *Prevotella intermedia* (AP014598.1) | BAU18623.1 | BAU18624.1 | 6 | N | N | N | 1134 |
| *Prevotella intermedia* ZT (ATMK01000017.1) | KJJ86756.1 | KJJ86755.1 | 2 | ? | ? | ? | 1126 |
| *Prevotella aurantiaca* JCM 15754 (NZ__BAKF01000019.1) | WP__025000926.1 | WP__036889078.1 | 5 | ? | ? | ? | 1125 |
| *Prevotella pleuritidis* F0068 (NZ__AWET01000045.1) | WP__021584635.1 | WP__021584705.1 | 6 | ? | ? | ? | 1140 |
| *Prevotella pleuritidis* JCM 14110 (NZ__BAJN01000005.1) | WP__036931485.1 | WP__024991772.1 | 7 | ? | ? | ? | 1117 |
| *Prevotella falsenii* DSM 22864 = JCM 15124 (NZ__BAJY01000004.1) | WP__036884929.1 | WP__051527348.1 | 10 | ? | ? | ? | 1134 |
| *Porphyromonas gulae* (NZ__JRAT01000012.1) | WP__039418912.1 | WP__052073447.1 | 11 | Y | Y | Y | 1176 |
| *Porphyromonas* sp. COT-052 OH4946 (NZ__JQZY01000014.1) | WP__039428968.1 | WP__050563578.1 | 12 | ? | ? | ? | 1176 |
| *Porphyromonas gulae* (NZ__JRFD01000046.1) | WP__039442171.1 | WP__050563578.1 | 9 | ? | ? | ? | 1175 |
| *Porphyromonas gulae* (NZ__JRAJ01000010.1) | WP__039431778.1 | WP__046201041.1 | 2 | ? | ? | ? | 1176 |
| *Porphyromonas gulae* (NZ__KQ040500.1) | WP__046201018.1 | WP__046201041.1 | 4 | ? | ? | ? | 1176 |
| *Porphyromonas gulae* (NZ__JRAL01000022.1) | WP__039434803.1 | WP__039434800.1 | 20 | ? | ? | ? | 1176 |
| *Porphyromonas gulae* (NZ__JRAI01000002.1) | WP__039419792.1 | WP__052078041.1 | 9 | ? | ? | ? | 1120 |
| *Porphyromonas gulae* (NZ__JRAK01000129.1) | WP__039426176.1 | WP__039426172.1 | 6 | ? | ? | ? | 1120 |
| *Porphyromonas gulae* (NZ__KN294104.1) | WP__039437199.1 | WP__052102013.1 | 0 | ? | ? | ? | 1120 |
| *Porphyromonas gingivalis* TDC60 (NC__015571.1) | WP__013816155.1 | WP__043890185.1 | 2 | Y | Y | Y | 1120 |
| *Porphyromonas gingivalis* ATCC 33277 (NC__010729.1) | WP__012458414.1 | WP__012458413.1 | 4 | Y | Y | Y | 1120 |
| *Porphyromonas gingivalis* A7A1-28 (NZ__CP013131.1) | WP__058019250.1 | WP__043898408.1 | 6 | Y | Y | Y | 1176 |
| *Porphyromonas gingivalis* JCVI SC001 (APMB01000175.1) | EOA10535.1 | EOA10563.1 | 5 | ? | ? | ? | 1176 |

TABLE 1-continued

| | | | | | | | |
|---|---|---|---|---|---|---|---|
| | | Representative Type VI-B Effectors and Accessory Proteins | | | | | |
| Species (Genome Accession) | Cas13b Accession | Csx27/28 Accession | # Spacers | CRISPR- Cas? | Cas1? | Cas2? | Cas13b size (aa) |
| *Porphyromonas gingivalis* W50 (NZ_AJZS01000051.1) | WP_005874195.1 | WP_010955981.1 | 2 | ? | ? | ? | 1176 |
| *Porphyromonas gingivalis* (NZ_CP011995.1) | WP_052912312.1 | WP_010955981.1 | 7 | Y | Y | Y | 1176 |
| *Porphyromonas gingivalis* AJW4 (NZ_CP011996.1) | WP_053444417.1 | WP_043898408.1 | 11 | N | N | N | 1120 |
| *Porphyromonas gingivalis* (NZ_CP007756.1) | WP_039417390.1 | WP_021665928.1 | 5 | Y | Y | Y | 1120 |
| *Porphyromonas gingivalis* (NZ_LOEL01000001.1) | WP_061156470.1 | WP_021663076.1 | 5 | ? | ? | ? | 1120 |

Kit

The terms "kit" and "kit of parts" as used throughout this specification refer to a product containing components necessary for carrying out the specified methods (e.g., methods for detecting, quantifying or isolating intestinal epithelial cells, intestinal epithelial stem cells, intestinal immune cells, or respiratory epithelial cells (preferably epithelial cells, e.g., tuft cells) as taught herein), packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively.

Typically, kits and kit of parts are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridisation probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris(hydroxymethyl)-aminomethane) buffers or maleate buffers, or mixtures thereof), enzymes (such as for example but without limitation thermostable DNA polymerase), detectable labels, detection reagents, and control formulations (positive and/or negative), useful in the specified methods. Typically, the kits and kit of parts may also include instructions for use thereof, such as on a printed insert or on a computer readable medium. The terms may be used interchangeably with the term "article of manufacture", which broadly encompasses any man-made tangible structural product, when used in the present context.

In certain embodiments, the kit of parts or article of manufacture may comprise a microfluidic system.

The invention having now been described by way of written description, those of skill in the art will recognize that the invention can be practiced in a variety of embodiments and that the foregoing description and examples below are for purposes of illustration and not limitation of the claims that follow.

Although the present invention and its advantages have been described in detail, it should be understood that various changes, substitutions and alterations can be made herein without departing from the spirit and scope of the invention as defined in the appended claims.

The invention is further described in the following examples, which do not limit the scope of the invention described in the claims.

EXAMPLES

Example 1—A Single-Cell Atlas Identifies all Known Populations of Epithelial Cells in the Small Intestine Here, Applicants performed an scRNA-seq survey of 53,193 epithelial cells of the small intestine (SI) in homeostasis and during infection. Applicants identified gene signatures, key transcription factors (TFs) and specific G protein-coupled receptors (GPCRs) for each major small intestinal differentiated cell type. Applicants distinguished proximal and distal enterocytes and their stem cells, established a novel classification of different enteroendocrine subtypes, and identified previously unrecognized heterogeneity within both Paneth and tuft cells. Finally, Applicants demonstrated how these cell types and states adaptively change is response to different infections.

Applicants profiled a total of 53,193 individual cells across this study (Table 2). Applicants estimated the required cell numbers using a general statistical model based on the negative binomial distribution for random sampling (Methods). There are seven known cell-types in the intestinal epithelium, and in order to provide an unbiased estimate, Applicants arbitrarily allow for as many as twice this number. The statistical framework suggested that to achieve a 99% probability of sampling at least 50 cells from each of 14 expected cell types, where the rarest cell type is present at a fraction of 1%, Applicants needed to sequence 7,500 cells (Methods).

TABLE 2

| Dataset | Number of cells | Single-cell platform |
|---|---|---|
| Atlas (droplet) | 7216 | 3'-droplet Full-length plate |
| Atlas (plate) | 1522 | |
| Infection models (10X) | 9842 | 3'-droplet |
| *Salmonella* infection | 2,029 | 3'-droplet Full-length plate |
| Infection models (SS2) | 389 | |

TABLE 2-continued

| Dataset | Number of cells | Single-cell platform |
|---|---|---|
| RANKL-treated organoids | 5434 | 3'-droplet |
| Follicle-associated epithelium (FAE) | 4700 | 3'-droplet |
| Spatial regions | 11665 | 3'-droplet |
| Paneth cell enrichment | 10396 | 3'-droplet |
| Total | 53193 | |

Applicants used droplet-based massively-parallel single cell RNA-Seq[24] (Methods) to transcriptionally profile EpCAM[+] epithelial cells from the small intestine of C57BL/6 wild-type and Lgr5-GFP knock-in mice[6] (FIG. 1a). Applicants measured 8,882 single-cell profiles, removed 1,402 low quality cells (<800 genes detected; Methods) and 264 contaminating immune cells (Methods), retaining 7,216 cells for all subsequent analyses (median 42,697 transcripts per cell, median 1,659 genes detected per cell; FIG. 7a), with excellent reproducibility between replicates (n=6 mice, mean r=0.95, FIG. 7c-f).

Unsupervised clustering of the data partitioned the cells into 15 distinct groups. First, Applicants built a k-nearest neighbor graph on a low-dimensional representation of the cellular expression data using principal component analysis (PCA), and partitioned this graph into 15 discrete clusters using the Infomap algorithm[25,26], each comprising transcriptionally similar cells (Methods). The clusters, each of which contained cells from all mice and replicate experiments (FIG. 7c,g), were visualized using t-stochastic neighborhood embedding[26-28] (tSNE) (FIG. 1b).

Applicants labeled the 15 clusters post hoc based on the expression of signatures of known marker genes (FIG. 7g), showing that each is associated with a distinct cell type or state, including the major post-mitotic cell-types: enterocyte, goblet, Paneth, enteroendocrine and tuft cells (FIG. 1b). Applicants scored proliferating cells with a cell-cycle signature that Applicants previously developed from single-cell profiles[29] to distinguish between dividing stem or progenitor cells and fully differentiated, post-mitotic cells. To enrich for M cells, found only above Peyer's patches, Applicants isolated and analyzed the follicle associated epithelium (FAE) in a separate set of experiments (below). The enteroendocrine, Paneth, goblet, stem and tuft cells were each represented by a single (1:1 matching) cluster (FIG. 1b and FIG. 7g). While the term 'enterocytes' is occasionally used to refer to all intestinal epithelial cells, in this study Applicants use the term to refer exclusively to absorptive enterocytes, which are the most abundant cell type in the intestinal epithelium[1]. This subset of cells was partitioned across seven clusters representing distinct stages of maturation (FIG. 1b, FIG. 7g). Of note, a recent study[30] identified the same major cell-type clusters of IECs without these distinctions between various stages of enterocyte differentiation. The proportions of common differentiated IEC types, such as goblet cells (7.1%) and enterocyte (44.6%), were consistent with their expected abundances given the crypt-enriched isolation protocol Applicants used (Methods, FIG. 7d), with the exception of Paneth cells, which were under-represented in the data (3.6% compared to the expected 5%[31]). Conversely, the proportions of enteroendocrine and tuft cells were 4.3% and 2.3%, respectively, significantly higher than current estimates[11, 12, 14]. To improve Paneth cell capture, Applicants devised a sorting strategy to better capture large cells. Profiling an additional 10,396 epithelial cells identified 1,449 Paneth cells (13.9%) in two distinct clusters (FIG. 10M), but no additional novel cell-types. Applicants thus expect that all cell-types with >0.75% prevalence were detected in the survey at 99% confidence.

Applicants validated the atlas by independently profiling single epithelial cells that were sorted by FACS followed by an established full-length scRNA-seq protocol[32] (FIG. 1a and FIGS. 7b and 2a). Applicants profiled 1,853 single cells, filtered isolated immune cells and lower quality cells (<3,000 genes per cell; Methods), and retained a high-quality subset of 1,522 single cells for analysis, with high reproducibility across mice (n=10 mice, FIG. 8a). The measured cell profiles had much higher coverage (median 1.06 million reads per cell, median of 6,009 genes per cell; FIG. 7b). The same clustering procedure (using the 15 significant PCs in this data; Methods) identified 8 clusters, and overall recapitulated the same post-mitotic cluster groups (FIG. 8a), but without finer distinctions by maturity and location among the enterocytes (below), as expected given the much smaller cell number. This highlights the importance of collecting a large number of scRNA-seq profiles to make finer distinctions[26].

Figure 27:
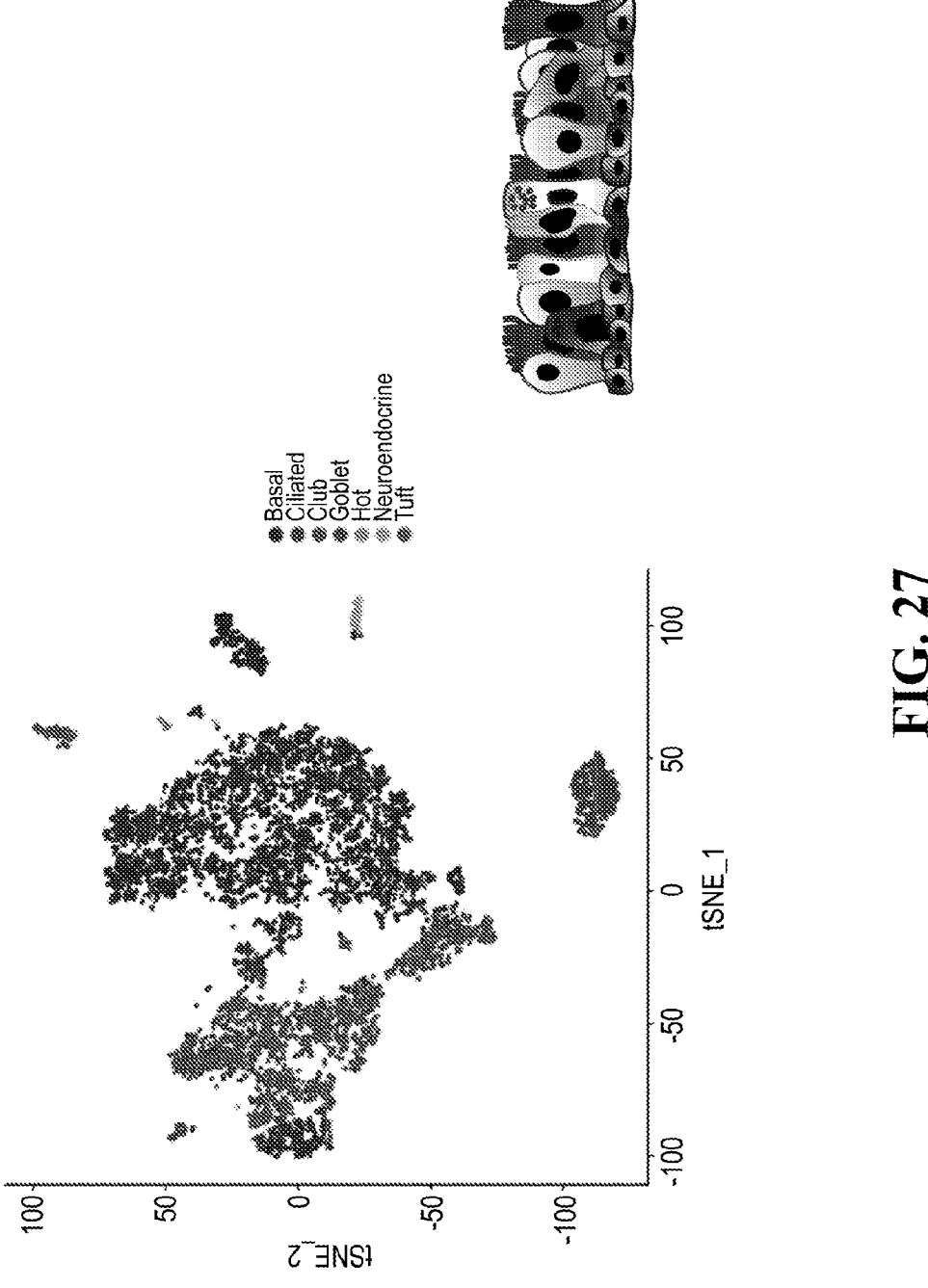
FIG. 27—Cell types in trachea—sets forth clustering of single cells based on tSNE analysis.
Figure 28:
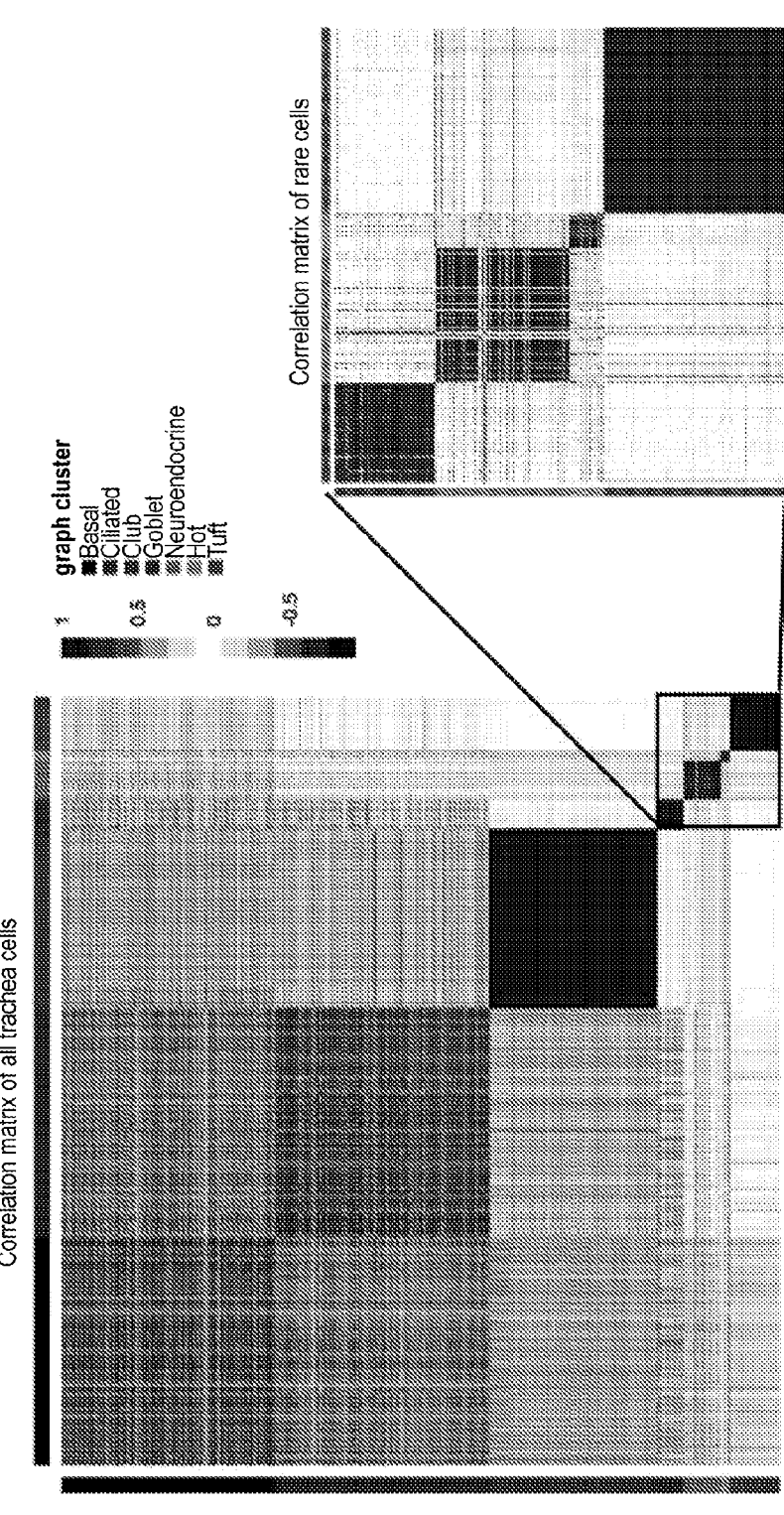
FIG. 28—Cell type clusters—sets forth a heatmap showing clusters of cells in the trachea.
Figure 29:
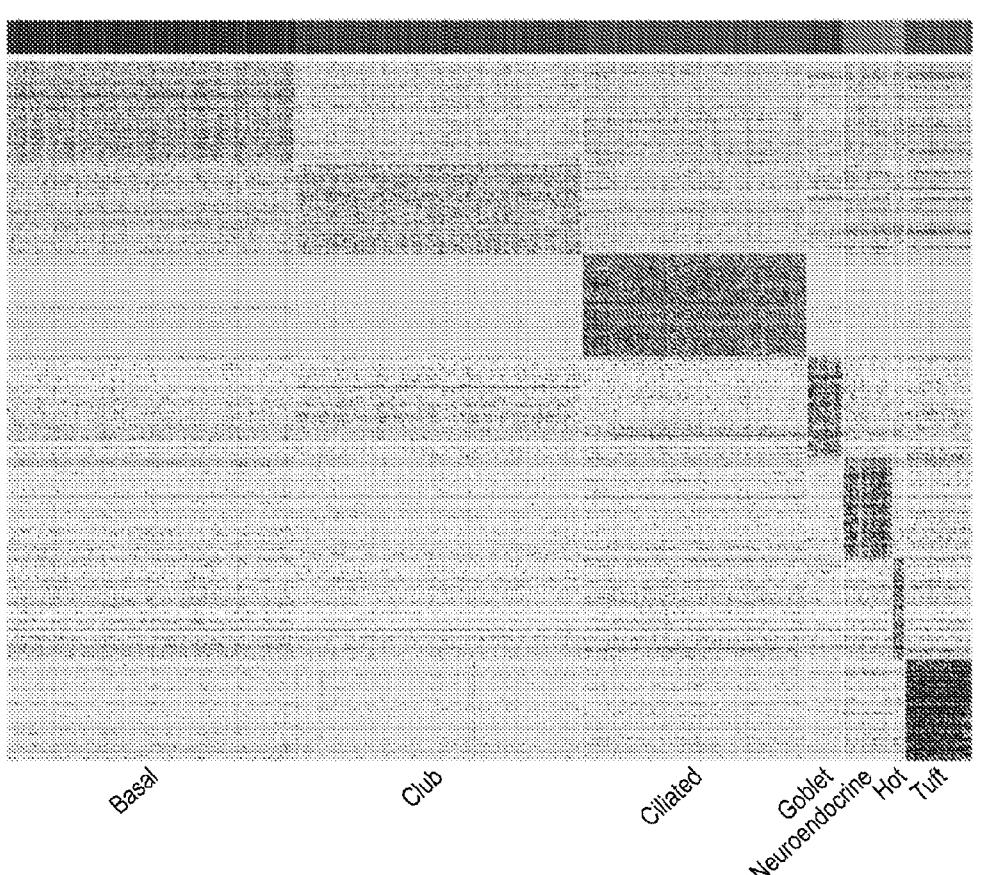
FIG. 29—Cell type signatures—sets forth a heat map showing cell type specific gene signatures.
Figure 30:
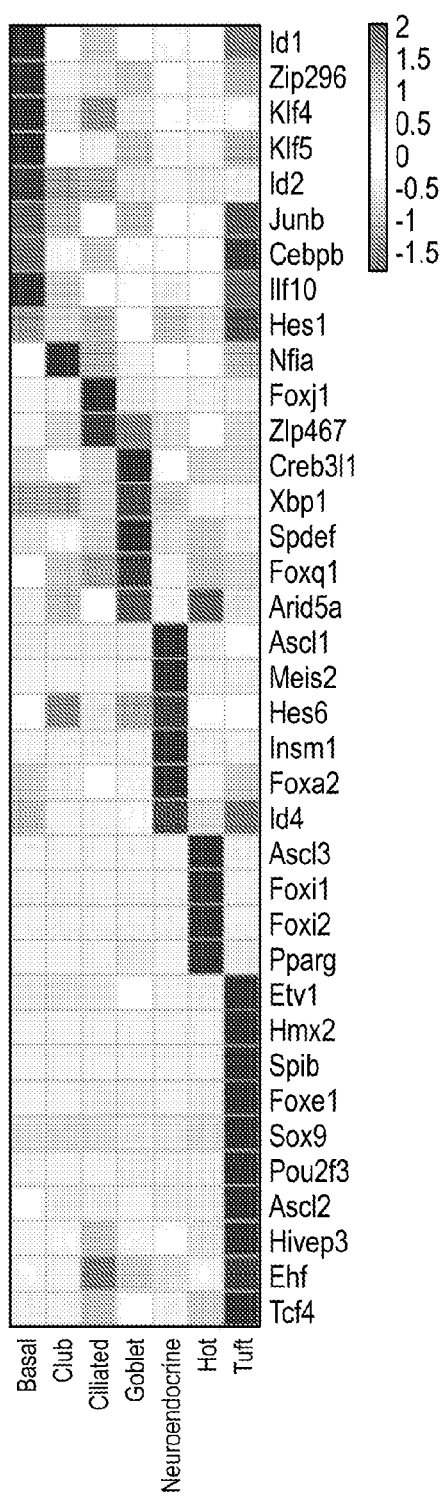
FIG. 30—Transcription factors—sets forth cell type specific transcription factor expression in the trachea.

Applicants also profiled trachea single cells and verified a tuft cell gene signature that was consistent across the intestine and trachea (FIG. 27-29). Applicants identified transcription factors specific to tuft cells in the trachea and these were consistent with transcription factor expression in the intestine (FIG. 30).

Figure 1C:
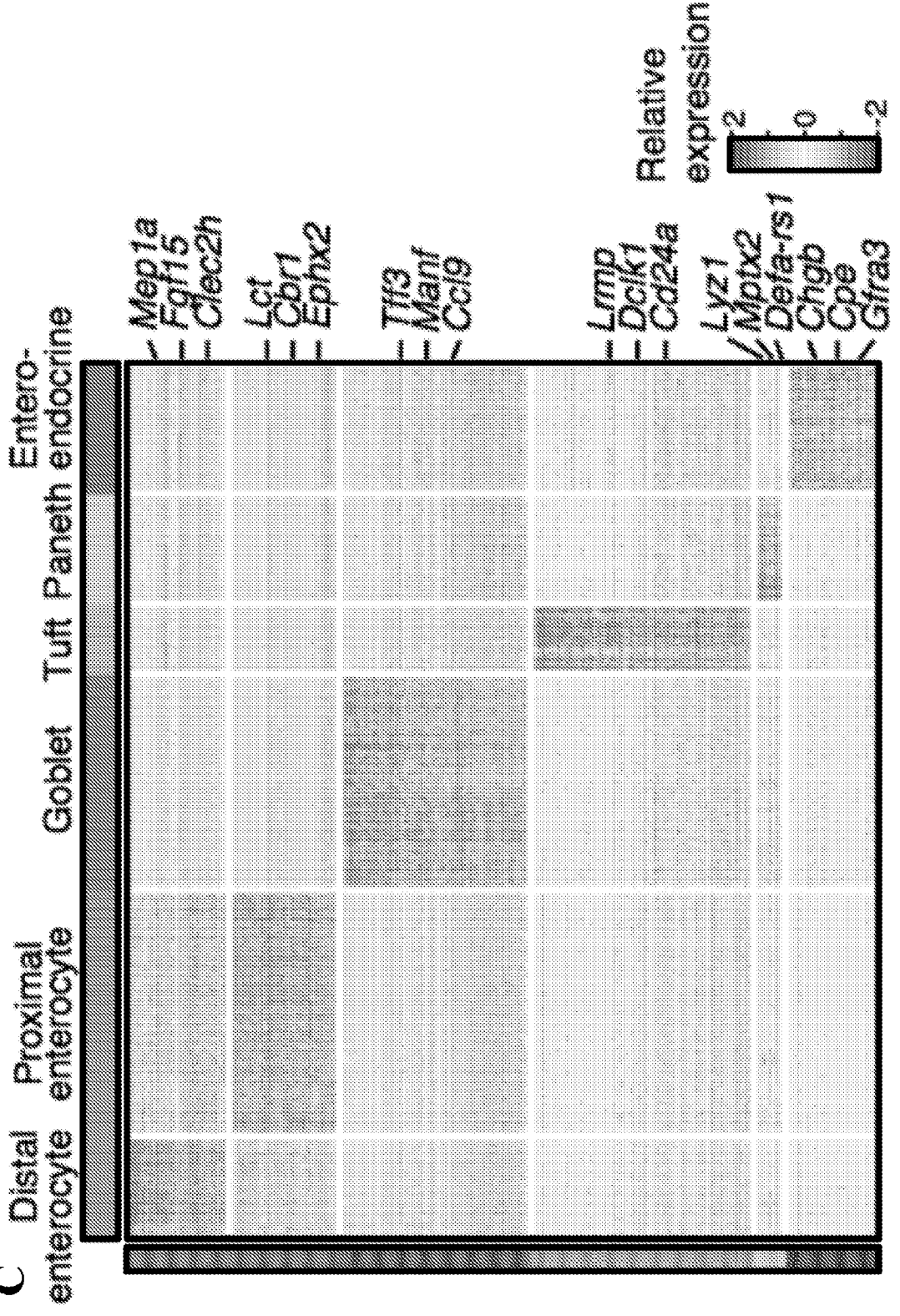
Figure 10H:
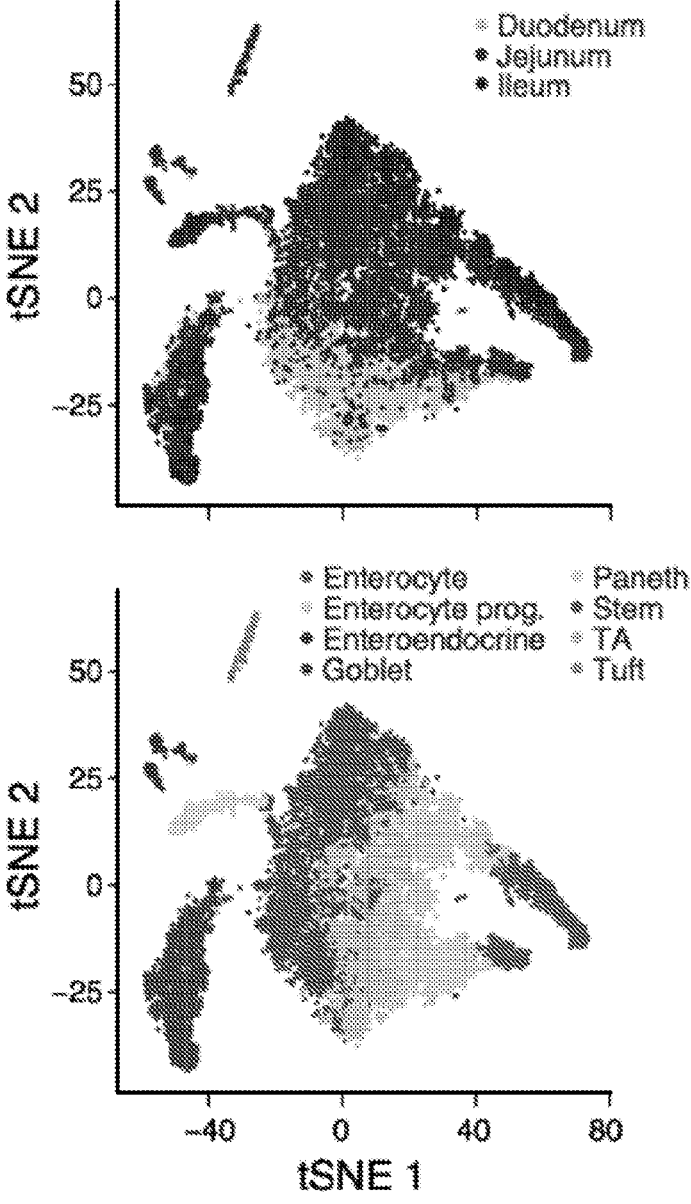
FIG. 10H shows single-cell profiles from regional sites of the small intestine. tSNE embedding of 11,665 single cells extracted from three regions of the small intestine (duodenum, jejunum and ileum), shaded by the region of origin (top, legend) or their assignment to cell-type by unsupervised clustering (bottom, legend). n=2 mice.
Figure 10I:
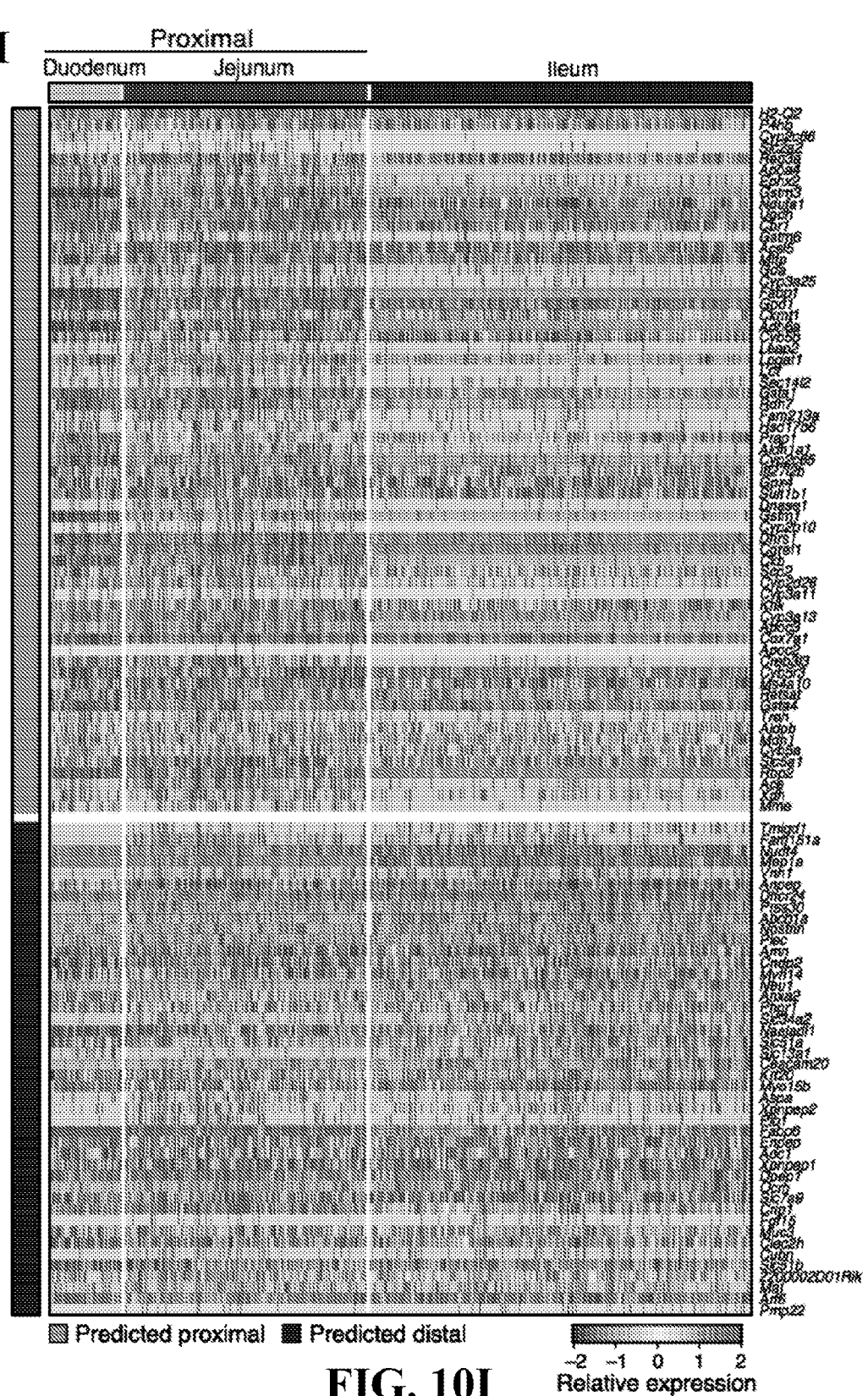
FIG. 10I shows validation of predicted regional markers. Heatmap shows the expression level (row-wise Z-score, bar) in each of the 1,041 enterocytes (columns) analyzed from three regions of the small intestine (duodenum, jejunum and ileum; bar, top) of 108 genes (rows) predicted to be markers of proximal (light grey) and distal (dark grey) enterocytes (bar, left) using unsupervised cluster analysis (FIG. 1B,C).
Figure 10J:
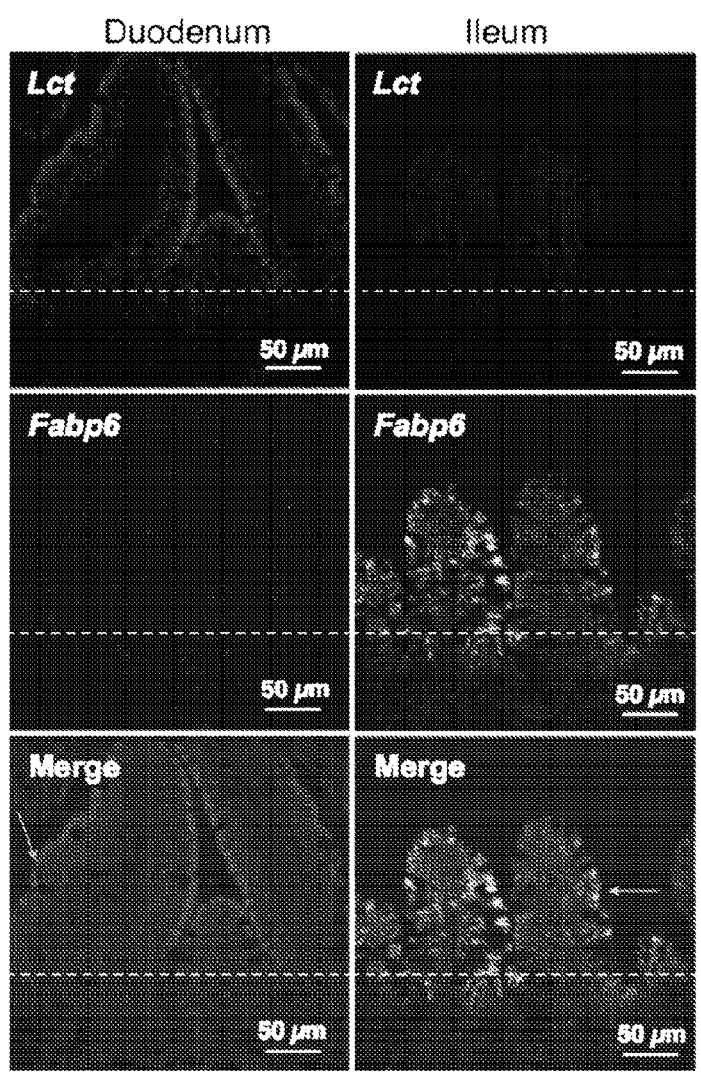
FIG. 10J shows validation of proximal and distal enterocyte markers. smFISH of Lct and Fabp6 (white) in the duodenum (proximal small intestine, top) and the ileum (distal small intestine, bottom). Dotted line indicates the boundary between the crypt region (below) and the villi (above). Scale bar, 50 μm.
Figure 10K:
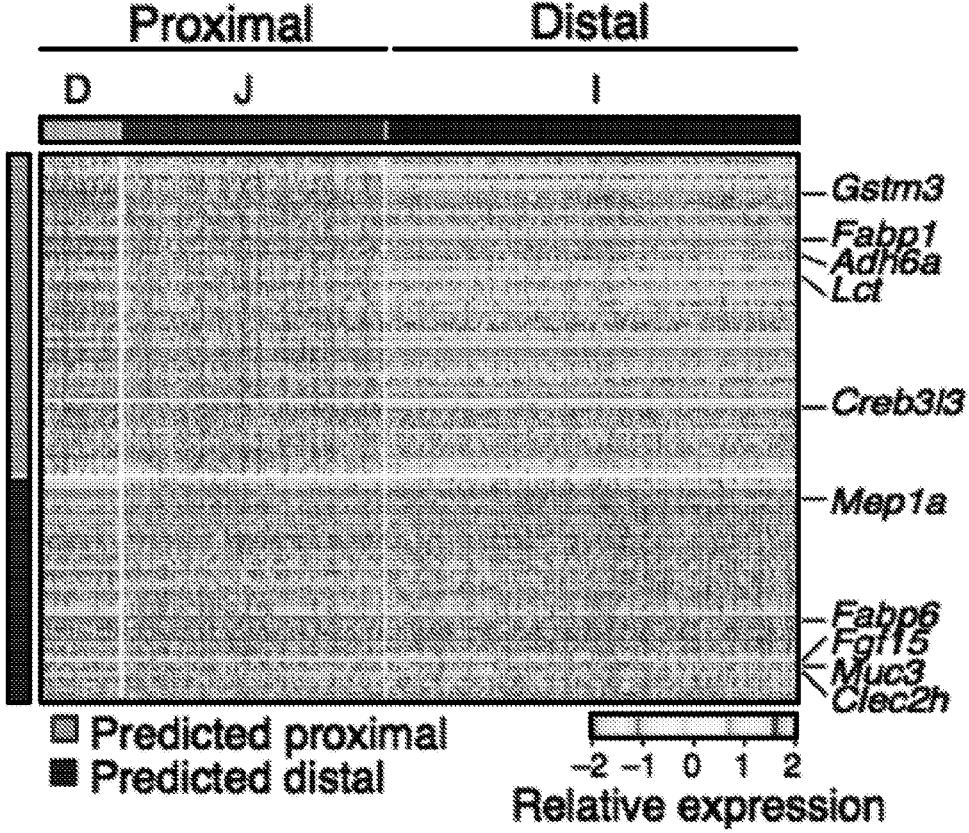
FIG. 10K shows regional enterocyte signatures. Relative expression of genes (rows) across cells (columns), sorted by region.
Figure 10L:
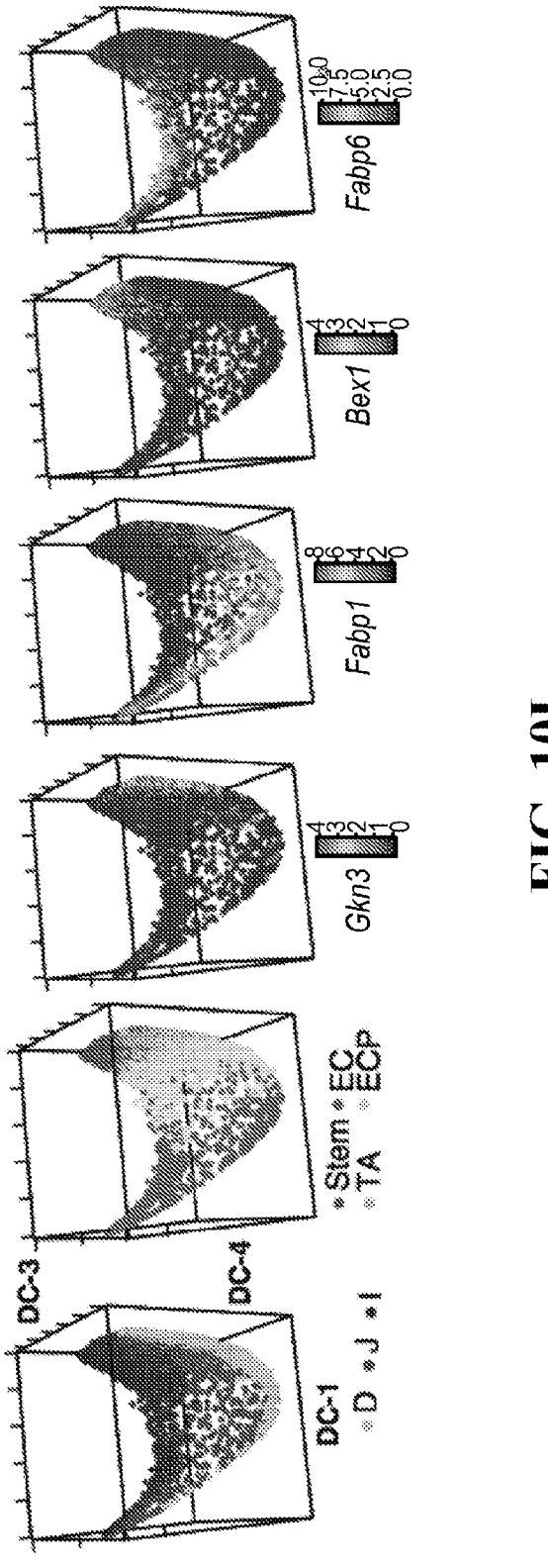
FIG. 10L shows regional differences in [SC differentiation. Diffusion-map embedding of 8,988 cells shaded by region (left), cluster (center left), or expression of novel regional markers of ISCs (Gkn3, Bex]) or enterocytes (Fabp1, Fabp6).
Figure 10M:
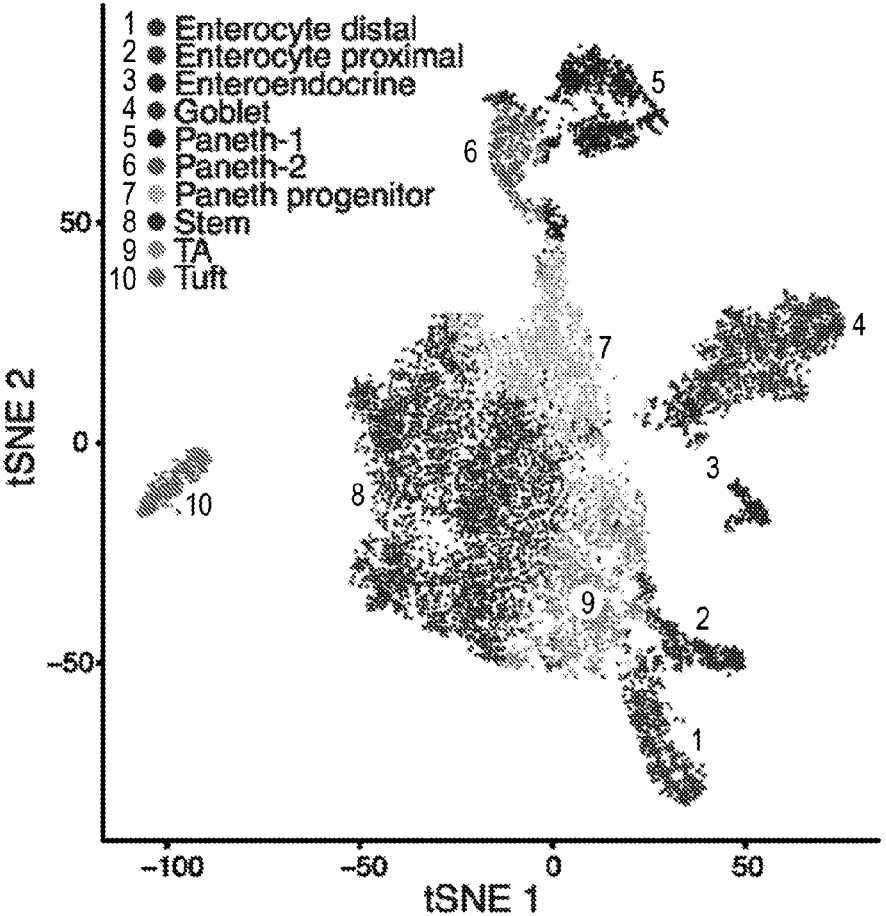
FIGS. 10M-P show regional variation in Paneth cell sub-types and stem cell markers.
Figure 10N:
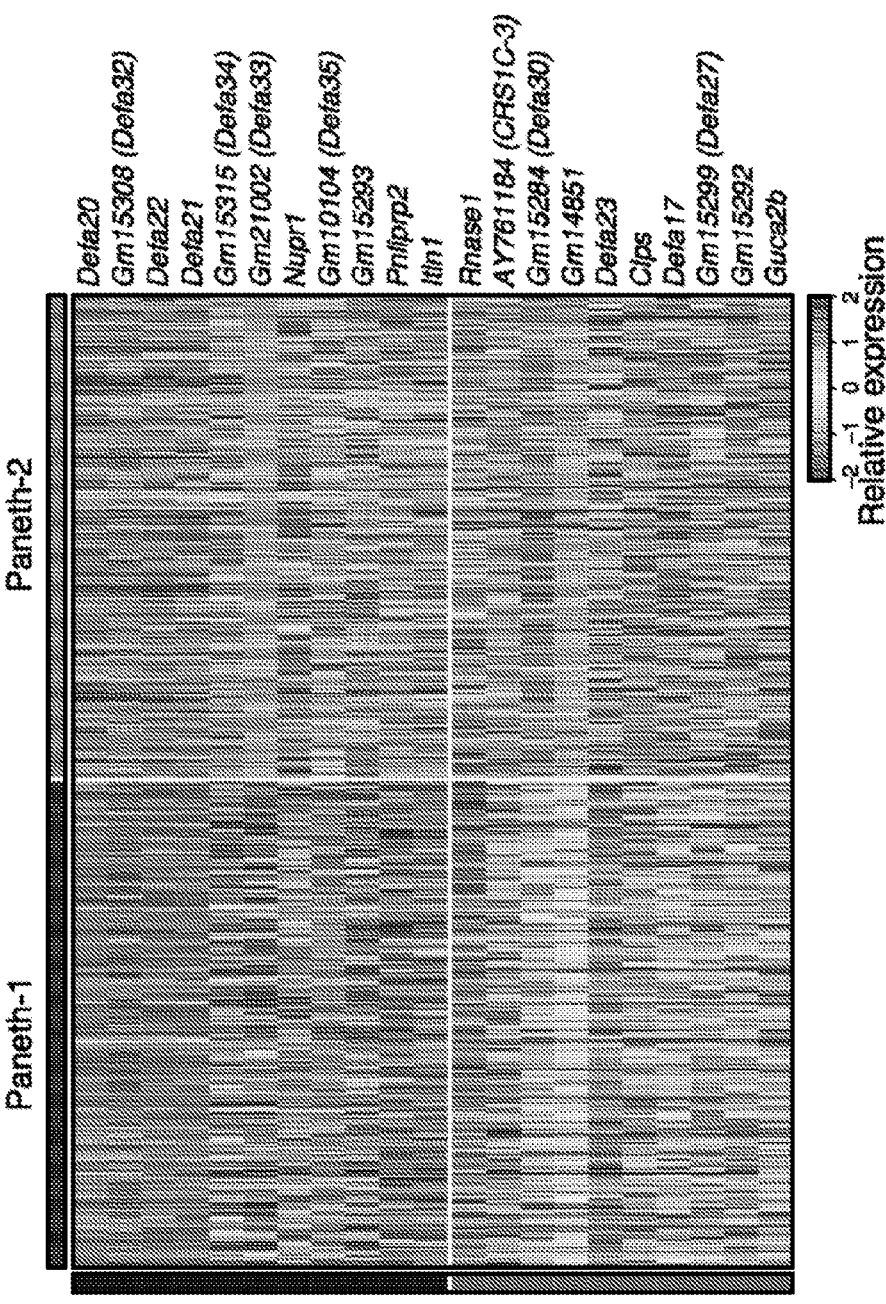

Example 2—Distinct Cell Types are Characterized by Specific Signatures, TFs and Receptors Relying on the high congruence between the two approaches, Applicants defined high-confidence consensus expression signatures for each cell type (Methods), highlighting known markers (corroborating the labels) and novel ones suggesting specific functions (FIG. 1c, FIG. 8b and Tables 3-5). For example, the Paneth cell consensus signature identified Mptx2, a mucosal pentraxin, with unknown function[33], (FIG. 1c, FIG. 8b,c, Table 5), which Applicants validated using single-molecule fluorescence in situ hybridization (smFISH, Methods) (FIG. 1d,e). From the deeper, full length RNA-seq dataset, Applicants also identified Mptx1, another mucosal pentraxin, as specific to Paneth cells (FDR<0.001, Mann-Whitney U-test, Table 4). Other Pentraxins include C reactive protein (CRP) and serum amyloid P component protein (SAP), secreted proteins that play a role in host defense against pathogenic bacteria[34]. In addition, the two Paneth cell subsets expressed distinct panels of anti-microbial alpha-defensins (FIG. 10n).

TABLE 3

Marker genes (3' droplet-based data) for intestinal epithelial cell-types

| Entero-endocrine | Enterocyte Immature Distal | Enterocyte Immature Proximal | Enterocyte Mature Distal | Enterocyte Mature Proximal | Goblet | Paneth | Stem | TA (G2) | Tuft |
|---|---|---|---|---|---|---|---|---|---|
| Chgb | Reg3g | Casp6 | Tmigd1 | Apoa4 | Agr2 | Gm15284 | Gkn3 | Stmn1 | Lrmp |
| Chga | Gsdmc4 | | Fabp6 | Fabp1 | Spink4 | Gm14851 | | Tubb5 | Alox5ap |
| Gfra3 | Prss32 | | Slc51b | Apoc2 | Fcgbp | Defa21 | | | Rgs13 |
| Cpe | Krt8 | | Slc51a | Rbp2 | Tff3 | Defa22 | | | Sh2d6 |
| Tac1 | | | Mep1a | Apoc3 | Muc2 | AY761184 | | | Ltc4s |
| Fam183b | | | Fam151a | Leap2 | Zg16 | Defa24 | | | Avil |
| Hmgn3 | | | Naaladl1 | Cyp2b10 | Clca1 | Defa17 | | | Hck |
| Cck | | | Slc34a2 | Cyp3a11 | Ccl6 | Lyz1 | | | Dclk1 |
| Fev | | | Plb1 | Lct | Klk1 | Defa-rs1 | | | Snrnp25 |
| Gch1 | | | Nudt4 | Gsta1 | Tpsg1 | Defa3 | | | Cd24a |
| Pcsk1n | | | Dpep1 | Gstm1 | Ccl9 | Mptx2 | | | Trpm5 |
| Bex2 | | | Pmp22 | Gstm3 | Txndc5 | Ang4 | | | Kctd12 |
| Neurog3 | | | Xpnpep2 | Ephx2 | Smim14_ ENSMUSG00000037822 | Defa26 | | | Aldh2 |
| Ngfrap1 | | | Muc3 | Ms4a10 | Tspan13 | Gm15292 | | | Il13ra1 |
| Vwa5b2 | | | Neu1 | Fam213a | Atoh1 | | | | Gng13 |
| Resp18 | | | Clec2h | Cbr1 | Lrrc26 | | | | Tmem176a |
| Sct | | | Phgr1 | Adh6a | Ramp1 | | | | Skap2 |
| Aplp1 | | | 2200002D01Rik | Cyb5r3 | Galnt12 | | | | Ptpn6 |
| Scgn | | | Prss30 | Dhrs1 | Mmp7 | | | | Ly6g6f |
| Neurod1 | | | Cubn | Ifi27l2b | Qsox1 | | | | Fyb |
| Nkx2-2 | | | Plec | Cyb5a | Fkbp11 | | | | Adh1 |
| Insm1 | | | Fgf15 | Cyp3a25 | Rep15 | | | | Tmem176b |
| Vim | | | Crip1 | Gda | Tmsb10 | | | | Hpgds |
| Rbp4 | | | Krt20 | Ckb | Pla2g10 | | | | Reep5 |
| Isl1 | | | Dhcr24 | Prap1 | Tsta3 | | | | Ptpn18 |
| Ddc | | | Myo15b | Cgref1 | Pdia6 | | | | Spib |
| Mtch1 | | | Amn | Dnase1 | Sdf2l1 | | | | Bpgm |
| Tph1 | | | Enpep | Aldh1a1 | S100a6 | | | | Galk1 |
| Cldn4 | | | Anpep | Khk | Manf | | | | Matk |
| Scg5 | | | Slc7a9 | Lpgat1 | Slc12a8 | | | | Tuba1a |
| Maged1 | | | Ocm | Treh | Creb3l1 | | | | 1810046K07Rik |
| Rprml | | | Anxa2 | Reg3a | Sh3bgrl3 | | | | Hmx2 |
| Cryba2 | | | Aoc1 | Acsl5 | Spdef | | | | Ccdc28b |
| Rph3al | | | Ceacam20 | Ace | Tpd52 | | | | Ethe1 |
| Celf3 | | | Arf6 | Aldob | Pdia5 | | | | Limd2 |
| Cacna1a | | | Abcb1a | H2-Q2 | Cmpk1 | | | | Sh2d7 |
| Trp53i11 | | | Xpnpep1 | Rdh7 | Serp1 | | | | Ccdc109b |
| Gpx3 | | | Vnn1 | Ckmt1 | Tmed3 | | | | Tspan6 |
| Pcsk1 | | | Cndp2 | Cyp3a13 | Selm | | | | Smpx |
| Fabp5 | | | Nostrin | P4hb | Creb3l4 | | | | Vav1 |
| Fxyd6 | | | Slc13a1 | Mdh1 | Smim6 | | | | Ly6g6d |
| Cplx2 | | | Aspa | Ppap2a | Krtcap2 | | | | Pik3r5 |
| Cdkn1c | | | Maf | Slc2a2 | Bace2 | | | | Nebl |
| Rundc3a | | | Myh14 | Cox7a1 | Stard3nl | | | | Plcg2 |
| Pycr2 | | | | Sec14l2 | Bcas1 | | | | Rbm38 |
| Myl7 | | | | Gsta4 | Nans | | | | Vdac3 |
| Ffar2 | | | | Mme | C1galt1c1 | | | | Krt18 |
| Prnp | | | | Retsat | Xbp1 | | | | Asah1 |
| Rimbp2 | | | | Mttp | Hpd | | | | Cd47 |
| Slc25a4 | | | | Creb3l3 | Slc50a1 | | | | Krt23 |
| Bambi | | | | Slc5a1 | Guk1 | | | | Bcl2l14 |
| Itm2c | | | | Sult1b1 | Tmed9 | | | | Lima1 |
| Cacna2d1 | | | | Hsd17b6 | Ssr4 | | | | Pygl |
| Fgd2 | | | | Scp2 | Hgfac | | | | Itpr2 |
| Gadd45a | | | | Cyb5b | Ostc | | | | Inpp5j |
| Cited2 | | | | Cyp2c65 | Creld2 | | | | Pea15a |
| Olfm1 | | | | Gpx4 | Sec61b | | | | Rac2 |
| Slc39a2 | | | | Xdh | Gale | | | | Pou2f3 |
| Ptov1 | | | | Cyp2d26 | Kdelr2 | | | | Atp2a3 |
| Rab3c | | | | Ugdh | Ssr2 | | | | Bmx |
| Tox3 | | | | Gstm6 | Ern2 | | | | Acot7 |
| Cdkn1a | | | | Ndufa1 | Ergic1 | | | | Gnai2 |
| Anxa6 | | | | Gpd1 | AW112010 | | | | Alox5 |
| Krt7 | | | | Cyp2c66 | Gcnt3 | | | | Ppp3ca |
| Btg2 | | | | | Guca2a | | | | Ptgs1 |
| Cnot6l | | | | | Klf4 | | | | Calm2 |
| Riiad1 | | | | | Sep15 | | | | Zfp428 |
| Marcksl1 | | | | | Galnt7 | | | | Tmem141 |
| Pax6 | | | | | Uap1 | | | | Myo1b |
| Wbp5 | | | | | Dnajc10 | | | | Siglecf |
| Scg3 | | | | | Ddost | | | | Pla2g4a |
| Nisch | | | | | Oit1 | | | | Inpp5b |
| Gstz1 | | | | | Foxa3 | | | | Fam221a |

TABLE 3-continued

Marker genes (3' droplet-based data) for intestinal epithelial cell-types

| Enteroendocrine | Enterocyte Immature Distal | Enterocyte Immature Proximal | Enterocyte Mature Distal | Enterocyte Mature Proximal | Goblet | Paneth | Stem | TA (G2) | Tuft |
|---|---|---|---|---|---|---|---|---|---|
| Bax | | | | | Tm9sf3 | | | | Bub3 |
| Gm43861 | | | | | Cracr2b | | | | Arpc5 |
| Slc18a1 | | | | | Vimp | | | | Pla2g16 |
| Gng4 | | | | | Capn9 | | | | 1110007C09Rik |
| | | | | | Scin | | | | Gimap1 |
| | | | | | Pdia3 | | | | Coprs |
| | | | | | Rnase1 | | | | Lect2 |
| | | | | | Calr | | | | Nrgn |
| | | | | | Wars | | | | Agt |
| | | | | | Snhg18 | | | | Ffar3 |
| | | | | | Dap | | | | Tmem45b |
| | | | | | Ttc39a | | | | Ccdc23 |
| | | | | | Dad1 | | | | Rgs2 |
| | | | | | Tnfaip8 | | | | Mlip |
| | | | | | Tram1 | | | | Csk |
| | | | | | Kdelr3 | | | | 2210016L21Rik |
| | | | | | Arf4 | | | | St6galnac2 |
| | | | | | Cmtm7 | | | | Ildr1 |
| | | | | | | | | | Gprc5c |
| | | | | | | | | | Mocs2 |
| | | | | | | | | | Nrep |
| | | | | | | | | | Pik3cg |
| | | | | | | | | | Malat1 |
| | | | | | | | | | Sec14l1 |
| | | | | | | | | | Ndufaf3 |
| | | | | | | | | | Inpp5d |
| | | | | | | | | | Pim3 |
| | | | | | | | | | Tmem9 |
| | | | | | | | | | Gga2 |
| | | | | | | | | | Nt5c3 |

Significance cut-offs: FDR (max): 0.05, Log2 fold-change: 0.5

Significance cut-offs: FDR (max):0.05, Log 2 fold-change: 0.5

TABLE 4

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Gfra3 | Mep1b | Slc16a1 | Ccnb1 | Clca3 | Defa23 | Lgr5 | | Alox5ap |
| Chgb | Anpep | | Cdc20 | Zg16 | Gm15284 | Gkn3 | | Hck |
| Trp53i11 | Gsta1 | | Cenpa | Fcgbp | Defa17 | Ascl2 | | Lrmp |
| Neurod1 | Apoa1 | | Cdkn3 | Tff3 | Defa-rs7 | Olfm4 | | Avil |
| Vwa5b2 | Gm3776 | | Cdc25c | Agr2 | AY761184 | Rgmb | | Trpm5 |
| Cck | Igsf9 | | Ccnb2 | Scin | Defa-rs1 | Igfbp4 | | Spib |
| Rfx6 | Il18 | | Kif22 | Pdia5 | Gm7849 | 2210407C18Rik | | Rgs13 |
| Prnp | Ace2 | | Ube2c | Tpsg1 | Gm14851 | Jun | | Ltc4s |
| Pcsk1 | Creb3l3 | | Sapcd2 | Chst4 | Defa3 | Pdgfa | | Pygl |
| Syt13 | Krt20 | | Rbp7 | Bcas1 | Defa22 | Soat1 | | Sh2d7 |
| Rph3al | Slc9a3 | | Ccna2 | Bace2 | Gm21498 | Tnfrsf19 | | Dclk1 |
| Fabp5 | Dpep1 | | Aurka | Galnt12 | Defa26 | Cyp2e1 | | Alox5 |
| Pam | Slc25a45 | | Cdkn2d | Rep15 | Defa4 | Fstl1 | | Pik3r5 |
| Scgn | Rbp2 | | Kif23 | S100a6 | Defa20 | H2-Eb1 | | Fyb |
| Aplp1 | Ms4a18 | | Nek2 | Capn9 | Defa25 | Ifitm3 | | Vav1 |
| Fev | Reg3b | | Birc5 | Spdef | Gm14850 | Prelp | | Matk |
| Scg5 | Reg3a | | Plk1 | Atoh1 | Defa5 | Scn2b | | Tspan6 |
| Celf3 | Clec2h | | Tacc3 | Guca2a | Defa24 | A930009A15Rik | | Strip2 |
| Resp18 | Slc51b | | Melk | Pla2g10 | Gm15292 | H2-Ab1 | | Pou2f3 |
| Neurog3 | Cyp2d26 | | Cdca3 | Muc2 | Defa-ps1 | Slc1a2 | | 1810046K07Rik |
| Maged1 | Adh6a | | Hmmr | Mlph | Gm15315 | Cd74 | | Ptpn6 |
| Scg3 | Bco2 | | Spc25 | AW112010 | Mptx2 | Sp5 | | Bmx |
| Pax4 | Slc3a1 | | Tpx2 | Scnn1a | Gm15299 | Noxa1 | | Tuba1a |
| Olfm1 | Cyp3a13 | | Arhgef39 | Ern2 | Gm10104 | Rgcc | | Espn |
| Cplx2 | Slc16a5 | | Bub1b | Ttc39a | Lyz1 | Sorbs2 | | Plcb2 |
| Isl1 | Btnl1 | | 1190002F15Rik | Liph | Clps | Sectm1b | | Ffar3 |
| Gpx3 | 2010106E10Rik | | Kif4 | C1galt1c1 | Defa21 | H2-Aa | | Ccdc109b |
| Anxa6 | Maob | | Mad2l1 | Kcnk6 | Reg4 | Cdo1 | | Plcg2 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Gng4 | Sis | Fbxl8 | | Creb3l4 | Pnliprp2 | Slc14a1 | | Ly6g6f |
| Mreg | Acad11 | Gpsm2 | | Slc12a8 | Defa6 | Clca2 | | Hpgds |
| Map1b | Edn2 | Ckap2l | | Efcab4a | Pla2g2a | Tifa | | Pea15a |
| Bex2 | Spink3 | Knstrn | | Ptprr | Itln1 | Pls3 | | Ly6g6d |
| Baiap3 | H2-Q1 | Id1 | | Klk1 | Mmp7 | Hmgcs2 | | Pik3cg |
| Disp2 | Sult2b1 | Cmc2 | | Tnfaip8 | Gm21002 | Arid5b | | Inpp5d |
| 1700086L19Rik | Slc7a7 | 1810065E05Rik | | Lrrc26 | Gm7861 | Agr3 | | Ccdc28b |
| Lrp11 | 1700019G17Rik | Cenpe | | C1galt1 | Ang4 | Slc12a2 | | Snrnp25 |
| Rimbp2 | Dgat2 | Pif1 | | Galnt7 | Gm15308 | Rassf5 | | Kctd12 |
| Snap25 | Enpep | Ckap5 | | Fam174b | Habp2 | Rnf43 | | Siglec5 |
| Klhdc8b | Fmo5 | Cnih4 | | Sgsm3 | Pnliprp1 | Nrn1 | | Skap2 |
| Foxa2 | 2010001E11Rik | Spc24 | | Galnt3 | Gm6696 | Lamb3 | | Ccdc129 |
| Gck | Fam3b | | | Spats2l | Mptx1 | Cd44 | | Nebl |
| Pcsk1n | Slc26a6 | | | Ccl9 | Fam46c | Axin2 | | Gprc5c |
| Gdap1l1 | Mpp1 | | | Sytl2 | Samd5 | Slc27a2 | | Rgs22 |
| Map3k15 | Ces1f | | | Car8 | Lyz2 | Afap1l1 | | Gfi1b |
| Kcnh6 | Apoa4 | | | Uap1 | C4bp | Ccdc3 | | Hmx3 |
| Kcnb2 | Slc5a11 | | | Asph | 1810010D01Rik | Lrig1 | | Cbr3 |
| Prodh2 | 2010003K11Rik | | | Slc50a1 | Apoc2 | Noxo1 | | Pfkfb3 |
| Bex1 | Eci3 | | | Smim14 | AY761185 | Cdk6 | | Prss53 |
| Lhfpl2 | Cyp4f14 | | | Creb3l1 | Defb1 | Amica1 | | Itpr2 |
| Fam183b | Btnl6 | | | Hgfac | Pla2g2f | Tgif1 | | Limd2 |
| Nkx2-2 | Ace | | | Stard3nl | Copz2 | Tns3 | | Cd300lf |
| Pax6 | Hsd17b6 | | | Tspan13 | Scgb2b7 | Nr2e3 | | Chn2 |
| Adprm | Rdh7 | | | Gsn | Scgb2b19 | Efna4 | | Smpx |
| Dbpht2 | Alpi | | | Capn8 | Scgb2b20 | Rnf32 | | Ptgs1 |
| Myt1 | Gpd1 | | | Gcnt3 | Klf15 | Prss23 | | A4galt |
| Kcnk16 | Ptprh | | | Txndc5 | Sntb1 | 2010009K17Rik | | Rac2 |
| Tac1 | Papss2 | | | Atp2c2 | Ggh | Smoc2 | | Csk |
| Scarb1 | Ggt1 | | | Hpd | Cd244 | Mecom | | Slco4a1 |
| Acadsb | Aldh1a1 | | | Bhlhe40 | Gm15293 | Esrrg | | Ptpn18 |
| Vim | Naaladl1 | | | Tfcp2l1 | Gm7325 | Aqp1 | | Chat |
| Xpnpep2 | Agpat9 | | | Qsox1 | Fzd9 | Znrf3 | | Hebp1 |
| Acsl6 | H2-Q2 | | | St3gal6 | Fgfrl1 | Grb7 | | Ppp1r14c |
| Bcmo1 | Hsd17b2 | | | Rap1gap | Tesc | Phgdh | | Dgki |
| Parp6 | Exoc3l4 | | | Kctd14 | Slc1a4 | 2410004N09Rik | | Inpp5j |
| Plxnb1 | Hpgd | | | Kdelr3 | Lamb1 | Clca4 | | Tppp3 |
| Cnot6l | Gnpda1 | | | Galnt10 | Darc | Aqp4 | | Gng13 |
| Ncald | Gm1332 | | | Dnajc10 | Ddx26b | Lcp1 | | Ildr1 |
| Scg2 | Ms4a10 | | | Sytl4 | Slc30a2 | E030011005Rik | | Cwh43 |
| Phldb2 | Gm7092 | | | Hid1 | Hspb8 | Snhg1 | | Il17rb |
| Peg3 | Ugt2a3 | | | Samhd1 | Sync | BC064078 | | Ncf2 |
| Mapre3 | Upp1 | | | Fkbp11 | Slc16a7 | Car12 | | Fut2 |
| Ids | Lrrc19 | | | Galnt5 | Hapln4 | Zbtb38 | | Coprs |
| Amigo2 | Fmo4 | | | Tmed3 | Insrr | Cdca7 | | Ddah1 |
| Dner | Hkdc1 | | | Ica1 | Acvr1c | Fam13a | | Tmem116 |
| Syp | Nr1h3 | | | Pqlc3 | Syne4 | Shisa2 | | Sucnr1 |
| Tox3 | Themis3 | | | Tmem123 | Acox2 | Dtx4 | | Tmem176a |
| Insm1 | Agmo | | | Sdf2l1 | Dkk3 | Slc19a2 | | Ccrl1 |
| Adora3 | Slc6a20a | | | S100a14 | Ang2 | Fam115c | | 1110007C09Rik |
| Tmem106c | Soat2 | | | Ergic1 | Ang6 | Mir703 | | Adcy5 |
| Sstr1 | Ces2a | | | Efcab4b | Thbs1 | Cd14 | | Fnbp1 |
| Cbfa2t2 | Bcl2l15 | | | Foxa3 | Dll3 | Mettl20 | | Plk2 |
| Slc39a2 | Entpd5 | | | Stx17 | Ang5 | Myo9a | | Hmx2 |
| Rasd1 | Cndp2 | | | AI597468 | | App | | Tmem141 |
| Cacna2d1 | Tmem37 | | | Fxyd3 | | Clic6 | | Krt23 |
| Ngfrap1 | Gda | | | Cd97 | | Wee1 | | Gprc5a |
| Rab36 | Abcg5 | | | Csrp1 | | 2410006H16Rik | | Rgs2 |
| Akna | Ces2c | | | Pdia6 | | Lancl1 | | Camk2b |
| Ghrl | Mogat2 | | | Tinagl1 | | 1500012F01Rik | | Fes |
| Gpr116 | Abhd3 | | | Rcan3 | | Casp12 | | Bpgm |
| 2610301B20Rik | St3gal4 | | | Fam114a1 | | Sh3rf1 | | Acacb |
| Rbfox2 | Gm8909 | | | Cmtm7 | | Lrp4 | | Il13ra1 |
| Pde1c | Slc5a1 | | | Ppapdc1b | | Arhgef26 | | Zfp428 |
| Mapk8ip2 | Tubal3 | | | Mon1a | | Etv6 | | Ppp1r3b |
| Scn3a | Gstm3 | | | Slc7a4 | | 1700024F13Rik | | Ccnj |
| Sstr5 | Sphk1 | | | Tnfrsf21 | | Cttnbp2 | | Bcl2l14 |
| Lypd1 | Slc26a3 | | | Tor3a | | Slc16a13 | | Tmem229a |
| Marcks | Tmem106a | | | Adrbk1 | | Htr4 | | Ethe1 |
| Riiad1 | Slc27a4 | | | P2rx4 | | Pdxk | | Runx1 |
| Trit1 | Sowaha | | | Myo5c | | Immp2l | | Gga2 |
| Ptpru | Slc6a4 | | | Nipal2 | | Rps15a-ps6 | | Apobec1 |
| Apbb1 | Mme | | | Tmem39a | | Rps15a-ps4 | | Serpini1 |
| Galr3 | Adamtsl5 | | | Sil1 | | Nap1l1 | | St6galnac6 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Rapgef4 | Aldh1l1 | | | Slc17a9 | | Sdc4 | | Fbxl21 |
| Sphkap | Gpt | | | Mcf2l | | Epn3 | | 9030624J02Rik |
| Golim4 | Igsf5 | | | Rasa4 | | Sipa1l1 | | Inpp5b |
| Nefm | Emp1 | | | Cgref1 | | Wfdc15b | | Samd14 |
| Cdk2ap1 | Cox7a1 | | | Galk2 | | Zfp341 | | Pgm2l1 |
| Tubb3 | Ugt2b5 | | | Wars | | Ngef | | Pla2g4a |
| Tmem182 | Apoc3 | | | Gm9994 | | Nrg4 | | Ptprc |
| Fam135a | Abcg8 | | | Edem1 | | Csad | | Aldh2 |
| Fam43a | Ugt2b36 | | | Mia3 | | Rpl34-ps1 | | Ifi27l1 |
| Golga7b | Pex11a | | | Slc35a1 | | Rin2 | | Pnpla3 |
| Slc26a4 | Osgin1 | | | Tm9sf3 | | Cd81 | | Jarid2 |
| Chd7 | Gsta4 | | | Fhl1 | | Irf2bp2 | | Rgs19 |
| Cerkl | Slc28a1 | | | Sec24d | | Sesn3 | | Reep5 |
| Cplx1 | Gm11437 | | | Sel1l3 | | Phlpp1 | | Tiparp |
| Galr1 | Nat8 | | | Tmed9 | | Yap1 | | Gnai2 |
| Gpr119 | Nr1i3 | | | Cd9 | | Mfge8 | | Fam49a |
| Fam160a2 | Slc51a | | | Rasd2 | | Zfp825 | | Cacna2d2 |
| Pcp4l1 | Fabp1 | | | Edem2 | | Itga1 | | Ypel2 |
| Efcab1 | Abcc2 | | | Golph3l | | Pcdh8 | | Cd24a |
| Maml3 | Apob | | | Arfip2 | | Vdr | | Acot7 |
| Ap3b2 | Mical2 | | | Tsta3 | | Kcnq1 | | Svil |
| Trf | Mgat4c | | | Tvp23b | | Slc28a2 | | Abhd16a |
| Rab31 | H2-Bl | | | Rnf39 | | Zfp36l1 | | Fam101a |
| Hnrnph3 | Hdhd3 | | | E130003G02Rik | | Urod | | Trim40 |
| Ffar1 | Sec23a | | | Aacs | | Rgs12 | | Trak1 |
| Emb | Slc7a9 | | | Chrm1 | | Nfib | | Sec14l1 |
| Th | Tmem86a | | | Fut4 | | Sdsl | | 4930539E08Rik |
| Ptprn | Npc1l1 | | | Vps37c | | Nfia | | Smtn |
| Prkar1b | Btnl2 | | | Creld2 | | | | Galk1 |
| Dock4 | Acot9 | | | Ikbip | | | | Tbc1d1 |
| Kirrel2 | Paqr7 | | | Nans | | | | Tmem176b |
| Sh2d5 | Cblc | | | Tpd52 | | | | Fcna |
| Tmem130 | Tmem253 | | | Tmem214 | | | | Abhd2 |
| Pde11a | Smlr1 | | | Anxa3 | | | | Hsbp1l1 |
| Nek5 | Abhd6 | | | Rassf6 | | | | Slc4a8 |
| Azi1 | Amn | | | Bcat2 | | | | Myo1b |
| 5430425J12Rik | Pbld2 | | | Tmem159 | | | | Tmem38b |
| Pnmal1 | Mttp | | | Stxbp6 | | | | Hk1 |
| Dnahc9 | Ap2a2 | | | Slc30a7 | | | | Neurl1a |
| Rnf122 | Ptk6 | | | Mansc1 | | | | Dmxl2 |
| Chst11 | Vwce | | | Gfpt1 | | | | Bub3 |
| Tekt2 | Cideb | | | Gmppb | | | | Ptprj |
| Mum1l1 | Sco2 | | | Sybu | | | | Trib2 |
| Trpm2 | Gramd3 | | | Srd5a1 | | | | Stard5 |
| Map9 | Apol10a | | | Tram1 | | | | Ubtd1 |
| Ctif | Dpyd | | | Slc39a7 | | | | Slc41a3 |
| Btbd17 | Abat | | | Tmem248 | | | | Plekhg5 |
| Lrrc16b | Slc46a1 | | | Bet1l | | | | Rbm38 |
| Rufy2 | Adtrp | | | Sec23ip | | | | Fam57a |
| Ambp | Xdh | | | Cog6 | | | | Eef2k |
| Pkia | Tgfbi | | | Rab3d | | | | Cables2 |
| Pitpnc1 | Chp2 | | | D630039A03Rik | | | | Fbxo25 |
| Mapkbp1 | Gyk | | | Prrc1 | | | | Ap1s2 |
| Unc13a | Khk | | | Appl2 | | | | 1300002K09Rik |
| Gatm | Lct | | | 1810055G02Rik | | | | Ero1lb |
| Slc35d3 | Atp6v0a2 | | | Synj2 | | | | Clmn |
| Spred3 | Rhbg | | | 1700066B19Rik | | | | Fam49b |
| Zc3h12c | Tmem82 | | | Arfgap1 | | | | Cpvl |
| Mapk15 | Galm | | | Oit1 | | | | Prr15 |
| March4 | AA986860 | | | Ehd4 | | | | Lpcat4 |
| Pax6os1 | Shpk | | | Stx5a | | | | Tmem74b |
| Neurod2 | Slc15a1 | | | Plcb1 | | | | Mn1 |
| Cidea | Cyp4f40 | | | Ptger4 | | | | Eppk1 |
| Klhl32 | Sult1b1 | | | Slc39a11 | | | | Samd9l |
| Hrh3 | Slc13a1 | | | 5033406O09Rik | | | | Tmem245 |
| Slc8a1 | Cml1 | | | Pllp | | | | Glyctk |
| Klhl31 | Pm20d1 | | | Gpr20 | | | | Aldh3a2 |
| Gfra1 | Fahd1 | | | Spink4 | | | | Ppp3ca |
| Adgb | Trim31 | | | Nfkb2 | | | | Cpne3 |
| Lhx1 | H2-T3 | | | Tmco3 | | | | Slc4a7 |
| Plk5 | 0610005C13Rik | | | Mllt3 | | | | Nfatc1 |
| | Optn | | | Gmppa | | | | Kit |
| | Clec2e | | | D10Bwg1379e | | | | Fam117b |
| | Myo7a | | | Cdk5rap3 | | | | Nradd |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Slc37a4 | | | Smim6 | | | | Tmem121 |
| | Ppargc1a | | | Parm1 | | | | Cpm |
| | Stom | | | Fam69a | | | | Asah1 |
| | Reep6 | | | 1810007106Rik | | | | Slc9a9 |
| | Cmbl | | | Kcnh3 | | | | Ubl7 |
| | Cdkn2b | | | Tspan1 | | | | Abca3 |
| | Pgm2 | | | B3gnt7 | | | | Pde6d |
| | Maf | | | Entpd4 | | | | Bmp2 |
| | Mia2 | | | Kdelr2 | | | | Kdm4a |
| | Slc11a2 | | | Sppl2a | | | | Camkk2 |
| | Spsb1 | | | Impad1 | | | | Arhgap8 |
| | Tmem236 | | | Mgat3 | | | | Agt |
| | Cd36 | | | Cpd | | | | Ptpra |
| | Treh | | | Asns | | | | Adh1 |
| | Gstk1 | | | Hyou1 | | | | Dusp14 |
| | Lipe | | | Uba7 | | | | Clic4 |
| | Tmem139 | | | Dnajc3 | | | | Gimap1 |
| | Cyp2c66 | | | Golt1b | | | | Cpne5 |
| | Gsdmd | | | Pygb | | | | Ceacam2 |
| | Ocm | | | Manf | | | | Zfp710 |
| | Srxn1 | | | Xbp1 | | | | Gcnt1 |
| | Lmbr1l | | | Galnt16 | | | | B4galt5 |
| | Lpgat1 | | | Hspa13 | | | | Suco |
| | Fez2 | | | Rab27b | | | | Pim3 |
| | Slc52a2 | | | Rasef | | | | Ogdhl |
| | Mocos | | | Itga2 | | | | Oas1g |
| | Nek3 | | | Gorasp1 | | | | Dcp1b |
| | Tm6sf2 | | | Pck1 | | | | Myzap |
| | Agpat2 | | | Pgm3 | | | | Cdkn1a |
| | Slc23a2 | | | Galnt6 | | | | Cd37 |
| | Xkr9 | | | Vimp | | | | Brms1 |
| | Tob1 | | | Golga5 | | | | Lrrc42 |
| | Clcn2 | | | Sec16a | | | | Pld2 |
| | Hectd3 | | | Eif2ak3 | | | | Tmem9 |
| | Tbc1d22a | | | Osbpl2 | | | | Cpeb4 |
| | Naip1 | | | Zfp467 | | | | Ssx2ip |
| | Ctss | | | Hdlbp | | | | Ddah2 |
| | Slc9a2 | | | Cbfa2t3 | | | | Tmem65 |
| | Cdc42ep2 | | | Zbp1 | | | | 5430417L22Rik |
| | 9030617O03Rik | | | B3gnt5 | | | | 2210016L21Rik |
| | Mall | | | Far1 | | | | Msi2 |
| | Pla2g12b | | | 0610007N19Rik | | | | B4galt4 |
| | Rhod | | | Zfp330 | | | | Rabgap1l |
| | Kbtbd11 | | | Gcc2 | | | | Pik3r3 |
| | Acox1 | | | Lman1 | | | | Nt5c3 |
| | Arhgap26 | | | Lamc2 | | | | Palld |
| | Trim30d | | | Herpud1 | | | | AA467197 |
| | Tcn2 | | | Slc10a7 | | | | Pip5k1b |
| | Mylk | | | Serp1 | | | | Krt18 |
| | Thnsl2 | | | Scamp1 | | | | Map1a |
| | Fam213b | | | Gal3st2 | | | | Lmf1 |
| | Dhrs1 | | | Odf21 | | | | Arhgef28 |
| | Adh4 | | | Hilpda | | | | Nsfl1c |
| | Dgkq | | | Cog3 | | | | Txndc16 |
| | Ces2e | | | Alyref2 | | | | Pstpip2 |
| | Aldh1a7 | | | Galnt4 | | | | Ttll11 |
| | Myo5b | | | Prr24 | | | | Exph5 |
| | Dnm1 | | | Litaf | | | | 2700086A05Rik |
| | Frk | | | Fam98a | | | | Gadd45a |
| | Tsc22d3 | | | Pcsk9 | | | | Plekhs1 |
| | Slc35f5 | | | Zbtb8a | | | | Fam188a |
| | 2200002D01Rik | | | Tmem63a | | | | Jmy |
| | Cyp2c65 | | | Dap | | | | Atat1 |
| | S100g | | | Trim47 | | | | Arhgef2 |
| | Ugdh | | | Ssr3 | | | | Lmbr1 |
| | Cyp2c68 | | | Edem3 | | | | Rhoc |
| | Hagh | | | Tst | | | | Card10 |
| | Xpnpep1 | | | Ang | | | | Kcnj16 |
| | Cobl | | | Slc38a10 | | | | Arhgap4 |
| | Epb4.1l3 | | | Guk1 | | | | Acsl4 |
| | Mep1a | | | Pcsk7 | | | | Rhog |
| | Hnf4g | | | Trabd | | | | Fam221a |
| | Parp9 | | | Gfi1 | | | | Dynlt1b |
| | Cyp2j6 | | | Gnpnat1 | | | | C2 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Sgpl1 | | | Pdxdc1 | | | | Zbtb41 |
| | Pccb | | | Hspa5 | | | | Socs1 |
| | Abcg2 | | | Slc35a2 | | | | Atp6ap1 |
| | Slc2a2 | | | Slc37a3 | | | | Fam171a1 |
| | Ephx2 | | | Arl1 | | | | Wnk2 |
| | Kcnk5 | | | Smim5 | | | | Kcnd3 |
| | Lrp1 | | | Ccnd3 | | | | Slc27a1 |
| | Tmem135 | | | Sar1a | | | | Atxn1 |
| | Dak | | | F2rl1 | | | | Rabgap1 |
| | Dusp12 | | | Stt3a | | | | Myrfl |
| | Gpr128 | | | Tdrd7 | | | | Crot |
| | Abcb1a | | | Spcs3 | | | | Tm4sf4 |
| | Tmem252 | | | Sidt1 | | | | Ube2j1 |
| | Slc7a8 | | | Pdia3 | | | | Sort1 |
| | 4931406C07Rik | | | Lss | | | | Lima1 |
| | Tm4sf5 | | | Cmpk1 | | | | Mov10 |
| | Akr1b7 | | | Naga | | | | Lca5 |
| | Tmem230 | | | Sh3bgrl3 | | | | Gimap9 |
| | Acbd4 | | | Slc41a2 | | | | Mlip |
| | Crat | | | Ostc | | | | 1110008P14Rik |
| | Pcsk5 | | | Fgfr3 | | | | Ckap4 |
| | Galt | | | Fut8 | | | | Tor4a |
| | Gm10768 | | | Ggcx | | | | Rmdn1 |
| | Cyp3a25 | | | Plac9a | | | | Oas2 |
| | Gstp2 | | | Sec61b | | | | Dsp |
| | Ilvbl | | | Bscl2 | | | | Sox9 |
| | Urgcp | | | Golm1 | | | | Osbpl3 |
| | Chchd7 | | | Klf4 | | | | Kif21b |
| | Car4 | | | Ssr4 | | | | Tbcb |
| | Slc13a2 | | | Srprb | | | | Arap2 |
| | Epha1 | | | Yipf6 | | | | Casp3 |
| | Dab1 | | | Clptm1l | | | | Enc1 |
| | Gstm6 | | | Id4 | | | | Il25 |
| | Sept9 | | | Arf4 | | | | Lman2l |
| | Adipor2 | | | Gale | | | | Zmiz1 |
| | Cast | | | Eif4ebp1 | | | | Nav2 |
| | Abp1 | | | Srpr | | | | Atp2a3 |
| | Casp6 | | | Tbc1d30 | | | | Gimap8 |
| | Itga3 | | | Akr1c14 | | | | Folr1 |
| | Rilp | | | Zc3h7a | | | | Fn1 |
| | Tmem41a | | | D17Wsu104e | | | | Hspa4l |
| | Nkiras2 | | | S100a16 | | | | Sufu |
| | March6 | | | Mknk2 | | | | Atp8a1 |
| | Gm9926 | | | Tmprss2 | | | | Vps53 |
| | Plin3 | | | Tc2n | | | | Rgs14 |
| | Rab11fip3 | | | Slc35c1 | | | | Gm17660 |
| | Retsat | | | Ufsp2 | | | | Pdcl |
| | Arg2 | | | Tmem165 | | | | Shkbp1 |
| | Slc39a5 | | | Tmsb10 | | | | Oas1a |
| | Pepd | | | Sec62 | | | | Pkp1 |
| | Idh1 | | | Bet1 | | | | Ccdc23 |
| | Ccdc134 | | | Cyp51 | | | | Il4ra |
| | Mgam | | | Fam3c | | | | 1700112E06Rik |
| | Ugt2b34 | | | Mfsd7a | | | | Dvl1 |
| | Ceacam20 | | | Slc37a1 | | | | Zfhx3 |
| | Slc2a9 | | | Cmtm8 | | | | Adam22 |
| | Frmd8 | | | Adam9 | | | | Gramd1c |
| | Smpdl3a | | | Art2a-ps | | | | Tmem45b |
| | Apol10b | | | Capns1 | | | | Unc5b |
| | Slc5a9 | | | Syt7 | | | | Mical3 |
| | Gna11 | | | Pdia4 | | | | Kctd13 |
| | Pls1 | | | Slc22a23 | | | | Ak7 |
| | Rab17 | | | Yipf5 | | | | Tcta |
| | Lgals3 | | | H2-T9 | | | | Nek7 |
| | Slc25a37 | | | Atf4 | | | | D730039F16Rik |
| | Ppap2a | | | Ick | | | | Plekho2 |
| | Gpr155 | | | Srm | | | | Myo6 |
| | Cml5 | | | Plaur | | | | Chdh |
| | Spns2 | | | Pyroxd1 | | | | Opn3 |
| | Acot11 | | | Fry | | | | Tle3 |
| | Vmp1 | | | Cyp2j9 | | | | Ttll10 |
| | Mertk | | | Sep15 | | | | Strada |
| | 2510049J12Rik | | | Sc4mol | | | | Ypel3 |
| | Zzef1 | | | Stk38l | | | | Cmip |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Bche | | | Bmp8a | | | | Cachd1 |
| | Abcd3 | | | Spryd3 | | | | Pigc |
| | Aqp11 | | | Gne | | | | Atp6v1d |
| | Gcnt2 | | | Aldh3b2 | | | | Rdx |
| | Acsl5 | | | Rell1 | | | | S100a11 |
| | Gng12 | | | Krtcap2 | | | | Spa17 |
| | Cda | | | Sec23b | | | | Gimap5 |
| | Fcgrt | | | St3gal1 | | | | Cystm1 |
| | Gm6034 | | | Tmem56 | | | | Zdhhc17 |
| | Sema4g | | | Tulp4 | | | | Lect2 |
| | Zfyve21 | | | Capn7 | | | | Vdac3 |
| | Pfkfb4 | | | Gpr180 | | | | Hspb11 |
| | D130043K22Rik | | | Txndc11 | | | | Gm4952 |
| | Cyp4v3 | | | Copb2 | | | | Slc16a2 |
| | C530008M17Rik | | | Calr | | | | Abhd5 |
| | Ptdss1 | | | Homer2 | | | | Rhbdf1 |
| | Gm766 | | | Ssr2 | | | | Cblb |
| | Tbc1d24 | | | Tbrg1 | | | | Nfe2l3 |
| | Cyb5b | | | Jtb | | | | Pla2g16 |
| | Maoa | | | Syvn1 | | | | Sept8 |
| | Vat1 | | | Morf4l2 | | | | Gpcpd1 |
| | Ehhadh | | | Rpn2 | | | | Psd3 |
| | Naprt1 | | | Ugp2 | | | | Anxa11 |
| | Slc3a2 | | | H13 | | | | Slc25a12 |
| | Dhrs11 | | | Slc16a6 | | | | Ehf |
| | Sh3tc1 | | | Slc39a1 | | | | Akr1b10 |
| | Irak2 | | | Gm1123 | | | | Dapp1 |
| | Btnl4 | | | Copg1 | | | | Vmn2r26 |
| | Stx12 | | | Ssr1 | | | | Esyt1 |
| | Dgat1 | | | Tmed2 | | | | Ppt1 |
| | Acaa1a | | | Ank3 | | | | Cd47 |
| | Cyp4f16 | | | Tmbim4 | | | | Chi3l1 |
| | Btnl5 | | | Rpn1 | | | | Mical1 |
| | Snx9 | | | Uggt1 | | | | Gna14 |
| | Ahnak | | | Utp11l | | | | Pacs2 |
| | Fam109a | | | Ppib | | | | Lyn |
| | Edn3 | | | Camsap3 | | | | Rmnd5a |
| | Ccl25 | | | Ddost | | | | Ankrd12 |
| | Zdhhc7 | | | Mesdc1 | | | | BC022687 |
| | Ppp1r14d | | | 4930404N11Rik | | | | Rit1 |
| | Slc43a2 | | | Sh3bgrl2 | | | | Camta2 |
| | Faah | | | Golgb1 | | | | Mocs2 |
| | Tymp | | | B3gnt3 | | | | Usp49 |
| | Acy1 | | | Dcbld2 | | | | Nrbp2 |
| | Cyb5r3 | | | Spcs2 | | | | Ifnar2 |
| | Rnf13 | | | Sec61a1 | | | | Epha4 |
| | Rxra | | | Cant1 | | | | Arl5a |
| | Dqx1 | | | Tpcn1 | | | | Rgl2 |
| | Snx13 | | | Gorasp2 | | | | St18 |
| | Acnat1 | | | Pmm2 | | | | BC016579 |
| | Ticam1 | | | Ano7 | | | | Tead1 |
| | Sidt2 | | | Rrbp1 | | | | Enpp4 |
| | Fam78a | | | Pacsin1 | | | | Tmem158 |
| | Aldh18a1 | | | Srp72 | | | | Tnfaip3 |
| | Rmdn3 | | | Tnk2 | | | | Gys1 |
| | Sat1 | | | Eif2ak4 | | | | Hivep2 |
| | Ckmt1 | | | Sec22b | | | | Cap1 |
| | Txlng | | | Tars | | | | Slc4a2 |
| | Slc31a1 | | | Slc1a5 | | | | Map4k4 |
| | Slc25a36 | | | Copb1 | | | | Desi1 |
| | Slc25a34 | | | Yif1b | | | | H2-D1 |
| | AU040320 | | | Etnk1 | | | | Man2a1 |
| | Marc2 | | | Ramp1 | | | | Cyp17a1 |
| | Aldob | | | Cltb | | | | Cyhr1 |
| | Gm7030 | | | Slc22a15 | | | | Morf4l1 |
| | Decr1 | | | Kif13a | | | | Mllt4 |
| | Sh3d21 | | | Yipf3 | | | | Phf17 |
| | Ugt1a1 | | | Ift20 | | | | Stox2 |
| | Ccs | | | Ufl1 | | | | Hist3h2a |
| | Kifc3 | | | Tm9sf2 | | | | Hdac6 |
| | Slc18b1 | | | Syngr2 | | | | Prox1 |
| | Aprt | | | Nucb1 | | | | Dtnb |
| | Slc22a1 | | | Gmds | | | | Lrch4 |
| | Acp6 | | | Sec61g | | | | Spire2 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Ogdh | | | Rfc1 | | | | Klf6 |
| | Tfg | | | C2cd2l | | | | Rab5b |
| | Tstd1 | | | Smim3 | | | | Anxa4 |
| | Klc4 | | | Hsp90b1 | | | | Rab4b |
| | Itpk1 | | | Srp9 | | | | Iqsec1 |
| | Bmp3 | | | Ost4 | | | | Pdpk1 |
| | Pld1 | | | Tmem183a | | | | Stk40 |
| | Ezr | | | Dnajb11 | | | | Gde1 |
| | Coro2a | | | Tom1l1 | | | | Mtmr11 |
| | Ckb | | | Sh3pxd2a | | | | Cib2 |
| | Farp2 | | | Ier3ip1 | | | | March2 |
| | Pxdc1 | | | | | | | Capg |
| | Sar1b | | | | | | | Narf |
| | Scp2 | | | | | | | Mgst3 |
| | Ggact | | | | | | | Angel1 |
| | Cst6 | | | | | | | Bicd1 |
| | Sft2d2 | | | | | | | Ifitm1 |
| | Abr | | | | | | | Stx3 |
| | Glt28d2 | | | | | | | S100a1 |
| | Slc34a2 | | | | | | | Omd |
| | Fam160a1 | | | | | | | 0610040J01Rik |
| | Pcyt1a | | | | | | | Arpc5 |
| | Tep1 | | | | | | | Homer3 |
| | Hadha | | | | | | | Cdc42se1 |
| | Ccdc88c | | | | | | | Abcc3 |
| | Lpcat3 | | | | | | | Hsf2 |
| | Tbc1d14 | | | | | | | Pnpla6 |
| | Gucd1 | | | | | | | Ccdc68 |
| | Acadm | | | | | | | Fryl |
| | 2210404O07Rik | | | | | | | Lmtk2 |
| | Mvp | | | | | | | Tas1r3 |
| | Actn4 | | | | | | | 4931406H21Rik |
| | Tspan15 | | | | | | | Uspl1 |
| | Rufy3 | | | | | | | Ajuba |
| | Mcu | | | | | | | Kalrn |
| | Spint1 | | | | | | | Basp1 |
| | Sfxn1 | | | | | | | Pip5kl1 |
| | Alas1 | | | | | | | Slc26a2 |
| | Nipsnap3b | | | | | | | Atp2b2 |
| | Tor1aip2 | | | | | | | Smug1 |
| | Casp1 | | | | | | | Myadm |
| | Bpnt1 | | | | | | | D330041H03Rik |
| | Baiap2l1 | | | | | | | Wdfy2 |
| | Ifngr2 | | | | | | | Trim38 |
| | Pex19 | | | | | | | Arf3 |
| | Myl12b | | | | | | | Scand1 |
| | 0610008F07Rik | | | | | | | Dpysl2 |
| | Atp1a1 | | | | | | | Ndufaf3 |
| | Itfg3 | | | | | | | Sik1 |
| | Dnpep | | | | | | | Wdr7 |
| | Akr7a5 | | | | | | | Sfxn3 |
| | Dlst | | | | | | | Kcnq4 |
| | Ugt1a7c | | | | | | | Mll1 |
| | Myo1d | | | | | | | Hsbp1 |
| | Tmem120a | | | | | | | Calml4 |
| | Cdh17 | | | | | | | Atf7ip |
| | Acaa2 | | | | | | | Gpr137b-ps |
| | Apol11b | | | | | | | Hap1 |
| | Hadh | | | | | | | Kctd15 |
| | Casp7 | | | | | | | Prcp |
| | Acp5 | | | | | | | 9430023L20Rik |
| | Rfk | | | | | | | Gmip |
| | Aldh9a1 | | | | | | | Cmtm3 |
| | Vipr1 | | | | | | | Madd |
| | Txndc17 | | | | | | | Krt222 |
| | Phgr1 | | | | | | | Nsf |
| | Eno1 | | | | | | | Klhl28 |
| | Hsd17b4 | | | | | | | Pparg |
| | Slc39a4 | | | | | | | Eml3 |
| | Nlrp6 | | | | | | | Phlda1 |
| | Pttg1ip | | | | | | | P2rx1 |
| | Il17rc | | | | | | | Pde9a |
| | Sqrdl | | | | | | | Otud7b |
| | Netl | | | | | | | Tfpi2 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Lad1 | | | | | | | Rilpl2 |
| | Gm5177 | | | | | | | Klf3 |
| | Mdh2 | | | | | | | Gyg |
| | 2210016F16Rik | | | | | | | 4930455F23Rik |
| | Erbb3 | | | | | | | Armcx1 |
| | Proz | | | | | | | Lzts2 |
| | Tax1bp3 | | | | | | | Plek |
| | Pgd | | | | | | | Vamp8 |
| | Sult1d1 | | | | | | | Stat2 |
| | Gpi1 | | | | | | | Znf512b |
| | Prap1 | | | | | | | Ptplad1 |
| | Lypla1 | | | | | | | 1110058L19Rik |
| | | | | | | | | Tmem160 |
| | | | | | | | | Tmem51 |
| | | | | | | | | Cdhr5 |
| | | | | | | | | Stk38 |
| | | | | | | | | Atp13a2 |
| | | | | | | | | Nptn |
| | | | | | | | | Sirt5 |
| | | | | | | | | Gabarapl2 |
| | | | | | | | | Nudt14 |
| | | | | | | | | 2010111I01Rik |
| | | | | | | | | Alkbh7 |
| | | | | | | | | Slc18a3 |
| | | | | | | | | 4930427A07Rik |
| | | | | | | | | Ttll7 |
| | | | | | | | | Acss2 |
| | | | | | | | | Siae |

Significance cut-offs: FDR (max): 0.05, Log2 fold-change: 0.5

TABLE 5

Consensus (full-length platebased and 3' droplet-based)
signatures for post-mitotic intestinal epithelial cells

| Goblet | Paneth | Tuft | Enteroendocrine | Enterocyte (Proximal) | Enterocyte (Distal) |
|---|---|---|---|---|---|
| Agr2 | Gm15284 | Alox5ap | Chgb | Gsta1 | Tmigd1 |
| Fcgbp | AY761184 | Lrmp | Gfra3 | Rbp2 | Fabp6 |
| Tff3 | Defa17 | Hck | Cck | Adh6a | Slc51b |
| Clca1 | Gm14851 | Avil | Vwa5b2 | Apoa4 | Slc51a |
| Zg16 | Defa22 | Rgs13 | Neurod1 | Reg3a | Mep1a |
| Tpsg1 | Defa-rs1 | Ltc4s | Fev | Creb3l3 | Fam151a |
| Muc2 | Defa3 | Trpm5 | Aplp1 | Cyp3a13 | Naaladl1 |
| Galnt12 | Defa24 | Dclk1 | Scgn | Cyp2d26 | Slc34a2 |
| Atoh1 | Defa26 | Spib | Neurog3 | Ms4a10 | Plb1 |
| Rep15 | Defa21 | Fyb | Resp18 | Ace | Nudt4 |
| S100a6 | Lyz1 | Ptpn6 | Trp53i11 | Aldh1a1 | Dpep1 |
| Pdia5 | Gm15292 | Matk | Bex2 | Rdh7 | Pmp22 |
| Klk1 | Mptx2 | Snrnp25 | Rph3al | H2-Q2 | Xpnpep2 |
| Pla2g10 | Ang4 | Sh2d7 | Scg5 | Hsd17b6 | Muc3 |
| Spdef | | Ly6g6f | Pcsk1 | Gstm3 | Neu1 |
| Lrrc26 | | Kctd12 | Isl1 | Gda | Clec2h |
| Ccl9 | | 1810046K07Rik | Maged1 | Apoc3 | Phgr1 |
| Bace2 | | Hpgds | Fabp5 | Gpd1 | 2200002D01Rik |
| Bcas1 | | Tuba1a | Celf3 | Fabp1 | Prss30 |
| Slc12a8 | | Pik3r5 | Pcsk1n | Slc5a1 | Cubn |
| Smim14 | | Vav1 | Fam183b | Mme | Plec |
| Tspan13 | | Tspan6 | Prnp | Cox7a1 | Fgf15 |
| Txndc5 | | Skap2 | Tac1 | Gsta4 | Crip1 |
| Creb3l4 | | Pygl | Gpx3 | Lct | Krt20 |
| C1galt1c1 | | Ccdc109b | Cplx2 | Khk | Dhcr24 |
| Creb3l1 | | Ccdc28b | Nkx2-2 | Mttp | Myo15b |
| Qsox1 | | Plcg2 | Olfm1 | Xdh | Amn |
| Guca2a | | Ly6g6d | Vim | Sult1b1 | Enpep |
| Scin | | Alox5 | Rimbp2 | Treh | Anpep |
| Ern2 | | Rimbp2 | Anxa6 | Lpgat1 | Slc7a9 |
| AW112010 | | Pou2f3 | Scg3 | Dhrs1 | Ocm |
| Fkbp11 | | Gng13 | Ngfrap1 | Cyp2c66 | Anxa2 |
| Capn9 | | Bmx | Insm1 | Ephx2 | Aoc1 |
| | | Ptpn18 | | | |

TABLE 5-continued

| | | | | Enterocyte | Enterocyte |
| | | | | (Proximal) | (Distal) |
| --- | --- | --- | --- | --- | --- |
| | | | Consensus (full-length platebased and 3' droplet-based) signatures for post-mitotic intestinal epithelial cells | | |
| Goblet | Paneth | Tuft | Enteroendocrine | | |
| Stard3nl | | Nebl | Gng4 | Cyp2c65 | Ceacam20 |
| Slc50a1 | | Limd2 | Pax6 | Cyp3a25 | Arf6 |
| Sdf2l1 | | Pea15a | Cnot61 | Slc2a2 | Abcb1a |
| Hgfac | | Tmem176a | Cacna2d1 | Ugdh | Xpnpep1 |
| Galnt7 | | Smpx | Tox3 | Gstm6 | Vnn1 |
| Hpd | | Itpr2 | Slc39a2 | Retsat | Cndp2 |
| Ttc39a | | Il13ra1 | Riiad1 | Ppap2a | Nostrin |
| Tmed3 | | Siglecf | | Acsl5 | Slc13a1 |
| Pdia6 | | Ffar3 | | Cyb5r3 | Aspa |
| Uap1 | | Rac2 | | Cyb5b | Maf |
| Gcnt3 | | Hmx2 | | Ckmt1 | Myh14 |
| Tnfaip8 | | Bpgm | | Aldob | |
| Dnajc10 | | Inpp5j | | Ckb | |
| Ergic1 | | Ptgs1 | | Scp2 | |
| Tsta3 | | Aldh2 | | Prap1 | |
| Kdelr3 | | Pik3cg | | | |
| Foxa3 | | Cd24a | | | |
| Tpd52 | | Ethe1 | | | |
| Tmed9 | | Inpp5d | | | |
| Spink4 | | Krt23 | | | |
| Nans | | Gprc5c | | | |
| Cmtm7 | | Reep5 | | | |
| Creld2 | | Csk | | | |
| Tm9sf3 | | BCl2l14 | | | |
| Wars | | Tmem141 | | | |
| Smim6 | | Coprs | | | |
| Manf | | Tmem176b | | | |
| Oit1 | | 1110007C09Rik | | | |
| Tram1 | | Ildr1 | | | |
| Kdelr2 | | Galk1 | | | |
| Xbp1 | | Zfp428 | | | |
| Serp1 | | Rgs2 | | | |
| Vimp | | Inpp5b | | | |
| Guk1 | | Gnai2 | | | |
| Sh3bgrl3 | | Pla2g4a | | | |
| Cmpk1 | | Acot7 | | | |
| Tmsb10 | | Rbm38 | | | |
| Dap | | Gga2 | | | |
| Ostc | | Myo1b | | | |
| Ssr4 | | Adh1 | | | |
| Sec61b | | Bub3 | | | |
| Pdia3 | | Sec14l1 | | | |
| Gale | | Asahi | | | |
| Klf4 | | Ppp3ca | | | |
| Krtcap2 | | Agt | | | |
| Arf4 | | Gimap1 | | | |
| Sep15 | | Krt18 | | | |
| Ssr2 | | Pim3 | | | |
| Ramp1 | | 2210016L21Rik | | | |
| Calr | | Tmem9 | | | |
| Ddost | | Lima1 | | | |
| | | Fam221a | | | |
| | | Nt5c3 | | | |
| | | Atp2a3 | | | |
| | | Mlip | | | |
| | | Vdac3 | | | |
| | | Ccdc23 | | | |
| | | Tmem45b | | | |
| | | Cd47 | | | |
| | | Lect2 | | | |
| | | Pla2g16 | | | |
| | | Mocs2 | | | |
| | | Arpc5 | | | |
| | | Ndufaf3 | | | |

Significance cut-offs: FDR (max): 0.05, Log2 fold-change: 0.5 in both datasets

Figure 8A:
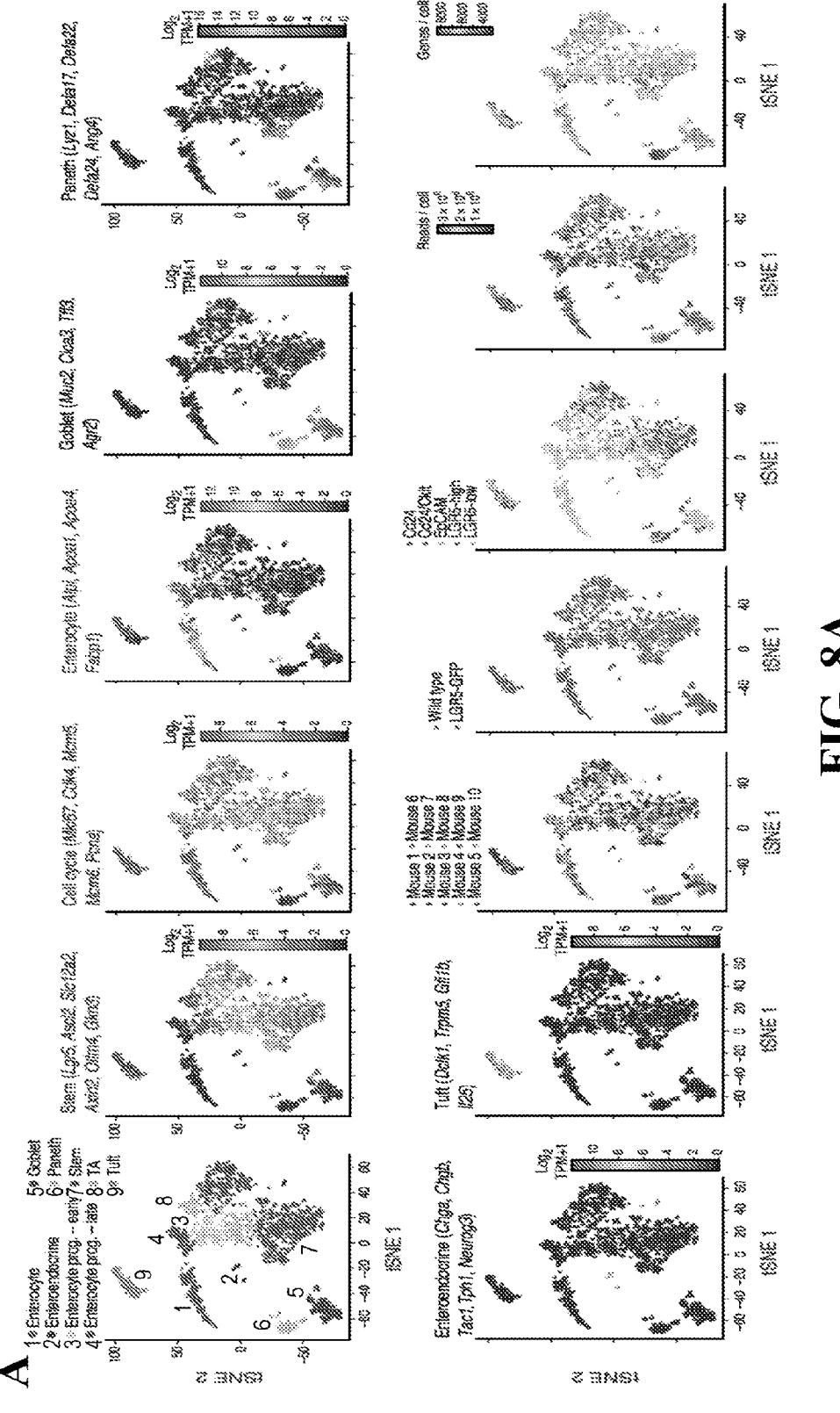
Figure 8D:
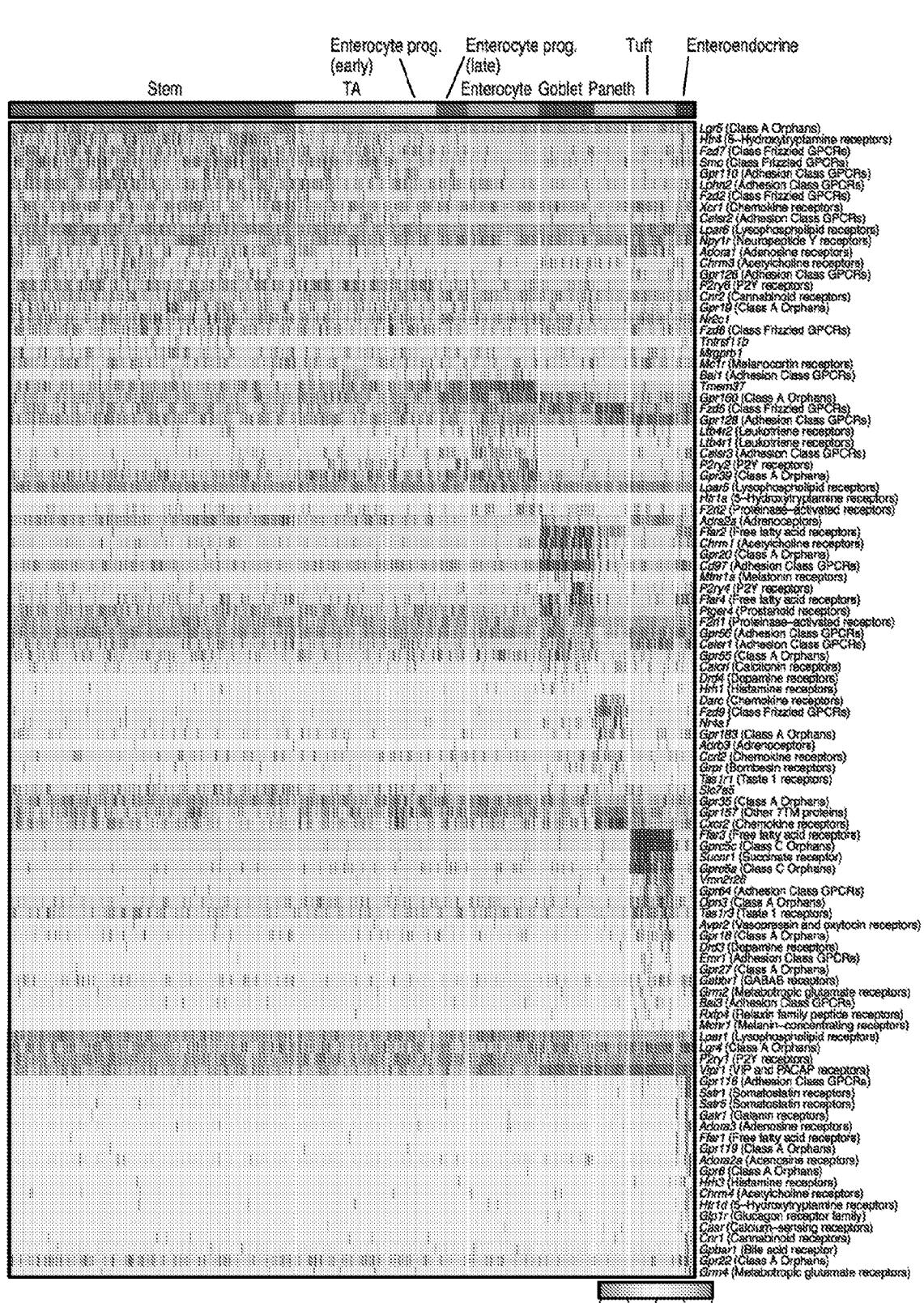
Figure 8E:
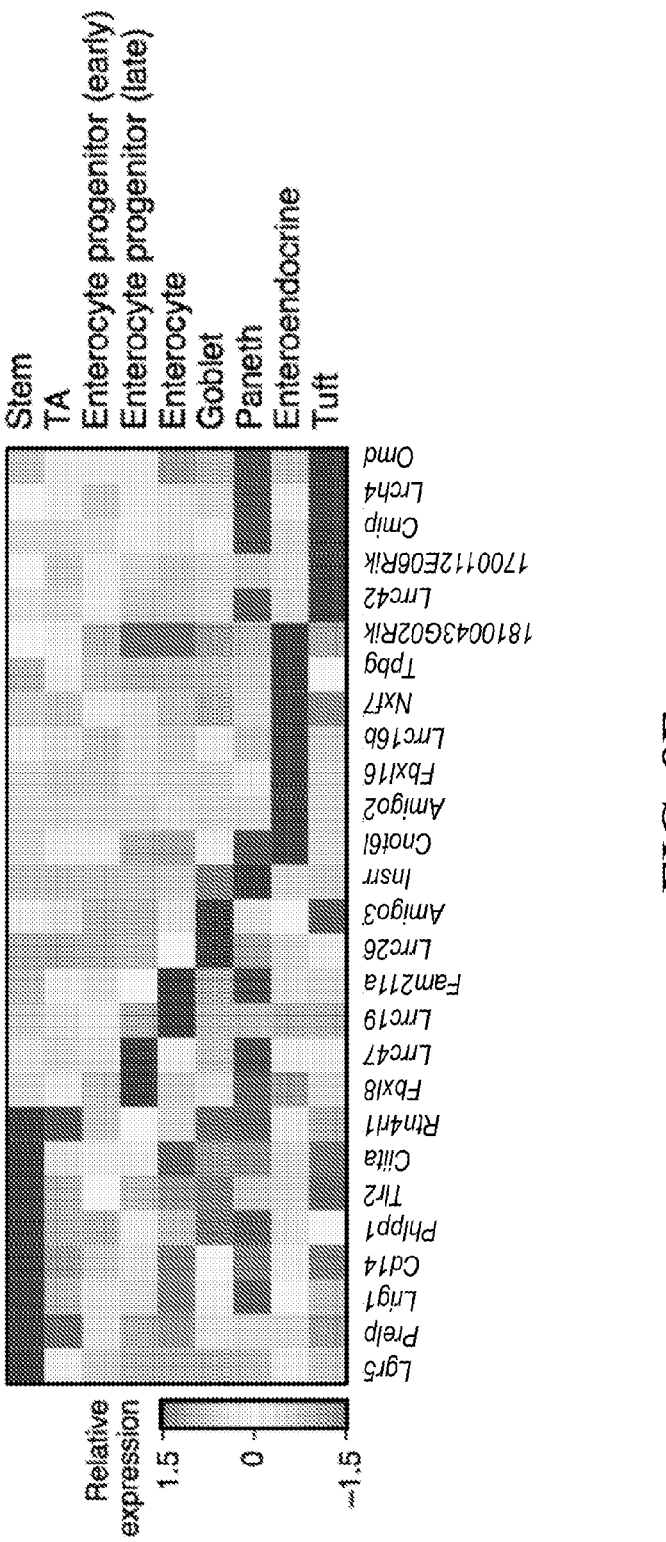

Next, leveraging the higher sensitivity of the plate-based, full-length scRNA-seq data, Applicants also identified enriched TFs, GPCRs and leucine-rich repeat (LRR) proteins (Methods) for each of the major cell types (FIG. 1f,g, FIG. 8d,e and Table 6). Among TFs, these included several Kruippel-like family (KLF) TFs specific to secretory subtypes, such as Klf4, a known regulator of goblet cell development[35], and novel KLFs, including Klf15, expressed at significantly higher levels by Paneth cells, and Klf3 and Klf6 by tuft cells. Among cell-type enriched GPCRs (FIG. 1g, FIG. 8d and Table 6), the known sensory cell types (tuft and EECs) were most prominently represented, each with more than 10 enriched receptors. These included many nutrient-sensing receptors expressed on the EECs (e.g., Gpbar1-a, a bile acid receptor[36], and Gpr119, a sensor for food intake and glucose homeostasis[37]) and Drd3, a dopamine receptor (FIG. 8*d*) enriched in tuft cells. The family of pattern recognition receptors (PRR) containing LRR domains are variably deployed on surfaces of the normal intestinal epithelium. Interestingly, Tlr2 and its co-receptor Cd14 had a significantly higher expression (FDR<0.5, Methods) in the stem cell population (FIG. 8*e*). In sum, Applicants identified and characterized all major cell-types of the villous epithelium at single-cell resolution.

TABLE 6A

| Transcription factors (TFs) (full-length plate-based data) | | | | | | | | |
|---|---|---|---|---|---|---|---|---|
| Stem | TA | Enterocyte progenitor (early) | Enterocyte progenitor (late) | Enterocyte | Goblet | Paneth | Enteroendocrine | Tuft |
| Ascl2 | Zfp808 | Zbtb44 | Id1 | Creb3l3 | Spdef | Klf15 | Neurod1 | Spib |
| Jun | Ctcf | Zfp72 | Pias4 | Nr1h3 | Atoh1 | Nr4a1 | Rfx6 | Pou2f3 |
| Sp5 | Zfp101 | Zfp709 | Foxm1 | Nr1i3 | Creb3l4 | Zfp667 | Fev | Gfi1b |
| Arid5b | Zfp652 | | Nfyc | Maf | Creb3l1 | | Neurog3 | Hmx3 |
| Tgif1 | | | Mycn | Tsc22d3 | Bhlhe40 | | Pax4 | Hmx2 |
| Nr2e3 | | | Hmgb2 | Hnf4g | Foxa3 | | Isl1 | Runx1 |
| Mecom | | | | Rxra | Nfkb2 | | Foxa2 | Jarid2 |
| Esrrg | | | | Batf2 | Xbp1 | | Nkx2-2 | Nfatc1 |
| Zbtb38 | | | | Zbtb7b | Zfp467 | | Pax6 | Zfp710 |
| Etv6 | | | | | Litaf | | Myt1 | Zbtb41 |
| Tgif2 | | | | | Zbtb8a | | Peg3 | Sox9 |
| Nr1d2 | | | | | Klf4 | | Tox3 | Zmiz1 |
| Zfp341 | | | | | Id4 | | Insm1 | Zfhx3 |
| Hes1 | | | | | Atf4 | | Etv5 | Nfe2l3 |
| Nfix | | | | | Dnajc1 | | Sox4 | Ehf |
| Repin1 | | | | | Tulp4 | | Zfp68 | Camta2 |
| Zfp825 | | | | | Foxp1 | | Lmx1a | St18 |
| Vdr | | | | | Nfxl1 | | Lcorl | Tead1 |
| Gtf2i | | | | | | | Zfp7 | Hivep2 |
| Nfib | | | | | | | Vezf1 | Prox1 |
| Nfia | | | | | | | Gm5595 | Klf6 |
| Relb | | | | | | | Pbx1 | Hsf2 |
| Hmga1-rs1 | | | | | | | Zfp787 | Pparg |
| Pms1 | | | | | | | Zfp62 | Klf3 |
| Gm6710 | | | | | | | Hhex | Stat2 |
| Atf7 | | | | | | | Etv1 | Znf512b |
| Zfp956 | | | | | | | Zfp92 | |
| Esr1 | | | | | | | Neurod2 | |
| Hmga2 | | | | | | | Zfp329 | |
| 0610010B08Rik | | | | | | | Zfp71-rs1 | |
| Hmga1 | | | | | | | Zfp30 | |
| Myc | | | | | | | Zkscan1 | |
| Zfp317 | | | | | | | Lhx1 | |
| Nfic | | | | | | | Rcor2 | |
| Zfp13 | | | | | | | Zfp266 | |
| Bcl6 | | | | | | | Sp4 | |
| Foxq1 | | | | | | | Atoh8 | |
| Zfp119b | | | | | | | Bach1 | |
| Hnf4a | | | | | | | Zfp236 | |
| Trp53 | | | | | | | Rfx2 | |
| Zfp369 | | | | | | | Zfp189 | |
| Zfp1 | | | | | | | Plag1 | |
| | | | | | | | Zfp821 | |
| | | | | | | | Zglp1 | |
| | | | | | | | Nanog | |

TABLE 6B

| G-coupled protein receptors (GPCRs) (full-length plate-based data) | | | | | | | | |
|---|---|---|---|---|---|---|---|---|
| Stem | TA | Enterocyte progenitor (early) | Enterocyte progenitor (late) | Enterocyte | Goblet | Paneth | Entero-endocrine | Tuft |
| Lgr5 | | | | Gpr128 | Cd97 | Fzd9 | Adora3 | Ffar3 |
| Htr4 | | | | Gpr160 | Chrm1 | Darc | Sstr1 | Gprc5c |
| Fzd7 | | | | Lpar1 | Ptger4 | Ccrl2 | Gpr116 | Sucnr1 |
| Gpr110 | | | | | Gpr20 | | Sstr5 | Ccrl1 |
| Lphn2 | | | | | F2rl1 | | Gpr22 | Gprc5a |
| | | | | | Ffar2 | | Galr3 | Opn3 |
| | | | | | Mtnr1a | | Galr1 | Vmn2r26 |
| | | | | | P2ry4 | | Gpr119 | Tas1r3 |
| | | | | | | | Ffar1 | |
| | | | | | | | Adora2a | |
| | | | | | | | Cxcr7 | |
| | | | | | | | Gpr6 | |
| | | | | | | | Hrh3 | |
| | | | | | | | Gpbar1 | |
| | | | | | | | Chrm4 | |
| | | | | | | | Glp1r | |
| | | | | | | | Htr1d | |

TABLE 6C

| Leucine-rich repeat (LRR) proteins (full-length plate-based data) | | | | | | | | |
|---|---|---|---|---|---|---|---|---|
| Stem | TA | Enterocyte progenitor (early) | Enterocyte progenitor (late) | Enterocyte | Goblet | Paneth | Entero-endocrine | Tuft |
| Lgr5 | | | Fbxl8 | Lrrc19 | Lrrc26 | Insrr | Cnot6l | Lrrc42 |
| Prelp | | | Lrrc47 | Fam211a | Amigo3 | | Amigo2 | 1700112E06Rik |
| Lrig1 | | | | | | | Fbxl16 | Cmip |
| Cd14 | | | | | | | Lrrc16b | Lrch4 |
| Phlpp1 | | | | | | | Nxf7 | Omd |
| Tlr2 | | | | | | | Tpbg | |
| Ciita | | | | | | | 1810043G02Rik | |
| Rtn4rl1 | | | | | | | | |

Significance cut-offs: FDR (max): 0.5

Example 3—Distinct Regulators are Associated with the Proliferation-Differentiation and Proximal-Distal Axes The largest components of variation (PC-1 and PC-2) between single cells in the atlas reflect the processes of proliferation and differentiation in the small intestine (FIG. 9a). Applicants thus used the cell-type signatures (Table 4) to embed each cell in a three-dimensional space (FIG. 2a), such that its location corresponds to its lineage fate, and to its stage of differentiation towards that fate (Methods). Applicants confirmed that Lgr5-expressing cells were positioned at the base of the embedding (FIG. 2a, left). Scoring of a cell-cycle state signature[29] highlighted the presence of rapidly proliferating cells above the stem cells (FIG. 2a, center), with a somewhat lower expression of stemness related genes, but not yet expressing markers for differentiated cell types, corresponding to TA progenitor cells, as previously suggested[38]. The distinct "leaves" on top reflected Muc2-expressing goblet cells, Dclk1-expressing Tuft cells, and Chgb-expressing EECs (FIG. 9b), whereas the expression of the enterocyte marker Alpi gradually increased along a dense branch of cells moving towards the enterocyte lineage (FIG. 2a, right). Although the vast majority of these Alpi-expressing cells are well on their way to the enterocyte lineage, a small subset co-expresses Alpi and crypt-specific markers (Slc12a2, Ascl2, Axin2, and Lgr5) (data not shown), consistent with a recent report[39].

Focusing on the abundant population of enterocytes, Applicants used diffusion maps[40] to place them in a pseudo-temporal order (FIG. 2b-e). Several recent studies[41,42] have shown that cellular differentiation and fate determination can be modeled as a dynamic process on a high-dimensional manifold, which can be inspected by ordering cells—sampled simultaneously from an ongoing asynchronous process—in pseudo-time. In this case, considering the first and third diffusion components (DC-1 and 3) highlighted a trajectory from stem-like to progenitor to immature enterocytes (FIG. 2b, FIG. 9c-e and FIG. 10a-c).

Figure 10O:
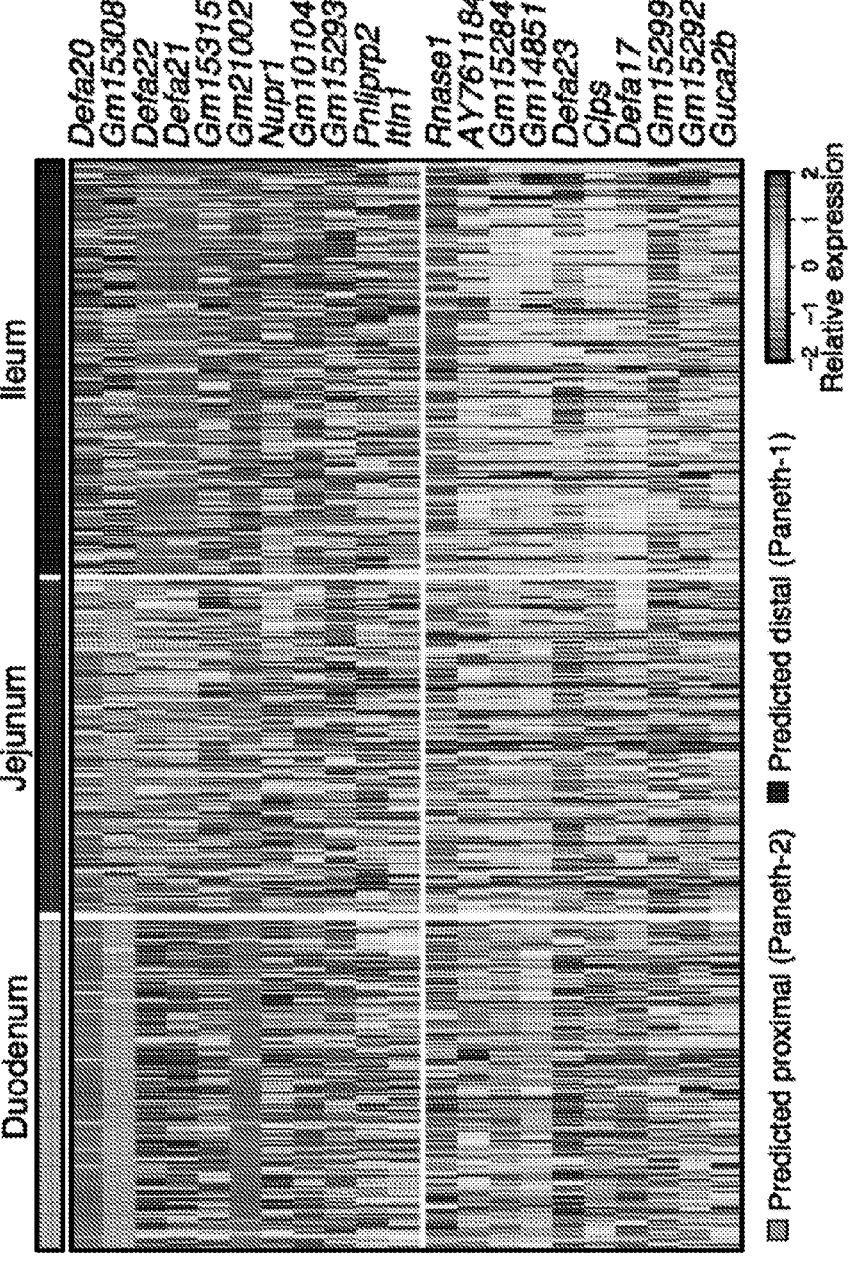
Figure 10P:
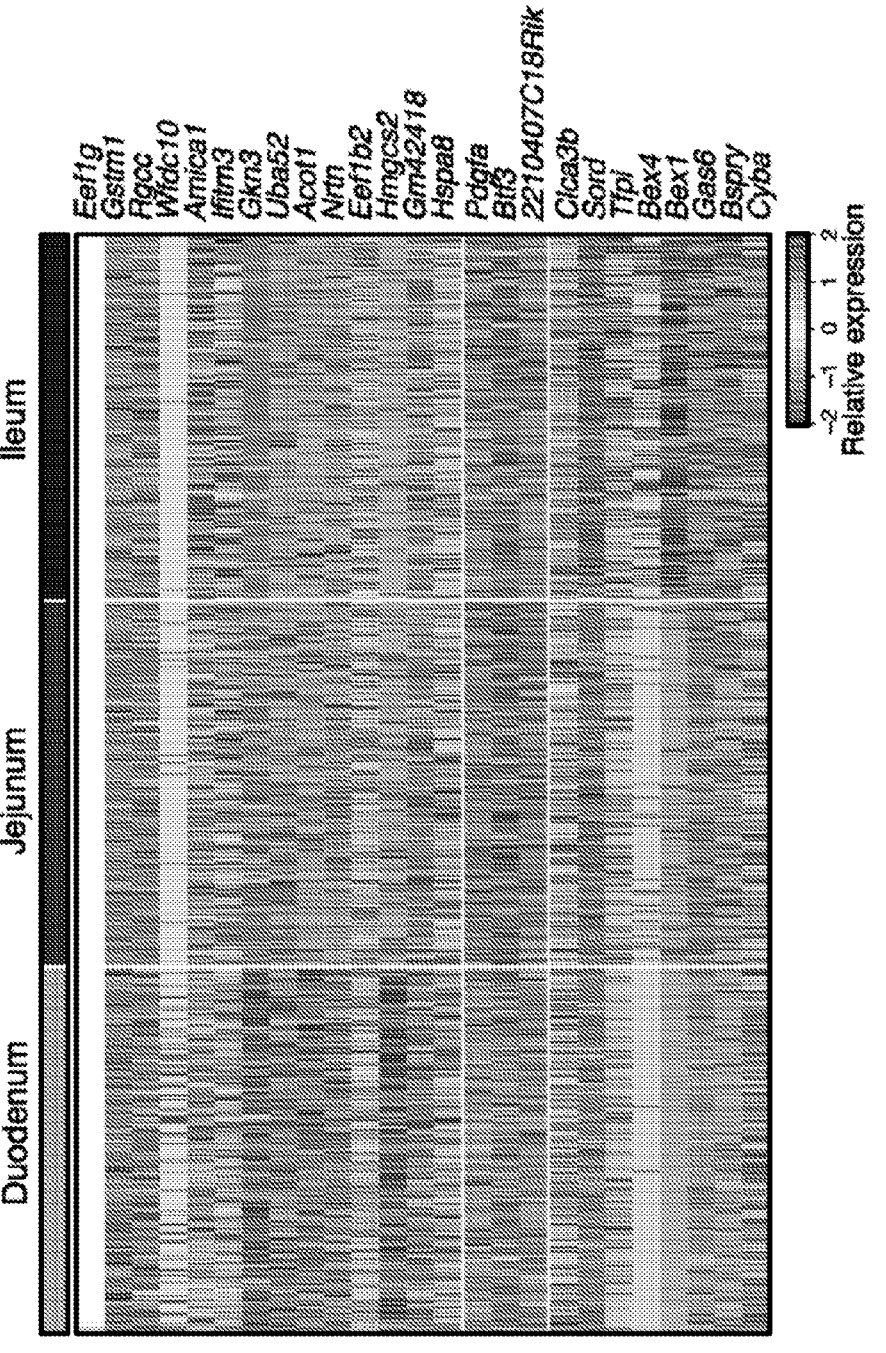
Figure 10Q:
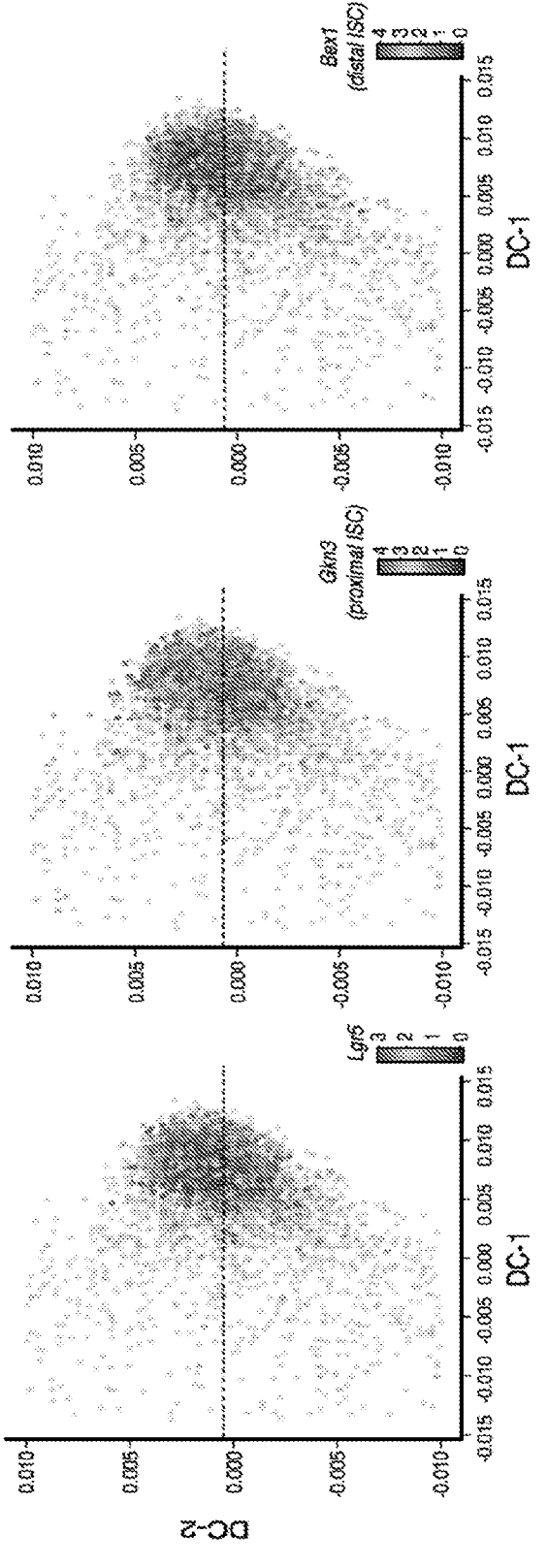

DC-2 captured a process of branching lineage commitment between enterocytes of the proximal (duodenum and jejunum) and distal (ileum) small intestine (FIG. 2c, FIG. 10d-f), emphasizing the adaptation of enterocytes to absorb different carbon sources, from easy to digest carbohydrates to more complex molecules such as fat. Applicants tested this prediction, by profiling another 11,665 single cells from the duodenum, jejunum and ileum separately (n=2 mice, FIG. 10h), and recovering genes differentially expressed in the 1,041 absorptive enterocytes from the different regions (Methods). Indeed, of the 64 and 44 genes identified as signature genes for mature proximal and distal enterocytes, respectively, (Methods, FIG. 1c and Table 3), 60 and 23, respectively, were also differentially expressed (FDR<0.05 Mann-Whitney U-test) between proximal (duodenum and jejunum) and distal (ileum) regions (FIG. 10i). Furthermore, smFISH confirmed the regional distribution of enterocytes expressing Lct and Fabp6 markers[43] in the duodenum and ileum, respectively (FIG. 10j). Most marker genes of the two Paneth cell subsets (FIG. 10n) are enriched (FDR<0.05) in proximal or distal gut respectively, confirming that they reflect regional distinctions (FIG. 10o); the novel marker Mptx2 showed no regional specificity (Table 10). Finally, the stem cells in each region also express region-specific markers (FIG. 10p), which when examined in either the non-regional (Fig. q) or the regional (FIG. 10l) diffusion maps mark distinct ISC subsets, each likely foreshadowing the eventual distinct enterocytes from the corresponding region (FIG. 10l).

Enteroendocrine cells (EECs) in the small intestine are a major site of hormone production, and were reported to comprise 8 distinct sub-classes, traditionally classified by the primary hormone they produce[11, 47, 48], such that cells expressing Sct, Cck, Gcg or GIP were traditionally termed S, I, L and K cells, respectively[12]. However, significant crossover between traditional subtypes has been observed[12, 22], such that the same hormone may be expressed by more than one type. Thus, a classification based on a single "marker" hormone may not represent the true diversity and function of EECs (Gribble and Reimann, 2016), and may limit the ability in follow up studies based on these genes.

Applicants identified a cluster of EECs in both the whole SI (FIG. 1b, 310 cells) and regional datasets (FIG. 10h, 239 cells) based on expression of known markers, including Chromogranin A (Chga) and B (Chgb), which this study

TABLE 10

DE results [droplet-data], ranked by Log2 fold-change Paneth-1 (distal) vs. Paneth-2 (proximal)

| Gene symbol | Mean expression (Log2 TPM + 1) Paneth-1 | Mean expression (Log2 TPM + 1) Paneth-2 | log2fc | p | p. adj |
|---|---|---|---|---|---|
| Defa20 | 8.43307629 | 4.191569275 | 4.241507015 | 4.59E−198 | 1.29E−193 |
| Gm15308 | 6.747161753 | 2.622293721 | 4.124868032 | 1.82E−194 | 2.55E−190 |
| Defa22 | 8.938663197 | 4.944112099 | 3.994551098 | 2.63E−177 | 2.45E−173 |
| Defa21 | 8.979216936 | 5.396694643 | 3.582522293 | 3.65E−165 | 2.56E−161 |
| Guca2a | 3.927258003 | 1.966457829 | 1.960800174 | 3.25E−158 | 1.82E−154 |
| Gm15315 | 2.93782559 | 1.484980923 | 1.452844667 | 1.03E−82 | 2.40E−79 |
| Gm21002 | 1.426481352 | 0.165194501 | 1.261286851 | 2.44E−108 | 9.77E−105 |
| Nupr1 | 2.47171844 | 1.419388432 | 1.052330007 | 2.80E−90 | 7.85E−87 |
| Gm10104 | 3.266743446 | 2.254967422 | 1.011776024 | 1.48E−90 | 4.61E−87 |
| Gm1123 | 1.646936159 | 0.685262667 | 0.961673491 | 4.34E−71 | 8.69E−68 |
| Agr2 | 2.958898977 | 2.108410455 | 0.850488522 | 9.78E−50 | 1.61E−46 |
| Muc2 | 2.572337443 | 1.749806632 | 0.822530811 | 6.74E−49 | 1.05E−45 |
| Gm15293 | 1.67374113 | 0.895914849 | 0.777826282 | 1.16E−44 | 1.55E−41 |
| Pnliprp2 | 2.801230998 | 2.134237786 | 0.666993213 | 1.69E−11 | 7.07E−09 |
| Tspan1 | 1.333205915 | 0.716544122 | 0.616661793 | 2.21E−46 | 3.09E−43 |
| Itln1 | 7.721067156 | 7.13664624 | 0.584420916 | 1.35E−15 | 8.40E−13 |
| Pglyrp1 | 2.681719453 | 2.143612461 | 0.538106992 | 5.20E−43 | 6.62E−40 |
| mt-Atp6 | 4.984661454 | 4.469107748 | 0.515553706 | 6.48E−12 | 2.79E−09 |
| Guca2b | 3.555007019 | 4.08419426 | −0.529187242 | 2.46E−42 | 3.00E−39 |
| Gm15292 | 4.123432202 | 4.663038688 | −0.539606487 | 1.24E−25 | 1.20E−22 |
| Gm15299 | 2.822490385 | 3.416108207 | −0.593617822 | 5.07E−36 | 5.91E−33 |
| Defa17 | 4.869214625 | 5.476804872 | −0.607590247 | 3.46E−58 | 6.45E−55 |
| Clps | 5.793805073 | 6.504310944 | −0.710505871 | 1.18E−50 | 2.07E−47 |
| Defa23 | 2.958117378 | 3.6903216 | −0.732204222 | 3.84E−21 | 3.36E−18 |
| Gm14851 | 8.518496669 | 9.343126247 | −0.824629578 | 3.56E−83 | 9.06E−80 |
| Gm15284 | 9.174886103 | 10.05353355 | −0.878647448 | 6.25E−73 | 1.35E−69 |
| AY761184 | 8.318749405 | 9.553086427 | −1.234337022 | 4.50E−104 | 1.57E−100 |
| Rnase1 | 1.026127868 | 2.459104539 | −1.432976671 | 3.18E−111 | 1.48E−107 |

Finally, Applicants identified TFs with specific expression patterns in different regions of the diffusion map (Methods), associating regulators with early enterocyte lineage commitment (known: Sox4[44], and novel: Batf2, Mxd3 and Foxm1) (FIG. 2d and FIG. 10g), or with proximal and distal intestinal identity (known: Gata4, Nr1 h4[45-46] and novel: Creb3l3, Jund, Osr2, Nr1i3) (FIG. 2e).

Figure 3A:
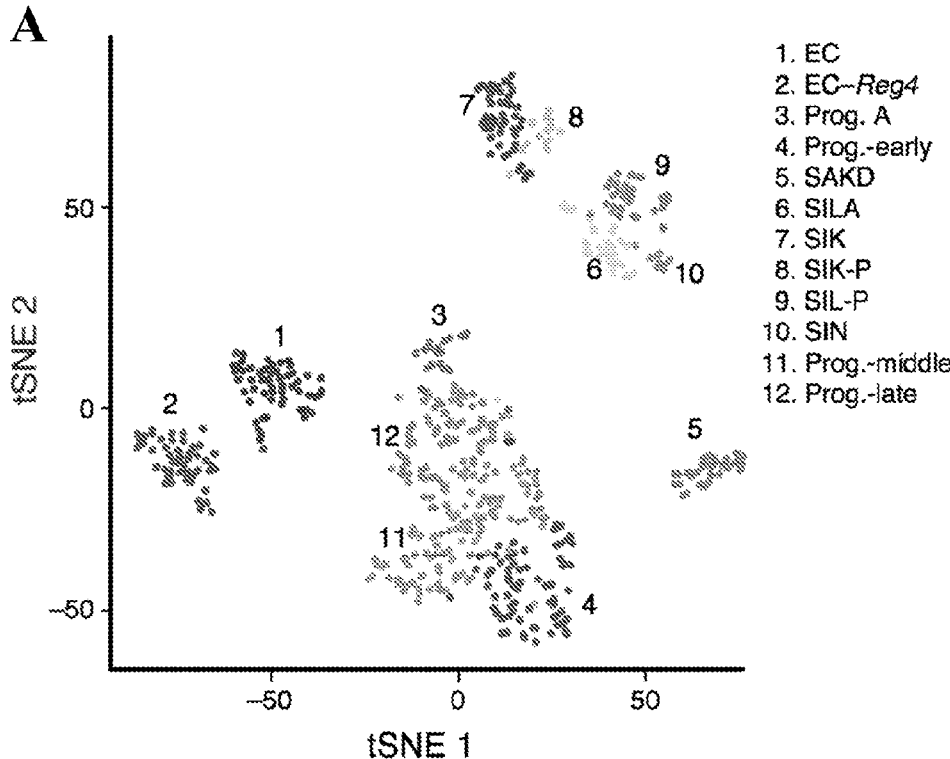
Figure 3B:
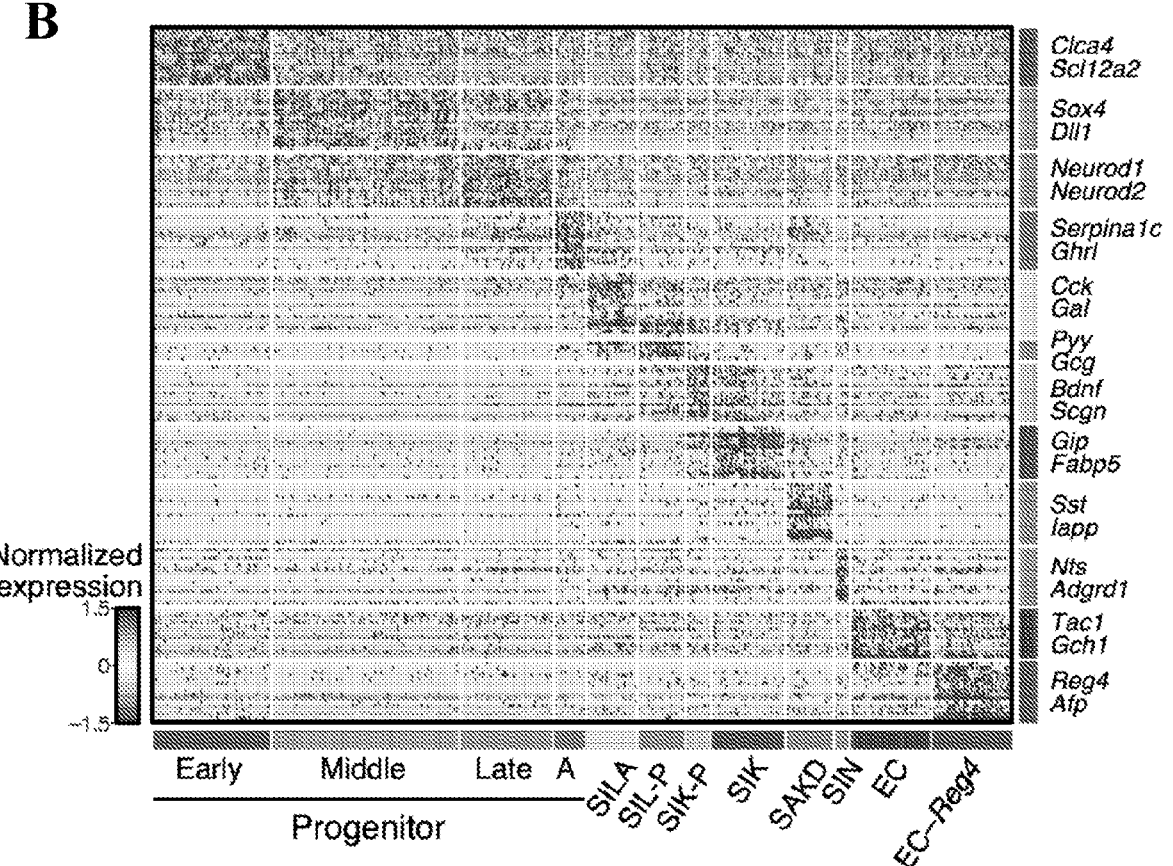
Figure 11E:
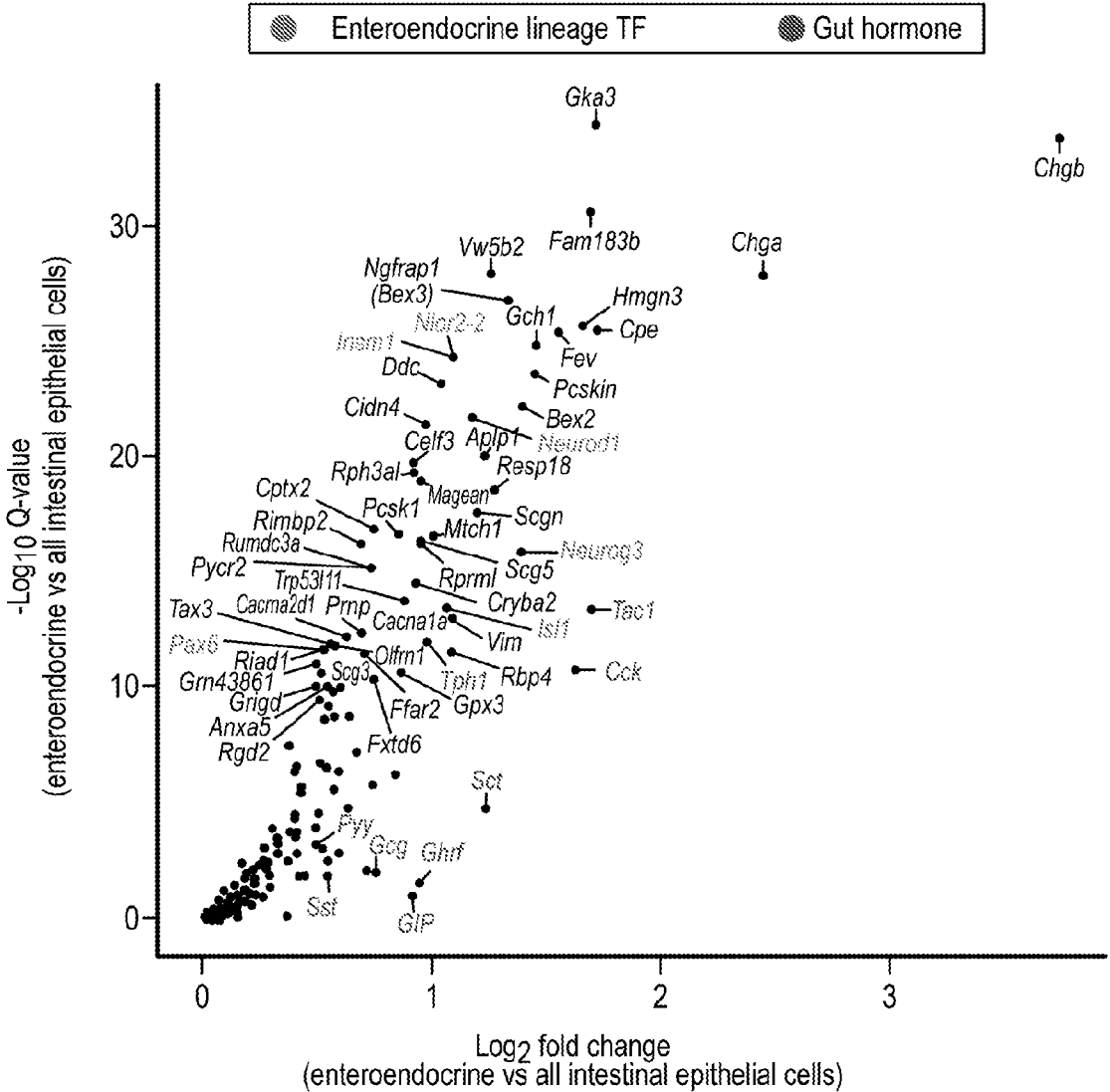

Example 4—Taxonomy of Enteroendocrine Cells is Defined by Hierarchical Hormone Expression Enteroendocrine cells (EECs) are key sensors of nutrients and microbial metabolites[11,12] that secrete diverse hormones and function as metabolic signal transduction units[146].

confirmed as the two best markers for this group identified by the unbiased analysis (FIG. 11e), along with GDNF family receptor alpha-3 (Gfra3) as a novel and specific marker (FIG. 11e), for a total of 533 EECs (Methods). To define putative EEC subtypes ab initio, Applicants separately clustered these 533 cells, and distinguished 12 clusters (FIG. 3a, FIG. 11a), each supported by a distinct gene signature (FIG. 3b, Table 7, Methods). Four of the EEC groups expressed markers of EEC precursors (Neurog3, Neurod1, Sox4), while the other eight represented mature EEC subsets. A recent study of scRNA-seq of organoid derived EECs showed EEC heterogeneity but with fewer EEC subsets[53].

TABLE 7

Summary of marker genes for enteroendocrine subsets

| Progenitor (early) | Progenitor (late) | Progenitor (mid) | Progenitor (A) | SAKD | SILA |
|---|---|---|---|---|---|
| Pycard | Tubb3 | Fcgbp | Maged2 | Sst | Cck |
| Oat | Neurod1 | Tff3 | Cdkn1a | Iapp | Parm1 |
| Clca3b | Neurod2 | Bcl2 | Serpina1c | Hhex | Scg2 |
| Cps1 | Gadd45a | Aldob | Acsl1 | Acot7 | Tspan13 |
| Dbi | Drap1 | Gadd45g | Ceacam10 | Rgs4 | Cpn1 |
| Prap1 | Btbd17 | Litaf | Zcchc12 | BC048546 | Crp |
| Ppp1r1b | Mrfap1 | Sox4 | Cxxc4 | Arg1 | Anpep |
| Hspe1 | Cyth2 | Slc39a2 | Il11ra1 | Asic5 | 0610011F06Rik |
| Mgst1 | Mapk15 | Tmsb10 | Cdkn1c | Kcnk2 | Gal |
| Gpx1 | Vasp | Fuca1 | Mboat4 | Fam151a | Fars2 |
| Pigr | Esd | Prom1 | 1500009L16Rik | Th | Hepacam2 |
| Tkt | Trp53i11 | Dll1 | Krt18 | Pdx1 | Gpr119 |
| Hspd1 | Clta | Mfge8 | Bambi | Fam46a | Gclm |
| C1qbp | Eif4a1 | Hmgb3 | Rgs17 | Serpina1a | Tm4sf4 |
| Cd74 | Btg2 | Top1 | Arx | Hgfac | Agr3 |
| Ccl25 | Tubb5 | Ddit4 | Plb1 | Tmem108 | Gnai1 |
| Mt1 | Dbn1 | Nek6 | Fxyd2 | Cd24a | Tm4sf5 |
| Csrp2 | Ypel3 | Gpx2 | Trp53i13 | Rbpms | Sult1d1 |
| Kcne3 | Psmd10 | Slc25a5 | Necab2 | | Krt20 |
| Cldn15 | Fhl2 | Pdha1 | Serpina1d | | Upp1 |
| Slc12a2 | Yipf4 | Txndc5 | Tuba1a | | Nr4a2 |
| Mrpl12 | Cct2 | Casp6 | Gng4 | | Itm2b |
| Amica1 | Rnase4 | Eif4g2 | Ghrl | | |
| Nop10 | Krt7 | Nme1 | Card19 | | |
| Tuba1b | Eif3l | Fubp1 | Arhgap22 | | |
| Mcm6 | Prmt1 | Llph | Fam183b | | |
| Pglyrp1 | Npc2 | Rps10 | Nefm | | |
| Banf1 | Gltscr2 | Bok | Isl1 | | |
| Aprt | Cdk2ap1 | Vgll4 | Akr1c19 | | |
| Reg3g | Tsg101 | Rnase1 | Cd177 | | |
| Idh3a | Eif3h | Rps4x | H1fx | | |
| 2810417H13Rik | Jund | Rpl26 | Capsl | | |
| Anp32b | Zfos1 | Eef1g | Nefl | | |
| Tomm5 | Mtch1 | Acadsb | Nkx2-2 | | |
| Phb2 | Cdk4 | Rps25 | Serpina1e | | |
| Fgfbp1 | Hpcal1 | Lypd1 | | | |
| Sdc4 | Hnrnpk | Hmgn1 | | | |
| Ncl | Fgd2 | Rps26 | | | |
| Lypd8 | Rph3al | Rps8 | | | |
| Ccnd2 | Prdx2 | Cd9 | | | |
| Ran | Crybb1 | Shfm1 | | | |
| Dmbt1 | Dact2 | Rps5 | | | |
| Reg3b | Csnk1a1 | Srsf2 | | | |
| Sdha | Calm2 | Sap30 | | | |
| Chchd10 | Eif3f | Hdac2 | | | |
| Aldh1b1 | Marcksl1 | Rplp0 | | | |
| Lgals9 | Hspa8 | Rps3 | | | |
| Atp5o | Tead2 | Cdc14b | | | |
| Snrpd2 | Srsf6 | Hnrnpab | | | |
| Ociad2 | Rcor2 | Qsox1 | | | |
| Hmgb2 | Adrm1 | Rpl8 | | | |
| Hspa9 | Eef2 | Sypl | | | |
| Prss32 | H3f3a | Tubb2b | | | |
| Tjp3 | Krt8 | Ywhaq | | | |
| Ndufb9 | Cd63 | | | | |
| Lsm2 | Psmc6 | | | | |
| Mcm2 | 2700060E02Rik | | | | |
| Dtymk | Neurog3 | | | | |
| Lsm4 | Ppib | | | | |
| Nucks1 | Tmem176b | | | | |
| Naa10 | Btf3 | | | | |
| Ranbp1 | Uqcrc2 | | | | |
| Nlrp6 | Pcbp1 | | | | |
| Cyc1 | Tpm4 | | | | |
| G3bp1 | Naca | | | | |
| Cox7b | Pcbp2 | | | | |
| Ube2c | Ooep | | | | |
| Cdca7 | Pfdn5 | | | | |
| Ndufv1 | Psma7 | | | | |
| Cenpa | Smarcd2 | | | | |
| Rnf186 | Sdcbp | | | | |
| Siva1 | Pdap1 | | | | |
| Cyba | Hn1 | | | | |
| 2700094K13Rik | Smim6 | | | | |
| Dctpp1 | Akr1c12 | | | | |
| Cdca8 | Cct4 | | | | |

TABLE 7-continued

Summary of marker genes for enteroendocrine subsets

| | |
|---|---|
| Snrpd1 | Cpt2 |
| Alyref | Ftl1 |
| Nhp2 | Igsf8 |
| Ldha | Commd3 |
| Tsfm | Hsp90ab1 |
| Mapk13 | Ppp1r14b |
| Aqp1 | Gadd45gip1 |
| H2-Ab1 | Rps21 |
| Mif | Akr1c13 |
| Mlec | Eif3k |
| Sri | Stard10 |
| Hes1 | Vwa5b2 |
| Pmf1 | Serbp1 |
| Lsm3 | |
| Rnaseh2c | |
| Marc2 | |
| Lyar | |
| Ppa1 | |
| Tomm40 | |
| B2m | |
| Plcb3 | |
| Uqcrc1 | |
| Cox5a | |
| Timm10 | |
| Exosc5 | |
| Cct3 | |
| Aars | |
| Mecr | |
| Spc24 | |
| Epcam | |
| Lmnb1 | |
| Prdx4 | |
| Gar1 | |
| Aadac | |
| Snrpb | |
| Kcnq1 | |
| Trim28 | |
| Cox6a1 | |
| Mettl1 | |
| Cox5b | |
| Ybx1 | |
| Ndufs7 | |
| Acat1 | |
| Ifrd2 | |
| Hsd17b10 | |
| Psme2 | |
| Ascl2 | |
| Atp5h | |
| Cebpb | |
| Cldn3 | |
| Cdca3 | |
| Agmat | |
| Snrpg | |
| Anapc13 | |
| Eif3b | |
| Pycrl | |
| Atp5j | |
| Cldn7 | |
| Fh1 | |
| Phb | |
| Sdhb | |
| Nxt1 | |
| Slc25a3 | |
| Myb | |
| Cox7a2 | |
| H2-DMa | |
| Vipr1 | |
| Fam195a | |
| H2-Eb1 | |
| Sdsl | |
| Mcm5 | |
| Cluh | |
| Eif5a | |
| Aimp2 | |
| Emg1 | |
| Rps27l | |
| Mcm3 | |
| Srsf7 | |

TABLE 7-continued

| Summary of marker genes for enteroendocrine subsets |
| --- |
| Uqcrq |
| Trap1 |
| Tmem147 |
| Atp5d |
| Rpl39 |
| B4galnt1 |
| Rcc2 |
| Farsb |
| H2afx |
| Uqcr10 |
| Ifngr1 |
| Tyms |
| Hnrnpu |
| Ivns1abp |
| Atad3a |
| Tk1 |
| Ifitm3 |
| Klf5 |
| Abhd11os |
| Gmnn |
| Kcnn4 |
| Galk1 |
| Ruvbl2 |
| H2afv |
| Tfrc |
| H2afj |
| Atpif1 |
| Prelid1 |
| Slc39a5 |
| Bdh1 |
| Timm9 |
| Noxo1 |
| Bola3 |
| Ndufa4 |
| Pdss1 |
| Txn2 |
| Npm3 |
| Rpl13 |
| Ccnb2 |
| Ccdc34 |
| S100a10 |
| Tmsb4x |
| Pa2g4 |
| Rpsa |
| Cdk2ap2 |
| Uqcr11 |
| Birc5 |
| Top2a |
| Anp32e |
| 2200002D01Rik |
| Rpl12 |
| Car9 |
| Gjb1 |
| Eef1d |
| Prdx6 |
| Atp5j2 |
| Ddx39 |
| Rpl7 |
| Txn1 |
| Rps15 |
| Rps16 |
| Cox8a |
| Ndufa5 |
| Aoc1 |
| Mgam |
| Serinc3 |
| Rfc3 |
| Rrm1 |
| Haus4 |
| Stmn1 |
| Rsl1d1 |
| Rps19 |
| Ccnd1 |
| Gcat |
| Dhrs4 |
| Atp5b |
| Fth1 |
| Rplp1 |

TABLE 7-continued

Summary of marker genes for enteroendocrine subsets

Hnrnpa2b1
Pabpc1
Cox6c
Pebp1
Gm1123
Rpl37
Rpl18
Otc
Lig1
Vsig10
Atp5a1
Cks1b
Rpl34
Abhd11
Rplp2
Rps20
Shmt1
Gnb2l1
Dut
Nasp

| SIK | SIK-P | SIL-P | SIN | EC | EC Reg4 |
|---|---|---|---|---|---|
| Gip | Car8 | Pyy | Nts | Tac1 | Reg4 |
| Rbp2 | Cdhr5 | Gcg | Crip1 | Vim | Afp |
| Pkib | Bdnf | Rnf130 | Sct | Gch1 | S100a1 |
| Tpst1 | Hexb | Nostrin | Adgrd1 | Fev | Chga |
| Phlda1 | Gatm | Gpbar1 | Car4 | Scn3a | Ambp |
| Acadl | Rnf32 | Scin | Agr2 | Slc25a35 | Tpbg |
| Fabp5 | Entpd5 | | Id3 | Pdk3 | Apoc3 |
| Fam213a | Itm2c | | 4930539E08Rik | Slc38a11 | Gstt1 |
| Itpr1 | Fam105a | | Tppp3 | Tmem158 | Gstk1 |
| Tmprss7 | 1700086L19Rik | | Tnks1bp1 | Cox7a2l | Rgs2 |
| Fam167a | Il17re | | S100a11 | Igfbp3 | Mapk14 |
| Nrn1 | Tmem163 | | Ece1 | Mnx1 | Apoa1 |
| Gpx3 | Gm14964 | | Tmem38a | Serpinb1a | Rab3b |
| Rhou | Scgn | | Scg3 | Fam204a | Cyp2d26 |
| Bnip3 | Scarb1 | | Fxyd5 | Cyp4b1 | Gsdmd |
| Rogdi | Prps1 | | Espn | Hmgn3 | Serpinf2 |
| Scp2 | Pax6 | | Ffar1 | Glud1 | C1qa |
| Fabp1 | Resp18 | | Dnajc12 | Sepp1 | Me2 |
| Rbp4 | Slc6a19 | | Gchfr | Tph1 | Ucn3 |
| Tspan7 | 1110032F04Rik | | Uchl1 | Pfn1 | Ica1 |
| | Anxa6 | | Gcnt3 | Gspt1 | Ptprn |
| | Anxa5 | | Nrp1 | Gm43861 | Upb1 |
| | 1110017D15Rik | | Rprml | Bax | Itpr3 |
| | Cib2 | | Banf2 | Ddt | Psat1 |
| | Scg5 | | Qpct | Sec61b | Fxyd6 |
| | Abcc8 | | Myl7 | | Rpp25 |
| | Gmpr | | Sis | | Prodh2 |
| | Ffar4 | | Gucy2c | | Gde1 |
| | | | Disp2 | | C1qtnf4 |
| | | | Rab37 | | Ndufv3 |
| | | | Bcam | | Pcsk1 |
| | | | | | Tmem106a |
| | | | | | Bex2 |
| | | | | | Rhoc |
| | | | | | Trpa1 |
| | | | | | Slc18a1 |
| | | | | | Uqcc2 |
| | | | | | Ndufa2 |
| | | | | | Igfbp4 |
| | | | | | Ttr |
| | | | | | Acvrl1 |
| | | | | | Atp6v1b2 |
| | | | | | Atp5e |
| | | | | | Camk2n1 |
| | | | | | Lmx1a |
| | | | | | Qdpr |
| | | | | | Ssbp2 |
| | | | | | Rab3c |
| | | | | | S100a13 |
| | | | | | Edf1 |
| | | | | | Chgb |
| | | | | | Ddc |
| | | | | | Ngfrap1 |
| | | | | | Comt |
| | | | | | Minos1 |

TABLE 7-continued

| Summary of marker genes for enteroendocrine subsets |
| --- |
| Tmigd3 |
| Tceb2 |
| Atp5k |
| Pkdcc |
| Atp5g1 |
| Gars |
| Rbp1 |

Significance cut-offs: FDR (Fisher's combined): 0.01, Log2 fold-change: 0.1, Fraction-expressing: 0.25

Figure 3C:
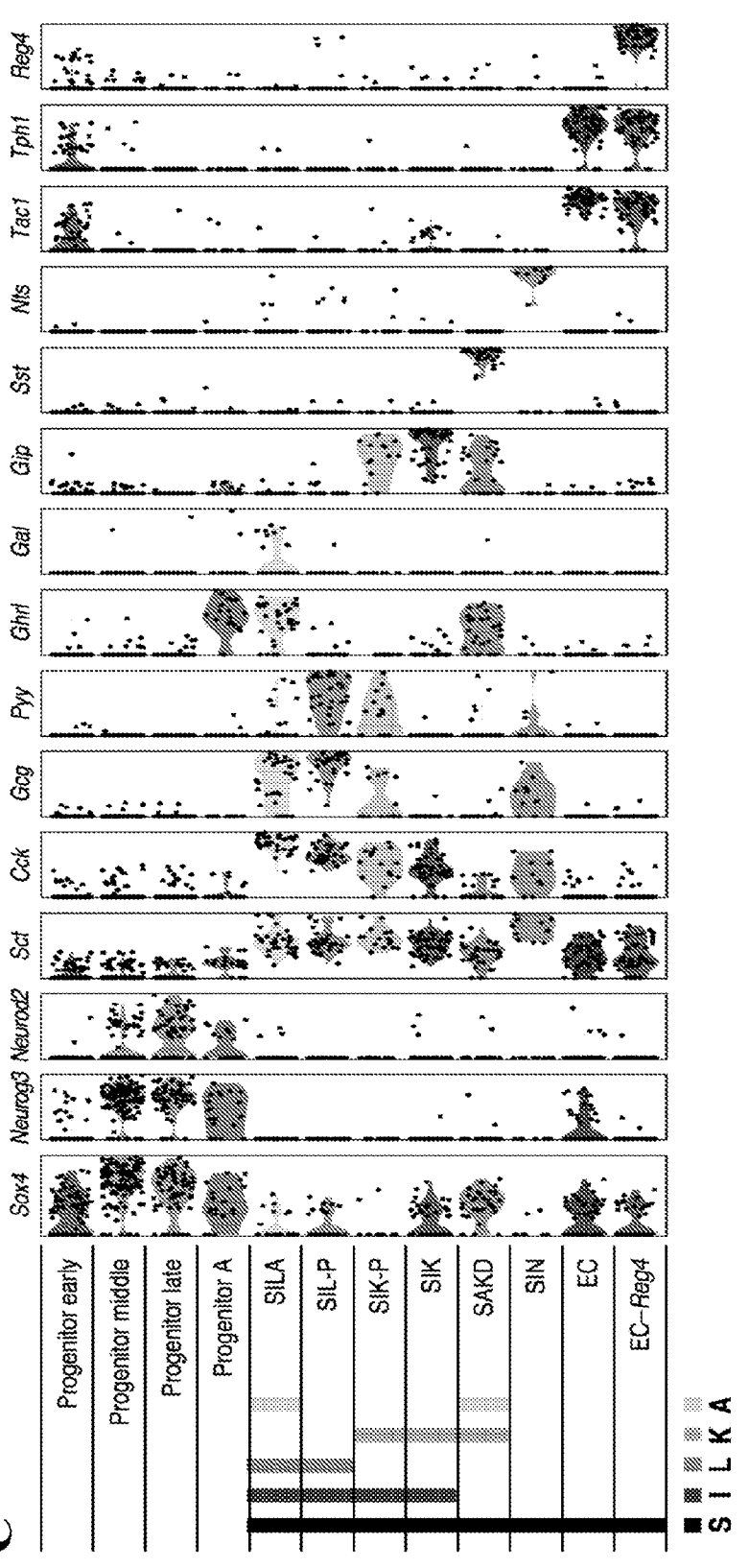

Applicants then compared this ab initio taxonomy to the canonical classification by the expression of the marker hormones in each cluster (FIG. 3c). Consistent with earlier reports[22,49], several key hormones were expressed across multiple clusters rather than in a single group of cells. For example, Secretin (Sct), previously reported to be produced solely by S-cells[11], was expressed by cells in all mature EEC clusters, albeit at varying levels (FIG. 3c). Similarly, Cholecystokinin (Cck), the canonical marker for I-cells[49], was expressed in cells spanning five clusters. This surprisingly broad expression pattern of several hormones, particularly Sct and Cck, was reproducible and concordant in the high-coverage full-length scRNA-seq data, with excellent agreement in detection frequency across all GI hormones (FIG. 11b). In some cells, Cck was co-expressed with both glucagon (Gcg) and Ghrelin (Ghrl), the markers of L- and A-cells, respectively. Notably, Cck-expressing cells are a subset of those expressing Sct, and Gcg and Ghrl expression induces a further subdivision of the cells (FIG. 3c and FIG. 11c-d), which Applicants validated using smFISH (FIG. 3d).

Applicants placed each cluster of mature EECs in the new taxonomy (FIG. 3c and FIG. 1id) and labeled it by the expression of canonical hormones if over 50% of the cells in the subset express a particular hormone, using bootstrap resampling-based hierarchical clustering (FIG. 12a) and cell-cell correlations (FIG. 12b) to assess the relationships between subsets. For example, in this taxonomy the Sct+/Cck+/Gcg+/Ghrl+ subset—the components of which were traditionally termed S, I, L and A cells respectively[12]—is annotated with the label S-I-L-A (FIG. 3c), which Applicants subsequently validated (FIG. 3d). Within each cluster, the marker hormones are co-expressed in individual cells, and therefore generally do not partition into further subsets (FIG. 11c-d). In addition to the more broadly expressed hormones, several hormones are subset-specific (FIG. 3c and FIG. 12c). In particular, Galanin (Gal) is specific to SILA, Neurotensin (Nts) to SIN, Nesfatin-1 (Nucb2) to SA, and Amylin (Iapp) and Somatostatin (Sst) to SAKD. This taxonomy represents a "snapshot" of the subsets of post-mitotic EECs: although Applicants did not see evidence for transitional states, Applicants cannot rule out the possibility of cells transitioning between hormonal profiles, especially in light of the current number of EECs in the cell atlas.

Some EEC subsets are preferentially localized to specific regions of the small intestine. Specifically, SILA, expressing Ghrelin (Ghrl), the hunger hormone[50], together with GCG, the incretin hormone[51], are enriched in the duodenum (FDR<0.25, χ² test, Methods), while SIL-P and SIK-P, both expressing the hormone Peptide YY, which reduces appetite upon feeding[52], are found mainly in the ileum (FDR<0.1, χ²test) (FIG. 3e and FIG. 11a), consistent with the roles of these hormones in the regulation of appetite[11].

Applicants note that a recent study[53] used scRNA-seq of 145 organoid-derived EECs to identify seven subsets. The present taxonomy of 12 subsets from 533 in vivo cells includes all those mature identified subsets[53], an additional three novel subsets (FIG. 12e, grey shading), including SIN, a particularly rare Nts-expressing subset, as well as a further sub-division of SIL and SIK cells that are enriched in the ileum, SIL-P and SIK-P.

Example 5—Two Sub-Types of Enterochromaffin Cells are Distinguished by Reg4 Expression Mature enterochromaffin cells (EC), EECs that secrete serotonin, regulate gut motility and secretory reflexes[54] and are implicated in diverse pathologies[55], partition into two clusters in the taxonomy. Both are readily identified by the expression of two canonical EC markers: Preprotachykinin-1 (Tac1), a precursor for neurokinin A and substance P, and Tryptophan hydroxylase 1 (Tph1), the rate-limiting enzyme in the biosynthesis of serotonin[56] (FIG. 3c and FIG. 11c-d). Comparing the gene signatures for the two clusters (FIG. 3b) highlighted Reg4 (regenerating islet-derived protein 4) and Afp as the top markers of one cluster ("EC-Reg4"), whereas Reg4 is barely detectable in the other cluster ("EC") (FIG. 3c). Although a recent single-cell study[23] suggested that Reg4 is a pan-enteroendocrine cell marker based on 238 cells from gut organoids, of the 7,216 cells Applicants profiled here, Reg4 is expressed in a subset of 35 out of 52 enterochromaffin cells (FIG. 3b-c and FIG. 11c-d), as well as in Paneth cells and in goblet cells (FIG. 12d). Applicants validated the partitioning of ECs by Reg4-specific expression in situ, validating the presence of two subsets of ECs (FIG. 3f).

As enteroendocrine cells play a central role in sensing luminal nutrients, Applicants examined the expression of genes encoding GPCRs in these cells, identifying those expressed significantly higher (FDR<0.25, Mann-Whitney U-test) in a given subset (FIG. 12f). Notably, the free fatty acid receptors 1 and 4 showed specific expression patterns. Ffar1 was highest in SIN cells, and also expressed by the Cck-expressing subsets previously collectively termed I-cells (STL-P, SILA and SIK-P), while Ffar4 was highest in the GIP-expressing subsets (SIK and SIK-P). These receptors are known to induce the expression of GIP and Gcg to maintain energy homeostasis[51]. Ffar2 was expressed by some progenitors and by EC cells, but notably absent from GIP-expressing cells, while the oleoylethanolamide receptor Gpr119, important for food intake and glucose homeostasis[37], was expressed highest in SILA cells.

Example 6—Two Subgroups of Tuft Cells with Immune and Neuronal-Like Expression Programs Tuft cells are the chemosensory cells of the gut and are enriched for taste-sensing molecules[148]. Tuft cells, a relatively poorly characterized epithelial cell type, were recently shown to play a key role in the T helper 2 (Th2) response to parasitic worm infection, through secretion of the Inter-leukin-25 (Il25), a potent chemoattractant for type II innate lymphoid cells[14-16].

Figure 2F:
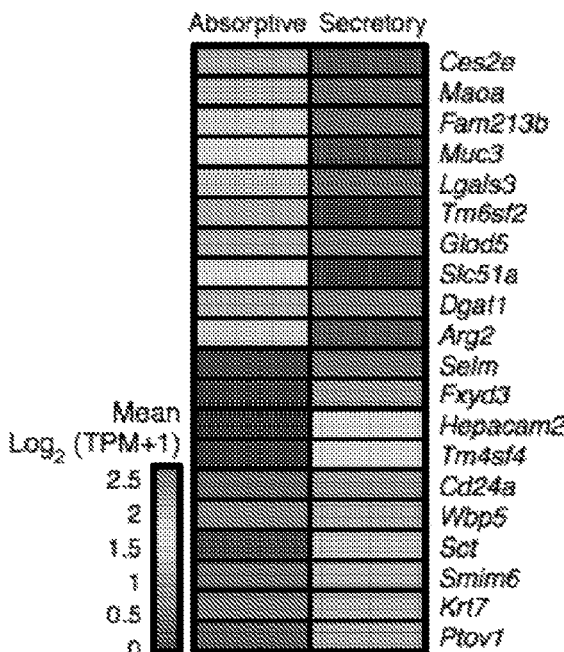
Figure 8F:
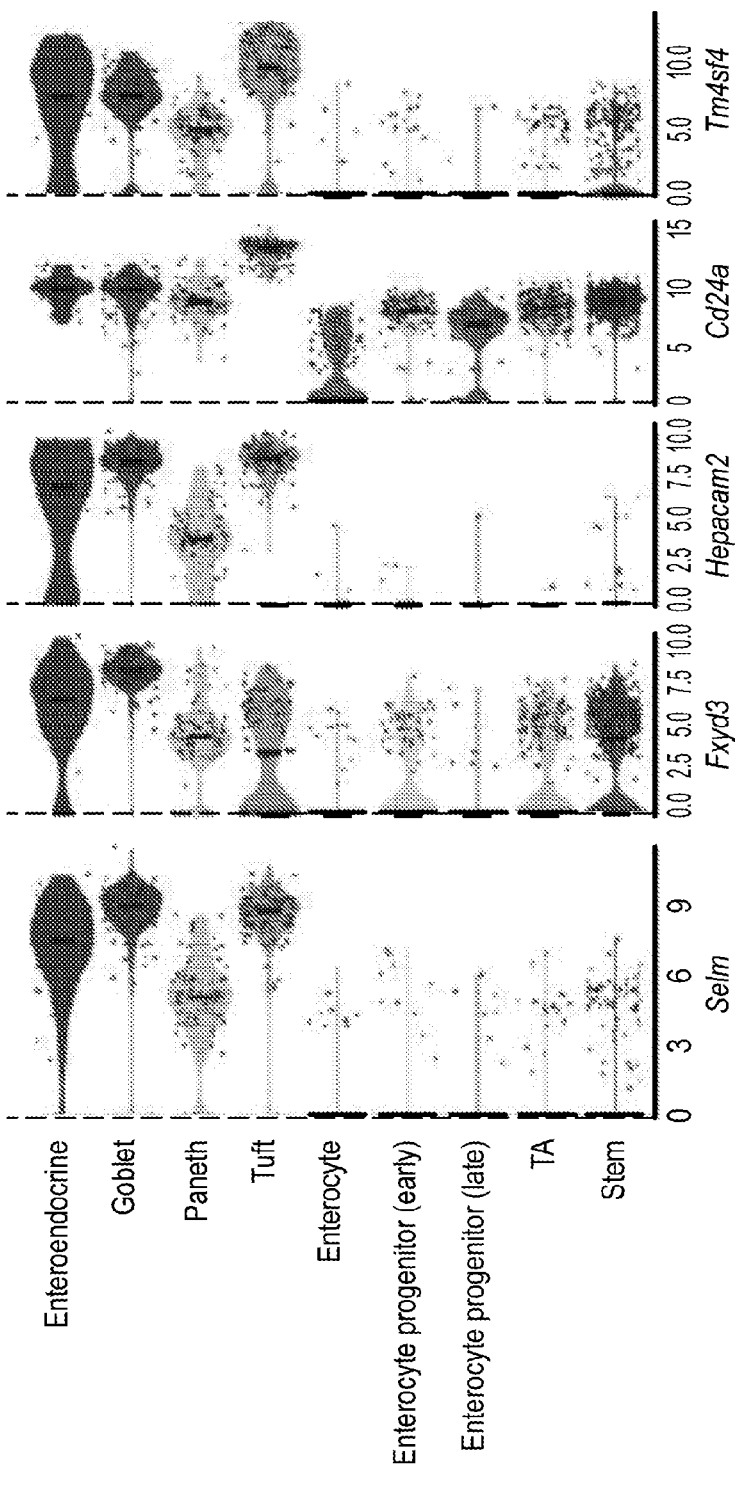

This study obtained sets of marker genes distinguishing the absorptive and secretory lineages and noticed that the known secretory lineage marker Cd24a (Sato et al., 2009) was indeed one of the specific markers for the secretory lineage (FIG. 2f). However, although Cd24a is broadly expressed by all secretory IECs, it was found to be expressed at a significantly higher level in tuft cells (FDR<0.05 Mann-Whitney U-test, FIG. 1C, FIG. 8F), which this study then confirmed at the protein level, observing a strong enrich-ment for tuft cells in a FACS sorted population of CD24+ high cells. This study therefore suggests that Hepacam2, a cell-surface marker, may be more useful to enrich for secretory cells without bias towards tuft cells (FIG. 8F).

A previous study[21] defined a tuft cell signature based on expression profiles of a bulk population of cells isolated using the cell surface marker Trpm5. The bulk signature had both neuronal and inflammation related gene modules; these could in principle be explained by either co-expression in the same cells or in distinct sub-types.

Figure 4A:
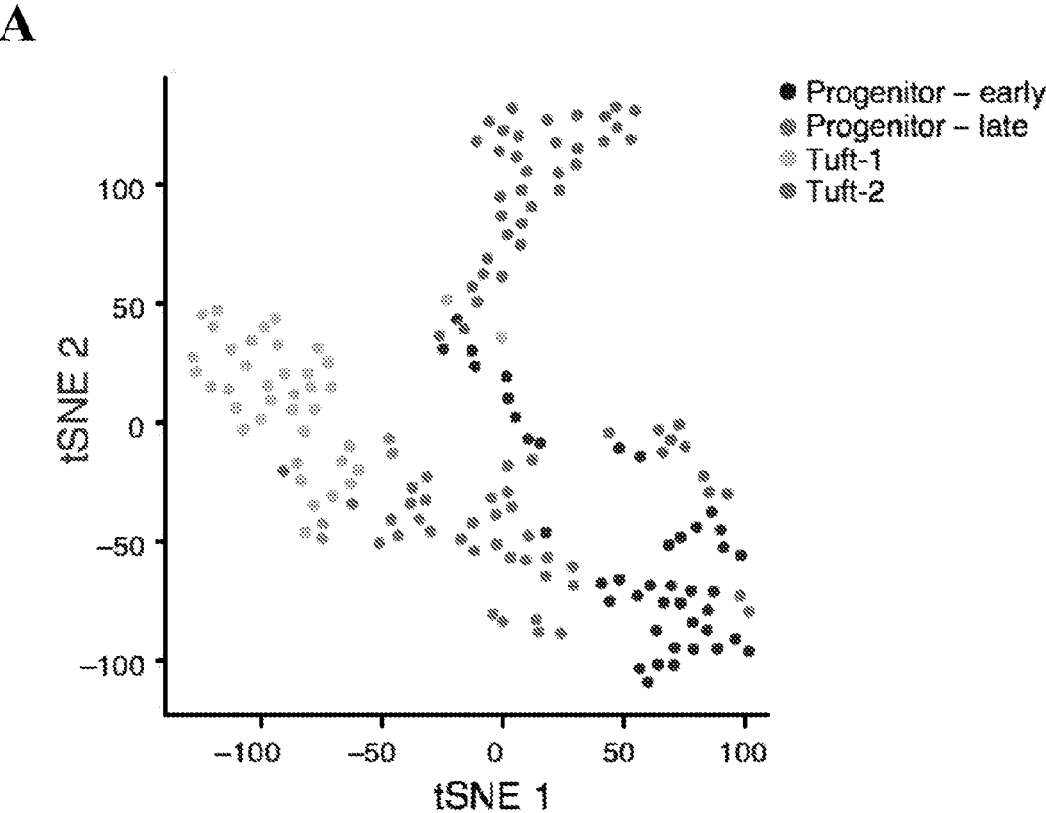
Figure 4B:
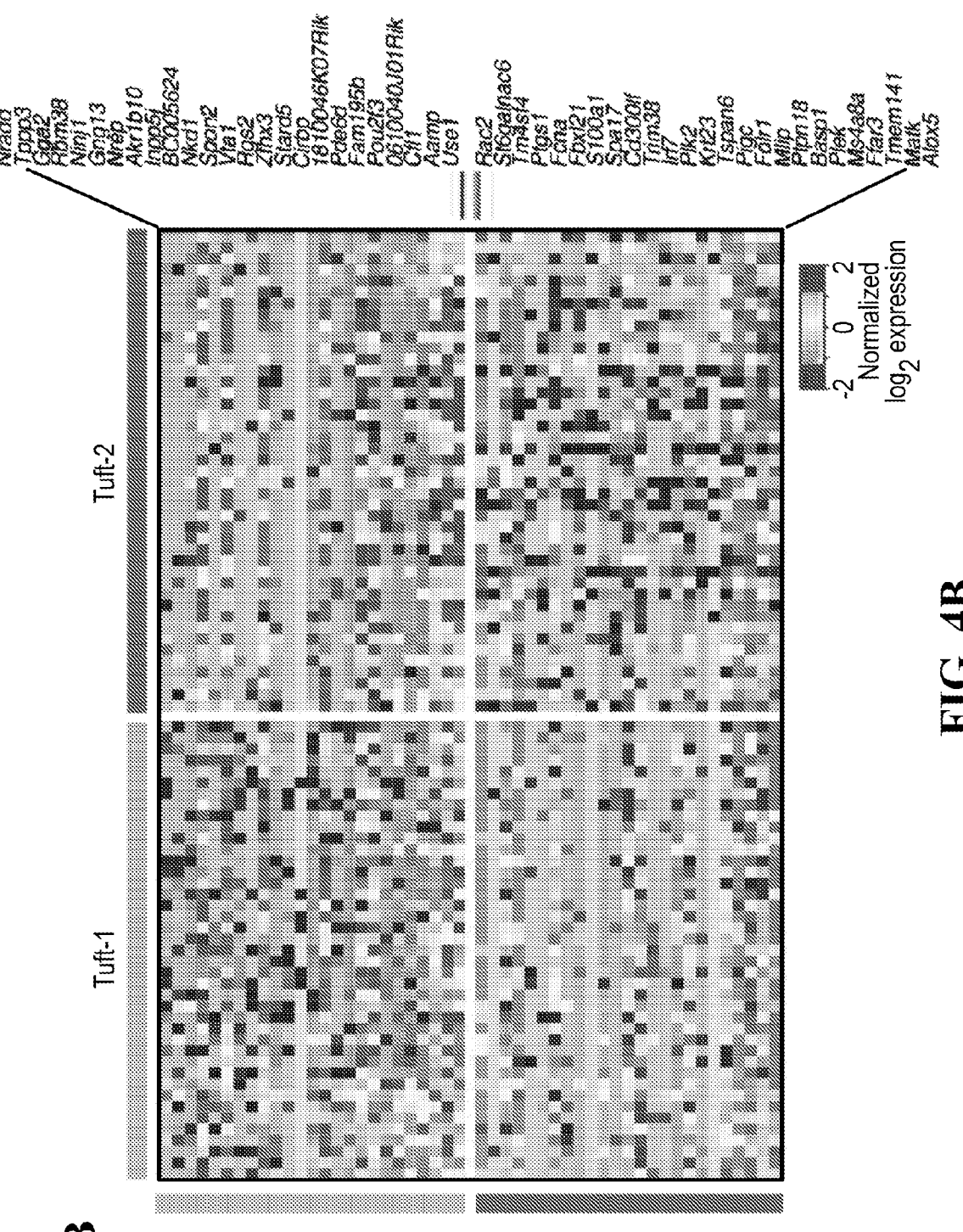
Figure 13A:
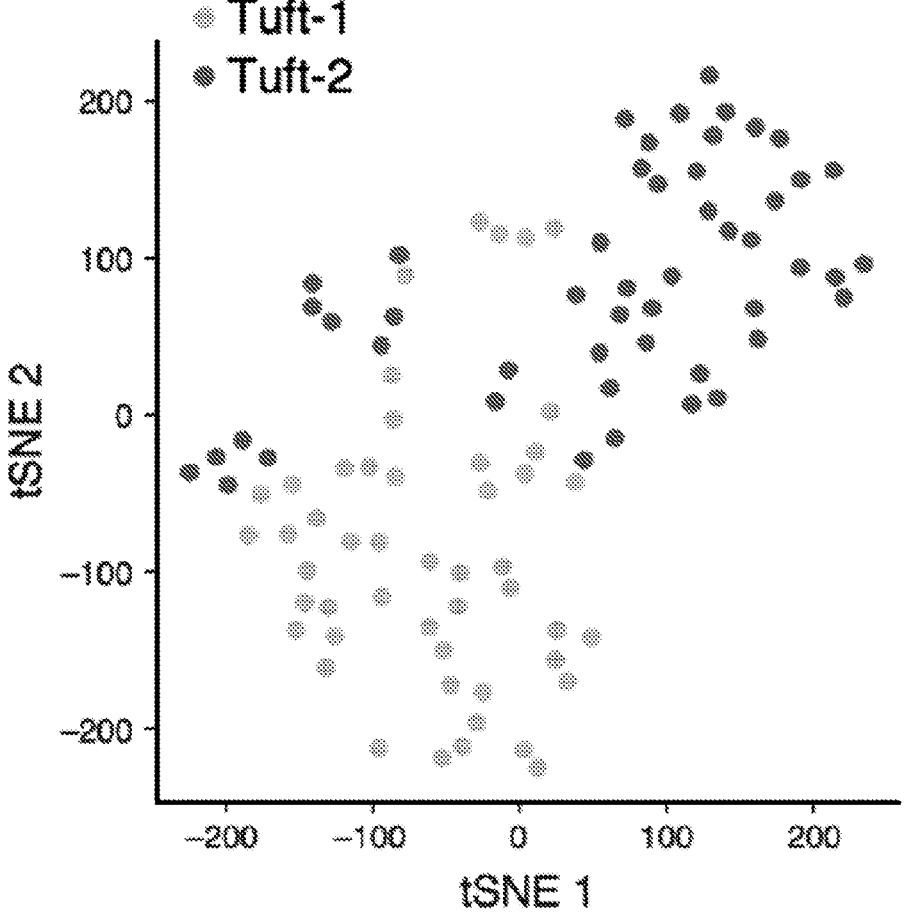
Figure 13B:
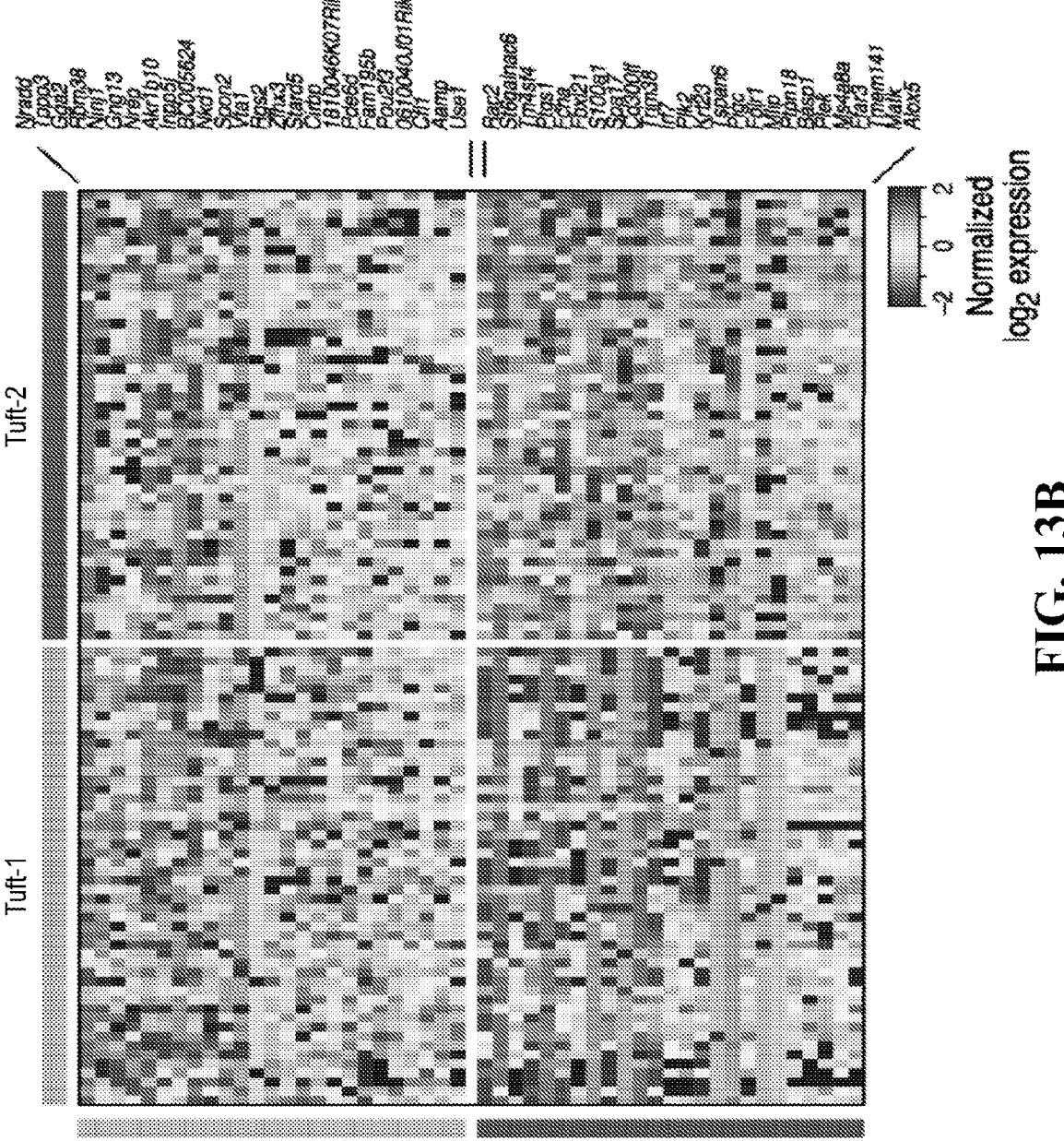

To distinguish these possibilities, Applicants re-clustered the 166 cells in the tuft cell cluster (FIG. 1b, FIG. 7g), and found that the cells not only readily partitioned into pro-genitors (early and late) and mature tuft cells, but that the 84 mature tuft cells were further partitioned into two major sub-clusters (Methods), which Applicants termed Tuft-1 and Tuft-2 (FIG. 4a). Tuft-1 and Tuft-2 cells showed no signifi-cant distinction in spatial location along the SI (data not shown). Applicants confirmed the same sub-division by independent clustering of the 101 mature tuft cells (enriched by CD24a+ sorting) in the deeper, full length scRNA-seq dataset (FIG. 13a). These two datasets enabled us to define a consensus signature, of 30 and 74 specific markers for the Tuft-1 and Tuft-2 clusters respectively, identified indepen-dently in both the 3' droplet and full-length datasets (FDR<0.01, Mann-Whitney U-test, Methods, FIG. 4b, FIG. 13b and Table 8).

TABLE 8

| Summary of marker genes for tuft cell subsets | | | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| Nradd | Il13ra1 | Nradd | Siglec5 | Rac2 | Rac2 |
| Endod1 | Ywhaq | Tppp3 | Rac2 | Matk | St6galnac6 |
| Tppp3 | Tsc22d1 | Gga2 | Ptprc | Nrgn | Tm4sf4 |
| Gga2 | Rgs13 | Rbm38 | St6galnac6 | Siglecf | Ptgs1 |
| Rbm38 | Stx7 | Ninj1 | Tm4sf4 | Alox5 | Fcna |
| Ldhb | Ppp3ca | Gng13 | Smpx | Cd300lf | Fbxl21 |
| Slc44a2 | Nebl | Nrep | Ptgs1 | Ccdc28b | S100a1 |
| Stoml1 | Gng13 | Akr1b10 | C2 | Trpm5 | Spa17 |
| BC016579 | Skp1a | Inpp5j | Cpvl | Hck | Cd300lf |
| Rabl5 | Rbm38 | BC005624 | Fcna | Ptgs1 | Trim38 |
| Cbr3 | Nradd | Nkd1 | Fbxl21 | Tuba1a | Irf7 |
| Ninj1 | Calm2 | Spon2 | Ceacam2 | Ptpn18 | Plk2 |
| Cnp | Tppp3 | Vta1 | S100a1 | Tm4sf4 | Krt23 |
| Wdr6 | Rnf128 | Rgs2 | Spa17 | Ms4a8a | Tspan6 |
| Gadd45a | Sh3bgrl | Zfhx3 | Sucnr1 | Sh2d6 | Pigc |
| Gng13 | Rab10 | Stard5 | Gde1 | Krt23 | Folr1 |
| Usp11 | Ctsc | Cirbp | Kcnj16 | Folr1 | Mlip |
| Mblac2 | Nkd1 | 1810046K07Rik | AA467197 | S100a1 | Ptpn18 |
| Pik3r3 | Ppp1ca | Pde6d | Cd300lf | Ccnj | Basp1 |
| Nrep | Cirbp | Fam195b | Trim38 | Ptpn6 | Plek |
| Akr1b10 | Krcc1 | Pou2f3 | Vmn2r26 | Reep5 | Ms4a8a |
| Sphk2 | Use1 | 0610040J01Rik | Gcnt1 | Atp2a3 | Ffar3 |
| Ddah2 | Ckap4 | Cfl1 | Irf7 | Krt18 | Tmem141 |
| Haghl | Zfp428 | Aamp | Plk2 | Hebp1 | Matk |
| Suv420h2 | Nrep | Use1 | Glyctk | Agt | Alox5 |
| H2-L | Rsrp1 | H3f3b | Krt23 | Ffar3 | Ccnj |
| Ulk1 | Cetn2 | Cyb5r4 | Tmem116 | H2-D1 | S100a11 |
| Atp4a | Bri3 | Trappc3 | Fam188a | Romo1 | Gm4952 |
| Gltpd1 | Myo6 | Runx1 | Bmp2 | Yipf1 | Ncf2 |
| Ift43 | Vdac3 | Pla2g4a | Ctsc | Ift172 | Cfb |
| Usp11 | Chmp5 | | Tspan6 | Ly6g6f | Cpne3 |
| Mical1 | Hsbp1l1 | | Slc25a20 | 9030624J02Rik | Sdcbp2 |
| Homer3 | Dpcd | | Pigc | Basp1 | Col15a1 |
| Trafd1 | Eif1b | | Folr1 | Mien1 | Ly6g6f |
| Ldlrad4 | Ube2d3 | | Mlip | Mlip | Man2a1 |
| Pir | Pla2g4a | | B4galt4 | Tubb4b | Agt |
| Atp6v0c-ps2 | St3gal6 | | Txndc16 | Pnpla6 | Nrgn |
| Anapc2 | Bpgm | | Ptpn18 | Plk2 | Snrnp25 |
| Grpel2 | Lima1 | | Ccdc23 | Lman2l | Tmem245 |
| Tanc2 | Cby1 | | Capg | Tmem176a | Hck |
| Mta2 | Dazap2 | | Ly6g6d | H2afj | Gimap1 |
| Ankrd63 | Cdc42se1 | | Basp1 | Elovl1 | Gprc5c |
| Exoc7 | Nsfl1c | | Abhd4 | Col15a1 | Coprs |
| Med27 | Aamp | | Plek | Tmem98 | Stk40 |
| Rmnd5a | Gdi2 | | Ms4a8a | Tspan6 | Tuba1a |
| Gpm6b | Mff | | Cwh43 | Fbp2 | Ttll10 |
| Plscr3 | Fkbp1a | | Tm7sf2 | Snrnp25 | Tmem176a |
| Dcxr | Hpgds | | Lect2 | Fes | Tubb4b |
| Stau1 | Scamp3 | | Ffar3 | Fdps | Romo1 |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Inpp5j | Sub1 | | Adam22 | Irf7 | Fbp2 |
| Bin3 | Degs2 | | Oas1g | Ctsa | Dclk1 |
| Ssh1 | Wbp2 | | Slc2a1 | S100a11 | Tax1bp1 |
| Ap1s2 | Rnf5 | | Tmem141 | Lmf1 | Fes |
| Svil | Galk1 | | Gm17660 | Gprc5c | Hebp1 |
| Chd6 | Med10 | | Suco | Sh2d7 | Skap2 |
| Gimap8 | Tnfsf13os | | Matk | Fbxl21 | Clec4a1 |
| Bloc1s2a | Ola1 | | Ccdc109b | Tmem245 | Cox17 |
| Zfp191 | Rhoa | | Alox5 | Fcnaos | Mien1 |
| Nbeal2 | Psmd8 | | Acsl4 | Car7 | Car7 |
| Plekhg5 | Pla2g12a | | Trim40 | Aldh2 | Reep5 |
| Gtf2ird1 | Mpg | | Slc41a3 | D17Wsu92e | Tmem80 |
| Ogfr | Mtfr1l | | Ccnj | Sdcbp2 | Ccdc28b |
| Hmg20b | Fam96a | | Rdx | Cox17 | Krt18 |
| Cdc42ep1 | Trappc1 | | Rmdn1 | Hypk | Ift172 |
| Gna14 | Srp14 | | Plekho2 | Tmem80 | Ptpn6 |
| Zfp810 | Cystm1 | | Cfi | Dyrk4 | Pnpla6 |
| Marveld2 | Tcta | | Car2 | Ubl7 | Isg15 |
| Thtpa | Pnrc1 | | Apobec1 | Fcna | Tmem57 |
| BC005624 | Ninj1 | | Mboat1 | Tmem141 | Abhd16a |
| Tcp11l2 | Ube2l3 | | Ccdc68 | Rtp4 | 1700112E06Rik |
| Shkbp1 | Cryzl1 | | Smg7 | Vav1 | Map1a |
| Pcyox1l | Lpcat4 | | Rgs13 | Man2a1 | Shf |
| Tmem131 | Rab3ip | | Oas2 | Trak1 | H2-D1 |
| Ssna1 | Fam103a1 | | Rhoc | Gimap1 | Lmf1 |
| Nkd1 | Zbtb20 | | Rnasel | Uba1 | |
| Ndufaf3 | Ociad2 | | Pparg | S100a13 | |
| Zfp872 | Cyb5r4 | | Gnai1 | Gucy2c | |
| Amz2 | Rab18 | | Bmx | Sec14l1 | |
| Cyb561d1 | H3f3a | | Atp2b2 | Atg101 | |
| Zfp444 | Leprot | | Dynlt1b | Ltc4s | |
| Src | Rab14 | | Sept8 | Lamtor4 | |
| Anxa11 | Fam195b | | Il17rb | Sfxn3 | |
| Pgm2l1 | Lrrc42 | | Kalrn | Fam98c | |
| Nsmce1 | Akr1b10 | | Opn3 | Map1a | |
| Snapc3 | Cyhr1 | | Dnase1l1 | Stk40 | |
| Abi2 | Cfl1 | | Ero1lb | Pigc | |
| Smug1 | Camk2d | | Asl | Isg15 | |
| Slco3a1 | Gm10384 | | Lrrc42 | Pradc1 | |
| Myo10 | Dcp1b | | Ifitm1 | Cpne3 | |
| Kcnn4 | Acss2 | | Atp6v0c | Dclk1 | |
| Ehmt2 | Prom1 | | Enpp4 | Fip1l1 | |
| Snap47 | Cutc | | Samd9l | Plek | |
| Snapin | Gng5 | | Abhd5 | Arhgap1 | |
| Tas1r3 | Dnaja2 | | S100a11 | Pqlc1 | |
| Ssh2 | Pold4 | | Fut2 | Tax1bp1 | |
| Fn1 | Dynlt3 | | Gm4952 | Abcc3 | |
| Tchp | Prdx2 | | Ccrl1 | 1700112E06Rik | |
| Nrbp2 | Rbm39 | | Tmem74b | Snf8 | |
| Atxn7l1 | Asah1 | | Enc1 | Sez6l2 | |
| Kif3b | Trappc6b | | Ncf2 | Gm4952 | |
| Ppp2r3d | Tm2d1 | | Scd2 | Zdhhc16 | |
| Atf7ip | 1810046K07Rik | | Il10rb | Rpp21 | |
| Adnp | Snx2 | | Kirrel3 | Adcy5 | |
| Dnahc8 | Cd24a | | Gpr64 | Slc4a2 | |
| Ctxn1 | Trappc3 | | Hist2h2aa1 | Tusc2 | |
| Tcf4 | Zfhx3 | | Rhbdf1 | Mrpl46 | |
| Cyth1 | Trappc6a | | Cfb | Clec4a1 | |
| Zscan21 | Capza2 | | Gm14288 | Csk | |
| Dync1i2 | Itfg1 | | A4galt | Cfb | |
| Nlrc4 | Dnaja1 | | Pmel | Kdm4a | |
| Ttc1 | Zfp410 | | Ifi27l1 | Trim38 | |
| Afap1l2 | Itpr2 | | Oas1a | Sdf4 | |
| Plod3 | Pop7 | | Cpne3 | Bst2 | |
| Utrn | Brk1 | | Rps6ka2 | Ap2s1 | |
| Kdm2a | Sept7 | | Tmem246 | Stat2 | |
| Etv4 | Anxa4 | | Sdcbp2 | 1810037I17Rik | |
| Maml1 | Mast4 | | Col15a1 | Coprs | |
| Spon2 | Tmx1 | | Ly6g6f | Pik3cg | |
| Gata5 | 1700123020Rik | | Man2a1 | Plcg2 | |
| Tln1 | Gstm7 | | Chat | Cd37 | |
| Akap8l | Stxbp3 | | Rgs22 | Ttll10 | |
| F730043M19Rik | Dctn6 | | Pold4 | Skap2 | |
| Arl10 | Rassf6 | | Kctd13 | Dmxl2 | |
| Vta1 | Immp1l | | Cdhr2 | Mrpl41 | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Tbx3 | Pnrc2 | | Apip | Tmem57 | |
| Rbm5 | Sdcbp | | Gabarapl2 | St6galnac6 | |
| Gm6756 | Sdhaf4 | | Gpcpd1 | Cutal | |
| Epb4.1l1 | C2cd4b | | Pcdh20 | Shf | |
| Il4ra | Arl2 | | D730039F16Rik | Lpp | |
| Rgs2 | Slc44a3 | | Agt | Ncf2 | |
| Pcdh1 | Vapb | | Nrgn | Ap1s1 | |
| Arid3b | H3f3b | | Snrnp25 | Abhd16a | |
| Map1s | Pou2f3 | | Fam167a | Dalrd3 | |
| Ctnnal1 | Inpp5j | | Etohi1 | Spa17 | |
| Acap3 | Lpar6 | | Siae | Pde2a | |
| Mboat2 | Akirin2 | | Gstt1 | Cyp51 | |
| Unc45a | Map1lc3b | | Ndst1 | Scand1 | |
| Zfhx3 | Chmp3 | | Rhog | Trim31 | |
| Stard5 | Fnta | | Pot1a | Lrrc41 | |
| Hps5 | Phpt1 | | Tmem245 | | |
| Arrdc1 | Commd7 | | Hck | | |
| Taf8 | Syf2 | | Rab13 | | |
| Rac3 | Cdc42 | | Smyd1 | | |
| Gnb2 | Acot7 | | 2810468N07Rik | | |
| Ehmt1 | Mea1 | | Gimap1 | | |
| Inpp5b | Vapa | | Tmem219 | | |
| Pam16 | Ccdc109b | | Gprc5c | | |
| Cdc25b | Pip5k1b | | Slc6a8 | | |
| Gfod1 | Vta1 | | Coprs | | |
| B9d2 | Ube2r2 | | Fam49a | | |
| Wdr85 | Klf9 | | Uox | | |
| Atf6b | 0610040J01Rik | | Tmem121 | | |
| Gatad2a | Ndfip2 | | Tmem241 | | |
| Wdr13 | Actr10 | | Mgll | | |
| Zfhx2 | Manbal | | Hrsp12 | | |
| Ccdc92 | Morf4l2 | | Tcta | | |
| Nfe2l3 | Pigyl | | Tmc5 | | |
| Tead2 | Runx1 | | 1700011H14Rik | | |
| Rmnd5b | Rnf6 | | Mtmr11 | | |
| Dock7 | Ghitm | | Neurl1a | | |
| Wnk2 | Pim3 | | Stk40 | | |
| Snapc2 | Tank | | Klhl28 | | |
| Dixdc1 | Nubp2 | | Nek7 | | |
| Neu2 | Lsm1 | | Ak7 | | |
| Mcc | Zfand6 | | Tuba1a | | |
| Ythdf2 | Uros | | Slc16a3 | | |
| Stx4a | Snapc5 | | Prkce | | |
| Flii | Frg1 | | Neu1 | | |
| Mmp14 | Malat1 | | Irs2 | | |
| Hgs | Pla2g16 | | Tslp | | |
| Ptprf | 9130230L23Rik | | Ypel3 | | |
| Puf60 | Gga2 | | Ablim3 | | |
| Aldh7a1 | Tmem30b | | Crip1 | | |
| Prpf6 | Ube2k | | Gm14440 | | |
| Gdpd5 | Mocs2 | | Ppp1r3b | | |
| Gramd4 | Slmo2 | | Ppt1 | | |
| Mov10 | Atp6v1g1 | | Cdhr5 | | |
| Hipk3 | Dnajb1 | | Ttll10 | | |
| Mthfd1l | Stra6l | | Fbxo9 | | |
| Fam216a | Slc25a11 | | Gimap3 | | |
| Rab4b | Smim8 | | 1110032A03Rik | | |
| Sh3glb2 | Tpgs2 | | Rbpms | | |
| Cdc14b | Bub3 | | Cadps2 | | |
| Tmem63b | Rit1 | | Loh12cr1 | | |
| Leng1 | Hsbp1 | | Ccser2 | | |
| Nab2 | M6pr | | Tmem176a | | |
| AW554918 | Gemin7 | | Tubb4b | | |
| 4931428F04Rik | Cpq | | P2rx1 | | |
| Ddx42 | Jade1 | | Romo1 | | |
| Cttn | BC004004 | | Chac2 | | |
| Mtfmt | Sirt2 | | Ccbe1 | | |
| Stox2 | Tspan31 | | Lyn | | |
| Cirbp | Atg3 | | Bnip3 | | |
| Gm8096 | Bbs4 | | L1cam | | |
| Usf2 | Wbscr22 | | Fbp2 | | |
| Kcnh8 | Rgs2 | | Wdfy2 | | |
| Fam89b | Plaa | | Nsf | | |
| Fundc1 | Nudt14 | | Nfatc1 | | |
| Arhgef2 | Msi2 | | Rpl30 | | |

TABLE 8-continued

| Summary of marker genes for tuft cell subsets | | | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| Myo7b | Dnlz | | Necap1 | | |
| 1810046K07Rik | Akr1b3 | | Nlrx1 | | |
| Afap1 | Maf1 | | Ydjc | | |
| Gtdc1 | Pde6d | | Oasl2 | | |
| Chd4 | Stard5 | | Dpysl2 | | |
| Dclk3 | Phax | | Parp4 | | |
| C230052I12Rik | Slc23a3 | | Gm6644 | | |
| 2410018L13Rik | Prelid2 | | 1700047I17Rik2 | | |
| Arid2 | Strbp | | Fyb | | |
| Commd4 | Pea15a | | Gmpr | | |
| Pigv | Chn2 | | Enpp3 | | |
| St5 | Cmip | | Nptn | | |
| Pde6d | Diablo | | Serpini1 | | |
| Traf7 | Txndc9 | | Slc4a8 | | |
| Fam195b | Alox5ap | | Gprc5a | | |
| Ubn2 | 0610009L18Rik | | Fabp1 | | |
| Lzts2 | Taf12 | | Gm14295 | | |
| Mark2 | Acer3 | | Dclk1 | | |
| Pou2f3 | Mpv17l2 | | Terf2 | | |
| Csk | Nck1 | | Tax1bp1 | | |
| Plekhm2 | Tmbim1 | | Klf6 | | |
| Abhd8 | Metap2 | | Mn1 | | |
| Dopey2 | Hnrnpk | | Pygl | | |
| Ppil2 | Yif1b | | Sema7a | | |
| Hdac6 | Stat6 | | Chmp2a | | |
| Tmem158 | Dctn2 | | Sh3kbp1 | | |
| Vezt | Siah1a | | Bicd1 | | |
| Adora1 | Spon2 | | Atp6v1d | | |
| Fhad1 | Shisa5 | | Avpi1 | | |
| Gripap1 | Ppp1r35 | | Xaf1 | | |
| Sptbn1 | Arpc1b | | Atp6v0d1 | | |
| Tcea2 | Ppp6c | | Gm14436 | | |
| Sugp2 | BC005624 | | Sema5b | | |
| Efs | | | Chi3l1 | | |
| Sbf1 | | | Slc25a12 | | |
| Lrrc16a | | | Fes | | |
| Nsd1 | | | Fam177a | | |
| 0610040J01Rik | | | Hebp1 | | |
| Jup | | | Klf7 | | |
| Cacnb3 | | | Nudt8 | | |
| Stub1 | | | Tesk2 | | |
| Mob3a | | | Inpp5d | | |
| Zdhhc8 | | | Lrp12 | | |
| Hmx2 | | | Fam83d | | |
| Ywhab | | | Skap2 | | |
| AI846148 | | | Atg3 | | |
| Tet1 | | | Wdfy1 | | |
| Rab1b | | | Hipk1 | | |
| Hes6 | | | Efhd2 | | |
| Slc4a7 | | | Krt222 | | |
| 2410004B18Rik | | | Trappc2 | | |
| Rest | | | Lipo1 | | |
| Abca7 | | | Syne2 | | |
| 1110004F10Rik | | | Clec4a1 | | |
| 9230110C19Rik | | | Ptpra | | |
| Kdm6b | | | Ttll7 | | |
| Gas8 | | | Lyrm2 | | |
| Cgn | | | Cox17 | | |
| Tnrc18 | | | Tm2d1 | | |
| Taok2 | | | Strip2 | | |
| Gpsm1 | | | Dock8 | | |
| Setx | | | Sdf2 | | |
| Patz1 | | | Hyi | | |
| Esyt1 | | | Gpr18 | | |
| Junb | | | Cables2 | | |
| Ntng2 | | | Sertad1 | | |
| Ncs1 | | | Mien1 | | |
| Ppm1m | | | Fam57a | | |
| Atxn2l | | | Ptpre | | |
| Arpc1a | | | 1810058I24Rik | | |
| Smarce1 | | | Car7 | | |
| Tmem231 | | | Lmtk2 | | |
| Cish | | | Tnnt1 | | |
| Agrn | | | Ypel5 | | |
| Abcc5 | | | Gtf2b | | |

TABLE 8-continued

| Summary of marker genes for tuft cell subsets | | | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| Plekhg2 | | | Zdhhc20 | | |
| Ssbp3 | | | Mapre2 | | |
| Sbk1 | | | Sik1 | | |
| 2700086A05Rik | | | Erp29 | | |
| Kdm5a | | | Tmem229a | | |
| Cfl1 | | | Gas7 | | |
| Ppp6r2 | | | Rnasek | | |
| Jmy | | | Tuba4a | | |
| Oas1h | | | Ppp1r14c | | |
| Fgf12 | | | Pacs2 | | |
| Mau2 | | | Pnpla3 | | |
| Irf2bpl | | | Reep5 | | |
| Ogdhl | | | Rbm4b | | |
| Trerf1 | | | Tmem80 | | |
| Lamtor5 | | | Kctd15 | | |
| Lmnb2 | | | Capn1 | | |
| Dync1h1 | | | Ifnar2 | | |
| Dpp3 | | | Xrcc4 | | |
| Aldh4a1 | | | Tspan17 | | |
| Wwc1 | | | Hdac1 | | |
| Zfp459 | | | Ccdc28b | | |
| Pion | | | Tspan8 | | |
| Strn4 | | | Grina | | |
| Ppp2r5c | | | Fam46a | | |
| Stx8 | | | 4930539E08Rik | | |
| Wdr78 | | | Casp3 | | |
| Dsp | | | Adam1b | | |
| 9030624G23Rik | | | Mxd1 | | |
| Kifc2 | | | Fdft1 | | |
| Senp7 | | | Kcns3 | | |
| Aamp | | | Slc9a6 | | |
| 4931406H21Rik | | | Vamp4 | | |
| Gtf2f1 | | | Cd47 | | |
| Oas1c | | | Slc52a3 | | |
| Cachd1 | | | Gm3002 | | |
| Fis1 | | | Apba3 | | |
| Use1 | | | Syne3 | | |
| Kit | | | Krt18 | | |
| Zdhhc17 | | | Map1lc3a | | |
| Tmem9 | | | Rusc1 | | |
| H3f3b | | | Dctn3 | | |
| Narf | | | Gnat3 | | |
| Kcnh2 | | | Homer1 | | |
| Ddx17 | | | Gngt2 | | |
| Micall1 | | | Slc39a13 | | |
| Dnajb2 | | | Rgs19 | | |
| Ik | | | Emc2 | | |
| Flt3l | | | Tusc3 | | |
| Igfbp7 | | | Vps53 | | |
| Chdh | | | Gpr137b-ps | | |
| Pak1 | | | Kif2a | | |
| Hoxa5 | | | Ildr1 | | |
| Rnf114 | | | Limd2 | | |
| Mlec | | | Gm10406 | | |
| Rbm42 | | | Rab11a | | |
| Kdm4d | | | Ift172 | | |
| Fam50a | | | Tmem256 | | |
| Irgq | | | 6330407A03Rik | | |
| Irf5 | | | Fbxo36 | | |
| Cenpt | | | Ptpn6 | | |
| Iqsec1 | | | Exph5 | | |
| Dvl3 | | | Arl6 | | |
| Figf | | | Stx7 | | |
| Tmed1 | | | Dcaf15 | | |
| Znf512b | | | Lap3 | | |
| Podxl2 | | | Nav2 | | |
| Cyb5r4 | | | Lrrc57 | | |
| Plekha6 | | | Prox1 | | |
| Trappc3 | | | Pnpla6 | | |
| Snn | | | Syap1 | | |
| Zdhhc24 | | | Itih5 | | |
| Runx1 | | | Rock2 | | |
| Cd9912 | | | Isg15 | | |
| Zc3h11a | | | Tprg1 | | |
| Gse1 | | | Amdhd2 | | |

TABLE 8-continued

| Summary of marker genes for tuft cell subsets | | | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| Cdx1 | | | Unc13d | | |
| Camkk1 | | | AI462493 | | |
| Jag2 | | | Ampd3 | | |
| Arid4b | | | Gm14308 | | |
| 2310011J03Rik | | | Ell2 | | |
| Rnf111 | | | 0610031J06Rik | | |
| Eif4h | | | Zdhhc9 | | |
| Rraga | | | Zfp868 | | |
| Dyrk1b | | | Gys1 | | |
| Nfe2l1 | | | Tmem57 | | |
| Csrnp1 | | | Hspb11 | | |
| Cyld | | | Nebl | | |
| Tnip1 | | | Fbxo25 | | |
| Atp6v1e2 | | | Gbp3 | | |
| Tet3 | | | Cdkl2 | | |
| Pvrl1 | | | Zdhhc12 | | |
| Prpf38b | | | Gclm | | |
| Pla2g4a | | | Gm3317 | | |
| Pfkfb3 | | | Gm3494 | | |
| Ubr4 | | | 4833418N02Rik | | |
| Ppp2r1a | | | Ube2j1 | | |
| Polb | | | Htatsf1 | | |
| Igsf8 | | | Kif3a | | |
| Tmem223 | | | Lca5 | | |
| Tiam2 | | | Taf9b | | |
| Sptan1 | | | H2-Ke6 | | |
| Zmym3 | | | Bmyc | | |
| Shoc2 | | | Mtmr7 | | |
| Tnfrsf25 | | | Abhd16a | | |
| Celf1 | | | Itsn2 | | |
| Map4k4 | | | Atp6v0a1 | | |
| Hyal2 | | | Adra2a | | |
| Tjp3 | | | Dcp1b | | |
| Morf4l1 | | | Snx18 | | |
| Ccdc115 | | | Pxmp4 | | |
| Phip | | | Smap1 | | |
| Gclc | | | Cmip | | |
| Pcdhga5 | | | Atp6v0b | | |
| Polr3g | | | Dnahc6 | | |
| Pnn | | | 1700112E06Rik | | |
| Fam129b | | | Cpm | | |
| Trio | | | Arhgap4 | | |
| 4931440P22Rik | | | Ccdc129 | | |
| Lepre1 | | | Fnta | | |
| Agpat1 | | | Ccndbp1 | | |
| Kank1 | | | Itfg1 | | |
| Pard6g | | | Map1a | | |
| Mapk1ip1l | | | Efnb2 | | |
| Tmub2 | | | Shf | | |
| Fgd6 | | | H2-D1 | | |
| Safb2 | | | Tbcb | | |
| Bahd1 | | | Phf1 | | |
| Ajuba | | | Cry2 | | |
| Pou2f1 | | | Iqce | | |
| Pdlim5 | | | Cript | | |
| Dnmt3a | | | Sema3b | | |
| Fcho2 | | | Adh1 | | |
| Trib2 | | | Crot | | |
| Bptf | | | Eppk1 | | |
| Ctnna1 | | | B3gat3 | | |
| 2310035C23Rik | | | Arl8a | | |
| R3hdm4 | | | Gadd45g | | |
| | | | Alkbh7 | | |
| | | | Cib2 | | |
| | | | 2010012O05Rik | | |
| | | | Cic | | |
| | | | A630075F10Rik | | |
| | | | Gm14420 | | |
| | | | Rabgef1 | | |
| | | | Lgals8 | | |
| | | | Lmf1 | | |

TABLE 8-continued

| | | Summary of marker genes for tuft cell subsets | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| | | | Bad | | |
| | | | Cdipt | | |
| | | | Kank3 | | |
| | | | Mtpn | | |
| | | | Atp6v1e1 | | |
| | | | OTTMUSG00000016609 | | |
| | | | Myl6 | | |
| | | | Gfi1b | | |
| | | | Pigyl | | |
| | | | Ccdc126 | | |
| | | | Ocel1 | | |
| | | | Bloc1s1 | | |
| | | | Eml6 | | |
| | | | Kcnd3 | | |
| | | | Nfat5 | | |
| | | | Gm5617 | | |
| | | | Sos1 | | |
| | | | Mania | | |
| | | | Acer3 | | |
| | | | Gm2382 | | |
| | | | Suox | | |
| | | | Chuk | | |
| | | | Coq10b | | |
| | | | Dhcr24 | | |
| | | | Srpx2 | | |
| | | | Epb4.1l4b | | |
| | | | Gemin7 | | |
| | | | Rab44 | | |
| | | | Elp5 | | |
| | | | Rasa2 | | |
| | | | Calml4 | | |
| | | | Slco4a1 | | |
| | | | Slc25a17 | | |
| | | | Arhgap5 | | |
| | | | Rbms3 | | |
| | | | Neat1 | | |
| | | | Nab1 | | |
| | | | Rdh14 | | |
| | | | 1700030A11Rik | | |
| | | | Tfpi2 | | |
| | | | Ccnc | | |
| | | | Zfp428 | | |
| | | | B3gnt6 | | |
| | | | Ddt | | |
| | | | Ostf1 | | |
| | | | Cdk11b | | |
| | | | Tmem79 | | |
| | | | Gm14306 | | |
| | | | Vps13a | | |
| | | | Fam3a | | |
| | | | Clca5 | | |
| | | | Dcaf12 | | |
| | | | Mbd6 | | |
| | | | Gramd1b | | |
| | | | Tbcc | | |
| | | | Wsb2 | | |
| | | | Tmem8 | | |
| | | | B4galt6 | | |
| | | | Psd3 | | |
| | | | Marveld3 | | |
| | | | Synrg | | |
| | | | Krcc1 | | |
| | | | Tshz1 | | |
| | | | Rogdi | | |
| | | | Rap2a | | |
| | | | Gm6249 | | |
| | | | Apc | | |
| | | | Enpp5 | | |
| | | | Otud7b | | |
| | | | Rilpl2 | | |
| | | | Stambpl1 | | |
| | | | Samd14 | | |
| | | | Ccdc104 | | |
| | | | Atp2b1 | | |
| | | | Phtf2 | | |

TABLE 8-continued

| Summary of marker genes for tuft cell subsets | | | | | |
|---|---|---|---|---|---|
| Tuft-1 (plate) | Tuft-1 (droplet) | Tuft-1 (consensus) | Tuft-2 (plate) | Tuft-2 (droplet) | Tuft-2 (consensus) |
| | | | Ndrg1 | | |
| | | | Srp19 | | |
| | | | Tspyl1 | | |
| | | | B3galt5 | | |
| | | | Aldoc | | |

Significance cut-offs: FDR (Fisher's combined): 0.01, Log2 fold-change: 0.25

The Tuft-2 cell signature is enriched for immune-related genes (FDR<0.001, FIG. 13c-d), whereas genes related to neurogenesis and neuronal development (e.g., Nradd, Ninj1, Plekhg5 and Nrep) are among the most specific markers for the Tuft-1 cluster (FIG. 13d). Irf7 is the only Tuft-2 specific TF and may be a target used for modulating activity of Tuft-2 cells. This supports the hypothesis that the previously reported inflammation and neuronal signatures in bulk data[21] belonged to distinct tuft cell subsets. These two subsets may reflect dynamic states, transient stages of maturity, or two distinct bona-fide cell types.

As tuft cells were recently shown to be important for communication with gut-resident immune cells[14-16], Applicants examined their expression of genes encoding epithelial cytokines. Both groups expressed Il25, consistent with recent findings[14], but neither expressed Il33 (in both data-sets) (FIG. 4c), which may be due to the low level of this transcript. However, the expression of thymic stromal lymphopoietin (TSLP), an important Th2 promoting cytokine[13, 57] was significantly higher in the Tuft-2 group (FDR<0.1, Mann-Whitney U-test) (FIG. 4c), a finding Applicants confirmed using smFISH and qPCR (FIG. 4d-e). TSLP expression by the Tuft-2 subset may, along with Il25, contribute to the induction of the Th2 response to intestinal parasites.

Finally, the Tuft-2 signature revealed that Ptprc, the gene encoding the pan-immune marker CD45, is expressed strongly and exclusively by Tuft-2 cells (FIG. 4f), a finding Applicants validated at the mRNA level in situ by co-FISH (FIG. 4g, top-left), at the protein level using FACS (FIG. 4g, top right) and by an immunofluorescence assay (IFA) (FIG. 4g lower panels and FIG. 13e). Finally, sorting for EpCAM+ CD45+ cells (n=3 mice) followed by 3' droplet scRNA-seq of 332 cells, showed a strong enrichment for Tuft-2 cells (FIG. 4h and FIG. 13f). Applicants note that Applicants used a lenient sorting gate to ensure Applicants obtain sufficient numbers of these rare tuft cells, which led to a higher contamination rate of T cells, which Applicants removed using unsupervised clustering (T cell expression of Ptprc is ~25% higher than in sorted CD45+ Tuft-2 cells). To Applicants knowledge, this is the first finding of CD45+ cells from a non-hematopoietic lineage, and highlights the challenges associated even with even well-established molecular markers of cell types.

Taken together, the data suggests that tuft cells are a population of two distinct sub-types; Tuft-1 cells, with neuron-like features that may transmit taste-chemosensory signals to enteric neurons (Westphalen et al., 2014) and Tuft-2 cells with immune-like features that in addition to the taste-chemosensory ability, may communicate with immune cells, as suggested before (Gerbe et al., 2016; Howitt et al., 2016; von Moltke et al., 2016) to boost type-2 immunity upon signals from the lumen.

Figure 34:
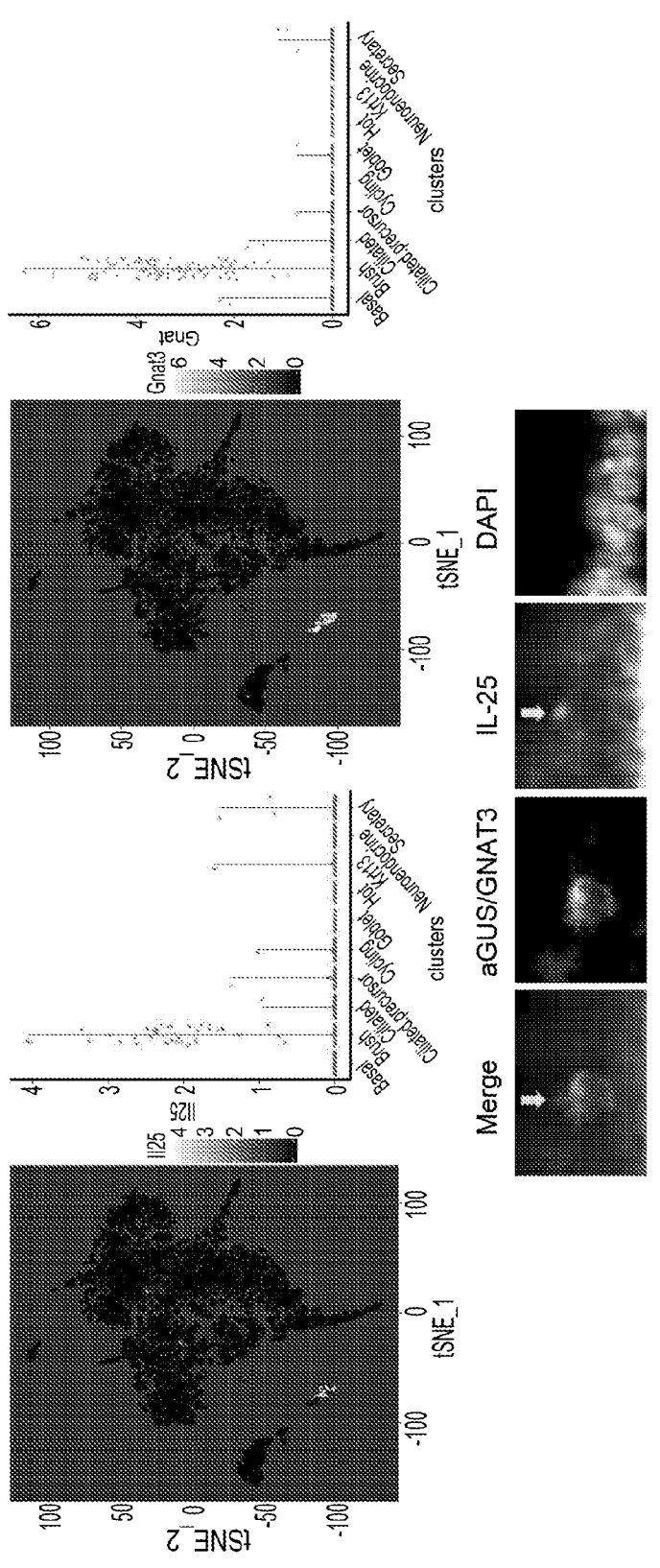
FIG. 34—shows the Respiratory Tuft Cell produces ILC2-modulating IL-25.
Figure 35:
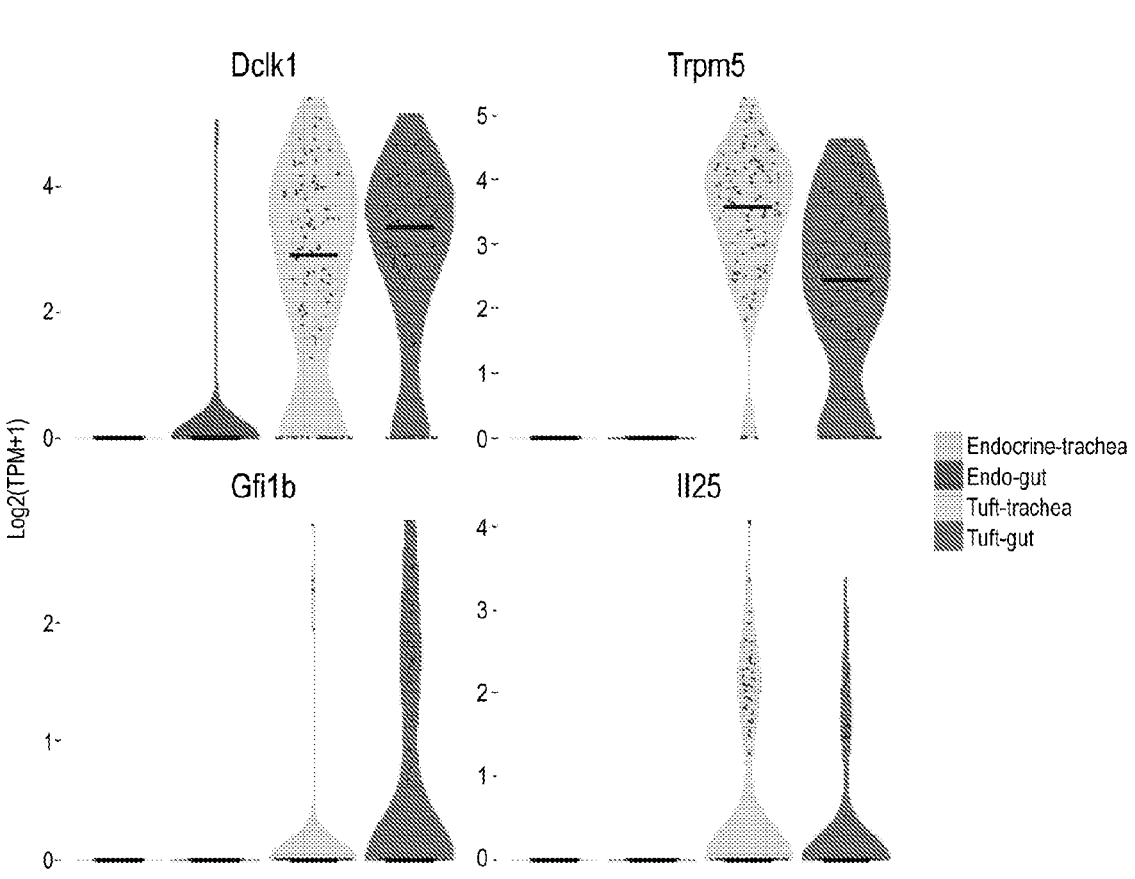
FIG. 35—shows tuft cell markers—sets forth violin plots showing tuft cell specific expression in the trachea and gut.
Figure 36:
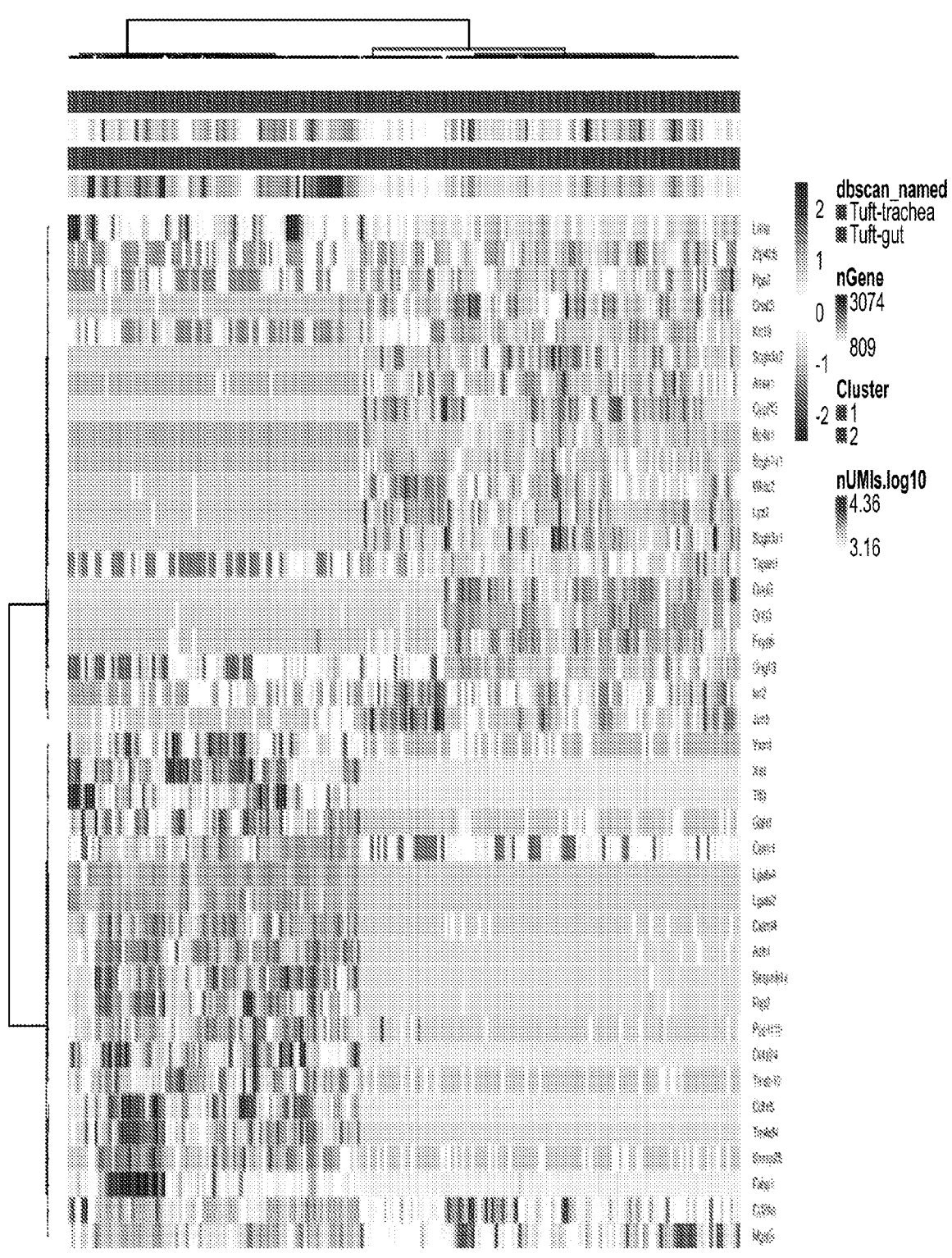
FIG. 36—shows tuft cell markers in gut and trachea—sets forth a heat map showing differential expression in the gut and trachea.

The Tuft-1 and Tuft-2 signatures were also examined in cells obtained from the trachea. Applicants found that the respiratory Tuft cells included both subtypes of Tuft cells as in the gut, suggesting that they perform similar roles in the trachea (e.g., T helper 2 (Th2) response, ILC2 response). Applicants identified transcription factors that were exclusively expressed in trachea Tuft cells. The transcription factors expressed exclusively in Tuft cells included Etv1, Hmx2, Spib, Foxe1, Sox9, Pou2f3, Ascl2, Ehf and Tcf4 (FIG. 30). Applicants further analyzed genes specific to tuft cells in both the trachea and gut and found that tuft cells secreted IL-25 (FIG. 34, 35). Applicants also analyzed genes specific to the gut and trachea (FIG. 36).

Example 7—Identification and Characterization of Microfold (M) Cells In Vivo

Surprisingly, the Tuft-2 subset expressed several of the genes previously reported to be specific to microfold (M) cells[17,58], including Rac2, Siglecf, and Gfi1b (Growth Factor Independent 1B Transcription Repressor), at a significantly higher mean level than Tuft-1 cells (p<1×10⁻⁵, Mann-Whitney U-test, FIG. 5a, FIG. 14a). M cells are derived from the common Lgr5+ stem cells of the intestinal epithelium[17], but reside exclusively above Peyer's patches (PP) within a distinct flat epithelial tissue known as the follicle associated epithelia (FAE). The FAE comprises a small fraction of the total intestinal epithelium (<1%)[18], and since M cells represent only a subset of the FAE, they were not detected in the initial atlas, as noted above (FIG. 1b). There are two alternative explanations for the observed overlap between Tuft-2 and M cell marker genes: (1) Tuft-2 cells are in fact rare M cells with an atypical location, that is, the previously proposed villous M cells[59], or (2) Tuft-2 cells are indeed a subset of tuft cells, which nevertheless express some M cell-related genes.

Figure 14E:
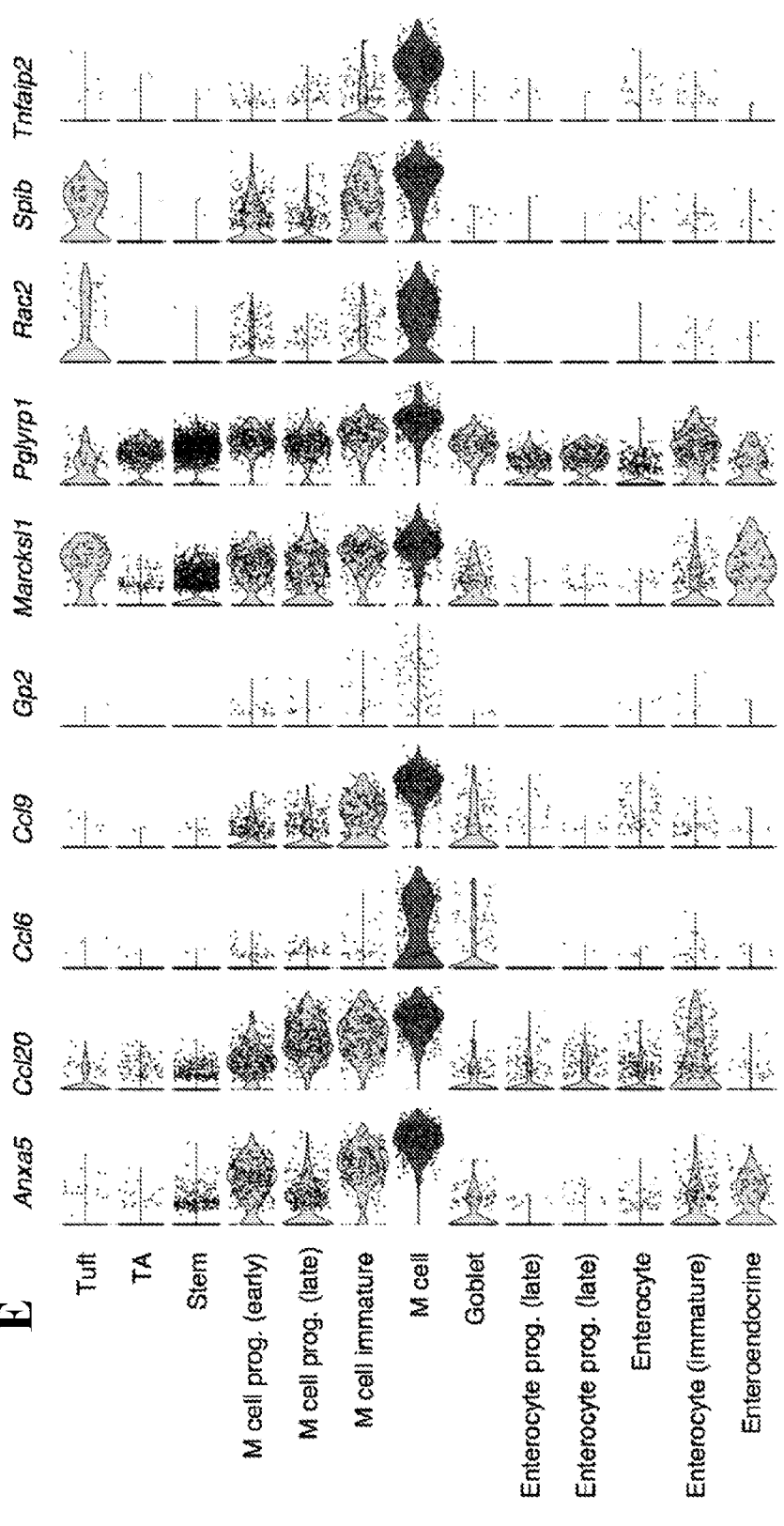
Figure 14F:
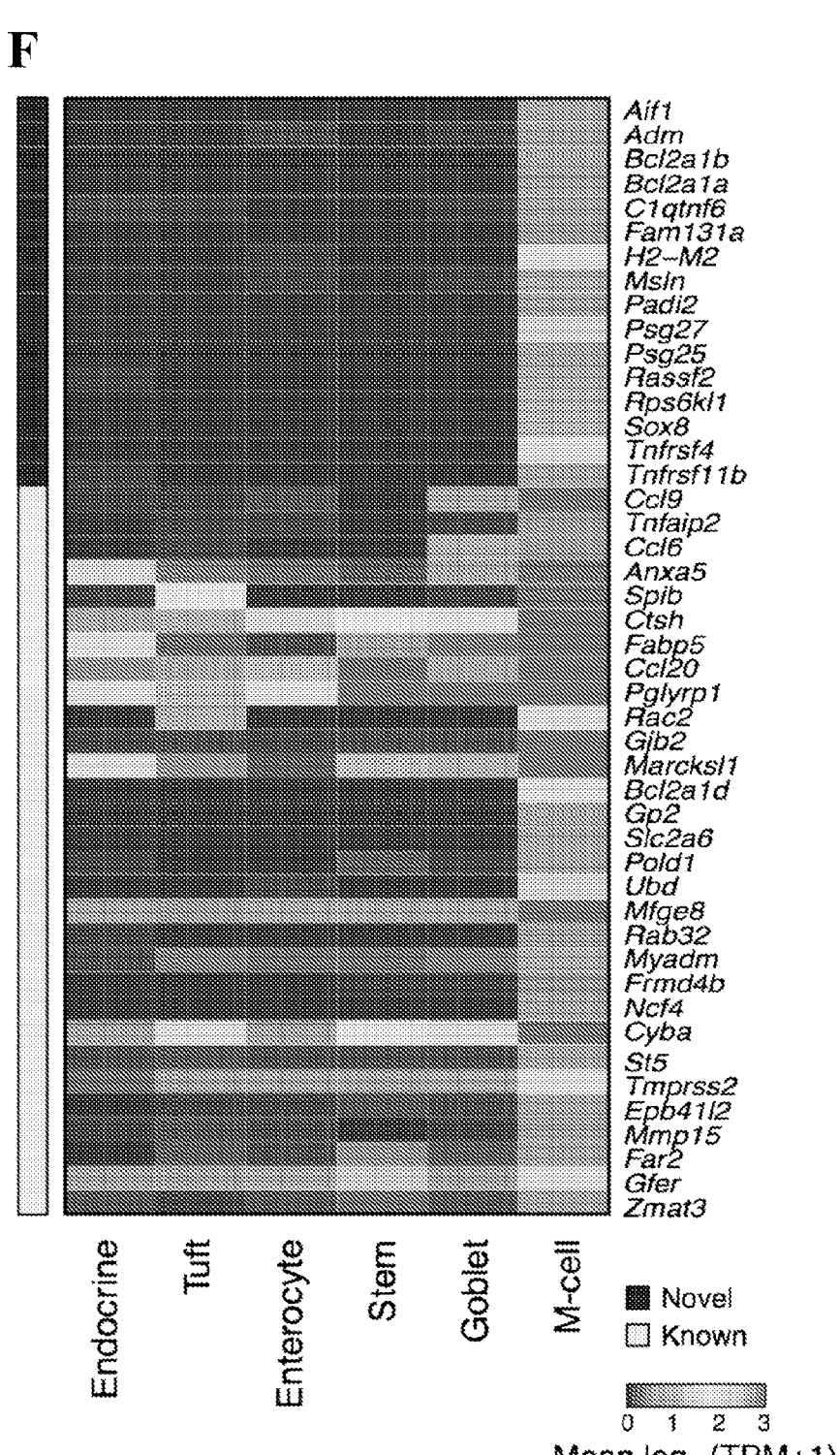
Figure 14I:
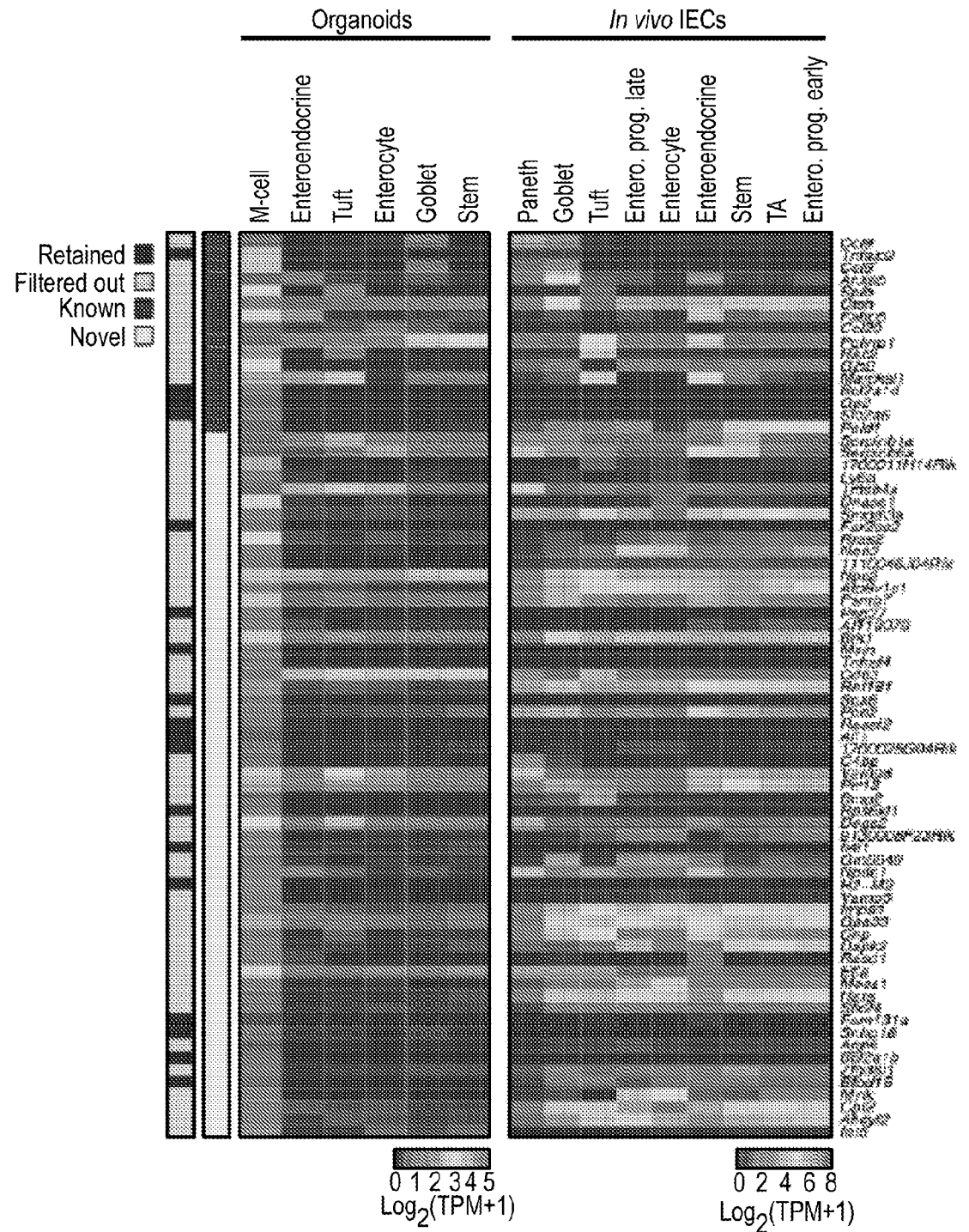

To distinguish between these possibilities, Applicants used both ex vivo and in vivo strategies, to determine an M cell signature at the single-cell level. First, Applicants used an ex vivo model of M cell differentiation, analyzing 5,434 cells from small intestinal organoids treated with RANKL[17] for 0, 3, and 6 days (FIG. 5b-c, FIG. 14b). One cluster of 378 cells (FIG. 5b) recovered by unsupervised clustering (Methods), was labeled as differentiated M cells by the expression of known M cell marker genes[58], not expressed by Tuft-2 cells, including Gp2 and Tnfaip2 (M-see) (FIG. 14c-e). Based on this cluster, Applicants constructed signatures (FIG. 14i, Methods) of M cell specific genes and TFs in vitro (FIG. 14f-g, Table 9, Methods), highlighting several immune factors (e.g., Spib, Irf2, and Irf6).

TABLE 9

| Summary of marker genes for Microfold (M) cells | |
|---|---|
| In vivo | In vitro |
| Ccl20 | Ccl9 |
| Clu | Serpinb1a |
| Mfge8 | Serpinb6a |
| Anxa5 | Tnfaip2 |
| Pglyrp1 | 1700011H14Rik |
| Ctsh | Ccl6 |
| Serpinb6a | Ly6a |
| H2-M2 | Anxa5 |
| Gp2 | Spib |
| Ubd | Ctsh |
| Lamp1 | Fabp5 |
| Cxcl16 | Ccl20 |
| Cyba | Pglyrp1 |
| Scd1 | Tmsb4x |
| 1700011H14Rik | Rac2 |
| Aif1 | Dnase1 |
| Ctsd | Smpdl3a |
| Tnfaip2 | Far2os2 |
| Far2os2 | Rras2 |
| Slc2a6 | Nqo2 |
| Adgrd1 | Gjb2 |
| Ncf4 | 1110046J04Rik |
| Rnf128 | Npc2 |
| Il4i1 | Atp6v1c1 |
| Far2 | Marcksl1 |
| BC021614 | Psmb7 |
| D630011A20Rik | Psg27 |
| Vcam1 | AI118078 |
| Stx11 | Brk1 |
| Sdhaf1 | Msln |
| Ces1b | Tnfrsf4 |
| Itga3 | Cd63 |
| Msln | Rnf181 |
| Scarb2 | Sox8 |
| Tnfrsf4 | Pon2 |
| Fam98a | Bcl2a1d |
| Tmsb4x | Rassf2 |
| Nfkbia | Aif1 |
| Rnase1 | 1700025G04Rik |
| Vamp5 | C4bp |
| Gulo | Vamp8 |
| | Prr13 |
| | Bmp2 |
| | Rps6kl1 |
| | Degs2 |
| | 9130008F23Rik |
| | Il4i1 |
| | Gm5549 |
| | Npdc1 |
| | Gp2 |
| | H2-M2 |
| | Vamp5 |
| | Impa1 |
| | Gpa33 |
| | Cnp |
| | Dapk2 |
| | Rasd1 |
| | Etfa |
| | Mocs1 |
| | Slc2a6 |
| | Hars |
| | Stk24 |
| | Fam131a |
| | Snhg18 |
| | Pold1 |
| | Agps |
| | Bcl2a1b |
| | Zfp36l1 |
| | Btbd16 |
| | Mylk |

TABLE 9-continued

| Summary of marker genes for Microfold (M) cells | |
|---|---|
| In vivo | In vitro |
| | Cpt2 |
| | Ahcyl2 |
| | Ier5 |

Significance cut-offs:
in vivo: FDR (Fisher's combined): 0.001, Log2 fold-change: 0.5
in vivo: FDR (max): 0.05, Log2 fold-change: 0.5

Figure 5D:
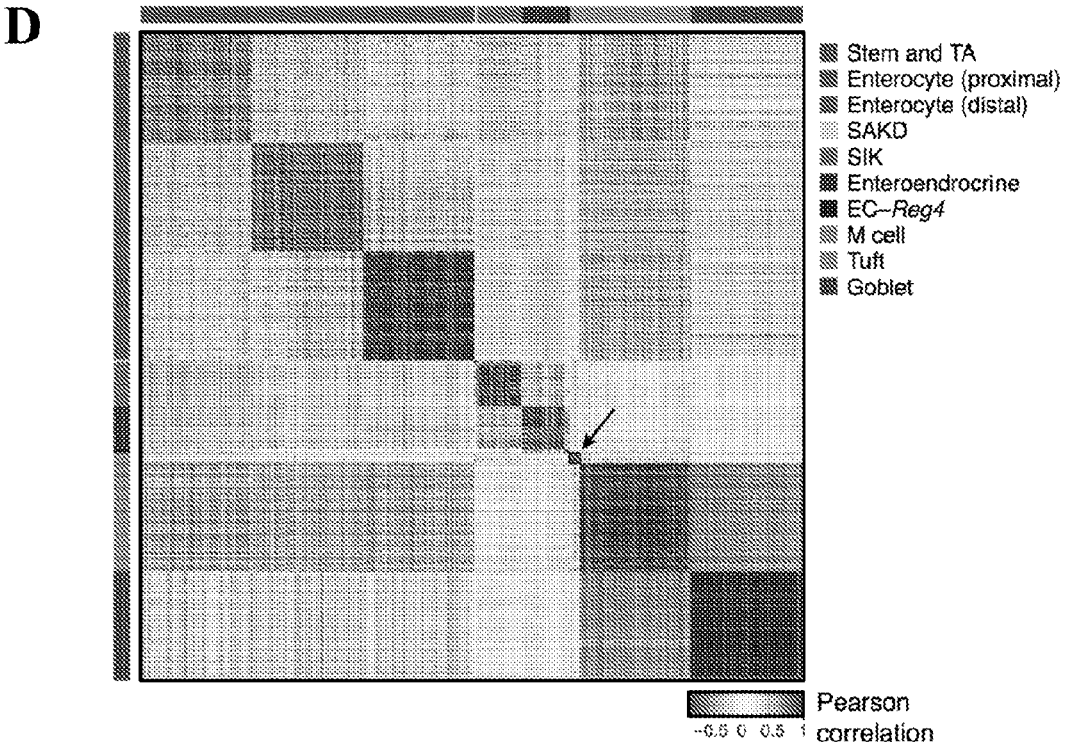

Next, to confirm the relevance of these signatures to M cells in vivo, Applicants profiled 4,700 EpCAM⁺ cells from FAE of WT and Gfi1b-GFP labeled knock-in mice, a known marker for both tuft and M cells[17,60] (n=5 mice). A cluster of 18 cells (FIG. 5d, arrow; Methods), was enriched for known M cell markers (FDR<0.05, Mann-Whitney U-test), including Gp2, Ccl20, Tnfaip2, and Anxa5 (FIG. 5e). These cells also expressed high levels of the M cell signature genes derived from the in vitro data ($p<10^{-4}$, Mann-Whitney U-test, FIG. 14h). Applicants then defined an in vivo signature of enriched markers and TFs (FIG. 5e-f, Methods). Notably, only one of the 7,216 cells in the sampling of the intestinal epithelium is positive for this M cell signature (data not shown), indicating that: (1) M cells are not readily obtained from scRNA-seq of epithelia without enrichment; (2) Peyer's patch M cells are extremely rare, and require specific FAE enrichment; the statistical model suggests that cells present at 0.07% or lower would be undetected with high (95%) probability (Methods); (3) Tuft-2 cells are not M cells, despite some genes expressed by both cell types; and (4) villous M cells are undetectable in the data. Applicants cannot rule out the possibility that Tuft-2 cells may have been previously erroneously termed "villous M cells", because of the partial similarity in some of their features.

Example 8—Pathogen-Specific Recalibration of
Cell Proportions and Cell States in Response to
Bacterial and Helminth Infections Immune and epithelial cell decisions to tolerate or elicit an immune response to specific gut pathogens play a key role in maintaining gut homeostasis[2]. Because the epithelial cells of the small intestine are generated in an ongoing, continuous and rapid process of differentiation from stem cells throughout life, it is likely that following infection with a pathogen, there are changes both in the relative composition of IEC sub-types and in the internal state of each type, as well as in global expression changes across multiple cell types. These three types of signals are challenging to distinguish in bulk analysis, whereas single-cell analysis can readily dissect each aspect.

Applicants therefore investigated the IEC responses to a common pathogenic bacterium, *Salmonella enterica*, which induces enteritis within hours[61,62], and to the helminth *Heligmosomoides polygyrus*, a parasitic worm that damages the integrity of the small intestine and elicits a strong Th2 response[63]. Applicants profiled individual IECs using droplet-based 3' scRNA-seq two days after *Salmonella* (n=2 mice, 1,770 cells) or 3 days (n=2 mice, 2,121 cells) and 10 days (n=2 mice, 2,711 cells) after *H. polygyrus* infections, as well as 3,240 cells from control mice (n=4 mice). Applicants profiled an additional 389 cells with the deeper, full-length scRNA-seq, which Applicants used to obtain high-confidence 'consensus' differentially expressed genes for all comparisons that are independent of cell-type.

Figure 6H:
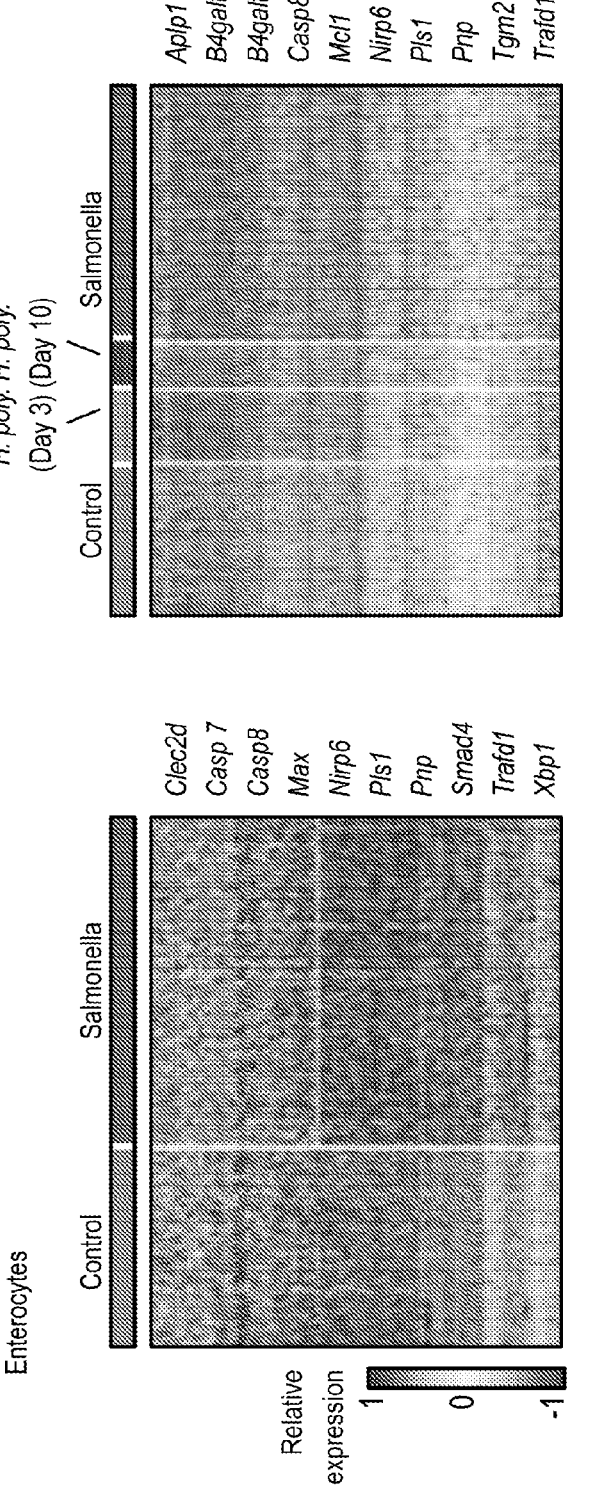
Figure 15A:
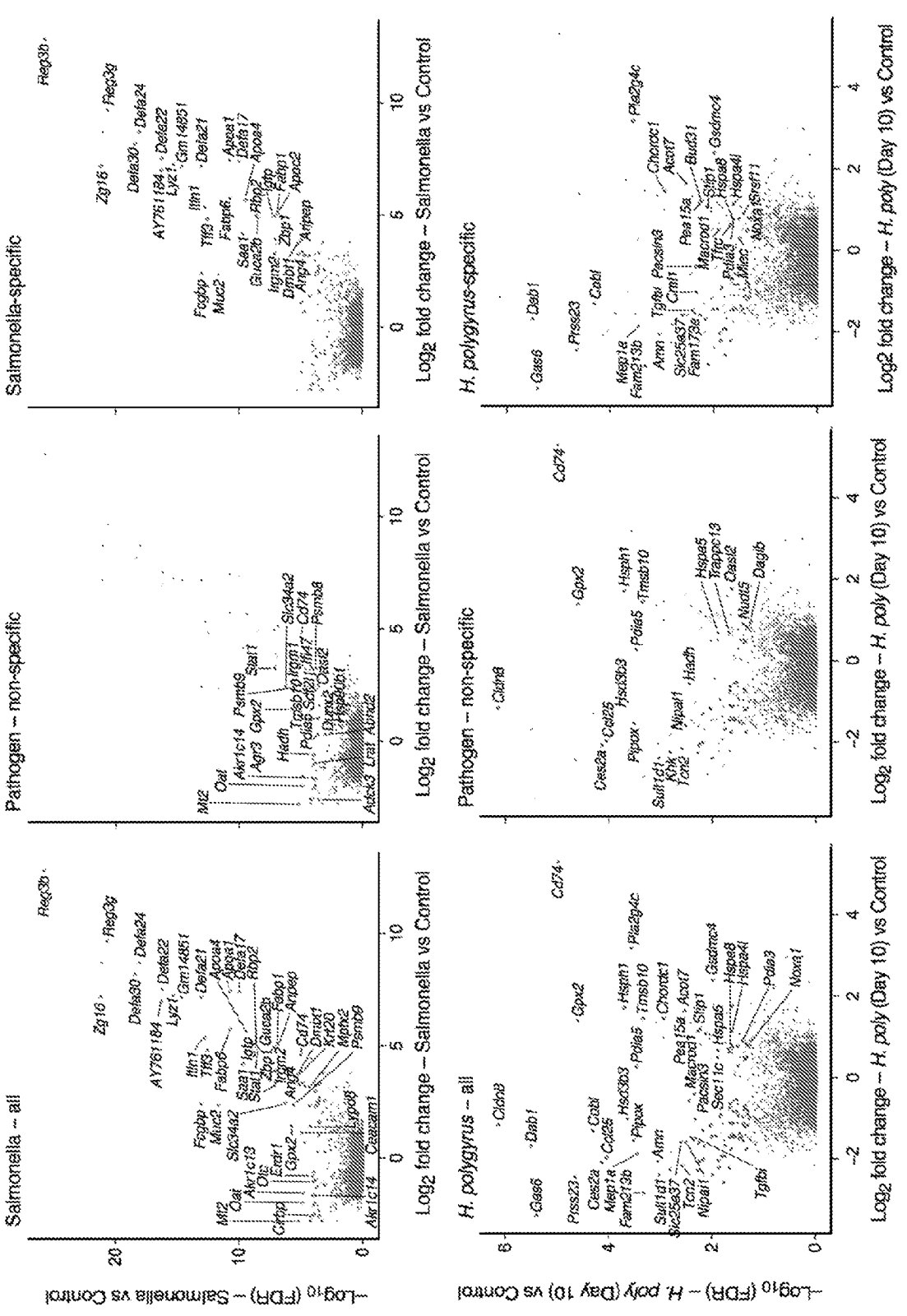

First, Applicants investigated the global effects of infection with *Salmonella*. In infected IECs, 571 genes were up-regulated vs. control cells (FDR<0.25, likelihood-ratio test, FIG. 15a, top left) and these genes were enriched (FDR<0.001, hypergeometric test) for pathways involved in defense response to bacterium (FIG. 6a). Also up-regulated were genes involved in acute inflammatory programs such as the interferon-inducible GTPase (Igtp) and DNA-dependent activator of IFN-regulatory factors (Zbp1), or with a protective role in *Salmonella* infection, such as the anti-microbial lectins Reg3b and Reg3 g[64,65] (FIG. 6b, top). In addition, Applicants identified a non-specific inflammatory response—a minority (112/571; 19%) of the genes up-regulated in response to *Salmonella* infection are also regulated in the same way in response to *H. polygyrus* (FDR<0.25, likelihood-ratio test), and are likely associated with a generalized acute stress response (FIG. 15a, middle panels). Indeed, genes known to be involved in stress responses such as Gpx2, Hspa1 and Hsph5 were among those up-regulated in response to both pathogens (FIGS. 15a and 10a). In particular, the invariant chain of MHC class II, Cd74, was also strongly induced (FDR<0.001, likelihood-ratio test) in both responses (FIG. 16a).

Second, Applicants identified cell-type-specific responses to *Salmonella* infection, most notably, an increase in the expression of both anti-microbial peptides and the mucosal pentraxin, Mptx2 (FIG. 1) in Paneth cells under infection (FIG. 15d). Comparing enterocytes in control and *Salmonella*-infected mice (424 vs. 705 cells) (FIG. 6e, top), Applicants found 40 enterocyte-specific genes significantly up-regulated (FDR<0.1, likelihood-ratio test), including the innate immune-related genes Tnfsf10 and Nlrp6. Among these cell-type-specific genes, 26 (65%) are induced in a *Salmonella*-specific manner (FIG. 6e, bottom, Methods), including several previously implicated in the response to *Salmonella* infection, such as Tgm2[66]. Comparing single enterocytes in control and *Salmonella*-infected mice (424 vs. 705 cells) (FIG. 6h), this study found significant up-regulation of innate immune-related molecules including Clec2d, Nlrp6 and Smad4 and (FIG. 6h, left). this study further refined the list to 52 *Salmonella*-specific genes (Methods) and found several genes previously implicated in the response to *Salmonella* infection such as Tgm2, Nlrp6 and Casp8 (FIG. 6h, right) (Man et al., 2013; Rodenburg et al., 2007; Wlodarska et al., 2014). Thus, the dramatic elevation in the number of enterocytes together with the retuning of their intrinsic cell states suggests an unappreciated crucial role of these absorptive cells in anti-microbial defense. In addition, the pro-inflammatory apolipoproteins[67] Serum Amyloid A1 and 2 (Saal and Saa2) were induced in the distal enterocytes, under *Salmonella* infection, with higher levels of Saa1 and Saa2 (FIG. 15a,c).

Notably, as a result of infection, some anti-microbial genes, that are enterocyte-specific in homeostatic conditions, are induced at two levels: (1) further induction in enterocytes; and (2) global induction in non-enterocyte cells, generating an overall elevated response of the tissue. Specifically, in control mice, expression of the Reg3 gene-family (Reg3a-g) was mainly restricted to absorptive enterocytes (Table 3-4). Upon *Salmonella* infection not only was their expression further elevated in absorptive enterocytes (FIG. 6b top, dots), but Reg3b and Reg3 g, largely undetectable in other cell types pre-infection, were up-regulated in all cell-types post-infection (FIG. 6b top, grey dots). Thus, the IEC response to *Salmonella* involves the induction in all cells of anti-microbial genes, including Clec2 h, Anpep, and Enpep, that are only expressed in enterocytes in homeostasis (FIG. 6b top, FIG. 15b).

Third, Applicants systematically distinguished the contribution of changes in cell intrinsic expression programs vs. shifts in cell composition. Applicants used unsupervised clustering to determine the proportion of each of the different IEC populations (FIG. 6d), visualized by tSNE embeddings (FIG. 6c). Applicants observed a dramatic shift in cell proportions following *Salmonella* infection (FIG. 6d; Methods), with a substantial increase in the frequency of mature absorptive enterocytes (from 13.1% on average in control to 21.7% in infection; FIG. 6d) and a significant reduction in the proportion of TA (52.9% to 18.3%) and stem (20.7% to 6.4%) cells. Applicants initially recovered a low number of Paneth cells (Methods), and thus analyzed an additional 2,029 cells from an additional experiment (droplet-based scRNA-seq; n=4, *Salmonella*-treated mice), and found a substantial increase in mature Paneth cell proportions (from 1.1% to 2.3%, FDR<0.01), in agreement with a previous study that showed more positive staining of Paneth cells in *Salmonella* infection[68] (FIG. 15d-e). These results suggest that the IEC response to *Salmonella* infection includes the induction of specific differentiation towards absorptive enterocytes and Paneth cells, most likely to increase production of anti-microbial peptides.

Next, analyzing IECs during infection with *H. polygyrus*, Applicants found a distinct recalibration of cell composition and cell states than in *Salmonella*. There are 299 genes up-regulated in *H. polygyrus* infected vs. control mice, 187 of which (62%) were specific to the *H. polygyrus* response (FDR<0.25, likelihood-ratio test, FIG. 15a, bottom panels). These *H. polygyrus*-specific genes were enriched with inflammatory response molecules, including Dnaja1, Vcp, Noxa1 andPsmd6, the phospholipase Pla2 g4c (FIG. 15a, bottom right), and the tuft cell markers Acot7, Peal5a and Avil (FIG. 15a bottom panels). This again suggested a change in cell composition, which Applicants then tested by unsupervised clustering. Indeed, at ten days post infection, there is a striking increase in goblet cells—known to be important for the epithelial response to the parasite[69] (on average, from 7.0% to 11.8%, FDR<1×10⁻⁵, Wald test, Methods), and a reduction in enterocyte proportions (15.3% to 4.9%, FDR<1×10⁻¹⁰, Wald test) (FIG. 6d). Tuft cell proportions were increased substantially at day three (1.9% to 6.3%, FDR<1×10⁻⁵, Wald test), with a further increase by day ten (to 8.5%, FDR<1×10⁻¹⁰, Wald test) (FIG. 6d). Within the tuft cell subset (409 cells overall, FIG. 16b-c) there was a significant elevation (17.2% to 43.0%, FDR<0.05, Wald test) in the proportion of immune-like Tuft-2 cells by day 10 (FIG. 6f), reflecting changes in tuft cell states along with the dynamic expansion in the overall tuft cell population in response to the parasite.

Figure 6I:
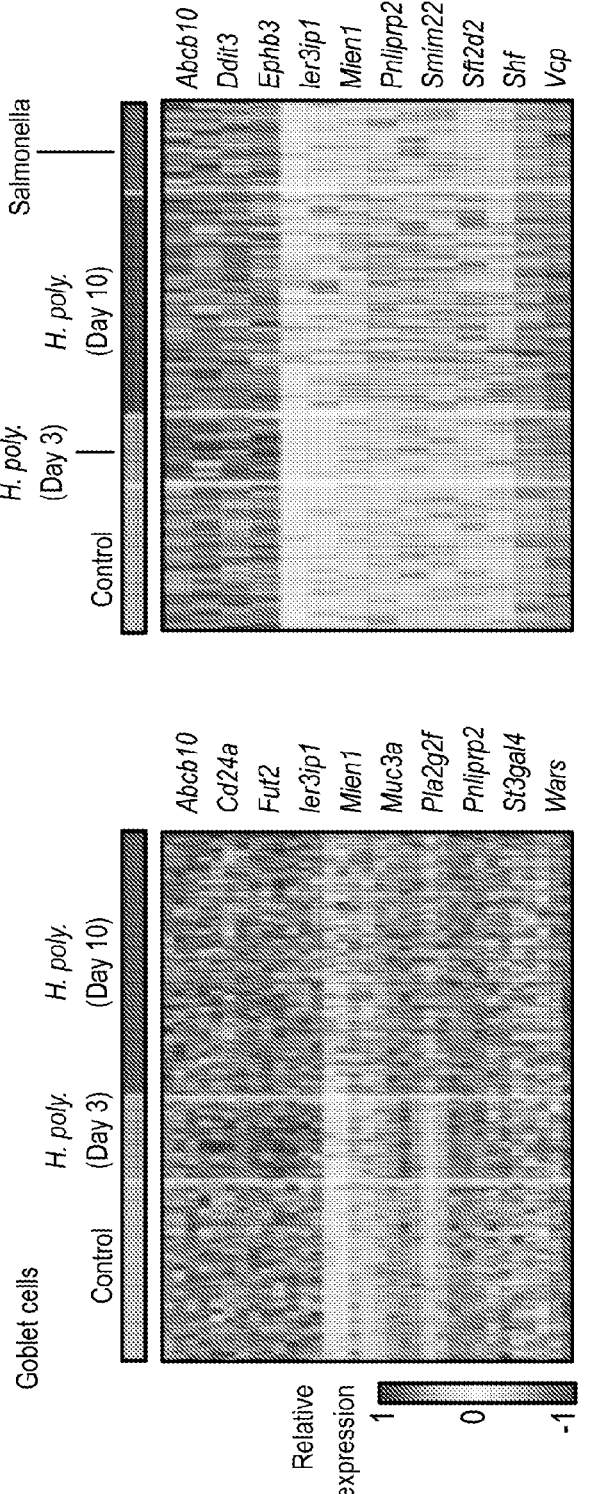

In addition to changes in cell proportions, within goblet cells there was a strong induction (FDR<1×10⁻⁵, likelihood-ratio test; FIG. 6g) of several genes previously implicated in anti-parasitic immunity, including RELMβ[69] (Retnlb, FIG. 16d), but also in genes (e.g., Wars and Pnlipr2; FIG. 6g), previously reported to be expressed in response to parasitic infection[70], but not known to be expressed by goblet cells. Further refining this gene set to those specific to the *H. polygyrus* pathogen revealed an up-regulation of genes related endoplasmic reticulum stress, specifically Ddit3, Ier3ip1 and Sft2d2, possibly involved in processing of secreted mucins to respond to the worm (FIG. 6i, right). Thus, *H. polygyrus* infection elicits shifts in both cell composition and cell state, with early expansion of tuft cells to initiate the Th2 response[14], and later expansion of goblet cell numbers to help prevent attachment of the helminth to the epithelial barrier via secreted mucins[71], along with an increase in the expression of key genes in the expanded goblet cells.

Table Legends

Table 2| Summary of single-cell RNAseq experiments. This table provides the number (after quality filtering, see Methods) of individual intestinal epithelial cells profiled in each of the in this study.

Table 3| Cell-type specific signature genes—droplet-based dataset. This table provides the lists of genes specific to each of the identified clusters of intestinal epithelial cells, identified using 3' droplet-based scRNA-seq data (FIG. 1B).

Table 4|Cell-type specific signature genes—plate-based dataset. This table provides the lists of genes specific to each of the identified clusters of intestinal epithelial cells, identified using full-length plate-based scRNA-seq data (Extended Data FIG. 2A).

Table 5|Consensus cell-type specific signature genes—both datasets. This table provides high-confidence lists of genes specific to each subtype of intestinal epithelial cells in both 3' droplet-based and full-length plate-based scRNA-seq datasets.

Table 6| Cell-type specific TFs and receptors. This table provides lists of genes annotated as either transcription factors (TFs), G protein-coupled receptors (GPCRs), or leucine-rich repeat (LRR) proteins, enriched in each subtype of intestinal epithelial cells in full-length plate-based scRNA-seq data.

Table 7| Enteroendocrine cell subset signature genes. This table provides the lists of genes specific to each of the identified clusters of enteroendocrine cells, identified using 3' droplet-based scRNA-seq data.

Table 8|Consensus tuft cell subset signature genes. This table provides the lists of genes specific to each of the identified subsets of tuft cells, identified using both 3' droplet-based and full-length plate-based scRNA-seq data.

Table 9| In vitro and in vivo M cell signature genes. This table provides the lists of genes specific to intestinal microfold (M) cells, using 3' droplet-based scRNA-seq data from in vitro cells derived from RANKL-treated organoids, and in vivo cells derived from the follicle associated epithelia (FAE) of wild-type mice.

Table 10| Markers of proximal and distal Paneth cells. This table provides estimates of differential gene expression between two subsets of Paneth cells identified by clustering and interpreted (post-hoc) as derived from proximal and distal small intestine (FIG. 10).

Example 9—Discussion

The intestinal epithelium is the most diverse epithelial tissue in the body, composed of functionally and molecularly specialized subtypes. Here, Applicants dissected it into its different components using massively parallel scRNA-seq, analyzing a total of 53,193 IECs, to create a high-resolution single-cell atlas of the mouse intestinal epithelium, and reveal even further diversity than was previously appreciated. Using unsupervised analyses, Applicants identified and characterized the transcriptomes of the major differentiated epithelial cell-types: enterocyte, goblet, Paneth, enteroendocrine, tuft and microfold. Applicants also derived specific gene signatures for intestinal stem, transit-amplifying and various enterocyte precursor cells. For each major cell-type Applicants obtained specific markers, TFs and GPCRs and high-confidence consensus signatures from two complementary scRNA-seq methods (3' and full-length).

The single-cell profiling of tens of thousands of intestinal epithelial cells revealed coherent cell-specific transcriptional programs, some revising predicted marker expression, which Applicants validated in situ and in prospectively isolated cells. This emphasized the utility of unsupervised profiling of tissues to define new cell-type gene signatures, rather than solely relying on previously annotated individual marker genes, which may lead to biased isolation of subtypes. For example, Applicants discovered and validated that tuft cells are composed of two subsets, one of which expresses neuron-related genes which might mediate interaction with the enteric nervous system, while the other expresses genes related to inflammation and immunity, including the immune-cell marker gene Ptprc (CD45). This CD45+ tuft population expresses the epithelial cytokine TSLP, which may represent an additional mechanism by which epithelial cells communicate with gut-resident immune cells. Further studies would be required to determine whether the Tuft-1 and Tuft-2 cells represent two different developmental fates, or alternative cell states. In another example, Applicants found that several known tuft cell markers are also expressed by M cells, which may have confounded studies based on those markers. Using single-cell profiling Applicants resolve this ambiguity, providing novel specific markers and TFs to distinguish these rare cells, which may enable further insights into M cell biology.

The large number of cells profiled allowed Applicants to assess heterogeneity even within rare subpopulations such as enteroendocrine cells (EECs). From 533 EECs extracted from 18,881 epithelial cells (Table 2), Applicants identified and characterized the transcriptomes of 12 subsets, 8 of which are mature. Interestingly, EECs were more abundant than expected and partitioned into two main groups, enterochromaffin (2 subsets) and Secretin[high] (6 subsets) cells (FIG. 3). The Reg4 gene, a previously proposed marker for all EECs[23], was in fact expressed only in one of the groups of enterochromaffin cells. The in vivo sampling of EECs encompasses the subsets found in an organoid-derived EECs single-cell study[53], and highlights three additional mature EEC subsets (FIG. 12E). Two of these subsets (SIL-P and SIK-P) are enriched in the ileum, while SILA were found mainly in the duodenum, consistent with the regulatory roles of the hormones Ghrelin—an appetite stimulant—and GLP-1 and PYY, which together act as an 'ileal brake', a feedback loop which limits gastric emptying as nutrients arrive in the distal gut[11]. Further, Applicants found that most EEC subsets express more than one GI hormone and defined a novel taxonomy reflecting each subset's unique hormonal expression profile. An open challenge is to understand the specific role of each of these novels subsets in the orchestration of appetite, gut motility, nutrient absorption, or in the onset and treatment of diseases, such as Type 2 diabetes and obesity.

Molecular Underpinning for the Integration of Lumen Signals by the Gut Epithelium IECs play barrier roles, absorb nutrients, integrate and relay signals from the environment to the immune and enteric nervous systems[12]. The atlas resolves the cellular populations that are implicated in sensory pathways at unprecedented resolution. For example, Applicants found that two of the 10 most enterocyte-specific TFs were from the nuclear receptor (NR) family of proteins. These genes are crucial for sensing and metabolism of various substances. In particular, lipid homeostasis (Nrlh3), and sensing of endobiotic and xenobiotic substances, Nrli3.

Similarly, Applicants provide an enhanced map of the GPCRs expressed by all cells, and particularly by EEC subsets. Most notably, the important cannabinoid receptor Gpr119[37] was enriched in the novel SILA subset (FDR<0.05, FIG. 12F), which co-expresses Ghrl and Gcg, genes encoding gut hormones that regulate appetite and satiety. Furthermore, several GPCRs enriched in EECs (FDR<0.05, FIG. 8d) may mediate communication with enteric neurons, including the metabotropic glutamate (Grm4) and acetylcholine (Chrm4) receptors. Additionally, the important neurotrophic cytokine brain-derived neurotrophic factor (Bdnf) was enriched in SIK-P cells (FDR<0.01, FIG. 3B), a possible additional EEC-neuron channel of communication. Tuft cells were also enriched for GPCR expression, supporting recent studies that they are specialized for chemosensory properties, especially taste sensing[72]. Indeed, the gene encoding taste receptor type 1 member 3 (Tas1r3) was expressed exclusively by tuft cells. Like EECs, tuft cells were enriched (FDR<0.05) for genes encoding GPCRs that sense nutrients, such as Ffar3 and Sucnr1 and for gamma-aminobutyric acid B (GABAB, Gabbr1) and dopamine (Drd3) receptors that may be involved in further crosstalk with enteric neurons.

The Adaptive Response of the Intestinal Epithelium to Pathogens Combines Cell Intrinsic and Cell Composition Changes Although many studies have shown an expansion of goblet cells and recently tuft cells in response to parasites[13-15], this analysis revealed that this dynamic restructuring of the epithelial barrier is specific to the identity of the individual pathogen and distinguished cell composition changes from changes in cell intrinsic programs. After infection with the parasitic worm H. polygyrus, there is, as reported, dramatic expansion of secretory cell types, initially an expansion of tuft cells, followed several days later by goblet cell metaplasia. While the overall Tuft cell population increased, the relative proportion of immune-like Tuft-2 subset was particularly expanded. In contrast, the pathogenic bacterium Salmonella enterica induced a strong expansion of absorptive enterocytes and Paneth cells. These dynamic shifts in epithelial composition constitute a generic response mechanism in which differentiation pathways are redirected to enhance the epithelial barrier under pathogenic insult.

These compositional changes are accompanied and enhanced by cell intrinsic changes to regulatory programs, both within specific cell types and across multiple cell types. During helminth infection, goblet cells induce the antiparasitic molecules Retnlb, Wars and Pnliprp2. Upon Salmonella infection, Paneth cells not only increase in number, but also upregulate various genes encoding anti-microbial peptides (e.g., Lyz1, Defa5), and the mucosal pentraxin, Mptx2. Moreover, Applicants uncovered a novel epithelial cell response to Salmonella, where the expression of genes that are cell-type-specific in homeostatic conditions is broadened across multiple cell types during infection: the antimicrobial C-type lectins Reg3b and Reg3 g, known to be crucial for preventing attachment of bacteria to the epithelium[73], are expressed only by enterocytes in normal conditions, but were globally up-regulated by all cells following Salmonella infection. This could only be distinguished by single-cell analysis.

In single-cell RNA sequencing there is a trade-off between sequencing fewer cells deeply and sequencing many cells at a lower coverage. This study pursued both directions simultaneously for maximal information capture, and showed that the very large cell numbers achievable with droplet-based methods enabled the discovery of extremely rare subtypes (Shekhar et al., 2016), while the high coverage (an average of more than 6,000 genes detected per cell) obtained by the plate-based data enabled the detection of less abundant mRNA molecules such as transcription factors, which frequently play important regulatory roles in gut function. Further, the high number of cells this study obtained from the rapidly differentiating intestinal epithelium constitutes a dense sampling of a dynamic process, and therefore provided a high level of 'pseudo-temporal' resolution. This enabled Applicants to profile gradual shifts in differentiation of the absorptive enterocytes, subsequently identifying both known and novel TFs such as Gata4 (Bosse et al., 2006) and Gata5 which are expressed coherently during differentiation toward proximal or distal mature enterocyte, respectively.

This study provides a detailed reference dataset and specific hypotheses for follow-up studies, including cell-type specific gene markers, TFs and GPCRs that may open the possibilities for novel clinical interventions in pathologies such as obesity, type-2 diabetes, and allergies. For example, the Tuft-2 cells, which secrete Th2-recruiting epithelial cytokines, may provide insight into mechanisms underlying food allergies. Furthermore, the characterization of epithelial differentiation dynamics in response to two enteric pathogens, may help find ways to manipulate epithelial cell differentiation to minimize gut pathologies, such as acute or chronic gut inflammation, identify cell-specific epithelial cell markers for restitution and inflammation resolution.

Understanding the development, differentiation and function of an organ, such as the intestine, requires the identification and characterization of all of its component cell types. In the small bowel, intestinal epithelial cells (IECs) sense and respond to microbial stimuli and noxious substances, provide crucial barrier function and participate in the coordination of immune responses. Here, this study profiled 24,423 individual IECs from mouse small intestine and intestinal organoid cultures. Taken together, the examples above demonstrate that using unsupervised clustering, Applicants defined specific gene signatures for major IEC lineages, including the identification of Mptx2, a mucosal pentraxin, as a novel Paneth cell marker responsive to Salmonella infection. In addition, this study identified unexpected diversity of rare hormone-secreting enteroendocrine populations, revealing co-expression programs of gut hormone genes, previously thought to represent different enteroendocrine subtypes, and constructed a novel hierarchical classification of these cells. this study also distinguished two subtypes of Dclk1-positive tuft cells, one of which (Tuft-2) expresses both the epithelial cytokine Tslp and the pan-immune cell marker Ptprc (CD45), which has not been previously associated with any non-hematopoietic cell type.

Finally, this study characterized how the intrinsic state and proportion of these cell types are reshaped in response to Salmonella enterica and Heligmosomoides polygyrus infections. Salmonella infection led to an increased number of Paneth cells and enterocytes, and a Paneth cell-specific up-regulation of both defensins and pentraxins, including Mptx1 and Mptx2. An absorptive enterocyte-specific anti-microbial program was broadly activated across all IEC types, demonstrating a previously uncharacterized cellular plasticity in response to pathogens. In contrast, H. polygyrus led to expansion of goblet and tuft cell populations. This increase in tuft cells was driven by an expansion of the Cd45+ Tuft-2 group. The comprehensive atlas highlights new markers and transcriptional programs, novel allocation of sensory molecules to cell types and organizational principles of gut homeostasis and physiology.

Example 10—Gut Atlas Analysis in Human Colon from Healthy Subjects

Applicants have generated a foundational resource in the healthy gut for: (1) Cell composition (i.e., changes in proportions of different cell types/states), (2) Cell intrinsic states (i.e., changes in gene expression within a cell type), (3) Cell-cell interactions (i.e., changes in cell-cell interaction mechanisms), and (4) the relevant cell types for each gene (e.g., GWAS genes).

Applicants used droplet-based scRNA-seq of colonoscopy samples from healthy individuals to generate the cell atlas. The samples were obtained from 10 healthy individuals (37,435 non-inflamed cells). The samples were small biopsies containing about <80,000 cells. The biopsies were fresh and dislocation and processing were performed by applicants.

Figure 17:
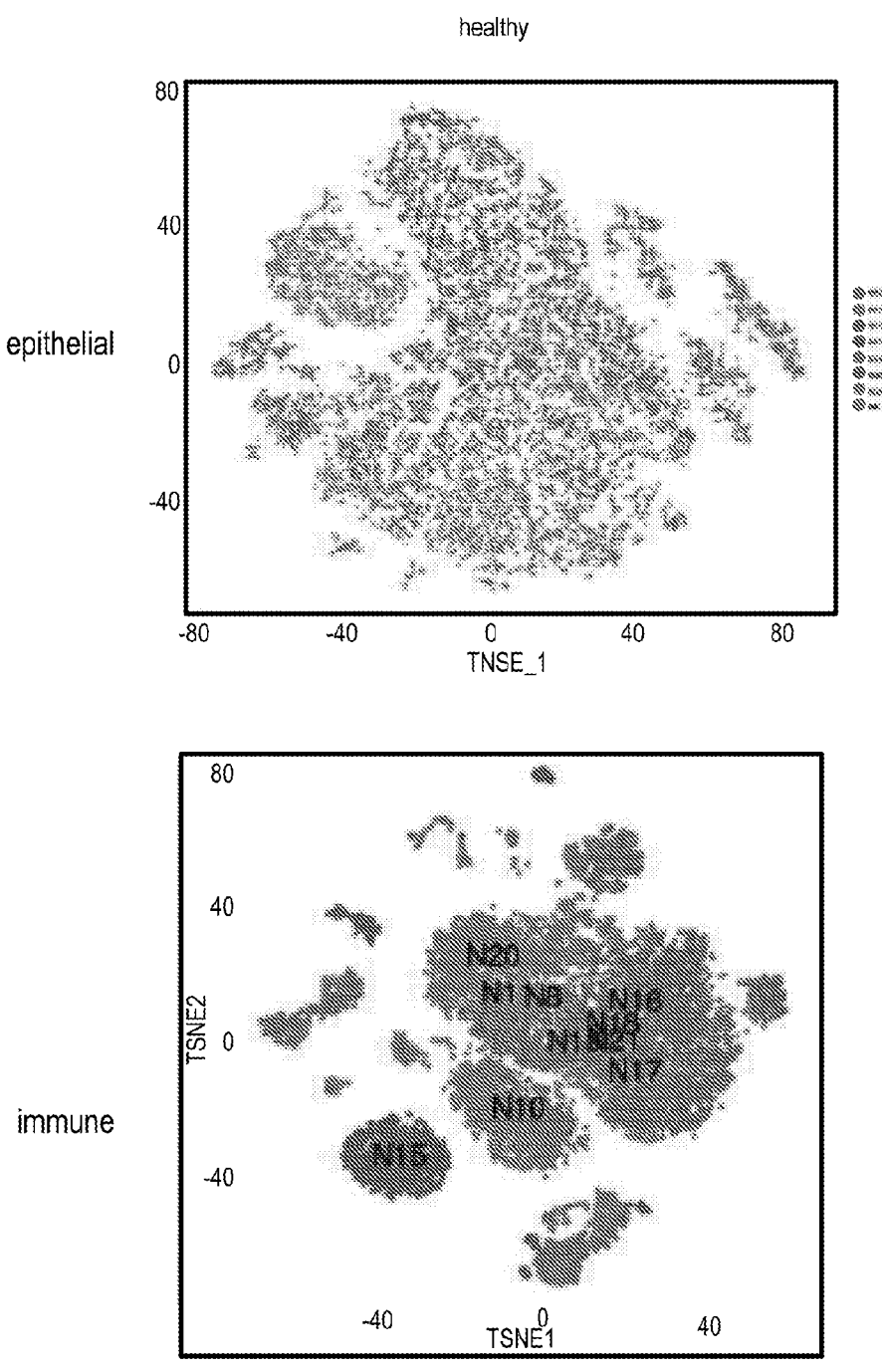
FIG. 17—illustrates that epithelial cells in healthy cells partition by cell type in tSNE plots.
Figure 18:
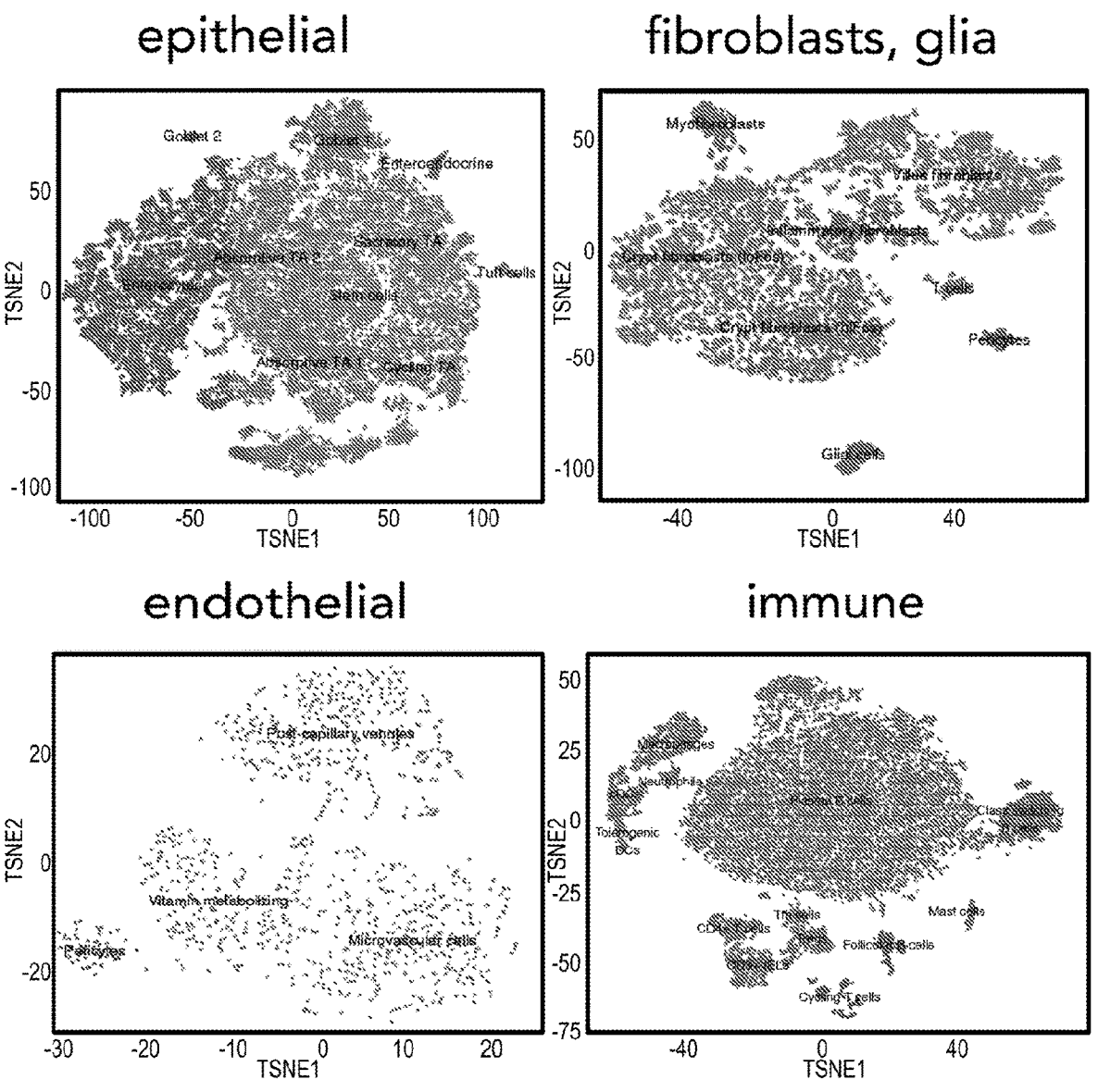
FIG. 18—illustrates that the atlas uncovers almost all cell types and subtypes in the colon.
Figure 19:
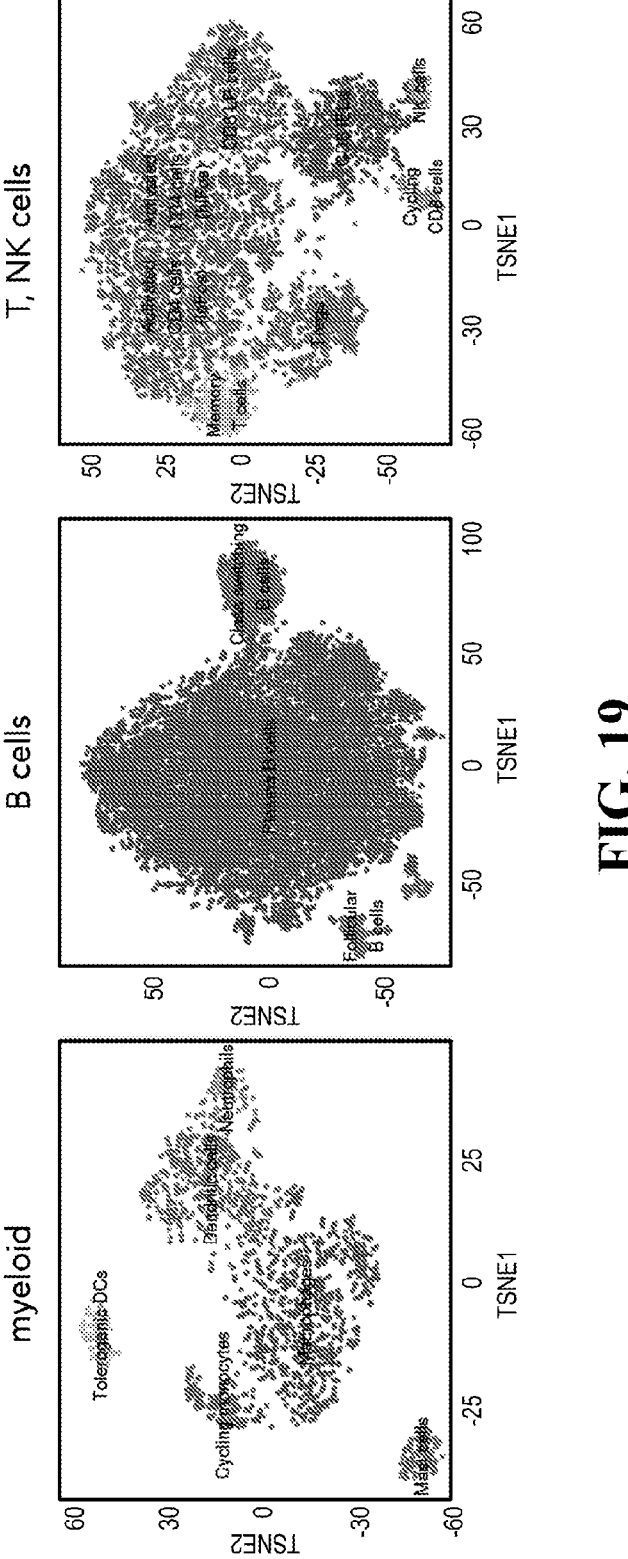
FIG. 19—illustrates that the atlas uncovers almost all cell types and subtypes in the colon.

FIG. 17 shows that clustering analysis partitioned cells by cell type in the healthy samples. FIGS. 18 and 19 show that the atlas uncovers almost all cell types and subtypes in the colon. Applicants identified the following cell types and subtypes in the colon: Plasma B cells, Class switching B cells, Follicular B cells, T cells, Macrophages, Dendritic cells, Mast cells, Cycling monocytes, Tolerogenic DCs, Neutrophils, Activated CD4 cells loFos, Activated CD4 cells hiFos, CD8 IELs, CD8 LP cells, Tregs, Memory T cells, NK cells, Cycling CD8 cells, Microvascular cells, Post-capillary venules, Vitamin metabolizing, Endothelial pericytes, Enterocytes, Tuft cells, Goblet 2, Absorptive TA 1, Secretory TA, Absorptive TA 2, Cycling TA, Goblet 1, Stem cells, Enteroendocrine, Glial cells, Inflammatory fibroblasts, Fibroblast pericytes, Myofibroblasts, Villus fibroblasts, Crypt fibroblasts (hiFos) and Crypt fibroblasts (loFos). Applicants identified markers specific for each cell type. Table 15 A-D shows the top 250 genes expressed in each cell type.

TABLE 15A

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| HERPUD1 | IGLL5 | CD79A | PRSS23 | DARC | CD320 | RGS5 | RPL15 | AZGP1 | MUC2 |
| IGJ | IGJ | MS4A1 | RGCC | NPC2 | RAMP2 | HIGD1B | RPS2 | LRMP | TFF1 |
| SSR4 | TMSB10 | CD79B | PLVAP | CLDN5 | CLDN5 | CD320 | RPL13 | SH2D6 | RPL13 |
| SEC11C | CFL1 | VPREB3 | VWA1 | CPE | PLVAP | PLVAP | RPS6 | MARCKSL1 | ZG16 |
| XBP1 | TMSB4X | TCL1A | PASK | MADCAM1 | SLC9A3R2 | CLDN5 | GUCA2A | AVIL | RPL10 |
| MZB1 | PFN1 | FCRLA | GNG11 | CLU | GNG11 | CRIP2 | RPL10 | BIK | RPL15 |
| FKBP11 | MYL6 | CD37 | CA4 | DUSP23 | IGFBP4 | RAMP2 | CRIP2 | SH2D7 | RPS4X |
| DERL3 | FTH1 | CD19 | CD36 | JAM2 | TXNIP | CAV1 | RPL32 | HCK | RPS2 |
| SPCS2 | GAPDH | SMIM14 | CD320 | PLVAP | ENPP2 | ESAM | RPS4X | ANXA4 | RPS18 |
| TNFRSF17 | ACTB | CST3 | VWF | LY6E | CLEC14A | GNG11 | RPS19 | PTGS1 | RPS19 |
| CD79A | IGLL1 | CD63 | ENG | ECSCR | TMEM88 | CD36 | SLC26A3 | ALOX5 | RPL32 |
| SSR3 | TNFRSF17 | LTB | RAMP2 | SDCBP | ESAM | COX4I2 | RPLP1 | ANXA13 | FCGBP |
| UBE2J1 | CD79A | LIMD2 | SLC9A3R2 | TSPAN7 | CRIP2 | NDUFA4L2 | RPS18 | KRT18 | RPL19 |
| SPCS1 | DERL3 | CD22 | ESAM | EGFL7 | SPARCL1 | IGFBP4 | PLAC8 | IL17RB | S100P |
| DNAJB9 | MT-CO1 | BLK | CRIP2 | VWF | HLA-E | MGP | CEACAM7 | TPM1 | CEACAM5 |
| EAF2 | MZB1 | LGALS3 | GSN | GNG11 | RAMP3 | EGFL7 | FXYD3 | TRPM5 | TSPAN1 |
| FKBP2 | SERF2 | PTPRCAP | SPARCL1 | RAMP2 | CD59 | TMEM88 | KRT20 | EIF1B | RPL11 |
| MANF | AL928768.3 | AL928768.3 | FKBP1A | APLNR | CAV1 | SPARCL1 | FABP1 | BMX | RPS9 |
| PRDX4 | ACTG1 | HLA-DQA1 | TMEM204 | RAMP3 | VAMP5 | RBP7 | PRAP1 | HPGDS | RPS14 |
| SDF2L1 | RPL28 | CD53 | ITM2B | ITM2B | IFI27 | IGFBP7 | TSPAN1 | POU2F3 | FXYD3 |
| SERP1 | RPS24 | BANK1 | RBP5 | CTNNAL1 | JAM2 | MYL9 | CEACAM5 | GNG13 | RPL10A |
| AL928768.3 | MT-CO3 | RHOH | TM4SF18 | IGFBP4 | ECSCR | SLC9A3R2 | SDCBP2 | HTR3E | RPL35 |
| SPCS3 | ATP5E | S100A6 | RAMP3 | NNMT | SEPW1 | TINAGL1 | SRI | PSTPIP2 | LYPD8 |
| CYBA | COX4I1 | GPR18 | EGFL7 | HLA-E | EGFL7 | NOTCH3 | MS4A12 | SPIB | RPL12 |
| WT1-AS | HLA-A | CORO1A | HSPG2 | GIMAP7 | BCAM | CLEC14A | PHGR1 | PLCG2 | RPS5 |
| CRELD2 | PPAPDC1B | BCAS4 | CCDC85B | GPR126 | GIMAP7 | TXNIP | C19orf33 | ELF3 | MUC1 |
| VIMP | GNG7 | CXCR5 | ECSCR | ICAM1 | CD36 | ENPP2 | RPS8 | MATK | ENTPD8 |
| SEC61B | UBA52 | CD74 | TMEM88 | HHEX | NPDC1 | JAM2 | RPS9 | KRT8 | RPLP1 |
| PDIA6 | ICAM3 | SERPINA9 | SDPR | GIMAP4 | RBP7 | SDPR | RPL10A | C11orf53 | RPS8 |
| HSP90B1 | UQCR11 | LRMP | VAMP5 | TNFSF10 | GSN | GIMAP7 | CTD-2228K2.5 | TFF3 | RPL35A |
| GNG7 | RPS12 | FCGRT | BCAM | LINC01013 | CYYR1 | RAMP3 | RPL35 | EPCAM | RPL26 |
| PPAPDC1B | SSR4 | EAF2 | CAV1 | AC011526.1 | SDPR | TM4SF1 | MISP | RASSF6 | CLDN4 |
| CD27 | S100A6 | RGS13 | MGP | CLEC14A | EFNA1 | ECSCR | GUCA2B | RGS13 | RPS13 |
| FAM46C | PPDPF | CXCR4 | EMCN | IGFBP7 | ICAM2 | HLA-E | RPS5 | FYB | TFF3 |
| PDIA4 | RPL31 | POU2AF1 | ELTD1 | NPDC1 | TM4SF1 | CYYR1 | TMEM54 | CRYM | REP15 |
| ISG20 | CHCHD2 | SMARCB1 | PLAT | NCOA7 | EMCN | IFITM3 | RPS7 | PRSS3 | FAM3D |
| PABPC4 | BTF3 | CD52 | KDR | CAV1 | IFITM3 | SPARC | SLC51B | IGJ | RPS27A |
| TRAM1 | SRP14 | SPIB | CLEC14A | LMO2 | MGP | A2M | RPL19 | TREH | RPS3 |
| ANKRD37 | CD27 | MGST3 | HLA-E | SNCG | TSPAN7 | GSN | RPL11 | SPINT2 | GNB2L1 |
| RPL36AL | TOMM7 | BLNK | IGFBP7 | CTGF | FKBP1A | CALD1 | CDHR5 | IL13RA1 | RPS7 |
| C19orf10 | PFDN5 | HLA-DRA | FLT1 | TM4SF1 | IL3RA | HSPA1A | RPL5 | NMU | RPS16 |
| CCR10 | MYL12B | CD72 | PODXL | FAM213A | IFITM1 | CAV2 | RPL35A | SOX4 | CLDN7 |
| IGLL5 | YBX1 | POU2F2 | SEPW1 | SPARCL1 | PODXL | CCDC85B | RPS13 | DPYSL3 | RPL6 |
| HSPA5 | EAF2 | ACTR3 | IGFBP4 | CRIP2 | IFITM2 | VWF | CLDN7 | ASCL2 | RPLP2 |
| ACTB | UBE2J1 | FCRL2 | HTRA1 | ITM2A | TGFBR2 | VAMP5 | RPL12 | LGALS4 | RPS15 |
| LMAN2 | SRGN | HMGN1 | SPARC | FAM167B | STOM | ZFP36 | RPS23 | HEPACAM2 | RPS15A |
| MEI1 | RPL30 | CD40 | CAV2 | FKBP1A | PPA1 | HLA-C | CEACAM1 | LGALS1 | MUC13 |
| DUSP5 | EIF3K | ARPC2 | SLC14A1 | ESAM | ENG | HSPB1 | CA2 | HOTAIRM1 | RPLP0 |
| SELK | NDUFA11 | GGA2 | AC011526.1 | IFITM3 | HES1 | HLA-DRA | ANPEP | PLEKHB1 | SDCBP2 |

TABLE 15A-continued

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| UBC | CYTIP | EZR | SH3BP5 | TMEM100 | CD34 | EGR1 | LYPD8 | CLDN4 | RPL8 |
| FCRL5 | RPL23 | HERPUD1 | FAM167B | CCL14 | VWF | TM4SF18 | KRT8 | PPAP2C | ELF3 |
| CST3 | TRAM1 | NCF1 | FAM213A | BCAM | HLA-C | IFI27 | LINC01133 | PPDPF | GDPD3 |
| TXNDC11 | ATP5G2 | IRF8 | SNCG | GIMAP1 | RBP5 | CSRP2 | RPS3 | PTPN18 | NACA |
| UAP1 | FAM46C | HLA-DPA1 | GIMAP7 | CD34 | CAV2 | JUNB | RPS12 | OGDHL | RPS12 |
| PIM2 | TCEB2 | HLA-DQB1 | CDC37 | IFI27 | SLC14A1 | NOSTRIN | RPLP0 | MDK | RPL23A |
| CFL1 | PTMA | HLA-DPB1 | IFITM3 | TGFBR2 | PRSS23 | FOS | RPL26 | FXYD3 | RPL5 |
| SPAG4 | ERLEC1 | LAPTM5 | RP11-536O18.2 | CYBA | PLAT | CDH5 | GNB2L1 | OCIAD2 | CLDN3 |
| YPEL5 | SH3BGRL3 | UBE2J1 | PAP2A | RBP5 | CDC37 | RNASE1 | SFN | RP11-93B14.5 | PHGR1 |
| PFN1 | EDF1 | HLA-DOB | TSC22D1 | CYYR1 | A2M | GADD45B | RPS15A | CLDN3 | RPS23 |
| S100A6 | HM13 | FCER2 | IFITM2 | ZNF385D | CCDC85B | IFITM2 | RPL14 | ESPL1 | C19orf33 |
| TPD52 | RPS7 | C12orf75 | ICAM2 | NRN1 | TNFSF10 | FRZB | RPS14 | FABP1 | GUCA2B |
| CHPF | KDELR1 | SWAP70 | PTRF | HLA-DRA | EPAS1 | IER2 | PRSS3 | ALOX5AP | PLAC8 |
| RP11-290F5.1 | ARHGDIB | HMCES | EHD4 | ADIRF | RNASE1 | ENG | LGALS3 | ANXA3 | RPL4 |
| HSPA1B | FKBP11 | BTG1 | NQO1 | CD320 | OAZ2 | CTGF | RPL6 | CD74 | BCAS1 |
| POU2AF1 | PABPC4 | P2RX5 | CLDN5 | CD59 | SRP14 | JUN | RPL4 | FURIN | RPS6 |
| JUN | SPCS3 | LY86 | CD59 | SRPX | CTGF | ICAM2 | RPS16 | PPP1R1B | RPL13A |
| BTG2 | RPL38 | CYTIP | COL4A1 | ENG | HLA-DRB1 | BGN | RPS15 | MT-CO3 | TBX10 |
| TXNDC15 | COX6B1 | METAP2 | PPAP2B | CFI | GIMAP4 | TPP3 | RPL23A | ANKS4B | TUBB2A |
| TSC22D3 | ALDOA | CD180 | HLA-C | HLA-A | HLA-DRA | FOSB | PTMA | HSPB1 | TM4SF5 |
| TMEM258 | RPS11 | AICDA | CXorf36 | HSPB1 | ELTD1 | RBP5 | PKIB | NCMAP | SMIM6 |
| TMED10 | CLIC1 | CD9 | NPDC1 | HLA-DPB1 | ITM2B | HLA-DPB1 | RPS27A | DEFB1 | VSIG2 |
| MCL1 | TPI1 | LY9 | ARHGAP29 | PIM3 | FAM107A | HES1 | AMN | ZFP36 | SERPINA1 |
| TMSB10 | TXNDC15 | HLA-DRB1 | ANGPT2 | HLA-DRB5 | AC011526.1 | HLA-DRB1 | RPL27A | CC2D1A | IFI27 |
| TPST2 | RPL10A | ANXA2 | HSPB1 | SEPW1 | APP | HLA-DRB5 | GPA33 | COX5A | LGALS9B |
| ACTG1 | CHST12 | ISG20 | CD34 | SDPR | MPZL2 | MGLL | GCNT3 | MT-CO1 | KRT20 |
| NR4A1 | NDUFA13 | SEPW1 | TM4SF1 | ENPP2 | IGFBP7 | SLC14A1 | PRDX6 | EHF | ZG16B |
| S100A10 | TRMT112 | ARHGDIB | APP | NOSTRIN | TMEM204 | SEPW1 | AGPAT2 | CALM2 | MT-CO1 |
| TNFRSF18 | DPP7 | HMGA1 | BAALC | DNAJA1 | GPR146 | EPAS1 | AOC1 | SOX9 | PTMA |
| ERLEC1 | IFNAR2 | TCEA1 | C16orf80 | PTRF | CD74 | FKBP1A | SULT1A2 | IFT172 | SERINC2 |
| NUCB2 | RPL11 | POLD4 | EFNA1 | KCTD12 | FLT1 | ITM2B | MEP1A | 7SK | RPL14 |
| TMSB4X | MYL12A | CD83 | ACVRL1 | IFITM2 | C16orf80 | SNCG | RPL8 | ITM2C | TRIM31 |
| RPN2 | RPSA | BASP1 | LXN | HLA-DRB1 | ACVRL1 | C8orf4 | RPL31 | CASP6 | RPL24 |
| SUB1 | RPL26 | STAG3 | IGFBP3 | MYCT1 | FAM167B | SOCS3 | SMIM22 | EMP3 | AMN |
| PNOC | ISG20 | S100A11 | CYYR1 | GIMAP5 | MMRN2 | LDB2 | TMIGD1 | COX6C | TPSG1 |
| SELM | ATP6V1G1 | SNX29P2 | MYL12A | CCDC85B | MGLL | ELTD1 | KRT19 | ATP1A1 | FFAR4 |
| SLAMF7 | RPL27 | TPD52 | MGLL | CNN3 | HLA-DPB1 | PLAT | CA4 | PHGR1 | KLK1 |
| IFNAR2 | POU2AF1 | IFI27 | HLA-A | LMCD1 | NOSTRIN | EMCN | CLDN3 | CCDC115 | TMEM54 |
| DDOST | ALG5 | ARPC3 | HLA-DRA | KANK3 | GIMAP1 | ID3 | SERINC2 | GFI1B | RPL27A |
| MYL12B | PSMA7 | HTR3A | STOM | CD74 | BST2 | GIMAP4 | RPL13A | HSPA1A | RPS20 |
| TNFRSF13B | RPL24 | GCSAM | EGLN3 | HLA-DPA1 | HYAL2 | PRSS23 | PIGR | S100A11 | CDHR5 |
| FGF23 | SLC25A3 | PNOC | ROBO4 | HLA-C | TIMP3 | BST2 | NEAT1 | KIAA1324 | CLTB |
| LMAN1 | SEC62 | E2F5 | SPTBN1 | CDH5 | TM4SF18 | CD59 | RPL29 | EPS8L3 | RPL29 |
| ANKRD28 | CNPY2 | CD27 | ABI3 | ADM5 | HHEX | FAM167B | FTH1 | NREP | CREB3L1 |
| CD38 | BST2 | RAC2 | HLX | NFKBIA | GIMAP5 | TSC22D1 | TST | HLA-DPB1 | RPL3 |
| ICAM3 | TMEM230 | AC023590.1 | RASIP1 | SPARC | RPLP1 | HSPA1B | CLCA4 | HLA-DRA | EPCAM |
| GAPDH | RPL37 | STX7 | HLA-B | PALMD | SLCO2A1 | RGS16 | RPL7A | HLA-DRB1 | FOXA3 |
| DNAJB11 | CD63 | LYL1 | TGFBR2 | CHCHD10 | SNCG | PDGFRB | PPP1R14D | MYO1B | RPL31 |
| ARF4 | SLAMF7 | TMSB10 | S100A13 | LPCAT4 | FAM213A | ADIRF | MUC12 | B2M | CAPN8 |
| AC104699.1 | LGALS1 | UCP2 | MMRN2 | ERG | HLA-DPA1 | GJA4 | MUC13 | GADD45B | GPA33 |
| CDK2AP2 | GYPC | IL32 | IVNS1ABP | SH3BP5 | HEY1 | TGFBR2 | TMEM171 | KLK11 | CFDP1 |

TABLE 15A-continued

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| TMEM59 | RPS9 | HLA-DMA | CTGF | STXBP6 | SOX17 | KLF2 | HIST1H1C | CLRN3 | TMSB10 |
| ALG5 | NDUFA4 | SELT | F2RL3 | BST2 | PTRF | MFGE8 | CLDN4 | ATP2A3 | RPS25 |
| C16orf74 | COX5B | LAT2 | ENPP2 | CAV2 | EMP2 | APP | C2orf88 | NDUFB4 | RPS24 |
| SRPRB | DUSP5 | IFITM3 | WWTR1 | SMAD1 | RPL12 | PODXL | TRIM31 | COX7A2 | AQP8 |
| CIRBP | RPS13 | BFSP2 | EXOC3L2 | CLIC2 | NKX2-3 | TIMP3 | MYO15B | S100A14 | KRT18 |
| FTH1 | HNRNPDL | GDI2 | B2M | IFIT1 | SYNPO | HLA-A | ETHE1 | EIF5 | RPL30 |
| TMED2 | LRPAP1 | HLA-DMB | NOTCH4 | TPD52L1 | SOCS3 | BCAM | RPL18 | PRDX2 | FAM177B |
| RGS2 | PARK7 | HHEX | GABARAPL2 | SOCS3 | NRN1 | SLC2A3 | RPS25 | CYB5A | RPL18 |
| IGFBP7 | MEI1 | LGALS4 | IFI27 | GALNT15 | RPLP0 | DNAJA1 | S100A6 | C15orf48 | LGALS4 |
| RABAC1 | RPL19 | EPCAM | S100A16 | HLA-DQA1 | IFIT3 | MCAM | RETSAT | CLDN7 | RPL7A |
| CD74 | RHEB | MZB1 | HES1 | CYP1B1 | CDH5 | SERPING1 | RPS20 | CHPT1 | SPATS2L |
| SSR2 | VIM | SIT1 | GMFG | ICAM2 | HLA-A | CD74 | CES2 | CKB | KRT8 |
| ARHGDIB | RPL32 | PLEKHF2 | IL3RA | HSPA1A | IER2 | SYNPO | CA1 | COX7C | PRR15L |
| DNAJB1 | COX7C | TNFRSF13B | GAS6 | IRF1 | TSC22D1 | ISYNA1 | RPL24 | SLC25A6 | PRSS3 |
| CYTIP | COX6A1 | RHOC | IDO1 | FBLN2 | RND1 | COX7A1 | RPL3 | MAP7 | DHRS9 |
| ZBP1 | PTPRCAP | OAZ1 | COL4A2 | HYAL2 | KANK3 | LHFP | RPL28 | VSNL1 | PIGR |
| HM13 | SMARCB1 | KRT18 | MSN | EIF1 | THBD | SRGN | C11orf86 | MT-ND4 | NEAT1 |
| AMPD1 | COMMD3 | LCP1 | FSCN1 | SELP | NQO1 | THBD | SPINT2 | BUB3 | PLA2G10 |
| MYL12A | LSP1 | HVCN1 | HHEX | LIFR | C8orf4 | EFNA1 | RPL30 | KRT19 | EEF1D |
| RHOC | PSENEN | C15orf48 | MYCT1 | S100A16 | LDB2 | MMRN2 | RPLP2 | CCDC28B | RPL27 |
| GSN | RPS25 | KRT8 | ACE | TCF4 | ARHGAP29 | HLA-DPA1 | CYSTM1 | SRI | SCNN1A |
| IFI27 | ARL6IP4 | ITM2B | TSPAN7 | MPZL2 | C10orf10 | FAM107A | SLC26A2 | SMIM22 | FABP1 |
| REEP5 | EMC4 | MBD4 | EPAS1 | YBX3 | EHD4 | IRF1 | MT-CO1 | FBP1 | RPL28 |
| TMEM208 | ARPC3 | BIK | FAM110D | EGR1 | HSPB1 | CLIC2 | RPSA | H1F0 | SMIM22 |
| SDC1 | ATP5O | TXN | C9orf5 | ARL2 | HLA-DRB5 | PTRF | COL17A1 | ALDH2 | FAM101A |
| GLA | MT-ND4 | CCND3 | CALCRL | MTUS1 | GABARAPL2 | CYGB | S100A10 | PAFAH1B3 | FTL |
| TUBA1A | GMFG | DEF8 | HLA-DRB1 | B2M | NOTCH4 | RPLP0 | LINC00035 | MAOB | FAU |
| EEF1D | SRPRB | RASGRP2 | SOX18 | SNHG7 | GPR116 | PPA1 | MYH14 | HLA-DRB5 | HIST1H1C |
| KDELR2 | ATP5B | MARCKSL1 | FABP5 | FAM110D | HEG1 | MYCT1 | EPCAM | HLA-DMA | PARM1 |
| B4GALT3 | NDUFA1 | NEIL1 | GALNT18 | CALCRL | CLIC2 | H3F3B | RPS24 | ACTG1 | CEACAM6 |
| PDE4B | RPL37A | SUGCT | ITM2A | ELTD1 | SRGN | B2M | C15orf48 | MIEN1 | CEACAM7 |
| RGCC | RAC1 | RP11-164H13.1 | A2M | PIR | FABP5 | SPINT2 | NACA | MT-CYB | GSN |
| LGALS1 | EIF3F | RFTN1 | IFITM1 | JUNB | NFIB | GPX3 | HSD17B2 | HOXB6 | ARL14 |
| RGS1 | DNAJB1 | ITM2C | IGFBP6 | IL3RA | AIF1L | TSPAN7 | SLC17A4 | TIMP1 | MISP |
| LGALS3 | ATP5J | MT2A | NOSTRIN | RNASE1 | ADAM15 | COL18A1 | TMSB10 | GPX2 | CA2 |
| PDK1 | MT-ATP6 | TNFAIP8 | JAM2 | IL33 | NOV | FLT1 | RPL36 | ZFHX3 | GUCA2A |
| TMEM176B | RPS20 | ZCCHC7 | RNASE1 | VGLL4 | C9orf3 | SOD3 | EEF1D | CD9 | MLPH |
| SH3BGRL3 | MGAT1 | LINC00926 | MYL12B | IFIT3 | S100A16 | EIF1 | SLC44A4 | MALAT1 | CEACAM1 |
| IFITM3 | CRELD2 | AIM2 | SLCO2A1 | EFEMP1 | SH3BP5 | COL1A2 | CDKN2B-AS1 | RPL37A | SPINT2 |
| KIAA0125 | UBL5 | STK17A | CALM1 | AC116035.1 | HLA-B | PPAP2B | LGALS4 | NCK2 | YBX1 |
| MYL6 | MT-CYB | CISD3 | NES | KLF4 | B2M | TCF4 | IFI27 | TAS1R3 | RPL36 |
| SRGN | SELM | CYB561A3 | KANK3 | TESC | PIK3R3 | SERTAD1 | PPDPF | PIK3CG | SCGB2A1 |
| RP11-492E3.2 | VAMP2 | SLBP | ARHGAP18 | EPCAM | PLLP | STOM | BTNL3 | RBM38 | C15orf48 |
| TRIB1 | OSTC | TMEM156 | RND1 | STOM | C10orf54 | C16orf80 | NPM1 | LDHA | NAAA |
| CITED2 | ICAM2 | BACH2 | FTH1 | CD55 | SPARC | HLA-DMA | BTNL8 | COX5B | MT-ND2 |
| ID2 | EMP3 | LMNA | CLIC2 | RND1 | CFI | APOLD1 | ELF3 | ESPN | RPSA |
| EV12B | NACA | ATP1A1 | LDB2 | CDC42EP3 | GAS6 | NRN1 | HN1 | ESYT2 | CLDN8 |
| KRTCAP2 | CALM2 | GYPC | MPZL2 | TIMP1 | PPAP2A | HES4 | POLD4 | PSMD9 | ASS1 |
| BEX5 | RPS3 | RMI2 | PEA15 | HES1 | LY6E | SOX17 | ST14 | ANXA2 | S100A6 |
| CISD2 | NDUFS8 | PPP1CC | MCAM | TSPAN4 | SERTAD1 | LGALS1 | SLC6A8 | MT-ND1 | POLD4 |
| SEPW1 | COX7A2 | UBE2N | DLL4 | PLK2 | TIE1 | ZFP36L1 | CLTB | TXN | MXD1 |

TABLE 15A-continued

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| ANXA1 | PLP2 | AGR2 | MFNG | ATP5G3 | MYCT1 | REM1 | LAMB3 | STMN1 | PFDN5 |
| RPN1 | CCR10 | PARP1 | C8orf4 | TXNIP | TMEM109 | ID1 | SLC51A | DEGS2 | SLC25A6 |
| EIF1 | TPD52 | MME | HLA-DMA | HLA-DMA | CD93 | NPDC1 | CLDN23 | PMM1 | MYO15B |
| FOSB | SELT | HCLS1 | HLA-DPB1 | BAG3 | RPS2 | AC011526.1 | CDHR2 | HOXA11-AS | MLLT3 |
| HAX1 | ZNF706 | PABPC1 | BST2 | PDLIM4 | GIMAP6 | CFI | TMEM45B | IP6K2 | TP53INP2 |
| IL32 | PIM2 | IGLL5 | PTPRB | MGP | ID1 | CYB5R3 | TMEM37 | TMEM176B | RPL18A |
| IFITM2 | HINT1 | RGS16 | TSPAN4 | ID3 | TAGLN2 | EFHD1 | CHP2 | ZNHIT3 | UBA52 |
| TMED4 | UAP1 | CD1C | ACTN4 | PHGR1 | ZFP36 | OAZ2 | GPRC5A | ATP5B | MT-CO2 |
| SEMA4A | SNRPD2 | RGS19 | IPO11 | TIE1 | S100A13 | CD34 | HPGD | IFITM2 | ST3GAL4 |
| RAB30 | S100A10 | PAX5 | DUSP6 | AGR2 | CYBA | NES | CKB | RPL36 | ITM2C |
| SLC17A9 | SLC35B1 | ETHE1 | TEK | SEMA6A | TACC1 | SRP14 | FCGBP | HMX2 | ATP5G2 |
| SLC38A5 | REEP5 | HLA-DQA2 | GUK1 | HLA-B | LAP3 | HHEX | AK1 | TSC22D3 | LMO7 |
| CAPZB | TMEM66 | DCK | ID3 | TAGLN2 | CFLAR | TMEM204 | ASS1 | ACADSB | RPL34 |
| PTPRCAP | ATRAID | ITSN2 | CDH5 | KRT222 | HSPA1A | C1QTNF1 | PRR15 | S100A4 | AGR2 |
| H3F3B | SOD1 | SH3B2 | IMP3 | TMEM176A | LMCD1 | GABARAPL2 | ITM2C | RHEB | AC009133.21 |
| COPE | RPS23 | SUSD3 | TBCD | SORBS2 | TINAGL1 | COL3A1 | TMPRSS2 | SPINT1 | SYTL2 |
| WNT10A | GUK1 | SRSF3 | CABP1 | ST8SIA4 | DLL4 | MYH9 | YBX1 | IMP4 | RAB27A |
| TMED9 | TMED4 | LYN | GIMAP1 | IFI16 | TNFRSF4 | DNAJB1 | S100A11 | LSMD1 | RPL37 |
| CUTA | RPS21 | SYPL1 | JUP | LGALS4 | PTP4A3 | PHGR1 | PRR13 | ATPIF1 | CKB |
| E2F5 | DNAJC1 | ARPC1B | TNFRSF4 | GIMAP8 | KDR | LGALS4 | KRT18 | ADH5 | VILL |
| HSPA1A | NDUFB2 | CTSD | ARHGDIB | KRT8 | SPTBN1 | ITGA7 | DHRS11 | H2AFJ | CA4 |
| SELT | MT-ND5 | IL16 | PRX | BAALC | HLX | HEY1 | HNRNPA1 | IGFBP2 | LINC01133 |
| HES1 | NUCB2 | GRB10 | FAM107A | FAM107A | ROBO4 | FAM222B | GNA11 | RAB4A | RP11-294O2.2 |
| EZR | PABPC1 | ZFAND6 | NRP1 | JUN | PTPRB | HSPG2 | NDRG1 | SPATS2L | S100A14 |
| DUSP1 | RPL12 | PRPSAP2 | SRGN | S100A13 | IFI6 | GPR116 | CCL15 | AFAP1L2 | MEP1A |
| RNU12 | ATF4 | MAP3K7CL | ERG | ZFP36 | FAM110D | TACC1 | RPL27 | WFDC2 | CYBA |
| PAIP2B | DNAJB9 | S100A10 | NKX2-3 | A2M | ATOH8 | BBX | SPINT1 | DNAJB1 | MT-CO3 |
| SPINK2 | B4GALT3 | PXK | CLIC4 | DTL | APLNR | SH3BP5 | DEFB1 | SKAP2 | PKIB |
| SLC35B1 | HNRNPA1 | RP11-960L18.1 | TUBA1B | EID1 | LPAR6 | C10orf10 | CFDP1 | HLA-DQB1 | KCNK1 |
| SMARCB1 | NEDD8 | CCR7 | SLC25A6 | PKP4 | PRMT1 | EHD2 | DHRS9 | ANXA5 | MAST2 |
| SEPP1 | CISD2 | LSM10 | LAYN | CCL21 | PALMD | TNS1 | PFDN5 | RPL31 | EIF4A1 |
| DNAJC1 | KRTCAP2 | LYPLA1 | TMEM255B | HLA-DQB1 | COL15A1 | FAM213A | PTPRH | PBXIP1 | CLDN23 |
| SELIL | ERGIC2 | DCAF12 | GIMAP4 | LIMCH1 | SEMA3G | LCN6 | FLNB | COL27A1 | HPGD |
| HSP90AA1 | UQCRQ | CTSH | LIMCH1 | GADD45B | NDUFA12 | PPP1R14A | ACAA2 | MT-ND5 | SMIM5 |
| AC093818.1 | CNBP | TMEM243 | THBD | CD9 | RGS3 | FAM110D | PRSS8 | RAB25 | MALAT1 |
| HLA-A | LAMTOR4 | TFEB | CD74 | CXorf36 | TMEM255B | RPLP1 | RPS11 | FRAT2 | SPINT1 |
| ICAM2 | COX6C | AC079767.4 | HLA-DPA1 | HAPLN3 | CHCHD10 | SDCBP | RPL37 | AOC1 | MT-ATP6 |
| TPI1 | CD44 | UBE2G1 | TSPAN12 | VIM | COX4I1 | SOX7 | C10orf99 | GSTP1 | PRSS8 |
| EMB | LMAN1 | WIPF1 | CDC42EP1 | ADCY4 | CD151 | GEM | RHOC | MT-CO2 | CLCA4 |
| QPCT | TMBIM4 | KIAA0125 | COX7A1 | WARS | ARL2 | EMP2 | RPL34 | RTN4 | MT-ND4 |
| SPATS2 | CST3 | HNRNPC | SCARF1 | PLAT | SLC25A6 | LMO2 | EIF4A1 | TUBA1A | RPS3A |
| RHOH | C4orf3 | FXYD3 | TXNIP | ACVRL1 | ID3 | NEAT1 | CDA | RPS27L | EEF2 |
| APOE | EIF4A2 | ID2 | SEMA3F | MEOX1 | SCARF1 | TIE1 | BLOC1S1 | CCDC14 | ST14 |
| MANEA | FXYD5 | CBX3 | RHOA | CYB5A | GALNT18 | IGFBP6 | HHLA2 | FUT3 | MUC12 |
| IRF4 | NDUFB8 | SNAP23 | LDHB | INPP1 | LIFR | COL4A1 | AHCYL2 | TP53I3 | HIST1H2AC |
| ANXA2 | AUP1 | MOB1A | SORBS2 | LDB2 | SWAP70 | APLNR | LDHB | MCL1 | RHOC |
| IFITM1 | DDOST | DBNL | TACC1 | IL1R1 | RPL29 | SEPP1 | GDPD3 | TSPO | RP11-665N17.4 |
| JSRP1 | GSTK1 | DOK3 | ITGA6 | TMEM176B | SEC14L1 | PLK2 | HRCT1 | ZFP36L1 | RPL37A |
| COMMD3 | C19orf43 | PLCG2 | KIFC3 | ARL4A | RPS19 | HYAL2 | MT-CO2 | CMTM8 | MT-ND1 |
| SRM | PRDX2 | KRT19 | LGALS4 | CTHRC1 | RPL10A | RPS29 | FAM3D | PRDX5 | TSPAN3 |
| CXCL14 | SKP1 | IGJ | TIE1 | PRCP | HLA-DMA | RNASET2 | ATP5G2 | HES6 | IGJ |
| | | SQRDL | | | | | | | |

TABLE 15A-continued

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| SMDT1 | A1BG | FCRL3 | HLA-DRB5 | IFIT2 | RRAS | TAGLN2 | FAM132A | PTMA | RPS11 |
| MT-CO3 | SAP18 | RRAS2 | PRDX1 | TMEM173 | LCN6 | SLCO2A1 | SLC9A3R1 | NDUFB11 | EIF1 |
| RPS5 | TMA7 | CERS4 | PELO | FAM198B | WARS | PKIG | PKP3 | CHN2 | KRT19 |
| IL2RG | UBE2D3 | OSER1 | TP53I11 | FABP1 | EPHX1 | KRT8 | STAP2 | TMEM63A | HSP90AB1 |
| SRPR | DHRS7 | LMO2 | SERPINI1 | GPR146 | DUSP6 | RPS2 | SLC22A18 | RASSF7 | BEST2 |
| ERGIC2 | RPS15 | TAGAP | PPA1 | MLEC | JUNB | CXorf36 | ESPN | VIL1 | RASEF |
| PTMS | LGALS3 | FTL | FAM101B | MMP28 | PRKCDBP | LRRC32 | MT-CO3 | MT-ATP6 | AOC1 |
| PLP2 | PSMB6 | BTK | S100A6 | SQSTM1 | RPL18 | RHOA | VIM | CERS6 | SPDEF |
| OSTC | SDF2L1 | ATP5I | PPFIBP1 | KRT18 | RALB | GIMAP1 | TJP3 | ID3 | LGALS9C |
| CNPY2 | CHID1 | ANP32B | RPL12 | SERTAD1 | SORBS2 | LIFR | PCK1 | CDH17 | NPM1 |
| S100A4 | ATP5G3 | PTPRC | TMEM173 | IFITM1 | EIF1 | HDAC7 | CTSA | TMSB10 | PCK1 |
| SRP14 | RBM39 | RCSD1 | ANKRD65 | LPAR6 | ALPL | TSPAN4 | BSG | ARPC1B | PABPC1 |
| PPIB | LAMP2 | RPS4Y1 | PLXNA2 | RASIP1 | FOS | C10orf54 | ARL14 | IFI6 | NLN |
| SIL1 | ATP6V0E1 | MLEC | APLN | ALDH1A1 | RPS5 | CYBA | TSPAN8 | FAM200B | SEPP1 |
| GLRX | ITM2B | GSTP1 | CD93 | MX1 | TMEM173 | IFIT3 | ENTPD8 | CDX2 | VIPR1 |
| CD69 | EV12B | CCNI | ITGA1 | PTPRB | CALM1 | HEG1 | CDH17 | HOXB9 | HNRNPA1 |
| RPL28 | EIF3H | C10orf54 | C10orf54 | NKX2-3 | KLF2 | GIMAP5 | MT-ND5 | COX6A1 | GPRIN2 |
| SLC25A4 | SEC11C | VAT1 | VAT1 | PPP1R15A | VWA1 | NQO1 | CDKN2B | AP1M2 | BTNL3 |
| TMBIM6 | UFM1 | KLHDC8B | KLHDC8B | NEAT1 | ADCY4 | IL3RA | PEX26 | RNF186 | QSOX1 |
| S100A11 | OS9 | NPM1 | PHGR1 | IGJ | NES | PTPRB | SLC25A6 | RPS21 | SMIM14 |
| TNFRSF4 | C11orf31 | SGPP1 | TTNAGL1 | MEIS2 | ETS2 | KANK3 | SLC25A5 | SHC1 | BTNL8 |
| LGALS4 | ANXA7 | HSH2D | CYBA | GIMAP6 | MGAT1 | IFITM1 | GGT6 | CD14 | ITLN1 |
| JTB | CALM1 | BLVRB | ME3 | SRGN | SERPING1 | NKX2-3 | LSR | DPP7 | NEDD4L |
| RPL8 | PSMB3 | ORAI2 | TNFSF10 | CLDN7 | SNX3 | TMEM176B | NLN | LYZ | GPR153 |
| THAP2 | TPT1 | TNFRSF17 | SERPINE1 | LAPTM4A | COX7A1 | GPRC5B | RPL18A | SEPP1 | TDP2 |
| COTL1 | TAPBP | ALOX5 | RHOC | PLA1A | ACTN4 | TCF21 | APOBEC3B | PERP | CYSTM1 |
| TIFA | CHPF | PTPN6 | EPHX1 | EPAS1 | CARHSP1 | NDUFA12 | PABPC1 | RNF24 | SH3BGRL3 |
| TXNIP | ERGIC3 | ACTG1 | NDUFA12 | SLC41A3 | ERG | ARIDSB | EIF1 | TBC1D2B | CDHR2 |
| FCRLA | DERL2 | GPSM3 | PTMA | LAYN | RPS4X | RAC1 | IL32 | MACROD1 | PTPRF |
| ENO1 | HIGD2A | MTMR14 | CCND1 | ASRGL1 | RAC1 | TNFSF10 | SULT1A1 | MYO10 | ISG20 |
| CD151 | 15-Sep | FAM65B | GIMAP5 | FOS | CYB5R3 | EPHX1 | LMO7 | RPS11 | LSR |
| BRSK1 | ARPC2 | TFF3 | RPLP1 | IFI6 | LRRC32 | PRKCDBP | CGN | IFITM3 | FBXO32 |
| ARPC1B | NDUFB4 | KLHL5 | GPX1 | CSF2RB | IMP3 | ITGA1 | RPL37A | EPHB3 | OASL |
| A2M | RPLP2 | GRB2 | RBP7 | CSRP2 | RNASET2 | PLAU | S100A14 | ASMTL | RPL23 |
| AC104024.1 | ST13 | GNG7 | KRT8 | C10orf128 | BTNL9 | FAM162B | LLGL2 | YPEL5 | CYP3A5 |
| LMTK3 | JTB | CCDC69 | SEC14L1 | DDX5 | RPL13 | DUSP1 | IFITM3 | H2AFY2 | SLC26A3 |
| SSR1 | ATP5D | CR2 | CHCHD10 | GBP2 | YBX3 | ACTN4 | MVP | STK38 | PRAP1 |
| RNASET2 | NUDT22 | TMEM141 | PKIG | IFI44L | HPCAL1 | APOL3 | CLCN2 | JUNB | MT-ND5 |
| COX5B | GNL3 | DDX39A | PSMB5 | TIMP3 | RPS18 | COL6A2 | TPRN | PPAP2A | SLC44A4 |
| SEC61A1 | NDUFB1L | SRGN | ARHGEF15 | EIF4A2 | ELK3 | ROBO4 | ACOX1 | LACTB2 | KCNK5 |
| HSH2D | NHP2L1 | MEF2C | SCARB1 | EVA1C | KLF4 | UBC | AKR1B10 | TAGLN2 | RASSF7 |
| ATP5E | ARF1 | HLA-DRB5 | PRKCH | IDH2 | PVRL2 | IGJ | CA12 | SMARCC1 | H2AFJ |
| DCN | SEC61A1 | LAMTOR4 | MCF2L | RAB13 | RHOC | WNT6 | MT-ATP6 | GAPDH | CA1 |
| CHID1 | CHMP2A | REL | GPR116 | NEDD9 | SNHG7 | TMEM255B | MPST | AC005355.2 | STARD10 |
| MT-CO1 | RPL14 | KIAA0226L | DYNLL1 | DNAJB4 | CTNNBIP1 | COL15A1 | TSPAN3 | TMPRSS2 | CDH1 |
| RP11-16E12.2 | NPM1 | PRDX5 | HEG1 | NR2F2 | RPL28 | ADAMTS1 | FAU | C7orf55 | STAP2 |
| ERGIC3 | ARMCX3 | CCDC109B | OSBPL1A | CAPG | RASIP1 | RPL10 | PARK7 | TSPAN13 | STX19 |
| TXNDC5 | SRPR | PPDPF | ARL2 | IPO11 | HYAL1 | PTMA | C1orf106 | SNX3 | PLAUR |

TABLE 15B

| Absorptive_TA_1 | Secretory_TA | Absorptive_TA_2 | Cycling_TA | Goblet_1 | Stem_cells |
|---|---|---|---|---|---|
| TXN | MT-ND1 | FABP1 | EPCAM | TFF3 | B2M |
| GPX2 | B2M | SELENBP1 | LGALS4 | KLK1 | LEFTY1 |
| MGST1 | TFF3 | CA2 | MGST1 | ITLN1 | TMSB4X |
| EPCAM | MT-ATP6 | LGALS4 | AGR2 | FCGBP | ASCL2 |
| AGR2 | PRDX5 | C15orf48 | C15orf48 | AGR2 | MT-ND4 |
| C15orf48 | MUC2 | S100A14 | GPX2 | CLCA1 | LGALS4 |
| PPP1R1B | FCGBP | PHGR1 | KRT8 | LRRC26 | SMOC2 |
| LGALS4 | KLK1 | KRT19 | CLDN7 | RETNLB | PRDX5 |
| HMGCS2 | RPL36 | ETHE1 | CLDN3 | MUC2 | RGMB |
| TSPAN8 | AGR2 | FXYD3 | PIGR | WFDC2 | MT-CYB |
| C10orf99 | PIGR | LGALS3 | HLA-DPA1 | SPINK1 | FXYD3 |
| UGT2B17 | ITLN1 | UQCRQ | PHGR1 | SPINK4 | GPX2 |
| ATP5B | GPX2 | PIGR | FXYD3 | KRT18 | CDCA7 |
| CLDN7 | ATP5G1 | COX5B | TXN | REP15 | MT-CO3 |
| S100A14 | MT-ND4 | MT-ND1 | ARHGDIB | ZG16 | TSPAN8 |
| PHGR1 | EPCAM | MT-CO2 | VIM | SERPINA1 | PHGR1 |
| ELF3 | LGALS4 | COX4I1 | ELF3 | TPSG1 | MT-ND2 |
| PIGR | ZG16 | C10orf99 | HLA-DPB1 | LGALS4 | MT-ND1 |
| CDX1 | MT1G | MT-CO3 | BST2 | ST6GALNAC1 | EPCAM |
| MT1G | CLDN3 | MT-ND4 | TUBB4B | FAM3D | ELF3 |
| CLDN3 | FABP1 | MT-ATP6 | CD74 | KRT8 | PIGR |
| FABP1 | PHGR1 | MT1G | KRT18 | EPCAM | HLA-C |
| FXYD3 | KRT8 | TST | S100A14 | STARD10 | MT-ATP6 |
| KRT8 | CLCA1 | ATP5G3 | MT1G | PHGR1 | MT-ND3 |
| COX5A | COX4I1 | KRT8 | ARPC1B | SMIM22 | KRT8 |
| ATP5G3 | CLDN7 | CA1 | ATP5G1 | FXYD3 | MT-CO1 |
| KRT18 | H3F3B | TMEM54 | HMGCS2 | GMDS | PPP1R1B |
| PRDX5 | FXYD3 | CHCHD10 | KRTCAP3 | HEPACAM2 | EPHB3 |
| CYC1 | MT-ND2 | ATP5G1 | CD9 | RNASE1 | SMIM22 |
| RPLP0 | RPS14 | SLC26A2 | HLA-DRB1 | KRT19 | KRT18 |
| ATP5G1 | MALAT1 | TXN | PPP1R1B | MT-ND1 | HSPB1 |
| MT1E | IGJ | B2M | CLDN4 | CLDN3 | CLDN7 |
| SLC25A5 | KRT18 | CLDN7 | TSPAN8 | VSIG2 | CLDN4 |
| TIMP1 | CLDN4 | CES2 | HLA-DRA | C15orf48 | RPS18 |
| LEFTY1 | RPL37A | COX7A2 | SUCLG1 | PIGR | C15orf48 |
| FAM3D | RPS29 | UQCR10 | CDX1 | CLDN7 | HMGCS2 |
| UQCRH | MT-CO2 | COX6C | NUPR1 | ANXA13 | HLA-B |
| KLF5 | RPS18 | COX6B1 | FAM3D | SPDEF | RPS24 |
| CHCHD10 | C15orf48 | HMGCS2 | CYC1 | MT-CO3 | RPS21 |
| CLDN4 | MT-CO3 | AKR1C3 | FABP1 | TMEM141 | CLDN3 |
| LGALS3 | TSPAN8 | CKB | PRDX5 | ANG | RPL36 |
| SUCLG2 | EIF1 | EPCAM | SMIM22 | COX6C | SPINK1 |
| CD9 | SPINK1 | HSD11B2 | LGALS1 | ELF3 | RPL37 |
| TSPO | RPL35 | AGR2 | TMEM141 | S100A14 | MT-CO2 |
| KRT19 | SMIM22 | SMIM22 | TMEM54 | HMGCS2 | RPS6 |
| SMIM22 | SPINK4 | MT-ND5 | CKB | BEST2 | SLC12A2 |
| C19orf33 | STARD10 | AMN | CST3 | MB | RPL37A |
| NXPE4 | FAM3D | MGST1 | NDUFAB1 | FABP1 | S100A14 |
| B2M | MT-CYB | MT-CYB | C10orf99 | CREB3L1 | RPL31 |
| SUCLG1 | MT-ND3 | COX8A | ITM2C | RPL36 | RPL12 |
| ATP5A1 | RPS21 | C19orf33 | TMSB4X | GPX2 | MT1G |
| ATP5F1 | CD74 | TMEM141 | ARPC2 | CLDN4 | BST2 |
| GAPDH | HLA-DPA1 | COX6A1 | HLA-DRB5 | S100A6 | ACTB |
| COX4I1 | HLA-C | AKR7A3 | SPINK1 | RP11-234B24.2 | MARCKSL1 |
| COX5B | WFDC2 | MT1E | PLP2 | URAD | PDZK1IP1 |
| RP11-519G16.5 | ATP5I | GOLM1 | SPINT2 | TCEA3 | MGST1 |
| TMEM54 | TMEM141 | AKR1B10 | HLA-DMA | TSPAN8 | RNF186 |
| ETHE1 | ELF3 | PRSS3 | HLA-DMB | MT1G | GNB2L1 |
| UQCRC2 | RETNLB | CLDN3 | MT1E | TSPAN1 | RPS3 |
| CA2 | TIMP1 | CISD3 | COX5A | TMEM61 | RPLP0 |
| TMEM141 | HMGCS2 | ATP5D | ATP5B | RAP1GAP | ETS2 |
| HLA-E | RPS3 | MT-CO1 | ECH1 | C10orf99 | HLA-A |
| CDX2 | PPP1R1B | MT-ND2 | TUBA1A | REG4 | CD63 |
| COX6C | RPS15 | CHP2 | IGJ | PRDX5 | CST3 |
| C1QBP | TMEM54 | H3F3B | FXYD5 | MT-ND4 | ARHGDIB |
| RPSA | KRT19 | KRT18 | SELENBP1 | CCL15 | FAM3D |
| KRTCAP3 | MT1E | NDUFA1 | ETFB | UQCRH | MT-ND5 |
| OLFM4 | ZFP36 | VSIG2 | HLA-DQB1 | H3F3B | CKB |
| UQCRFS1 | RPL12 | TIMP1 | SRI | NANS | RPS4X |
| S100A10 | KRTCAP3 | COX7C | KRT19 | NPDC1 | GSN |
| ATP5C1 | COX5B | FAM3D | KLF5 | MT-ATP6 | C10orf99 |
| H3F3B | IGLL5 | PDE4C | IGLL5 | MT-CYB | FABP1 |
| GSN | RPS9 | EIF1 | LGALS3 | MT-CO2 | ALDH1B1 |
| MRPL12 | MGST1 | COX5A | HADH | IGJ | MT1E |
| CD74 | C10orf99 | LGALS1 | CDX2 | MT-ND2 | TRABD2A |
| CKMT1B | RPL8 | CD74 | UQCRC1 | IGFBP2 | KLK1 |
| SLC25A6 | ITM2B | TSPAN1 | SMAGP | SPINT2 | SELENBP1 |
| ARHGDIB | RPLP2 | CLDN4 | TIMP1 | EIF1 | STARD10 |

TABLE 15B-continued

| | | | | | |
|---|---|---|---|---|---|
| RPS2 | CHCHD10 | TSPAN8 | ACTB | C2orf82 | AGR2 |
| MPC2 | UBC | SLC22A18AS | LY6E | COX5A | RPL26 |
| SELENBP1 | HLA-DRB1 | CYC1 | COA3 | IFI27 | SPINT2 |
| RPS24 | COX6B1 | MT-ND3 | COTL1 | HES6 | ARPC1B |
| RPS18 | ATP5D | ATPIF1 | IGFBP2 | COX5B | KRT19 |
| MAOA | NDUFB11 | UQCR11 | ACADS | TIMP1 | RPS5 |
| RPL8 | C19orf33 | ELF3 | PLA2G2A | CDC42EP5 | RPS2 |
| CKB | S100A14 | SDCBP2 | STARD10 | FOXA3 | RPL13 |
| MPST | HLA-DRA | ATP5I | CES2 | S100A4 | TFF3 |
| IGJ | RPS5 | IGJ | TST | PPDPF | S100A11 |
| TRABD2A | COX5A | CDX1 | LEFTY1 | ZG16B | MYL6 |
| ATP5O | RPS12 | TSPO | CKMT1B | MT-CO1 | AQP1 |
| RPS6 | RPL13 | SRI | ATP5G3 | IL1R2 | FERMT1 |
| HINT1 | ARHGDIB | UQCRC1 | CISD3 | TMEM176B | MT-ND4L |
| SPINK1 | C2orf82 | MGST3 | ISG15 | HSD11B2 | RABAC1 |
| HLA-DPA1 | RPS8 | S100A6 | RARRES2 | CD9 | HLA-DPA1 |
| ECH1 | RPS2 | MRPL41 | MPC2 | BTG1 | RPL29 |
| PHB | TCEA3 | TCEA3 | HLA-E | UQCR10 | LY6E |
| CES2 | HLA-DPB1 | NDUFB9 | ECHS1 | IFT172 | HLA-E |
| AKR1C3 | LEFTY1 | COX7B | CKMT1A | COX6B1 | SLC25A6 |
| CKMT1A | ACTB | ZFP36 | UQCRQ | TPM1 | TIMP1 |
| PLA2G2A | LRRC26 | ATP5J | GGH | ZFP36 | RPL8 |
| RPL5 | MUC5B | ATP5B | TSPO | SERF2 | CD74 |
| UQCR10 | NUPR1 | SLC39A5 | MPST | TSTA3 | RPL35A |
| IGFBP2 | MT-ND5 | KRTCAP3 | ATP5F1 | MGST1 | RPL10A |
| COX7C | CKB | NXPE4 | COX4I1 | TSPAN13 | KRTCAP3 |
| COX6B1 | UQCR10 | GPT | ATPIF1 | C19orf33 | UBB |
| LCN2 | SELENBP1 | MS4A12 | CYCS | MT-ND3 | RPS12 |
| RPL7A | RPL27A | ANXA5 | UQCRH | ATP5G3 | KLF5 |
| ZFP36 | MT-CO1 | ACADS | ZFP36 | FAM195A | NOS2 |
| RPS8 | UQCRQ | SLPI | MACROD1 | ITM2B | RPL5 |
| CMBL | STRA13 | PXMP2 | COX5B | RAB25 | OLFM4 |
| FAM84A | RPL7A | NDUFB2 | STAP2 | FTL | SOX4 |
| PEBP1 | RPL32 | FAM162A | RPLP0 | CDX1 | RPL32 |
| S100A4 | RPS19 | DBI | RP11-519G16.5 | STAP2 | RPS23 |
| STARD10 | CISD3 | ARHGDIB | COX6C | DNAJA1 | SEPP1 |
| HLA-C | TPSG1 | PPP1R14D | RGS10 | TMEM54 | GUK1 |
| IGFBP7 | AMN | GPX2 | SLC44A4 | FABP2 | COX5A |
| PPP1R14D | URAD | UQCRH | NANS | ATP5I | RPS8 |
| HLA-DPB1 | MT2A | TMEM45B | NDUFV1 | CHCHD10 | MLXIP |
| PDE4C | RPLP1 | CYSTM1 | RPS18 | ARPC1B | CEACAM5 |
| RPS3A | TSPO | MYO1A | B2M | TSTD1 | RPS19 |
| PCK1 | COX6C | CDHR5 | NBL1 | UBC | QTRT1 |
| GSTA1 | RPL18 | SLC44A4 | ALDH2 | PPP1R1B | IFITM3 |
| RPL26 | DUSP1 | DHRS11 | GNAI2 | DDX5 | STXBP6 |
| STAP2 | HERPUD1 | ADIRF | C1QBP | ACTB | RPL14 |
| RPS3 | RPS6 | PPP1R1B | S100A4 | MLPH | CDX1 |
| RPL10A | TMSB10 | CKMT1B | MLEC | ETHE1 | RPL30 |
| SEPP1 | RPSA | MT1M | SUCLG2 | SH3BGRL3 | RPS9 |
| ATP5I | ARPC1B | HLA-C | MINOS1 | KIAA1324 | RHOC |
| FAM162A | DDX5 | ITM2B | S100A10 | KRT20 | RPL7A |
| UQCRC1 | ATP5G3 | PKIB | OAZ1 | HSPA1A | CDX2 |
| TCEA3 | UQCRH | USMG5 | PSAP | STRA13 | HLA-DRB1 |
| CHP2 | NDUFA1 | FAM195A | ATP5I | IFITM2 | IFI27 |
| RPL31 | ANXA5 | FCGBP | TIMM13 | CKB | RPS14 |
| ATP5D | TIMM13 | IFITM3 | SEPP1 | AC011523.2 | IFITM2 |
| RPL37A | HLA-B | MPC2 | HSPD1 | HLA-C | TXN |
| SRI | COX8A | S100A10 | RPL36 | UGT2B17 | RPL34 |
| HLA-DRB1 | CDX1 | MISP | UQCRFS1 | ENTPD8 | ISG15 |
| SELK | HLA-E | STAP2 | ATP5A1 | COX4I1 | HLA-DPB1 |
| TSPAN1 | SEPP1 | MGAT4B | ANXA5 | CST3 | IGJ |
| RPS23 | CDC42EP5 | SULT1A1 | HLA-C | RGCC | PFN1 |
| SOCS3 | SNX3 | PYCARD | S100A6 | B2M | AP003774.1 |
| RAB25 | CYC1 | ATP1A1 | SFN | RAB15 | GPR160 |
| MT1X | HLA-DRB5 | DNAJA1 | ATP5O | CD74 | H3F3B |
| COX6A1 | MRPL12 | ZG16 | AP1M2 | NDUFA1 | CD9 |
| NACA | HLA-DMA | ASL | MT2A | MT1E | CDHR1 |
| RPS29 | IFITM2 | NPM1 | RAC2 | ERI3 | HLA-DRB5 |
| GMDS | RPL28 | MPST | RGCC | TST | HLA-DMA |
| COA3 | RPL38 | MUC4 | GSN | ERN2 | S100A4 |
| UBC | RPS11 | UBC | STRA13 | TNNC2 | NUPR1 |
| RPL36 | DNAJA1 | SLC26A3 | ATP5J2 | NEURL1 | RPL18 |
| SPINT2 | HLA-A | SLC51B | CA2 | GSN | RPL27A |
| ITM2C | RPL37 | URAD | PEBP1 | LGALS3 | RPS15 |
| IFITM3 | COX7C | HLA-B | TYMP | CAMK2N1 | HLA-DRA |
| RPL13A | ETHE1 | S100A4 | PRDX2 | SMAGP | RPS15A |
| DNPH1 | HLA-DQB1 | HLA-E | H3F3B | IFITM3 | ANXA5 |
| ISG15 | MZT2B | CDH17 | SQRDL | TSPO | RPL38 |
| SLC25A3 | LITAF | CKMT1A | GJB1 | CAPN9 | TMEM54 |
| UGT2A3 | ISG15 | ANPEP | PBK | MALAT1 | FXYD5 |

TABLE 15B-continued

| | | | | | |
|---|---|---|---|---|---|
| SLC39A5 | TRABD2A | SLC25A5 | RPL37A | CDX2 | RPL24 |
| RPL12 | MZT2A | ABCC3 | UCP2 | TMEM176A | RPS29 |
| RPL29 | TSC22D3 | UQCRFS1 | TPM4 | IGLL5 | PSMB9 |
| FAM195A | TSTD1 | IGLL5 | CHCHD10 | SLC44A4 | ARSE |
| URAD | ARPC2 | DUSP1 | TMEM98 | TTC39A | RPSA |
| NDUFA10 | ECI1 | TRMT112 | ADIRF | COX7B | RPL11 |
| SQRDL | ETFB | IFITM2 | DDT | OAZ1 | CTSC |
| HSPD1 | MPC2 | SHD | AKR1B10 | COX8A | EEF1B2 |
| DDT | IGFBP2 | JUNB | S100A16 | JUNB | ARPC2 |
| IFITM2 | PLA2G2A | TSC22D3 | PLEKHJ1 | UQCRQ | CAPZB |
| NUPR1 | TST | ATP5E | LGALS3BP | MARCKSL1 | ZKSCAN1 |
| TPI1 | GSTP1 | TMSB10 | ARPC3 | SCNN1A | TYMP |
| NOX1 | HIST1H4C | TXNDC17 | NOX1 | LYPD8 | KIAA1324 |
| ACADS | SDCBP | HLA-DRA | EEF1B2 | COX7A2 | LRIG1 |
| ATPIF1 | DNPH1 | SQRDL | FAM162A | CTD-2547H18.1 | IMPDH2 |
| TSC22D3 | RPL31 | CIRBP | RPS14 | RASD1 | GLTSCR2 |
| TMSB10 | SOCS3 | SERINC2 | GGCT | CIRBP | RNF43 |
| RPS27A | S100A4 | DDT | RPS8 | KRTCAP3 | RPS27A |
| ANXA5 | PRDX2 | LDHB | TCEA3 | H1F0 | ATP1A1 |
| PRSS3 | RP11-357H14.17 | NDUFB7 | GMDS | NXPE4 | PSME2 |
| TFF3 | COX7B | CMBL | RPS6 | RPS24 | RPL23 |
| GOLM1 | HSPA1A | IFI27 | ETHE1 | RPL37A | RPS7 |
| RPS15A | RARRES2 | AOC1 | LAMTOR4 | PCBD1 | DYNLL1 |
| HLA-B | CLUH | RAB25 | MT-ND1 | YPEL5 | RPLP2 |
| MACROD1 | RPLP0 | KLF5 | RPL8 | HLA-E | LGR5 |
| PXMP2 | MPST | PCK1 | SH3BGRL3 | MUC1 | OAZ1 |
| TST | SPINT2 | SPINT2 | HLA-B | ITM2C | SOCS3 |
| COX7A2 | TXN | TCEB2 | IMPDH2 | ATP5G1 | EIF3D |
| AP1M2 | GSN | NDUFA2 | TUFM | KCNMA1 | SUCLG1 |
| TUBB | UQCRC1 | C2orf82 | PXMP2 | PRR15L | HSPA1A |
| IGLL5 | CES2 | HERPUD1 | NDUFA10 | RPL26 | URAD |
| GJB1 | RPL29 | S100A16 | LYZ | HLA-DRB1 | PTGDR |
| EIF1 | ATPIF1 | GSN | PHB | CYC1 | CHDH |
| ARPC1B | ST6GALNAC1 | HNRNPA1 | VIL1 | AGR3 | KCNN4 |
| CISD3 | MGAT4B | BCL2L15 | NDUFA1 | FFAR4 | PSMA7 |
| PKIB | MLEC | LAPTM4A | ACTR3 | AMN | TAGLN2 |
| GPR160 | REP15 | UGT2B17 | HINT1 | RPS29 | C19orf33 |
| MRPS33 | IFI27 | STARD10 | RAB25 | SCGB2A1 | EPHB2 |
| DCTPP1 | FBL | EID1 | IRF8 | KLF5 | ETHE1 |
| AKR1B1 | DNAJB1 | NDUFB3 | CHP2 | DUSP1 | PABPC1 |
| CDH17 | UQCR11 | MRPL12 | AKR1B1 | DNAJC12 | SELM |
| AKR7A3 | RNASE1 | ESRRA | FCGRT | MUC4 | ITM2B |
| HSPA1A | NDUFS5 | MT2A | RPS3 | ATP5J2 | IGLL5 |
| RPS14 | IMPA2 | PNRC1 | RPL26 | RAB27A | MPST |
| PLP2 | DDT | NDUFV1 | RPL10A | COX7C | UQCRH |
| RGS10 | MYL12A | GJB1 | HOXB7 | IL32 | UBC |
| MT-CYB | RHOA | MYO1D | MAOA | PSAP | TDGF1 |
| TKT | RPL11 | NAP1L1 | AMN | RP11-357H14.17 | PPAP2C |
| MDH2 | RPL10A | VIL1 | TSPAN1 | HLA-DRA | NQO1 |
| ITM2B | NDUFB7 | DDX5 | MT1M | HSPA8 | RARRES2 |
| HLA-DRA | RAB25 | TMC4 | MRPL12 | MUC5B | S100A6 |
| EEF1B2 | SUCLG1 | NDUFS7 | ITM2B | PLA2G10 | HLA-DQB1 |
| DUSP1 | FAM195A | SOCS3 | NPC2 | MPC2 | TSC22D3 |
| PSMB9 | MUC4 | MAOA | NXPE4 | DUSP2 | CDKN1A |
| AMN | SFN | KRT20 | UQCRC2 | TRABD2A | TGIF1 |
| AKR1B10 | MT1X | PLCD3 | SDC1 | DYRK4 | AP000344.3 |
| FBL | GCHFR | SFN | ACAT1 | KLK15 | C10orf54 |
| NDUFAB1 | MUC1 | ROMO1 | IFITM2 | LXN | SH3BGRL3 |
| DBI | FKBP1A | SSR2 | RPS21 | NDUFB4 | WNK2 |
| CBLC | DCTPP1 | CFTR | CENPW | BCAS1 | PSAP |
| GNB2L1 | RPS16 | LDHD | H2AFZ | CREB3L4 | AXIN2 |
| NDUFV1 | SLC44A4 | HLA-A | DNPH1 | MRPL27 | MYC |
| CST3 | PSAP | NDUFB10 | LAD1 | TYMP | RGCC |
| YBX1 | TSPAN1 | CD9 | GADD45B | HSPA1B | LGALS3 |
| MARCKSL1 | CD9 | SUCLG1 | IGFBP7 | CTSC | IFITM1 |
| RPS7 | NME1 | C19orf70 | TUBA1C | CLRN3 | CYBA |
| TIMM13 | NDUFS8 | MINOS1 | PRSS8 | TXN | EPB41L4A-AS1 |
| CYCS | C14orf2 | MT1H | RPSA | PDZK1IP1 | MYL12B |
| NDUFA9 | ATP6V0E1 | LAMTOR4 | RPS12 | CYBA | ZNF703 |
| RPS5 | CENPM | RNF186 | RP11-357H14.17 | HPCAL1 | MYB |
| TUFM | UBE2D3 | EIF4A1 | CNN2 | CMAS | ZFP36 |
| ATP5G2 | CA2 | PLAC8 | MRPS25 | LINC00261 | S100A16 |
| RARRES3 | JUNB | PLA2G10 | SLIRP | NDUFA4 | TMEM141 |
| RPL32 | LAPTM4A | SLC22A18 | UGT2B17 | GUCA2A | CA2 |
| PPIA | S100A11 | SELK | NDUFS8 | SLC25A5 | TMEM176B |
| CYSTM1 | RPL26 | PAPSS2 | PPT1 | KREMEN1 | SMAGP |
| JUNB | PXMP2 | HINT1 | HSPA1A | PNRC1 | ATP5G2 |
| SLC44A4 | CTSC | ATP5J2 | MDH2 | NEDD4L | PERP |
| DNAJB9 | RPL19 | SEPP1 | PRDX4 | DNAJB1 | CFD |
| RNF186 | VSIG2 | MVP | ATP5D | AOC1 | HSPA5 |

TABLE 15B-continued

| PSAP | NBL1 | GIPC1 | RPS29 | ISG15 | RPS11 |
|---|---|---|---|---|---|
| RPL18 | CENPV | HRCT1 | COX6B1 | FAM162A | S100A13 |
| CASP6 | ADIRF | MT1X | UQCR10 | CKMT1A | RPS13 |
| S100A13 | CDHR1 | HLA-DRB1 | RPL7A | C9orf152 | PTPRO |
| IMPDH2 | ITM2C | NDRG1 | SERINC2 | ATP2C2 | NACA |
| EEF2 | TMSB4X | ID1 | NDUFB7 | S100A10 | RPL15 |
| RPL13 | STAP2 | PTMA | MRPL16 | KLK3 | RAB25 |
| MTCH2 | RAB7A | EEF1D | HERPUD1 | C12orf57 | RPS20 |
| RPL14 | GMDS | ITM2C | RPL13 | SLC12A2 | RHOA |
| RPL3 | TMEM176B | PADI2 | TPM1 | DCTPP1 | MYL12A |
| RPL11 | FOS | NDUFB1 | SH3YL1 | TMSB10 | COPE |
| RPS9 | TRPM4 | DPP7 | HSD17B11 | GADD45B | VAMP8 |

| Enteroendocrine | Glial_cells | Inflammatory_fibroblasts | Fibroblast_pericytes |
|---|---|---|---|
| PCSK1N | CRYAB | VCAM1 | RGS5 |
| CRYBA2 | ALDH1A1 | NNMT | BGN |
| SCGN | GPM6B | LUM | CSRP2 |
| CHGA | PLP1 | SOD2 | NDUFA4L2 |
| PYY | SPP1 | CCL2 | MYL9 |
| SCG5 | S100B | TDO2 | MFGE8 |
| GCG | FXYD1 | COL3A1 | TINAGL1 |
| FEV | PRNP | C1S | TSC22D1 |
| MS4A8 | PMP22 | MFAP4 | COX4I2 |
| TTR | CLU | C1R | FRZB |
| CACNA1A | TUBA1A | MMP2 | ADIRF |
| PRDX5 | CD9 | CTSK | TPPP3 |
| HLA-C | MPZ | PDPN | HIGD1B |
| HOXB9 | SPARC | FBLN1 | COL18A1 |
| FXYD3 | NRXN1 | DCN | GPX3 |
| STARD10 | DKK3 | CTSC | SOD3 |
| RAB26 | CYR61 | RARRES2 | IGFBP7 |
| B2M | LGI4 | GPX3 | NET1 |
| LGALS4 | MATN2 | APOE | CALD1 |
| PHGR1 | TUBB2B | SELM | 4-Sep |
| RAB3B | ANXA2 | CALD1 | TPM2 |
| KRT18 | PMEPA1 | IFITM3 | SERPINI1 |
| MARCKSL1 | PCSK2 | TMEM176A | NOTCH3 |
| MDK | PEBP1 | CYGB | PGF |
| SLC29A4 | GFRA3 | DYNLT1 | HES4 |
| KRT8 | CAPS | COL1A2 | ACTA2 |
| EPCAM | CALM2 | ADAMDEC1 | MGP |
| ELF3 | MYOT | WARS | ISYNA1 |
| SST | L1CAM | TMEM176B | PDGFRB |
| HLA-B | S100A1 | COL6A2 | SPARC |
| TMSB4X | COMT | CFD | FAM162B |
| ARX | CD59 | GGT5 | HSPB1 |
| VIM | PLEKHB1 | NDN | H2AFJ |
| CLDN3 | TIMP3 | FOXF1 | BCAM |
| HLA-DPA1 | CDH19 | NINJ1 | PLXDC1 |
| C15orf48 | SMIM5 | PLAU | CD36 |
| FABP1 | TSPAN11 | LAP3 | CAV1 |
| RPL37A | NTM | EMILIN1 | DSTN |
| MLXIPL | C8orf4 | IGFBP7 | PRSS23 |
| COX6C | CNN3 | STMN2 | REM1 |
| C19orf77 | MAL | CXCL14 | LHFP |
| HLA-DRA | FIBIN | EPSTI1 | COL4A2 |
| NEUROD1 | FBLN2 | HAPLN3 | RGS16 |
| CPE | CCL2 | CD63 | LURAP1L |
| SMIM22 | CBR1 | GBP1 | TPM1 |
| TSPAN1 | FGFBP2 | SPARC | TAGLN |
| HLA-DRB1 | ARHGAP15 | COL1A1 | EGR1 |
| TFF3 | LGALS1 | PKIG | IFITM3 |
| IGJ | JUN | LGALS1 | HLA-C |
| HLA-DPB1 | PRKCDBP | SERPING1 | EHD2 |
| CLDN4 | SNCA | CFH | MEST |
| ITM2B | RPS6 | DMKN | PKIG |
| SEPP1 | IGFBP7 | SERPINF1 | LGALS1 |
| IFITM3 | NDRG2 | PAQR5 | STOM |
| RTN1 | COL9A3 | THY1 | A2M |
| SPINK1 | ST6GALNAC2 | SOD3 | STEAP4 |
| LDHA | TTR | COL6A1 | PTGIR |
| VWA5B2 | TMEM176B | CNOT4 | RPLP2 |
| CD74 | RPS2 | LINC01082 | PTK2 |
| RPL36 | FOS | TNFRSF1A | RBPMS |
| SOX4 | AP1S2 | PMP22 | EPS8 |
| SCT | WISP2 | GSTT1 | PPP1R14A |
| BEX2 | HES1 | SGCE | SRGN |
| ISL1 | VIM | TPM2 | COL3A1 |
| ANXA5 | RGS16 | A2M | GEM |

TABLE 15B-continued

| | | | |
|---|---|---|---|
| GSN | FEZ1 | TFPI | CRIP2 |
| RPS29 | SORBS2 | CLEC11A | ZFP36L1 |
| S100A14 | FCGR2B | FTH1 | ARID5A |
| HOXB8 | IFITM3 | MFGE8 | ARVCF |
| CHGB | RP4-792G4.2 | SPON2 | EPHX1 |
| GUCY2C | RHOB | GBP4 | HLA-A |
| FXYD5 | TMEM176A | C2 | ADAMTS1 |
| CLDN7 | ART3 | SFTA1P | PRKCDBP |
| HLA-DMA | EGR1 | LAPTM4A | MAP3K7CL |
| HLA-DRB5 | RPL8 | TIMP1 | NDUFAF4 |
| KRT19 | TUBB2A | CDH11 | C1R |
| PRDX2 | PDLIM4 | LY6E | CALM2 |
| SPINT2 | IL11RA | PLAT | C8orf4 |
| EIF1 | RPS19 | CEBPB | SDC2 |
| ETV1 | ANXA5 | APOL1 | TCF21 |
| HLA-E | SOCS3 | PROCR | ESAM |
| QPCT | RPS18 | TMEM205 | HEYL |
| KIF12 | PHLDA3 | GADD45G | KNOP1 |
| DDC | NRN1 | EVA1A | EFHD1 |
| LITAF | TSPAN15 | ICAM1 | SERPING1 |
| TMEM141 | MIA | FHL2 | RCAN2 |
| TMEM61 | COL18A1 | KLF6 | C1QTNF1 |
| MT-ND3 | RPLP1 | LGALS3BP | RBPMS2 |
| COX5A | SPARCL1 | RCN1 | SERPINH1 |
| IGLL5 | TPT1 | BST2 | NDRG2 |
| LY6E | C1orf198 | CCL8 | FXYD6 |
| MPC2 | SCCPDH | GALNT11 | COL6A1 |
| IFITM2 | S100A10 | IGFBP3 | GPRC5C |
| UCP2 | S100A4 | ECM1 | MAP1LC3A |
| NDUFB11 | RPL11 | CYR61 | RERG |
| COX6B1 | RASSF4 | F3 | GUCY1B3 |
| HEPACAM2 | TNFAIP6 | HSD11B1 | ASPN |
| HLA-A | SGCE | CEBPD | EPAS1 |
| COX4I1 | COL1A2 | IGFBP6 | CTSF |
| CXXC4 | NNMT | EFEMP2 | UBA2 |
| KIAA1324 | CADM4 | SEPP1 | GUCY1A3 |
| TPH1 | TAX1BP3 | PRR24 | RPS14 |
| VAMP5 | RPL19 | COL18A1 | LRRC32 |
| ATP5G1 | RPS3 | NAB2 | MSC |
| RPS9 | TFAP2A | SCARA5 | NR2F2 |
| MT-ND4 | RCAN1 | TNFAIP6 | LGALS3BP |
| SLC25A6 | IER2 | TNIP2 | ANGPT2 |
| MT-ND1 | MYL9 | TCF21 | CD151 |
| ERI3 | RPS14 | PRR16 | SORBS3 |
| ZFP36 | GPNMB | IFI35 | MCAM |
| S100A11 | TUBA1B | PTGIR | COL1A2 |
| RPS14 | GPX3 | BRCC3 | GNG11 |
| NPC2 | FAM210B | EID1 | PTMS |
| PCBD1 | ID3 | POSTN | MYH11 |
| RPS21 | CADM2 | PSMA2 | RNASET2 |
| CKB | GATM | APOC1 | RPLP1 |
| ATP5G2 | HSPB2 | CXCL1 | THY1 |
| GPBAR1 | RHOC | S100A13 | TGFBI |
| SELENBP1 | RPLP2 | CD302 | COL6A2 |
| NDUFA3 | RPL18 | RBP1 | ASAH1 |
| SMIM6 | NGFR | EMP3 | PLOD2 |
| RPS11 | HSPA2 | BSG | RARRES2 |
| KLK1 | ASPA | SPG20 | EFEMP1 |
| BAIAP3 | FST | TNFRSF11B | SOCS3 |
| RPS2 | MARCKS | UBE2L6 | RPS18 |
| RPS18 | KCNMB4 | IL7 | RPS19 |
| RPL12 | SBSPON | PSME2 | LBH |
| MYL12A | PSAP | SCT | SELM |
| TM4SF5 | OLFML2A | IL11 | NEXN |
| CADPS | RPL10 | SRGN | CDS2 |
| C21orf58 | SEPP1 | IGJ | GADD45B |
| DNAJC12 | C1S | ARID5B | COX7A1 |
| CTSC | RPL13A | EDEM2 | FKBP7 |
| PPT1 | CXXC5 | PSMA4 | HLA-B |
| RARRES1 | S100A6 | TAP2 | CD248 |
| RPS3 | EMP2 | IFI6 | PTRF |
| DNAJA1 | RPL13 | FBLIM1 | F2R |
| SNX3 | MXRA8 | COL5A2 | MRVI1 |
| NGFRAP1 | SERPING1 | FOSB | NFASC |
| ISG15 | RPS4X | ATP5E | PPIL4 |
| CDX1 | RPL31 | PCOLCE | STK16 |
| RPL38 | RPL28 | COL14A1 | SMDT1 |
| C12orf75 | SRGN | ETHE1 | NF2 |
| TAX1BP3 | FGL2 | CDK2AP2 | ATF3 |
| RPS8 | TBCB | IFITM2 | APOE |

TABLE 15B-continued

| | | | |
|---|---|---|---|
| PPP1R1B | ENTPD2 | ANXA5 | FLNA |
| LYZ | SELM | TRIM47 | TUBA1A |
| HMGCS2 | PHLDA1 | TSPAN4 | RRAD |
| PAM | EID1 | PDGFRA | TRIB2 |
| PLA2G12A | NGFRAP1 | ISG15 | OAZ2 |
| ACTB | ANGPTL7 | CD276 | RPL19 |
| SPINK4 | RPS8 | ADM | HRC |
| IFITM1 | RPL26 | APH1A | HCFC1R1 |
| COX8A | JUNB | IL34 | HEY2 |
| IGFBP2 | SLITRK6 | FILIP1L | C11orf96 |
| TSTD1 | RPS12 | MAD2L2 | LAPTM4A |
| LYPD8 | RPL15 | ADD3 | RPL27A |
| RPSA | RPL12 | TAGLN2 | RPL11 |
| C4orf48 | SLC22A17 | PHGR1 | ARHGEF17 |
| HLA-DQB1 | RERG | SQSTM1 | CACNA1H |
| GPX2 | PCBP4 | PLAC9 | TGFB1I1 |
| MLXIP | CADM1 | MESDC2 | COTL1 |
| LAP3 | RPS23 | NR2F1 | PLEKHA4 |
| ATP5E | ATF3 | SERPINH1 | RPS13 |
| HSPA1A | RPS27A | NUBP2 | GULP1 |
| AGR2 | ITPR1 | LAMA4 | PARM1 |
| TNNC1 | LGALS3BP | CYB5R1 | OLFM2 |
| TPPP3 | FSTL3 | TSPAN9 | RPS5 |
| SOCS3 | RPS5 | SEC63 | RASL12 |
| MT-ATP6 | FAU | DKK3 | S100A10 |
| QTRT1 | RPL32 | F10 | RPS6 |
| HERPUD1 | ZFP36L1 | AGT | ITGA7 |
| ETFB | SOD1 | COX5B | DOCK7 |
| MRPL41 | SERTAD1 | BBIP1 | ANGPT1 |
| CD55 | RPS16 | TNIP1 | CD74 |
| PEMT | PCMT1 | COTL1 | CLMN |
| PRSS3 | RARRES2 | IFIT1 | ENTPD3 |
| C10orf54 | ITGB1BP1 | IFITM1 | RPL36 |
| CKMT1A | RPLP0 | PTGDS | MAB21L2 |
| TCEA3 | CTNNAL1 | CD40 | ILK |
| TYMP | RPS20 | ALDH1A3 | COASY |
| S100A4 | HSPA1A | ACP5 | RPL28 |
| PSMB9 | YWHAE | NUPR1 | MSRB3 |
| RPL18 | CST3 | GSN | CYGB |
| RPS15 | RPS9 | OS9 | PDE1A |
| MT1G | SLC15A3 | MRFAP1 | FHL2 |
| RPL32 | CLIC4 | CLEC2B | CCL2 |
| PIGR | DYNLL1 | ARHGDIB | ZNF580 |
| MT-CO3 | RPS15A | GNG11 | CASC3 |
| CUTA | RPSA | NUMA1 | SH3BGRL3 |
| KIAA1456 | MT2A | PPAP2B | HLA-F |
| CTSD | S100A16 | LGALS4 | TMEM98 |
| RAC1 | WDR86 | SYPL1 | RRAGA |
| QDPR | DLX2 | FBN1 | LINC00152 |
| C19orf45 | GSN | FABP1 | LGI4 |
| RPL13 | LAMP1 | TMEM119 | MXRA8 |
| WFDC2 | ID4 | MMP3 | GPI |
| HSPB1 | POLR2F | ATPIF1 | 10-Sep |
| RPL31 | RXRG | S100A3 | MYLK |
| CD59 | SECISBP2L | C1RL | CCDC146 |
| OCIAD2 | RPS7 | AKR1B1 | PTP4A3 |
| KIAA1377 | TMOD2 | HTRA3 | NNT-AS1 |
| CENPV | RPL6 | NBL1 | ARHGAP29 |
| EMC10 | SH3BGRL3 | SLC9A3R2 | FILIP1 |
| PLAUR | DEPDC7 | TYMP | SCN4B |
| DNAJB9 | ERBB3 | PUS3 | FOS |
| RPL37 | PON2 | EZR | RPS15 |
| EPHB3 | STARD13 | PRKCDBP | MOCS1 |
| GADD45B | RPL23A | ANG | PPP1R15A |
| HIST1H4C | SCD | OLFML3 | EPC1 |
| SERINC2 | GRAMD3 | CXCL6 | FXYD5 |
| CTSS | AHNAK | GPX8 | VIM |
| URAD | CDC42EP1 | CPQ | SERTAD3 |
| RGS2 | IFIT3 | CCL13 | RPL8 |
| NDUFA11 | RPL27A | TNFRSF12A | ID3 |
| ATP6AP2 | RPL5 | PGRMC1 | HN1 |
| NUDT16L1 | C1R | PSMB9 | EFEMP2 |
| RPL27A | ST3GAL6 | MDK | LSP1 |
| NFASC | ANK3 | PUSL1 | C1QTNF2 |
| RGS10 | RBMS1 | MYL9 | HOXB-AS1 |
| RPS12 | RPS13 | EPCAM | TMC4 |
| NPDC1 | PLSCR4 | PTGES | PLEKHH2 |
| RP11-279F6.1 | MAPRE2 | CAPG | C1S |
| GCHFR | CADM3 | AGTRAP | C1orf54 |
| RPS4X | IER3 | VAMP5 | IFIT1 |

TABLE 15B-continued

| | | | |
|---|---|---|---|
| SYT7 | DST | CD320 | IRF1 |
| GRN | RPL4 | RAB13 | HSPA2 |
| RASD1 | PFN1 | TLCD1 | DDX5 |
| CCDC24 | RTN4 | MEG3 | CDK19 |
| RPLP2 | TIMP4 | TMEM100 | LIG1 |
| UQCR11 | TALDO1 | RFK | CTDSP1 |
| COX5B | SH3BGR | SAMD11 | TYROBP |
| RHOA | FADS3 | CTC-276P9.1 | SDHD |
| ANG | PHLDB1 | HOXA10 | RPS3 |
| RPL28 | ZFYVE21 | UGCG | PDLIM2 |
| MT-CO2 | IL32 | CTSL | CYP4X1 |
| ARPC1B | ST3GAL4 | LEPROT | NUP85 |
| ISYNA1 | H3F3B | C12orf44 | TPD52L2 |
| TMEM54 | TMEM59L | WFDC1 | CARKD |
| COX7C | UBR4 | ARHGAP24 | CBWD1 |
| TPM4 | UBA52 | CLDN3 | SPRED1 |
| GNG4 | LHPP | TRPA1 | MRPS6 |
| PDZK1IP1 | CTNNA1 | HAPLN1 | ISCA1 |
| NDUFB4 | ZNF428 | TRAFD1 | SLC25A4 |
| WNK2 | ARMCX1 | INTS12 | FRMD3 |
| SAT1 | CMTM5 | TPST1 | EBF1 |
| ANXA2 | TNFRSF12A | PAPPA | TIMP1 |
| TIMM13 | RPL29 | FAM105A | LPL |
| UQCR10 | RPS29 | COPA | GNAI1 |
| PRR15L | ARHGAP12 | EHD2 | RSBN1L |

TABLE 15C

| Myofibroblasts | Villus_fibroblasts | Crypt_fibroblasts_(hiFos) | Crypt_fibroblasts_(loFos) | T_cells |
|---|---|---|---|---|
| ACTA2 | NSG1 | ADAMDEC1 | CFD | DCN |
| TAGLN | F3 | CFD | DCN | LUM |
| MYL9 | FRZB | DCN | ADAMDEC1 | CFD |
| TPM2 | CXCL14 | C1S | FBLN1 | ADAMDEC1 |
| PDLIM3 | DMKN | LUM | LUM | C1R |
| ACTG2 | VSTM2A | FBLN1 | MFAP4 | C1S |
| HHIP | POSTN | HAPLN1 | C1R | FBLN1 |
| SOSTDC1 | BMP4 | CCL8 | APOE | TCF21 |
| MYLK | ENHO | C1R | C1S | APOE |
| FHL1 | PLAT | MFAP4 | SOD3 | COL3A1 |
| HSD17B6 | MMP2 | APOE | TCF21 | CXCL12 |
| MYL6 | EDNRB | CTSC | COL1A2 | MFAP4 |
| TPM1 | HSD17B2 | CCL2 | ABCA8 | GPX3 |
| MYH11 | COL6A1 | COL1A2 | COL3A1 | HAPLN1 |
| DSTN | COL6A2 | TCF21 | CTSC | CFH |
| CNN1 | SDC2 | COL3A1 | CYGB | SERPINF1 |
| NDUFA4 | AGT | CYGB | CXCL12 | COL1A2 |
| TGFB1I1 | TMEM176B | ABCA8 | CXCL14 | CCL2 |
| NPNT | IGFBP3 | SOD3 | CTSK | PPAP2B |
| DCN | NBL1 | STMN2 | TMEM176B | PLAC9 |
| PDLIM7 | CYGB | CXCL14 | GPX3 | PTN |
| PRKCDBP | FENDRR | PROCR | RBP1 | PTGDS |
| WFDC1 | RARRES2 | GPX3 | PROCR | IGFBP7 |
| CXCL14 | FOXF1 | CXCL12 | COL6A2 | PROCR |
| COL3A1 | MFGE8 | A2M | PLAC9 | COL6A2 |
| COL1A2 | CAV1 | RBP1 | CCL8 | CTSC |
| SMTN | ECM1 | COL1A1 | PTN | CXCL14 |
| FLNA | TPM2 | SERPINF1 | IGFBP7 | SOD3 |
| HHIP-AS1 | MFAP4 | PTN | LINC01082 | CYGB |
| C1S | PDGFRA | CCL13 | CALD1 | CCL13 |
| SELM | COL3A1 | TMEM176B | A2M | CCL8 |
| PPIC | COL1A2 | CTSK | TMEM176A | IFITM3 |
| LUM | GPX3 | LINC01082 | COL1A1 | PMP22 |
| PPP1R14A | C1S | PPAP2B | SERPINF1 | CCL11 |
| ADAMDEC1 | LGALS1 | GSN | IFITM3 | RARRES2 |
| COL1A1 | CALD1 | CFH | CFH | GSN |
| TM4SF1 | TMEM119 | IGFBP7 | ADH1B | CD2 |
| COL6A2 | FAM150B | CCL11 | SERPING1 | COL14A1 |
| NBL1 | WFDC1 | CLEC11A | CCL2 | ADH1B |
| NEXN | APLP2 | ADH1B | CLEC11A | SCARA5 |
| LGALS1 | COL1A1 | GGT5 | HAPLN1 | A2M |
| C1R | BMP5 | PLAC9 | GGT5 | COL1A1 |
| ILK | PDLIM1 | SCARA5 | RARRES2 | FXYD1 |
| KCNMB1 | TMSB4X | VCAM1 | SCARA5 | DKK3 |
| SPARC | SCPEP1 | DKK3 | CCL13 | CALD1 |
| CSRP1 | PDGFD | COL6A2 | LGALS3BP | CD3D |
| MFAP4 | MMP11 | PMP22 | GSN | PPAP2A |

TABLE 15C-continued

| | | | | |
|---|---|---|---|---|
| CALD1 | MMP1 | TMEM176A | MMP2 | ADAM28 |
| IGFBP7 | SPARC | SEPP1 | DKK3 | TMEM176B |
| LINC01082 | TMEM176A | MATN2 | CCL11 | CLEC11A |
| HSPB1 | IGFBP7 | PPAP2A | PMP22 | CTSK |
| APOE | PROCR | CYR61 | PPAP2B | EFEMP1 |
| POSTN | LGALS3BP | CALD1 | HAAO | PCOLCE |
| APOC1 | PPP1R14A | ADAM28 | ADAM28 | CD69 |
| FBLN1 | PKIG | RARRES2 | CD63 | EMILIN1 |
| TMEM176B | IGFBP6 | MMP2 | PCOLCE | STMN2 |
| SPARCL1 | TRPA1 | BMP4 | BMP4 | MMP2 |
| CAV1 | TIMP1 | SERPING1 | COL6A1 | GGT5 |
| LMOD1 | MYL9 | VIM | SEPP1 | HAAO |
| AOC3 | MRPS6 | SGCE | SPON2 | NDN |
| CFD | PCOLCE | EFEMP1 | SPARC | SPON2 |
| RBPMS | SLITRK6 | PCOLCE | PPP1R14A | RBP1 |
| TCEAL4 | C1R | IFITM3 | PPAP2A | CD52 |
| IFITM3 | IFITM3 | ECM1 | FHL2 | THY1 |
| TUBB6 | TCF21 | LTBP4 | LGALS1 | BMP4 |
| MMP2 | SERPINF1 | PTGDS | PTGDS | VCAN |
| MXRA8 | TGFBI | LAPTM4A | MFGE8 | GNG11 |
| CD151 | REEP2 | SPARC | EMILIN1 | SCT |
| TCF21 | SOX6 | CD63 | VIM | PPP1R14A |
| ACTN1 | TSLP | COL6A1 | PRKCDBP | ABCA8 |
| PDIA5 | CLEC11A | PPP1R14A | THY1 | LAPTM4A |
| PMP22 | INSC | SPON2 | SELM | TMEM176A |
| EFEMP2 | CTC-276P9.1 | HAAO | GNG11 | LGALS1 |
| LGALS3BP | SRGN | FOS | LAPTM4A | LTB |
| CD9 | RBP4 | SNAI2 | LTBP4 | LINC01082 |
| EMILIN1 | LTBP4 | NNMT | TIMP1 | PAMR1 |
| TUBA1A | PITX1 | FHL2 | STMN2 | PLTP |
| GSN | LAPTM4A | GNG11 | EFEMP2 | IGFBP6 |
| MRGPRF | EMILIN1 | MEG3 | SNAI2 | NDUFA4L2 |
| MFGE8 | MAGED2 | TM4SF1 | ECM1 | VIM |
| COL6A1 | GLP2R | FABP4 | SGCE | SELM |
| UBE2E3 | LAMA4 | EMILIN1 | VCAM1 | CIRBP |
| C9orf3 | A2M | LGALS3BP | IL34 | FABP4 |
| PTMS | PROM1 | EFEMP2 | IGFBP6 | S100A4 |
| SERPINF1 | RGS10 | CXCL1 | SPARCL1 | QSOX1 |
| JUNB | LHFP | LGALS1 | NOVA1 | RGCC |
| RCN1 | BAMBI | PLAT | FBLN5 | FBLN5 |
| FXYD1 | RBPMS | IGFBP6 | NGFRAP1 | PLAT |
| CES1 | ANXA5 | SOCS3 | PLTP | MEG3 |
| NUPR1 | AKR1B1 | TPM2 | MATN2 | SRGN |
| RARRES2 | BSG | SMPDL3A | FXYD1 | TIMP1 |
| SRGN | PRR16 | NDN | EDIL3 | GSTT1 |
| FN1 | MAP1B | SELM | TPM2 | EMID1 |
| SDC2 | GADD45G | FXYD1 | SFTA1P | SERPING1 |
| FOXF1 | TSPAN4 | C2 | TSPAN4 | CD3E |
| PCOLCE | S100A13 | PLTP | MEG3 | ANXA1 |
| SERPING1 | GLT8D2 | VCAN | EPHX1 | LTBP4 |
| SCPEP1 | HSPB1 | NGFRAP1 | QSOX1 | CCL5 |
| AC131025.8 | C11orf96 | QSOX1 | MYL9 | SPARCL1 |
| SGCE | EFEMP2 | SDC2 | SRGN | MXRA8 |
| MIR145 | FGF9 | EPHX1 | TM4SF1 | IFI27L2 |
| CRYAB | EID1 | GSTM3 | EFEMP1 | FN1 |
| LTBP1 | PTMS | SPARCL1 | PLAT | GSTM3 |
| CRIP2 | COL5A1 | TIMP1 | OLFML3 | MYL9 |
| DUSP1 | MXRA8 | FHL1 | GSTM3 | PHGR1 |
| CERCAM | FKBP10 | SRGN | CCDC80 | CD63 |
| TPPP3 | PTGDR2 | COLEC11 | DPT | SEPP1 |
| SH3BGRL | CPE | EDIL3 | RAB13 | TPM2 |
| VIM | SGCE | IL34 | ITIH5 | GATA3 |
| CKB | TNC | PRKCDBP | NNMT | TFPI |
| NGFRAP1 | TAGLN | C11orf96 | SDC2 | LEPROT |
| PTCH1 | DCN | ARHGDIB | FSTL1 | C16orf89 |
| SOD3 | TXNL1 | FBLN5 | LOXL1 | SGCE |
| COL4A2 | EMID1 | SFTA1P | FABP4 | LGALS3BP |
| LRRC17 | CRISPLD2 | EID1 | S100A13 | LCK |
| GNG11 | SRPX2 | FXYD6 | COL14A1 | DPT |
| CYBA | C1orf21 | MYL9 | NDN | SNAI2 |
| RBP1 | NDN | THY1 | MXRA8 | ZFP36L1 |
| IER2 | ISCU | LINC01116 | UBE2E3 | IL32 |
| CPQ | CD9 | TFPI | FHL1 | TSC22D3 |
| MAP1LC3A | ACP1 | LOXL1 | TAC3 | LAMB1 |
| BMP5 | PALLD | MXRA8 | IFITM2 | MATN2 |
| OSR1 | F2R | IRF1 | EID1 | C6orf48 |
| AKR7A2 | BST2 | PITX1 | PITX1 | SPARC |
| NDN | CPM | MFGE8 | C2 | CNBP |
| PKIG | SELM | UBE2E3 | LRP1 | NANS |
| S100A13 | PTN | FGF7 | NUPR1 | FSTL1 |

TABLE 15C-continued

| | | | | |
|---|---|---|---|---|
| HMG20B | WNT5B | SERPINH1 | VKORC1 | EEF1D |
| RP11-332H18.4 | SERPING1 | OLFML3 | APOC1 | AEBP1 |
| CFH | RBP1 | ARID5B | FKBP10 | SERPINH1 |
| GAS6 | FBLN1 | PPIC | FXYD6 | NNMT |
| FOSB | NDUFA4L2 | RAB13 | LAMA4 | WNT2B |
| LPP | PCDH18 | CFL1 | PPIC | C11orf96 |
| PALLD | APOD | JUNB | DMKN | PDPN |
| TTLL7 | KREMEN1 | KCNS3 | EMID1 | GZMK |
| IGFBP5 | TUBA1A | S100A13 | NDUFA4L2 | ELANE |
| LAPTM4A | ID1 | CEBPD | PLAU | TRIM22 |
| WLS | ADM | TSPAN4 | FOXF1 | CLEC14A |
| EDNRB | PRKCDBP | APOC1 | FN1 | PITX1 |
| FAM127A | IFITM1 | LAMA4 | GLT8D2 | SLC25A5 |
| ARHGDIB | CXCL12 | C6orf48 | COL5A1 | CXCL1 |
| CSRP2 | TSHZ2 | ZFP36L1 | CTC-276P9.1 | COL6A3 |
| TIMP2 | LRRN4CL | GLT8D2 | COLEC11 | IDH2 |
| MAMDC2 | PTCH1 | NDUFA4L2 | CFL1 | COLEC11 |
| P2RY14 | LAMB1 | EMID1 | EHD2 | COX5A |
| S100A4 | HHIP | CCL7 | RBPMS | MXRA5 |
| TRIP6 | VIM | SRPX | COL18A1 | EDIL3 |
| SH3BGRL3 | NNMT | TIMP3 | SCPEP1 | EFEMP2 |
| CBR1 | CIRBP | ANGPTL4 | SMPDL3A | PPIC |
| MMP14 | CAPZB | SCPEP1 | WFDC1 | TDO2 |
| SEPW1 | CD63 | DPT | DUSP1 | C4orf3 |
| MFAP5 | TGFB1I1 | ADM | COX5A | VPS25 |
| FENDRR | IL32 | GADD45B | FOSB | FNDC1 |
| CALU | PLK2 | NUPR1 | C6orf48 | CYP7B1 |
| TMEM176A | TBX2 | LRP1 | SERPINE2 | SPRY1 |
| CTSK | ANGPTL4 | CYBA | FAM127A | PCDH7 |
| C1QTNF2 | PCSK6 | RAB34 | TMEM119 | ZFP36L2 |
| SNAI2 | TSPAN2 | PRNP | GSTM5 | DMKN |
| COL4A1 | WLS | EGR1 | CPQ | ALDOA |
| CD63 | AEBP1 | ZFP36 | RAB34 | COL6A1 |
| COX7A1 | SCUBE2 | PROS1 | AKR1B1 | HTRA3 |
| LOXL2 | LANCL2 | ITIH5 | CD81 | PRKCDBP |
| CYB5R3 | LOXL2 | CD81 | SLC9A3R2 | CXCR4 |
| FOS | FIP1L1 | CIRBP | TNFAIP6 | KRT8 |
| IL32 | RTN4 | FOXF1 | FILIP1L | KLRB1 |
| RPL28 | ADH5 | CCDC80 | VCAN | PHLDA1 |
| CFL2 | TM4SF1 | NEGR1 | TGFB1I1 | FGF7 |
| LTBP4 | C7orf50 | COX5A | COL15A1 | LAMA4 |
| EHD2 | IL1R1 | NOVA1 | ATRAID | TAC3 |
| ITM2C | EMP3 | FN1 | TFPI | COL18A1 |
| STMN2 | CYBA | CPQ | WNT2B | SPINT2 |
| BSG | CAV2 | ID3 | SERPINH1 | THNSL2 |
| VCAN | TMEM100 | FKBP10 | PRNP | NEXN |
| LAMB1 | MAP1LC3A | BST2 | CTSF | RNASE1 |
| MAP1B | IFI27 | WFDC1 | MDK | FXYD6 |
| VCL | SEMA4D | TDO2 | ACTA2 | LOXL1 |
| P2RX1 | PXDN | DMKN | CST3 | CD81 |
| WNT2B | HAAO | COL5A2 | KLF6 | TMEM66 |
| PARVA | NPY | COL14A1 | TGFBI | CRIP2 |
| S100A6 | RGCC | PGRMC1 | TIMP3 | TIMP3 |
| ECM1 | SGCB | PHGR1 | ABCA6 | H3F3B |
| TCEAL1 | FHL1 | SH3BGRL3 | FGF7 | IRF1 |
| LAMA4 | TPBG | ANXA5 | CYBRD1 | ECM1 |
| VKORC1 | NUPR1 | EHD2 | MMP23B | IFI27 |
| NME4 | TBX3 | TAC3 | EVA1A | DDR2 |
| TMEM98 | RGS1 | VASN | PTMS | SLC9A3R2 |
| RPLP2 | LEPROT | SLC25A5 | TNFRSF1A | SGCA |
| TIMP1 | GNAI1 | AEBP1 | C7 | CD74 |
| CD74 | MSC | RBPMS | RP11-14N7.2 | COL15A1 |
| PPP1CC | PTX3 | CCNI | RGCC | SFTA1P |
| A2M | ACTA2 | CNBP | CDH11 | CDK2AP2 |
| CTSS | CD74 | SPRY1 | FGFR4 | PTGER2 |
| PTS | LRP1 | SEC11C | BST2 | FABP1 |
| PPAP2A | TMEM98 | PLAU | IGFBP5 | TNFAIP3 |
| TTC3 | PLBD1 | IFITM2 | CXCL1 | FGFR2 |
| ADH5 | CPQ | 4-Sep | CP | FHL1 |
| MCL1 | VASN | GSTM5 | C16orf89 | KRT18 |
| FAM105A | AMPD3 | ABCA6 | LINC01116 | RND3 |
| MAGED2 | IGFBP5 | FILIP1L | CIRBP | SCPEP1 |
| NKX2-3 | MXRA5 | MT-ND2 | SAMD11 | MAPK10 |
| RAB34 | PHGR1 | LEPROT | SAT1 | LY6E |
| SGCA | STMN2 | FSTL1 | SH3BGRL3 | CLEC2B |
| CCDC107 | GULP1 | MT-CO2 | MIR497HG | FTH1 |
| SERPINH1 | CCDC68 | TUBA1A | PHGR1 | NUPR1 |
| FILIP1L | SPON2 | HES1 | HTRA3 | CD5 |
| MINOS1 | CH25H | CSF1 | AEBP1 | IL34 |
| AEBP1 | PLAU | CDK2AP2 | TMEM9 | EMP3 |

TABLE 15C-continued

| | | | | |
|---|---|---|---|---|
| NEO1 | MRVI1 | CDH11 | S100A4 | NUDT16L1 |
| EID1 | CD151 | PFN1 | SCT | CCDC80 |
| PDGFC | CNTFR | HTRA3 | MXRA5 | IL1R1 |
| DCTN2 | COL6A3 | RND3 | CNBP | EVL |
| CBR3 | PDLIM4 | HSPA1A | IFITM1 | RP11-14N7.2 |
| RCAN2 | CYTL1 | JUN | PDLIM3 | CSF1 |
| RERG | COL4A5 | MT-ND4 | KCNS3 | GNAO1 |
| CLEC11A | HMGB1 | CST3 | ISLR | LRP1 |
| FSTL1 | ST5 | HINT1 | HSPA8 | ITIH5 |
| C2 | GADD45B | TNFAIP6 | PFN1 | MFGE8 |
| FHL3 | ID3 | CHL1 | BDH2 | DUSP2 |
| TGM2 | CYR61 | ADAMTS1 | ELANE | FHL2 |
| MORF4L2 | CTSF | ACTA2 | HINT1 | TRAT1 |
| TMEM47 | CTSK | SERPINE2 | WARS | FARP1 |
| ISG20 | ENPP6 | C16orf89 | COX7A1 | MRPL23 |
| ACTB | LUM | MYL12A | PAMR1 | TM4SF1 |
| CD99 | HOXA10 | RCN1 | LY6E | LAMA2 |
| EFEMP1 | SERPINH1 | IGJ | CRYAB | GZMA |
| ZYX | FILIP1L | TMEM98 | MYL12A | PAM |
| SAMD11 | SEC62 | ELANE | SPRY1 | RNASET2 |
| SSPN | GPC1 | MAMDC2 | IL6ST | GPC6 |
| RBBP7 | ARPC1B | CTC-276P9.1 | ANGPTL1 | IL7R |
| CPED1 | PDPN | CD302 | GAS6 | IFITM2 |
| RGS10 | TUSC3 | PCDH18 | NENF | FBN1 |
| CREB3 | RP11-332H18.4 | FAM92A1 | RUNX1T1 | ACTA2 |
| DDAH2 | C12orf57 | GRK5 | CYBA | RARRES3 |
| SEPP1 | NOVA1 | WNT2B | ANXA1 | ADM |
| MIR143HG | WFS1 | MDK | NEGR1 | FKBP10 |
| NENF | NGFRAP1 | POSTN | CYCS | COL5A1 |
| PITX1 | CDH11 | ISLR | COL6A3 | CCDC127 |
| COL6A3 | OLFML3 | EPHA7 | SLC25A5 | GAPDH |
| KANK2 | ZFP36L1 | ANGPTL1 | PAM | MGST1 |
| NUDT4 | PDE1A | PHLDA1 | IL32 | VKORC1 |
| ARHGEF25 | ECHDC2 | HSD11B1 | CRIP2 | HSD11B1 |
| MMP23B | BRK1 | FTH1 | TDO2 | DUSP23 |
| THYN1 | HLA-A | RGCC | COL4A2 | CHCHD10 |
| RGS1 | TCF4 | IL6ST | RGS1 | SSBP3 |
| ARPC1B | SEC11C | SMIM10 | PCDH18 | NGFRAP1 |
| RCN3 | COL4A6 | TMEM150C | P4HA2 | ARHGAP24 |
| SQRDL | RCAN2 | CTSF | CYB5R3 | EID1 |
| APCDD1 | SCARB2 | ATP6AP2 | TSTD1 | ID4 |
| RP11-532F6.3 | MMP14 | AKR1B1 | EEF1D | C11orf58 |
| NDUFB9 | SH3BGRL3 | SVEP1 | MT-CO2 | CREG1 |

| Macrophages | Dendritic_cells | Mast_cells | Cycling_monocytes | Tolerogenic_DCs |
|---|---|---|---|---|
| FTL | CST3 | TPSAB1 | FTL | SNX3 |
| C1QB | CLEC10A | VWA5A | PSAP | CPVL |
| C1QC | HLA-DPB1 | LTC4S | MS4A6A | IDO1 |
| PSAP | HLA-DPA1 | C1orf186 | GPX1 | CST3 |
| C1QA | HLA-DQB1 | CPA3 | AIF1 | CLEC9A |
| CTSB | FCER1A | SLC18A2 | C1QA | LGALS2 |
| CD68 | HLA-DQA1 | HPGDS | C1QC | C1orf54 |
| CTSD | HLA-DRA | MAOB | C1QB | HLA-DPB1 |
| TYROBP | HLA-DRB1 | HDC | CST3 | DNASE1L3 |
| SAT1 | CD74 | CLU | TYROBP | IRF8 |
| LGMN | AIF1 | NFKBIZ | IGSF6 | HLA-DPA1 |
| FCER1G | LST1 | RP11-354E11.2 | CD68 | CD74 |
| MS4A7 | IL1B | SAMSN1 | CTSB | HLA-DQB1 |
| MS4A6A | LYZ | GATA2 | DNASE1L3 | LSP1 |
| AIF1 | CPVL | ANXA1 | FCER1G | COTL1 |
| ACP5 | AMICA1 | GLUL | MS4A7 | HLA-DQA1 |
| MS4A4A | HLA-DMA | FCER1A | MS4A4A | HLA-DRA |
| DNASE1L3 | TYROBP | KRT1 | NPC2 | AIF1 |
| GPX1 | FCER1G | CAPG | LYZ | HLA-DQB2 |
| IGSF6 | SPI1 | CTSG | IL1B | HLA-DRB1 |
| FUCA1 | MS4A6A | PPP1R15A | VSIG4 | SPI1 |
| FCGRT | HLA-DQB2 | SLC45A3 | LST1 | LYZ |
| SEPP1 | HLA-DMB | HPGD | SDS | HLA-DOB |
| HLA-DMB | CFP | HS3ST1 | CTSD | HLA-DRB5 |
| NPC2 | HLA-DRB5 | GMPR | GRN | HLA-DQA2 |
| HLA-DPA1 | IGSF6 | KIT | CPVL | ACTB |
| STAB1 | LGALS2 | RGS13 | FGL2 | LST1 |
| HLA-DQA1 | PLAUR | CD9 | SPI1 | RGS10 |
| HLA-DPB1 | CD83 | FCER1G | HLA-DPB1 | BATF3 |
| RNASET2 | IFI30 | NFKBIA | SAT1 | CADM1 |
| LST1 | PLD4 | BTK | CD74 | MPEG1 |
| LYZ | CD1C | HSP90AB1 | HLA-DRB1 | ASB2 |
| HLA-DRA | MNDA | CD44 | HLA-DQA1 | C1orf162 |
| CD14 | COTL1 | MITF | HLA-DPA1 | PPT1 |

TABLE 15C-continued

| | | | | |
|---|---|---|---|---|
| HLA-DMA | GPX1 | SERPINB1 | RNASE6 | FGL2 |
| GPNMB | HLA-DQA2 | LMNA | FAM26F | S100A6 |
| HLA-DRB1 | ITGB2 | ADRB2 | PLAUR | HLA-DMB |
| PLA2G7 | SGK1 | VIM | CTSZ | BASP1 |
| APOC1 | GPR183 | TYROBP | HLA-DRA | CD83 |
| CD74 | FGL2 | SRGN | HLA-DRB5 | KIAA0226L |
| SDS | C1orf162 | IL1RL1 | RNASET2 | HLA-DMA |
| CTSS | SRGN | SDPR | PLA2G7 | SGK1 |
| LAPTM5 | FAM26F | FAM46A | SEPP1 | TMSB4X |
| CD163L1 | LY86 | BTG2 | CD14 | RGCC |
| RNASE6 | RNASE6 | ALOX5 | HLA-DQB1 | PLEK |
| VSIG4 | RGS2 | NSMCE1 | STAB1 | S100B |
| HLA-DQB1 | DNASE1L3 | CTNNBL1 | HLA-DMA | SERPINF2 |
| GRN | CTSH | MIR24-2 | LAPTM5 | ARPC2 |
| ADORA3 | CD1E | LEO1 | CLEC10A | SMCO4 |
| CTSZ | FCGR2B | SDCBP | ACP5 | ITGB2 |
| S100A11 | MS4A7 | PTGS1 | HLA-DMB | HCK |
| SPI1 | LAPTM5 | LAT2 | AP2S1 | CST7 |
| PLD3 | SAT1 | ALOX5AP | NCF4 | UCP2 |
| TREM2 | CD1D | FTH1 | S100A11 | WDFY4 |
| FOLR2 | C1QA | DDX5 | IGF1 | CPNE3 |
| CYBA | CXCL16 | AC020571.3 | A2M | TNNI2 |
| CST3 | ACTB | DNAJA1 | CCL3 | GLIPR1 |
| RNASE1 | RNASET2 | BACE2 | ITGB2 | DUSP2 |
| ATP6V1F | HCK | CD69 | SLC7A7 | PTPRE |
| CCL3 | CACNA2D3 | DUSP6 | CD300A | RNASET2 |
| SLC40A1 | CORO1A | MLPH | LGMN | ARPC1B |
| LIPA | MPEG1 | JUN | SLC40A1 | LY86 |
| GLUL | ARPC1B | IL1RAPL1 | TYMP | SLAMF8 |
| CSTB | VSIG4 | SIGLEC8 | C1orf162 | SLAMF7 |
| CPVL | BID | RAB27B | GLUL | C20orf27 |
| ASAH1 | STX11 | LAT | RGS10 | LIMD2 |
| VAMP8 | CTSS | UBB | VAMP8 | FLT3 |
| ATP6V0D2 | FTL | ACOT7 | SRGN | FAM49B |
| RENBP | SAMHD1 | STMN1 | P2RY6 | PARVG |
| CREG1 | GLIPR1 | FXYD5 | C1orf54 | CORO1A |
| CLEC10A | CSF2RA | EGR2 | MNDA | BID |
| FCGR2A | CD68 | ALDH1A1 | AMICA1 | GCSAM |
| FAM26F | LSP1 | NCOA4 | IFI30 | RAB32 |
| RGS10 | INSIG1 | GCSAML | CTSH | FAM26F |
| TMSB4X | IL8 | CD33 | FCGRT | CD9 |
| CTSL | NR4A3 | STX3 | CSF1R | LCP1 |
| NCF4 | ARPC3 | SVOPL | FCGR2A | ARHGDIB |
| AP2S1 | DUSP2 | ATP6V0A2 | TGFBI | CKS2 |
| LY86 | FAM110A | LAPTM4A | LGALS1 | SUSD3 |
| IGF1 | CD33 | HSP90AA1 | MPEG1 | PABPC1 |
| HLA-DRB5 | TMSB4X | CD63 | GPR183 | FKBP1B |
| FGL2 | C1QC | ANKRD28 | SERPINF1 | GSTP1 |
| AKR1B1 | CD86 | LAPTM5 | TBXAS1 | PPDPF |
| MALAT1 | RGS10 | EGR1 | IL8 | P2RY6 |
| AMICA1 | PHACTR1 | ARL5B | CTSS | FCER1G |
| APOE | PPDPF | CATSPER1 | APOC1 | NAP1L1 |
| IFI30 | AOAH | HSPH1 | RNF130 | CD48 |
| CD163 | PYCARD | KLRG1 | HCK | TYMP |
| ITGB2 | PTPRE | CLIC1 | ALOX5AP | LAPTM5 |
| HLA-DQB2 | ARHGDIB | TSC22D1 | CD36 | MT-ND2 |
| S100A9 | RNF130 | S100A4 | ADORA3 | ID2 |
| CD300A | PLEK | ATP6V1F | SIRPA | AMICA1 |
| UCP2 | TYMP | CTD-3203P2.2 | CYBA | AIM2 |
| CSF1R | GRN | SGK1 | PLD3 | CLNK |
| OAZ1 | NCF4 | RENBP | PDLIM1 | LGALS3 |
| GM2A | TBXAS1 | PLIN2 | RGS1 | IFI27 |
| PLAUR | C1QB | PTPN6 | GPNMB | CSF2RA |
| NPL | ARRB2 | ANXA2 | CD4 | VMO1 |
| HCK | IFI27 | FAM212A | RGS2 | DUSP4 |
| LILRB4 | UCP2 | FOSB | TIMP1 | ID3 |
| C1orf54 | ARL5B | ASAH1 | APOE | SAT1 |
| C5AR1 | DUSP1 | HSPA8 | OAZ1 | TLR10 |
| LGALS1 | CD48 | ASRGL1 | VIM | TYROBP |
| RNF130 | RHOG | LYL1 | ATP6V0B | MIR142 |
| CD209 | RGS1 | EIF4G2 | CORO1A | GPR183 |
| TTYH3 | NR4A2 | STXBP6 | HLA-DQA2 | TSPO |
| PRDX1 | NCF2 | TNFSF10 | CREG1 | MNDA |
| RAB42 | HCLS1 | GRAP2 | HLA-DQB2 | PFN1 |
| IL1B | ARPC2 | NFKBID | S100A9 | LGALS1 |
| FABP3 | PILRA | CSF2RB | PPT1 | GPX1 |
| MPEG1 | CD53 | RAC2 | LY86 | HSPA1A |
| CD36 | P2RY13 | NR4A1 | TXN | ACTG1 |
| SLC7A7 | CLEC4A | HSPA1B | EPCAM | CCND1 |
| NINJ1 | PPT1 | H3F3B | LILRB4 | CNN2 |

TABLE 15C-continued

| | | | | |
|---|---|---|---|---|
| C3AR1 | CHMP1B | SMYD3 | FUCA1 | LTB |
| CHMP1B | GPSM3 | MPP1 | FXYD5 | SAMHD1 |
| CAPG | ZNF385A | FAR2 | GNAI2 | NAAA |
| ADAP2 | ATF3 | LM04 | ADAP2 | ITM2C |
| OTOA | LITAF | SRSF5 | CSF2RA | HCLS1 |
| CFD | ZNF331 | ARHGDIB | LGALS4 | TACSTD2 |
| HSD17B14 | PARVG | EIF3D | NINJ1 | PSMB9 |
| CD83 | MIR142 | EGR3 | ATP5G1 | XCR1 |
| LILRB5 | NAMPT | CD82 | FCGR1A | PLCD1 |
| P2RY6 | P2RY6 | MYADM | EMP3 | SERPINB9 |
| CMKLR1 | FAM49B | TESPA1 | KRT18 | TMEM176B |
| SERPINF1 | FTH1 | RASSF5 | CAMK1 | GMFG |
| CTSC | GAPT | CALB2 | PHGR1 | COX7A2 |
| BLVRA | NPC2 | BIRC3 | CD163L1 | CD99 |
| TYMP | ITGB2- | HINT1 | KRT8 | PPM1J |
| TBXAS1 | HLA-DOA | CD22 | C3AR1 | H2AFY |
| RGS1 | CYBA | IL18 | IFI27 | PYCARD |
| CXCL16 | OAZ1 | HSPD1 | S100A4 | RGS1 |
| CD86 | PID1 | STXBP2 | RAB31 | TMEM59 |
| CD4 | CCL3 | MBOAT7 | DAB2 | SRGN |
| A2M | RILPL2 | RGCC | ANXA1 | ZYX |
| IL8 | CXCR4 | IER2 | ATP6V1F | CLEC7A |
| C1orf162 | CSF1R | MSRA | TUBB4B | NABP1 |
| NAGK | ARL4C | JUNB | CD209 | ZFP36L2 |
| ATP6V0B | PDLIM1 | BHLHE40 | TFF3 | ABI3 |
| HLA-DQA2 | IGJ | ARHGEF6 | LSP1 | MT-ND1 |
| FTH1 | NCF1 | CST3 | ARHGDIB | CD37 |
| CAMK1 | G0S2 | DUSP10 | UCP2 | FNBP1 |
| GPR34 | HSPA1A | SCYL1 | CXCL16 | EVI2A |
| SLAMF8 | VAMP8 | RGS10 | HBEGF | HAVCR2 |
| S100A6 | TNFSF13B | PRDX6 | ZNF331 | ARPC3 |
| IL18BP | H2AFY | ACTG1 | FCGR2B | CD63 |
| CTSH | OLR1 | CHST2 | CTSC | HES1 |
| ARHGDIB | HCST | CD37 | RB1 | KIAA1598 |
| PLTP | MT-CYB | DDX3X | SRI | VAC14 |
| COTL1 | TMEM59 | ESYT1 | YWHAH | IGFBP7 |
| ARL4C | CXorf21 | CRBN | RENBP | TAP1 |
| FPR3 | CNPY3 | SYTL2 | SGK1 | LDLRAD4 |
| SRGN | EIF4A1 | CTSD | CD163 | ELOVL5 |
| HMOX1 | THEMIS2 | HNRNPM | C5AR1 | IL16 |
| TNFSF13B | C20orf27 | P2RY14 | LILRB2 | RGS19 |
| CYBB | CD300A | CD83 | COTL1 | DUSP10 |
| LAIR1 | S100A11 | SLC2A6 | CLEC4A | PDLIM7 |
| GLIPR1 | YBX1 | CKS2 | TMSB4X | TWF2 |
| ITM2B | LGALS1 | ARHGAP18 | LAIR1 | CTSZ |
| YWHAH | IGFBP7 | TIMP3 | ASAH1 | IFITM3 |
| TGFBI | ANXA1 | TMEM154 | EEF2 | CXCR4 |
| HLA-DOA | PTPRC | CMA1 | PLD4 | COX5B |
| CCL4 | AGPAT9 | MALAT1 | MAFB | VIM |
| DAB2 | FCGR2A | RGS1 | RPL24 | SELPLG |
| EBI3 | CTSZ | DNAJB1 | FCER1A | CFL1 |
| GATM | PPIF | FCGRT | PLTP | ATG3 |
| ATOX1 | DOK2 | PFN1 | TUBA1B | C12orf5 |
| FCGR3A | MT-ND2 | EXD3 | RPS27A | PNMA1 |
| ARPC3 | GNA15 | LIF | GMFG | APOL3 |
| TNFAIP8L2 | KRT18 | GBE1 | AXL | RAB31 |
| ABI3 | HERPUD1 | CHORDC1 | CLEC7A | MT-CYB |
| RHOG | HBEGF | GAPT | PRDX5 | MYCL |
| RGS2 | SCIMP | HSPE1 | CD83 | IFNGR1 |
| CCL18 | LCP1 | ITM2B | HCST | GYPC |
| HN1 | PTGS2 | UBXN10 | GNPDA1 | GPSM3 |
| RAC1 | LIMD2 | CNIH1 | IGJ | PLEKHO1 |
| TMEM176B | PMAIP1 | SLC16A3 | TUBB | LSM6 |
| KRT8 | PABPC1 | GNPTAB | RPL31 | MSL3 |
| PYCARD | KDM6B | TSPO | DUSP1 | UQCR10 |
| PILRA | IL32 | RPL28 | RPL35A | LGALS4 |
| LGALS4 | FPR3 | MAML1 | P2RY13 | CXCR3 |
| SLCO2B1 | PFN1 | TUBA1B | CD9 | CIITA |
| SMS | BSG | UBE3A | BLVRA | BCL2A1 |
| CORO1A | GMFG | NFE2L2 | GLIPR1 | ROGDI |
| ZNF331 | SLC31A2 | SH3BGRL3 | TNFSF13B | TGFBI |
| ARRB2 | SNX10 | ELF1 | GATM | MIR4435-1HG |
| IFI27 | SEPW1 | PRKAR1A | OSM | CKLF |
| SIGLEC7 | ZFP36 | ENPP3 | CLDN7 | IGJ |
| GPR183 | FOSB | GALNT6 | NCF1 | BST2 |
| DOK2 | KYNU | CCL2 | CTSL | DGAT2 |
| CLEC4A | RGS19 | ACTR3 | GM2A | NDUFB9 |
| CECR1 | PHGR1 | TMEM66 | LRRC25 | COX6C |
| TMEM37 | SDS | NCF4 | C15orf48 | MT-ND5 |
| RHOC | AKIRIN2 | BEX4 | AKR1B1 | KLF6 |

TABLE 15C-continued

| | | | | |
|---|---|---|---|---|
| ANXA1 | DSTN | BLVRA | RAB42 | KRT18 |
| PHGR1 | VIM | SERP2 | GSN | 1-Mar |
| AP1B1 | S100A4 | TM6SF1 | TREM2 | EVI2B |
| NCF1 | RB1 | ITM2A | RPL34 | CPPED1 |
| GRB2 | ARPC5 | DHRS7 | SLCO2B1 | FERMT3 |
| GAL3ST4 | H3F3B | IFI27 | ADAMDEC1 | ST8SIA4 |
| ID1 | PAK1 | 2-Sep | TSPO | PTPRC |
| NINJ2 | RAB32 | CD84 | TRPM2 | GNAI2 |
| SDSL | CSF3R | HSPA9 | RPL18 | ATP5J |
| CD63 | GSN | FECH | RPL5 | GPR137B |
| ABHD12 | RAB31 | PRDX5 | H2AFZ | HSPA1B |
| GNPDA1 | ID3 | IFITM10 | SDSL | RNASE6 |
| CD81 | TNFAIP8L2 | HSPA1A | MT1E | AKIRIN2 |
| LRRC25 | SOD2 | DLC1 | FABP1 | LITAF |
| YBX1 | SLAMF8 | HIF1A | ENG | TOMM34 |
| GPSM3 | CCL3L1 | LYN | TNFAIP8L2 | PTPRCAP |
| TFPT | LILRB2 | DDX3Y | LIPA | AP1S2 |
| MKNK1 | PRDX5 | ZEB2 | NCF2 | BSG |
| SLC15A3 | ANXA5 | RHOG | ARL4C | MT-ND4 |
| BRI3 | RABAC1 | RBMX | MGST1 | MCL1 |
| ADAMDEC1 | S100A6 | CDK5 | GPSM3 | ACTR3 |
| IL2RA | FCGRT | DDX39A | RAC1 | CD40 |
| IGJ | COX6C | TMSB10 | CECR1 | MT-ATP6 |
| RB1 | CD52 | EIF1 | ARPC1B | PPA1 |
| MPP1 | NGFRAP1 | NEK6 | PARVB | KCNMB1 |
| SLC7A8 | PLEKHO1 | CSF2 | CYBB | MAP4K1 |
| TNFAIP2 | RAB20 | CSF1 | VMO1 | EPCAM |
| SCIMP | ITM2C | CXCL14 | SLC16A3 | MYADM |
| TFF3 | CEBPD | PIK3R6 | DOK2 | CAP1 |
| NCKAP1L | CD9 | GPR65 | TNFAIP2 | SIGLEC10 |
| FXYD3 | CD151 | RPS4Y1 | ARRB2 | CECR1 |
| ARPC1B | NUDT1 | VAV1 | ATPIF1 | ACTN1 |
| SIGLEC1 | CCDC88A | IL4R | COX5B | RAB7L1 |
| TUBA1B | MAT2A | SELM | ITGB7 | FAM110A |
| BSG | PRMT10 | EVL | NAGK | LINC00152 |
| EEF2 | GCA | HNRNPA2B1 | ATF3 | INPP5D |
| BST2 | LINC00936 | BCL2A1 | IL1RN | PHGR1 |
| HCST | COX5B | RALB | SUCLG1 | GRN |
| LGALS3 | MCL1 | CORO1A | HSD17B14 | AC093673.5 |
| MNDA | CARD9 | RAB32 | CD86 | C12orf57 |
| RAB20 | REL | WDR45B | KRT19 | PHACTR1 |
| FCGR1A | BCL2A1 | LINC00863 | TTYH3 | CD86 |
| PTAFR | TUBA1B | ABCB8 | ANXA5 | S100A4 |
| CD53 | FGR | EIF2AK1 | SOD2 | DAPP1 |
| HCLS1 | ABI3 | SAR1B | BST2 | RHOG |
| LSP1 | SOCS3 | RHBDD2 | CAPG | CYB5R3 |
| AGR2 | IFNGR1 | DHRS9 | FOLR2 | C10orf128 |
| C12orf57 | JUNB | SEMA7A | PRDX2 | RHOF |
| AOAH | GHRL | CCDC28A | STX11 | KRT8 |
| STMN1 | MT-ND5 | TRAPPC2P1 | SNCA | ANXA6 |
| GMFG | NAGK | IGFBP7 | PTGS2 | ITM2B |
| IRF8 | CIITA | GPR35 | CMKLR1 | SCNM1 |
| AXL | CPPED1 | PAK1 | ATP5B | PRDX5 |
| MMP14 | LGALS3BP | PARVB | RPL37A | CAT |
| C15orf48 | KLF4 | RARRES1 | RASSF4 | PTRHD1 |
| TRPM2 | WAS | IL5RA | S100A6 | CD72 |

TABLE 15D

| Neutrophils | Activated_CD4_cells_loFos | Activated_CD4_cells_hiFos | CD8_IELs | CD8_LP_cells | Tregs |
|---|---|---|---|---|---|
| S100A9 | RPLP1 | IL32 | CCL5 | CCL5 | IL32 |
| SOD2 | RPS3 | ANXA1 | CD7 | IL32 | CORO1B |
| IL1B | RPL10 | KLF6 | GZMA | NKG7 | BATF |
| PLAUR | IL32 | S100A4 | NKG7 | CCL4 | TIGIT |
| LST1 | RPS25 | CD69 | HOPX | GZMA | PFN1 |
| AIF1 | RPSA | DNAJA1 | IL32 | DUSP2 | BTG1 |
| SPI1 | RPL32 | HSPA8 | CKLF | CD8A | CD3D |
| G0S2 | ANXA1 | CD3D | KLRC2 | SH3BGRL3 | ARHGDIB |
| LYZ | RPLP2 | RPLP1 | CD160 | CST7 | CREM |
| SAT1 | RPL19 | LTB | GZMB | CD8B | ICA1 |
| FPR1 | RPS19 | CCL5 | PTPRCAP | CD52 | C9orf16 |
| TYROBP | TPT1 | CD52 | TMIGD2 | GZMK | DNPH1 |
| FCER1G | RPS15A | ID2 | HCST | ZFP36L2 | TNFRSF4 |
| SERPINA1 | RPLP0 | SH3BGRL3 | EVL | HCST | CARD16 |
| FTH1 | RPL13 | BTG1 | CD52 | HOPX | RAP1A |
| FCGR1A | RPL11 | TNFAIP3 | CD3D | PFN1 | LTB |

TABLE 15D-continued

| | | | | | |
|---|---|---|---|---|---|
| S100A8 | RPL28 | TNFRSF25 | GNLY | TMSB4X | ARPC1B |
| IGSF6 | RPS12 | CALM1 | CD3E | BTG1 | CTLA4 |
| CFP | RPL13A | TSC22D3 | SH3BGRL3 | GZMB | NDUFV2 |
| IL1RN | RPL30 | EIF1 | RAC2 | CD3D | FOXP3 |
| HLA-DRA | RPS27A | TMEM66 | CTSW | CD3E | PMVK |
| CTSS | RPL4 | CD2 | PHGR1 | GZMH | PBXIP1 |
| TYMP | RPS14 | ZFP36L2 | IGJ | CKLF | LCK |
| FAM26F | RPS6 | RPS3 | TMSB4X | MYL12A | CD63 |
| HLA-DQB1 | RPL23A | RPSA | GAPDH | CXCR4 | BIRC3 |
| FGL2 | RPS2 | CD3E | CORO1A | CFL1 | PTPRCAP |
| CPVL | CD52 | TMSB4X | ABI3 | NR4A2 | ITM2C |
| STX11 | RPS18 | RPS19 | PRF1 | B2M | UCP2 |
| HLA-DRB1 | RPL6 | SRSF7 | ACTB | ARHGDIB | IL2RG |
| CD14 | LTB | HSP90AA1 | CD3G | LYAR | AC017002.1 |
| FTL | RPL27A | DUSP1 | ARHGDIB | ANXA1 | SRGN |
| HLA-DPB1 | S100A4 | MYL12A | SIRPG | RPL28 | LGALS1 |
| HLA-DQA1 | RPL10A | ARHGDIB | LCK | CTSW | CD44 |
| COTL1 | RPL3 | ACTB | ACTG1 | TMEM66 | CALM3 |
| NCF2 | RPS16 | RPL28 | RARRES3 | C9orf142 | DUSP4 |
| HLA-DRB5 | RPS5 | CORO1A | PFN1 | PSMB9 | RGS1 |
| LILRB2 | IL7R | RPLP2 | CD247 | RPLP2 | TNFRSF1B |
| APOBEC3A | RPL31 | PFN1 | STK17A | RPS3 | MIR4435-1HG |
| EREG | RPL14 | ABRACL | CAPG | PTPRCAP | LAIR2 |
| C1orf162 | UBA52 | IL7R | TBC1D10C | LAG3 | ICOS |
| S100A11 | RPS15 | LEPROTL1 | XCL2 | CORO1A | TNFRSF18 |
| CDC42EP2 | RPL18 | RAC2 | FABP1 | HLA-B | HLA-A |
| PLEK | SH3BGRL3 | B2M | ARPC2 | GZMM | ACTB |
| MS4A7 | RPS20 | CD47 | CD96 | IFNG | SPOCK2 |
| LY86 | RPS13 | IFITM3 | C9orf142 | TUBA4A | ANKRD12 |
| HLA-DPA1 | RPL27 | APRT | LGALS4 | ID2 | EIF3H |
| IFI30 | RPS8 | HLA-DRA | FTH1 | S100A4 | GSTP1 |
| HLA-DMB | EEF1B2 | RPLP0 | XCL1 | RPS19 | B2M |
| LGALS2 | RPS23 | IL2RG | CD8A | CD69 | CORO1A |
| ITGB2 | RPS4X | TPT1 | 1-Sep | CD7 | CD27 |
| C5AR1 | RPL12 | RPL10 | CST3 | ACTB | CCL5 |
| SRGN | ARHGDIB | CD53 | AC092580.4 | HLA-A | LAT |
| CYBA | RPS3A | DNAJB1 | CFL1 | CD2 | PKM |
| TIMP1 | RPL35A | PTGER4 | CST7 | PSME1 | PPP1R18 |
| CD74 | RPL5 | ID3 | CLIC1 | ALOX5AP | ANXA1 |
| CST3 | RPL15 | PPP2R5C | PPP1CA | RPL27A | EEF1D |
| CD36 | RPL37 | CD40LG | IL2RB | HSPA8 | HINT1 |
| TNFSF13B | RPL8 | HLA-DPB1 | ALOX5AP | LEPROTL1 | IL10 |
| MS4A6A | TMEM66 | CKLF | TIGIT | SRGN | RAC2 |
| BID | RPL34 | RPS12 | RPS19 | HSPB1 | ASB2 |
| GBP1 | CD3D | RPS27A | IGLL5 | SRRT | LAG3 |
| GLRX | RPL29 | PHLDA1 | PLEKHF1 | RPS27A | FOS |
| NFKBIA | IGFBP7 | RPL19 | ACAP1 | RPL30 | ATP5L |
| MNDA | PTGER4 | FTL | PTPN6 | CXCR3 | TBC1D4 |
| CXCL10 | RPL35 | DRAP1 | P2RY11 | CALM1 | COTL1 |
| ACTB | CD3E | CD63 | ID2 | KLF6 | RPL28 |
| FCN1 | RPS7 | DEDD2 | MYL12A | RPL13A | RHOH |
| IL8 | TOMM7 | GPSM3 | FASLG | CREM | NINJ2 |
| ARPC1B | CXCR4 | DDX5 | CYTIP | BIN1 | RHOG |
| HLA-DQA2 | MYL12A | 1-Sep | KLRD1 | RPL23A | GMFG |
| PILRA | RPL18A | UBE2D3 | DRAP1 | APRT | CST3 |
| LILRB1 | BTG1 | CFL1 | CD8B | RPS20 | CD52 |
| FGR | RPL9 | GRN | CLIC3 | HLA-C | PPP1R2 |
| NINJ1 | RPL7A | PSMB9 | IFITM3 | CYBA | UBE2D2 |
| CD86 | TMSB4X | TPM3 | CXCR3 | ABRACL | FYB |
| LINC00877 | CD63 | CD48 | PPP1R18 | TC2N | TNFRSF9 |
| OAZ1 | CORO1A | RPL14 | RPS4Y1 | 1-Sep | PTTG1 |
| TREM1 | FAU | PDCL3 | ACTR3 | CD99 | CD2 |
| ASGR1 | CD2 | SAMSN1 | GRN | EVL | TRAF3IP3 |
| HLA-DMA | TNFAIP3 | PSME2 | RGL4 | ICAM3 | NTMT1 |
| TNFAIP2 | RPL36 | RPS6 | TPI1 | IFITM3 | RPS15A |
| ARPC3 | CCL5 | SRGN | COTL1 | LCK | ADTRP |
| CAMK1 | EEF1D | RPL32 | TRAPPC1 | C12orf75 | CACYBP |
| S100A4 | GPSM3 | ALOX5AP | KLRC1 | ARPC2 | S100A4 |
| CPPED1 | LDHB | RPS20 | HSPA1A | FYN | GPR183 |
| RAB20 | RPS9 | ARHGDIA | CIB1 | XCL1 | JUN |
| RIPK2 | LEPROTL1 | SOCS1 | PSMB10 | PRF1 | ENO1 |
| CXCL9 | PFN1 | DDIT4 | ITGA1 | PSAP | UBC |
| LAP3 | KLF6 | MIR24-2 | LAT2 | ATP5E | TNIP2 |
| ATP6V0B | CALM1 | HLA-B | CD244 | YPEL5 | 1-Sep |
| HCK | CD69 | HLA-DRB1 | ITGAE | DRAP1 | EVL |
| GCA | APRT | PGK1 | ENO1 | MCL1 | CXCR6 |
| RP11-290F20.3 | GLTSCR2 | LAPTM4A | BCAS4 | CRTAM | HSPA8 |
| LILRB4 | GPR183 | FDX1 | CDK2AP2 | PPP1CA | TAPSAR1 |
| CD37 | RPL26 | RPL27A | NFKBIA | RPLP1 | GNB2L1 |
| PRELID1 | RPL36AL | RPS4X | PTMA | RPS15A | XRCC6 |

TABLE 15D-continued

| | | | | | |
|---|---|---|---|---|---|
| RNASET2 | GIMAP7 | CITED2 | GIMAP7 | GSTK1 | CYTIP |
| GCH1 | HSPB1 | PSME1 | RPLP2 | TIMP1 | CD37 |
| CYBB | ABRACL | RAN | NPC2 | CLIC1 | RPL13A |
| NCF4 | PSAP | MALAT1 | ARPC1B | ID3 | NSA2 |
| IL23A | HLA-DPB1 | H3F3B | VASP | TMA7 | CD3E |
| RP11-701P16.5 | RPL24 | RPS15A | LSP1 | PTPRC | HMGN1 |
| SERPINB9 | HLA-DRB1 | FOSB | HERPUD1 | PPP2R5C | TRAPPC4 |
| MPEG1 | PTPRCAP | CXCR4 | RGCC | RGCC | TRAPPC1 |
| CCL3 | KLRB1 | BCAS2 | PTPN22 | RNF167 | SH2D1A |
| CFD | IFITM3 | ALG13 | CISH | MYL12B | TIMP1 |
| UBE2D1 | HLA-DPA1 | LCK | MATK | PSME2 | ARID5B |
| THEMIS2 | FTL | RPL11 | HSPA1B | HMOX2 | SKAP1 |
| STXBP2 | EVL | CDC42SE2 | SOCS3 | RPL13 | DOK2 |
| ARRB2 | APOE | RPL13 | RPS3 | CD59 | SNRPB |
| GPX1 | FXYD5 | CACYBP | RPL13A | SAMSN1 | ISG20 |
| TIFAB | CD74 | IDS | PSME1 | RARRES3 | TNFRSF14 |
| CORO1A | HLA-DRA | GALM | PTPN7 | TRAPPC1 | FXYD5 |
| DUSP2 | DDX5 | CD6 | CD2 | TAPBP | CDKN2A |
| TESC | RPS4Y1 | CCL20 | ASB2 | SH3KBP1 | RPL36AL |
| CD68 | RGCC | RPS2 | OSTF1 | APOBEC3G | PCBP1 |
| SPHK1 | TC2N | RPL31 | DOK2 | GLIPR2 | LAPTM5 |
| KYNU | HSPA1A | UBE2D2 | ITGB7 | PSMB10 | PTPN2 |
| BCL2A1 | CMPK1 | IL4I1 | MT-CO1 | DHRS7 | UXS1 |
| GLUL | CD6 | SLAMF1 | CD59 | RPL19 | PMAIP1 |
| BLVRA | IL2RG | FOS | TNFRSF18 | TSC22D3 | UGP2 |
| KDM6B | SRGN | MGAT4A | RPLP1 | MALAT1 | 9-Sep |
| NAMPT | NPM1 | TRMT112 | FCER1G | STK17A | ARF6 |
| SLC31A2 | TSC22D3 | FAM96B | LAG3 | DENND2D | CMC2 |
| NUP214 | PDCL3 | IL12RB1 | HSPB1 | RPL31 | LIMD2 |
| ABI3 | ZFP36L2 | SVIP | ARL6IP5 | ITM2A | PSME1 |
| SELK | CD59 | CCR6 | WAS | CDK2AP2 | LEPROTL1 |
| PSAP | CFL1 | RPL36AL | BUB3 | MZT2A | TMSB4X |
| SAMSN1 | SOCS1 | PLP2 | RGS1 | RGS1 | IGBP1 |
| PPIF | NACA | CYCS | CD69 | SOCS1 | PYHIN1 |
| ATF5 | RPL38 | TTC39C | SLC16A3 | GUK1 | BCAS2 |
| AMICA1 | CKLF | HLA-DPA1 | HLA-DRA | GRAP2 | PHLDA1 |
| IGJ | CD37 | NOP58 | RPS3A | C19orf60 | PRR13 |
| ITM2C | SH2D2A | ENO1 | PTTG1 | TNFAIP3 | ZNHIT1 |
| YBX1 | GNB2L1 | MYADM | LDLRAD4 | IL2RG | SOD1 |
| ACSL1 | IGJ | RPS25 | CD53 | DDX5 | MAPK1IP1L |
| RNASE6 | BTF3 | HNRNPA0 | PSAP | EEF1D | OSER1 |
| ZFAND5 | NPC2 | JUN | PTGER2 | RPS12 | CASP4 |
| GRN | CXCL14 | YPEL5 | SH3BP1 | ARPC1B | RGCC |
| WAS | CCDC109B | PPP1R15A | CHMP4A | PTGER4 | NAMPT |
| TNFAIP8 | LGALS1 | SERP1 | IDH2 | ZNF331 | 6-Sep |
| JUN | HSPA8 | RPS14 | RPS27A | BUB3 | IDI1 |
| ASGR2 | CRIP1 | EVL | LSM2 | RBM8A | GBP2 |
| CXCL2 | HSPA1B | PSAP | EEF1A1 | CAP1 | SSU72 |
| FCGR1B | CCR6 | FAU | HCLS1 | RPS18 | COPE |
| LIMD2 | RPS29 | RPL13A | MYL12B | 7-Sep | YWHAZ |
| DOK2 | PFDN5 | PTPRCAP | CRIP1 | C19orf24 | COMMD3 |
| PFN1 | TTC39C | TAGAP | PABPC1 | HLA-DRB1 | GLRX |
| LILRA2 | RPS21 | DHRS7 | LYAR | FAM177A1 | RBBP4 |
| PYCARD | C9orf142 | H2AFZ | FYN | CRIP1 | PTPRC |
| ISG15 | RPL37A | AMD1 | BIN1 | ABT1 | HIGD2A |
| KMO | RPL17 | CD74 | RGS19 | CXCL14 | SMS |
| IL10 | PABPC1 | ODF2L | DEF6 | RPS25 | CCL20 |
| CTSH | EIF1 | SND1 | RPL18A | SNRPB | ANP32A |
| CD48 | GSTK1 | OSTF1 | IFI27 | RPS2 | NPM1 |
| RTN1 | ARL4A | ERP29 | LCP1 | EIF1 | NAPA |
| IKZF1 | YPEL5 | PNP | HENMT1 | CTSB | APOE |
| SH3BGRL3 | CD7 | ARL4A | CXCR6 | BAX | RPL15 |
| C19orf38 | HCST | RPL30 | RPL9 | MFSD10 | HSPB11 |
| RIN3 | LAPTM5 | MRPL11 | FCGRT | RPL36AL | ACTR3 |
| PSME2 | ITM2C | AATF | RPS10 | RORA | CDC42SE2 |
| HCLS1 | ID2 | RPL4 | CCL4 | SRSF7 | TMEM66 |
| CD83 | FYB | MCL1 | RPS27 | HNRNPUL1 | SNX5 |
| AP1S2 | TUBA4A | JUNB | APOBEC3G | COPE | CHCHD10 |
| LCP1 | 1-Sep | BAZ1A | CD99 | FTL | ICAM3 |
| ITGAX | RPL22 | EIF4A3 | TPM3 | C9orf78 | JUNB |
| PKM | RORA | CREM | RPL17 | PDCL3 | LIMS1 |
| CFL1 | LAPTM4A | SRSF2 | GYPC | TAGAP | EPSTI1 |
| VAMP8 | PLD3 | RPS5 | GSTK1 | UBE2D3 | C19orf43 |
| IFNGR2 | SNRPD2 | MRPL34 | IL2RG | C14orf1 | PIM2 |
| NPC2 | METTL9 | SNHG8 | ATP5E | PLP2 | LINC00152 |
| RILPL2 | B2M | C9orf142 | GYG1 | GPSM3 | GTF3C6 |
| GPBAR1 | CACYBP | MTFP1 | FOSB | UBE2L3 | SOCS1 |
| CSF1R | SAMSN1 | RPS8 | SASH3 | GPR65 | RPL11 |
| OSM | HIGD2A | PRR5 | C19orf53 | ATP6V0E1 | UFC1 |
| CCRL2 | ARPC1B | ACTG1 | 7-Sep | RAC2 | TSC22D1 |

TABLE 15D-continued

| | | | | | |
|---|---|---|---|---|---|
| CLEC10A | 9-Sep | CHCHD7 | FXYD3 | KLRD1 | ARPC4 |
| IL4I1 | GPR171 | RPS13 | TSEN54 | HLA-DRA | NUDT1 |
| CD52 | AES | PTGER2 | COMMD8 | EBP | ANAPC16 |
| SYK | LAT | HSPE1 | CYBA | RPSA | TPRKB |
| CHMP1B | ACTB | TC2N | PSME2 | TMUB1 | PHGR1 |
| NLRP3 | NKG7 | SAP18 | EGR1 | RNF149 | WDR1 |
| HBEGF | DYNLT3 | RORA | CD74 | HLA-DQA1 | RPS2 |
| CCL3L1 | TRAT1 | CCDC109B | GZMM | GAPDH | CD58 |
| IFI27 | EIF3E | CDK2AP2 | CAPN12 | STUB1 | DDX5 |
| IL27 | RARRES3 | UBE2S | SPINT2 | SNRPD2 | RPS27A |
| ATP6V1F | OXNAD1 | LAT | C9orf78 | CSNK1D | SMCO4 |
| ARHGDIB | SERPINB6 | CD97 | POLR3GL | HSPA1A | EEF2 |
| TMSB10 | SPINT2 | GSTK1 | PDLIM1 | RPL14 | LDHB |
| VSIG4 | COMMD6 | PSENEN | C9orf16 | RALY | CUTA |
| ANXA2 | HNRNPA1 | LDHA | GUK1 | RPL22L1 | TNIP1 |
| VASP | ACP5 | EIF4A1 | CCND2 | FAM96B | SKP1 |
| PPDPF | RAP1A | FUS | GPR68 | TOMM7 | ITM2A |
| ARL5B | RPSAP58 | HNRNPUL1 | TNFSF14 | SNRPB2 | HCLS1 |
| MT-CYB | EEF1A1 | C14orf166 | RHOC | METTL5 | HLA-G |
| GBP5 | CREM | SPINT2 | IL16 | RPL32 | GYPC |
| PSTPIP2 | RCAN3 | SURF4 | SLC9A3R1 | PNN | RPS3 |
| GPR183 | CD48 | MZT2A | MIF | MBP | SH3BGRL3 |
| HCAR2 | SPOCK2 | CXXC1 | MT-CYB | CLDND1 | RPS27L |
| SAMHD1 | TNFSF13B | PCBP1 | TTC1 | GTF3A | GPX1 |
| HAPLN3 | EIF3H | RPS18 | SAT1 | ATF6B | SNRPB2 |
| CAPG | SAT2 | ANXA5 | TSC22D4 | CDC42SE2 | AKIRIN2 |
| EPSTI1 | LYAR | HMGN1 | LAPTM4A | ALG13 | PSMD8 |
| RNF130 | PLP2 | HCST | SCML4 | RPS16 | COX17 |
| ID3 | MZT2A | PSMA7 | PTPN4 | RBCK1 | UBE2I |
| CREM | MGAT4A | LAPTM5 | COMMD6 | CD9 | SELT |
| LITAF | SMDT1 | TIMP1 | HLA-DRB5 | CD74 | IL2RA |
| CXCL3 | ANXA5 | EML4 | RP11-47L3.1 | PHGR1 | FAIM3 |
| PLA2G7 | ENO1 | AMICA1 | SSNA1 | EPSTI1 | GK |
| UBE2E2 | TMEM14B | ICAM3 | CASP4 | CD53 | NAA38 |
| H2AFY | PSME1 | IL17A | CTSB | OAZ1 | PSMA2 |
| UBXN11 | CYCS | EIF1AX | ARPC3 | PPP1R18 | SNRPD2 |
| RGS2 | ATP5L | DYNLT3 | APRT | RPS14 | RPL24 |
| RHOG | RBM3 | IFITM2 | RPL7 | CSRNP1 | PIK3IP1 |
| CASP1 | ICAM3 | PRKCQ-AS1 | VAMP8 | BLVRB | ID3 |
| CD274 | ALOX5AP | RBL2 | RPL4 | RPL27 | SLAMF1 |
| HCAR3 | C19orf24 | HSP90B1 | HLA-DQB1 | RPL3 | RPL18 |
| LINC00936 | GMFG | SNRPB | FAM173A | OXNAD1 | UBXN1 |
| TUBA1B | NEAT1 | FERMT3 | SLA2 | NEDD8 | FTL |
| IL18BP | EGR1 | GHITM | GPR171 | C11orf31 | H2AFV |
| C12orf57 | PTPRC | SELT | SAMSN1 | HSPA9 | CMTM7 |
| EMG1 | CD97 | NFKBIA | PSMB9 | TPM3 | LINC00649 |
| PTGS2 | UBE2D2 | RPS16 | CD37 | CHMP4A | RPL34 |
| MYO1F | TXNIP | RPL22L1 | ANAPC16 | PSENEN | HSD17B10 |
| NADK | GTF3A | ISG20 | RPL21 | MLX | BAX |
| RABAC1 | RPS11 | SNRPD2 | RPSA | RPL34 | CLPP |
| A2M | PPP2R5C | IFI35 | HMOX2 | CIB1 | HSPA1B |
| GDI2 | SNRPG | CASP1 | LSM10 | OCIAD2 | CD7 |
| GLIPR1 | TMA7 | NPC2 | PSMD13 | SLC38A1 | RPS25 |
| HSPB1 | RPL22L1 | SLC1A5 | PGK1 | TADA3 | HLA-DRA |
| DSTN | IFITM2 | TRAPPC1 | TYROBP | IDH2 | ZNF706 |
| NMI | DUSP2 | TUBA4A | HLA-DRB1 | GHITM | RPL12 |
| CD9 | RPL23 | MAX | C11orf48 | NHP2L1 | DCXR |
| DUSP1 | SCML4 | UXT | RPL28 | ATP5D | CUL9 |
| MCL1 | C19orf53 | HSPB1 | GGA1 | ACADVL | RNF213 |
| BSG | GGA1 | RBM3 | EEF1D | ATP8A1 | ZC2HC1A |
| MT-ND3 | MZB1 | RAB8A | LAPTM5 | GATA3 | ALDOA |
| RNF19B | ARHGEF1 | TAPBP | GPR34 | NAA50 | G3BP2 |
| GLIPR2 | HERPUD1 | RPL23A | TSTA3 | AKR1A1 | HCST |
| PSMB9 | JUN | EMP3 | BANF1 | CD97 | CIB1 |
| GAPT | PHLDA1 | UBA52 | CDIP1 | MZB1 | PDCL3 |
| NAGK | PRKCQ-AS1 | CRIP1 | C11orf31 | MEA1 | SSBP1 |
| C10orf54 | ZFAS1 | NR4A2 | STXBP2 | PSMB8 | CCT7 |
| CTSB | EEF2 | TAP1 | RPL22 | MYEOV2 | HPRT1 |
| CD53 | COTL1 | SS18L2 | CALM1 | UBE2I | PTGES3 |
| CSF3R | TRAPPC6A | FLT3LG | RPL36A | ZFP36 | MRPS35 |
| SCIMP | CTSD | GPR183 | NUDT14 | FIBP | SRP19 |
| MT-ND4 | NDUFS5 | IRF1 | IRF2 | C14orf166 | HSP90B1 |
| PSMA4 | CLIC1 | CXCR3 | MRPL46 | SIGIRR | BUB3 |
| HCST | RPS24 | PPP6C | YPEL5 | RPL10 | BTG3 |

| Memory_T_cells | NK_cells | Cycling_CD8_cells | Inflammatory_CD2_DCs |
|---|---|---|---|
| LDHB | NKG7 | CD3D | LST1 |
| RPL11 | TYROBP | CD3E | IL4I1 |
| CCR7 | FCER1G | NKG7 | KRT86 |

TABLE 15D-continued

| | | | |
|---|---|---|---|
| RPS12 | XCL2 | CD2 | LTB |
| RPL32 | CTSW | CCL5 | FXYD5 |
| RPS3 | XCL1 | CD7 | ALDOC |
| RPL19 | CLIC3 | IL32 | KRT81 |
| RPLP2 | IL2RB | GZMA | ID2 |
| RPL13 | GZMB | CST3 | LTA4H |
| RPS15A | CCL4 | ITM2A | NFKBIA |
| RPS14 | GSTP1 | TUBB4B | ZFP36L1 |
| RPL23A | KLRC1 | CTSW | CASP3 |
| RPL31 | MATK | PTPRCAP | TNFRSF25 |
| RPSA | APOBEC3G | GZMB | HSPA8 |
| RPS4X | CST7 | VIM | MIR24-2 |
| RPL18 | GZMA | CD8A | LIF |
| RPS6 | GNLY | CD8B | TYROBP |
| RPS13 | GZMK | B2M | DUSP1 |
| RPL28 | CD7 | CD96 | NXT1 |
| RPL27A | KLRD1 | AC092580.4 | HNRNPA0 |
| RPS2 | HCST | SH3BGRL3 | MPG |
| RPS25 | EIF3G | CD3G | HMGN3 |
| LTB | PFN1 | RGL4 | CXCR4 |
| RPS18 | PRF1 | LGALS1 | NR4A1 |
| RPL30 | FGR | FCGRT | CSF2 |
| RPL4 | KRT81 | HCST | PRMT10 |
| RPS9 | HOPX | PLA2G16 | CD83 |
| RPL35A | CAPG | TMIGD2 | DNAJA1 |
| RPS27A | CCL3 | IFNG | H2AFY |
| RPS8 | KLRF1 | RAC2 | SRSF2 |
| RPL10A | MAP3K8 | GYPC | TMIGD2 |
| GNB2L1 | SRGN | SPINT2 | OTUD5 |
| CD63 | IFITM2 | LGALS4 | CD300LF |
| RPS23 | CD3D | HLA-DRA | SPINK2 |
| RPS20 | STK17A | CD69 | TPT1 |
| RPL14 | FAM177A1 | LY6E | TLE1 |
| RPL36 | PTP4A1 | LDHA | DLL1 |
| RPL37 | ITGB2 | ARHGDIB | PTGDR |
| RPL13A | CCL5 | GIMAP7 | NCOA7 |
| IL32 | BTG1 | SRGN | CD52 |
| RPL27 | NR4A2 | TBC1D10C | AMICA1 |
| PABPC1 | APMAP | CD52 | MAFF |
| RPL26 | DUSP2 | RPL8 | BIRC3 |
| RPL8 | PTGDR | EPCAM | JUNB |
| SELL | GZMH | RARRES3 | TOX2 |
| RPS21 | CORO1A | CD9 | DRAP1 |
| RPL5 | KRT86 | H2AFZ | CD69 |
| RPS15 | CD160 | ATPIF1 | IL23R |
| RPL10 | LAT2 | MSN | ARL4A |
| LGALS1 | ID2 | APOBEC3G | TCIRG1 |
| RPS16 | MIB2 | GZMM | UBB |
| BTG1 | ALOX5AP | SLC9A3R1 | IER2 |
| RPL34 | BCO2 | CDKN2A | CAT |
| RPL29 | NCR3 | COX5B | EIF1 |
| RPL12 | ARPC5L | C15orf48 | AREG |
| TMEM66 | MYL12A | ICAM3 | FOSB |
| FXYD5 | FTL | TXN | ZFP36 |
| ARHGDIB | CD97 | CD37 | TCP1 |
| RPS5 | PPP1R2 | SKAP1 | CD164 |
| RPLP1 | CD247 | PIM1 | DDX3X |
| RPS7 | GUPR2 | SLA2 | METTL9 |
| EEF1B2 | CLIC1 | TRAT1 | ZNF75A |
| RPS19 | SLC35E1 | CXCR3 | C16orf91 |
| CD52 | 7-Sep | TCEA2 | NR4A2 |
| FAU | CHST12 | PRKCH | TNFRSF18 |
| RPL7A | CDC42SE1 | ATP5B | MAP3K8 |
| GLTSCR2 | C20orf24 | EMP3 | TEX30 |
| NOSIP | LSP1 | MARCKSL1 | BZW1 |
| NPM1 | SAMD3 | HLA-DRB1 | H3F3B |
| LEF1 | PTPRCAP | HLA-B | DDX18 |
| RPL6 | HSPB1 | PEBP1 | MRPL18 |
| ZFP36L2 | ABHD17A | TRAF3IP3 | PRPF6 |
| RPL15 | RGCC | ATP5G1 | PRAM1 |
| EIF3E | CD44 | RPL37A | SLC43A2 |
| TCF7 | MAPK1 | HLA-DPB1 | RAN |
| HINT1 | LDLRAD4 | PRF1 | FCER1G |
| RPS29 | ACTB | HOPX | MGAT4A |
| RPLP0 | EVL | GSTP1 | SLC25A39 |
| UBA52 | TMIGD2 | PDLIM7 | NFKBIZ |
| LEPROTL1 | MRPL3 | CST7 | BLVRA |
| RPL22 | GZMM | GRN | FOS |
| RPL38 | ZFP36L2 | HLA-DPA1 | RNASET2 |
| ITM2C | NUDT14 | IFITM2 | IL2RG |

TABLE 15D-continued

| | | | |
|---|---|---|---|
| HSPA1A | TESC | LCK | EIF4A1 |
| RPL3 | SH2D1B | EVL | LINC00299 |
| TRAT1 | CHD2 | GZMK | EMP3 |
| EEF1D | FAM49B | SIRPG | DNAJB1 |
| EEF2 | VDAC1 | LGALS3 | IL7R |
| BTF3 | BIN2 | NANS | BST2 |
| LGALS3 | ARHGDIA | CD74 | CREM |
| SMDT1 | CDHR1 | CYC1 | SLC16A3 |
| PFDN5 | SIGIRR | AGR2 | KIAA1324 |
| TOMM7 | VPS37B | HLA-C | UNC93B1 |
| HNRNPA1 | TNFRSF18 | SH2D1A | ENO1 |
| EIF3F | GRK6 | LAPTM5 | SKIL |
| CCDC109B | DUSP1 | SLC25A5 | RNF139 |
| PTPRCAP | ZFP36 | CORO1A | HSP90AA1 |
| CD3D | SELM | HLA-A | BEX2 |
| CD37 | IDS | HSPD1 | TMEM243 |
| RPL23 | PRDX1 | RPL36 | DDIT4 |
| RPS3A | RHOF | IL2RB | RBM39 |
| PSAP | LGALS3 | LSP1 | SIK1 |
| GIMAP7 | CFL1 | TSPAN5 | PSMD13 |
| RPL24 | CMC1 | GCHFR | RASD1 |
| LIMD2 | RNF113A | ATP5G3 | AQP3 |
| RPL37A | IL2RG | HIST1H4C | MED30 |
| RPL9 | TIMM8B | GPX2 | HHEX |
| RPS11 | FASLG | RPL38 | ZNF331 |
| TRAF3IP3 | TMSB4X | SAMSN1 | BTG2 |
| RPS24 | SRSF5 | COX5A | RPL22L1 |
| PASK | LAMTOR5 | HN1 | NCR3 |
| TPT1 | AKNA | HLA-DQA1 | MYADM |
| NACA | USF2 | ATP5O | LPXN |
| CORO1A | RAC2 | UQCR10 | RBPJ |
| COX7C | NDUFB8 | UBE2C | UBE2S |
| IFITM3 | SDHC | GMFG | DPAGT1 |
| EIF3H | RANGRF | GNG2 | NHP2 |
| CXCR4 | KLRB1 | FYN | CYCS |
| ANAPC5 | PSMB2 | HES1 | PRR5 |
| RPL18A | SLC16A3 | GNLY | CCT4 |
| CD7 | RIN3 | ID2 | HMGN1 |
| DENND2D | RBM38 | UQCRQ | BCAS2 |
| MZT2A | IDI1 | XCL1 | BTG1 |
| RPL35 | UBXN2B | HLA-DMA | MAP2K1 |
| FAIM3 | LINC00667 | RPS29 | CXXC5 |
| OCIAD2 | CST3 | ANXA1 | ATG4B |
| GPSM3 | PPP5C | RGCC | SFPQ |
| C6orf48 | ID3 | CCNB1 | SRGN |
| UBB | DRAP1 | BST2 | NPC2 |
| RNF138 | NFKBIA | ATP5A1 | TUBA4A |
| CYTH1 | CCNL1 | CLEC2D | CALM1 |
| SERPINB6 | NXT1 | ECHS1 | TXK |
| CCL5 | ARID5A | CCNB2 | SPTLC2 |
| FAM177A1 | AGTRAP | ATP5J2 | ANP32A |
| DCXR | ARHGDIB | TNFRSF18 | CCR6 |
| NUCB1 | CBX3 | CKS2 | PROSC |
| DAP3 | TCEB2 | NCAPH | TXNL1 |
| P4HB | RPS3 | RPL5 | TRAF4 |
| FYB | ZNF814 | RAC1 | HSP90AB1 |
| HLA-DPA1 | LINC00996 | ARPC1B | SRSF5 |
| FOSB | PSMA7 | ABI3 | SLA |
| 6-Sep | CD69 | GPX1 | RNF19B |
| CHI3L2 | YPEL3 | MT1G | COL9A2 |
| ID3 | APRT | CYTIP | NFKB1 |
| CST3 | HMGN1 | SURF4 | PPP2CA |
| ARPC1B | CPNE1 | CTSH | NAP1L1 |
| JUNB | IGFBP7 | FXYD5 | SRP9 |
| RARRES3 | PPP1CA | PFKP | BEX4 |
| BEX2 | YWHAZ | CRIP1 | TMEM123 |
| ICOS | EBP | ZAP70 | TUBB4B |
| HLA-DRB1 | MIR24-2 | ICOS | LGALS3BP |
| IFITM1 | ZNF331 | MT1E | TNF |
| PFN1 | GCHFR | RPL12 | HSPD1 |
| CD3E | TRAPPC1 | RORA | SAMD10 |
| TBC1D10C | DDIT4 | IL2RG | CSTB |
| RNASET2 | GRB2 | IFI16 | CRIP1 |
| EIF2S3 | OCIAD2 | ETFB | CD47 |
| CASP8 | MPG | UPP1 | EMC10 |
| FXN | RALA | ATP5J | SACM1L |
| CYLD | C19orf25 | S100A4 | ANXA5 |
| SC5D | SNRPA1 | PSMB9 | IFI44L |
| LMNA | BUB3 | STK17A | CAPG |
| MAL | PLAC8 | RPS14 | FAM213B |

TABLE 15D-continued

| | | | |
|---|---|---|---|
| AIM1 | PDCD4 | KRT19 | EIF3D |
| TMSB4X | SLC25A39 | TIMM13 | EIF4G2 |
| MRPL16 | RPL7L1 | CD247 | ERBB2IP |
| COTL1 | NSMCE1 | RPS4Y1 | ARF1 |
| CRLF3 | BUD31 | RPL7A | PARL |
| H2AFV | PAPOLA | TMSB4X | HSPA5 |
| AAK1 | CALM1 | RPS18 | ZFAS1 |
| SLC2A3 | MRPS11 | GZMH | GSN |
| CTSD | C1orf162 | SRI | WDR45B |
| AC013264.2 | PSME2 | PIGR | TPM3 |
| TMSB10 | LDHB | KRT18 | SERTAD2 |
| 1-Sep | CD59 | COX4I1 | CA13 |
| IGBP1 | RBCK1 | CCL4 | AKAP17A |
| RPS4Y1 | GRN | CENPW | CUTA |
| ZFP36 | BCAP31 | STOM | CDC42SE1 |
| COMMD6 | AIM1 | CREM | PRKAR1A |
| DNMT1 | TGFB1 | PTTG1 | EPS8L2 |
| GIMAP4 | TIPARP | RPL35A | H2AFX |
| CXCL14 | MYO1F | FKBP11 | CXCL2 |
| YPEL5 | SF3B2 | PHB | ALG13 |
| WHSC1L1 | NDUFS8 | PTGER2 | SNRPB |
| ZNF331 | RTN3 | SUCLG1 | B3GALT5 |
| CD27 | NDUFA3 | ACAP1 | NRBP1 |
| GSTK1 | PPP1R14B | AIP | AUP1 |
| SSU72 | PTMA | PLEKHF1 | GPATCH3 |
| HLA-DPB1 | SH2D1A | UQCR11 | TRIAP1 |
| SPOCK2 | PIGX | HSPE1 | SF1 |
| TIMP1 | PTPN4 | TPM1 | GPR65 |
| SLC25A6 | JAK1 | HINT1 | VEZT |
| C1orf228 | IRF8 | DBI | PCBP1 |
| LCK | TADA3 | CCND3 | NR1H2 |
| NAA38 | HSPE1 | ITK | FKBP3 |
| DCK | GGA1 | RPS6 | TNFRSF4 |
| GPR18 | RTCA | CLDN7 | CD3E |
| CTSC | TLN1 | CD53 | GPR68 |
| HERPUD1 | TRMT2A | EEF2 | TNFSF4 |
| TPI1 | PSTPIP1 | SH2D2A | H2AFZ |
| RGCC | GGNBP2 | COX6B1 | PSME1 |
| LINC00861 | NHP2 | HMGA1 | JMY |
| CD59 | PSD4 | RNF187 | NUP54 |
| EVL | RTFDC1 | NDUFA11 | XCL1 |
| CORO1B | PSMD6 | HMGN1 | GNA15 |
| CYCS | DCXR | STMN1 | LTC4S |
| ZNHIT3 | TSPAN32 | UQCRC2 | TXNDC17 |
| TOMM20 | CUTC | LAT | GATA3 |
| TUBA4A | ATP6V1G1 | HLA-DQB1 | N4BP2L2 |
| 9-Sep | IFITM1 | AK2 | CTSH |
| DGUOK | C19orf66 | WDR54 | SLC39A4 |
| LYRM4 | PPP1R18 | RPS24 | PER1 |
| FTL | TMEM14C | TSC22D3 | AC022182.3 |
| JUN | ALKBH2 | MTPN | HCST |
| LAT | POLR2L | MYO1G | PCDH9 |
| PIK3IP1 | METRNL | KLRG1 | TPI1 |
| OAZ2 | SERBP1 | NRM | RP11-425D10.10 |
| FOS | C9orf16 | FOSL2 | SERTAD1 |
| HSPB1 | BHLHE40 | 1-Sep | KIT |
| AES | TSC22D4 | PRDX5 | ERGIC3 |
| COX4I1 | S100A6 | SSBP4 | ZNF814 |
| LRRFIP1 | RBM39 | RPS13 | FOSL2 |
| RAB1A | RNF125 | GIMAP1 | LYPLA2 |
| MALAT1 | MAFF | MPC2 | SIVA1 |
| RILPL2 | SLC9A3R1 | COX7C | JTB |
| HLA-DRA | STXBP2 | GMNN | ANP32E |
| GTF3A | CLDND1 | GNB2L1 | RNFT1 |
| ABHD14B | AP2M1 | PABPC1 | EIF5 |
| ACP5 | PSMD8 | HLA-DRB5 | BAD |
| CHCHD7 | VAPA | FAM162A | PNP |
| RAN | SOCS1 | OASL | HNRNPK |
| CD74 | HNRNPA2B1 | OSTF1 | MGMT |
| VAMP2 | DHRS7 | DOK2 | TCTN3 |
| APRT | AKIRIN2 | C1QBP | C6orf57 |
| C19orf43 | COA5 | LIMD2 | PCNP |
| TSC22D4 | COMMD6 | CD160 | TP53I13 |
| BRMS1 | ATG12 | TUBB | C3orf17 |
| RASAL3 | ARPC2 | RPL24 | MRPS15 |
| NDUFS6 | KLHDC4 | DDT | GPX7 |
| NPC2 | LRRFIP1 | GTPBP1 | CASP6 |
| LSM14A | APOBR | ATP2B4 | HLA-B |
| CCDC104 | ETF1 | NDUFC1 | CRTC2 |
| WDR82 | CASP4 | RAB27A | MBOAT7 |

TABLE 15D-continued

| MEA1 | CASP3 | PRDX3 | TNFAIP3 |
| GADD45B | CD53 | CXCR6 | DCAF11 |
| ANXA2 | U2AF1 | RPL23 | SRSF7 |
| CD28 | TSEN15 | CDC20 | PPP1R11 |
| FCGRT | AOAH | NASP | ZNF207 |
| LINC00649 | HLA-DPA1 | RHOF | FURIN |
| PHGR1 | OBFC1 | CDKN3 | WDR83OS |

Figure 23:
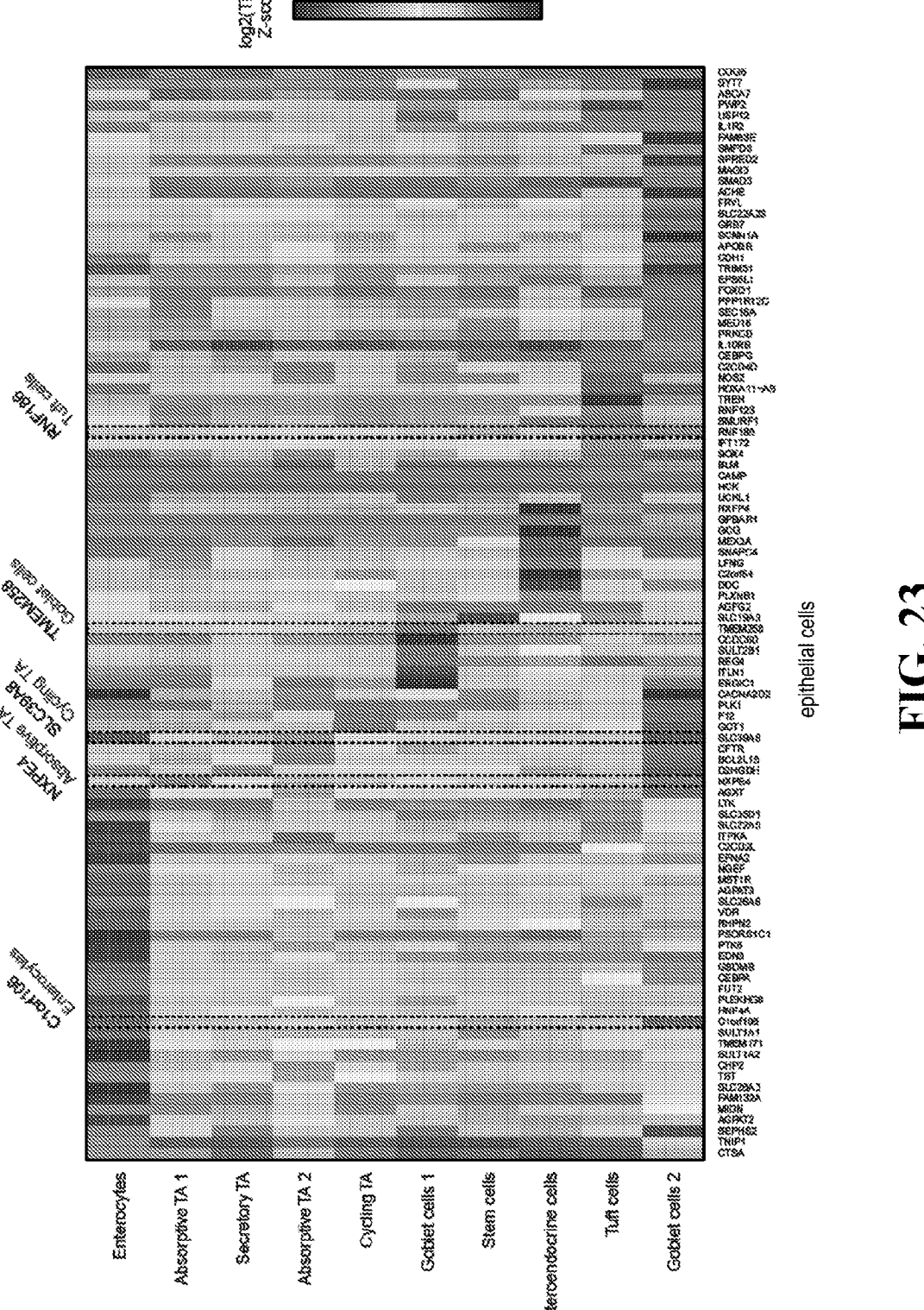
FIG. 23—illustrates the cell-of-origin for key IBD GWAS genes expressed in epithelial cells.
Figure 24:
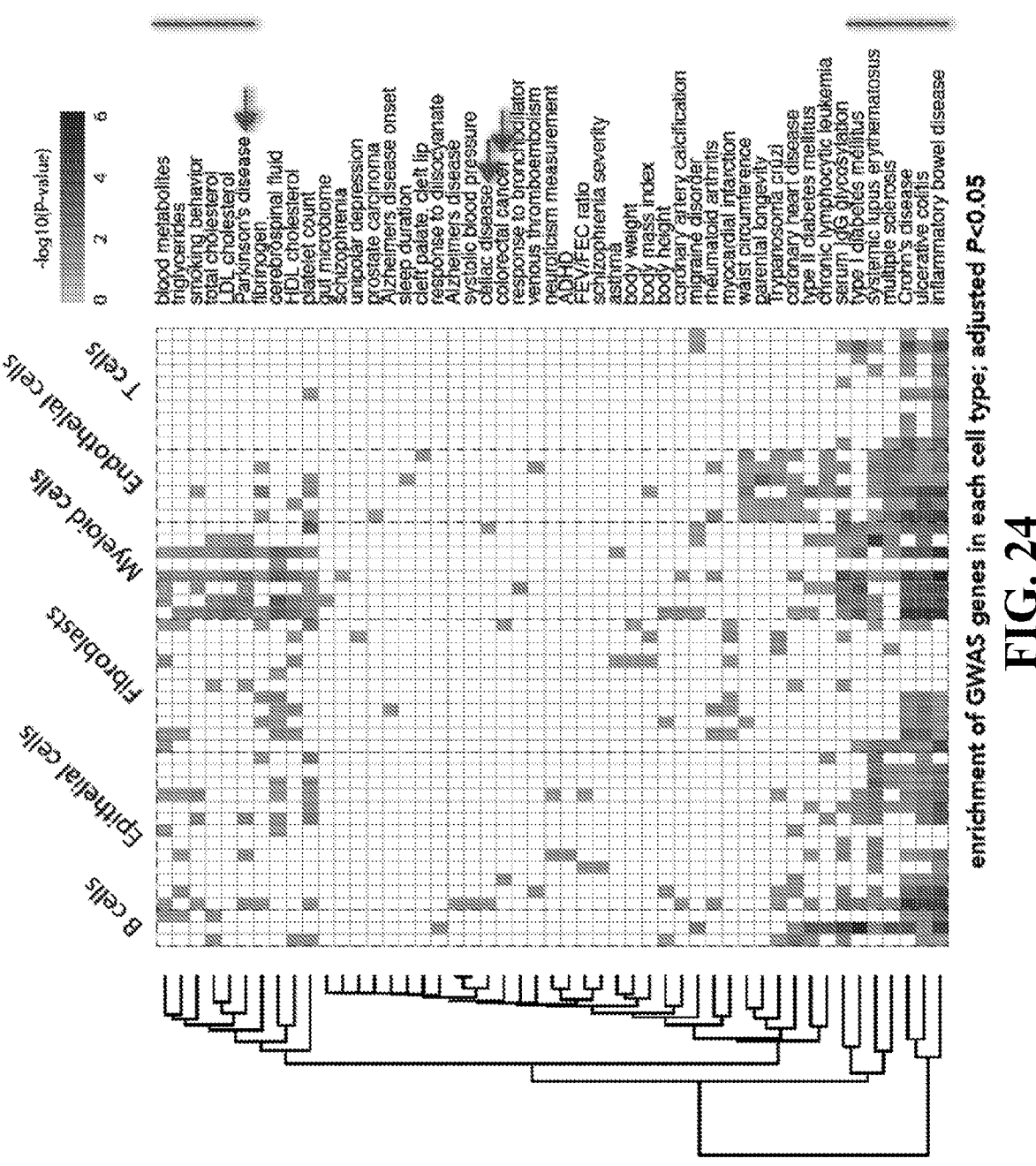
FIG. 24—illustrates that the atlas can be used to determine the cell-of-origin for GWAS genes for other indications.

Applicants were able to determine the cell of origin for genes associated with disease by genome wide association (GWAS) (e.g., IBD). Applicants show heatmaps for GWAS genes expressed in each cell type (FIGS. 20-24). Applicants show a heatmap for G-protein coupled receptors (GPCR), genes involved in cell-cell interactions, and in epithelial cells in the gut cell types. (FIGS. 21, 22 and 23). Key genes are highlighted in FIG. 23. FIG. 24 shows that genes associated with other disease indications can be localized to specific cell types in the atlas.

Figure 25:
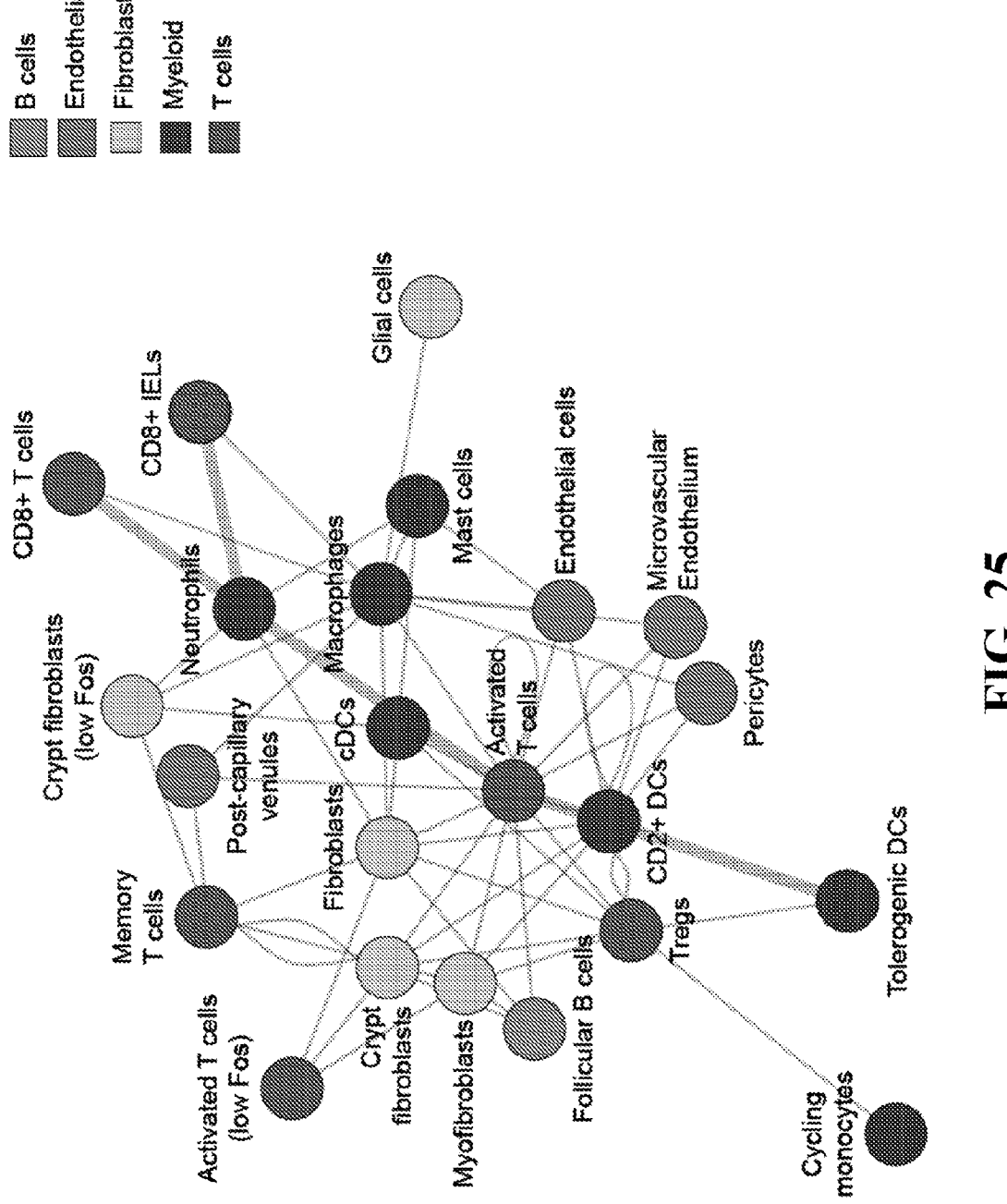
FIG. 25—illustrates that the atlas can be used to determine cell-cell interaction mechanisms.
Figure 26:
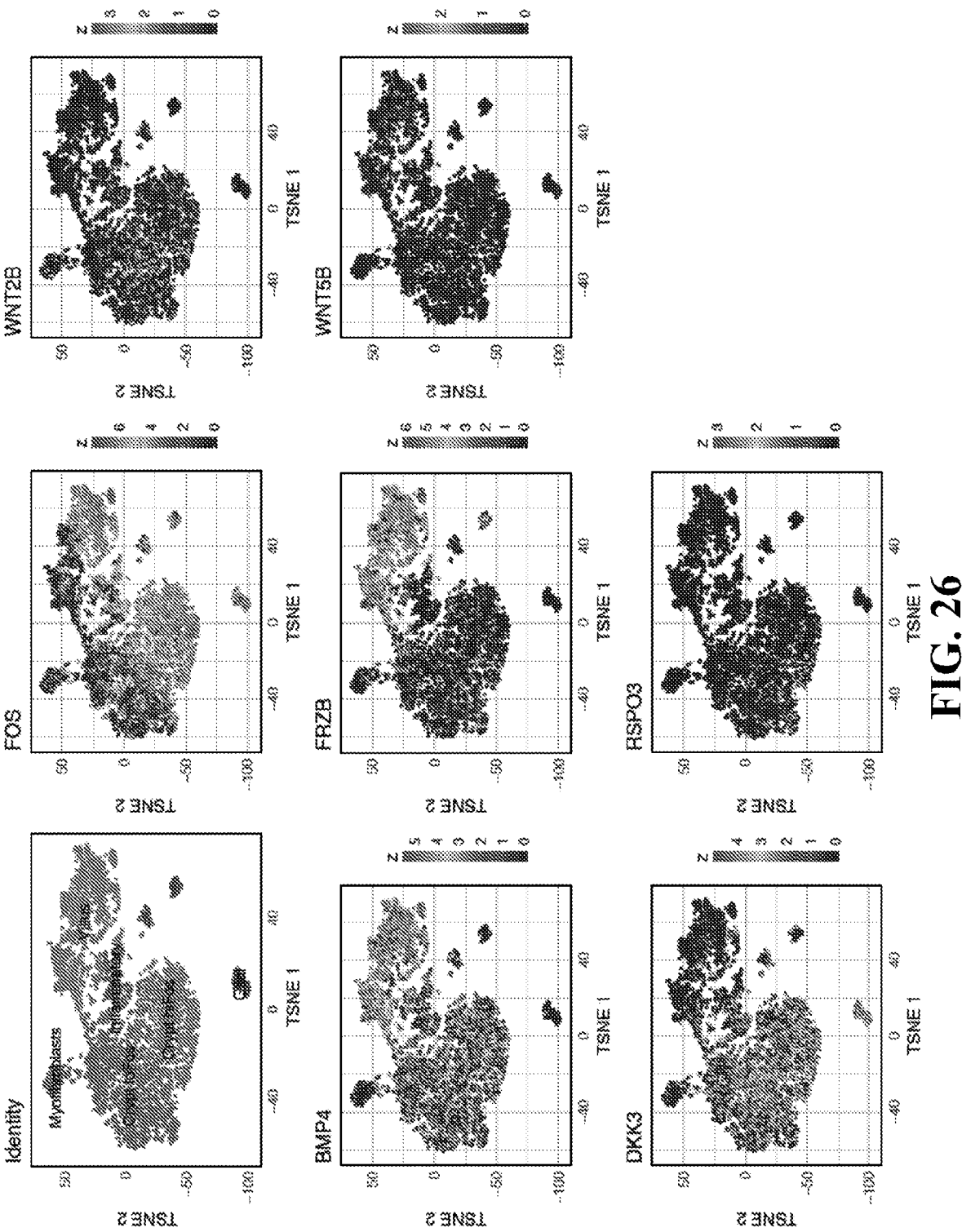
FIG. 26—illustrates that the atlas can be used to determine fibroblasts that support the stem cell niche.

Applicants also show that the atlas may be used to determine cell-cell interaction mechanisms within the gut (FIG. 25). Finally, Applicants show that fibroblasts that support the stem cell niche can be identified using the atlas (FIG. 26).

Example 11—the Tuft Cell is Dynamically Maintained by the Stem Cell Lineage

Figure 31:
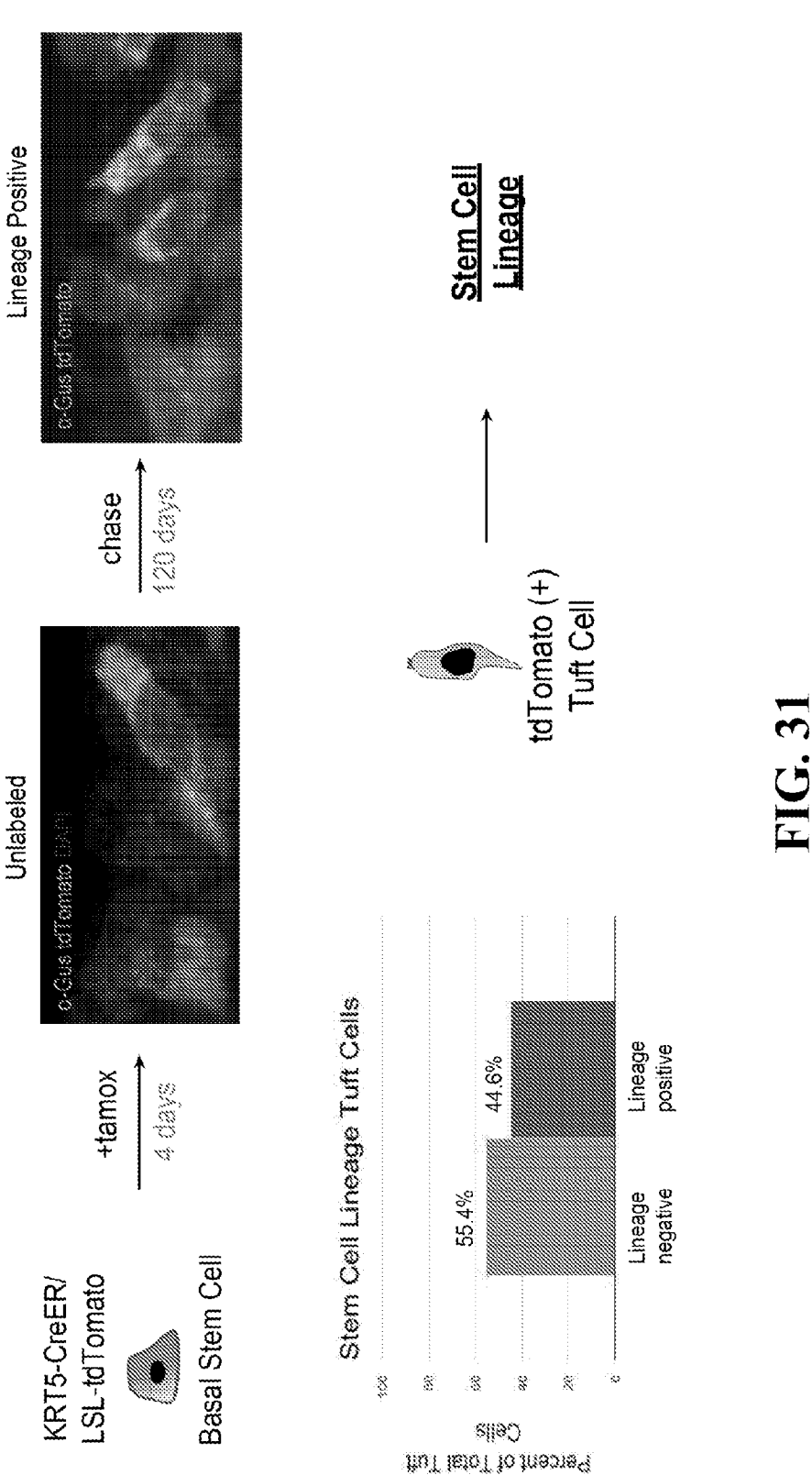
FIG. 31—shows the Tuft Cell is dynamically maintained by the Stem Cell lineage.
Figure 32:
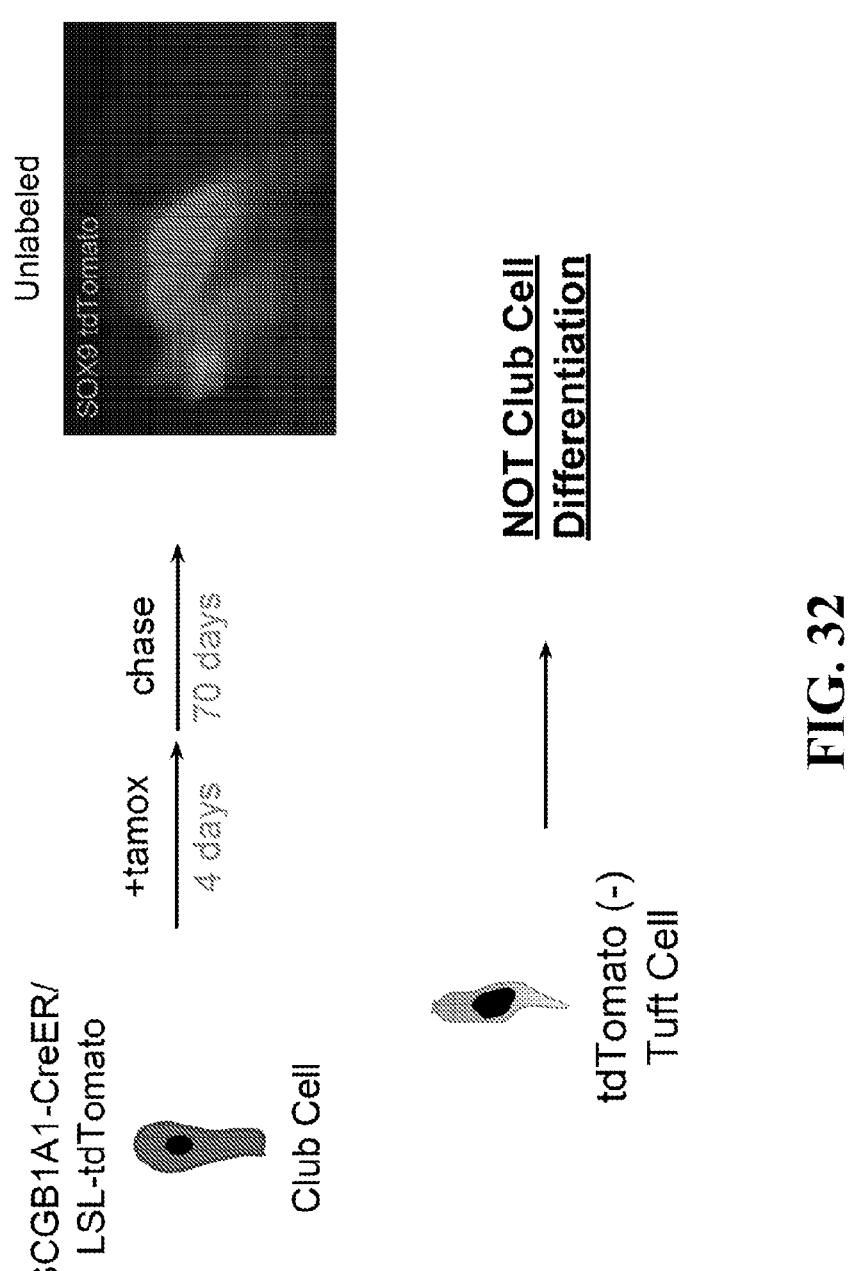
FIG. 32—shows the Tuft Cell is dynamically maintained by the Stem Cell lineage.
Figure 33:
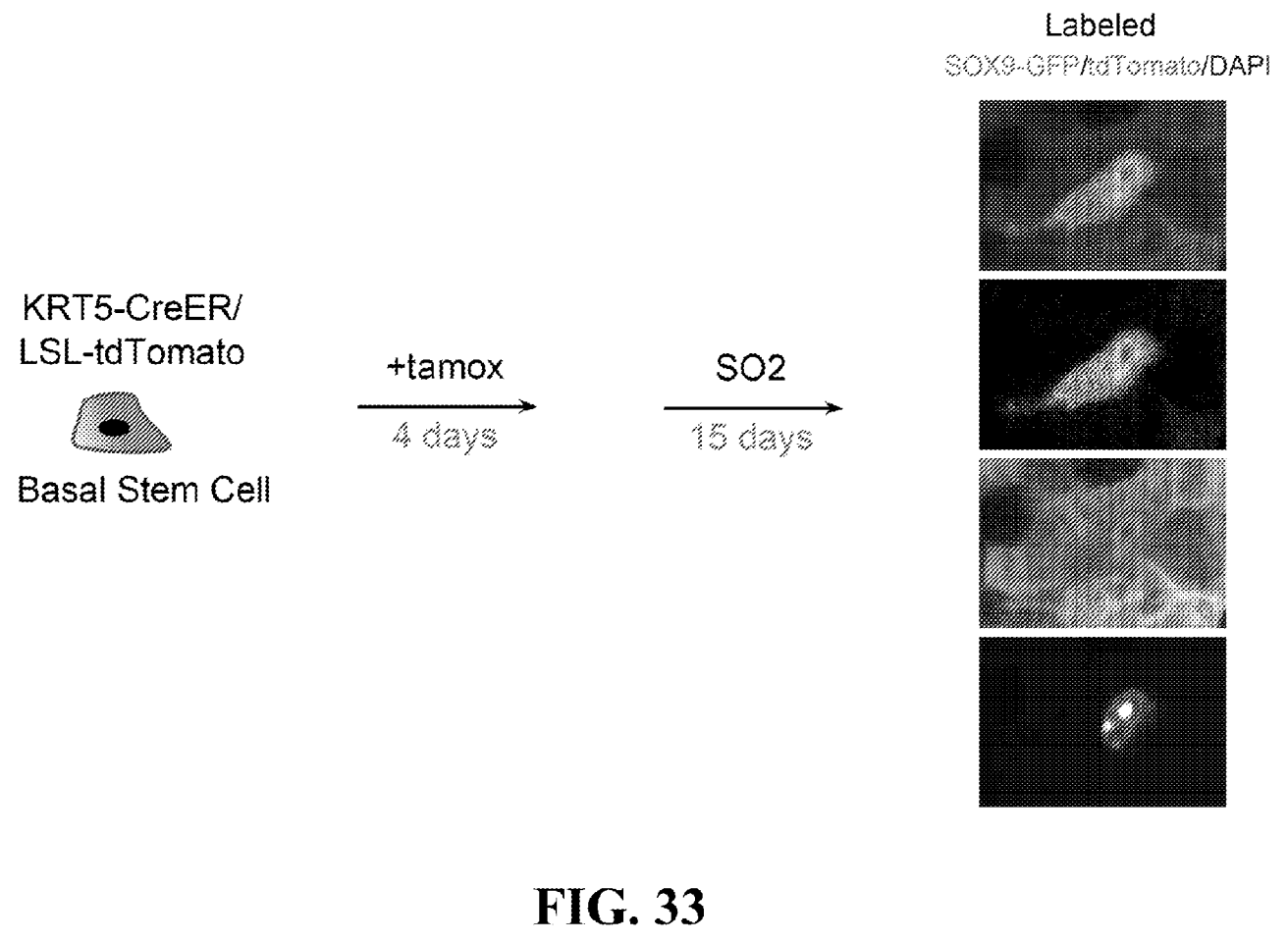

Using a cell lineage system Applicants show that tuft cells are maintained by basal stem cells in the trachea and not club cells (FIG. 31-33).

Example 12—Materials and Methods for Gut

Mice

All mouse work was performed in accordance with the Institutional Animal Care and Use Committees (IACUC) and relevant guidelines at the Broad Institute and MIT, with protocols 0055-05-15 and 0612-058-15. Seven to ten weeks old female or male C57BL/6J wild-type, Lgr5-EGFP-IRES-CreER$^{T2}$ (Lgr5-GFP), MHCII-KO, Foxp3-DTR, B6 Nude and TCRβ-KO mice, obtained from the Jackson Laboratory (Bar Harbor, ME) or Gfi1b$^{eGFP/+}$ (Gfi1b-GFP) were housed under specific-pathogen-free (SPF) conditions at the Broad Institute, MIT or at the Harvard T. H. Chan School of Public Health animal facilities. MHCII-EGFP was obtained from Hidde Ploegh's lab and Lgr5-tdTomato-MHCII-EGFP and H2-Ab1$^{fl/fl}$-Villin-CreER$^{T2}$ (MHCIIDgut) mice were crossed for this study. All mice were housed under specific-pathogen-free (SPF) conditions at either the Broad Institute or MIT animal facilities; infection experiments were conducted at the laboratory of Dr. HN Shi, maintained under specific pathogen-free conditions at Massachusetts General Hospital (Charlestown, MA), with protocol 2003N000158. BrdU and EDU incorporation: EdU was injected intraperitoneally (IP) into Lgr5-GFP mice at 100 mg kg$^{-1}$ for 2 or 4 hours before tissue collection.

*Salmonella enterica* and *H. polygyrus* infection. C57BL/6J mice (Jackson Laboratory) were infected with 200 third-stage larvae of *H. polygyrus* or 10$^8$ *Salmonella enterica* at the laboratory of Dr. HN Shi, maintained under specific pathogen-free conditions at Massachusetts General Hospital (Charlestown, MA), with protocol 2003N000158. *H. polygyrus* was propagated as previously described[76]. Mice were sacrificed 3 and 10 days after *H. polygyrus* infection. For the MHCII blocking experiment, mice infected with *H.*

*polygyrus* were injected with 500 g of blocking anti-mouse MHCII antibody (BioXCell) or Rat IgG2b isotype control (BioXCell) one-day prior to and for 2 consecutive days after *H. polygyrus* infection. For *Salmonella enterica*, mice were infected with a naturally streptomycin-resistant SL1344 strain of *S. typhimurium* (10$^8$ cells) as described[76] and were sacrificed 48 hours after infection.

Foxp3-DTR. Foxp3 and wild-type C57BL/6J mice were injected intraperitoneally with diphtheria toxin (DT) at 22.5 ng/g body weight every other day for one week and then sacrificed.

MHCII deletion in intestinal epithelial cells. Cre activity was induced in 7-10 weeks old mice by intraperitoneal injection (IP) of Tamoxifen (SIGMA), diluted in corn oil, 4 mg per injection, 3 times, every other day. Mice were sacrificed 10 days after the first injection.

Cell Dissociation and Crypt Isolation

Crypt isolation. The small intestine of C57BL/6J wild-type, Lgr5-GFP or Gfi1b-GFP mice was isolated and rinsed in cold PBS. For all mice, crypts were isolated from the whole small intestine or the duodenum, jejunum and ileum compartment to account for regional distribution of Lgr5+ stem cells. The small intestine was extracted and rinsed in cold PBS. The tissue was opened longitudinally and sliced into small fragments roughly 0.2 cm long. The tissue was incubated in 20 mM EDTA-PBS on ice for 90 min, while shaking every 30 min. The tissue was then shaken vigorously and the supernatant was collected as fraction 1 in a new conical tube. The tissue was incubated in fresh EDTA-PBS and a new fraction was collected every 30 min. Fractions were collected until the supernatant consistent almost entirely of crypts. The final fraction (enriched for crypts) was washed twice in PBS, centrifuged at 300 g for 3 min, and dissociated with TrypLE express (Invitrogen) for 1 min at 37° C. The single cell suspension was then passed through a 40 μm filter and stained for FACS sorting for either scRNA-seq method (below) or used for organoid culture.

FAE isolation. Epithelial cells from the follicle associated epithelium were isolated by extracting small sections (0.5 cm) containing Peyer's patches from the small intestine of C57Bl/6J or Gfi1b$^{eGFP/+}$ mice.

Immune cell isolation. Immune cells from the Lamina Propria were isolated enzymatically by incubating the small intestine with Liberase™ (100 ug/mL, Sigma) and DNaseI (100 ug/mL, Sigma) for 30 min at 37° C. Immune cells were also isolated from the mesenteric lymph nodes (mLN). Cells were then incubated with CD3, CD4, CD45, or CD11b FACS-labeled antibodies and sorted for scRNA-seq.

Cell Sorting

For plate-based scRNA-seq experiments, a fluorescence-activated cell sorting (FACS) machine (Astrios) was used to sort a single cell into each well of a 96-well PCR plate containing 5 μl of TCL buffer with 1% 2-mercaptoethanol. For EpCAM$^+$ isolation, cells were stained for 7AAD$^-$ (Life Technologies), CD45$^-$ (eBioscience), CD31$^-$ (eBioscience), Ter119$^-$ (eBioscience), EpCAM$^+$ (eBioscience), and for specific epithelial cells Applicants also stained for CD24$^{+/-}$ (eBioscience) and c-Kit$^{+/-}$ (eBioscience). To enrich for specific IEC populations, cells were isolated from Lgr5-GFP mice, stained with the antibodies mentioned above and gated on GFP-high (stem cells), GFP-low (TAs), GFP$^-$/CD24$^+$/c-Kit$^{+/-}$ (secretory lineages) or GFP$^-$/CD24$^-$/EpCAM$^+$ (epithelial cells). For Tuft-2 isolation, epithelial cells from 3 different mice were stained as above only this time Applicants used EpCAM$^+$/CD45$^+$ and sorted 2000 single cells. A population control of 200 cells was sorted into one well and a no-cell control was sorted into another well. After sorting, the plate was sealed tightly with a Microseal F and centrifuged at 800 g for 1 min. The plate was immediately frozen on dry ice and kept at −80° C. until ready for the lysate cleanup. Bulk population cells were sorted into an Eppendorf tube containing 100 µl solution of TCL with 1% 2-mercaptoethanol and stored at −80° C.

For droplet-based scRNA-seq, cells were sorted with the same parameters as described for plate-based scRNA-seq, but were sorted into an Eppendorf tube containing 50 µl of 0.4% BSA-PBS and stored on ice until proceeding to the GemCode Single Cell Platform or the Chromium Single Cell 3' Library.

Plate-Based scRNA-Seq

Single cells: Libraries were prepared using a modified SMART-Seq2 protocol as previously reported[32]. Briefly, RNA lysate cleanup was preformed using RNAClean XP beads (Agencourt) followed by reverse transcription with Maxima Reverse Transcriptase (Life Technologies) and whole transcription amplification (WTA) with KAPA Hot-Start HIFI 2× ReadyMix (Kapa Biosystems) for 21 cycles. WTA products were purified with Ampure XP beads (Beckman Coulter), quantified with Qubit dsDNA HS Assay Kit (ThermoFisher), and assessed with a high sensitivity DNA chip (Agilent). RNA-seq libraries were constructed from purified WTA products using Nextera XT DNA Library Preparation Kit (Illumina). On each plate, the population and no-cell controls were processed using the same method as the single cells. The libraries were sequenced on an Illumina NextSeq 500.

Bulk samples: Bulk population samples were processed by extracting RNA with RNeasy Plus Micro Kit (Qiagen) per the manufacturer's recommendations, and then proceeding with the modified SMART-Seq2 protocol following lysate cleanup, as described above.

Droplet-Based scRNA-Seq

Single cells were processed through the GemCode Single Cell Platform using the GemCode Gel Bead, Chip and Library Kits (10× Genomics, Pleasanton, CA), or the Chromium Single Cell 3' Library, Gel Bead and Chip Kits (10× Genomics, Pleasanton, CA), following the manufacturer's protocol. Briefly, single cells were sorted into 0.4% BSA-PBS. An input of 6,000 cells was added to each channel of a chip with a recovery rate of 1,500 cells. The cells were then partitioned into Gel Beads in Emulsion (GEMs) in the GemCode instrument, where cell lysis and barcoded reverse transcription of RNA occurred, followed by amplification, shearing and 5' adaptor and sample index attachment. Libraries were sequenced on an Illumina NextSeq 500.

Div-Seq

Lgr5-GFP mice were intraperitoneally (IP) injected with 100 mg kg, EdU (Click-iT Plus EdU Pacific Blue Flow Cytometry Assay Kit, Thermo Fisher Scientific) for 2 hours and then sacrificed. Crypts were isolated as described above and Lrg5$^{hi}$ cells were FACS sorted into PBS, spun down to remove the supernatant, flash frozen and stored in −80° C. Nuclei were then isolated using EZ Prep NUC-101 (Sigma)

per manufacturer's recommendation, and then incubated in the Click-iT Cocktail per manufacturer's recommendations for 30 min, washed in 1% BSA-PBS and counterstained with Vybrant DyeCycle Ruby stain (Thermo Fisher Scientific) for 15 min. Nuclei were then individually sorted into the wells of 96 well plates with TCL+1% 2-mercaptoethanol as described before[14] using FACS, based on positive Ruby and either EdU$^{high}$ or EdU$^{low}$. Plate-based single nucleus RNA-seq (snRNA-Seq) was then performed as described above for scRNA-seq.

Immunofluorescence and Single-Molecule Fluorescence In Situ Hybridization (smFISH)

Immunofluorescence (IFA) and immunohistochemistry (IHC): Staining of small intestinal tissues was conducted as described[13]. Briefly, tissues were fixed for 14 hours in formalin, embedded in paraffin and cut into 5 µm thick sections. Sections were deparaffinized with standard techniques, incubated with primary antibodies overnight at 4° C. and then with secondary antibodies at RT for 30 min. Slides were mounted with Slowfade Mountant+DAPI (Life Technologies, S36964) and sealed.

Single-molecule fluorescence in situ hybridization (smFISH): RNAScope Multiplex Fluorescent Kit (Advanced Cell Diagnostics) was used per manufacturer's recommendations with the following alterations. Target Retrieval boiling time was adjusted to 12 minutes and incubation with Protease IV at 40° C. was adjusted to 8 minutes. Slides were mounted with Slowfade Mountant+DAPI (Life Technologies, S36964) and sealed.

Combined IFA and smFISH was implemented by first performing smFISH as described above, with the following changes. After Amp 4, tissue sections were washed in washing buffer, incubated with primary antibodies overnight at 4° C., washed in 1×TBST 3 times and then incubated with secondary antibodies for 30 min at room temperature. Slides were mounted with Slowfade Mountant+DAPI (Life Technologies, S36964) and sealed.

Antibodies and Probes

Antibodies usedforIFA: rabbit anti-DCLK1 (1:200, Abcam ab31704), rat anti-CD45 (1:100, Biolegend 30-F11), goat anti-ChgA (1:100, Santa Cruz Sc-1488), mouse anti-E-cadherin (1:100, BD Biosciences 610181), rabbit anti-RELMP (1:200, Peprotech® 500-p215), rat anti-Lysozyme (1:200, Dako A0099) and anti-mouse I-A/I-E (1:100, Biolegend 107601). Alexa Fluor 488-, 594-, and 647-conjugated secondary antibodies were used and obtained from Life Technologies.

Probes used for single-molecule RNAscope (Advanced Cell Diagnostics): Cck (C1), Ghrl (C2), GCG (C3), Tph1 (C1), Reg4 (C2), TSLP (C1), Ptprc (C1) andMptx2 (C1). Probes used for single-molecule RNAscope (Advanced Cell Diagnostics): Lgr5 (C1, C3), Cyp2e1 (C2), Psrc1 (C1), Fgfr4 (C2), Cenpf (C3), mKi67 (C1, C3).

Th Cell Polarization In Vitro

CD4+naïve (CD44$^{lo}$CD62L$^+$ CD25$^-$) T cells were isolated from spleen and lymph nodes of 7-10 weeks old C57BL/6J mice using flow cytometry cell sorting. The purity of isolated T cell populations routinely exceeded 98%. Naïve T cells were stimulated with plate-bound anti-CD3 (145-2C11, 1 mg/ml) and anti-CD28 (PV-1, 1 mg/ml) and polarizing cytokines (Th1: 4 ng/ml IL-12; Th2: 4 ng/ml IL-4; Th17: 10 ng/ml IL-6, 2 ng/ml TGF-β1; iTreg: 5 ng/ml TGF-β1; all cytokines from R&D).

Intestinal Organoid Cultures

Organoid cultures. Following crypt isolation from the whole small intestine[142], the single cell suspension was resuspended in Matrigel® (BD Bioscience) with 1 µM Jagged-1 peptide (Ana-Spec). Roughly 300 crypts embedded in 25 µl of Matrigel® were seeded onto each well of a 24-well plate. Once solidified, the Matrigel® was incubated in 600 µl culture medium (Advanced DMEM/F12, Invitrogen) with streptomycin/penicillin and glutamax and supplemented with EGF (100 ng/mL, Peprotech®), R-Spondin-1 (600 ng/mL, R&D), Noggin (100 ng/mL, Peprotech®), Y-276432 dihydrochloride monohydrate (10 µM, Tocris™)), N-acetyl-1-cysteine (1 µM, Sigma-Aldrich), N2 (1×, Life Technologies), B27 (1×, Life Technologies) and Wnt3A (25 ng/mL, R&D Systems). Fresh media was replaced on day 3, and organoids were passaged by dissociation with TrypLE and resuspended in new Matrigel® on day 6 with a 1:3 split ratio. For selected experiments, organoids were additionally treated with RANKL (100 ng/mL, Biolegends). For T helper cell co-culture experiments, organoids were cultured with Th1, Th2, Th17 or iTregs. Roughly 10,000 T helper cells were added to each well of 500 organoids and were supplemented either to the medium or suspended in the Matrigel®. Treated organoids were dissociated and subjected to scRNA-seq using both methods.

Cytokine treated organoids. Organoids were additionally treated with 0.5U/ml IFNγ, 20 ng/ml IL-13, 20 ng/ml IL-17A or 10 ng/ml IL-10 in the culture medium for 3 days. Re-seeding after cytokine treatment. 500 organoids/well were treated with cytokines, as in the cytokine treated organoids above, collected after 3 days and then re-seeded at 500 organoids/well in media without cytokines. Each day, images were taken at 2× magnification and quantification of organoids number was performed with the ImageJ software. Two-Photon Intra-Vital Microscopy (2P-IVM) of T Cells and ISCs To generate gut-homing T cells visualized by 2P-IVM, a combination of modified protocols[143,144] was used. CD4+ T cells were isolated from spleen, pLN and mLN from β-actin-RFP mice using a MACS CD4 T cell positive-selection kit (Miltenyi clone L3T4) following the manufacturer's instructions. Plates were pre-treated with 5 ug/mL anti-CD3 (clone 145-2C11) and 1 ug/mL anti-CD28 (clone 37.51) and 1 Å~$10^6$ CD4+ T cells were added to each well for a final volume of 2.5 mL in complete RPMI1640 media supplemented with all-trans Retinoic Acid (100 nM, Sigma R2625). The T cells were cultured for 96 hours before replacing half of the volume with fresh media containing 20U/mL of rIL-2 and then cultured for another 48 hours. Before adoptive transfer into Lgr5-GFP hosts, the gut-homing phenotype was validated with flow cytometry for α4β7 and CCR9 expression. 1 Å~$10^7$ cells were then transferred into recipient mice for two hours, and treated with 20 ug of anti-CD3 (clone 2C11). 2P-IVM was performed 72 hours following transfer. The small intestine was surgically exposed through a laparotomy incision. Anesthetized mice were placed on a custom-built stage with a loop of the intact small intestine fixed to a temperature-controlled metallic support to facilitate exposure of the serosal aspect to a water-immersion 20× objective (0.95 numerical aperture) of an upright microscope (Prairie Technologies). A Mai Tai Ti:sapphire laser (Spectra-Physics) was tuned between 870 nm and 900 nm for multiphoton excitation and second-harmonic generation. For dynamic analysis of cell interaction in four dimensions, several X/Y sections (512×512) with Z spacing ranging from 2 µm to 4 µm were acquired every 15-20 seconds with an electronic zoom varying from 1× to 3×. Emitted light and second harmonic signals were directed through 450/80-nm, 525/50-nm and 630/120-nm bandpass filters and detected with non-descanned detectors. Post-acquisition image analysis, volume-rendering and four-dimensional time-lapse videos were performed using Imaris software (Bitplane scientific software).

Analysis

Pre-processing of droplet (10×) scRNA-seq data. Demultiplexing, alignment to the mm10 transcriptome and UMI-collapsing were performed using the Cellranger toolkit (version 1.0.1) provided by 10× Genomics. For each cell, Applicants quantified the number of genes for which at least one read was mapped, and then excluded all cells with either fewer than 800 detected genes. Expression values Ei,j for gene i in cell j were calculated by dividing UMI count values for gene i by the sum of the UMI counts in cellj, to normalize for differences in coverage, and then multiplying by 10,000 to create TPM-like values, and finally calculating $\log_2$ (TPM+1) values. Batch correction was performed using ComBat[78] as implemented in the R package sva[79], using the default parametric adjustment mode. The output was a corrected expression matrix, which was used as input to further analysis.

Selection of variable genes was performed by fitting a generalized linear model to the relationship between the squared co-efficient of variation (CV) and the mean expression level in log/log space, and selecting genes that significantly deviated ($P<0.05$) from the fitted curve, as previously described[80].

Pre-processing of SMART-Seq2 scRNA-seq data. BAM files were converted to merged, demultiplexed FASTQs using the Illumina provided Bcl2Fastq software package v2.17.1.14. Paired-end reads were mapped to the UCSC hg19 human transcriptome using Bowtie[81] with parameters "-q --phred33-quals-n 1 -e 99999999-1 25-I1-X 2000-a -m 15-S -p 6", which allows alignment of sequences with one mismatch. Expression levels of genes were quantified as using transcript-per-million (TPM) values calculated by RSEM[82] v1.2.3 in paired-end mode. For each cell, Applicants quantified the number of genes for which at least one read was mapped, and then excluded all cells with either fewer than 3,000 detected genes or a transcriptome-mapping of less than 40%.

Selection of variable genes was performed by fitting a generalized linear model to the relationship between the squared coefficient of variation (CV) and the mean expression level in log/log space, and selecting genes that significantly deviated ($p<0.05$) from the fitted curve, as previously described[80].

Dimensionality reduction usingPCA and tSNE. Applicants restricted the expression matrix to the subsets of variable genes and high quality cells noted above, and values were centered and scaled before input to PCA, which was implemented using the R function 'prcomp' from the 'stats' package for the SMART-seq2 dataset. For the droplet dataset, Applicants used a randomized approximation to PCA, implemented using the 'rpca' function from the 'rsvd' R package, with the parameter k set to 100. This low-rank approximation was used as it is several orders of magnitude faster to compute for very wide matrices. Given that many principal components (PCs) explain very little of the variance, the signal to noise ratio can be substantially improved by selecting a subset of n 'significant' PCs. After PCA, significant PCs were identified using the permutation test described in[83], implemented using the 'permutationPA' function from the 'jackstraw' R package. This test identified 13 and 15 significant PCs in the 10× and SMART-Seq2 datasets of FIG. 1, respectively. Only scores from these significant PCs were used as the input to further analysis.

For visualization, the dimensionality of the datasets was further reduced using the 'Barnes-hut' approximate version of the t-distributed stochastic neighbor embedding (tSNE)[84,85]. This was implemented using the 'Rtsne' function from the 'Rtsne' R package using 20,000 iterations and a perplexity setting that ranged from 10 to 30 depending on the size of the dataset. Scores from the first n PCs were used as the input to tSNE, where n was determined for each dataset using the permutation test described above.

Identifying cell differentiation trajectories using diffusion maps. Prior to running diffusion-map dimensionality reduction Applicants selected highly variable genes in the data as follows. Applicants first fit a null model for baseline cell-cell gene expression variability in the data based on a power-law relationship between coefficient of variation (CV) and the mean of the UMI-counts of all the expressed genes, similar to[86]. Next, Applicants calculated for each gene the difference between the value of its observed CV and that expected by the null model ($CV_{diff}$). The histogram of $CV_{diff}$ exhibited a "fat tail". Applicants calculated the mean $\mu$ and standard deviation $a$ of this distribution, and selected all genes with $CV_{diff} > \mu + 1.67\sigma$, yielding 761 genes that were used for further analysis.

Applicants performed dimensionality reduction using the diffusion map approach[40]. Briefly, a cell-cell transition matrix was computed using the Gaussian kernel where the kernel width was adjusted to the local neighborhood of each cell, following[87]. This matrix was converted to a Markovian matrix after normalization. The right eigenvectors $v_i$ ($i=0, 1, 2, 3, \ldots$) of this matrix were computed and sorted in the order of decreasing eigenvalues $\lambda_i$ ($i=0, 1, 2, 3, \ldots$) after excluding the top eigenvector $v_0$, corresponding to $\lambda_0=1$ (which reflects the normalization constraint of the Markovian matrix). The remaining eigenvectors $v_i$ ($i=1,2 \ldots$) define the diffusion map embedding and are referred to as diffusion components ($DC_k$ ($k=1, 2, \ldots$)). Applicants noticed a spectral gap between the $\lambda_4$ and the $\lambda_5$, and hence retained $DC_1$-$DC_4$.

Removing contaminating immune cells and doublets. Although cells were sorted prior to sequencing using EpCAM, a small number of contaminating immune cells were observed in the 10× dataset. These 264 cells were removed by an initial round of unsupervised clustering (density-based clustering of the tSNE map using 'dbscan'[88] from the R package 'fpc') as they formed an extremely distinct cluster. In the case of the SMART-Seq2 dataset, several cells were outliers in terms of library complexity, which could possibly correspond to more than one individual cell per sequencing library or 'doublets'. These cells were then removed by calculating the top quantile 1% of the distribution of genes detected per cell and removing any cells in this quantile.

Cluster analysis (e.g., k-NNgraph based clustering). To cluster single cells by their expression, Applicants used an unsupervised clustering approach, based on the Infomap graph-clustering algorithm[25], following approaches recently described for single-cell CyTOF data[89] and scRNA-seq[26]. Briefly, Applicants constructed a k-nearest-neighbor (k-NN) graph on the data using, for each pair of cells, the Euclidean distance between the scores of significant PCs to identify k nearest neighbors. The parameter k was chosen to be consistent with the size of the dataset.

Specifically, k was set to 200 and 80 for the droplet dataset of 7,216 cells (FIG. 1A), the SMART-Seq2 dataset of 1,522 cells (FIG. 8A). RANKL-treated organoids contained 5434 cells and k was set to 200, while the *Salmonella* and *H. polygyrus* dataset contained 9842 cells and k was set to 500. For cluster analyses within celltypes, specifically the EEC and tuft cell subsets, Applicants used the Pearson correlation distance instead of Euclidean, and set k=15, k=30 and k=40 for the enteroendocrine subtypes (533 cells), and 166 and 102 tuft cells in the 10× and SMART-Seq2 datasets respectively.

The nearest neighbor graph was computed using the function 'nng' from the R package 'cccd'. The k-NN graph was then used as the input to Infomap[25], implemented using the 'infomap.community' function from the 'igraph' R package.

Detected clusters were mapped to cell-types or intermediate states using known markers for intestinal epithelial cell subtypes. (7 FIGS. 7E and 7 FIG. 8A). In the case of the enteroendocrine cell (EEC) sub-analysis (FIG. 3), any group of EEC progenitor clusters with average pairwise correlations between significant PC scores r>0.85 was merged, resulting in 4 clusters, which were annotated as Prog. (a) based on high levels of Ghrl and Prog. (early), (mid) and (late)—based on decreasing levels of stem (Slc12a2, Ascl2, Axin2) and cell-cycle genes and increasing levels of known EEC regulatory factors (Neurod1, Neurod2 and Neurog3) from early to late (FIG. 11C). For the SMART-Seq2 dataset, two clusters expressing high levels of stem cell marker genes (FIG. 8A) were merged to form a 'Stem' cluster and two other clusters were merged to form a 'TA' cluster.

For the cluster analysis of the follicle-associated epithelium (FAE) dataset of 4700 cells, the M cells were exceedingly rare (0.38%), and therefore the 'ClusterDP' method[90] was used to identify them, as it empirically performed better than the kNN-graph algorithm on this dataset containing such a rare subgroup. As with the kNN methods, ClusterDP was run using significant (p<0.05) PC scores (19 in this case) as input, and was implemented using the 'findClusters' and 'densityClust' functions from the 'densityClust' R package using parameters rho=1.1 and delta=0.25.

Detected clusters were annotated by cell types or states using known markers for IEC subtypes. Specifically, for each known epithelial type Applicants selected five canonical marker genes (e.g., Lgr5, Ascl2, Slc12a2, Axin2 and Olfm4 for stem cells, or Lyz1, Defa17, Defa22, Defa24 and Ang4 for Paneth cells), and scored all clusters for their expression (see below for signature scoring procedure).

Extracting rare cell-types for further analysis. The initial clustering of the whole-gut dataset (7,216 cells, FIG. 1B) showed a cluster of 310 EECs and 166 tuft cells. The tuft cells were taken 'as is' for the sub-analysis (FIG. 4A-B), while the EECs were combined with a second cluster of 239 EECs identified in the regional dataset (FIG. 10H) for a total of 533 EECs. A group of 16 cells co-expressed EEC markers Chga, Chgb with markers of Paneth cells including Lyz1, Defa5 and Defa22, and were therefore interpreted as doublets, and removed from the analysis, leaving 533 EECs, which were the basis for the analysis in FIG. 3. To compare expression profiles of enterocytes from proximal and distal small intestine (FIG. 10I), the 1,041 enterocytes identified from 11,665 cells in the regional dataset (FIG. 10H) were used.

Defining cell-type signatures. To identify maximally specific genes for cell-types, Applicants ran differential expression tests between each pair of clusters for all possible pairwise comparisons. Then, for a given cluster, putative signature genes were filtered using the maximum FDR Q-value and ranked by the minimum log 2 fold-change. The minimum fold-change and maximum Q-value represent the weakest effect-size across all pairwise comparisons, therefore this a stringent criterion. Cell-type signature genes shown in (FIG. 1C, FIG. 14H, and Tables 3-5 and 9) were obtained using a maximum FDR of 0.05 and a minimum log 2 fold-change of 0.5.

In the case of signature genes for subtypes within cell-types (FIG. 3B, FIG. 4B and FIG. 13B), an aggregate p-value (across the pairwise tests) for enrichment was computed using Fisher's method—a more lenient criterion than simply taking the maximum p-value—and a maximum FDR Q-value of 0.01 was used, along with a cutoff of minimum log 2 fold-change of 0.25 for tuft cell subsets (FIG. 4B, FIG. 13B and Table 8) and 0.1 for enteroendocrine subsets (FIG. 3B, Table 7). Due to low cell numbers (n=18), this Fisherp-value was also used for the in vivo M cell signature, with an FDR cutoff of 0.001 (FIG. 5D), Table 9). Marker genes were ranked by minimum log 2 fold-change. Differential expression tests were carried out using the Mann-Whitney U-test (also known as the Wilcoxon rank-sum test) implemented using the R function 'wilcox.test'. For the infection experiments (FIG. 6), Applicants used a two part 'hurdle'-model to control for both technical quality and mouse-to-mouse variation. This was implemented using the R package MAST[91], and p-values for differential expression were computed using the likelihood-ratio test. Multiple hypothesis testing correction was performed by controlling the false discovery rate[92] using the R function p.adjust.

Gene sets associated with G1/S and G2/M phases of the cell-cycle were downloaded from cell.com/cms/attachment/2051395126/2059328514/mmc2.xlsx [Macosko 2015]. A set of cell-cycle genes to assess overall proliferation (see below for scoring procedure) was defined as the union of the G1/S and G2/M sets.

Scoring cells using signature gene sets. To obtain a score for a specific set of n genes in a given cell, a 'background' gene set was defined to control for differences in sequencing coverage and library complexity between cells in a manner similar to[29]. The background gene set was selected to be similar to the genes of interest in terms of expression level. Specifically, the 10n nearest neighbors in the 2-D space defined by mean expression and detection frequency across all cells were selected. The signature score for that cell was then defined as the mean expression of the n signature genes in that cell, minus the mean expression of the IOn background genes in that cell.

Estimates of cell type samplingfrequencies. For each cell-type the probability of observing at least n cells in a sample of size k is modeled using the cumulative distribution function of a negative binomial NBcdf(k, n, p), where p is the relative abundance of this cell type. For m cell types with the same parameter p the overall probability of seeing each type at least n times is NBcdf(k; n, p)^m. Such analysis can now be performed with user specified parameters at satijalab.org/howmanycells.

EEC dendrogram. Average expression vectors were calculated for all 12 EEC subset clusters, using $\log_2(TPM+1)$ values, and restricted to the subset of 1,361 genes identified as significantly variable between EEC susbsets (p<0.05), as described above. The average expression vectors including these genes were hierarchically clustered using the R package pvclust (Spearman distance, ward.D2 clustering method), which provides bootstrap confidence estimates on every dendrogram node, as an empirical p-value over 100, 000 trials (FIG. 12A).

Cell-type specific TFs, GPCRs and LRRs. A list of all genes identified as acting as transcription factors in mice was obtained from AnimalTFDB 93, downloaded from: bioguo.org/AnimalTFDB/BrowseAllTF.php?spe=Mus_musculus. The set of G-protein coupled receptors (GPCRs)

was obtained from the UniProt database, downloaded from: uniprot.org/uniprot/?query=family %3A %22 g+protein+coupled+receptor %22+AND+organis m %3A %22Mouse+%5B10090%5D %22+AND+reviewed %3Ayes&sort=score. Functional annotations for each protein (FIG. 8D) were obtained from the The British Pharmacological Society (BPS) and the International Union of Basic and Clinical Pharmacology (IUPHAR) data, downloaded from: guideto-pharmacology.org/GRAC/GPCRListForward?class=A. The list of leucine-rich repeat proteins (LRRs) was taken from 94. To map from human to mouse gene names, human and mouse orthologs were downloaded from Ensembl (latest release 86, ensembl.org/biomart/martview), and human and mouse gene synonyms from NCBI (ftp.ncbi.nlm.nih.gov/gene/DATA/GENE_INFO/Mammalia/). For each human LRR gene, all human synonyms were mapped to the orthologous gene in mouse using the ortholog list, and mouse gene names were mapped to those in the single-cell data using the synonym list.

Cell-type enriched TFs, GPCRs and LRRs were then identified by intersecting the list of genes enriched in to each cell type with the lists of TFs, GPCRs and LRRs defined above. Cell-type enriched genes were defined using the SMART-Seq2 dataset, as those with a minimum log 2 fold-change of 0 and a maximum FDR of 0.5, retaining a maximum of 10 genes per cell type in FIG. 1F, FIG. 1G, and FIG. 8E, while complete lists are provided in Table 6. In addition, a more extensive panel of cell-type specific GPCRs was identified (FIG. 8D) by selecting a more lenient threshold. This was achieved by comparing each cell-type to all other cells, instead of the pairwise comparisons described in the previous section, and selecting all GPCR genes differentially expressed (FDR<0.001).

Testing for changes in cell type proportions. Applicants model the detected number of each cell-type in each analyzed mouse as a random count variable using a Poisson process. The rate of detection is then modeled by providing the total number of cells profiled in a given mouse as an offset variable, while the condition of each mouse (treatment or control) was provided as a covariate. The model was fit using the R command 'glm' from the 'stats' package. The p-value for the significance of the effect produced by the treatment was then assessed using a Wald test on the regression coefficient.

In the case of the assessment of the significance of spatial distributions of enteroendocrine (EEC) subsets (FIG. 3E), the comparison involved more than two groups. In particular, the null hypothesis was that the proportion of each EEC subset detected in the three intestinal regions (duodenum, jejunum, and ileum) was equal. To test this hypothesis Applicants used analysis of variance (ANOVA) with a $\chi^2$-test on the Poisson model fit described above, implemented using the 'anova' function from the 'stats' package.

Specifically, given that m and n total cells (of all cell types) are sequenced in a treatment and control condition respectively, Applicants test, for a given cell type, whether the number of k and q of observed cells of type C in total and treatment condition respectively, significantly deviates from a null model given by the hypergeometric distribution. The probability of observing these values was calculated using the R function 'phyper' from the 'stats' package, using the command:

P=phyper(q, k, m, n)

and was reported as a hypergeometric p-value.

Gene set enrichment and GO analysis. GO analysis was performed using the 'goseq' R package[95], using significantly differentially expressed genes (FDR<0.05) as target genes, and all genes expressed with $\log_2(\text{TPM}+1) > 3$ in at least 10 cells as background.

REFERENCES FOR EXAMPLES 1-12

1 Clevers, H. Wnt/beta-catenin signaling in development and disease. *Cell* 127, 469-480, doi:10.1016/j.cell.2006.10.018 (2006).

2 Peterson, L. W. & Artis, D. Intestinal epithelial cells: regulators of barrier function and immune homeostasis. *Nature reviews. Immunology* 14, 141-153, doi:10.1038/nri3608 (2014).

3 Ferraris, R. P., Villenas, S. A. & Diamond, J. Regulation of brush-border enzyme activities and enterocyte migration rates in mouse small intestine. *The American journal of physiology* 262, G1047-1059 (1992).

4 Sato, T. et al. Single Lgr5 stem cells build crypt-villus structures in vitro without a mesenchymal niche. *Nature* 459, 262-265, doi:10.1038/nature07935 (2009).

5 Gerbe, F., Legraverend, C. & Jay, P. The intestinal epithelium tuft cells: specification and function. *Cellular and molecular life sciences: CMLS* 69, 2907-2917, doi:10.1007/s00018-012-0984-7 (2012).

6 Barker, N. et al. Identification of stem cells in small intestine and colon by marker gene Lgr5. *Nature* 449, 1003-1007, doi:10.1038/nature06196 (2007).

7 Barker, N., van Oudenaarden, A. & Clevers, H. Identifying the stem cell of the intestinal crypt: strategies and pitfalls. *Cell stem cell* 11, 452-460, doi:10.1016/j.stem.2012.09.009 (2012).

8 Clevers, H. The intestinal crypt, a prototype stem cell compartment. *Cell* 154, 274-284, doi:10.1016/j.cell.2013.07.004 (2013).

9 Salzman, N. H., Ghosh, D., Huttner, K. M., Paterson, Y. & Bevins, C. L. Protection against enteric *salmonellosis* in transgenic mice expressing a human intestinal defensin. *Nature* 422, 522-526, doi:10.1038/nature01520 (2003).

10 Pelaseyed, T. et al. The mucus and mucins of the goblet cells and enterocytes provide the first defense line of the gastrointestinal tract and interact with the immune system. *Immunological reviews* 260, 8-20, doi:10.1111/imr.12182 (2014).

11 Gribble, F. M. & Reimann, F. Enteroendocrine Cells: Chemosensors in the Intestinal Epithelium. *Annual review of physiology* 78, 277-299, doi:10.1 146/annurev-physiol-021115-105439 (2016).

12 Furness, J. B., Rivera, L. R., Cho, H. J., Bravo, D. M. & Callaghan, B. The gut as a sensory organ. *Nature reviews. Gastroenterology & hepatology* 10, 729-740, doi:10.1038/nrgastro.2013.180 (2013).

13 Biton, M. et al. Epithelial microRNAs regulate gut mucosal immunity via epithelium-T cell crosstalk. *NatImmunol* 12, 239-246, doi:10.1038/ni.1994 (2011).

14 Howitt, M. R. et al. Tuft cells, taste-chemosensory cells, orchestrate parasite type 2 immunity in the gut. *Science* 351, 1329-1333, doi:10.1 126/science.aaf1648 (2016).

15 von Moltke, J., Ji, M., Liang, H. E. & Locksley, R. M. Tuft-cell-derived IL-25 regulates an intestinal ILC2-epithelial response circuit. *Nature* 529, 221-225, doi:10.1038/nature16161 (2016).

16 Gerbe, F. et al. Intestinal epithelial tuft cells initiate type 2 mucosal immunity to helminth parasites. *Nature* 529, 226-230, doi:10.1038/nature16527 (2016).

17 de Lau, W. et al. Peyer's patch M cells derived from Lgr5(+) stem cells require SpiB and are induced by RankL in cultured "miniguts". *Molecular and cellular biology* 32, 3639-3647, doi:10.1128/MCB.00434-12 (2012).

18 Mabbott, N. A., Donaldson, D. S., Ohno, H., Williams, I. R. & Mahajan, A. Microfold (M) cells: important immunosurveillance posts in the intestinal epithelium. *Mucosal immunology* 6, 666-677, doi:10.1038/mi.2013.30 (2013).

19 Heinz, S., Romanoski, C. E., Benner, C. & Glass, C. K. The selection and function of cell type-specific enhancers. *Nature reviews. Molecular cell biology* 16, 144-154, doi:10.1038/nrm3949 (2015).

20 Wagner, A., Regev, A. & Yosef, N. Revealing the vectors of cellular identity with single-cell genomics. *Nat Biotechnol* 34, 1145-1160, doi:10.1038/nbt.3711 (2016).

21 Bezencon, C. et al. Murine intestinal cells expressing Trpm5 are mostly brush cells and express markers of neuronal and inflammatory cells. *The Journal of comparative neurology* 509, 514-525, doi:10.1002/cne.21768 (2008).

22 Habib, A. M., Richards, P., Rogers, G. J., Reimann, F. & Gribble, F. M. Co-localisation and secretion of glucagon-like peptide 1 and peptide YY from primary cultured human L cells. *Diabetologia* 56, 1413-1416, doi:10.1007/s00125-013-2887-z (2013).

23 Grun, D. et al. Single-cell messenger RNA sequencing reveals rare intestinal cell types. *Nature* 525, 251-255, doi:10.1038/nature14966 (2015).

24 Zheng, G. X. et al. Haplotyping germline and cancer genomes with high-throughput linked-read sequencing. *Nat Biotechnol* 34, 303-311, doi:10.1038/nbt.3432 (2016).

25 Rosvall, M. & Bergstrom, C. T. Maps of random walks on complex networks reveal community structure. *Proceedings of the National Academy of Sciences* 105, 1118-1123, doi:10.1073/pnas.0706851105 (2008).

26 Shekhar, K. et al. Comprehensive Classification of Retinal Bipolar Neurons by Single-Cell Transcriptomics. *Cell* 166, 1308-1323.e1330, doi:10.1016/j.cell.2016.07.054 (2016).

27 Amir el, A. D. et al. viSNE enables visualization of high dimensional single-cell data and reveals phenotypic heterogeneity of leukemia. *Nat Biotechnol* 31, 545-552, doi:10.1038/nbt.2594 (2013).

28 van der Maaten, L. & Hinton, G. Visualizing Data using t-SNE. *J Mach Learn Res* 9, 2579-2605 (2008).

29 Kowalczyk, M. S. et al. Single-cell RNA-seq reveals changes in cell cycle and differentiation programs upon aging of hematopoietic stem cells. *Genome Research* 25, 1860-1872, doi:10.1101/gr.192237.115 (2015).

30 Yan, K. S. et al. Non-equivalence of Wnt and R-spondin ligands during Lgr5+ intestinal stem-cell self-renewal. *Nature* 545, 238-242, doi:10.1038/nature22313 (2017).

31 Garabedian, E. M., Roberts, L. J., McNevin, M. S. & Gordon, J. I. Examining the role of Paneth cells in the small intestine by lineage ablation in transgenic mice. *J Biol Chem* 272, 23729-23740 (1997).

32 Picelli, S. et al. Full-length RNA-seq from single cells using Smart-seq2. *Nature protocols* 9, 171-181, doi:10.1038/nprot.2014.006 (2014).

33 van der Meer-van Kraaij, C. et al. Dietary modulation and structure prediction of rat mucosal pentraxin (Mptx) protein and loss of function in humans. *Genes & nutrition* 2, 275-285, doi:10.1007/s12263-007-0058-x (2007).

34 Du Clos, T. W. Pentraxins: structure, function, and role in inflammation. *ISRN inflammation* 2013, 379040, doi:10.1155/2013/379040 (2013).

35 Katz, J. P. et al. The zinc-finger transcription factor Klf4 is required for terminal differentiation of goblet cells in the colon. *Development* 129, 2619-2628 (2002).

36 Duboc, H., Tache, Y. & Hofmann, A. F. The bile acid TGR5 membrane receptor: from basic research to clinical application. *Dig Liver Dis* 46, 302-312, doi:10.1016/j.dld.2013.10.021 (2014).

37 Overton, H. A., Fyfe, M. C. & Reynet, C. GPR119, a novel G protein-coupled receptor target for the treatment of type 2 diabetes and obesity. *Br J Pharmacol* 153 Suppl 1, 576-81, doi:10.1038/sj.bjp.0707529 (2008).

38 Kim, T. H. et al. Single-Cell Transcript Profiles Reveal Multilineage Priming in Early Progenitors Derived from Lgr5(+) Intestinal Stem Cells. *Cell Rep* 16, 2053-2060, doi:10.1016/j.celrep.2016.07.056 (2016).

39 Tetteh, P. W. et al. Replacement of Lost Lgr5-Positive Stem Cells through Plasticity of Their Enterocyte-Lineage Daughters. *Cell stem cell* 18, 203-213, doi:10.1016/j.stem.2016.01.001 (2016).

40 Coifman, R. R., et al. Geometric diffusions as a tool for harmonic analysis and structure definition of data: diffusion maps. *Proceedings of the National Academy ofSciences of the United States of America* 102, 7426-7431, doi:10.1073/pnas.0500334102 (2005).

41 Trapnell, C. et al. The dynamics and regulators of cell fate decisions are revealed by pseudotemporal ordering of single cells. Nat Biotechnol 32, 381-386, doi:10.1038/nbt.2859 (2014).

42 Bendall, S. C. et al. Single-cell trajectory detection uncovers progression and regulatory coordination in human B cell development. *Cell* 157, 714-725, doi:10.1016/j.cell.2014.04.005 (2014).

43 Kohlnhofer, B. M., Thompson, C. A., Walker, E. M. & Battle, M. A. GATA4 regulates epithelial cell proliferation to control intestinal growth and development in mice. *Cell Mol Gastroenterol Hepatol* 2, 189-209, doi:10.1016/j.jcmgh.2015.11.010 (2016).

44 Basak, O. et al. Mapping early fate determination in Lgr5+ crypt stem cells using a novel Ki67-RFP allele. *EMBO J*33, 2057-2068, doi:10.15252/embj.201488017 (2014).

45 Beuling, E. et al. GATA factors regulate proliferation, differentiation, and gene expression in small intestine of mature mice. *Gastroenterology* 140, 1219-1229 e1211-1212, doi:10.1053/j.gastro.2011.01.033 (2011).

46 Battle, M. A. et al. GATA4 is essential for jejunal function in mice. *Gastroenterology* 135, 1676-1686 e1671, doi:10.1053/j.gastro.2008.07.074 (2008).

47 Sjolund, K., Sanden, G., Hakanson, R. & Sundler, F. Endocrine cells in human intestine: an immunocytochemical study. *Gastroenterology* 85, 1120-1130 (1983).

48 Cheng, H. & Leblond, C. P. Origin, differentiation and renewal of the four main epithelial cell types in the mouse small intestine. III. Entero-endocrine cells. *The American journal of anatomy* 141, 503-519, doi:10.1002/aja.1001410405 (1974).

49 Egerod, K. L. et al. A major lineage of enteroendocrine cells coexpress CCK, secretin, GIP, GLP-1, PYY, and neurotensin but not somatostatin. *Endocrinology* 153, 5782-5795, doi:10.1210/en.2012-1595 (2012).

50 Klok, M. D., Jakobsdottir, S. & Drent, M. L. The role of leptin and ghrelin in the regulation of food intake and body weight in humans: a review. *Obes Rev* 8, 21-34, doi:10.1111/j.1467-789X.2006.00270.x (2007).

51 Ichimura, A., Hirasawa, A., Hara, T. & Tsujimoto, G. Free fatty acid receptors act as nutrient sensors to regulate energy homeostasis. *Prostaglandins Other Lipid Mediat* 89, 82-88, doi:10.1016/j.prostaglandins.2009.05.003 (2009).

52 Karra, E., Chandarana, K. & Batterham, R. L. The role of peptide YY in appetite regulation and obesity. *J Physiol* 587, 19-25, doi:10.1113/jphysiol.2008.164269 (2009).

53 Basak, O. et al. Induced Quiescence of Lgr5+ Stem Cells in Intestinal Organoids Enables Differentiation of Hormone-Producing Enteroendocrine Cells. *Cell stem cell* 20, 177-190 e174, doi:10.1016/j.stem.2016.11.001 (2017).

54 Gershon, M. D. & Tack, J. The serotonin signaling system: from basic understanding to drug development for functional GI disorders. *Gastroenterology* 132, 397-414, doi:10.1053/j.gastro.2006.11.002 (2007).

55 Ramage, A. G. & Villalon, C. M. 5-hydroxytryptamine and cardiovascular regulation. *Trends in pharmacological sciences* 29, 472-481 (2008).

56 Reigstad, C. S. et al. Gut microbes promote colonic serotonin production through an effect of short-chain fatty acids on enterochromaffin cells. *FASEB J* 29, 1395-1403, doi:10.1096/fj.14-259598 (2015).

57 Ziegler, S. F. & Artis, D. Sensing the outside world: TSLP regulates barrier immunity. *Nat Immunol* 11, 289-293, doi:10.1038/ni.1852 (2010).

58 Terahara, K. et al. Comprehensive gene expression profiling of Peyer's patch M cells, villous M-like cells, and intestinal epithelial cells. *Journal of immunology* 180, 7840-7846 (2008).

59 Jang, M. H. et al. Intestinal villous M cells: an antigen entry site in the mucosal epithelium. *Proceedings of the National Academy of Sciences of the United States of America* 101, 6110-6115, doi:10.1073/pnas.0400969101 (2004).

60 Vassen, L., Okayama, T. & Moroy, T. Gfi1b:green fluorescent protein knock-in mice reveal a dynamic expression pattern of Gfi1b during hematopoiesis that is largely complementary to Gfi1. *Blood* 109, 2356-2364, doi:10.1182/blood-2006-06-030031 (2007).

61 Coburn, B., Grassl, G. A. & Finlay, B. B. *Salmonella*, the host and disease: a brief review. *Immunology and cell biology* 85, 112-118, doi:10.1038/sj.icb.7100007 (2007).

62 Darwin, K. H. & Miller, V. L. Molecular basis of the interaction of *Salmonella* with the intestinal mucosa. *Clinical microbiology reviews* 12, 405-428 (1999).

63 Reynolds, L. A., Filbey, K. J. & Maizels, R. M. Immunity to the model intestinal helminth parasite Heligmosomoides polygyrus. *Seminars in immunopathology* 34, 829-846, doi:10.1007/s00281-012-0347-3 (2012).

64 Loonen, L. M. et al. REG3gamma-deficient mice have altered mucus distribution and increased mucosal inflammatory responses to the microbiota and enteric pathogens in the ileum. *Mucosal immunology* 7, 939-947, doi:10.1038/mi.2013.109 (2014).

65 van Ampting, M. T. et al. Intestinally secreted C-type lectin Reg3b attenuates *salmonellosis* but not listeriosis in mice. *Infection and immunity* 80, 1115-1120, doi:10.1128/IAI.06165-11 (2012).

66 Rodenburg, W. et al. *Salmonella* induces prominent gene expression in the rat colon. *BMC Microbiol* 7, 84, doi:10.1186/1471-2180-7-84 (2007).

67 Eckhardt, E. R. et al. Intestinal epithelial serum amyloid A modulates bacterial growth in vitro and pro-inflammatory responses in mouse experimental colitis. *BMC Gastroenterol* 10, 133, doi:10.1186/1471-230X-10-133 (2010).

68 Martinez Rodriguez, N. R. et al. Expansion of Paneth cell population in response to enteric *Salmonella enterica* serovar *Typhimurium* infection. *Infection and immunity* 80, 266-275, doi:10.1128/IAI.05638-11 (2012).

69 Artis, D. et al. RELMbeta/FIZZ2 is a goblet cell-specific immune-effector molecule in the gastrointestinal tract. *Proceedings of the National Academy of Sciences of the United States of America* 101, 13596-13600, doi:10.1073/pnas.0404034101 (2004).

70 Datta, R. et al. Identification of novel genes in intestinal tissue that are regulated after infection with an intestinal nematode parasite. *Infection and immunity* 73, 4025-4033, doi:10.1128/IAI.73.7.4025-4033.2005 (2005).

71 Birchenough, G. M., Johansson, M. E., Gustafsson, J. K., Bergstrom, J. H. & Hansson, G. C. New developments in goblet cell mucus secretion and function. *Mucosal immunology* 8, 712-719, doi:10.1038/mi.2015.32 (2015).

72 Young, R. L. et al. Expression of taste molecules in the upper gastrointestinal tract in humans with and without type 2 diabetes. *Gut* 58, 337-346, doi:10.1136/gut.2008.148932 (2009).

73 Mukherjee, S. & Hooper, L. V. Antimicrobial defense of the intestine. *Immunity* 42, 28-39, doi:10.1016/j.immuni.2014.12.028 (2015).

74 Rubin, D. B. The Bayesian bootstrap. *The Annals of Statistics* 9, 130-134 (1981).

75 Kobayashi, A. et al. Identification of novel genes selectively expressed in the follicle-associated epithelium from the meta-analysis of transcriptomics data from multiple mouse cell and tissue populations. *DNA research: an international journal for rapid publication of reports on genes and genomes* 19, 407-422, doi:10.1093/dnares/dss022 (2012).

76 Su, L. et al. Development of fatal intestinal inflammation in MyD88 deficient mice co-infected with helminth and bacterial enteropathogens. *PloS Negl Trop Dis* 8, e2987, doi:10.1371/journal.pntd.0002987 (2014).

77 Schneider, C. A., Rasband, W. S. & Eliceiri, K. W. NIH Image to ImageJ: 25 years of image analysis. *Nat Methods* 9, 671-675 (2012).

78 Johnson, W. E., Li, C. & Rabinovic, A. Adjusting batch effects in microarray expression data using empirical Bayes methods. *Biostatistics (Oxford, England)* 8, 118-127, doi:10.1093/biostatistics/kxj037 (2007).

79 Leek, J. T., Johnson, W. E., Parker, H. S., Jaffe, A. E. & Storey, J. D. The sva package for removing batch effects and other unwanted variation in high-throughput experiments. *Bioinformatics* 28, 882-883, doi:10.1093/bioinformatics/bts034 (2012).

80 Brennecke, P. et al. Accounting for technical noise in single-cell RNA-seq experiments. *Nature Methods* 10, 1093-1095, doi:10.1038/nmeth.2645 (2013).

81 Langmead, B., Trapnell, C., Pop, M. & Salzberg, S. L. Ultrafast and memory-efficient alignment of short DNA sequences to the human genome. *Genome Biology, doi:* 10.1186/gb-2009-10-3-r25) (2009).

82 Li, B. & Dewey, C. N. RSEM: accurate transcript quantification from RNA-Seq data with or without a reference genome. *BMC Bioinformatics* 12, 323, doi:10.1186/1471-2105-12-323 (2011).

83 Buja, A. & Eyuboglu, N. Remarks on Parallel Analysis. *Multivariate Behavioral Research* 27, 509-540, doi:10.1207/s15327906mbr2704_2 (1992).

84 van der Maaten, L. Accelerating t-SNE using Tree-Based Algorithms. *The Journal of Machine Learning Research* 15, 3221-3245 (2014).

85 van der Maaten, L. & Hinton, G. Visualizing Data using t-SNE. *The Journal of Machine Learning Research* 9, 2579-2605 (2008).

86 Zeisel, A. et al. Cell types in the mouse cortex and hippocampus revealed by single-cell RNA-seq. *Science* 347, 1138-1142, doi:10.1 126/science.aaa1934 (2015).

87 Haghverdi, L., Buettner, F. & Theis, F. J. Diffusion maps for high-dimensional single-cell analysis of differentiation data. *Bioinformatics* 31, 2989-2998, doi:10.1093/bioinformatics/btv325/-/DC1 (2015).

88 Ester, M., Kriegel, H. P., Sander, J. & Xu, X. A density-based algorithm for discovering clusters in large spatial databases with noise. *Kdd* (1996).

89 Levine, J. H. et al. Data-Driven Phenotypic Dissection of AML Reveals Progenitor-like Cells that Correlate with Prognosis. *Cell,* 1-15, doi:10.1016/j.cell.2015.05.047 (2015).

90 Rodriguez, A. & Laio, A. Machine learning. Clustering by fast search and find of density peaks. *Science* 344, 1492-1496, doi:10.1126/science.1242072 (2014).

91 Finak, G. et al. MAST: a flexible statistical framework for assessing transcriptional changes and characterizing heterogeneity in single-cell RNA sequencing data. *Genome Biol* 16, 278, doi:10.1186/s13059-015-0844-5 (2015).

92 Benjamini, Y. & Hochberg, Y. Controlling the False Discovery Rate: A Practical and Powerful Approach to Multiple Testing. *Journal of the Royal Statistical Society. Series B Methodological* 57, 289-300 (1995).

93 Zhang, H.-M. et al. AnimalTFDB: a comprehensive animal transcription factor database. *Nucleic Acids Research* 40, D144-149, doi:10.1093/nar/gkr965 (2012).

94 Ng, A., Eisenberg, J. M. & Heath, R. in *Proceedings of the* . . . (2011).

95 Young, M. D., Wakefield, M. J., Smyth, G. K. & Oshlack, A. Gene ontology analysis for RNA-seq: accounting for selection bias. *Genome Biology* 11, doi:10.1186/gb-2010-11-2-r14 (2010).

96 Barker, N. Adult intestinal stem cells: critical drivers of epithelial homeostasis and regeneration. Nat Rev Mol Cell Biol 15, 19-33, doi:10.1038/nrm3721 (2014).

97 Potten, C. S., Owen, G. & Booth, D. Intestinal stem cells protect their genome by selective segregation of template DNA strands. J Cell Sci 115, 2381-2388 (2002).

98 Tirosh, I. et al. Dissecting the multicellular ecosystem of metastatic melanoma by single-cell RNA-seq. Science 352, 189-196, doi:10.1126/science.aad0501 (2016).

99 Patel, A. P. et al. Single-cell RNA-seq highlights intratumoral heterogeneity in primary glioblastoma. Science 344, 1396-1401, doi:10.1126/science.1254257 (2014).

100 Hayami, S. et al. Overexpression of the JmjC histone demethylase KDM5B in human carcinogenesis: involvement in the proliferation of cancer cells through the E2F/RB pathway. Molecular Cancer 9, 59-14, doi: 10.1186/1476-4598-9-59 (2010).

101 Roesch, A. et al. A Temporarily Distinct Subpopulation of Slow-Cycling Melanoma Cells Is Required for Continuous Tumor Growth. Cell 141, 583-594, doi:10.1016/j.cell.2010.04.020 (2010).

102 Oki, T. et al. A novel cell-cycle-indicator, mVenus-p27K-, identifies quiescent cells and visualizes GO-G1 transition. Scientific Reports 4, 1-10, doi:10.1038/srep04012 (2014).

103 Munoz, J. et al. The Lgr5 intestinal stem cell signature: robust expression of proposed quiescent ' +4& apos; cell markers. The EMBO Journal 31, 3079-3091, doi:10.1038/emboj.2012.166 (2012).

104 Habib, N. et al. Div-Seq: Single-nucleus RNA-Seq reveals dynamics of rare adult newborn neurons. Science 353, 925-928, doi:10.1126/science.aad7038 (2016).

105 Kambayashi, T. & Laufer, T. M. Atypical MHC class II-expressing antigen presenting cells: can anything replace a dendritic cell?Nature reviews. Immunology 14, 719-730, doi:10.1038/nri3754 (2014).

106 Thelemann, C. et al. Interferon-gamma induces expression of MHC class II on intestinal epithelial cells and protects mice from colitis. PloS One 9, e86844, doi: 10.1371/journal.pone.0086844 (2014).

107 Bland, P. MHC class II expression by the gut epithelium. Immunol Today 9, 174-178, doi:10.1016/0167-5699 (88)91293-5 (1988).

108 Salomon, P., Pizzimenti, A., Panja, A., Reisman, A. & Mayer, L. The expression and regulation of class II antigens in normal and inflammatory bowel disease peripheral blood monocytes and intestinal epithelium. Autoimmunity 9, 141-149 (1991).

109 Howie, D., Garcia Rueda, H., Brown, M. H. & Waldmann, H. Secreted and transmembrane 1A is a novel co-stimulatory ligand. PloS One 8, e73610, doi:10.1371/journal.pone.0073610 (2013).

110 Madsen, L. et al. Mice lacking all conventional MHC class II genes. Proc Natl Acad Sci USA 96, 10338-10343 (1999).

111 Huch, M. et al. In vitro expansion of single Lgr5+ liver stem cells induced by Wnt-driven regeneration. Nature 494, 247-250, doi:10.1038/nature1 1826 (2013).

112 Boes, M. et al. T-cell engagement of dendritic cells rapidly rearranges MHC class II transport. Nature 418, 983-988, doi:10.1038/nature01004 (2002).

113 Noah, T. K., Donahue, B. & Shroyer, N. F. Intestinal development and differentiation. Exp Cell Res 317, 2702-2710, doi:10.1016/j.yexcr.2011.09.006 (2011).

114 van Es, J. H. et al. Notch/gamma-secretase inhibition turns proliferative cells in intestinal crypts and adenomas into goblet cells. Nature 435, 959-963, doi:10.1038/nature03659 (2005).

115 Saha, S. et al. Macrophage-derived extracellular vesicle-packaged WNTs rescue intestinal stem cells and enhance survival after radiation injury. Nat Commun 7, 13096, doi:10.1038/ncomms13096 (2016).

116 Lindemans, C. A. et al. Interleukin-22 promotes intestinal-stem-cell-mediated epithelial regeneration. Nature 528, 560-564, doi:10.1038/nature16460 (2015).

117 Aurora, A. B. & Olson, E. N. Immune modulation of stem cells and regeneration. Cell stem cell 15, 14-25, doi:10.1016/j.stem.2014.06.009 (2014).

118 Burzyn, D. et al. A special population of regulatory T cells potentiates muscle repair. Cell 155, 1282-1295, doi:10.1016/j.cell.2013.10.054 (2013).

119 Stappenbeck, T. S. & Miyoshi, H. The role of stromal stem cells in tissue regeneration and wound repair. Science 324, 1666-1669, doi:10.1126/science.1172687 (2009).

120 Griffin, A. J. & McSorley, S. J. Development of protective immunity to Salmonella, a mucosal pathogen with a systemic agenda. Mucosal Immunol 4, 371-382, doi: 10.1038/mi.2011.2 (2011).

121 Pashine, A., John, B., Rath, S., George, A. & Bal, V. Th1 dominance in the immune response to live Salmonella typhimurium requires bacterial invasiveness but not persistence. Int Immunol 11, 481-489 (1999).

122 Sokol, C. L. et al. Basophils function as antigen-presenting cells for an allergen-induced T helper type 2 response. Nat Immunol 10, 713-720, doi:10.1038/ni.1738 (2009).

123 Nozaki, K. et al. Co-culture with intestinal epithelial organoids allows efficient expansion and motility analysis of intraepithelial lymphocytes. J Gastroenterol 51, 206-213, doi:10.1007/s00535-016-1170-8 (2016).

124 Jager, A., Dardalhon, V., Sobel, R. A., Bettelli, E. & Kuchroo, V. K. Th1, Th17, and Th9 effector cells induce experimental autoimmune encephalomyelitis with different pathological phenotypes. J Immunol 183, 7169-7177, doi:10.4049/jimmunol.0901906 (2009).

125 Sato, T. & Clevers, H. Growing self-organizing mini-guts from a single intestinal stem cell: mechanism and applications. Science 340, 1190-1194, doi:10.1126/science.1234852 (2013).

126 Farin, H. F. et al. Paneth cell extrusion and release of antimicrobial products is directly controlled by immune cell-derived IFN-gamma. J Exp Med 211, 1393-1405, doi:10.1084/jem.20130753 (2014).

127 Cordier, A. C. & Haumont, S. M. Development of thymus, parathyroids, and ultimo-branchial bodies in NMRI and nude mice. The American journal of anatomy 157, 227-263, doi:10.1002/aja.1001570303 (1980).

128 Mombaerts, P. et al. Mutations in T-cell antigen receptor genes alpha and beta block thymocyte development at different stages. Nature 360, 225-231, doi:10.1038/360225a0 (1992).

129 Kim, J. M., Rasmussen, J. P. & Rudensky, A. Y. Regulatory T cells prevent catastrophic autoimmunity throughout the lifespan of mice. Nat Immunol 8, 191-197, doi:10.1038/ni1428 (2007).

130 Liberzon, A. et al. Molecular signatures database (MsigDB) 3.0. Bioinformatics 27, 1739-1740, doi: 10.1093/bioinformatics/btr260 (2011). 131 Ali, N. et al. Regulatory T Cells in Skin Facilitate Epithelial Stem Cell Differentiation. Cell 169, 1119-1129 e1111, doi:10.1016/j.cell.2017.05.002 (2017).

132 Hashimoto, K., Joshi, S. K. & Koni, P. A. A conditional null allele of the major histocompatibility IA-beta chain gene. Genesis 32, 152-153 (2002).

133 el Marjou, F. et al. Tissue-specific and inducible Cre-mediated recombination in the gut epithelium. Genesis 39, 186-193, doi:10.1002/gene.20042 (2004).

134 Ivanov, I I et al. Induction of intestinal Th17 cells by segmented filamentous bacteria. Cell 139, 485-498, doi: 10.1016/j.cell.2009.09.033 (2009).

135 Tanoue, T., Atarashi, K. & Honda, K. Development and maintenance of intestinal regulatory T cells. Nature reviews. Immunology 16, 295-309, doi:10.1038/nri.2016.36 (2016).

136 Ritsma, L. et al. Intestinal crypt homeostasis revealed at single-stem-cell level by in vivo live imaging. Nature 507, 362-365, doi:10.1038/nature12972 (2014).

137 Snippert, H. J. et al. Intestinal crypt homeostasis results from neutral competition between symmetrically dividing Lgr5 stem cells. Cell 143, 134-144, doi:10.1016/j.cell.2010.09.016 (2010).

138 Buczacki, S. J. A. et al. Intestinal label-retaining cells are secretory precursors expressing Lgr5. Nature 495, 65-69, doi:10.1038/nature11965 (2013).

139 Sangiorgi, E. & Capecchi, M. R. Bmil is expressed in vivo in intestinal stem cells. Nature Genetics 40, 915-920, doi:10.1038/ng.165 (2008).

140 Shalek, A. K. et al. Single-cell RNA-seq reveals dynamic paracrine control of cellular variation [Supplementary Information]. Nature, 1-28, doi:10.1038/nature13437 (2014).

141 Su, L. et al. Coinfection with an intestinal helminth impairs host innate immunity against Salmonella enterica serovar Typhimurium and exacerbates intestinal inflammation in mice. Infect Immun 82, 3855-3866, doi: 10.1128/IAI.02023-14 (2014).

142 Matsumoto, T. et al. Retinol Promotes In Vitro Growth of Proximal Colon Organoids through a Retinoic Acid-Independent Mechanism. PloS One 11, e0162049, doi: 10.1371/journal.pone.0162049 (2016).

143 Iwata, M. et al. Retinoic acid imprints gut-homing specificity on T cells. Immunity 21, 527-538, doi: 10.1016/j.immuni.2004.08.011 (2004).

144 Esplugues, E. et al. Control of TH17 cells occurs in the small intestine. Nature 475, 514-518, doi:10.1038/nature10228 (2011).

145 Barriga, F. M. et al. Mex3a Marks a Slowly Dividing Subpopulation of Lgr5+ Intestinal Stem Cells. Cell Stem Cell 20, 801-816 e807, doi:10.1016/j.stem.2017.02.007 (2017).

146 Worthington, J. J., Reimann, F. & Gribble, F. M. Enteroendocrine cells-sensory sentinels of the intestinal environment and orchestrators of mucosal immunity. *Mucosal immunology*, doi:10.1038/mi.2017.73 (2017).

147 Yan, K. S. et al. Intestinal Enteroendocrine Lineage Cells Possess Homeostatic and Injury-Inducible Stem Cell Activity. *Cell Stem Cell* 21, 78-90 e76, doi:10.1016/j.stem.2017.06.014 (2017).

148 Gerbe, F. & Jay, P. Intestinal tuft cells: epithelial sentinels linking luminal cues to the immune system. *Mucosal immunology* 9, 1353-1359, doi:10.1038/mi.2016.68 (2016).

149 van der Flier, L. G., and Clevers, H. (2009). Stem cells, self-renewal, and differentiation in the intestinal epithelium. Annu Rev Physiol 71, 241-260.

150 Lei, N.Y., Jabaji, Z., Wang, J., Joshi, V. S., Brinkley, G. J., Khalil, H., Wang, F., Jaroszewicz, A., Pellegrini, M., Li, L., et al. (2014). Intestinal subepithelial myofibroblasts support the growth of intestinal epithelial stem cells. PloS One 9, e84651.

151 Shale, M., Schiering, C., and Powrie, F. (2013). CD4(+) T-cell subsets in intestinal inflammation. Immunol Rev 252, 164-182.

152 Dombrowski, Y., O'Hagan, T., Dittmer, M., Penalva, R., Mayoral, S. R., Bankhead, P., Fleville, S., Eleftheriadis, G., Zhao, C., Naughton, M., et al. (2017). Regulatory T cells promote myelin regeneration in the central nervous system. Nat Neurosci 20, 674-680.

153 Arpaia, N., Green, J. A., Moltedo, B., Arvey, A., Hemmers, S., Yuan, S., Treuting, P. M., and Rudensky, A. Y. (2015). A Distinct Function of Regulatory T Cells in Tissue Protection. Cell 162, 1078-1089.

154. Ali, N., Zirak, B., Rodriguez, R. S., Pauli, M. L., Truong, H. A., Lai, K., Ahn, R., Corbin, K., Lowe, M. M., Scharschmidt, T. C., et al. (2017). Regulatory T Cells in Skin Facilitate Epithelial Stem Cell Differentiation. Cell 169, 1119-1129 e1111.

155. Kaser, A., Lee, A. H., Franke, A., Glickman, J. N., Zeissig, S., Tilg, H., Nieuwenhuis, E. E., Higgins, D. E., Schreiber, S., Glimcher, L. H., et al. (2008). XBP1 links ER stress to intestinal inflammation and confers genetic risk for human inflammatory bowel disease. Cell 134, 743-756.

156. Strober, W., and Ehrhardt, R. O. (1993). Chronic intestinal inflammation: an unexpected outcome in cytokine or T cell receptor mutant mice. Cell 75, 203-205.

157. Mombaerts, P., Mizoguchi, E., Grusby, M. J., Glimcher, L. H., Bhan, A. K., and Tonegawa, S. (1993). Spontaneous development of inflammatory bowel disease in T cell receptor mutant mice. Cell 75, 274-282.

158. Ramilowski, J. A., Goldberg, T., Harshbarger, J., Kloppmann, E., Lizio, M., Satagopam, V. P., Itoh, M., Kawaji, H., Carninci, P., Rost, B., et al. (2015). A draft network of ligand-receptor-mediated multicellular signalling in human. Nat Commun 6, 7866.

159. Beyaz, S., Mana, M. D., Roper, J., Kedrin, D., Saadatpour, A., Hong, S. J., Bauer-Rowe, K. E., Xifaras, M. E., Akkad, A., Arias, E., et al. (2016). High-fat diet enhances stemness and tumorigenicity of intestinal progenitors. Nature 531, 53-58.

160. Grun, D., Lyubimova, A., Kester, L., Wiebrands, K., Basak, O., Sasaki, N., Clevers, H., and van Oudenaarden, A. (2015). Single-cell messenger RNA sequencing reveals rare intestinal cell types. Nature, 1-23.

161 Erichson N. Benjamin, V. S., Brunton Steven L., Kutz J. Nathan (2016). Randomized Matrix Decompositions using R. arXiv preprint.

Example 13—an Atlas of the Airway Epithelial Hierarchy Reveals CFTR-Expressing Ionocytes

INTRODUCTION

The airways are responsible for conducting oxygen from the atmosphere to the distal gas-exchanging alveoli, and are the locus of major diseases including asthma, COPD, and cystic fibrosis. The cells of epithelium include basal stem cells, secretory club cells, and ciliated cells that sweep debris out of the airway[1]. Rare cell types such as neuroendocrine (NE), goblet, and tuft cells have only recently been investigated, and their functions remain poorly understood. Diseases of the airway occur at distinct sites along the respiratory tree. Such localized disease presentations have been attributed to physical factors governing the deposition of inhaled particulates, toxins, smoke and allergens to particular regions of the airway[2]. An open question is whether disease heterogeneity is similarly a reflection of intrinsic cellular heterogeneity along the airway tree. Single-cell RNA-seq (scRNA-seq) opens the way to address these questions. Early scRNA-seq studies such as LungMAP[3] have demonstrated the ability to probe epithelial cell-type diversity and lineage hierarchy[4] in the developing lung. Here, Applicants combined massively-parallel single-cell RNA-seq and in vivo lineage tracing to study the cellular composition and hierarchy of the adult murine tracheal airway epithelium. Applicants now demonstrate that a finer comprehensive taxonomy of the cellular composition of this airway epithelium and its developmental hierarchies identifies new cell types, new developmental paths, and reframes the understanding of both cystic fibrosis, a prototypical Mendelian disease, and a complex multigenic disease like asthma.

Results

A Single-Cell Census Reveals New Disease-Associated Cell Types

Applicants initially profiled 7,491 high quality individual airway EpCAM+ epithelial cells from the tracheas of either C57BL/6 wild type mice (n=4) or FOXJ1-GFP ciliated cell reporter mice (n=2; Methods), using two complementary single-cell approaches: massively parallel droplet-based 3' scRNA-seq (k=7,193 cells) and deeper, full-length scRNA-seq (k=301 cells) (FIG. 37A, Methods, FIG. 43A,C).

Figure 43:
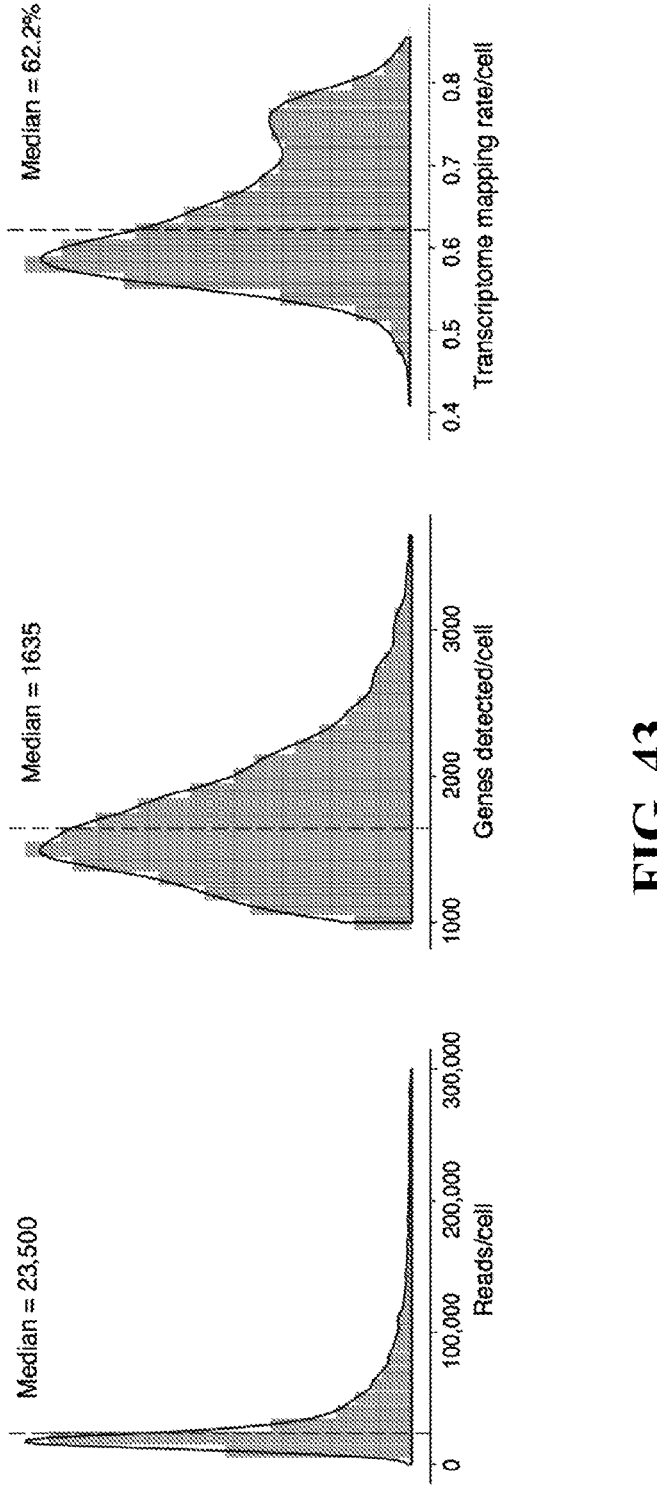
FIGS. 43A-D—Identifying tracheal epithelial cell types in 3' scRNA-seq.
Figure 43:
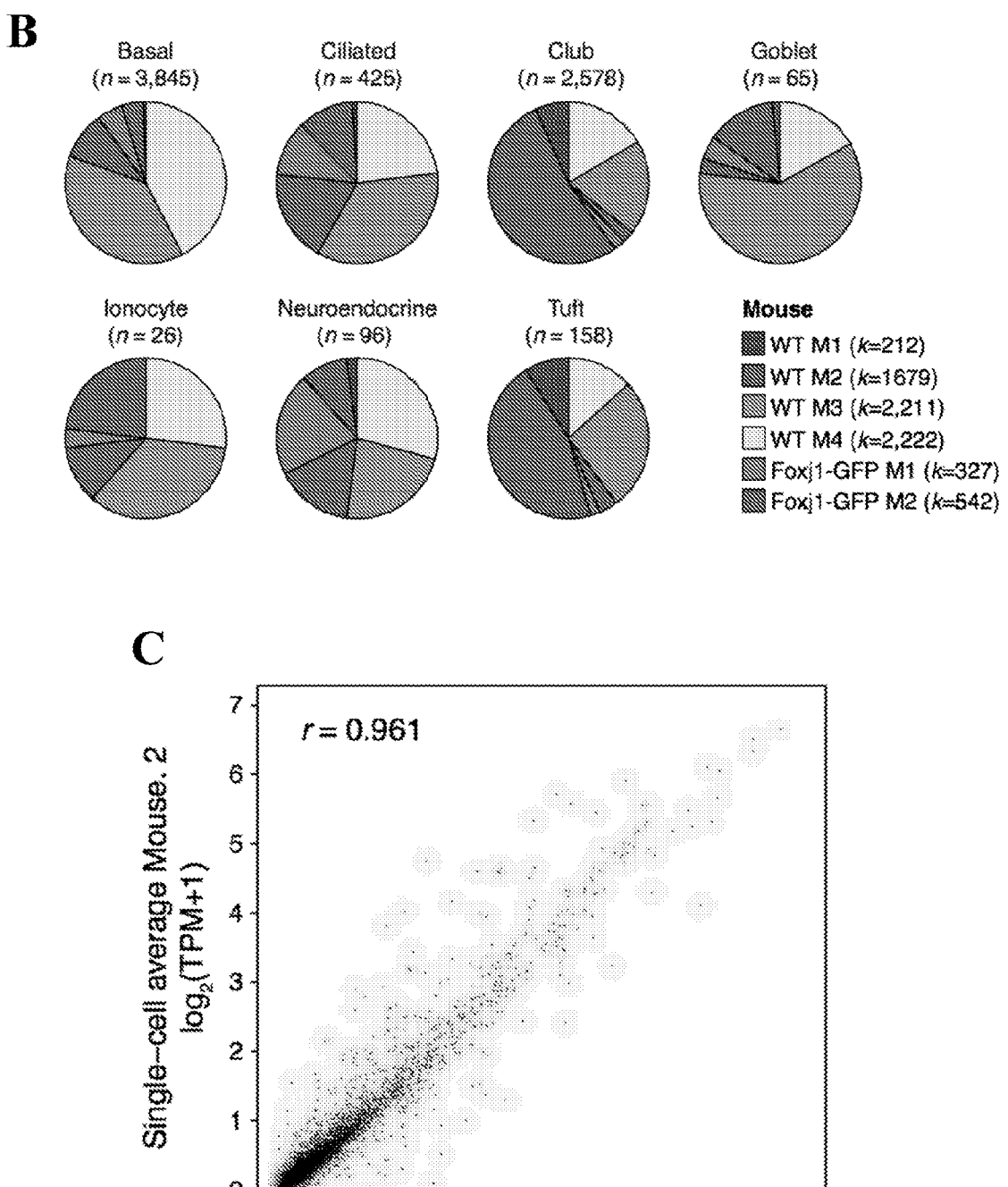
Figure 43:
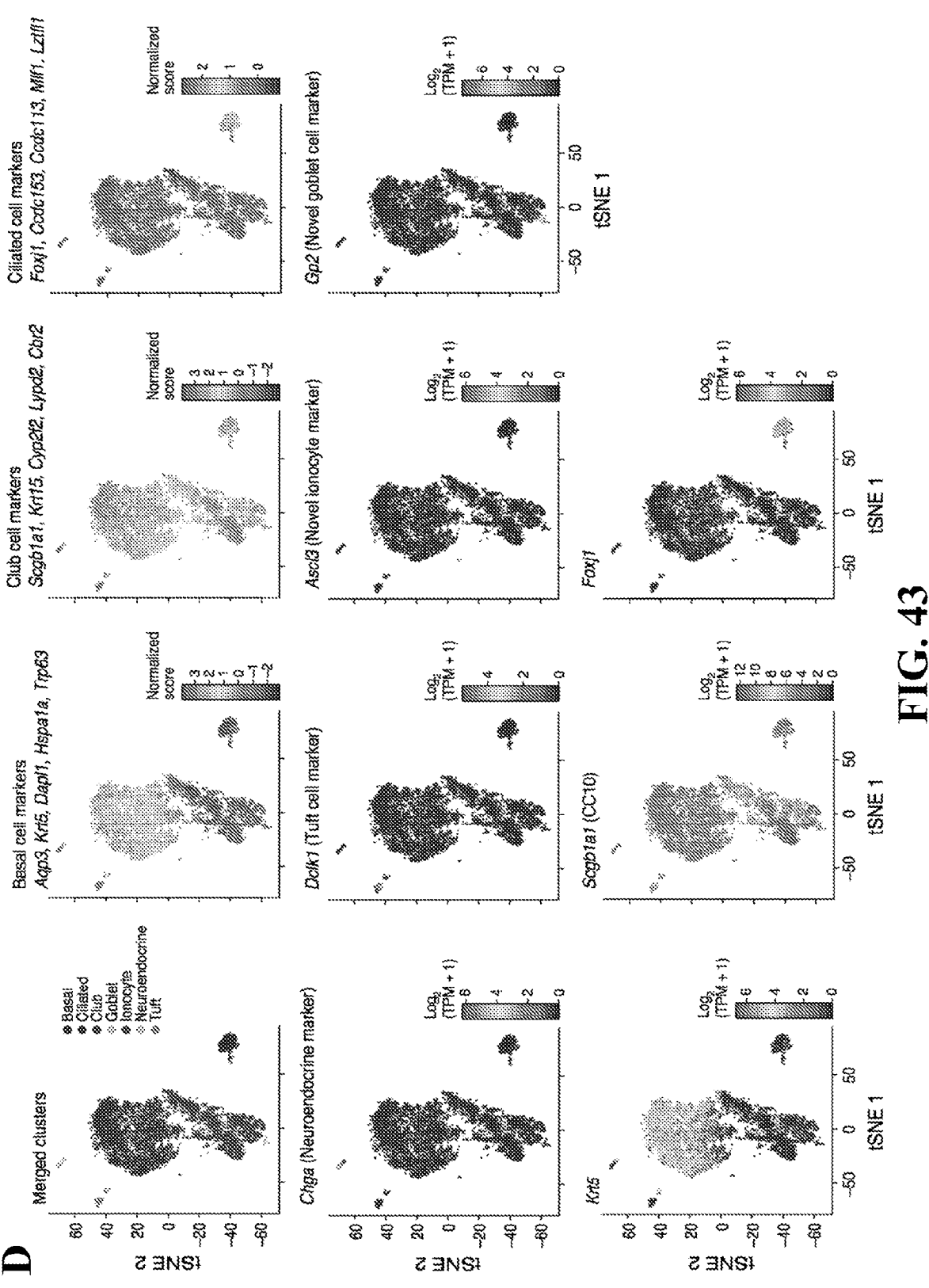
Figure 44:
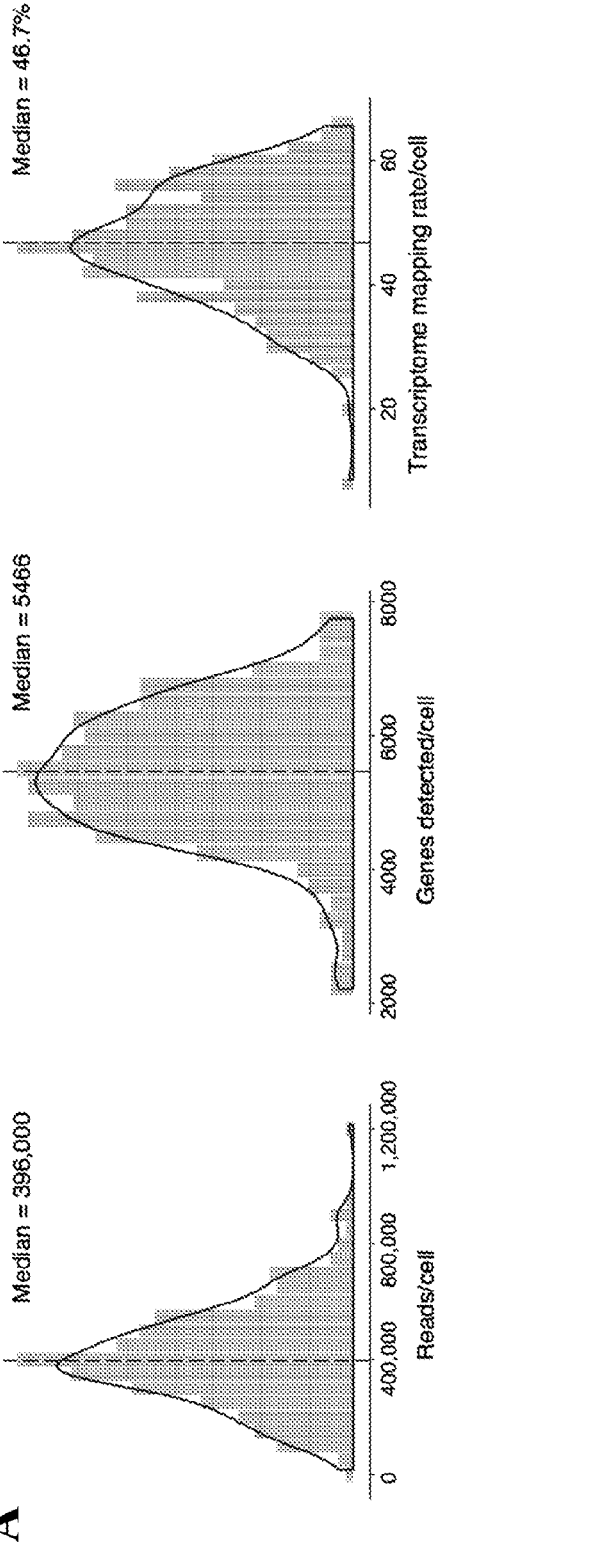
FIGS. 44A-D—Identifying tracheal epithelial cell types in full-length scRNA-seq.
Figure 44:
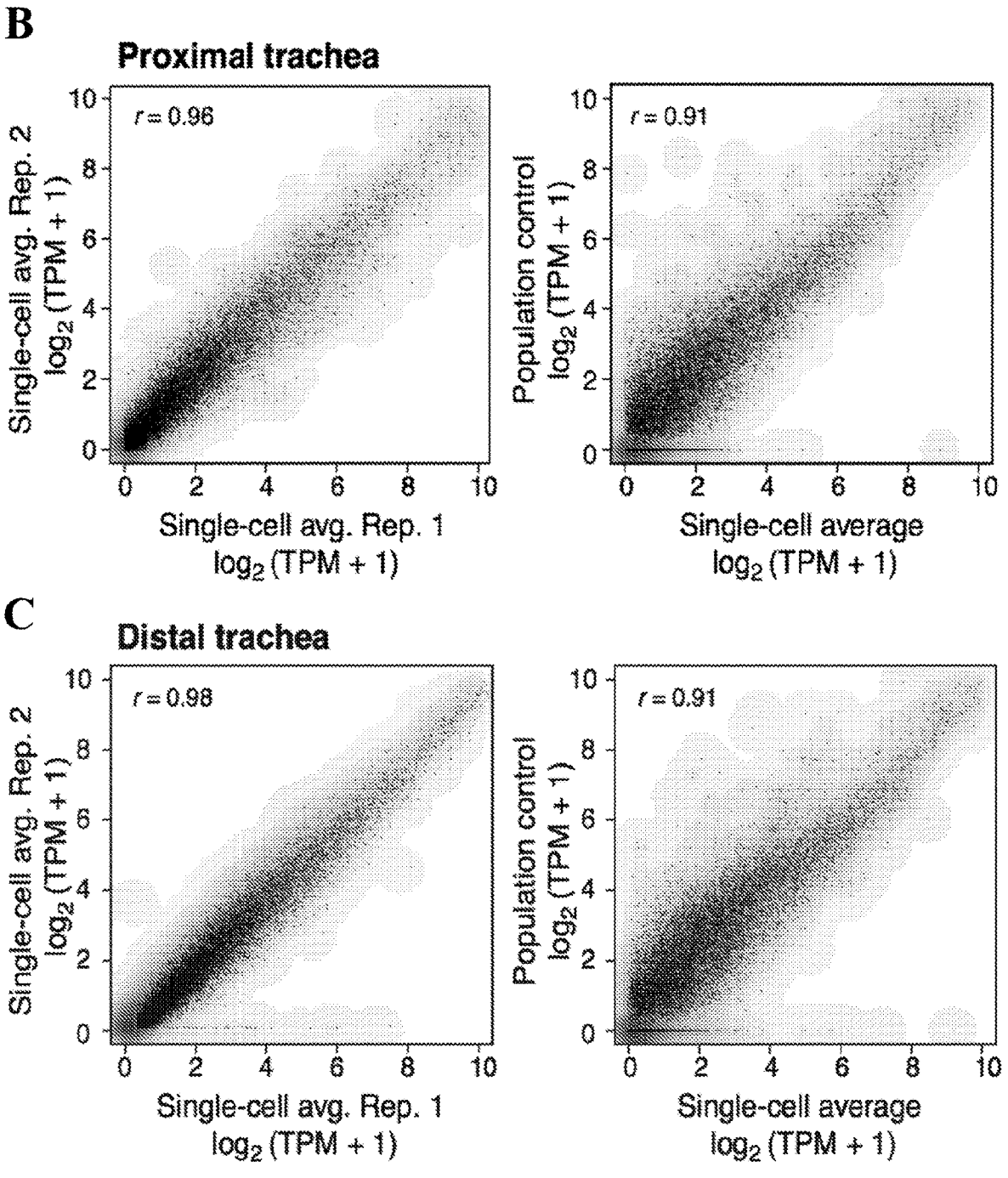
Figure 44:
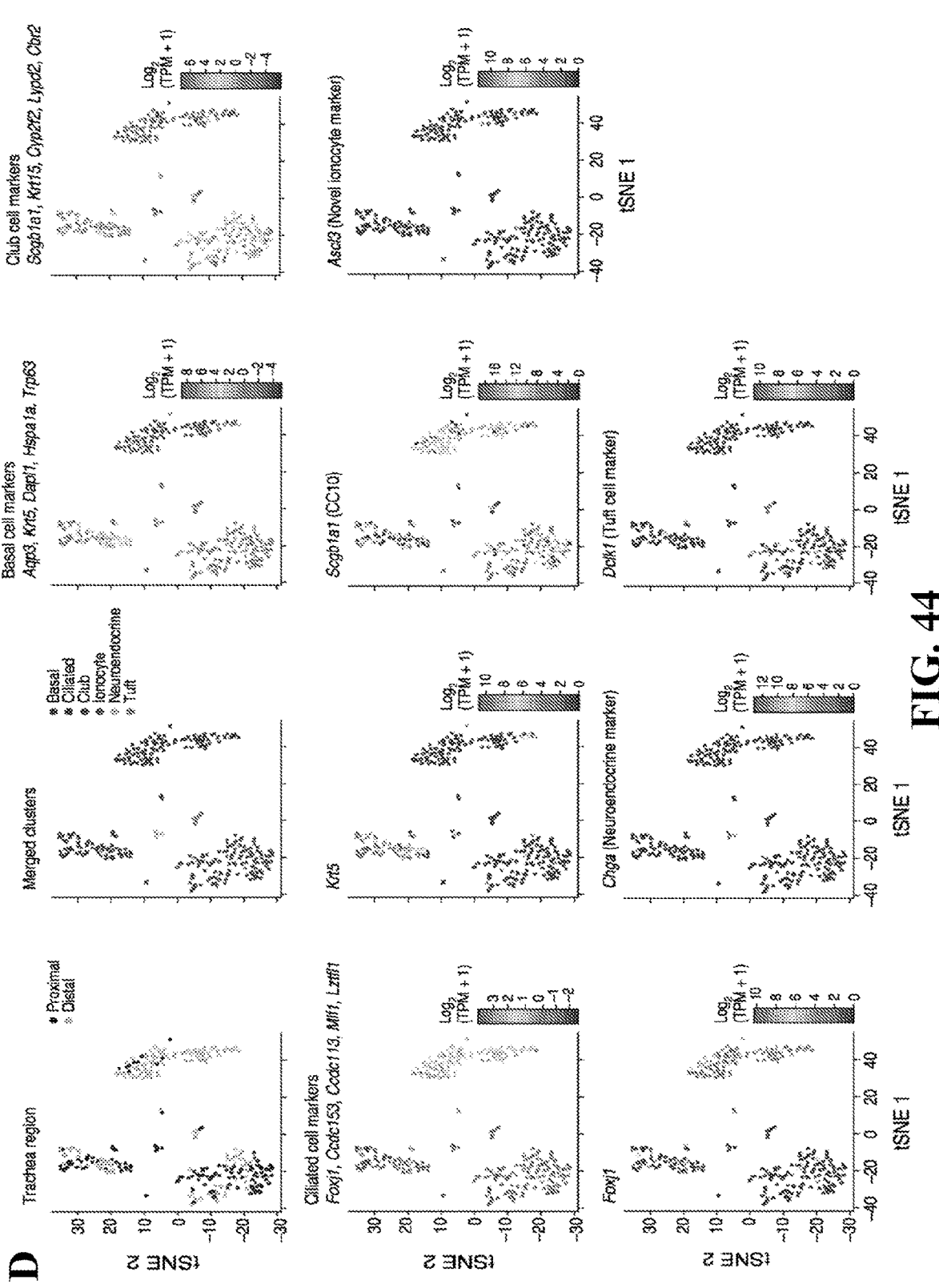
Figure 45:
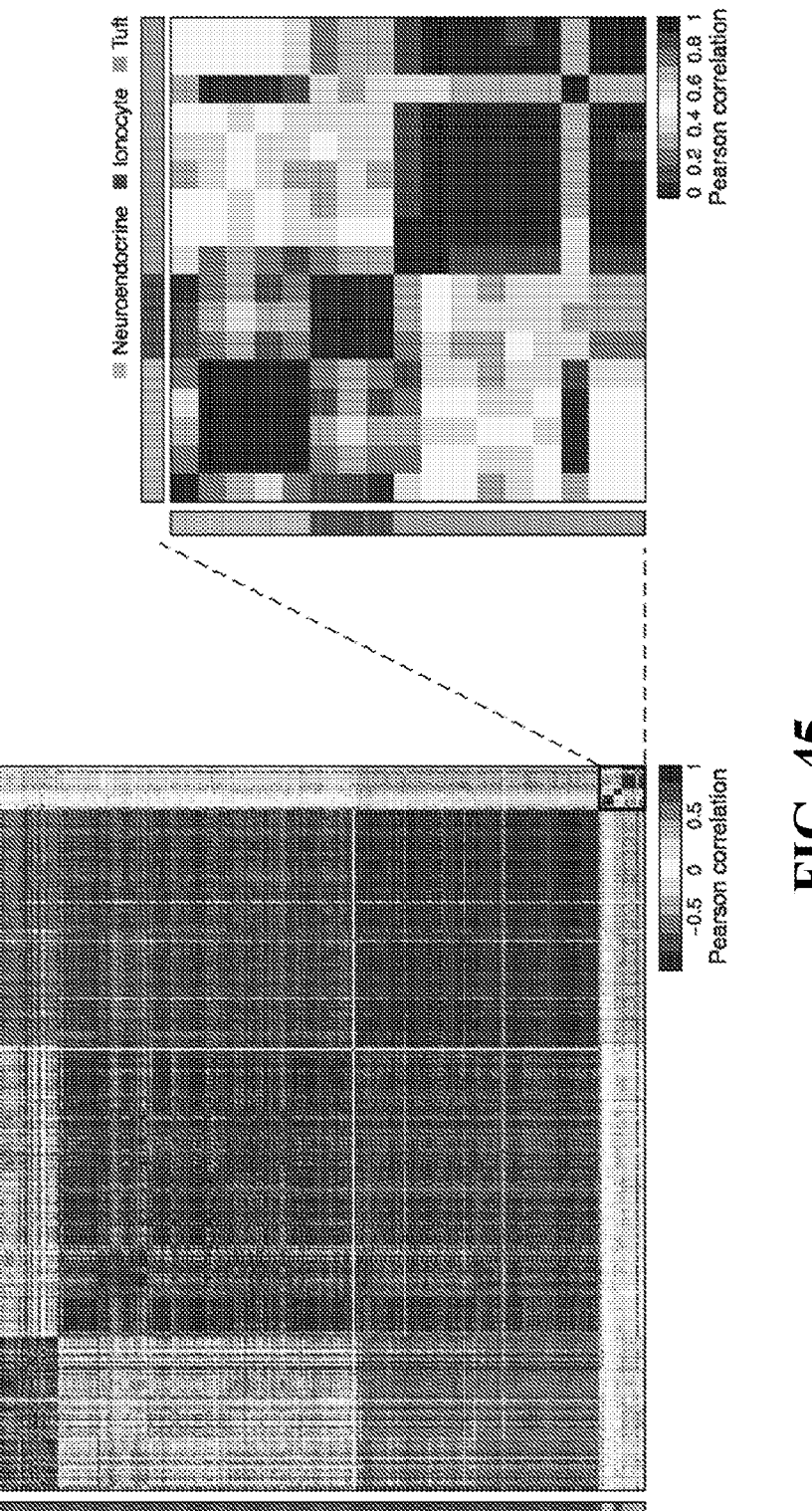
FIGS. 45A-E—High-confidence consensus cell type markers, and cell type-specific expression of asthma-associated genes.
Figure 45:
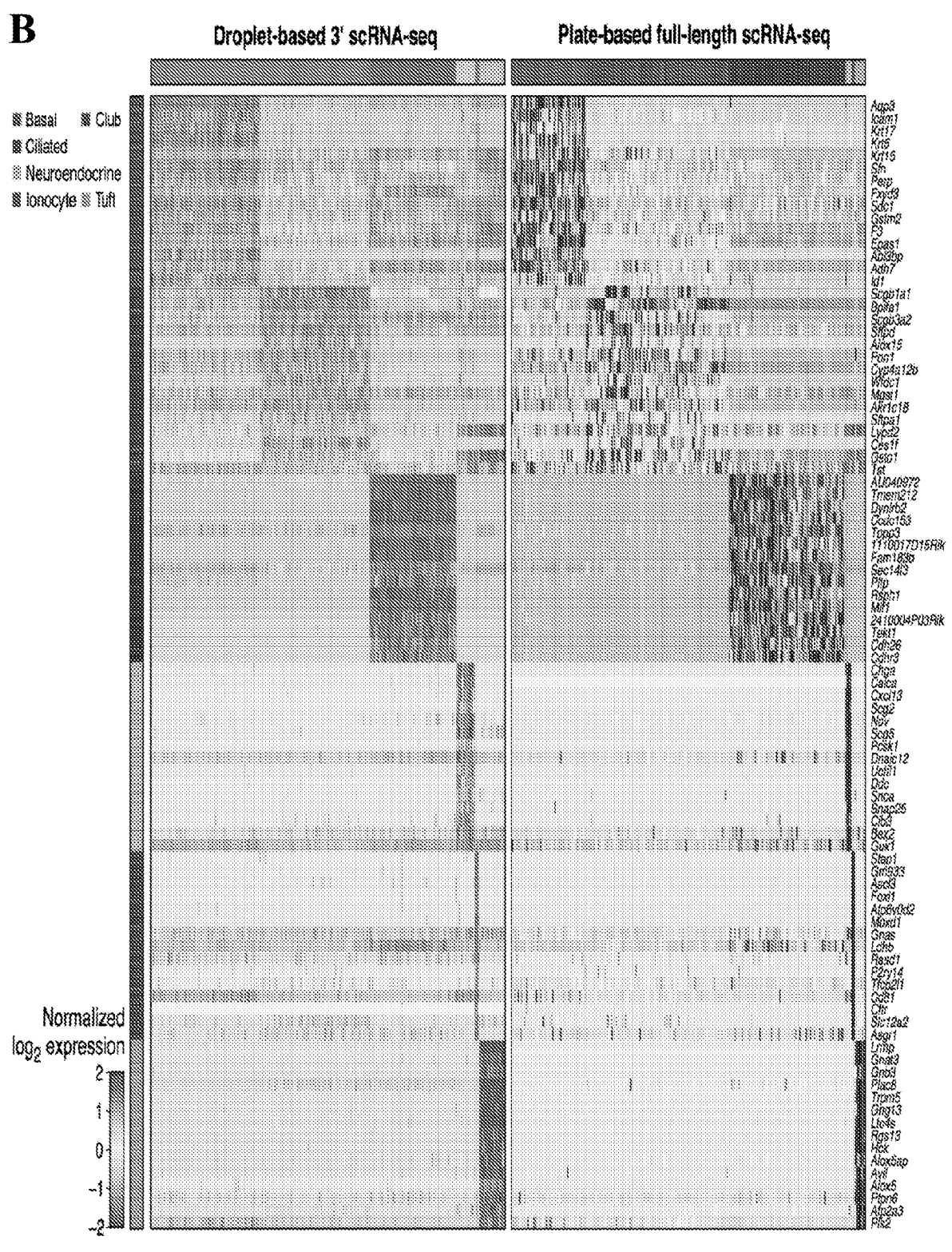
Figure 45:
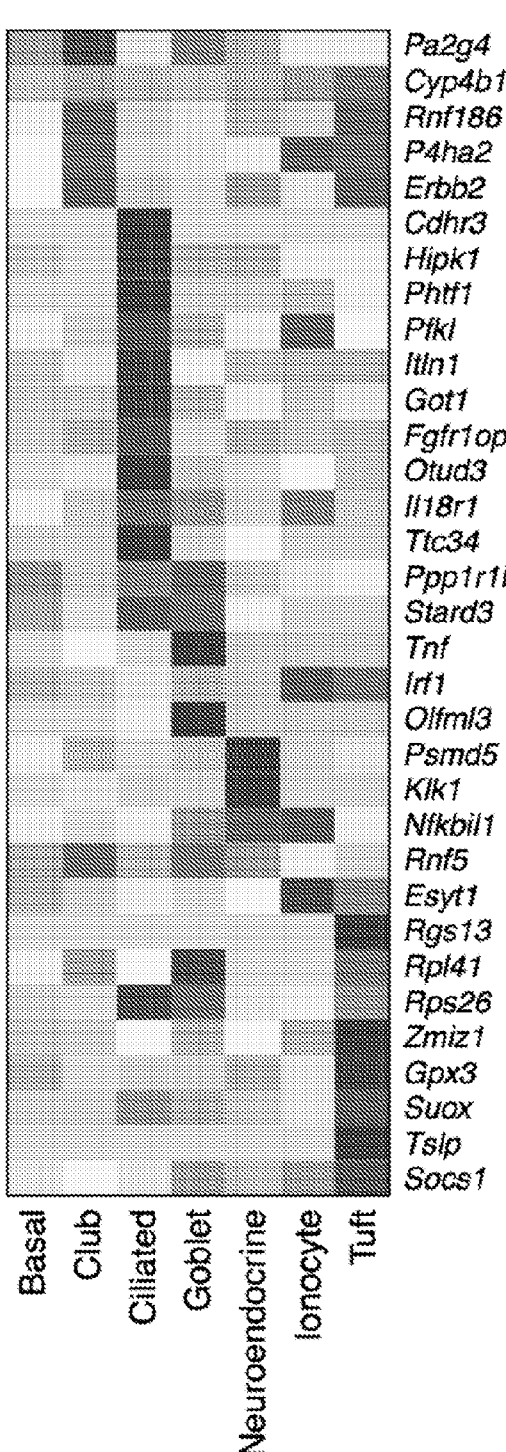
Figure 45:
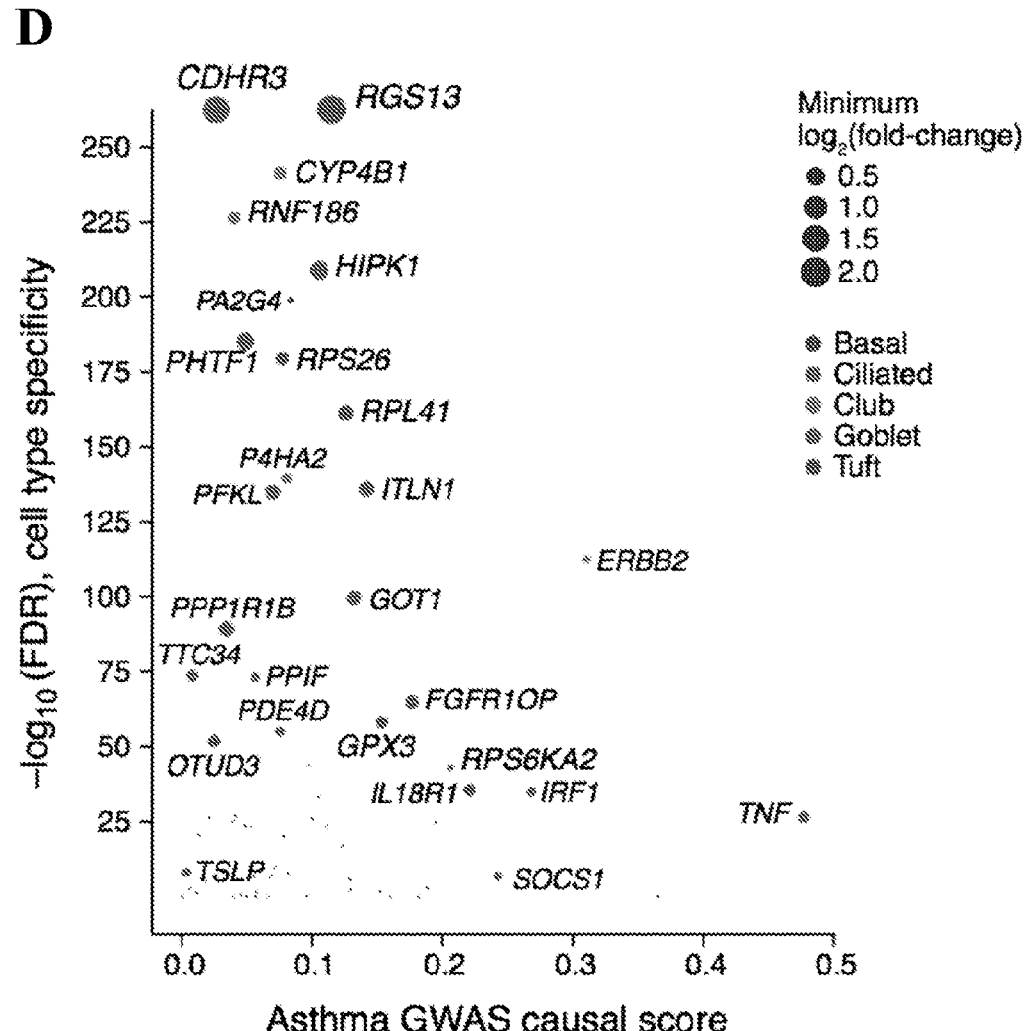
Figure 45:
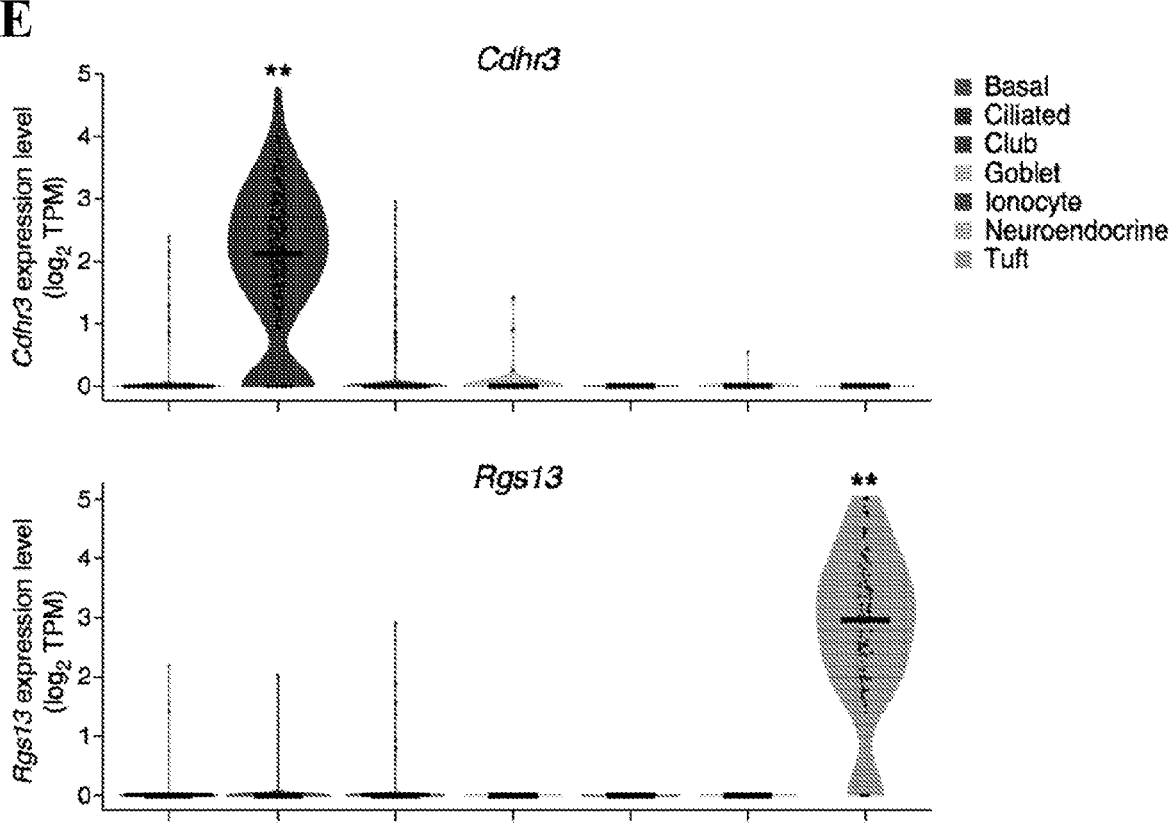

Applicants partitioned the cells into seven distinct clusters[5,6] (FIG. U37B-D, Methods), annotated post-hoc by the expression of known marker genes (FIG. 43D). Each cluster mapped one-to-one with a distinct cell type: three known major cell types (basal, club, and ciliated), three known rare cell types (tuft, NE, and goblet cells), and one additional cluster (FIG. 37B), whose expression signature was distinct from any known airway epithelial cell type, suggesting that this may be a previously unrecognized population. Applicants termed this cell type the pulmonary ionocyte, because of a conserved expression pattern with ionocytes, specialized cells that function to regulate ion transport and pH in freshwater fish skin and gill epithelia, *Xenopus* skin, and the mammalian kidney and epididymis. All clusters contained cells from all mice (n=6, FIG. 43B), except for the goblet cell cluster (five of six mice) and the unannotated cluster of exceedingly rare (0.31%) cells (four of six mice). Applicants validated the assignment of each cell type cluster with high quality full-length scRNA-Seq[7] of 301 EpCAM[+] CD45[−] epithelial cells from tracheas of C57BL/6 wild-type mice (n=3; FIGS. 44 and 45A,B) obtained from either proximal (cartilage 1-4) or distal (cartilage 9-12) tracheal segments (FIG. 37A, FIG. 44D, top left). Applicants did not detect a distinct goblet cell cluster in this small dataset, consistent with their low frequency (0.85% of epithelial cells, FIGS. 44D and 45A,B).

Figure 37:
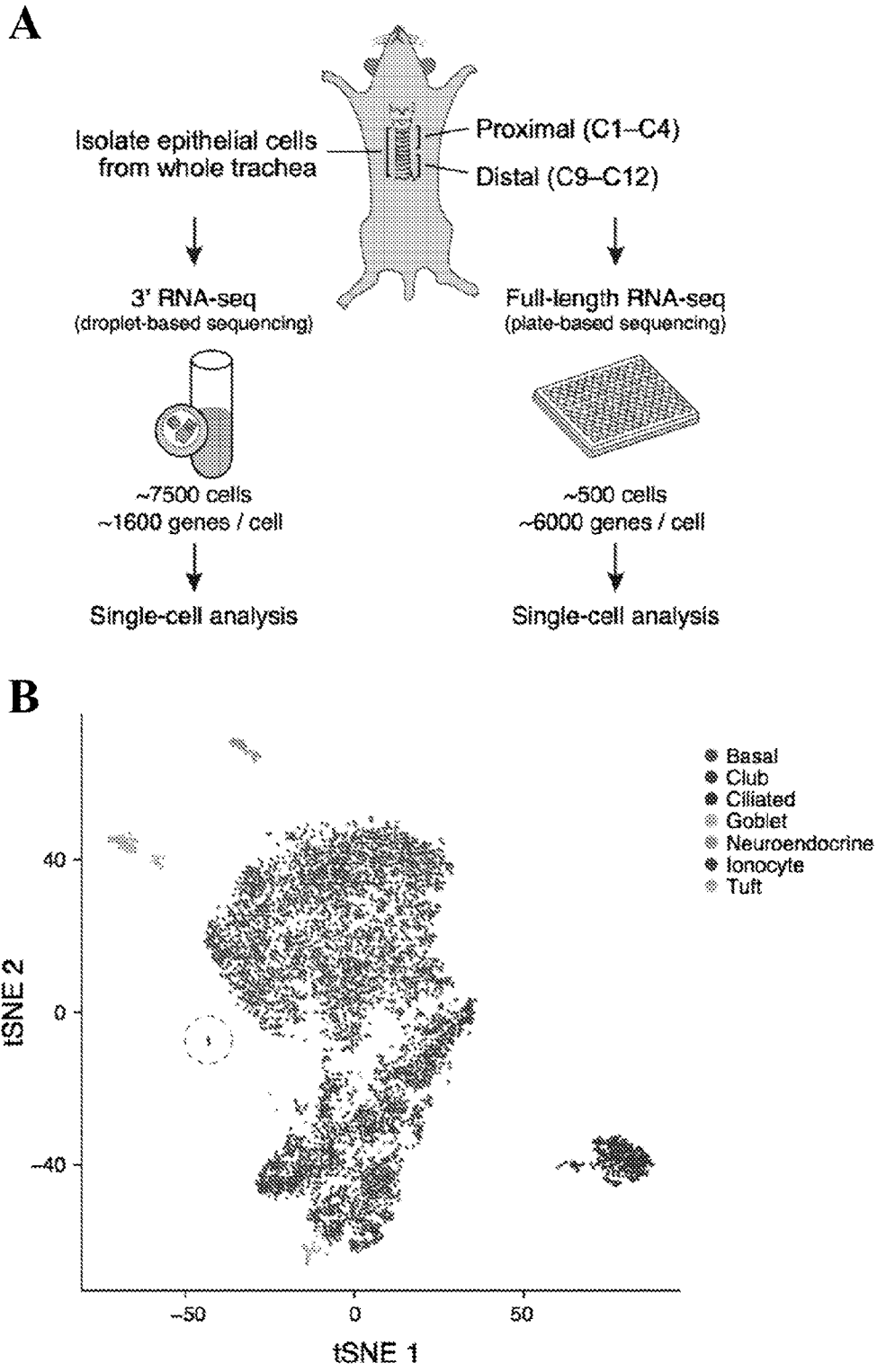
FIGS. 37A-E—A single-cell expression atlas of tracheal epithelial cells.
Figure 37:
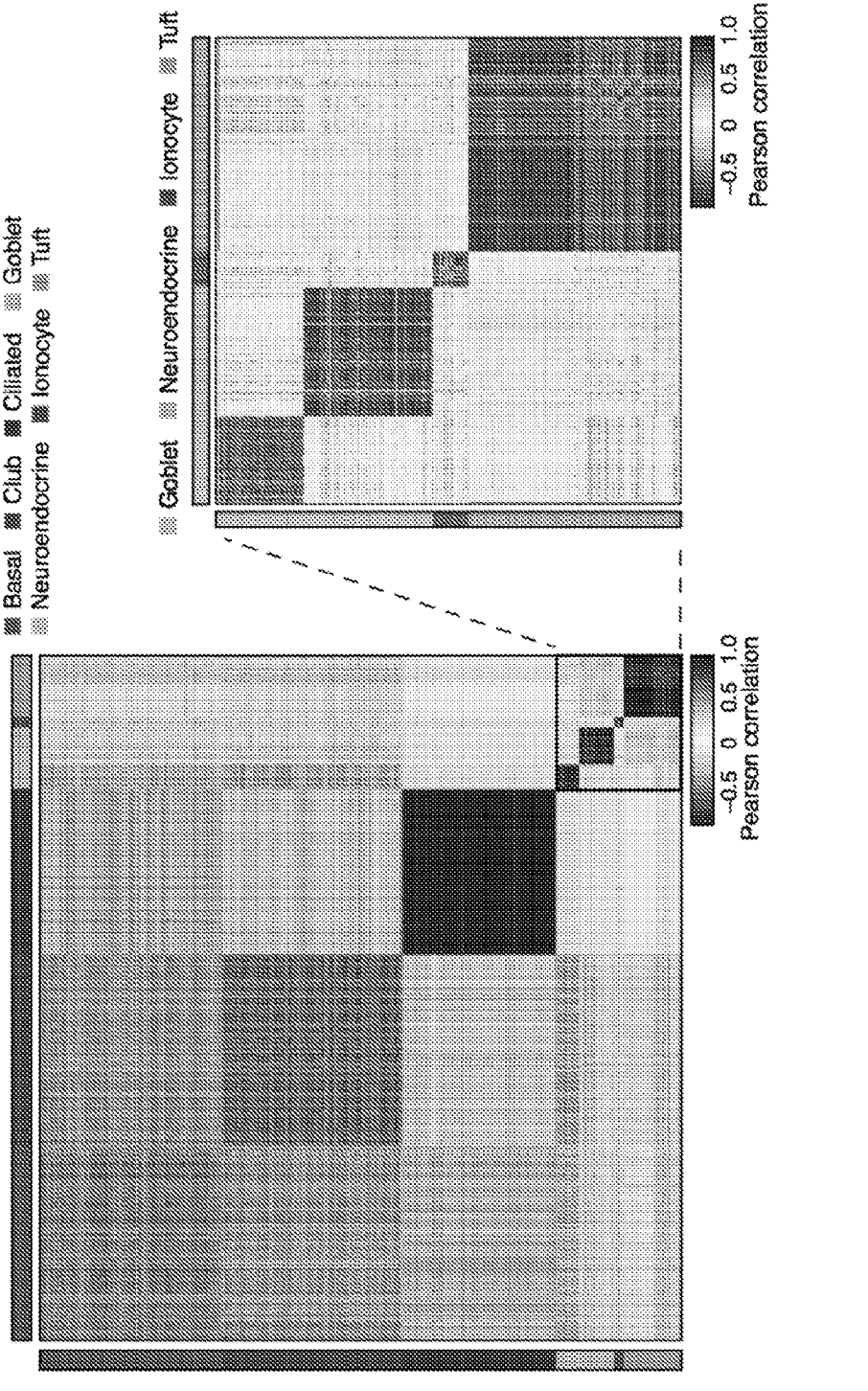
Figure 37:
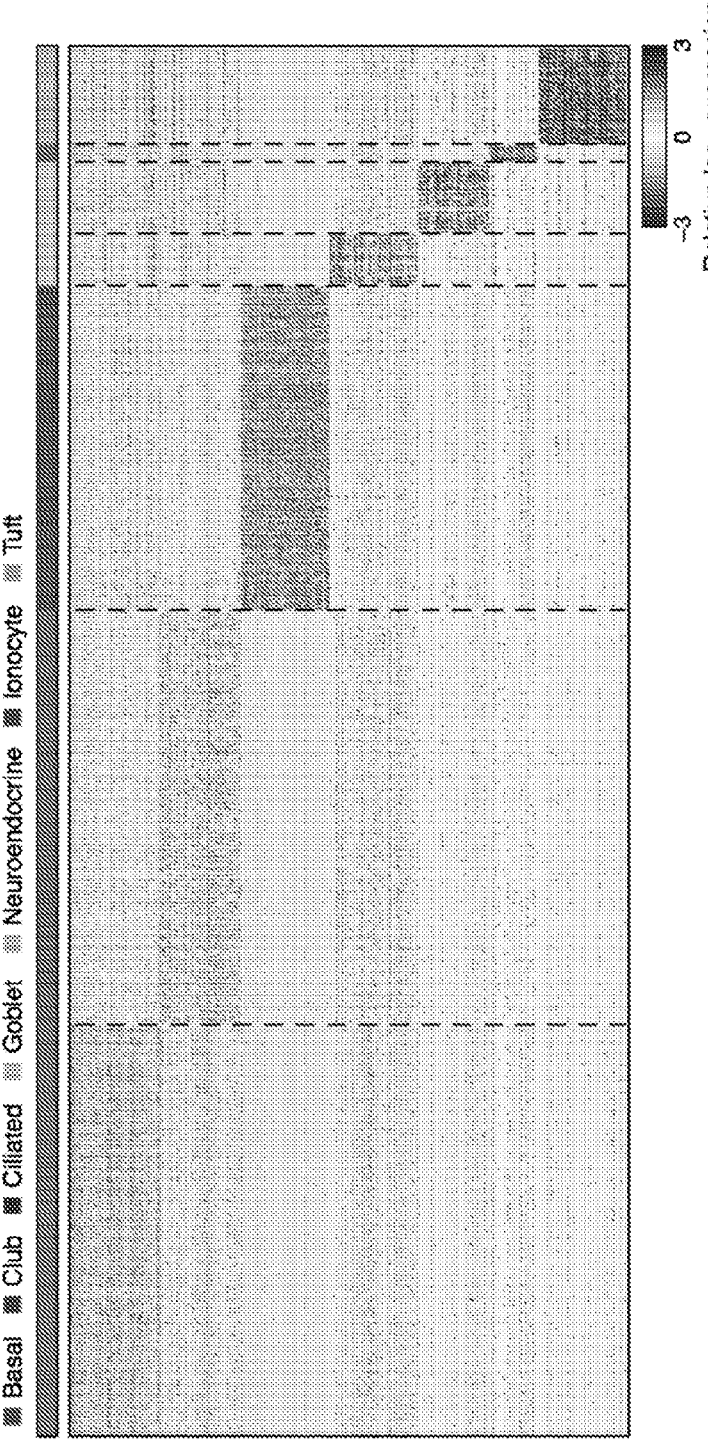
Figure 37:
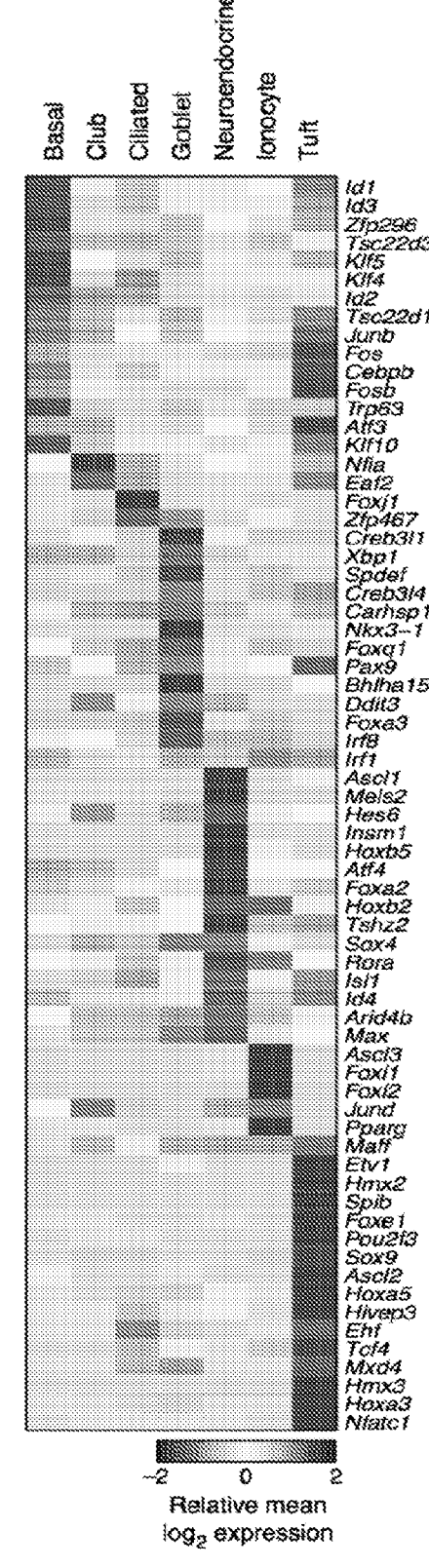

Applicants associated novel functions with rare cell types and highlighted new cell type-specific transcription factors (TFs) by defining cell type-specific expression signatures that are congruent between the two datasets (FDR<0.01, likelihood-ratio test, FIG. 37D,E, FIG. 45B). Basal cell type-specific TFs (FIG. 37E) included the canonical TF Trp63, as well as Klf4, Klf5, and K1f10, a family known to regulate proliferation and differentiation in epithelia[8]. In club cells, Applicants identify Nfia and Eaf2, which are the first TFs specifically associated with this cell type. Nfia is associated with the regulation of Notch signaling, which is required for club cell identity and maintenance[9]. Ascl1, Ascl2, and Ascl3, which are also associated with Notch signaling[10,11], are specifically enriched the rare NE, tuft, and ionocyte cells, respectively (FDR<0.0001, likelihood-ratio test). Tuft cells also expressed the known intestinal tuft cell TF Pou2f3[12] along with novel TFs Foxe1 and Etv1. Ionocytes were marked by the expression of Foxi1[13], whose ortholog is associated with ionocytes in *Xenopus*, as well as Foxi2. Finally, goblet cells specifically express the known goblet cell regulator Spdef as well as Foxq1, which is essential for mucin gene expression and granule content in gastric epithelia[14].

Some cell type-specific signature genes have previously been identified as risk genes in Genome-Wide Association Studies (GWAS) of asthma[15] (Methods, FIG. 45C-E). For example, the asthma-associated genes Cdhr3 and Rgs13[15] are specifically expressed in ciliated and tuft cells, respectively (FIG. 45C-E). Cdhr3 encodes a rhinovirus receptor and is associated with severe childhood asthma exacerbations[16,17], suggesting that exacerbations may be precipitated by rhinovirus infection of ciliated cells. Rgs13 was associated with asthma and IgE-mediated mast cell degranulation[18]; its specific expression in tuft cells (FIG. 45C-E), which play an immunomodulatory role in the intestines[12, 19, 20] suggests that they may also participate in driving asthmatic inflammation.

Figure 38:
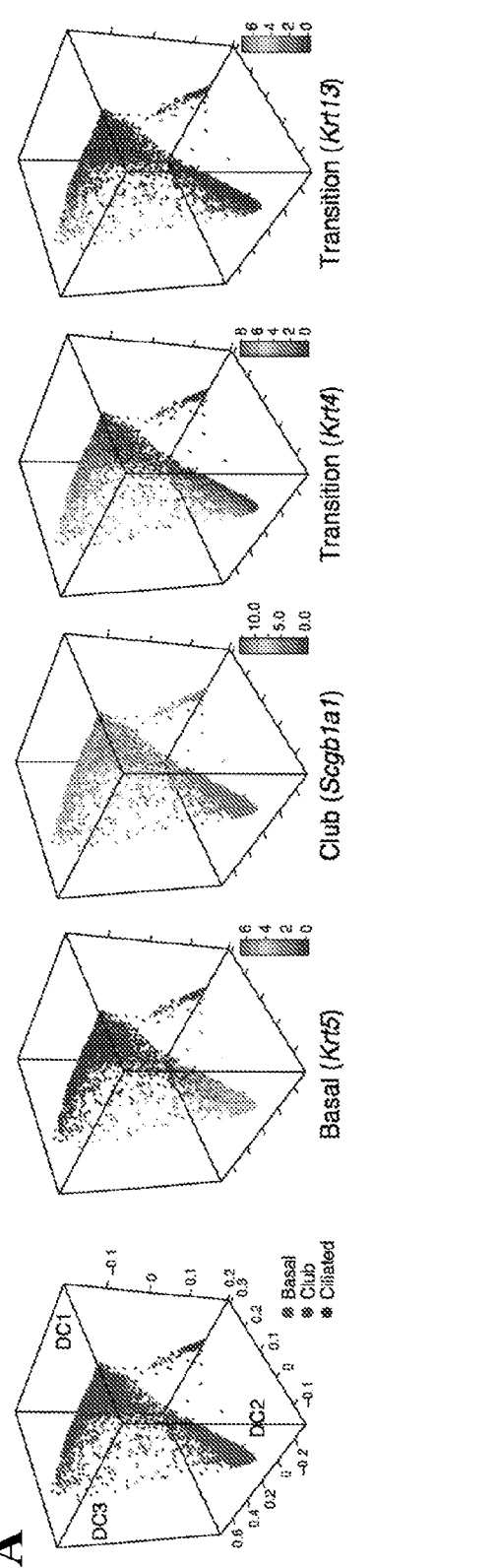
FIGS. 38A-I—Krt13$^+$ club cell progenitors exhibit rapid turnover and are found in hillocks.
Figure 38:
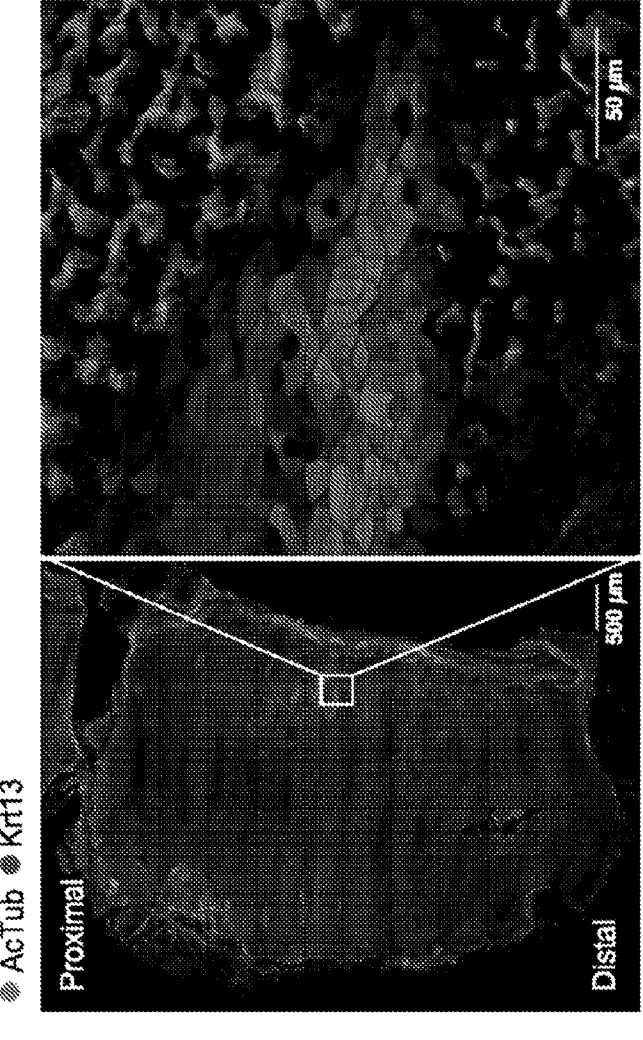
Figure 38:
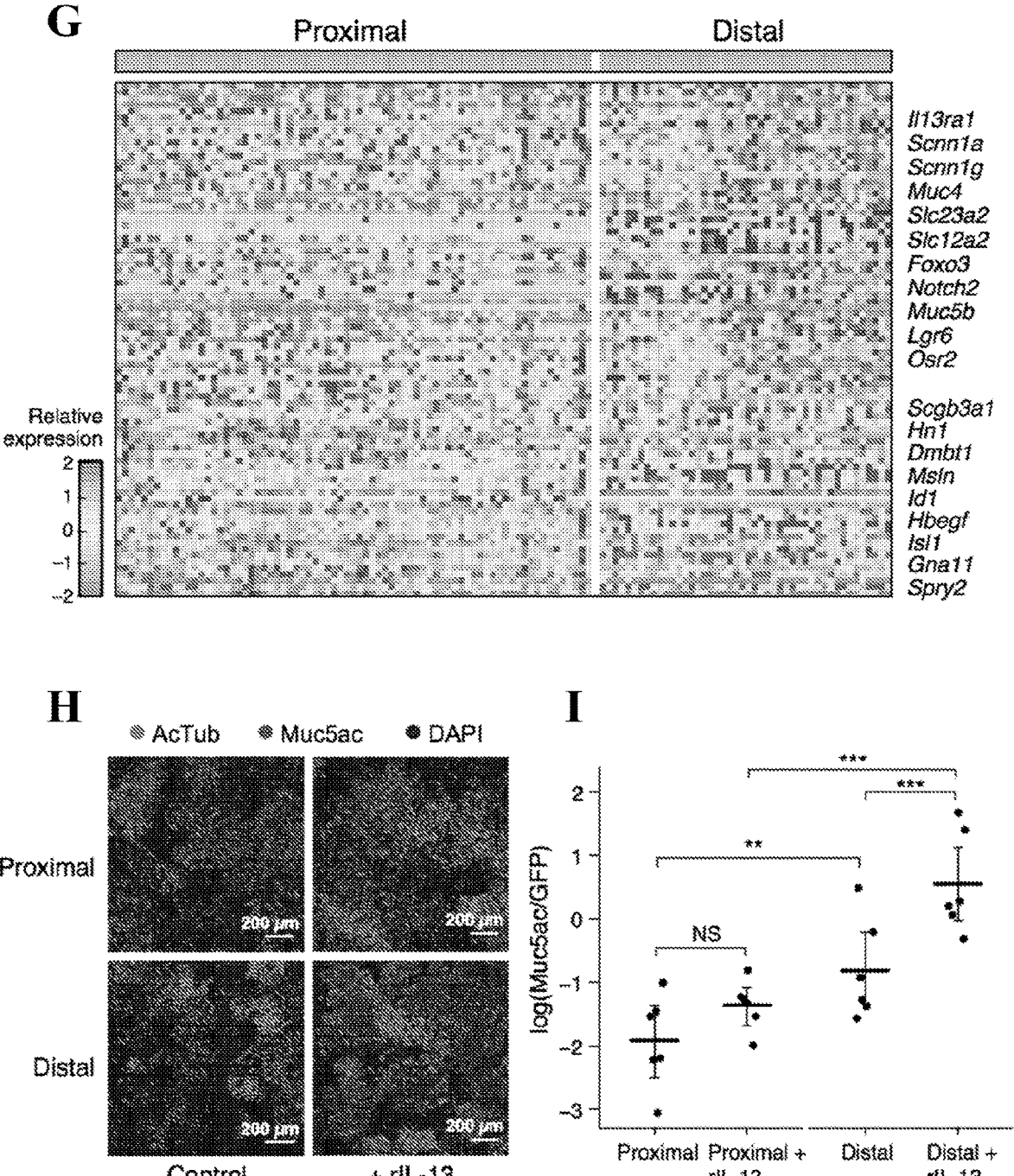

Some cell type-specific expression programs also vary along the proximodistal axis of the airway tree, mirroring the distribution of airway pathologies. In mouse, mucous metaplasia (an excess of mucus-producing goblet cells) occurs more prominently in the distal versus proximal trachea, and is the identifying epithelial pathology of asthma[21]. Notch signaling is required for this mucous metaplasia in mouse models[22]. Applicants found that 105 genes are differentially expressed (FDR<0.05, Mann-Whitney U-test) between club cells of the proximal versus distal trachea (FIG. 38G). In particular, Muc5b[23,24], Notch2[22], and Il13ra1[25] are all more prevalent in distal club cells, and all play known roles in mucous metaplasia. Indeed, when Applicants induced mucous metaplasia using recombinant murine IL-13 (rIL-13) in cultured proximal and distal airway epithelium, Applicants found a much higher induction of goblet cell differentiation in the distal epithelium, consistent with the increased expression of Il13ra1 in distal club cells (FIG. 38H,I, p<0.001, likelihood-ratio test).

A Novel Cell Population Organized in "Hillocks"

Figure 46:
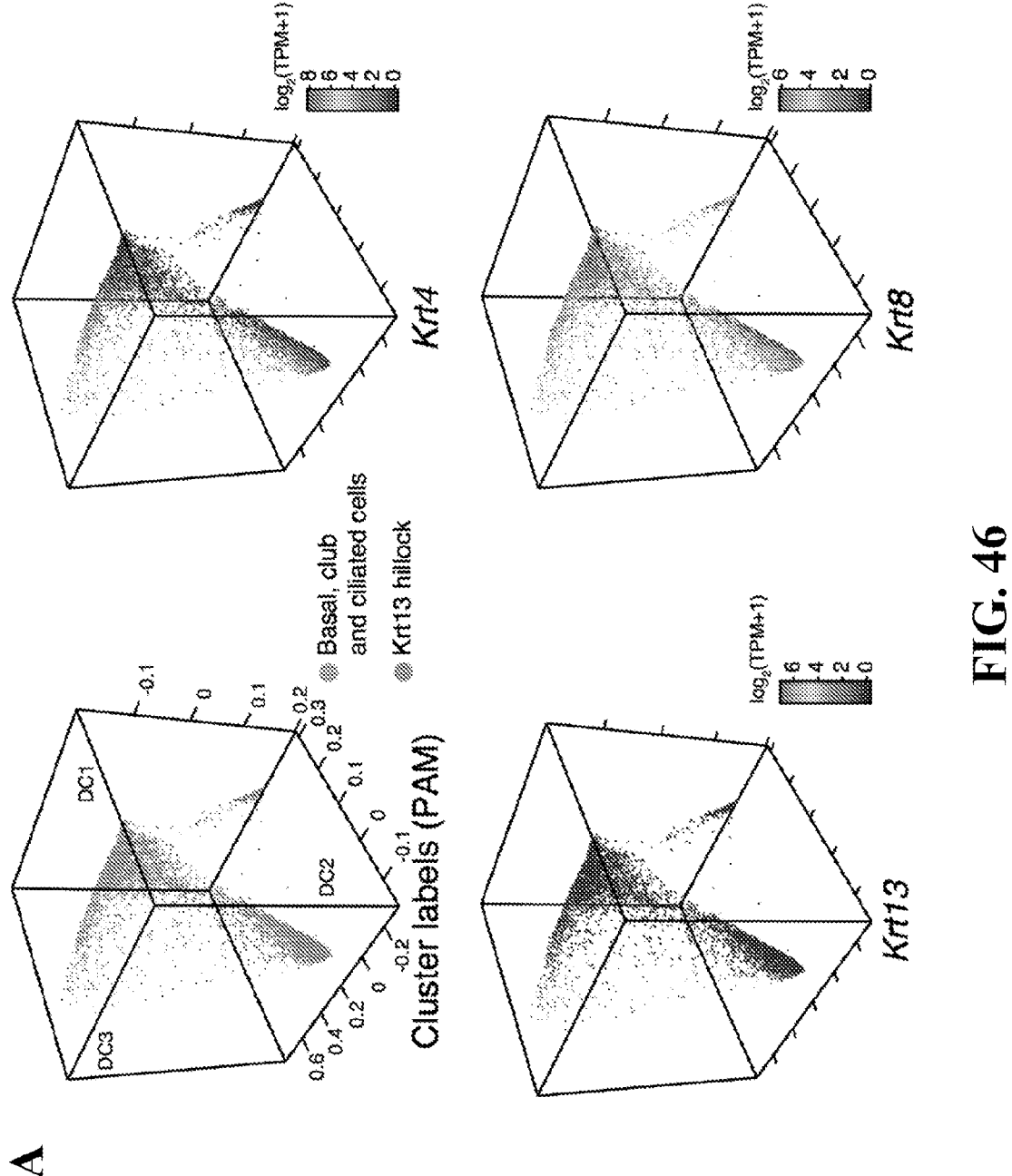
FIGS. 46A-E—Krt13[+] progenitors express a unique set of markers distinct from mature club cells.
Figure 46:
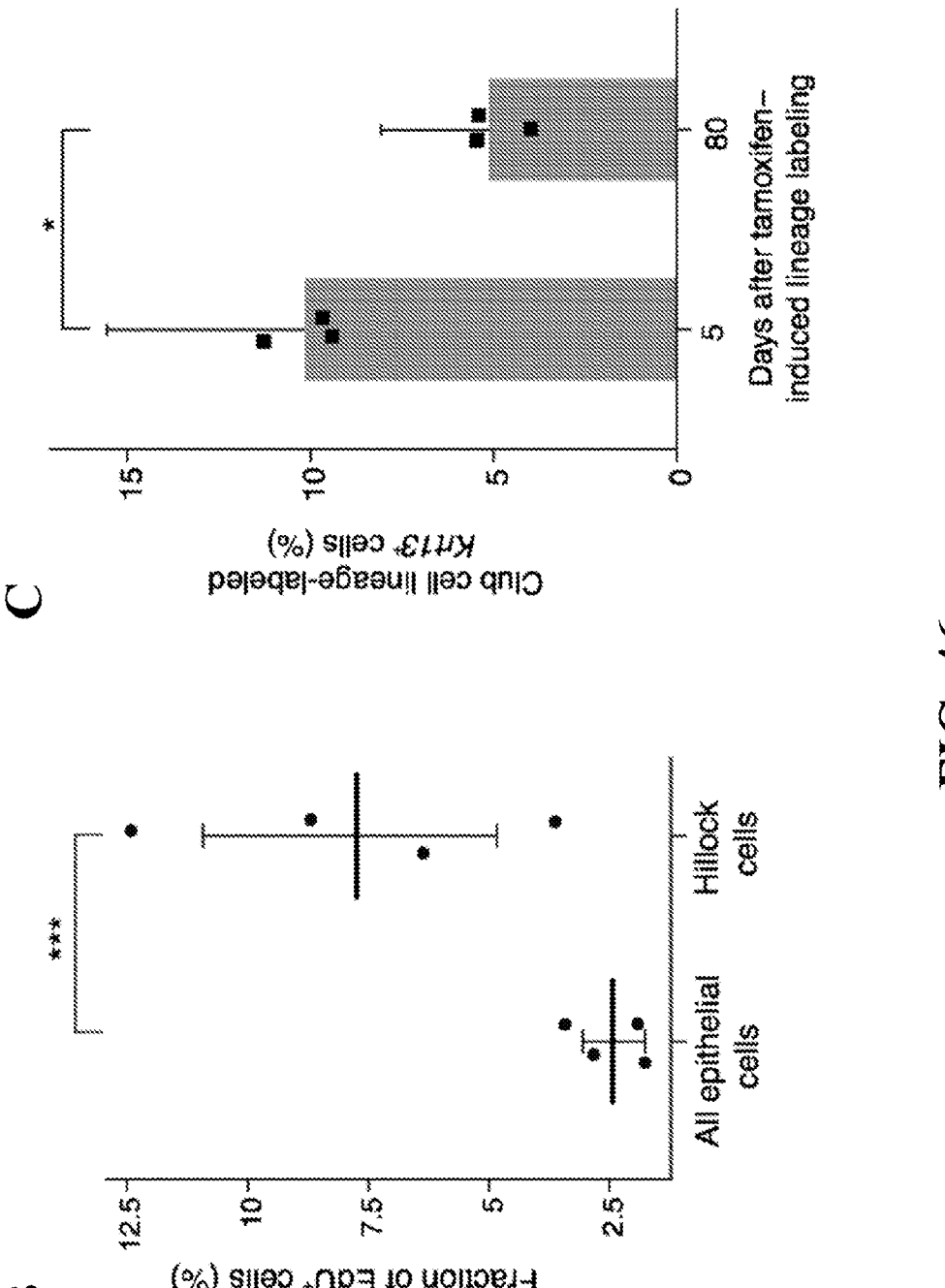
Figure 46:
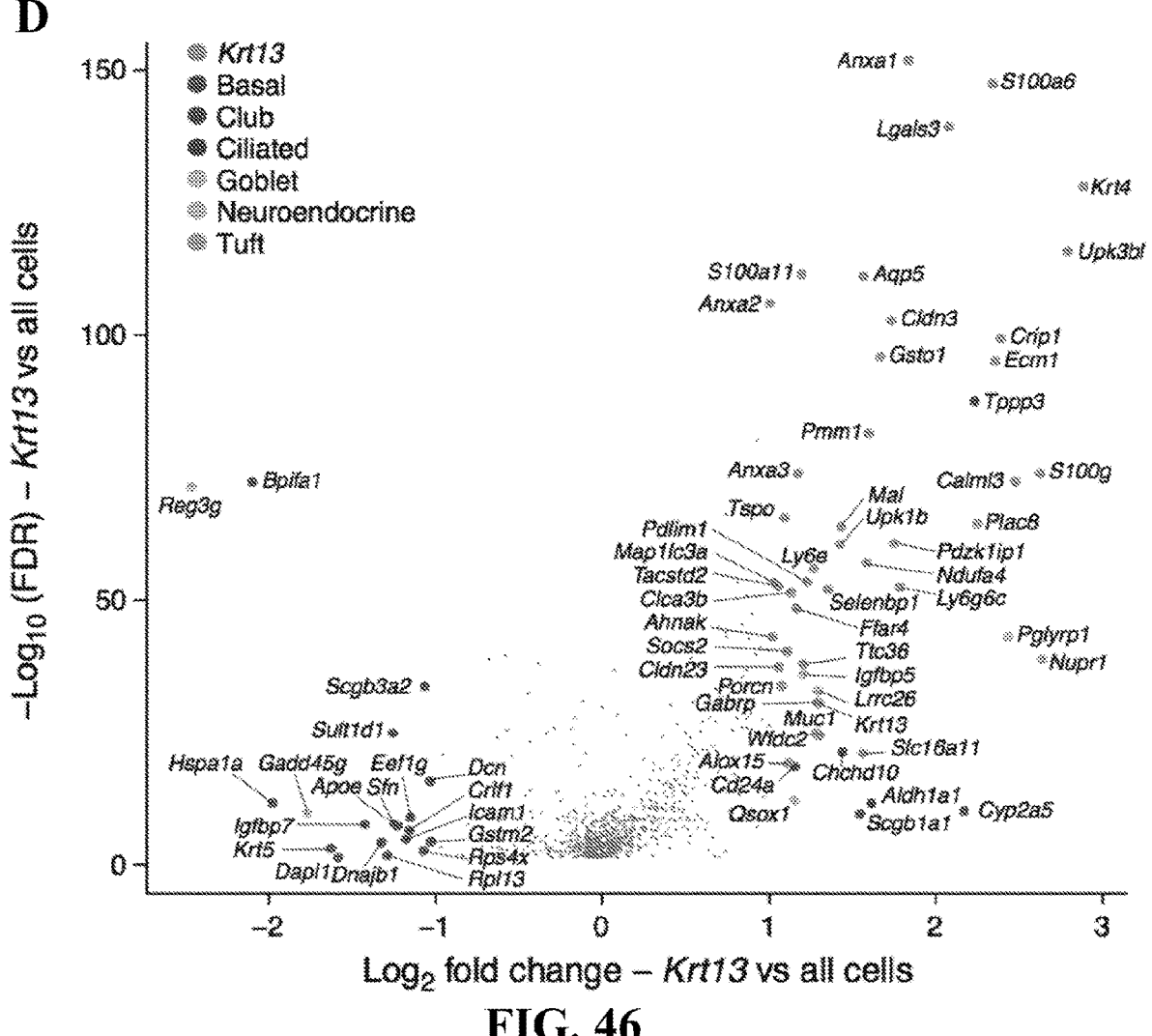
Figure 46:
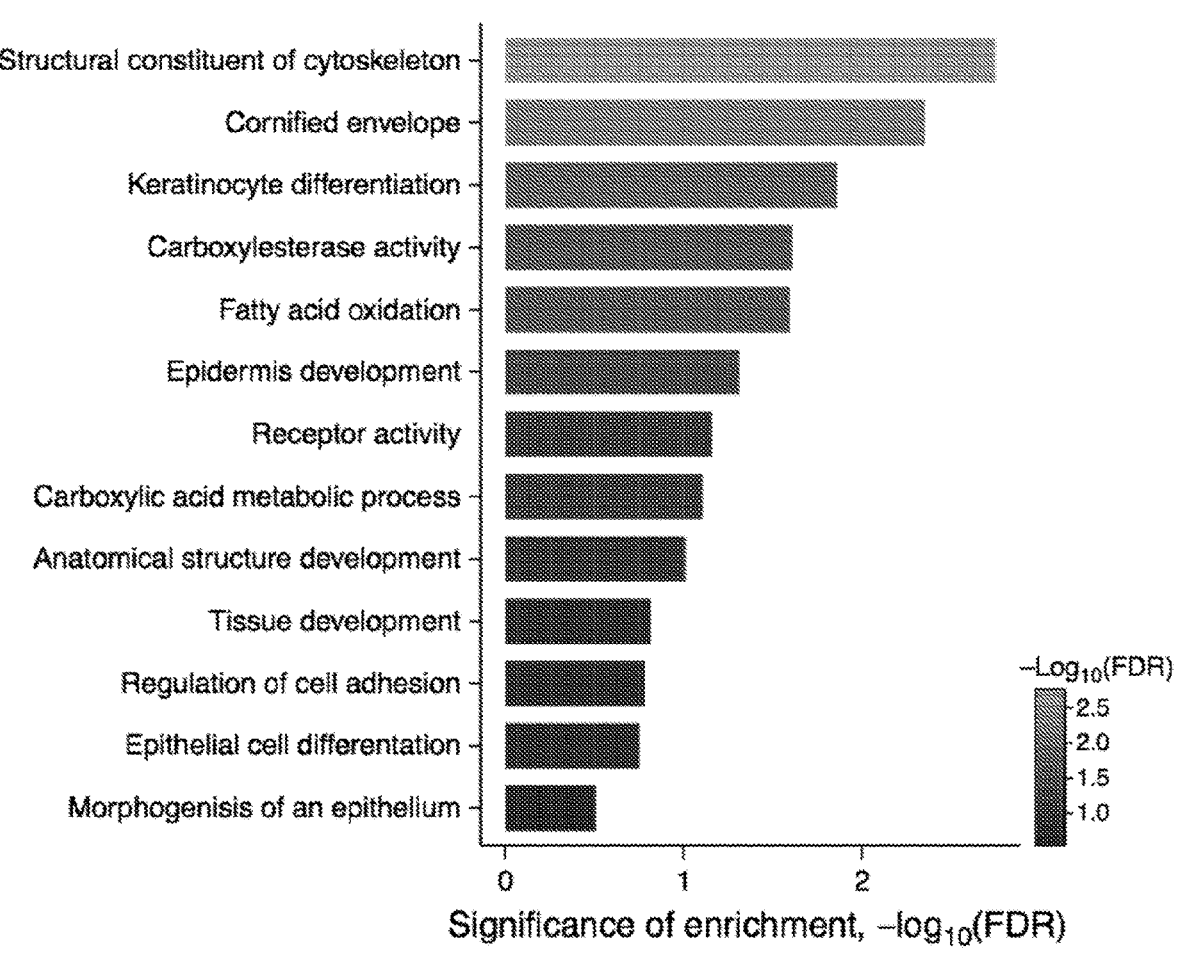
Figure 47:
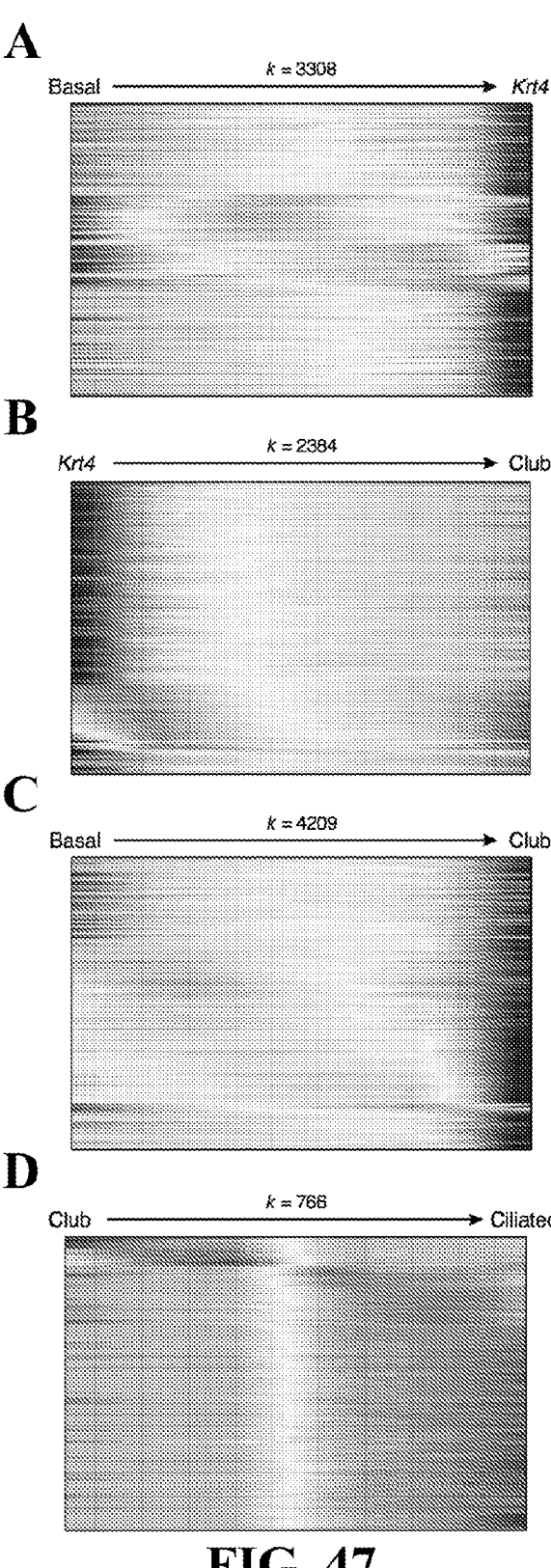
FIGS. 47A-H—Genes associated with cell fate transitions.
Figure 47:
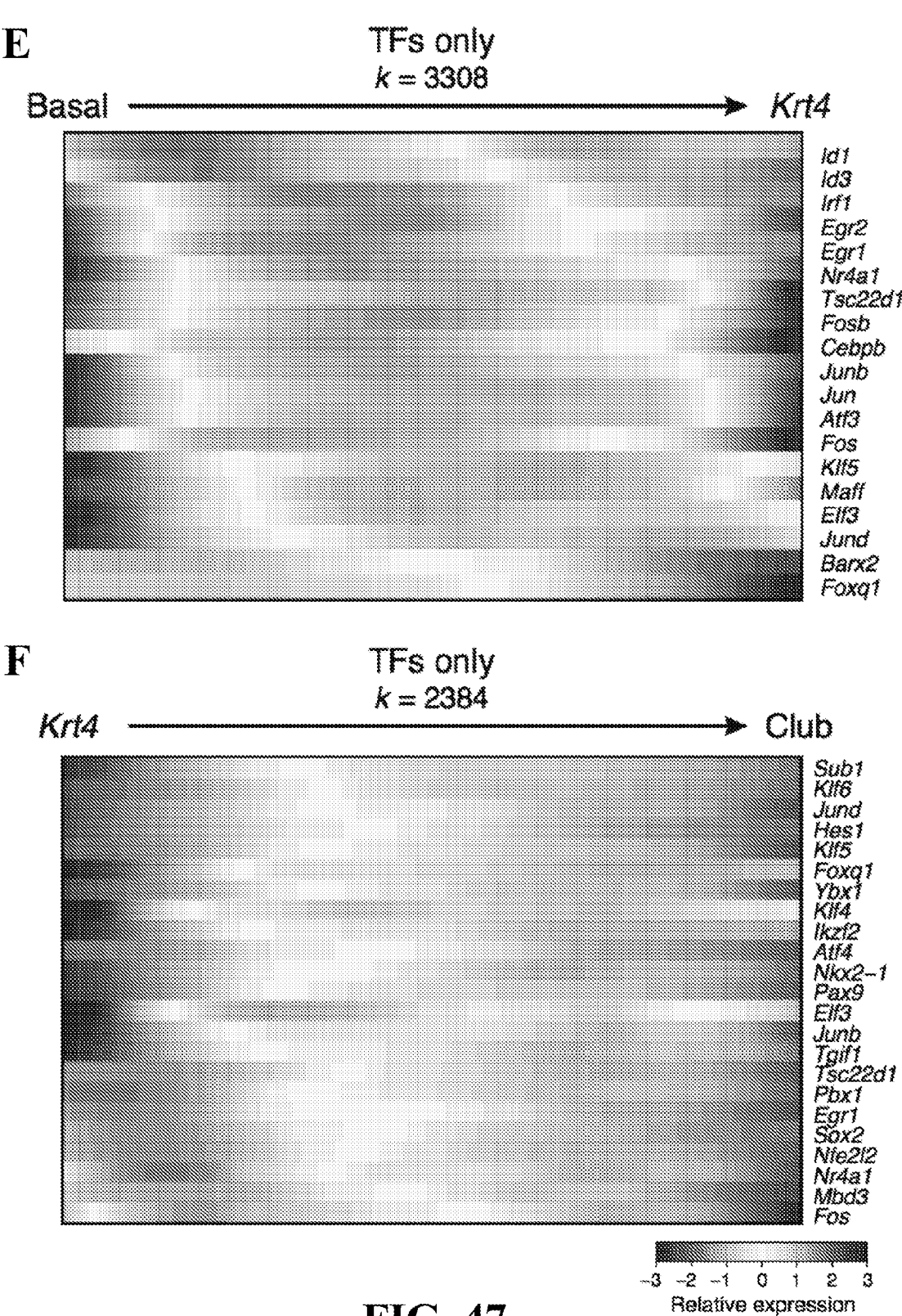
Figure 47:
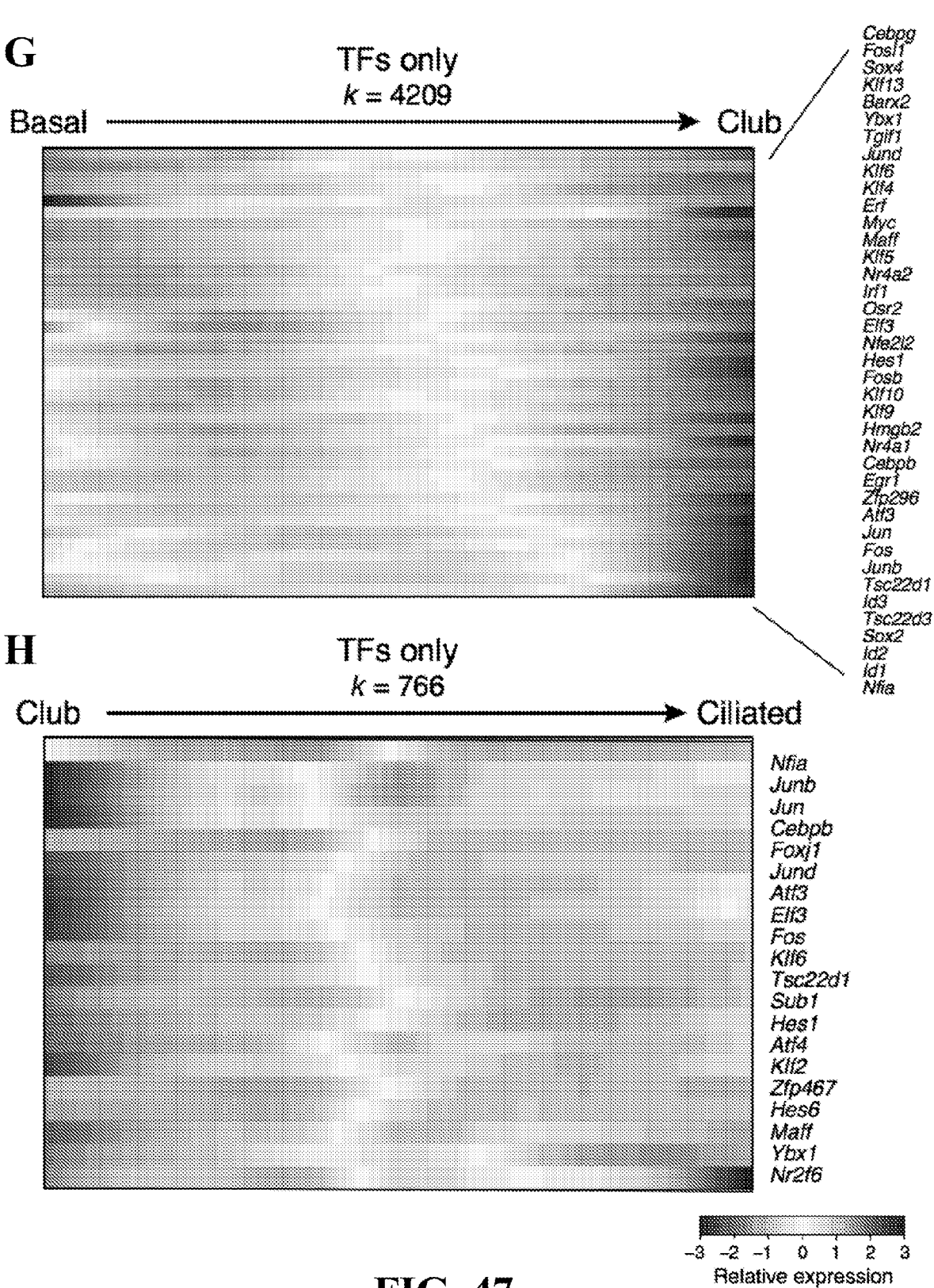

Cellular differentiation during adult tissue homeostasis in the trachea is an ongoing, asynchronous process. Applicants inferred trajectories of cell differentiation from pseudo-ordered putative transitional cells between the three common cell types (FIG. 38A,B, FIG. 46 and FIG. 47) using diffusion maps[26,27]. Applicants predicted which cells are in transition using curve fitting (Methods) and characterized gene programs and TFs that vary coherently along these trajectories (p<0.001, permutation test, Methods, FIG. 47). For example, the expression of the novel club cell TF Nfia diminished while the ciliated cell TF Foxj1 increased along the inferred trajectory from club to ciliated cells (FIG. 47H).

Surprisingly, the diffusion map revealed not only the canonical lineage path wherein basal cells produce club cells directly (DC1 and 2, k-555 cells, FIG. 38A,B), but also another path by which basal cells transition into club cells. This path was populated by novel transitional cells demarcated by the unique expression of Krt13 and Krt4 (FDR< 10[−5], likelihood-ratio test), two characteristic markers of squamous epithelia (DC2 and 3, k=1,908 cells, 38A,B). Conversely, Krt8, a prior marker of basal to luminal cell differentiation[28], is broadly expressed, and does not uniquely identify the novel cells (FIG. 46A, bottom right). Applicants did not detect any cells on a direct trajectory from basal to ciliated (38A,B), supporting previous reports that club cells are the primary source of ciliated cells during homeostasis[1,28].

Remarkably, the majority of Krt13[+] cells are confined to discrete structures comprised of contiguous groups of stratified cells with cuboidal morphology. Unlike the majority of the pseudostratified epithelium, these structures possess no ciliated cells (FIG. 38C). Scgb1a1[+]Krt13[+] club cells are located at the luminal surface (FIG. 38D,F). Additionally, there are scattered rare Krt13[+] cells throughout the epithelium (data not shown). Trp63[+]Krt13[+] cells are located in both the basal and intermediate strata of the structures, appearing as multiple layers of Trp63[+] cells. This pattern of layered Trp63[+] cells is not seen outside of the Krt13[+] regions. Applicants term these small mounds of distinct presumptive progenitors and their Krt13[+] club cell progeny "hillocks". The graded decrease of Trp63 expression and the graded increase of Scgb1a1 expression in cells along the basal to luminal axis of the hillock parallel the transition of Krt13[+] basal cells into Krt13[+] club cells, as predicted by the pseudo-ordering analysis (FIG. 38A).

To examine turnover in these unique progenitors, Applicants administered the thymidine analog 5-ethynyl-2'-deoxyuridine (EdU) to wild-type mice to label proliferating cells (Methods). The distribution of replicating cells varied across hillocks. In aggregate, Applicants found that 7.7% (95% CI [4.8%, 10.5%]) of Krt13[+] cells were EdU[+] vs. 2.4% (95% CI [1.8%, 3.1%]) of Krt13[−] cells in the neighboring pseudostratified epithelium (FIG. 46B, p<0.0001, likelihood-ratio test, n=4 mice). Thus, the topologically distinct hillocks represent discrete zones of unique cells that replicate faster than the adjoining pseudostratified epithelium (FIG. 38E,F).

Although club cells are known to dedifferentiate into stem cells following basal cell injury[29], Applicants did not find evidence of appreciable club cell dedifferentiation in hillocks under homeostatic conditions. Applicants generated an Scgb1a1-CreER LSL-tdTomato mouse strain to label hillock club cells and their progeny. After 8 weeks of homeostatic turnover, the hillock club cell lineage label was actually diluted from an initial 10.17% of all Krt13[+] club cells to only 5.12% of Krt13[+] club cells (FIG. 46B), consistent with ongoing cell turnover rather than dedifferentiation. This supports a model in which Trp63[+]Krt13[+] hillock progenitor cells rapidly produce hillock club cells that are then lost.

Krt13[+] hillock cells express unique gene modules associated with immunomodulation, squamous differentiation, and barrier function (FIG. 46D,E). Genes involved in squamous differentiation and the regulation of cellular adhesion and differentiation in squamous epithelia[30-32] include Ecm1, S100a11, and Cldn3 (FIG. 46D). Immune modulatory genes with asthma related functions[33, 34, 35] include Anxa1 and Lgals3 (FDR<$10^{-10}$ likelihood-ratio test). Overall, hillocks have attributes that normally would be predicted to play a role in regenerating epithelium: rapid turnover to replace damaged cells, squamous differentiation to enhance barrier function, and immunomodulation.

High Resolution Lineage Tracing Incorporating Cellular Dynamics with Pulse-Seq

During homeostatic turnover, basal stem cells self-renew and generate club cell progenitors, which in turn generate terminally differentiated ciliated cells[1,36]. However, the source of rare cells is unknown. The tuft cell lineage hierarchy has not been directly assessed in the airway epithelium, but it has been suggested that Gnat3[+] tuft cells in the trachea are static because they do not appreciably label with BrdU pulses[37]. Moreover, although prior lineage tracing has shown that Pgp9.5[+] NE cells are derived from basal cells during a 6 month lineage trace[28], no specific progenitor cell was identified as the immediate parent of mature NE cells.

Applicants developed a novel assay, Pulse-Seq, to monitor the generation of rare tuft cells, NE cells, and ionocytes (FIG. 39A). Pulse-Seq combines scRNA-seq and in vivo genetic lineage tracing of stem cells so that labeling of all their progeny can be monitored over a time course in the steady-state tracheal epithelium. Applicants crossed a basal cell-specific tamoxifen-inducible CreER driver to a reporter strain such that lineage-labeled basal stem cells and their subsequently labeled progeny will express membrane-localized eGFP (mG), while non-lineage-labeled cells will express membrane-localized tdTomato (mT) (Krt5-CreER/LSL-mT/mG) (Methods). Following tamoxifen-induced basal cell labeling, Applicants profiled 66,265 high quality labeled (mG[+]) and unlabeled (mT[+]) cells by scRNA-seq at day 0, 30, and 60 of homeostatic turnover (Methods; n=9 mice, 3 per time point). Applicants identified groups of cells corresponding to each of the seven epithelial cell types (Methods) and an additional group of proliferating cells, predominantly basal (FIG. 39B and FIG. 48B). For each subset, Applicants directly calculated the fraction of lineage-labeled cells at each time point (FIG. 39C,D). Applicants then used quantile regression to estimate the daily rate of change of this fraction, thereby estimating new cell generation (or the fraction of each cell-type that is produced from basal cells each day) (Methods, FIG. 39E, FIG. 48C). Confirming the specificity of the basal cell trace, at time point 0, 64.2% of the cells in the basal cluster are labeled, all non-basal cells were labeled at less than 3.3%, including less than 1.8% of the goblet, tuft, NE, and ionocyte cells (n=3 mice, FIG. 39C,D).

Cells that are not direct basal cell progeny would be expected to be labeled at low frequencies at early time points relative to those that arise directly. Indeed, in prior basal stem cell lineage traces, club cells were labeled earlier than ciliated cells. Subsequent club cell lineage traces confirmed that ciliated cells are produced from club cells in the steady-state epithelium, underscoring why basal cell lineage traces appear late in the ciliated cell population[1,36]. Using Pulse-Seq, Applicants showed that the fraction of labeled basal cells did not significantly change over the time course, consistent with the behavior of a self-renewing cell population (FIG. 48B). However, the fractions of labeled tuft, NE and ionocyte cells were substantially increased at day 30 and had further risen at day 60 (FIG. 39D). These rates are consistent with the club cell population at day 30 and 60 (FIG. 39D,E), suggesting that the rare cells are similarly immediate descendants of basal cells.

Applicants validated the result that basal cells are the direct parents of tuft cells using conventional in vivo lineage tracing of both basal and club cells separately along with subsequent in situ detection of tuft cells. Over a 30-day basal cell lineage trace (with Krt5-CreER/LSL-tdTomato mice), the proportion of lineage-labeled tuft cells dramatically increased (FIG. 39F), whereas club cell lineage tracing (with Scgb1a1-CreER/LSL-tdTomato mice) labeled only a modest fraction of Gnat3[+] tuft cells (FIG. 48D). Thus, basal cells are the predominant source of tuft cells (FIG. 39G), while club cells may provide a minor pathway of their differentiation. Applicants similarly verify that club cells do not substantially contribute to the ionocyte or NE cell populations following club cell lineage tracing (less than 3% labeling of each, FIG. 48E,F). While the fraction of labeled goblet and ciliated cells increased over time (p<0.05 in both cases, likelihood-ratio test), fewer cells were labeled by day 30 than for other cell types (FIG. 39D), and the rate of appearance of label within goblet cells was as low as that for ciliated cells (FIG. 39E). This is consistent with a model in which goblet cells are produced from club cells (FIG. 39G).

Figure 49:
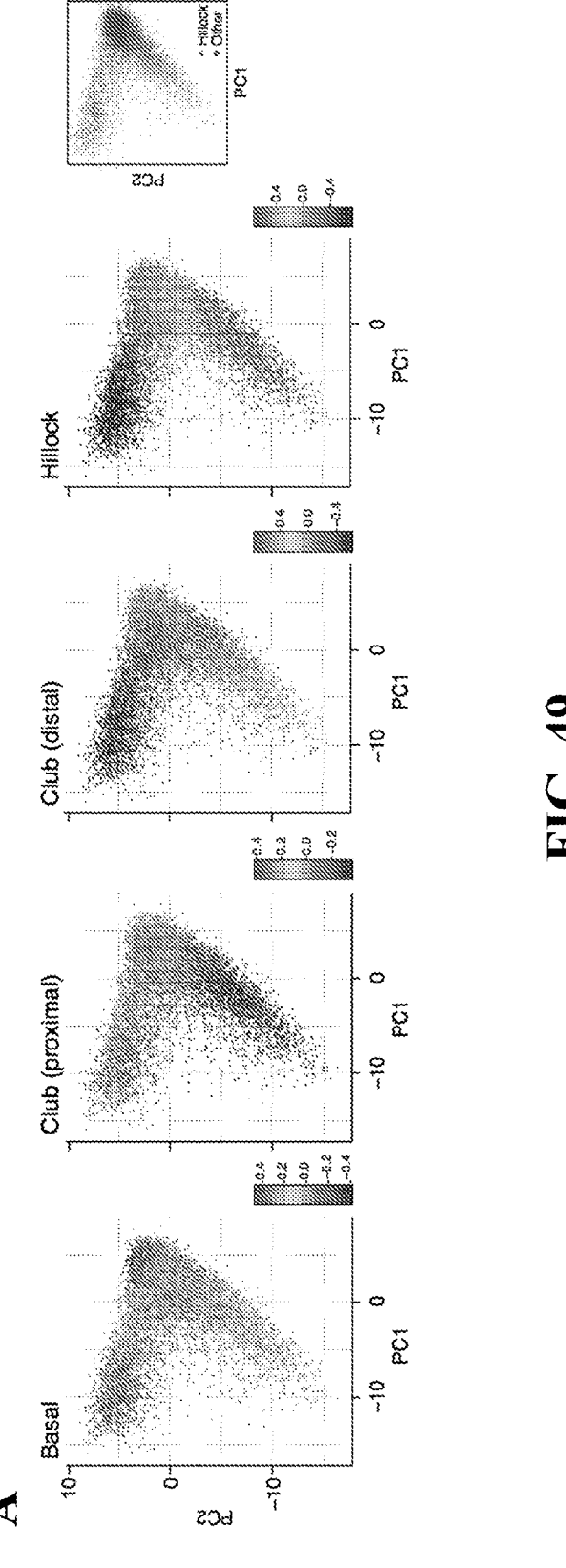
FIGS. 49A-E—Club cell heterogeneity and lineage tracing hillock-associated club cells using Pulse-Seq.
Figure 49:
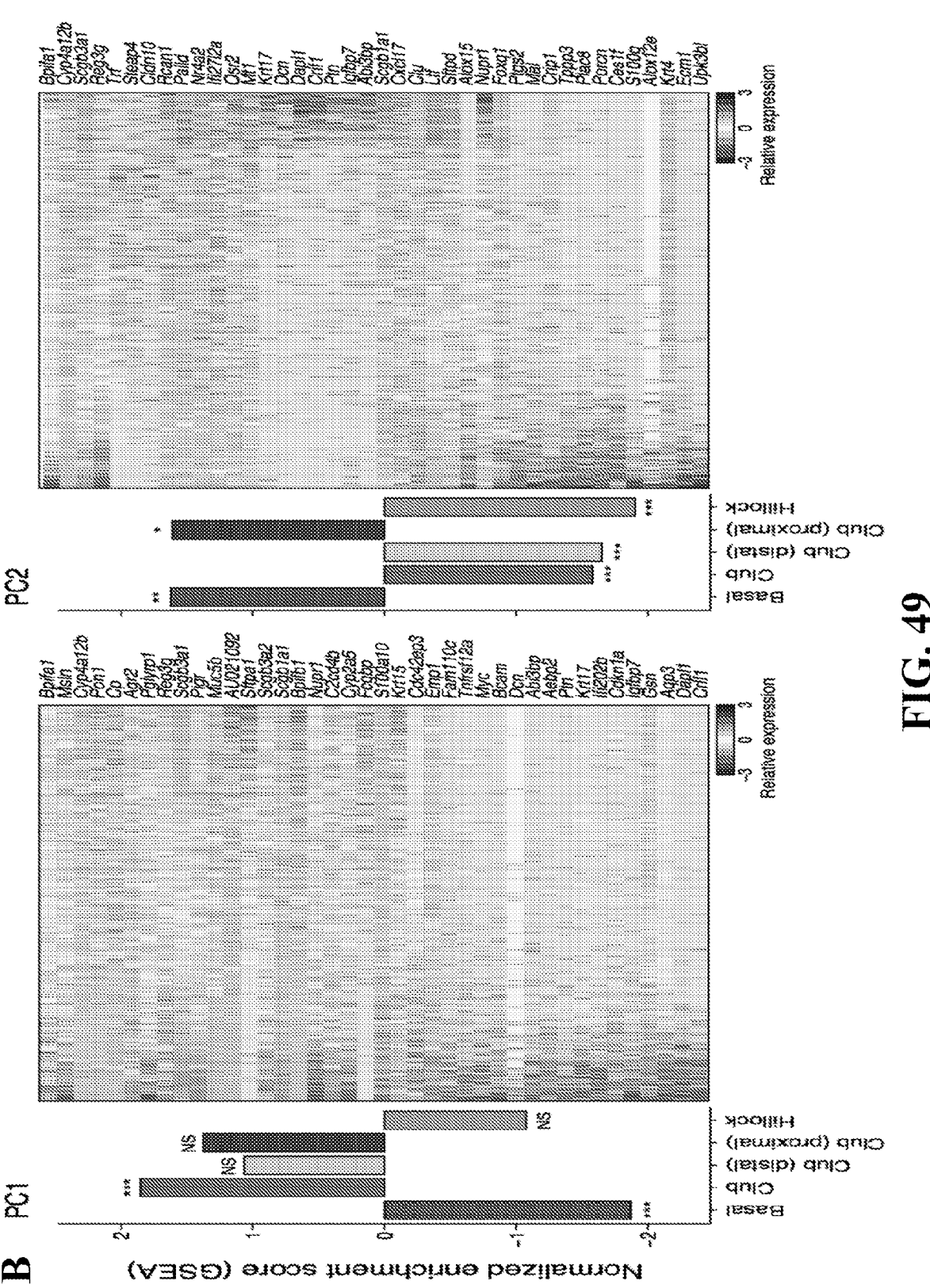

Finally, Applicants investigated the lineage of hillock-associated club cells identified by clustering of club cells (FIG. 49A,B, Methods). The fraction of labeled hillock-specific club cells increased more rapidly than the fraction of total labeled club cells (p<0.01, rank test, FIG. 49C-E) (compare FIG. 39E and FIG. 49D). This is consistent with the frequent EdU labeling observed within hillocks (FIG. 38E).

Distinct Types of Tuft and Goblet Cells

Applicants next tested if each of the rare cell populations (tuft, NE, goblet, ionocytes) are comprised of distinct subsets, by re-clustering the cells of each rare cell type from both droplet-based datasets combined (FIG. 37B and FIG. 39B, n=15 mice). The 892 tuft cells and 468 goblet cells each partitioned into three clusters, whereas neither the 276 ionocytes nor the 726 NE cells further partitioned (data not shown), as the latter do in the intestine.

The entire tuft cell population expressed a greater number of specific GPCRs than any other cell type (FDR<0.001 likelihood-ratio test, FIG. 50A), suggestive of a sensory specialization. These included Adora1 (involved in the regulation of respiratory rate in response to hypoxia[38]), Gpr64 (mediation of fluid exchange in the epididymis[39]), and the taste receptor cell transducer Gpr113[40]. They also express the alarmins Il25 and Tslp (FDR<$10^{-10}$, FIG. 50C), possibly linking their sensory function to the initiation of type-2 immunity in the airway, paralleling the gut[12, 19, 20]. Tuft cells possess unique lateral cytoplasmic extensions that traverse several cell diameters (FIG. 50D), perhaps extending their chemosensory span.

Figure 40:
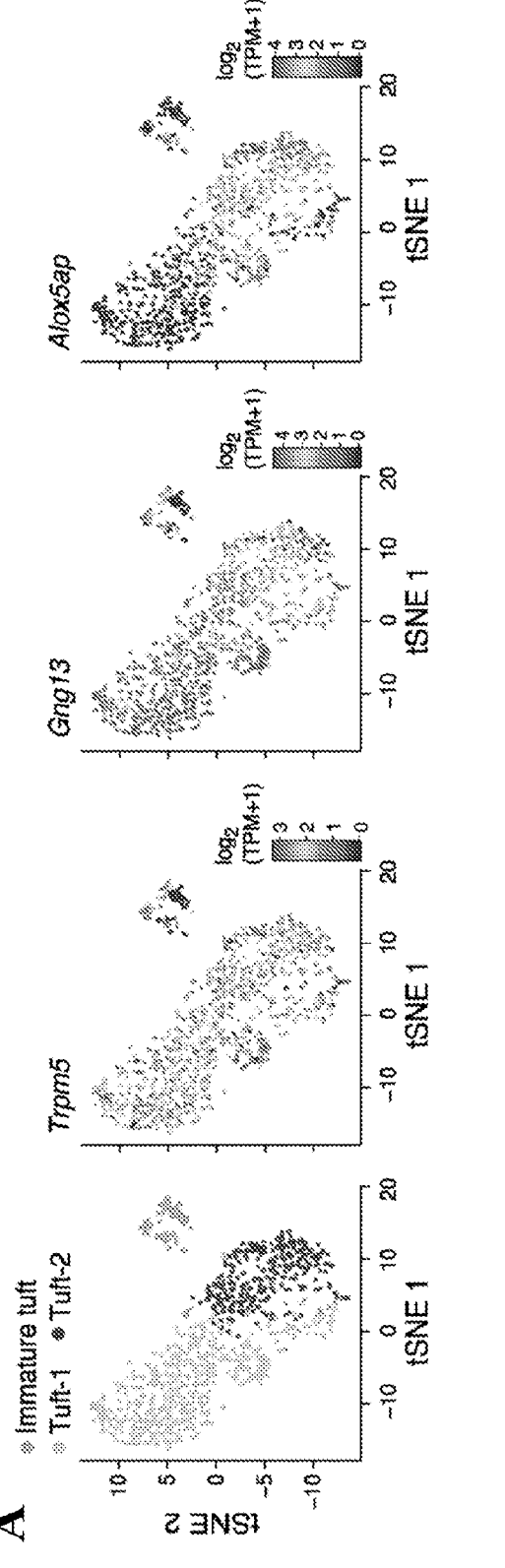
FIGS. 40A-H—Tuft and goblet cell subtypes display unique functional gene expression programs.
Figure 40:
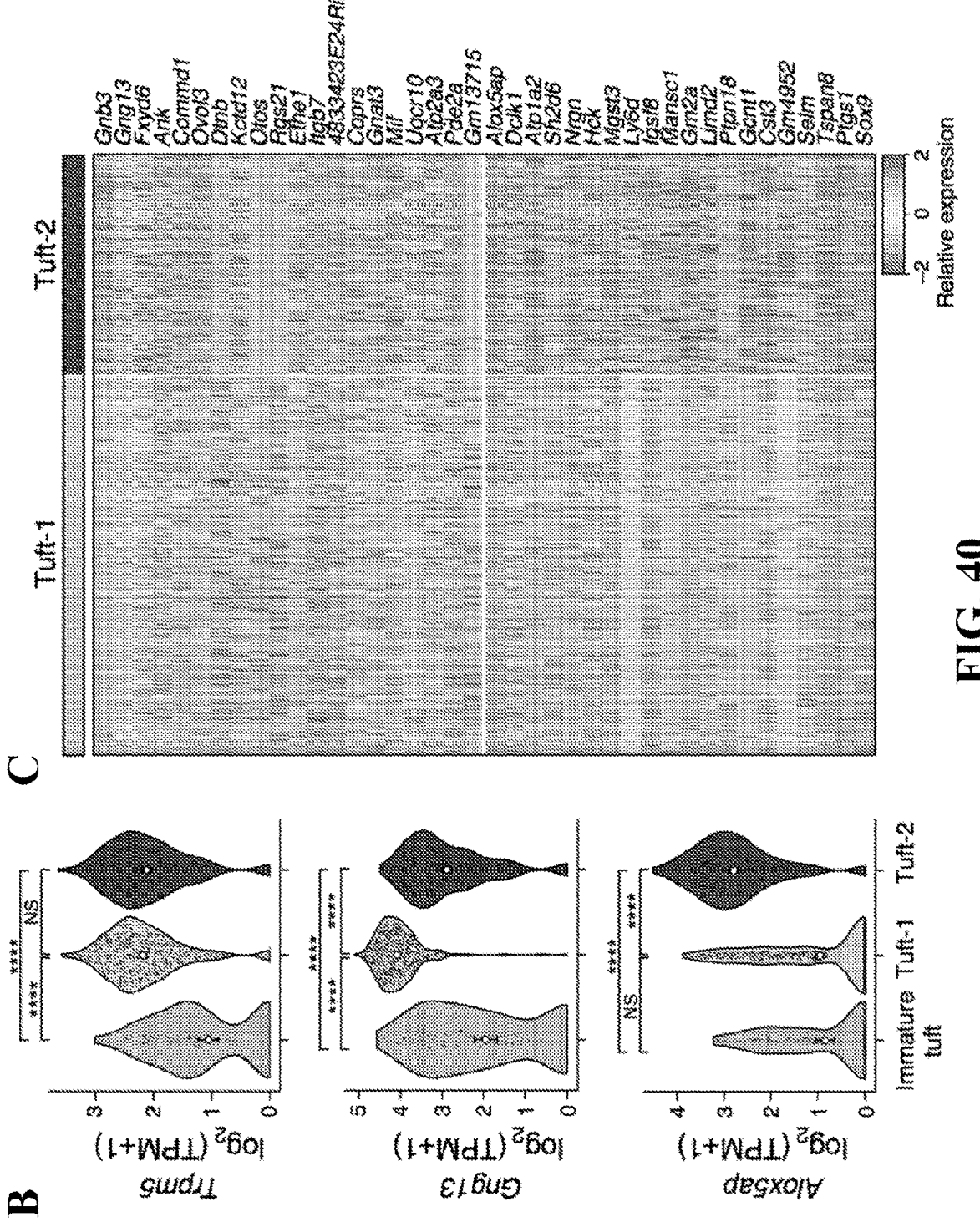
Figure 40:
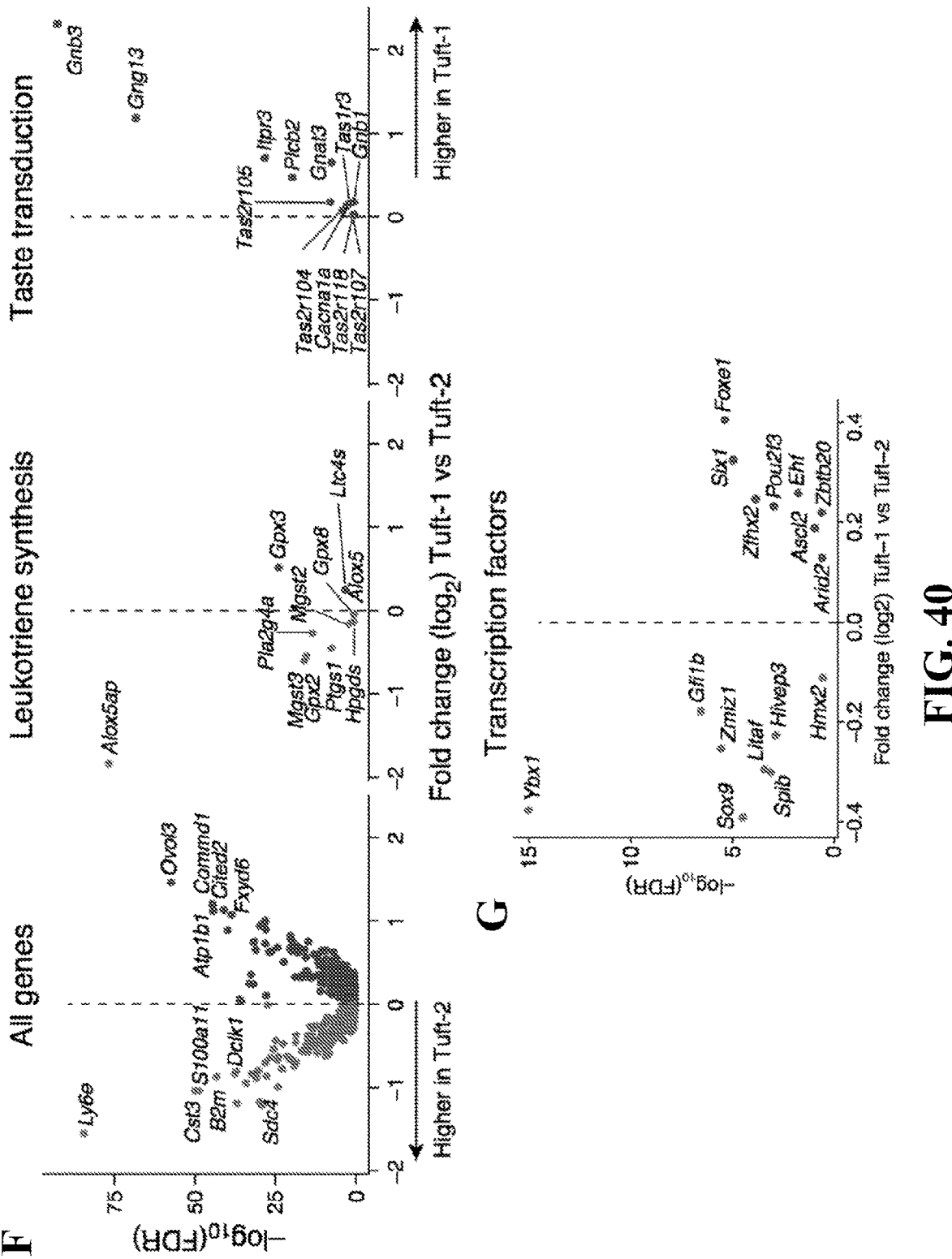
Figure 40:
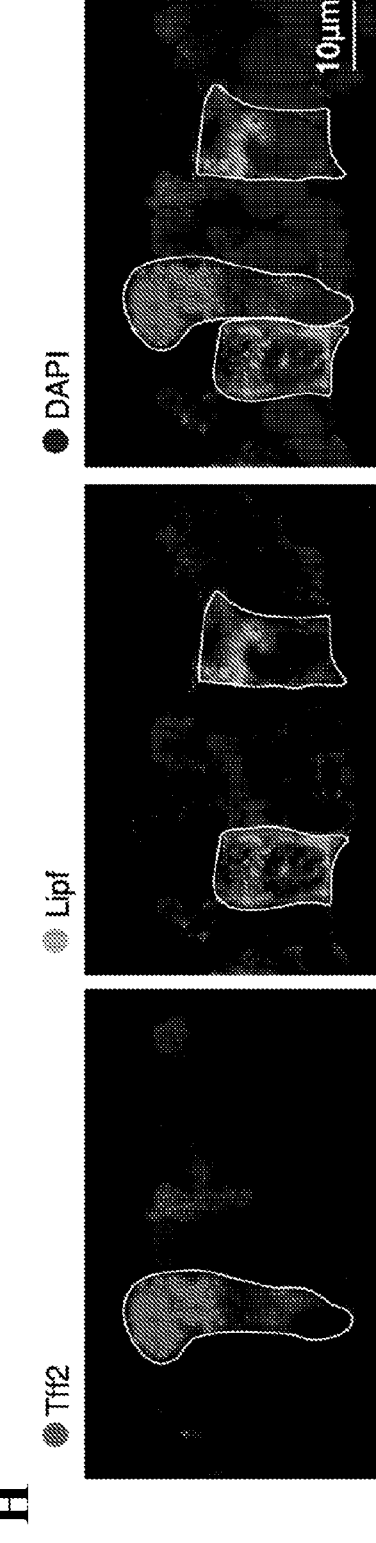

Applicants found one cluster of immature tuft cells and two clusters of mature tuft cells (FIG. 50E), which Applicants term tuft-1 and tuft-2 (FIG. 40). Cells in both the tuft-1 and tuft-2 clusters express the known tuft cell marker Trpm5, while the immature cells display low Trpm5 expression (FIG. 40A). The tuft-1 subset expresses genes that suggest a more prominent chemosensory function: elements of the taste transduction pathway (Gnb3, Gng13, Atp1b1, Fxyd6[41]), many type II taste receptors including those implicated in airway sensing of gram-negative bacterial infection (Tas2R38)[42,43] and regulation of breathing (Tas2R105, Tas2R108)[44-46], and the type I taste receptor Tas1r3 (FIG. 40F). Conversely, tuft-2 cells are associated with expression of inflammation, asthma and allergy-related genes (FIG. 40B-D,F) including Mgst3 and Alox5ap, both which are necessary for leukotriene biosynthesis[47,48] (FDR<0.05, hypergeometric test, FIG. 40B-D). They are also enriched, as in the gut, for the immune-cell associated Ptprc (CD45, FDR<0.1). Interestingly canonical tuft cell lineage TFs are specifically associated with the respective subsets, such as Pou2f3 (tuft-1) and Gfi1b, Spib, Sox9 (tuft-2, FDR<0.01, FIG. 40G).

Goblet cells also partitioned into one putative immature cell subset and two mature cell subsets, goblet-1 and goblet-2 (FIG. 40H and FIG. 50F-I). The most highly enriched marker across the entire goblet cell cluster was Gp2 (FIG. 37D and FIG. 43D), an M cell-specific marker in the intestinal epithelium, which binds pathogenic enterobacteria and initiates a mucosal immune response[49]. Goblet-1 cells are enriched for the expression of genes encoding key mucosal proteins (e.g, Tff1, Tff2, Muc5b[23], FDR<0.001, likelihood-ratio test, FIG. 50G-I) and regulators of mucus secretion (e.g., Lmanll, P2rx4[50-52], FDR<0.1, likelihood-ratio test). Applicants validated co-expression of Tff2 and Muc5ac in goblet-1 cells by antibody staining (FIG. 50I). Goblet-2 cells are distinguished by higher expression of Dcpl, Dccp2, andDccp3 (FIG. 50H), orthologs of the lectin-like secreted protein ZG16B[53], which physically aggregates bacteria[54] and of Lipf, a secreted gastric lipase that hydrolyses triglycerides (FIG. 40H and FIG. 50G,H). Applicants validated that Tff2 and Lipf are unique markers of the goblet-1 and goblet-2 cells, respectively (FIG. 40H). The Foxi1+ pulmonary ionocyte expresses CFTR in mouse and human Foxi1+ ionocytes are a new cell population, observed as a cluster of 26 cells in the initial dataset, and confirmed independently as a 276 cell cluster in the larger Pulse-Seq dataset. Applicants validated the presence of ionocytes using a transgenic Foxi1-GFP reporter mouse strain[55]. Foxi1-GFP+ cells co-labeled with anti-Foxi1 antibody, confirming the fidelity of the reporter line (FIG. 51A, left column). Ionocytes are labeled by the canonical airway markers Sox2 and Ttf1 (Nkx2-1) but are not labeled by the cell-type specific markers of any of the known airway epithelial cell types, confirming their distinct identity (FIG. 51A). Cell counting in three formalin-fixed whole-mounted tracheas (FIG. 51B, Methods), showed 1,038±501 ionocytes per trachea on average (~1% of all epithelial cells in the mouse trachea; compared to 0.36-0.42% detection by scRNA-seq).

Figure 41:
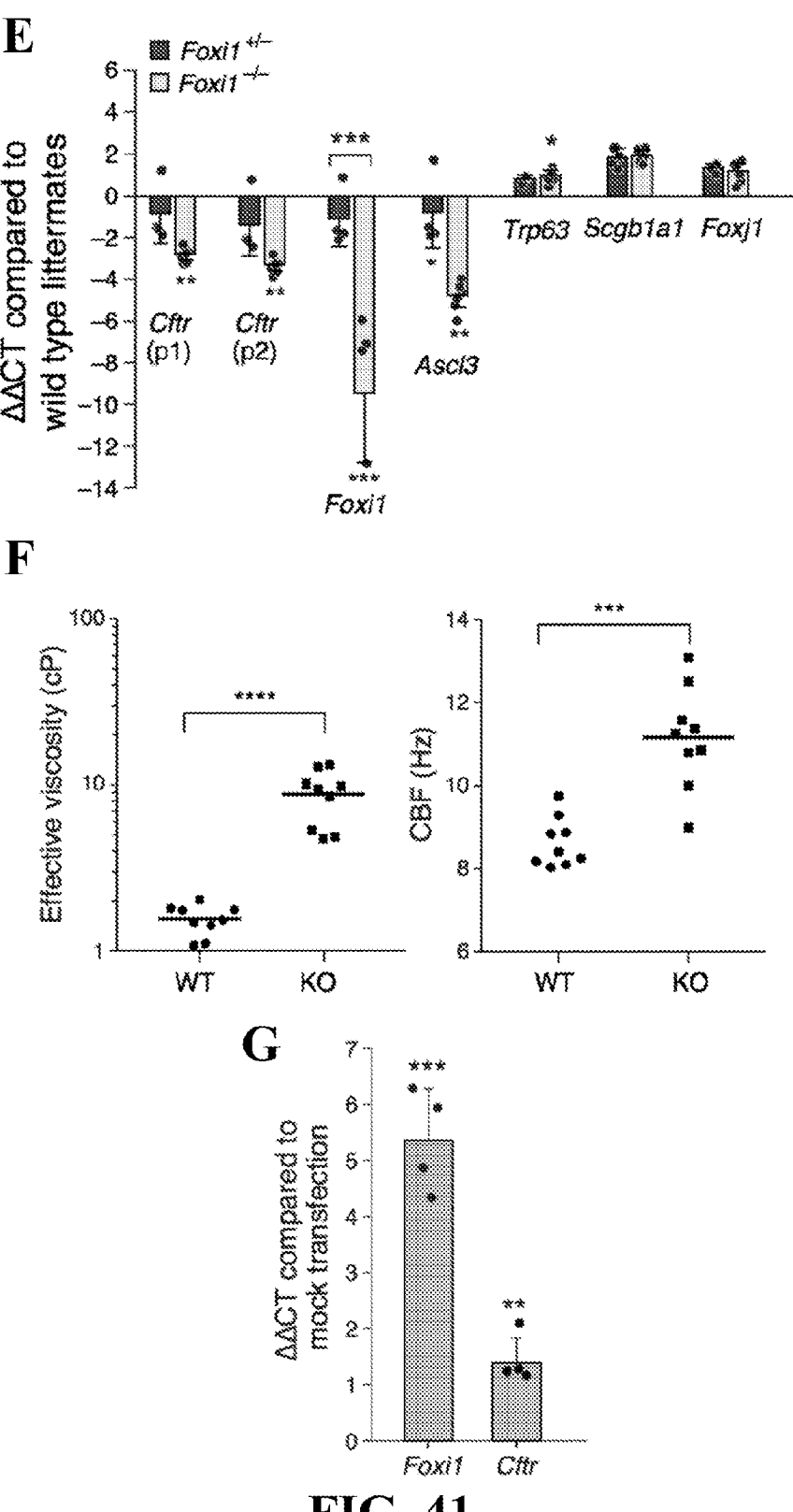
FIG. 41**E shows Foxi1-KO displays loss of expression of ionocyte TFs and Cftr in ALI cultured epithelia. Expression ($\Delta\Delta$CT, y-axis) of ionocyte (Cftr: −2.77 $\Delta\Delta$CT, 95% CI [±0.28], Foxi1: −9.46 $\Delta\Delta$CT, 95% CI [±3.32], Asc3: −4.77 $\Delta\Delta$CT, 95% CI [±0.57]) and basal (Trp63), club (Scgb1a1), or ciliated (Foxj1) markers (x-axis) in hetero- and homozygous KO (legend), normalized to wild type littermates. The mean of independent probes (p1 and p2) was used for Cftr. Heterozygous KO: n=4; homozygous KO: n=6, wild type: n=8, *p<0.05, p<0.01, Dunn's Method, error bars: 95% CI.

Based on their expression signature, pulmonary ionocytes resemble evolutionarily conserved V-ATPase-rich ionocytes in other organisms, where Foxi1 orthologs specify cell identity and regulate V-ATPase expression. In the multiciliated skin of *Xenopus*, ionocytes are specified by Foxi1[13]. Foxi3a and Foxi3b identify mitochondria-rich skin ionocytes in zebrafish[56]. Mammalian Foxi1 regulates V-ATPase in specialized cells of the inner ear, kidney, and epididymis that regulate ion transport and fluid pH[57,58]. Pulmonary ionocytes are similarly enriched in the expression of V-ATPase subunits Atp6v1c2 and Atp6v0d2 (FDR<0.0005, likelihood-ratio test, FIG. 41B top row, FIG. 45B) and are uniquely marked by an anti-ATP6v0d2 antibody (FIG. 41B, top row). Like tuft cells[37] (FIG. 50B) and zebrafish ionocytes[59], pulmonary ionocytes extend lateral processes some 10 μm-20 μm away from their cell bodies, contacting several additional epithelial cells beyond their immediate neighbors, as well as the basement membrane (FIG. 51C). Applicants speculate these processes may be involved in chemosensation and cell-to-cell communication.

Strikingly, the pulmonary ionocyte is specifically enriched for the expression of cystic fibrosis transmembrane conductance regulator (Cftr) mRNA (FDR<0.005 and FDR<$10^{-10}$ in the initial and Pulse-Seq dataset respectively, likelihood-ratio test, FIG. 41A,C, FIG. 45B), accounting, on average, for 55% of detected Cftr transcripts across all single cells profiled from the mouse tracheal epithelium, despite the fact that ionocytes comprise, on average, only 0.39% of the cells analyzed. Applicants confirmed the specific enrichment of Cftr in ionocytes by qRT-PCR of prospectively isolated populations of primary ionocytes (Foxi1-GFP) vs. ciliated cells (Foxj1-GFP) or bulk EpCAM+ epithelial cells (FIG. 41D), and at the protein level by Cftr staining of Foxi1-GFP+ cells in situ (FIG. 41B, bottom row).

Of note, Foxi1-GFP+ cells are detected in murine submucosal glands (FIG. 51D), which are implicated in the pathogenesis of cystic fibrosis[60] and have the highest levels of CFTR expression in human airways[61]. Ionocytes also specifically express Cochlin (Coch), a secreted protein that promotes antibacterial innate immunity against *Pseudomonas aeruginosa* and *Staphylococcus aureus*, the two most prominent pathogens in CF lung disease[62]. Deletion of Foxi1 in the mouse results in defective acidification of the epididymal lumen and male infertility[63], resembling the reduced fertility phenotype observed clinically in CF.

Analysis of epithelial cells derived from Foxi1 knockout (Foxi1-KO) mice shows that Foxi1 is required for the expression of the ionocyte TF Ascl3, and the majority of Cftr expression (FIG. 41E). Thus, loss of Foxi1 causes either loss of the ionocyte itself or a significant alteration in its transcriptional state. In contrast, epithelial cells derived from the Ascl3 knockout mouse displayed only moderately reduced Foxi1 and Cftr expression (FIG. 51E).

Ionocytes Regulate Epithelial Surface Physiology

Both the amount and viscosity of mucus in the airway surface liquid (ASL) is tightly regulated and this process is necessary for effective mucociliary clearance of debris and pathogens and is disturbed in diseases such as CF[64,65]. Several functional assays show that the loss of Foxi1 in mouse airway epithelium alters physiologic parameters that govern mucus clearance. Applicants assessed ASL depth, mucus viscosity, and ciliary beat frequency in the murine airway epithelium of Foxi1-KO with live imaging by micro-optical coherence tomography (μOCT) and particle tracking microrheology[64,66] (Methods). Strikingly, Foxi1-KO epithelia had increased optical density of airway mucus (FIG. 51F) and increased effective viscosity compared to wild type littermates (1.56+/−0.3 cP WT, 8.78+/−3.2 KO, p<0.0001 Mann Whitney U-test, FIG. 41F, left). Though modest in magnitude, these results are consistent with the increased mucus viscosity seen in animal models of cystic fibrosis[64,67]. Indeed, the changes in mucus viscosity are in line with those observed in primary human bronchial epithelial cells of CF patients as compared to normal individuals[64,68]. Ciliary beat frequency (CBF) significantly increased in the Foxi1-KO epithelium (FIG. 41F, right, 8.54+/−0.8 and 11.16+/−1.2 Hz in WT and KO, p<0.001, Mann Whitney U-test), consistent with mechanical feedback elicited by increased airway mucus viscosity[69]. In this model, as mechanical load increases, CBF increases until a failure threshold is reached. As with murine Cftr knockout models, neither depth (FIG. 52A) nor pH (FIG. 52B) of the ASL was significantly altered in Foxi1-KO epithelial cultures (Methods). In Cftr knockout models this lack of alteration in pH is attributed to low expression of $Na^+/K^+$ adenosine triphosphatase[70] and ASL depth is preserved through high compensatory upregulation of CaCC expression[71], as is also observed in murine $Cftr^{-/-}$ excised trachea (data not shown).

Applicants also tested whether Foxi1-KO epithelia display abnormal forskolin-induced and CFTR inhibitor $(CFTR_{inh}$-172)-blocked equivalent currents $(AIe_q)$ in measurements with the transepithelial current clamp system[72] (Methods). Paradoxically, Foxi1-KO mouse epithelium displayed increases in $CFTR_{inh}$-172-sensitive forskolin-induced currents under asymmetrical chloride (FIG. 51G,H). The reason for increased chloride currents in the setting of reduced Cftr expression of Foxi1-KO epithelium remains unclear, although cross-talk between cAMP and $Ca^{2+}$ pathways in mouse airways has been suggested to be partially responsible for a compensatory activation of forskolin-inducible currents in CF mouse airway epithelia[73]. The relevance of these findings and whether other non-ionocyte cell types contribute to Cftr currents in mouse airway epithelia in the setting of Foxi1 loss remain to be determined.

Since the ferret represents a more faithful model of human cystic fibrosis[74, 75], Applicants investigated the role of Foxi1 in regulating CFTR. CRISPR/dCas9VP64/p65-mediated transcriptional activation of Foxi1 increased airway epithelial expression of Cftr and other ionocyte genes as assessed by qRT-PCR (Methods, FIG. 41G). Importantly, Applicants found that ferret epithelial cultures subjected to Foxi1 transcriptional activation displayed significantly increased forskolin-induced $\Delta I_{sc}$ and CFTR (GlyH101) inhibitor $\Delta I_{sc}$ relative to mock-transfected controls (FIG. 41H, FIG. 52C). Thus, Foxi1 regulates CFTR expression and function in ferret airway epithelium.

The Pulmonary Ionocyte is the Predominant CFTR Expressing Cell in Human Airways

Human pulmonary ionocytes are the major source of CFTR in the airway epithelium as assessed by scRNA-Seq of healthy human lung from transplant material (FIG. 41J,K) and by RNA fluorescent in situ hybridization (RNA-FISH, Methods) of FOXI1 and CFTR in human bronchial airway epithelium (FIG. 41I). Among 78,217 cells from 5 regions along the airways of human lung (AT, AW, JR, AR, MS, J W et al, unpublished data), 765 ionocytes are detected by unsupervised clustering (FIG. 41J, left), with specific expression of FOXI1, ASCL3 and CFTR (FDR<$10^{-10}$, likelihood-ratio test, FIG. 41J,K), and a 14 gene cross-species consensus signature (FDR<$10^{-5}$, FIG. 41K). Ionocytes are detected at approximately the same fraction (0.5-1.5%) along the proximodistal axis from the carina to the secondary bronchus. As in mouse, FOXI1 expression is specific to ionocytes (FIG. 41J, middle), and CFTR is highly expressed in those cells (FIG. 41K, middle). Applicants do note however, that much lower expression is detected in a modest portion of some club and basal cells (FIG. 41J, right). In an accompanying study, FOXI1 transcriptional activation in human airway epithelial cultures results in increased ionocyte differentiation. Additionally, numbers of human ionocytes correlated with forskolin-induced CFTR (inh)-172 inhibitable short-circuit currents (Wingert et al.).

Taken together, these results identify the ionocyte as a novel rare airway epithelial cell type with unique morphology, expression profile, and role in regulating airway epithelial surface physiology. Though the loss of pulmonary ionocytes alters physiologic parameters that are also aberrant in cystic fibrosis, defining the role of the ionocyte in cystic fibrosis or any other airways disease requires future study.

DISCUSSION

Figure 42:
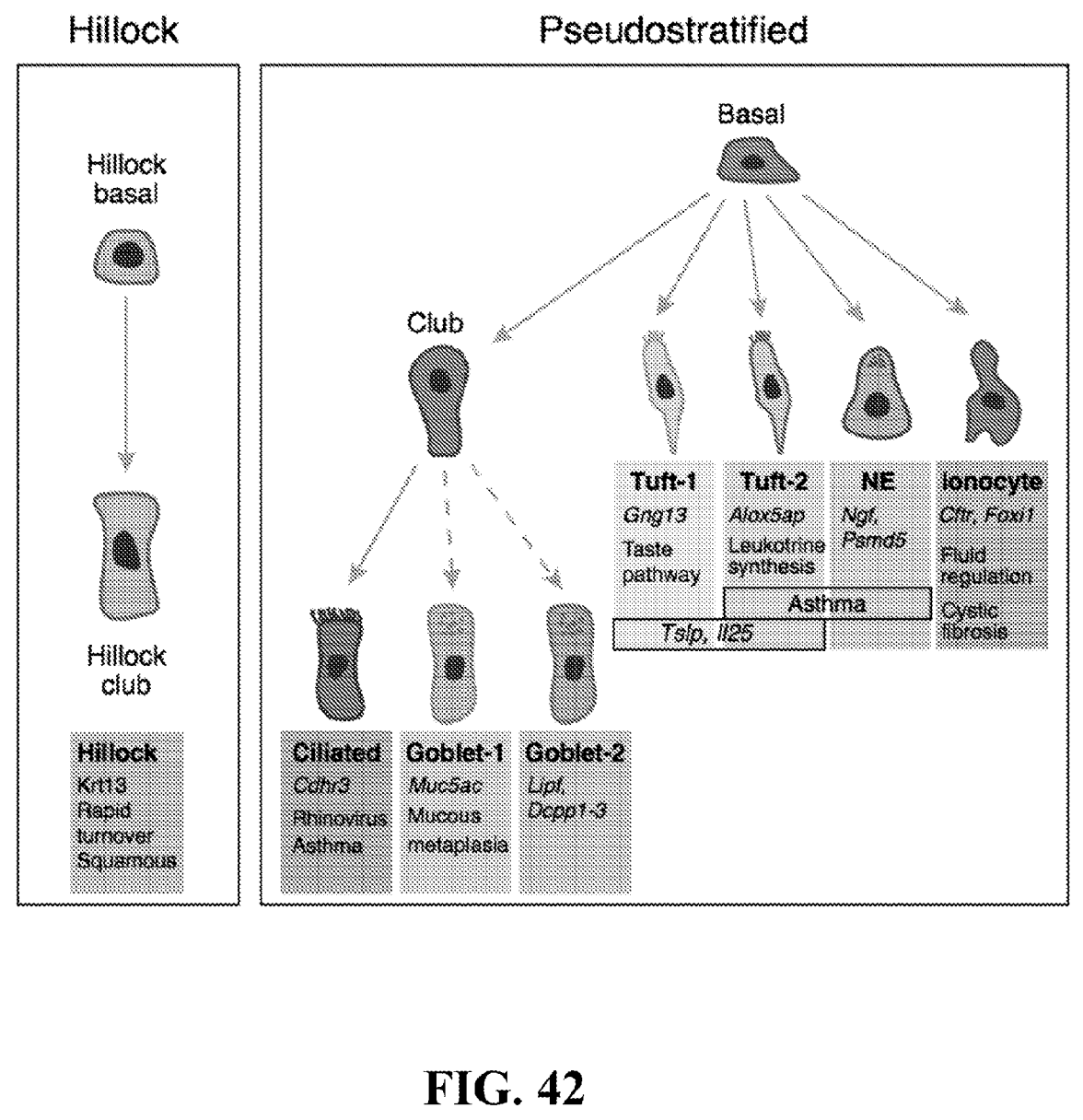

Applicants combined scRNA-seq and genetic lineage tracing to generate a revised hierarchy of the murine tracheal epithelium that includes a new cell type, the ionocyte, new subclasses of tuft and goblet cells, new transitional cells, a new structure (hillocks). Applicants also show that the basal cell is the direct parent cell of club, tuft, NE, and ionocyte cells (FIG. 42). An accompanying manuscript, using related but distinct models and computational approaches including murine tracheal regeneration models, identified similar cell types including the pulmonary ionocyte (Wingert et al.). The use of Pulse-Seq allowed Applicants to assess differentiation dynamics across multiple cell types and subtypes in a complex new lineage tree in a single internally controlled experiment. Surprisingly, Applicants show that ionocytes, NE cells, and tuft cells appear at approximately the same rate as club cells. Within hillocks, cells appear even more rapidly and are associated with squamous, barrier, and immunomodulatory features. However, their actual function and origin is mysterious.

Have Applicants catalogued the full range of biologically relevant epithelial cell types? Statistical modeling[76] suggests that with 66,000 cells Applicants should have detected any discrete cell type that comprises more than 0.035% of the total cell population with 99% confidence. As a caveat, the model assumes that one recovers cells in their correct in vivo proportions, but Applicants note some cell populations may require special dissociation conditions[76]. Importantly, injury and disease are likely to induce plasticity, thereby revealing new lineage paths. Indeed, cell states may change with disease and cell types not evident in the homeostatic epithelium may make an appearance.

The cell census allows one to reconstruct a hypothetical new cellular narrative of lung disease (FIG. 42). Disease genes associated with common diseases with complex genetic architecture, such as asthma, or with rare Mendelian genes, such as CF, can now be associated with particular cell types and subtypes. Generating comprehensive cell atlases of the healthy and diseased human lung and airways are a critical next step[77]. Lineage relationships, cell types, and cell type functionality may all be different in mouse and human. Indeed, Applicants focused on the murine trachea and even here Applicants have shown functional variation along this short anatomic span. As the human respiratory tree is so large, it will be important to sample single cells along its length.

Materials and Methods for Trachea

EXPERIMENTAL METHODS

Mouse models. The MGH Subcommittee on Research Animal Care approved animal protocols in accordance with NIH guidelines. Krt5-creER[80] and Scgb1a1-creER[36] mice were described previously. Foxi1-eGFP mice were purchased from GENSAT. C57BL/6J mice (stock no. 000664), LSL-mT/mG mice (mouse stock no. 007676), and LSL-tdTomato (stock no. 007914), Ascl3-EGFP-Cre mice (stock no. 021794), and Foxi1-KO mice (stock no. 024173) were purchased from the Jackson Laboratory. To label basal cells and secretory cells for in vivo lineage traces, Applicants administered tamoxifen by intraperitoneal injection (3 mg per 20 g body weight) three times every 48 hours to induce the Cre-mediated excision of a stop codon and subsequent expression of tdTomato. For Pulse-Seq experiments Applicants administered tamoxifen by intraperitoneal injection (2 mg per 20 g body weight) three times every 24 hours to induce the Cre-mediated excision of a stop codon and subsequent expression GFP. To label proliferating cells, Applicants administered 5-ethynyl-2'-deoxyuridine (EdU) per 25 g mouse by intraperitoneal injection (2 mg per 20 g body weight). 6-12-week-old mice were used for all experiments. Male C57BL/6 mice were used for the full length and initial 3' scRNA-seq experiments. Both male and female mice were used for lineage tracing and 'Pulse-Seq' experiments. Applicants used three mice for each lineage time point.

Immunofluorescence, microscopy and cell counting. Tracheae were dissected and fixed in 4% PFA for 2 h at 4° C. followed by two washes in PBS, and then embedded in OCT. Cryosections (6 μm) were treated for epitope retrieval with 10 mM citrate buffer at 95° C. for 10-15 minutes, permeabilized with 0.1% Triton X-100 in PBS, blocked in 1% BSA for 30 min at room temperature (27° C.), incubated with primary antibodies for 1 hour at room temperature, washed, incubated with appropriate secondary antibodies diluted in blocking buffer for 1 h at room temperature, washed and counterstained with DAPI.

In the case of whole mount trachea stains, tracheas were longitudinally re-sectioned along the posterior membrane, permeabilized with 0.3% Triton X-100 in PBS, blocked in 0.3% BSA and 0.3% Triton X-100 for 120 min at 37° C. on an orbital shaker, incubated with primary antibodies for 12 hours at 37° C. (again on an orbital shaker), washed in 0.3% Triton X-100 in PBS, incubated with appropriate secondary antibodies diluted in blocking buffer for 1 h at 37° C. temperature, washed in 0.3% Triton X-100 in PBS and counterstained with Hoechst 33342. They were then mounted on a slide between two magnets to ensure flat imaging surface.

The following primary antibodies were used: rabbit anti-Atp6v0d2 (1/300; pa5-44359, Thermo), goat anti-CC10 (aka Scgb1a1, 1:500; SC-9772, Santa Cruz), rabbit anti-CFTR (1:100; ACL-006, Alomone), mouse anti-Chromogranin A (1/500; sc-393941, Santa Cruz), rat anti-Cochlin (1/500; MABF267, Millipore), goat anti-FLAP (aka Alox5ap, 1:500; NB300-891, Novus), goat anti-Foxi1 (1:250; ab20454, Abcam), chicken anti-GFP (1:500; GFP-1020, Aves Labs), rabbit anti-Gnat3 (1/300; sc-395, Santa Cruz), rabbit anti-Gng13 (1:500; ab126562, Abcam), rabbit anti-Krt13 (1/500; ab92551, Abcam), goat anti-Krt13 (1/500; ab79279, Abcam), goat anti-Lipf (1:100; MBS421137, mybiosource.com), mouse anti-Muc5ac (1/500; mal-38223, Thermo), mouse anti-Muc5ac (1/500; mal-38223, Thermo), mouse anti-p63 (1:250; gtx102425, GeneTex), rabbit anti-Tff2 (1/500; 13681-1-AP, ProteinTech), rabbit anti-Trpm5 (1:500; ACC-045, Alomone), mouse anti-tubulin, acetylated (1:100; T6793, Sigma). All secondary antibodies were Alexa Fluor conjugates (488, 594 and 647) and used at 1:500 dilution (Life Technologies).

EdU was stained in fixed sections alongside the above antibody stains as previously described[81].

Confocal images for both slides and whole mount tracheas were obtained with an Olympus FV10i confocal laser-scanning microscope with a 60× oil objective. Cells were manually counted based on immunofluorescence staining of markers for each of the respective cell types. Cartilage rings (1 to 12) were used as reference points in all the tracheal samples to count specific cell types on the basis of immunostaining. Serial sections were stained for the antibodies tested and randomly selected slides were used for cell counting.

Cell dissociation and FACS. Airway epithelial cells from trachea were dissociated using papain solution. For whole trachea sorting, longitudinal halves of the trachea were cut into five pieces and incubated in papain dissociation solution and incubated at 37° C. for 2 h. For proximal-distal cell sorting, proximal (cartilage 1-4) and distal (cartilage 9-12) trachea regions were dissected and dissociated by papain independently. After incubation, dissociated tissues were passed through a cell strainer and centrifuged and pelleted at 500 g for 5 min. Cell pellets were dispersed and incubated with Ovo-mucoid protease inhibitor (Worthington biochemical Corporation, cat. no. LK003182) to inactivate residual papain activity by incubating on a rocker at 4° C. for 20 min. Cells were then pelleted and stained with EpCAM-PECy7 (1:50; 25-5791-80, eBioscience) and CD45, CD81, or basis of GFP expression for 30 min in 2.5% FBS in PBS on ice. After washing, cells were sorted by fluoresence (antibody staining and/or GFP) on a BD FACS Aria (BD Biosciences) using FACS Diva software and analysis was performed using FlowJo (version 10) software.

For plate-based scRNA-seq, single cells were sorted into each well of a 96-well PCR plate containing 5 μl of TCL buffer with 1% 2-mercaptoenthanol. In addition, a population control of 200 cells was sorted into one well and a no-cell control was sorted into another well. After sorting, the plate was sealed with a Microseal F, centrifuged at 800 g for 1 minute and immediately frozen on dry ice. Plates were stored at −80° C. until lysate cleanup.

For droplet-based scRNA-seq, cells were sorted into an Eppendorf tube containing 50 μl of 0.4% BSA-PBS and stored on ice until proceeding to the GemCode Single Cell Platform.

Plate-based scRNA-seq. Single cells were processed using a modified SMART-Seq2 protocol as previously described[4]. Briefly, RNAClean XP beads (Agencourt) were used for RNA lysate cleanup, followed by reverse transcription using Maxima Reverse Transcriptase (Life Technologies), whole transcription amplification (WTA) with KAPA HotStart HIFI 2× ReadyMix (Kapa Biosystems) for 21 cycles and purification using AMPure XP beads (Agencourt). WTA products were quantified with Qubit dsDNA HS Assay Kit (ThermoFisher), visualized with high sensitivity DNA Analysis Kit (Agilent) and libraries were constructed using Nextera XT DNA Library Preparation Kit (Illumina). Population and no-cell controls were processed with the same methods as singe cells. Libraries were sequenced on an Illumina NextSeq 500.

Droplet-based scRNA-seq. Single cells were processed through the GemCode Single Cell Platform per manufacturer's recommendations using the GemCode Gel Bead, Chip and Library Kits (10× Genomics, Pleasanton, CA). Briefly, single cells were partitioned into Gel Beads in Emulsion (GEMs) in the GemCode instrument with cell lysis and barcoded reverse transcription of RNA, followed by amplification, shearing and 5' adaptor and sample index attachment. An input of 6,000 single cells was added to each channel with a recovery rate of roughly 1,500 cells. Libraries were sequenced on an Illumina Nextseq 500.

qRT-PCR. FACS isolated cells were sorted into 150 μl TRIzol LS (ThermoFisher Scientific), while ALI culture membranes were submerged in 300 μl of standard TRIzol solution (ThermoFisher Scientific). A standard chloroform extraction was performed followed by an RNeasy column-based RNA purification (Qiagen) according to manufacturer's instructions. 1 μg (when possible, otherwise 100 ng) of RNA was converted to cDNA using SuperScript VILO kit with additional ezDNase treatment according to manufacturer's instructions (ThermoFisher Scientific). qRT-PCR was performed using 0.5 μl of cDNA, predesigned TaqMan probes, and TaqMan Fast Advanced Master Mix (ThermoFisher Scientific), assayed on a LightCycler 480 in 384 well format (Roche). Assays were run in parallel with the loading controls Hprt and Ubc, previously validated to remain constant in the tested assay conditions. Subsequent experiments using ferret epithelial cells were performed using the same methodology.

Single-molecule fluorescence in situ hybridization (smFISH). Intact primary human bronchus was obtained through the New England Organ Bank. Segments of bronchus were flash frozen by immersion in liquid nitrogen and embedded in OCT and 4 uM sections were collected. RNAScope Multiplex Fluorescent Kit (Advanced Cell Diagnostics) was used per manufacturer's recommendations, and confocal imaging was carried out as described above.

Transwell cultures. Cells were cultured and expanded in complete SAGM (small airway epithelial cell growth medium; Lonza, CC-3118) containing TGF-β/BMP4/WNT antagonist cocktails and 5 μM Rock inhibitor Y-27632 (Selleckbio, S1049). To initiate air-liquid interface (ALI) cultures, airway basal stem cells were dissociated from mouse tracheas and seeded onto transwell membranes. After reaching confluence, media was removed from the upper chamber. Mucociliary differentiation was performed with PneumaCult-ALI Medium (StemCell, 05001). Differentiation of airway basal stem cells on an air-liquid interface was followed by directly visualizing beating cilia in real time after 10-14 days.

Once air-liquid cultures were fully differentiated, as indicated by beating cilia, treatment cultures were supplemented with 10 ng/mL of recombinant murine IL-13 (Peprotech®-stock diluted in water and used fresh) diluted in PneumaCult-ALI Medium, while control cultures received an equal volume of water for 72 hours. After treatment, whole ALI wells were fixed in 4% PFA, immunostained in whole mount using the same buffers and imaged with a confocal microscope as described above.

Airway surface physiologic parameters. Epithelia derived from Foxi1-KO mice (wild type, heterozygous knockout, and homozygous knockout genotypes) were grown as ALI cultures in transwells as described above and OCT, particle-tracking microrheology, airway surface pH measurements, and equivalent current ($Ie_q$) assays were used to characterize their physiological parameters as described below.

μOCT methodologies have been used as previously described[64, 66, 69]. Briefly, Airway Surface Liquid (ASL) depth and ciliary beat frequency (CBF) were directly assessed via cross-sectional images of the airway epithelium with high resolution (<1 μM) and high acquisition speed (20,480 Hz line rate resulting in 40 frames/s at 512 line/frame). Quantitative analysis of images was performed in ImageJ[82]. To establish CBF, custom code in Matlab (Mathworks, Natick, MA) was used to quantify Fourier analysis of the reflectance of beating cilia. ASL depth was characterized directly by geometric measurement of the respective layers.

Particle-tracking microrheology was used to measure mucous viscosity following the methods detailed in Birket et al.[68]

Airway surface pH was measured by use of a small probe as described in Birket et al.[65]

Equivalent current ($I_{eq}$) assay on mouse ALI was carried out as described in Mou et al.[72] with these changes: benzamil was used at 20 uM and CFTR activation was done only with 10 uM forskolin.

Transcriptional activation of Foxi1 in ferret basal cell cultures. Lentivirus production and transduction. HEK 293T cells were cultured in 10% FBS, 1% penicillin/streptomycin DMEM. Cells were seeded at ~30% confluency, and then were transfected the next day at ~90% confluency. For each flask, 22 μg of plasmid containing the vector of pLent-dCas9-VP64 Blast or pLent-MS2-p65-HSF1 Hygromycin, 16 g of psPAX2, and 7 μg pMD2 (VSV-G) were transfected using calcium phosphate buffer. The next day after transfection, culture medium was removed and replaced with 2% FBS-DMEM medium and incubated for 24 h. Lentivirus supernatant was harvested 48 h after transfection, and the supernatant was centrifuged at 5000 rpm for 5 min. Lentivirus was filtered with a 0.45 μm PVDF filter, concentrated by Lentixconcentrator (Takara), aliquoted and stored at 80° C. Ferret basal cells were cultured in Pneumacult-Ex with medium supplemented with Pneumacult-Ex and supplemented with hydrocortisone and 1% penicillin/streptomycin and passaged at a 1:5 ratio. Cells were incubated with lentivirus for 24 h in growth media. At 72 h selection was initiated (10 μg/mL Blasticidin, 50 μg/mL Hygromycin). Selection was performed for 14 days for Hygromycin and Blasticidin with media changes every 24 h[83].

To generate sgRNA for transcriptional activation of Foxi1 in ferret cells, gBlocks were synthesized from IDT and included all components necessary for small guide (sg)RNA production, namely: T7 promoter, Foxi1 target specific sequence, guide RNA scaffold, MS2 binding loop and termination signal. gBlocks were PCR amplified and gel purified. PCR products were used as the template for in vitro transcription using MEGAshortscript T7 kit (Ambion). All sgRNAs were purified using MegaClear Kit (Ambion) and eluted in RNase-free water.

Foxi1 sgRNA was reverse transfected using Lipofectamine RNAiMAX Transfection Reagent (Life Science) into ferret basal cells that stably expresses dCas9-VP64 fusion protein and MS2-p65-HSF1 fusion protein. For the 0.33-cm$^2$ ALI inserts, (1 μg) sgRNA and Lipofectamine RNAiMAX was diluted in 50 μl of Opti-MEM. The solution was gently mixed, dispensed into insert and incubated for 20-30 min at room temperature. Next, 300,000 cells were suspended in 150 μl pneumacult-Ex plus medium and incubated for 24 h at 37° C. in a 5% $CO_2$ incubator.

Short circuit current measurements of CFTR-mediated chloride transport in ferret. Polarized ferret basal cells with activated Foxi1 expression as well as matched mock transfection controls (without DNA) were grown in ALI, and after three weeks short-circuit current ($I_{sc}$) measurements were performed as previously described[84]. The basolateral chamber was filled with high-chloride HEPES-buffered Ringer's solution (135 mM NaCl, 1.2 mM $CaCl_2$), 1.2 mM $MgCl_2$, 2.4 mM $KH_2PO_4$, 0.2 mM $K_2IPO_4$, 5 mM HEPES, pH 7.4). The apical chamber received a low-chloride HEPES-buffered Ringer's solution containing a 135-mM sodium gluconate substitution for NaCl. $I_{sc}$ was recorded using Acquire & Analyze software (Physiologic Instruments) after clamping the transepithelial voltage to zero. The following antagonists and agonists were sequentially added into the apical chamber: amiloride (100 μM) to block ENaC channels, apical DIDS (100 μM) to block calcium-activated chloride channels, forskolin (10 μM) and IBMX (100 μM) to activate CFTR, and GlyH101 (500 μM) to block CFTR.

Computational Methods

Pre-processing of 3' droplet-based scRNA-seq data. Demultiplexing, alignment to the mm10 transcriptome and UMI-collapsing were performed using the Cellranger toolkit (version 1.0.1, 10× Genomics). For each cell, Applicants quantified the number of genes for which at least one read was mapped, and then excluded all cells with fewer than 1,000 detected genes. Expression values $E_{i,j}$ for gene i in cell j were calculated by dividing UMI count values for gene i by the sum of the UMI counts in cell j, to normalize for differences in coverage, and then multiplying by 10,000 to create TPM-like values, and finally calculating $\log_2(\text{TPM}+1)$ values.

Selection of variable genes was performed by fitting a generalized linear model to the relationship between the squared co-efficient of variation (CV) and the mean expression level in log/log space, and selecting genes that significantly deviated (p<0.05) from the fitted curve, as previously described[85].

Both prior knowledge and this data show that different cell types have dramatically differing abundances in the trachea. For example, 3,845 of the 7,193 cells (53.5%) in the droplet-based dataset were eventually identified as basal cells, while only 26 were ionocytes (0.4%). This makes conventional batch correction difficult, as, due to random sampling effects, some batches may have very few (or even zero) of the rarest cells (FIG. 43b). To avoid this problem and simultaneously identify maximally discriminative genes, Applicants performed an initial round of clustering on the set of variable genes described above, and identified a set of 1,380 cell type-specific genes (FDR<0.01), with a minimum log 2 fold-change of 0.25. In addition, Applicants performed batch correction within each identified cluster, which contained only transcriptionally similar cells, ameliorating problems with differences in abundance. Batch correction was performed (only on these 1,380 genes) using ComBat[86] as implemented in the R package sva[87] using the default parametric adjustment mode. The output was a corrected expression matrix, which was used as input to further analysis.

Pre-processing of plate-based scRNA-seq data. BAM files were converted to merged, de-multiplexed FASTQs using the Illumina Bcl2Fastq software package v2.17.1.14. Paired-end reads were mapped to the UCSC mm10 mouse transcriptome using Bowtie[88] with parameters "-q --phred33-quals-n 1-e 99999999-1 25-I 1-X 2000-a -m 15-S -p 6", which allows alignment of sequences with one mismatch. Expression levels of genes were quantified as transcript-per-million (TPM) values by RSEM[89] v1.2.3 in paired-end mode. For each cell, Applicants determined the number of genes for which at least one read was mapped, and then excluded all cells with fewer than 2,000 detected genes. Applicants then identified highly variable genes as described above.

Dimensionality reduction by PCA and tSNE. Applicants restricted the expression matrix to the subsets of variable genes and high-quality cells noted above, and values were centered and scaled before input to PCA, which was implemented using the R function 'prcomp' from the 'stats' package for the plate-based dataset. For the droplet-based dataset, Applicants used a randomized approximation to PCA, implemented using the 'rpca' function from the 'rsvd' R package, with the parameter k set to 100. This low-rank approximation is several orders of magnitude faster to compute for very wide matrices. After PCA, significant PCs were identified using a permutation test as previously described[90], implemented using the 'permutationPA' function from the 'jackstraw' R package. Because of the presence of extremely rare cells in the droplet-based dataset (as described above), Applicants used scores from 10 significant PCs using scaled data, and 7 significant PCs using unscaled data. Only scores from these significant PCs were used as the input to further analysis.

For visualization purposes only (and not for clustering), dimensionality was further reduced using the Barnes-Hut approximate version of the t-distributed stochastic neighbor embedding (tSNE)[91,92]. This was implemented using the 'Rtsne' function from the 'Rtsne' R package using 20,000 iterations and a perplexity setting of 10 and 75 for plate- and droplet-based respectively. Scores from the first n PCs were used as the input to tSNE, where n was 11 and 12 for plate- and droplet-based data, respectively, determined using the permutation test described above.

Excluding immune, mesenchymal cells and suspected doublets. Although cells were sorted using EpCAM prior to scRNA-seq, 1,873 contaminating cells were observed in the initial droplet dataset, and were comprised of. 91 endothelial cells expressing Egfl7, Sh3g13 and Esam, 229 macrophages expressing MHCII (H2-Ab1, H2-Aa, Cd74), C1qa, and Cd68, and 1,553 fibroblasts expressing high levels of collagens (Col1a1, Col1a2, and Col3a1). Each of these cell populations was identified by an initial round of unsupervised clustering (density-based clustering of the tSNE map using 'dbscan'[55] from the R package 'fpc') as they formed extremely distinct clusters, and then removed. In the case of the Pulse-Seq dataset, the initial clustering step removed a total of 532 dendritic cells identified by high expression of Ptprc and Cd83. In addition, 20 other cells were outliers in terms of library complexity, which could possibly correspond to more than one individual cell per sequencing library, or 'doublets'. As a conservative precaution, Applicants removed these 20 possible doublet cells with over 3,700 genes detected per cell.

kNN-graph based clustering. To cluster single cells by their expression profiles, Applicants used unsupervised clustering, based on the Infomap community-detection algorithm[6], following approaches recently described for single-cell CyTOF data[93] and scRNA-seq[5]. Applicants constructed a k nearest-neighbor (k-NN) graph using, for each pair of cells, the Euclidean distance between the scores of significant PCs as the metric.

The number k of nearest neighbors was chosen in a manner roughly consistent with the size of the dataset, and set to 25 and 150 for plate- and droplet-based data respectively. For sub-clustering of rare cell subsets, Applicants used k=100, 50, 50 and 20 for tuft cells, neuroendocrine cells, ionocytes and goblet cells respectively. The k-NN graph was computed using the function 'nng' from the R package 'cccd' and was then used as the input to Infomap[6], implemented using the 'infomap.community' function from the 'igraph' R package.

Detected clusters were mapped to cell-types using known markers for tracheal epithelial subsets. In particular, because of the large proportion of basal and club cells, multiple clusters expressed high levels of markers for these two types. Accordingly, Applicants merged nine clusters expressing the basal gene score above a median $\log_2(\text{TPM}+1)$ >0, and seven clusters expressing the club gene score above median $\log_2(TPM+1) >1$. Calculation of a ciliated cell gene score showed only a single cluster with non-zero median expression, so no further merging was performed. This resulted in seven clusters, each corresponding 1 to 1 with a known airway epithelial cell type, with the exception of the ionocyte cluster, which Applicants show represents a novel subset.

Figure 50:
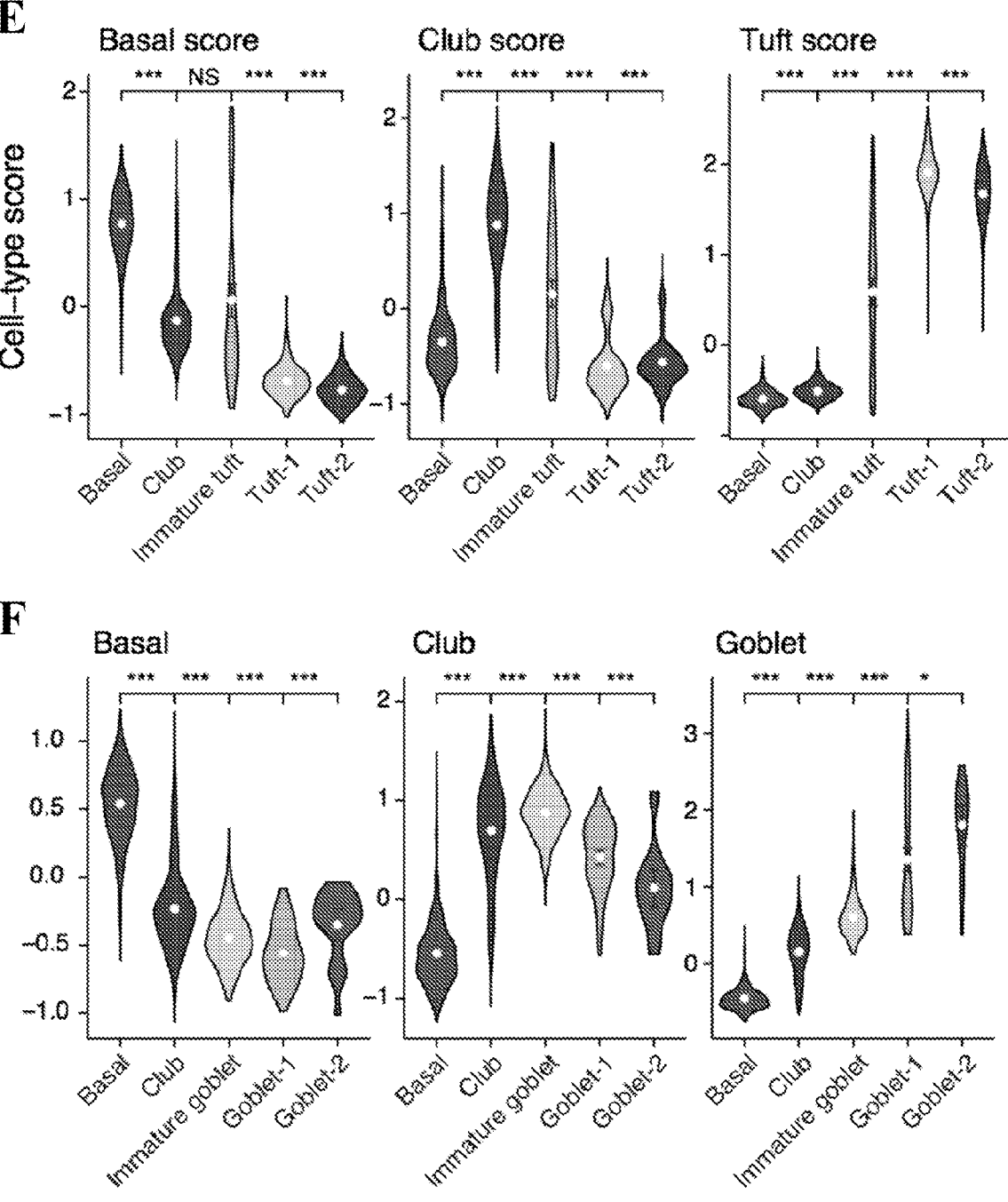
FIGS. 50A-I—Heterogeneity of rare tracheal epithelial cell types.
Figure 50:
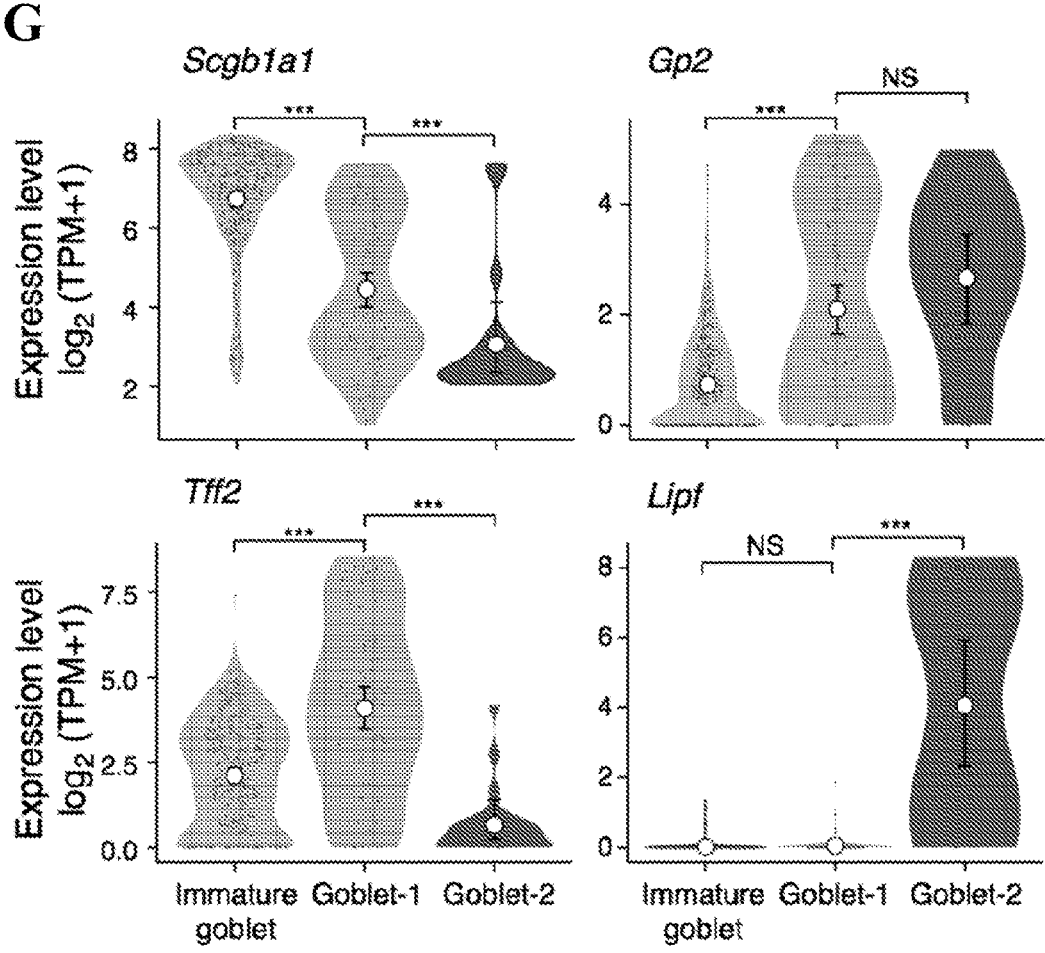
Figure 50:
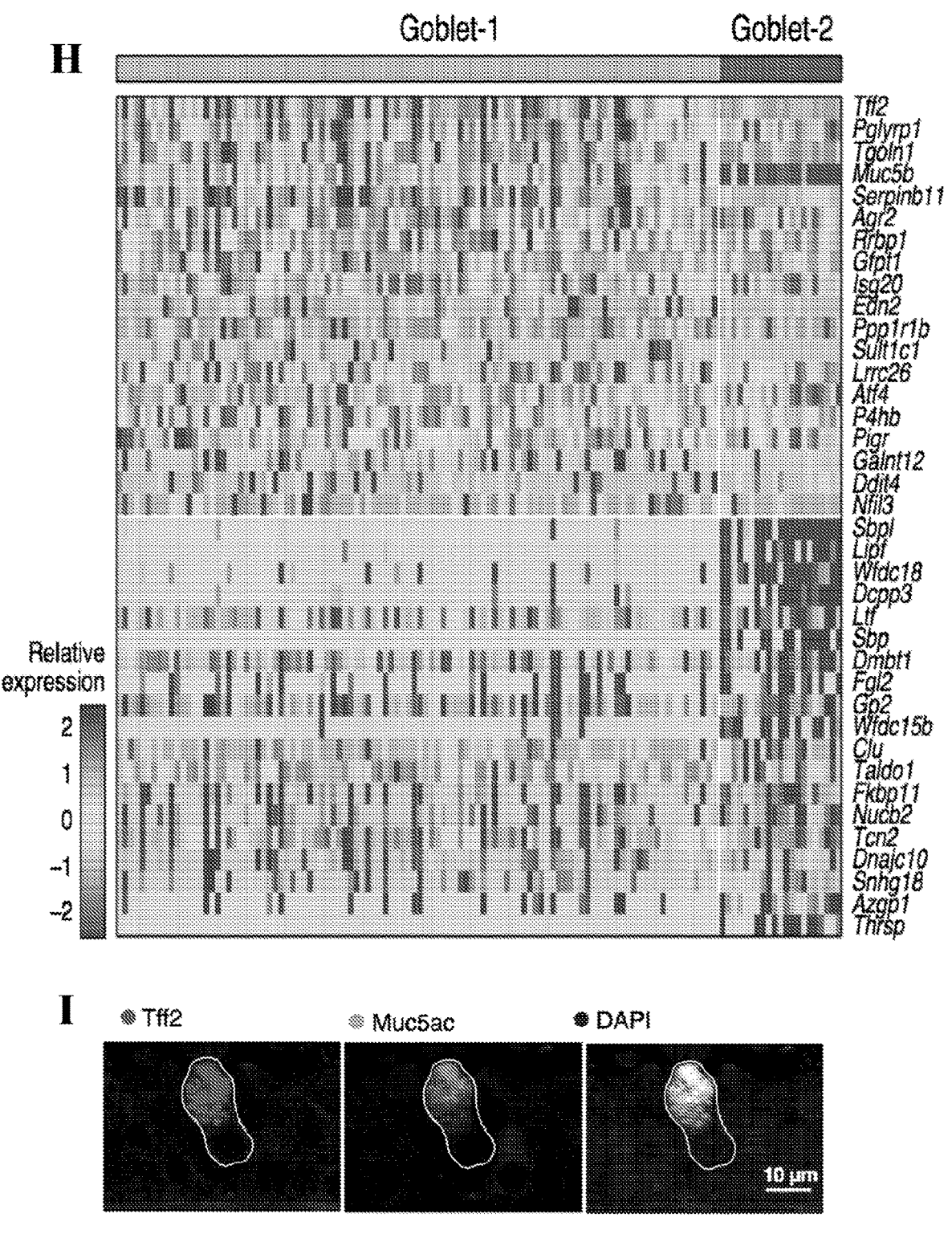
Figure 51:
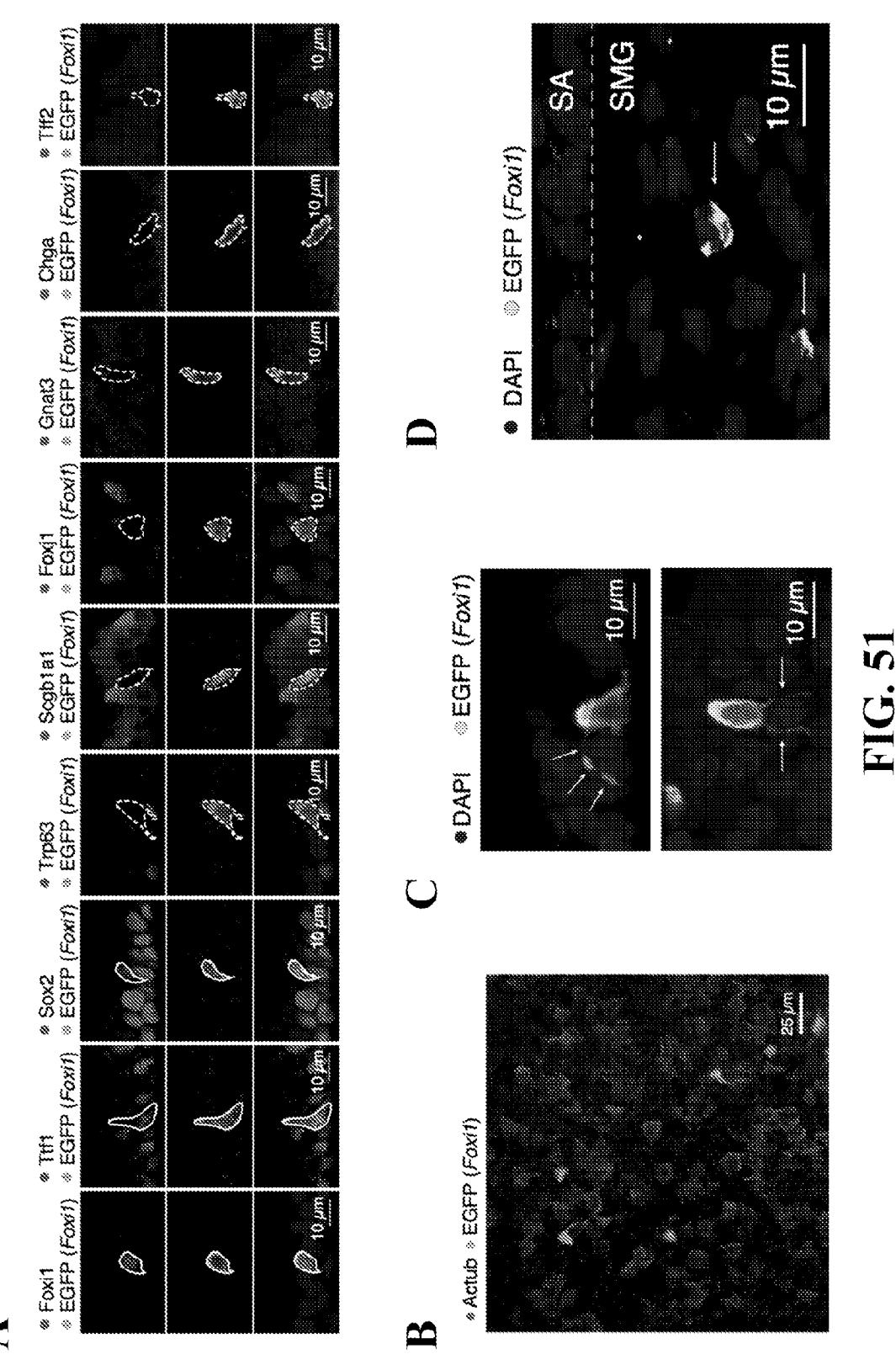
FIGS. 51A-H—Ionocyte characterization.
Figure 51:
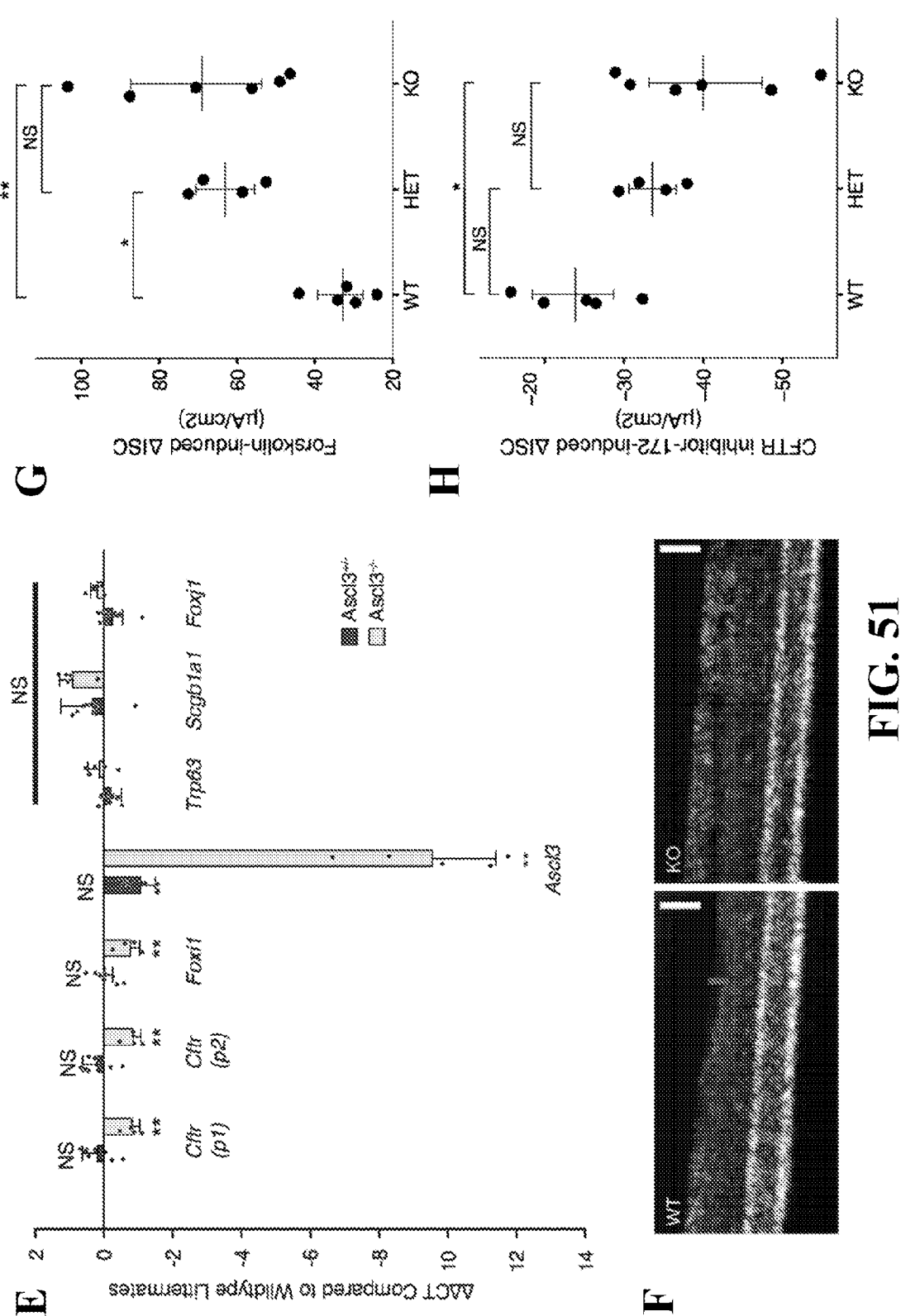

Rare cells (tuft, neuroendocrine, ionocyte and goblet) were sub-clustered to examine possible heterogeneity of mature types (FIG. 40 and FIG. 50). In each case, cells annotated as each type from the initial 3' droplet-based dataset (FIG. 37B and FIG. 43D) were combined with the corresponding cells from the Pulse-Seq dataset (FIG. 39B and FIG. 48A) before sub-clustering. In the case of goblet cells, sub-clustering the combined 468 goblet cells (k=20, above) partitioned the data into 7 groups, two of which expressed the novel goblet cell marker Gp2 (FIG. 37D) at high levels (median $\log_2(TPM+1) >1$). These two groups were annotated as mature goblet-1 and goblet-2 cells (FIG. 50F-J), while the five groups were merged and annotated as immature goblet cells.

Differential expression and cell-type signatures. To identify maximally specific genes for cell-types, Applicants performed differential expression tests between each pair of clusters for all possible pairwise comparisons. Then, for a given cluster, putative signature genes were filtered using the maximum FDR Q-value and ranked by the minimum log 2 fold-change (across the comparisons). This is a stringent criterion because the minimum fold-change and maximum Q-value represent the weakest effect-size across all pairwise comparisons. Cell-type signature genes for the initial droplet based scRNA-seq data (FIG. 37C) were obtained using a maximum FDR of 0.05 and a minimum log 2 fold-change of 0.5.

Where less cells were available, as is the case of full-length plate-based scRNA-seq data (FIG. 45B) or for sub-types within cell-types (FIG. 39C, FIG. 50C), a combined p-value across the pairwise tests for enrichment was computed using Fisher's method (a more lenient criterion) and a maximum FDR Q-value of 0.001 was used, along with a cutoff of minimum log 2 fold-change of 0.1 for tuft and goblet cell subsets (FIG. 39C, FIG. 50C). Larger clusters (basal, club, ciliated cells) were down-sampled to 1,000 cells for the pairwise comparisons. Marker genes were ranked by minimum log 2 fold-change. Differential expression tests were carried using a two part 'hurdle' model to control for both technical quality and mouse-to-mouse variation. This was implemented using the R package MAST[64], and p-values for differential expression were computed using the likelihood-ratio test. Multiple hypothesis testing correction was performed by controlling the false discovery rate[65] using the R function 'p.adjust'.

Assigning cell-type specific TFs, GPCRs and genes associated with asthma. A list of all genes annotated as transcription factors in mice was obtained from AnimalTFDB[94], downloaded from:

bioguo.org/AnimalTFDB/
BrowseAllTF.php?spe=Mus_musculus.

The set of G-protein coupled receptors (GPCRs) was obtained from the UniProt database, downloaded from:

uniprot.org/uniprot/?query=family %3A %22 g+protein+
coupled+receptor %22+AN D+organism %3A
%22Mouse+%5B10090%5D %22+AND+reviewed
%3Ayes&sort=score. To map from human to mouse gene names, human and mouse orthologs were downloaded from Ensembl latest release 86 at:

ensembl.org/biomart/martview, and human and mouse gene synonyms from: NCBI (ftp.ncbi.nlm.nih.gov/gene/DATA/GENE_INFO/Mammalia/).

Cell-type enriched TFs and GPCRs were then identified by intersecting the list of genes enriched in to each cell type with the lists of TFs and GPCRs defined above. Cell-type enriched TFs (FIG. 37E) and GPCRs (FIG. 50A) were defined using the 3' droplet-based and full-length plate-based datasets, respectively, as those with a minimum log 2 fold-change of 0.1 and a maximum FDR of 0.001, retaining a maximum of 10 genes per cell type in FIG. 37E.

Gene set or pathway enrichment analysis. GO analysis of enriched pathways in $Krt13^+$ hillocks (FIG. 45D) was performed using the 'goseq' R package[95], using significantly differentially expressed genes (FDR<0.05) as target genes, and all genes expressed with $\log_2(TPM+1) >3$ in at least 10 cells as background. For pathway and gene sets, Applicants used a version of MSigDB[78] with mouse orthologs, downloaded from: bioinfwehi.edu.au/software/MSigDB/. Association of principal components with cell-types (FIG. 49A, B) was computed using the Gene Set Enrichment Analysis (GSEA) algorithm[95] implemented using the 'fgsea' package in R. Genes that are involved in leukotriene biosynthesis and taste transduction pathways (FIG. 40F and FIG. 50B) were identified using KEGG and GO pathways. Specifically, genes in KEGG pathway 00590 (arachidonic acid metabolism) or GO terms 0019370 (leukotriene biosynthetic process) or 0061737 (leukotriene signaling pathway) were annotated as leukotriene synthesis-associated, while genes in KEGG pathway 04742 (taste transduction) were annotated as taste transduction-associated.

Statistical analysis of proximodistal mucous metaplasia. For the analysis in FIG. 38H,I, the extent of goblet cell hyperplasia was assessed using counts of $Muc5ac^+$ goblet cells, normalized to counts of $GFP^+$ ciliated cells. To quantify differences in the count values between the samples in different conditions (n=6, Foxj 1-GFP mice), Applicants fit a negative binomial regression using the 'glm.nb' function from the 'MASS' package in R. Pairwise comparisons between means for each condition were computed using post hoc tests and p-values were adjusted for multiple comparisons using Tukey's HSD, implemented using the function 'pairs' from the 'emeans' package in R.

Lineage inference using diffusion maps. Applicants restricted the analysis to the 6,848 cells in basal, club or ciliated cell clusters (95.2% of the 7,193 cells in the initial droplet dataset), since it was unlikely that rare cells (e.g., NE, tuft, goblet, and ionocyte cells) in transitional states will be sufficiently densely sampled. Next, Applicants selected highly variable genes among these three cell subsets as described above, and performed dimensionality reduction using the diffusion map approach[96]. Briefly, a cell-cell transition matrix was computed using the Gaussian kernel where the kernel width was adjusted to the local neighborhood of each cell, following the approach of Haghverdi et al.[97]. This matrix was converted to a Markovian matrix after normalization. The right eigenvectors $v_i(i=0, 1, 2, 3, \ldots)$ of this matrix were computed and sorted in the order of decreasing eigenvalues $\lambda_i(i=0, 1, 2, 3, \ldots)$, after excluding the top eigenvector $v_0$, corresponding to $\lambda_0=1$ (which reflects the normalization constraint of the Markovian matrix). The remaining eigenvectors $v_i(i=1, 2 \ldots)$ define the diffusion map embedding and are referred to as diffusion components ($DC_k(k=1, 2, \ldots)$). Applicants noticed a spectral gap between the $\lambda_3$ and the $\lambda_4$, and hence retained $DC_1$-$DC_3$ for further analysis.

To extract the edges of this manifold, along which cells transition between states (FIG. 38A), Applicants fit a convex hull using the 'convhulln' from the 'geometry' R package. To identify edge-associated cells, any cell within d<0.1 of an edge of the convex hull (where d is the Euclidean distance in diffusion-space) is assigned to that edge.

To identify cells associated with the Krt4+Krt13+ population, Applicants used unsupervised Partitioning Around Medoids (PAM) clustering of the cells in diffusion space with the parameter k=4. Edge-association of genes (or TFs) was computed as the autocorrelation (lag=25), implemented using the 'acf' function from the 'stats' R package. Empirical p-values for each edge-associated gene were assessed using a permutation test (1,000 bootstrap iterations), using the autocorrelation value as the test statistic.

Genes were placed in pseudotemporal order by splitting the interval into 30 bins from 'early' to 'late', and assigning each gene the bin with the highest mean expression. These data were smoothed using loess regression and then visualized as heatmaps (FIG. 47).

Pulse-Seq data analysis. For the much larger Pulse-Seq dataset (~66,700 cells), Applicants used a very similar, but more scalable, analysis pipeline, with the following modifications. Alignment and UMI collapsing was performing using the Cellranger toolkit (version 1.3.1, 10× Genomics). $Log_2(TPM+1)$ expression values were computed using Rcpp-based function in the R package 'Seurat' (v2.2). Applicants also used an improved method of identifying variable genes. Rather than fitting the mean-$CV^2$ relationship, a logistic regression was fit to the cellular detection fraction (often referred to as α), using the total number of UMIs per cell as a predictor. Outliers from this curve are genes that are expressed in a lower fraction of cells than would be expected given the total number of UMIs mapping to that gene, i.e., cell-type or state specific genes. Applicants used a threshold of deviance<−0.25, producing a set of 708 variable genes. Applicants restricted the expression matrix to this subset of variable genes and values were centered and scaled—while 'regressing out'[98] technical factors (number of genes detected per cell, number of UMIs detected per cell and cell-cycle score) using the 'ScaleData' function before input to PCA, implemented using 'RunPCA' in Seurat. After PCA, significant PCs were identified using the knee in the scree plot, which identified 10 significant PCs. Only scores from these significant PCs were used as the input to nearest-neighbor based clustering and tSNE, implemented using the 'FindClusters' (resolution parameter r=1) and 'RunTSNE' (perplexity p=25) methods respectively from the 'Seurat' package.

Once again due to their abundance, the populous basal, club and ciliated cells were spread across several clusters, which were merged using the strategy described above: 19 clusters expressing the basal score above mean $log_2(TPM+1)$>0, 12 expressing the club score above mean $log_2(TPM+1)$ >−0.1, and 2 clusters expressing the ciliated signature above were merged to construct the basal, club and ciliated subsets, respectively. Goblet cells were not immediately associated with a specific cluster, however, cluster 13 (one of those merged into the club cluster) expressed significantly elevated levels of goblet markers Tff2 and Gp2 (p<10^{-10}, likelihood-ratio test). Sub-clustering this population (resolution parameter r=1) revealed 6 clusters, of which two expressed the goblet score constructed using the top 25 goblet cell marker genes above mean $log_2(TPM+1)$ >1, which were merged and annotated as goblet cells. To identify the Krt4+/Krt13+ hillock-associated club cells, the remaining 17,700 club cells were re-clustered (resolution parameter r=0.2) into 5 clusters, of which one expressed much higher levels (p<10^{-10} in all cases) of Krt4, Krt13 and a hillock score constructed using the top 25 hillock marker genes, this cluster was annotated as 'hillock-associated club cells'.

Figure 39:
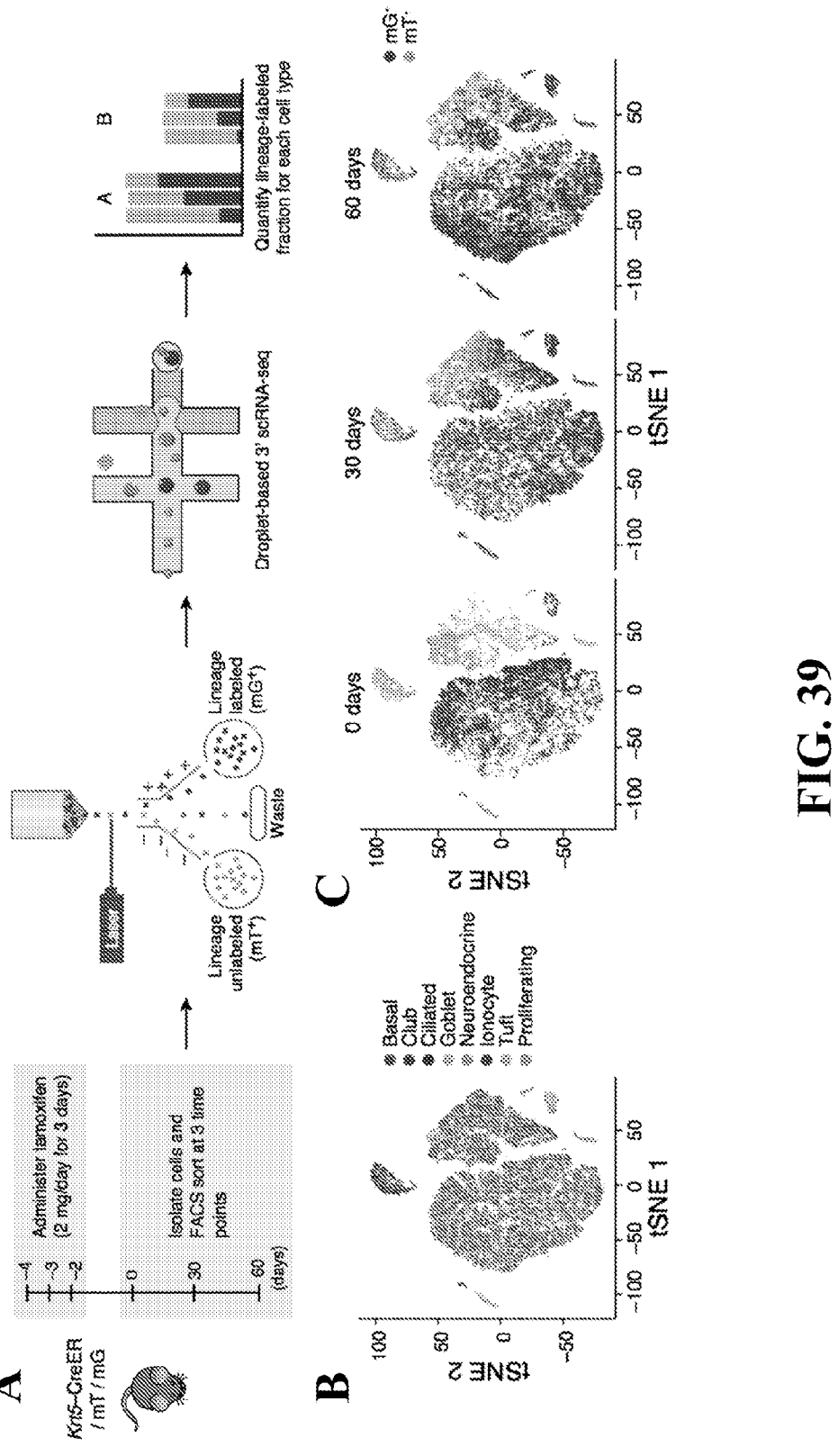
FIGS. 39A-G—Pulse-Seq reveals novel lineage paths and records cell dynamics with single-cell resolution.
Figure 48:
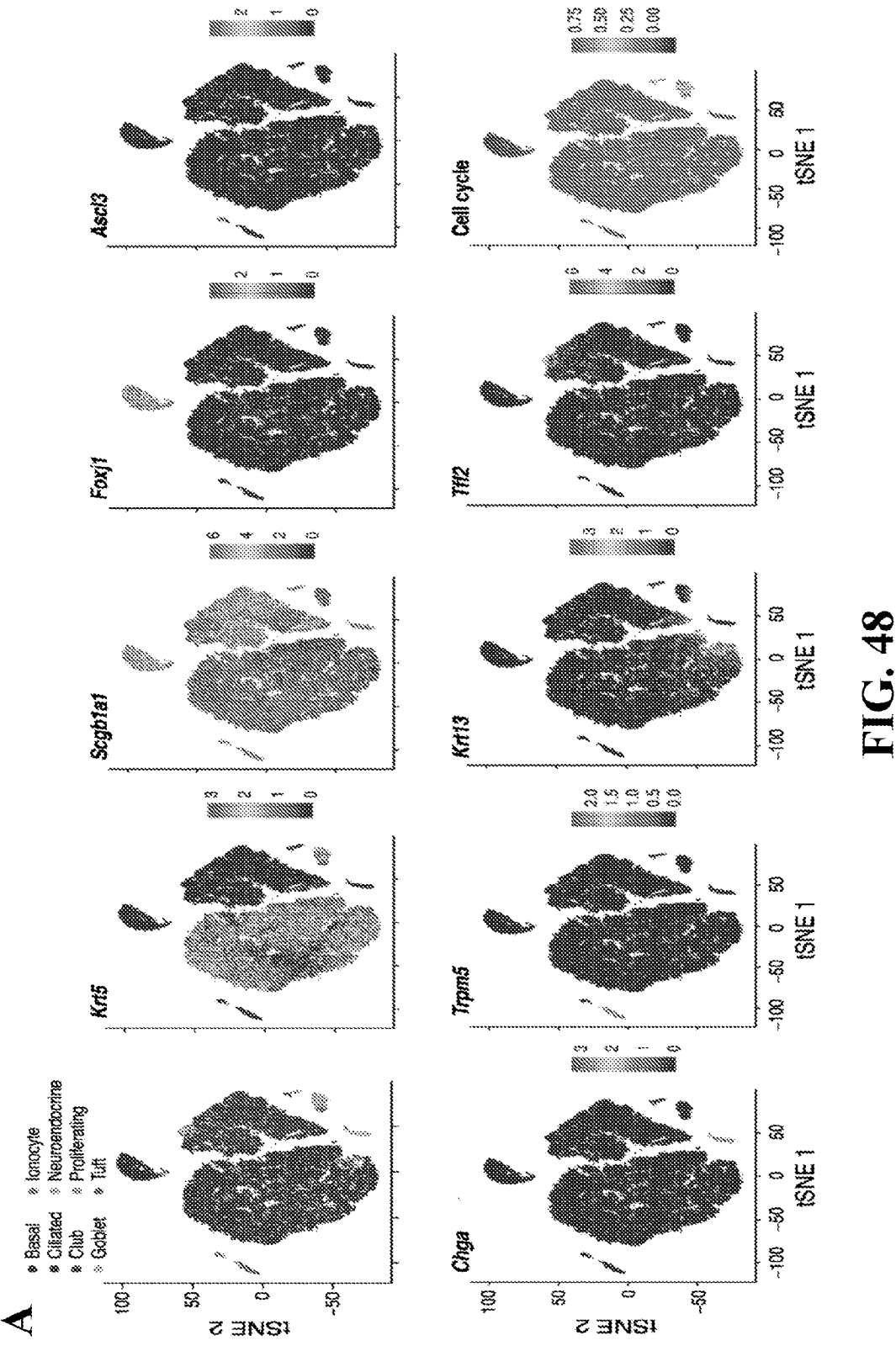
FIGS. 48A-F—Lineage tracing using Pulse-Seq.
Figure 48:
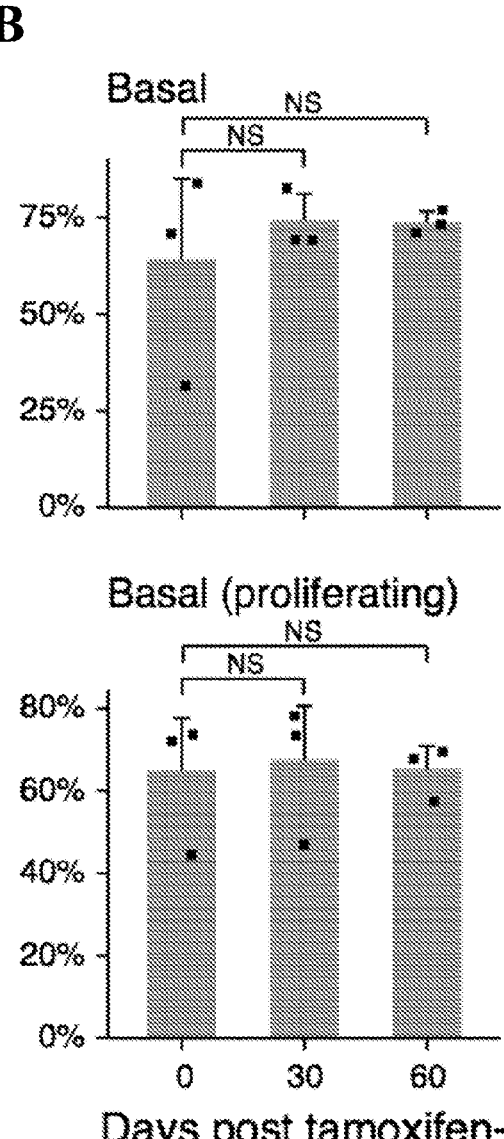
Figure 48:
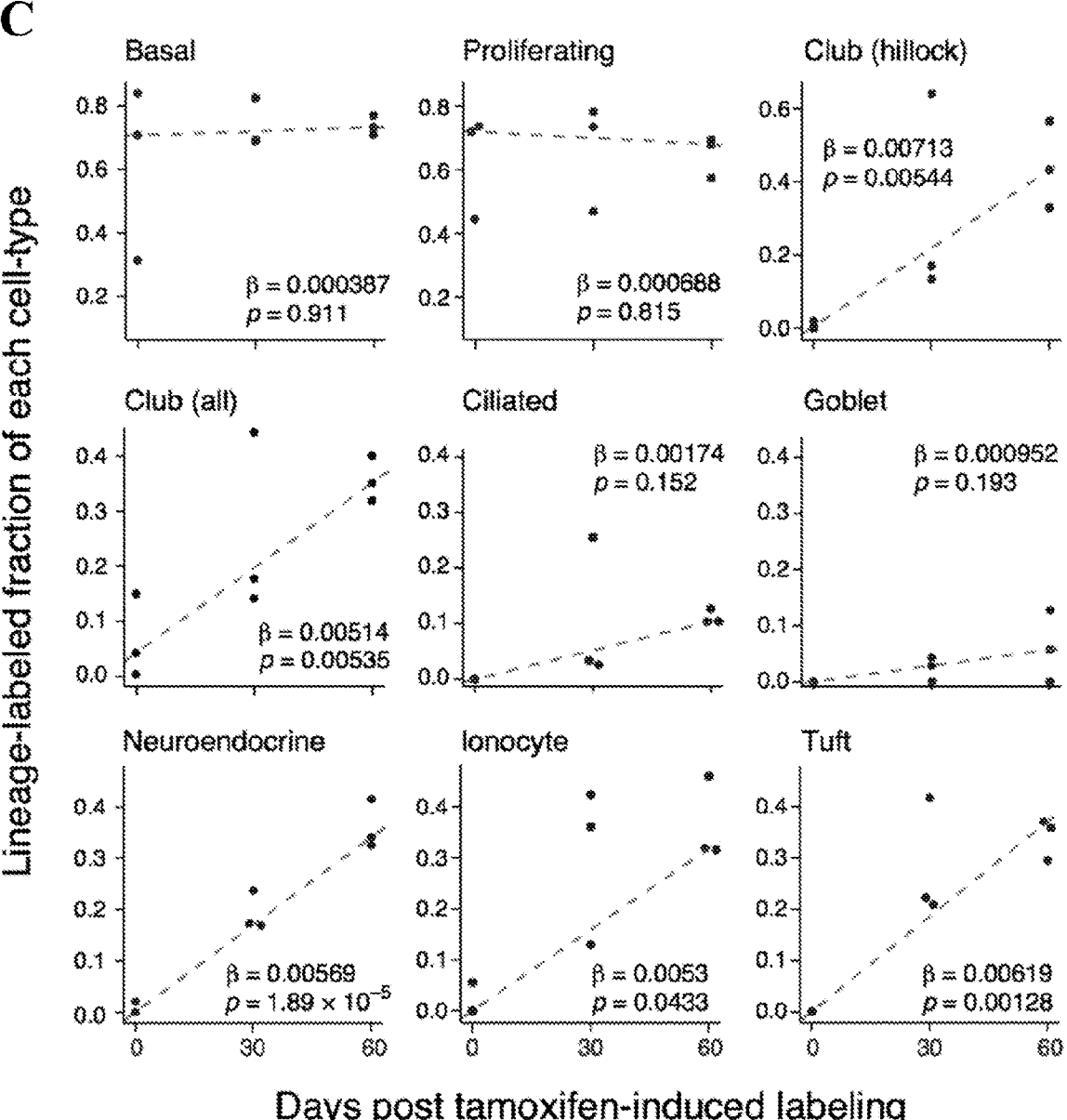

Estimating lineage-labeled fraction for Pulse-Seq and conventional lineage tracing. For any given sample (here, mouse) the certainty in the estimate of the proportion of labeled cells increases with the number of cells obtained; the more cells, the higher the precision of the estimate. Estimating the overall fraction of labeled cells (from conventional lineage tracing; FIG. 39F, FIG. 46 and FIG. 48, or Pulse-seq lineage tracing FIG. 39 and FIG. 48) based on the individual estimates from each mouse is analogous to performing a meta-analysis of several studies, each of which measures a population proportion; studies with greater power (higher n) carry more information, and should influence the overall estimate more, while low n studies provide less information and should not have as much influence. Generalized linear mixed models (GLMM) provide a framework to obtain an overall estimate in this manner[99]. Accordingly, Applicants implemented a fixed effects logistic regression model to compute the overall estimate and 95% confidence interval using the function 'metaprop' from the R package 'meta'[100].

Testing for difference in labeled fraction for Pulse-Seq and conventional lineage tracing. To assess the significance of changes in the labeled fraction of cells in different conditions, Applicants used a negative binomial regression model of the counts of cells at each time-point, controlling for variability amongst biological (mouse) replicates. For each cell-type, Applicants model the number of lineage-labeled cells detected in each analyzed mouse as a random count variable using a negative binomial distribution. The frequency of detection is modeled by using the natural log of the total number of cells of that type profiled in a given mouse as an offset. The time-point of each mouse (0, 30 or 60 days post tamoxifen) is provided as a covariate. The negative binomial model was fit using the R command 'glm.nb' from the 'MASS' package. The p-value for the significance of the change in labeled fraction size between time-points was assessed using a likelihood-ratio test, computing using the R function 'anova'.

Estimating turnover rate using quantile regression. Given the relatively few samples (n=9 mice) with which to model the rate of new lineage-labeled cells, Applicants used the more robust quantile regression[101], which models the conditional median (rather than the conditional mean, as captured by least-squares linear regression, which can be sensitive to outliers). The fraction of labeled cells in each mouse was modeled as a function of days post tamoxifen (FIG. 48C) using the function 'rq' from the R package 'quantReg'. Significance of association between increasing labeled fraction and time were computing using Wald tests implemented with the 'summary.rq' function, while tests comparing the slopes of fits were conducted using 'anova.rq'.

Statistical analysis of qRT-PCR data. ΔΔCT values were generated by normalization to the average of loading controls Hprt and Ubc, followed by comparison to wild type samples. Statistical analysis was performed at the ΔCT stage. For single comparisons, all datasets passed the Shapiro-Wilk normality test, which was followed by apost-hoc two-tailed t-test. For multiple comparisons, all datasets passed the Shapiro-Wilk normality test for equal variance. Data was then tested by two-way ANOVA, with sex as the second level of variance. In a few certain cases, sex trended towards significance, however, not enough to justify separate analysis. Post hoc multiple comparisons to the control group were performed using Dunn's Method. In the single case of Foxi1 KO (FIG. 41E), two heterozygous samples were identified as outliers and removed using a standard implementation of DBscan clustering using the full dataset of all genes assayed using qRT-PCR. These two samples exhibited gene expression closer to full Foxi1 knockouts and were removed from consideration. In all cases, error bars represent the calculated 95% CI, and *p<0.05, p<0.01, *p<0.001.

Data Availability. All data is deposited in GEO (GSE103354) and in the Single Cell Portal (portals.broadinstitute.org/single_cell/study/trachea-epithelium).

REFERENCES FOR EXAMPLE 13

1. Rock, J. R. et al. Basal cells as stem cells of the mouse trachea and human airway epithelium. *Proc. Natl. Acad. Sci. U.S.A* 106, 12771-12775 (2009).
2. Nunn's Applied Respiratory Physiology—8th Edition. Available at: elsevier.com/books/nunns-applied-respiratory-physiology/lumb/978-0-7020-6295-7. (Accessed: 5th April 2018).
3. Ardini-Poleske, M. E. et al. LungMAP: The Molecular Atlas of Lung Development Program. *Am. J. Physiol. Lung Cell. Mol. Physiol.* 313, L733-L740 (2017).
4. Treutlein, B. et al. Reconstructing lineage hierarchies of the distal lung epithelium using single-cell RNA-seq. *Nature* 509, 371-375 (2014).
5. Shekhar, K. et al. Comprehensive Classification of Retinal Bipolar Neurons by Single-Cell Transcriptomics. *Cell* 166, 1308-1323.e30 (2016).
6. Rosvall, M. & Bergstrom, C. T. Maps of random walks on complex networks reveal community structure. *Proc. Natl. Acad. Sci. U.S.A* 105, 1118-1123 (2008).
7. Picelli, S. et al. Full-length RNA-seq from single cells using Smart-seq2. *Nat. Protoc.* 9, 171-181 (2014).
8. Ghaleb, A. M. et al. *Kruppel-like factors* 4 *and* 5: the yin and yang regulators of cellular proliferation. *Cell Res.* 15, 92-96 (2005).
9. Pardo-Saganta, A. et al. Parent stem cells can serve as niches for their daughter cells. *Nature* 523, 597-601 (2015).
10. Sriuranpong, V. et al. Notch signaling induces rapid degradation of achaete-scute homolog 1. *Mol. Cell. Biol.* 22, 3129-3139 (2002).
11. Moriyama, M. et al. Multiple roles of Notch signaling in the regulation of epidermal development. *Dev. Cell* 14, 594-604 (2008).
12. Gerbe, F. et al. Intestinal epithelial tuft cells initiate type 2 mucosal immunity to helminth parasites. *Nature* 529, 226-230 (2016).
13. Quigley, I. K., Stubbs, J. L. & Kintner, C. Specification of ion transport cells in the *Xenopus* larval skin. *Dev. Camb. Engl.* 138, 705-714 (2011).
14. Verzi, M. P., Khan, A. H., Ito, S. & Shivdasani, R. A. Transcription factor foxq1 controls mucin gene expression and granule content in mouse stomach surface mucous cells. *Gastroenterology* 135, 591-600 (2008).
15. Li, M. J. et al. GWASdb v2: an update database for human genetic variants identified by genome-wide association studies. *Nucleic Acids Res.* 44, D869-876 (2016).
16. Bonnelykke, K. et al. A genome-wide association study identifies CDHR3 as a susceptibility locus for early childhood asthma with severe exacerbations. *Nat. Genet.* 46, 51-55 (2014).

17. Bochkov, Y. A. et al. Cadherin-related family member 3, a childhood asthma susceptibility gene product, mediates rhinovirus C binding and replication. *Proc. Natl. Acad. Sci. U.S.A* 112, 5485-5490 (2015).
18. Bansal, G., Xie, Z., Rao, S., Nocka, K. H. & Druey, K. M. Suppression of immunoglobulin E-mediated allergic responses by regulator of G protein signaling 13. *Nat. Immunol.* 9, 73-80 (2008).
19. Von Moltke, J., Ji, M., Liang, H.-E. & Locksley, R. M. Tuft-cell-derived IL-25 regulates an intestinal ILC2-epithelial response circuit. *Nature* 529, 221-225 (2016).
20. Howitt, M. R. et al. Tuft cells, taste-chemosensory cells, orchestrate parasite type 2 immunity in the gut. *Science* 351, 1329-1333 (2016).
21. Warburton, D. et al. The molecular basis of lung morphogenesis. *Mech. Dev.* 92, 55-81 (2000).
22. Danahay, H. et al. Notch2 is required for inflammatory cytokine-driven goblet cell metaplasia in the lung. *Cell Rep.* 10, 239-252 (2015).
23. Roy, M. G. et al. Muc5b is required for airway defence. *Nature* 505, 412-416 (2014).
24. Chen, Y., Zhao, Y. H. & Wu, R. In silico cloning of mouse Muc5b gene and upregulation of its expression in mouse asthma model. *Am. J. Respir. Crit. Care Med.* 164, 1059-1066 (2001).
25. Munitz, A., Brandt, E. B., Mingler, M., Finkelman, F. D. & Rothenberg, M. E. Distinct roles for IL-13 and IL-4 via IL-13 receptor alpha1 and the type II IL-4 receptor in asthma pathogenesis. *Proc. Natl. Acad. Sci. U.S.A* 105, 7240-7245 (2008).
26. Trapnell, C. et al. The dynamics and regulators of cell fate decisions are revealed by pseudotemporal ordering of single cells. *Nat. Biotechnol.* 32, 381-386 (2014).
27. Bendall, S. C. et al. Single-cell trajectory detection uncovers progression and regulatory coordination in human B cell development. *Cell* 157, 714-725 (2014).
28. Watson, J. K. et al. Clonal Dynamics Reveal Two Distinct Populations of Basal Cells in Slow-Turnover Airway Epithelium. *Cell Rep.* 12, 90-101 (2015).
29. Tata, P. R. et al. Dedifferentiation of committed epithelial cells into stem cells in vivo. *Nature* 503, 218-223 (2013).
30. Chan, I. The role of extracellular matrix protein 1 in human skin. *Clin. Exp. Dermatol.* 29, 52-56 (2004).
31. Sakaguchi, M. & Huh, N. S100A11, a dual growth regulator of epidermal keratinocytes. *Amino Acids* 41, 797-807 (2011).
32. Troy, T.-C., Arabzadeh, A., Yerlikaya, S. & Turksen, K. Claudin immunolocalization in neonatal mouse epithelial tissues. *Cell Tissue Res.* 330, 381-388 (2007).
33. D'Acquisto, F. et al. Annexin-1 modulates T-cell activation and differentiation. *Blood* 109, 1095-1102 (2007).
34. Ng, F. S. P. et al. Annexin-1-deficient mice exhibit spontaneous airway hyperresponsiveness and exacerbated allergen-specific antibody responses in a mouse model of asthma. *Clin. Exp. Allergy J. Br. Soc. Allergy Clin. Immunol.* 41, 1793-1803 (2011).
35. Zuberi, R. I. et al. Critical role for galectin-3 in airway inflammation and bronchial hyperresponsiveness in a murine model of asthma. *Am. J. Pathol.* 165, 2045-2053 (2004).
36. Rawlins, E. L. et al. The role of Scgb1a1+ Clara cells in the long-term maintenance and repair of lung airway, but not alveolar, epithelium. *Cell Stem Cell* 4, 525-534 (2009).

37. Saunders, C. J., Reynolds, S. D. & Finger, T. E. Chemosensory brush cells of the trachea. A stable population in a dynamic epithelium. *Am. J Respir. Cell Mol. Biol.* 49, 190-196 (2013).

38. Heitzmann, D. et al. The in vivo respiratory phenotype of the adenosine A1 receptor knockout mouse. *Respir. Physiol. Neurobiol.* 222, 16-28 (2016).

39. Davies, B. et al. Targeted deletion of the epididymal receptor HE6 results in fluid dysregulation and male infertility. *Mol. Cell. Biol.* 24, 8642-8648 (2004).

40. LopezJimenez, N. D. et al. Two novel genes, Gpr113, which encodes a family 2 G-protein-coupled receptor, and Trcg1, are selectively expressed in taste receptor cells. *Genomics* 85, 472-482 (2005).

41. Shindo, Y. et al. FXYD6, a Na, K-ATPase regulator, is expressed in type II taste cells. *Biosci. Biotechnol. Biochem.* 75, 1061-1066 (2011).

42. Adappa, N. D. et al. Genetics of the taste receptor T2R38 correlates with chronic rhinosinusitis necessitating surgical intervention. *Int. Forum Allergy Rhinol.* 3, 184-187 (2013).

43. Lee, R. J. et al. T2R38 taste receptor polymorphisms underlie susceptibility to upper respiratory infection. *J. Clin. Invest.* 122, 4145-4159 (2012).

44. Yoon, S.-Y. et al. Association between Polymorphisms in Bitter Taste Receptor Genes and Clinical Features in Korean Asthmatics. *Respir. Int. Rev. Thorac. Dis.* 91, 141-150 (2016).

45. Krasteva, G. et al. Cholinergic chemosensory cells in the trachea regulate breathing. *Proc. Natl. Acad. Sci. U.S.A* 108, 9478-9483 (2011).

46. Krasteva, G., Canning, B. J., Papadakis, T. & Kummer, W. Cholinergic brush cells in the trachea mediate respiratory responses to quorum sensing molecules. *Life Sci.* 91, 992-996 (2012).

47. Jakobsson, P. J., Mancini, J. A., Riendeau, D. & Ford-Hutchinson, A. W. Identification and characterization of a novel microsomal enzyme with glutathione-dependent transferase and peroxidase activities. *J. Biol. Chem.* 272, 22934-22939 (1997).

48. Dixon, R. A. et al. Requirement of a 5-lipoxygenase-activating protein for leukotriene synthesis. *Nature* 343, 282-284 (1990).

49. Hase, K. et al. Uptake through glycoprotein 2 of FimH (+) bacteria by M cells initiates mucosal immune response. *Nature* 462, 226-230 (2009).

50. Miklavc, P., Thompson, K. E. & Frick, M. A new role for P2x4 receptors as modulators of lung surfactant secretion. *Front. Cell. Neurosci.* 7, 171 (2013).

51. Zech, A. et al. P2rx4 deficiency in mice alleviates allergen-induced airway inflammation. *Oncotarget* 7, 80288-80297 (2016).

52. Burnstock, G. & Kennedy, C. P2X receptors in health and disease. *Adv. Pharmacol. San Diego Calif* 61, 333-372 (2011).

53. Mullins, J. J. et al. Identification of a human ortholog of the mouse Dcpp gene locus, encoding a novel member of the CSP-1/Dcpp salivary protein family. *Physiol. Genomics* 28, 129-140 (2006).

54. Bergstrom, J. H. et al. Gram-positive bacteria are held at a distance in the colon mucus by the lectin-like protein ZG16. *Proc. Natl. Acad. Sci. U.S.A* 113, 13833-13838 (2016).

55. Gong, S. et al. A gene expression atlas of the central nervous system based on bacterial artificial chromosomes. *Nature* 425, 917-925 (2003).

56. Esaki, M. et al. Mechanism of development of ionocytes rich in vacuolar-type H(+)-ATPase in the skin of zebrafish larvae. *Dev. Biol.* 329, 116-129 (2009).

57. Vidarsson, H. et al. The forkhead transcription factor Foxi1 is a master regulator of vacuolar H-ATPase proton pump subunits in the inner ear, kidney and epididymis. *PloS One* 4, e4471 (2009).

58. Overdier, D. G., Ye, H., Peterson, R. S., Clevidence, D. E. & Costa, R. H. The winged helix transcriptional activator HFH-3 is expressed in the distal tubules of embryonic and adult mouse kidney. *J. Biol. Chem.* 272, 13725-13730 (1997).

59. Jonz, M. G. & Nurse, C. A. Epithelial mitochondria-rich cells and associated innervation in adult and developing zebrafish. *J. Comp. Neurol.* 497, 817-832 (2006).

60. Hoegger, M. J. et al. Impaired mucus detachment disrupts mucociliary transport in a piglet model of cystic fibrosis. *Science* 345, 818-822 (2014).

61. Engelhardt, J. F. et al. Submucosal glands are the predominant site of CFTR expression in the human bronchus. *Nat. Genet.* 2, 240-248 (1992).

62. Py, B. F. et al. Cochlin produced by follicular dendritic cells promotes antibacterial innate immunity. *Immunity* 38, 1063-1072 (2013).

63. Blomqvist, S. R., Vidarsson, H., Soder, O. & Enerback, S. Epididymal expression of the forkhead transcription factor Foxi1 is required for male fertility. *EMBO J.* 25, 4131-4141 (2006).

64. Birket, S. E. et al. *A functional anatomic defect of the cystic fibrosis airway.* Am. J. Respir. Crit. Care Med. 190, 421-432 (2014).

65. Birket, S. E. et al. Development of an airway mucus defect in the cystic fibrosis rat. *JCI Insight* 3, (2018).

66. Liu, L. et al. Method for quantitative study of airway functional microanatomy using micro-optical coherence tomography. *PloS One* 8, e54473 (2013).

67. Tang, X. X. et al. Acidic pH increases airway surface liquid viscosity in cystic fibrosis. *J Clin. Invest.* 126, 879-891 (2016).

68. Birket, S. E. et al. Combination therapy with cystic fibrosis transmembrane conductance regulator modulators augment the airway functional microanatomy. *Am. J Physiol. Lung Cell. Mol. Physiol.* 310, L928-939 (2016).

69. Liu, L. et al. An autoregulatory mechanism governing mucociliary transport is sensitive to mucus load. *Am. J Respir. Cell Mol. Biol.* 51, 485-493 (2014).

70. Shah, V. S. et al. Airway acidification initiates host defense abnormalities in cystic fibrosis mice. *Science* 351, 503-507 (2016).

71. Tarran, R. et al. Regulation of murine airway surface liquid volume by CFTR and Ca2+-activated Cl— conductances. *J. Gen. Physiol.* 120, 407-418 (2002).

72. Mou, H. et al. Dual SMAD Signaling Inhibition Enables Long-Term Expansion of Diverse Epithelial Basal Cells. *Cell Stem Cell* 19, 217-231 (2016).

73. Grubb, B. R., Paradiso, A. M. & Boucher, R. C. Anomalies in ion transport in CF mouse tracheal epithelium. *Am. J. Physiol.* 267, C293-300 (1994).

74. Sun, X. et al. Lung phenotype of juvenile and adult cystic fibrosis transmembrane conductance regulator-knockout ferrets. *Am. J. Respir. Cell Mol. Biol.* 50, 502-512 (2014).

75. Sun, X. et al. Disease phenotype of a ferret CFTR-knockout model of cystic fibrosis. *J. Clin. Invest.* 120, 3149-3160 (2010).

76. Haber, A. L. et al. A single-cell survey of the small intestinal epithelium. *Nature* 551, 333-339 (2017).

77. Regev, A. et al. Science Forum: The Human Cell Atlas. *eLife* 6, e27041 (2017).

78. Liberzon, A. et al. Molecular signatures database (MSigDB) 3.0. *Bioinforma. Oxf Engl.* 27, 1739-1740 (2011).

79. Kowalczyk, M. S. et al. Single-cell RNA-seq reveals changes in cell cycle and differentiation programs upon aging of hematopoietic stem cells. *Genome Res.* 25, 1860-1872 (2015).

80. Van Keymeulen, A. et al. Distinct stem cells contribute to mammary gland development and maintenance. *Nature* 479, 189-193 (2011).

81. Salic, A. & Mitchison, T. J. A chemical method for fast and sensitive detection of DNA synthesis in vivo. *Proc. Natl. Acad. Sci. U.S.A* 105, 2415-2420 (2008).

82. Schneider, C. A., Rasband, W. S. & Eliceiri, K. W. NIH Image to ImageJ: 25 years of image analysis. *Nat. Methods* 9, 671-675 (2012).

83. Konermann, S. et al. Genome-scale transcriptional activation by an engineered CRISPR-Cas9 complex. *Nature* 517, 583-588 (2015).

84. Yan, Z. et al. Optimization of Recombinant Adeno-Associated Virus-Mediated Expression for Large Transgenes, Using a Synthetic Promoter and Tandem Array Enhancers. *Hum. Gene Ther.* 26, 334-346 (2015).

85. Brennecke, P. et al. Accounting for technical noise in single-cell RNA-seq experiments. *Nat. Methods* 10, 1093-1095 (2013).

86. Johnson, W. E., Li, C. & Rabinovic, A. Adjusting batch effects in microarray expression data using empirical Bayes methods. *Biostat. Oxf Engl.* 8, 118-127 (2007).

87. Leek, J. T., Johnson, W. E., Parker, H. S., Jaffe, A. E. & Storey, J. D. The sva package for removing batch effects and other unwanted variation in high-throughput experiments. *Bioinforma. Oxf Engl.* 28, 882-883 (2012).

88. Langmead, B., Trapnell, C., Pop, M. & Salzberg, S. L. Ultrafast and memory-efficient alignment of short DNA sequences to the human genome. *Genome Biol.* 10, R25 (2009).

89. Li, B. & Dewey, C. N. RSEM: accurate transcript quantification from RNA-Seq data with or without a reference genome. *BMC Bioinformatics* 12, 323 (2011).

90. Buja, A. & Eyuboglu, N. Remarks on Parallel Analysis. *Multivar. Behav. Res.* 27, 509-540 (1992).

91. Van Der Maaten, L. Accelerating t-SNE Using Tree-based Algorithms. *J Mach Learn Res* 15, 3221-3245 (2014).

92. Maaten, L. van der & Hinton, G. Visualizing Data using t-SNE. *J. Mach. Learn. Res.* 9, 2579-2605 (2008).

93. Levine, J. H. et al. Data-Driven Phenotypic Dissection of AML Reveals Progenitor-like Cells that Correlate with Prognosis. *Cell* 162, 184-197 (2015).

94. Zhang, H.-M. et al. AnimalTFDB: a comprehensive animal transcription factor database. *Nucleic Acids Res.* 40, D144-149 (2012).

95. *fgsea: Fast Gene Set Enrichment Analysis.* (Computer Technologies Laboratory, 2018).

96. Coifman, R. R. et al. Geometric diffusions as a tool for harmonic analysis and structure definition of data: multiscale methods. *Proc. Natl. Acad. Sci. U.S.A* 102, 7432-7437 (2005).

97. Haghverdi, L., Buettner, F. & Theis, F. J. Diffusion maps for high-dimensional single-cell analysis of differentiation data. *Bioinforma. Oxf Engl.* 31, 2989-2998 (2015).

98. Buettner, F. et al. Computational analysis of cell-to-cell heterogeneity in single-cell RNA-sequencing data reveals hidden subpopulations of cells. *Nat. Biotechnol.* 33, 155-160 (2015).

99. Pujana, M. A. et al. Network modeling links breast cancer susceptibility and centrosome dysfunction. *Nat. Genet.* 39, 1338-1349 (2007).

100. Stijnen, T., Hamza, T. H. & Ozdemir, P. Random effects meta-analysis of event outcome in the framework of the generalized linear mixed model with applications in sparse data. *Stat. Med.* 29, 3046-3067 (2010).

101. Koenker, R. & Hallock, K. F. Quantile Regression. *J. Econ. Perspect.* 15, 143-156 (2001).

The invention is further described by the following numbered paragraphs:

1. A method for identifying tuft cells in a sample, comprising detecting expression of any one or more of Cd24a, Tas1r3, Ffar3, Sucnr1, Gabbr1 or Drd3 protein or mRNA, wherein said expression indicates tuft cells.

2. The method of paragraph 1, further comprising detecting expression of any one or more of Ptprc or Tslp protein or mRNA, wherein said expression indicates a subset of tuft cells.

3. The method of paragraph 1, further comprising detecting expression of any one or more of Nrep, Nradd, Ninj1, and Plekhg5 protein or mRNA, wherein said expression indicates a subset of tuft cells.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for treating an inflammatory disease in a subject, comprising:

(i) detecting the presence of epithelial tuft cells by expression of a group of genes or polypeptides selected from the groups consisting of:

a) Lrmp, Dclk1, Cd24a, Tas1r3, Ffar3, Sucnr1, Gabbr1, Drd3, Etv1, Gfi1b, Hmx2, Hmx3, Runx1, Jarid2, Nfatc1, Zp710, Zbtb41, Spib, Foxe1, Sox9, Pou2f3, Ascl2, Fhf Tcf4, Gprc5c, Sucnr1, Ccrl1, CGprc5a, Opn3, Vmnn2r26 and Tas1r3;

b) Cd24a, Tas1r3, Ffar3, Sucnr1, Gabbr1 and Drd3:

c) Etv1, Gfi1b, Hmx2, Hmx3, Runx1, Jarid2, Nfatc1, Zfp710, Zbtb41, Spib, Foxe1, Sox9, Pou2f3, Ascl2, Ehf and Tcf4;

d) Etv1, Hmx2, Spib, Foxe1, Sox9, Pou2/3, Ascl2, Ehf and ift4;

e) Ffar3, Gprc5c, Sucnr1, Ccrl1, Gprc5a, Opn3, Vmn2r26 and Tas1r3;

f) Etv1, Hnx2, Spib, Foxe1, Pou2f3, Sox9, Ascl2, Hoxa5, Hivep3, Ehf, Tcf4, Mxd4, Hmx3, Hoxa3 and Nfatc1;

g) Lrmp, Gnat3, Gnb3, Plac8, Trpm5, Gng13, Ltc4s, Rgs13, Hck, Alox5ap, Avil, Alox5, PRtpn6, Atp2a3 and Plk2; and h) Rgs13, Rpl41, Pps26, Zmiz1, Gpx3, Suox, Tslp and Socs1;

(ii) contacting the epithelial tuft cells by administering to the subject a tuft cell modulating agent selected from a therapeutic antibody antagonist or a fragment thereof capable of binding to a surface receptor on the tuft cell in an amount sufficient to reduce the inflammatory response of epithelial tuft cells, wherein the surface receptor is capable of inducing an ILC class 2 inflammatory response.

2. The method of claim 1, wherein the tuft cell modulating agent comprises an agent capable of modulating the expression or activity of a transcription factor selected from the group consisting of Etv1, Hmx2, Spib, Foxe1, Pou2f3, Sox9, Ascl2, Hoxa5, Hivep3, Ehf, Tcf4, Mxd4, Hmx3, Hoxa3 and Nfatc1.

3. The method of claim 1, wherein the agent is administered to a mucosal surface.

4. The method of claim 1, wherein the epithelial tuft cells are detected using a technique selected from the group consisting of RT-PCR, RNA-seq, single cell RNA-seq, western blot, ELISA, flow cytometry, mass cytometry, fluorescence activated cell sorting, fluorescence microscopy, affinity separation, magnetic cell separation, microfluidic separation, and combinations thereof.

5. The method of claim 1, wherein the epithelial tuft cells comprise: a respiratory tuft cell, a gastrointestinal tuft cell, a subset of gastrointestinal tuft cells, or a subset of respiratory tuft cells.

6. The method of claim 5, wherein the respiratory tuft cell comprises: a laryngeal epithelial cell, a tracheal epithelial cell, a bronchial epithelial cell, or a submucosal gland cell.

7. The method of claim 5, wherein the gastrointestinal tuft cell comprises: an esophageal epithelial cell, a stomach epithelial cell, an intestinal epithelial cell, a laryngeal epithelial cell, a tracheal epithelial cell, a bronchial epithelial cell, or a submucosal gland cell.

8. The method of claim 1, wherein the epithelial tuft cells comprise an immune-like tuft cell further expressing a group of genes or polypeptides selected from the groups consisting of:

a) Ptprc (CD45) and Tslp;

b) Siglec5, Rac2 Ptprc, Sf6galnac6, Tm4sf4, Smpx, Ptgs1, C2, Gde1, Cpvl, S100a1, Fcna, Fbxl21, Ceacan2, Sucnr1, Spa17, Kcnj16, AA467197, Cd300lf; Trim38, Vmn2r26, Gcnt1, Irf7, Plk2, Glyctk and Tslp; and c) Lyn, Rhog, Il17rb, Irf7 and Rac2.

9. The method of claim 1, wherein the epithelial tuft cells comprise a neuronal-like tuft cell expressing a group of genes or polypeptides selected from the groups consisting of:

a) Nrep, Nradd, Ninj1, and Plekhg5; and b) Nradd, Endod1, Gga2, Rbm38, Slc44a2, Chr3, Ninj1, Mblac2, Usp11, Sphk2, Atp4a, Uspl1, Mcal1, Mta2, Inpp5j, Svil, Kcnn4, Dnahc8, Anxa11, Zfhx3, Lnpp5b, Tip3, Jup, and St5.

10. The method of claim 1, wherein the agent blocks activation of the surface receptor.

11. The method of claim 1, wherein the agent blocks binding of a ligand to the surface receptor.

12. The method of claim 1, wherein the agent is a blocking antibody.

13. The method of claim 3, wherein the mucosal surface is on a lung, a nasal passage, a trachea, a gut, an intestine, or an esophagus.

14. The method of claim 1, wherein the agent is administered by aerosol inhalation.

15. The method of claim 1, wherein the agent is administered by swallowing.

16. The method of claim 1, wherein the inflammatory disease comprises asthma, allergic asthma, therapy resistant-asthma, steroid-resistant severe allergic airway inflammation, systemic steroid-dependent severe eosinophilic asthma, chronic rhino-sinusitis (CRS), bronchitis, cystic fibrosis, infection, emphysema, lung cancer, pulmonary hypertension, chronic obstructive pulmonary disease, idiopathic pulmonary fibrosis, α-1-anti-trpysin deficiency, congestive heart failure, atopic dermatitis, food allergy, chronic airway inflammation, primary eosinophilic gastrointestinal disorder (EGID), eosinophilic esophagitis (EoE), eosinophilic gastritis, eosinophilic gastroenteritis, or eosinophilic colitis.

17. The method of claim 4, wherein the epithelial tuft cells are detected in a biopsy sample from the subject.

18. The method of claim 10, wherein the surface receptor comprises a G-protein coupled receptor (GPCR).

19. The method of claim 1, wherein the method reduces secretion of IL-25.

20. The method of claim 1, wherein the surface receptor is Sucnr1.

* * * * *

SEQUENCE LISTING

<160> NUMBER OF SEQ ID NOS: 2

<210> SEQ ID NO 1
<211> LENGTH: 288
<212> TYPE: PRT
<213> ORGANISM: Artificial Sequence
<220> FEATURE:
<223> OTHER INFORMATION: Synthetic

```
<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Pro Ala Pro Ser Pro Ala Phe
        50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
            115                 120                 125

Arg Pro Pro Arg Ala Lys Pro Ala Pro Arg Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
        210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
            275                 280                 285

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
        50                  55                  60

His Arg Val Ala Asp His Ala Gln Val Val Arg Val Leu Gly Phe Phe
```

-continued

```
65                    70                    75                    80

Gln Cys His Ser His Pro Ala Gln Ala Phe Asp Asp Ala Met Thr Gln
                85                    90                    95

Phe Gly Met Ser Arg His Gly Leu Leu Gln Leu Phe Arg Arg Val Gly
            100                   105                   110

Val Thr Glu Leu Glu Ala Arg Ser Gly Thr Leu Pro Pro Ala Ser Gln
            115                   120                   125

Arg Trp Asp Arg Ile Leu Gln Ala Ser Gly Met Lys Arg Ala Lys Pro
        130                   135                   140

Ser Pro Thr Ser Thr Gln Thr Pro Asp Gln Ala Ser Leu His Ala Phe
145                   150                   155                   160

Ala Asp Ser Leu Glu Arg Asp Leu Asp Ala Pro Ser Pro Met His Glu
                165                   170                   175

Gly Asp Gln Thr Arg Ala Ser
                180
```